(12) United States Patent
Mohammadi et al.

(10) Patent No.: US 10,703,788 B2
(45) Date of Patent: Jul. 7, 2020

(54) CHIMERIC FIBROBLAST GROWTH FACTOR 21 PROTEINS AND METHODS OF USE

(71) Applicant: New York University, New York, NY (US)

(72) Inventors: Moosa Mohammadi, Scarsdale, NY (US); Regina Goetz, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/895,770

(22) Filed: Feb. 13, 2018

(65) Prior Publication Data

US 2018/0186849 A1    Jul. 5, 2018

Related U.S. Application Data

(60) Continuation of application No. 15/289,447, filed on Oct. 10, 2016, now Pat. No. 9,926,355, which is a division of application No. 13/837,880, filed on Mar. 15, 2013, now Pat. No. 9,464,126.

(60) Provisional application No. 61/664,081, filed on Jun. 25, 2012, provisional application No. 61/656,778, filed on Jun. 7, 2012.

(51) Int. Cl.
| C07K 14/50 | (2006.01) |
| A61K 38/18 | (2006.01) |
| A61K 45/06 | (2006.01) |
| A61K 31/00 | (2006.01) |

(52) U.S. Cl.
CPC .............. *C07K 14/50* (2013.01); *A61K 31/00* (2013.01); *A61K 38/1825* (2013.01); *A61K 45/06* (2013.01); *C07K 14/501* (2013.01); *C07K 14/503* (2013.01); *C07K 2319/00* (2013.01); *G01N 2333/50* (2013.01); *G01N 2500/02* (2013.01); *G01N 2800/042* (2013.01)

(58) Field of Classification Search
None
See application file for complete search history.

(56) References Cited

U.S. PATENT DOCUMENTS

| 5,132,408 | A | 7/1992 | Baird et al. |
| 5,478,804 | A | 12/1995 | Calabresi et al. |
| 5,656,458 | A | 8/1997 | Barr |
| 6,326,484 | B1 | 12/2001 | Gage et al. |
| 6,982,170 | B1 | 1/2006 | Maciag et al. |
| 7,491,697 | B2 | 2/2009 | Beals et al. |
| 7,582,607 | B2 | 9/2009 | Frye et al. |
| 7,622,445 | B2 | 11/2009 | Frye et al. |
| 7,655,627 | B2 | 2/2010 | Frye et al. |
| 7,956,033 | B2 | 6/2011 | Cheng et al. |
| 8,168,591 | B2 | 5/2012 | Takada et al. |
| 8,642,546 | B2 | 2/2014 | Belouski et al. |
| 8,889,426 | B2 | 11/2014 | Mohammadi et al. |
| 8,889,621 | B2 | 11/2014 | Mohammadi et al. |
| 8,906,854 | B2 | 12/2014 | Jonker et al. |
| 8,951,966 | B2 | 2/2015 | Ling et al. |
| 8,999,929 | B2 | 4/2015 | Mohammadi et al. |
| 9,072,708 | B2 | 7/2015 | Jonker et al. |
| 9,272,017 | B2 | 3/2016 | Mohammadi et al. |
| 9,464,126 | B2 | 10/2016 | Mohammadi et al. |
| 9,474,785 | B2 | 10/2016 | Mohammadi et al. |
| 9,475,856 | B2 | 10/2016 | Mohammadi et al. |
| 9,550,820 | B2 | 1/2017 | Mohammadi et al. |
| 9,657,075 | B2 | 5/2017 | Mohammadi et al. |
| 9,907,830 | B2 | 3/2018 | Mohammadi et al. |
| 9,926,355 | B2 | 3/2018 | Mohammadi et al. |
| 9,926,356 | B2 | 3/2018 | Mohammadi et al. |
| 10,174,090 | B2 | 1/2019 | Mohammadi et al. |
| 10,364,278 | B2 | 7/2019 | Mohammadi et al. |
| 10,633,424 | B2 | 4/2020 | Mohammadi et al. |
| 2004/0259780 | A1 | 12/2004 | Glasebrook et al. |
| 2007/0142278 | A1 | 6/2007 | Beals et al. |
| 2007/0237768 | A1 | 10/2007 | Glaesner et al. |
| 2007/0265200 | A1 | 11/2007 | Glaesner et al. |
| 2007/0293430 | A1 | 12/2007 | Frye et al. |
| 2007/0299007 | A1 | 12/2007 | Frye et al. |
| 2008/0103096 | A1 | 5/2008 | Frye et al. |
| 2008/0255045 | A1 | 10/2008 | Cujec et al. |
| 2008/0261875 | A1 | 10/2008 | Etgen et al. |
| 2009/0111742 | A1 | 4/2009 | Kharitonenkov et al. |
| 2009/0118190 | A1 | 5/2009 | Beals et al. |
| 2009/0305986 | A1 | 12/2009 | Belouski et al. |
| 2010/0062984 | A1 | 3/2010 | Kumar et al. |
| 2010/0158914 | A1 | 6/2010 | Desnoyers |
| 2010/0184665 | A1 | 7/2010 | Suzuki et al. |

(Continued)

FOREIGN PATENT DOCUMENTS

| EP | 0 645 451 B1 | 8/2001 |
| WO | WO 2011/047267 A1 | 4/2011 |

(Continued)

OTHER PUBLICATIONS

Office Action for U.S. Appl. No. 15/289,447 dated Jun. 16, 2017.

(Continued)

*Primary Examiner* — Marianne P Allen
(74) *Attorney, Agent, or Firm* — Pepper Hamilton LLP

(57) ABSTRACT

The present invention relates to a chimeric protein that includes an N-terminus coupled to a C-terminus, where the N-terminus includes a portion of a paracrine fibroblast growth factor ("FGF") and the C-terminus includes a C-terminal portion of an FGF21 molecule. The portion of the paracrine FGF is modified to decrease binding affinity for heparin and/or heparan sulfate compared to the portion without the modification. The present invention also relates to pharmaceutical compositions including chimeric proteins according to the present invention, methods for treating a subject suffering from diabetes, obesity, or metabolic syndrome, and methods of screening for compounds with enhanced binding affinity for the βKlotho-FGF receptor complex involving the use of chimeric proteins of the present invention.

33 Claims, 13 Drawing Sheets

Specification includes a Sequence Listing.

(56) References Cited

U.S. PATENT DOCUMENTS

| | | |
|---|---|---|
| 2010/0216715 A1 | 8/2010 | Tagmose et al. |
| 2010/0285131 A1 | 11/2010 | Belouski et al. |
| 2010/0286042 A1 | 11/2010 | Imamura et al. |
| 2010/0323954 A1 | 12/2010 | Li et al. |
| 2011/0053841 A1 | 3/2011 | Yayon et al. |
| 2011/0104152 A1 | 5/2011 | Sonoda |
| 2011/0150901 A1 | 6/2011 | Smith et al. |
| 2011/0172401 A1 | 7/2011 | Cujec et al. |
| 2011/0190207 A1 | 8/2011 | Mohammadi et al. |
| 2011/0195077 A1 | 8/2011 | Gass et al. |
| 2012/0052069 A1 | 3/2012 | Belouski et al. |
| 2012/0288886 A1 | 11/2012 | Mohammadi et al. |
| 2013/0023474 A1 | 1/2013 | Ling et al. |
| 2013/0058896 A1 | 3/2013 | Takada et al. |
| 2013/0116171 A1 | 5/2013 | Jonker et al. |
| 2013/0184211 A1 | 7/2013 | Mohammadi et al. |
| 2013/0231277 A1 | 9/2013 | Mohammadi et al. |
| 2013/0331316 A1 | 12/2013 | Mohammadi et al. |
| 2013/0331317 A1 | 12/2013 | Mohammadi et al. |
| 2013/0331325 A1 | 12/2013 | Mohammadi et al. |
| 2014/0094406 A1 | 4/2014 | Mohammadi et al. |
| 2014/0107022 A1 | 4/2014 | Mohammadi et al. |
| 2014/0155316 A1 | 6/2014 | Mohammadi et al. |
| 2014/0171361 A1 | 6/2014 | Jonker et al. |
| 2014/0243260 A1 | 8/2014 | Mohammadi et al. |
| 2015/0111821 A1 | 4/2015 | Suh et al. |
| 2015/0343022 A1 | 12/2015 | Jonker et al. |
| 2016/0206695 A1 | 7/2016 | Suh et al. |
| 2017/0096462 A1 | 4/2017 | Mohammadi et al. |
| 2017/0101449 A1 | 4/2017 | Mohammadi et al. |
| 2017/0226172 A1 | 8/2017 | Mohammadi et al. |
| 2017/0355738 A1 | 12/2017 | Mohammadi et al. |
| 2018/0186850 A1 | 7/2018 | Mohammadi et al. |

FOREIGN PATENT DOCUMENTS

| | | |
|---|---|---|
| WO | WO 2011/130729 A2 | 10/2011 |
| WO | WO 2013/184958 A1 | 12/2013 |
| WO | WO 2013/184960 A2 | 12/2013 |
| WO | WO 2013/184962 A1 | 12/2013 |
| WO | WO 2015/149069 A1 | 10/2015 |

OTHER PUBLICATIONS

Office Action for U.S. Appl. No. 15/598,420 dated Jul. 5, 2018.
Restriction Requirement for U.S. Appl. No. 15/283,862 dated Feb. 22, 2018.
Restriction Requirement in U.S. Appl. No. 15/896,469 (dated Feb. 14, 2019).
Office Action in Canadian Patent Application No. 2,875,790 (dated Mar. 22, 2019).
Yie et al., "FGF21 N- and C-Termini Play Different Roles in Receptor Interaction and Activation," FEBS Lett. 583:19-24 (2009).
Andrukhova et al., "FGF23 Acts Directly on Renal Proximal Tubules to Induce Phosphaturia Through Activation of the ERK1/2-SKG1 Signaling Pathway," Bone 51(3):621-8 (Jun. 12, 2012).
Beenken et al., "Plasticity in Interactions of Fibroblast Growth Factor 1 (FGF1) N Terminus With FGF Receptors Underlies Promiscuity of FGF1," J. Biol. Chem. 287(5):3067-3078 (Nov. 4, 2011).
Jonker et al., "A PPARgamma-FGF1 Axis Is Required for Adaptive Adipose Remodelling and Metabolic Homeostasis," Nature 485(7398):391-394 (Apr. 22, 2012).
Wu et al., "A Unique FGF23 With the Ability to Activate FGFR Signaling Through Both alphaKlotho and betaKlotho," J. Mol. Biol. 418:82-89 (2012).
Beenken & Mohammadi, "The Structural Biology of the FGF19 Subfamily," Adv. Exp. Med. Biol. 728:1-24 (2012).
Wu et al., "C-Terminal Tail of FGF19 Determines Its Specificity Toward Klotho Co-Receptors," J. Biol. Chem. 283(48):33304-33309 (2008).
Goetz et al., "Conversion of a Paracrine Fibroblast Growth Factor Into an Endocrine Fibrobalst Growth Factor," J. Biol. Chem. 287(34):29134-29146 (Jun. 25, 2012).
Goetz et al., "Klotho Coreceptors Inhibit Signaling by Paracrine Fibroblast Growth Factor 8 Subfamily Ligands," Mol. Cell. Biol. 32(10):1944-1954 (Mar. 26, 2012).
Olsen et al., "Insights Into the Molecular Basis for Fibroblast Growth Factor Receptor Autoinhibition and Ligand-Binding Promiscuity,"Proc. Nat'l. Acad. Sci. USA 101(4):935-940 (2004).
Wei et al., "Fibroblast Growth Factor 21 Promotes Bone Loss by Potentiating the Effects of Peroxisome Proliferator-Activated Receptor Gamma," Proc. Nat'l. Acad. Sci. USA 109(8):3143-3148 (Feb. 21, 2012).
Wu et al., "Separating Mitogenic and Metabolic Activities of Fibroblast Growth Factor 19 (FGF19)," Proc. Nat'l. Acad. Sci. USA 107(32):14158-14163 (2010).
Wu et al., "FGF19-Induced Hepatocyte Proliferation Is Mediated Through FGFR4 Activation," J. Biol. Chem. 285(8):5165-5170 (2009).
Zhang et al., "Receptor Specificity of the Fibroblast Growth Factor Family," J. Biol. Chem. 281(23):15694-15700 (2006).
Presta et al., "Structure-Function Relationship of Basic Fibroblast Growth Factor: Site-Directed Mutagenesis of a Putative Heparin-Binding and Receptor-Binding Region," Biochem. Biophys. Res. Commun. 185(3):1098-1107 (1992).
Zakrzewska et al., "Increased Protein Stability of FGF1 Can Compensate for Its Reduced Affinity for Heparin," J. Biol. Chem. 284(37):25388-403 (2009).
Motomura et al., "An FGF1:FGF2 Chimeric Growth Factor Exhibits Universal FGF Receptor Specificity, Enhanced Stability and Augmented Activity Useful for Epithelial Proliferation and Radioprotection," Biochim. Biophys. Acta 1780(12):1432-40 (2008).
Nakayama et al., "Post Treatment With an FGF Chimeric Growth Factor Enhances Epithelial Cell Proliferation to Improve Recovery From Radiation-Induced Intestinal Damage," Int. J. Radiat. Oncol. Biol. Phys. 78(3):860-7 (2010).
Kharitonenkov et al., "The Metabolic State of Diabetic Monkeys is Regulated by Fibroblast Growth Factor-21," Endocrinology 148(2):774-81 (2007).
Igarashi et al., "Characterization of Recombinant Human Fibroblast Growth Factor (FGF)-10 Reveals Functional Similarities With Keratinocyte Growth Factor (FGF-7)," J. Biol. Chem. 273(21):13230-5 (1998).
International Search Report and Written Opinion for corresponding PCT/US13/44589 (dated Nov. 13, 2013).
Goetz et al., "Molecular Insights Into the Klotho-Dependent, Endocrine Mode of Action of Fibroblast Growth Factor 19 Subfamily Members,"Mol. Cell. Biol. 27(9):3417-3428 (2007).
Beenken, "Structural and Biochemical Studies of GFf-FGFR Complexes," Thesis (Sep. 2011).
Ge et al., "Characterization of a FGF19 Variant With Altered Receptor Specificity Revealed a Central Role for FGFR1c in the Regulation of Glucose Metabolism," PLoS One, 7(3):e33603 (Epub Mar. 23, 2012).
Wu et al., "FGF19 Regulates Cell Proliferation, Glucose and Bile Acid Metabolism Via FGFR4-Dependent and Independent Pathways," PLoS One 6(3):e17868 (Mar. 8, 2011).
Wu et al., "Selective Activation of FGFR4 by an FGF19 Variant Does Not Improve Glucose Metabolism in OB/OB Mice," Proc. Nat'l. Acad. Sci U.S.A. 106(34):14379-84 (2009).
Mohammadi et al., "Structural Basis for Fibroblast Growth Factor Receptor Activation," Cytokine & Growth Factor Reviews 16:107-137 (2005).
Hutley et al., "Fibroblast Growth Factor 1: A Key Regulator of Human Adipogenesis," Diabetes 53:3097-3106 (2004).
International Search Report and Written Opinion for PCT/US13/44594 (dated Nov. 13, 2013).
Imamura et al., "Recovery of Mitogenic Activity of a Growth Factor Mutant with Nuclear Translocation Sequence," Science 249:1567-1570 (Sep. 28, 1990).
International Search Report and Written Opinion for PCT/US13/44592 (dated Jan. 17, 2014).

(56) References Cited

OTHER PUBLICATIONS

Restriction Requirement for U.S. Appl. No. 13/838,350 (dated Jan. 30, 2014).
Office Action in U.S. Appl. No. 13/641,451 (dated Dec. 16, 2013).
Goetz et al., "Isolated C-Terminal tail of FGF23 Alleviates Hypophosphatemia by Inhibiting FGF23-FGFR-Klotho Complex Formation," PNAS 107(1):407-412 (Epub Dec. 4, 2009).
International Search Report and Written Opinion for PCT/US2013/028888 (dated Jul. 23, 2013).
Restriction Requirement in U.S. Appl. No. 14/176,992 (dated Mar. 7, 2014).
Office Action in U.S. Appl. No. 14/176,992 (dated Jun. 26, 2014).
International Search Report and Written Opinion for PCT/US14/17367 (dated Jun. 18, 2014).
Razzaque, "The FGF23-Klotho Axis: Endocrine Regulation of Phosphate Homeostasis," Nat. Rev. Endocrinol. 5(11):611-19 (2009).
Restriction Requirement in U.S. Appl. No. 13/784,289 (dated Sep. 3, 2014).
Restriction Requirement in U.S. Appl. No. 13/839,051 (dated Sep. 3, 2014).
Office Action in U.S. Appl. No. 13/838,350 (dated Jul. 17, 2014).
Restriction Requirement in U.S. Appl. No. 14/097,056 (dated Aug. 14, 2014).
Office Action in U.S. Appl. No. 13/839,051 (dated Dec. 11, 2014).
Office Action in U.S. Appl. No. 13/838,350 (dated Dec. 11, 2014).
Office Action in U.S. Appl. No. 13/784,289 (dated Mar. 4, 2015).
Office Action in U.S. Appl. No. 13/839,051, 11 pages (dated Aug. 6, 2015).
Office Action in U.S. Appl. No. 13/838,350, 11 pages (dated Aug. 3, 2015).
Restriction Requirement in U.S. Appl. No. 14/097,116, 9 pages (dated Dec. 11, 2014).
Restriction Requirement in U.S. Appl. No. 14/185,366, 9 pages (dated Jun. 4, 2015).
Office Action in U.S. Appl. No. 14/185,366, 10 pages (dated Jan. 15, 2016).
Abraham et al., "Human Basic Fibroblast Growth Factor: Nucleotide Sequence and Genomic Organization," *EMBO J.* 10:2523-2528 (1986).
Esch et al., "Primary Structure of Bovine Pituitary Basic Fibroblast Growth Factor (FGF) and Comparison with the Amino-Terminal Sequence of Bovine Brain Acidic FGF," PNAS 82:6507-6511 (1985).
Kurosu et al., "The Klotho Gene Family as a Regulator of Endocrine Fibroblast Growth Factors," Mol Cel Endocrin. 299:72-78 (2009).
Ono et al., "Novel Regulation of Fibroblast Growth Factor 2 (FGF2)-Mediated Cell Growth by Polysialic Acid," J. Biol. Chem. 287(6):3710-3722 (2012).

Schlessinger et al., "Crystal Structure of a Ternary FGF-FGRF-Heparin Complex Reveals a Dual Role for Heparin in FGFR Binding and Dimerization," Molecular Cell 6:743-750 (2005).
Thompson et al., "Energetic Characterization of the Basic Fibroblast Growth Factor-Heparin Interaction: Identification of the Heparin Binding Domains," Biochemistry 33:3831-3840 (1994).
Suh et al., "Endocrinization of FGF1 Produces a Neomorphic and Potent Insulin Sensitizer," Author Manuscript, Nature 513(7518):436-439 (2014).
Office Action in U.S. Appl. No. 13/784,289, 8 pages (dated Nov. 5, 2015).
Beenken et al., "The FGF Family: Biology, Pathophysiology and Therapy," Nat Rev Drug Discov. 8(3):235-53 (Mar. 2009).
Kurosu et al., "Tissue-specific Expression of βKlotho and Fibroblast Growth Factor (FGF) Receptor Isoforms Determines Metabolic Activity of FGF19 and FGF21," J. Biol. Chem. 282(37):26687-26695 (2007).
Micanovic et al., "Different Roles of N- and C- Termini in the Functional Activity of FGF21," J. Cell. Physiol. 219:227-234 (2009).
Kharitonenkov et al.,"FGF-21/FGF-21 Receptor Interaction and Activation is Determined by βKlotho," J. Cell. Physiol. 215:1-7 (2008).
Yao et al., "Expression and Pharmacological Evaluation of Fusion Protein FGF21-L-Fc," Acta Pharmaceutica Sinica 46(7):787-92 (2011) (Abstract in English).
Extended European Search Report for European Application No. 13799858.9, 13 pages (dated May 3, 2016).
Office Action in U.S. Appl. No. 13/839,051(dated May 25, 2016).
Patent Examination Report in Australian Patent Application No. 2014274604 (dated Oct. 16, 2015).
Office Action for Chinese Patent Application No. 201380039848.9 (dated Oct. 8, 2016) (Translation in English).
Pellegrini et al., "Crystal Structure of Fibroblast Growth Factor Receptor Ectodomain Bound to Ligand and Heparin," Nature 407:1029-1034 (2000).
Pellegrini et al., Protein Data Bank, 1E0O, "Crystal Structure of a Ternary FGF1-FGFR2-Heparin Complex," (Released Oct. 23, 2000).
Restriction Requirement in U.S. Appl. No. 13/837,880 (dated Sep. 3, 2014).
Office Action in U.S. Appl. No. 13/837,880 (dated Dec. 11, 2014).
Office Action in U.S. Appl. No. 13/837,880 (dated Aug. 4, 2015).
DiGabriele et al., "Structure of a Heparin-Linked Biologically Active Dimer of Fibroblast Growth Factor," *Nature* 393:812-17 (1998).
Second Office Action for Chinese Patent Application No. 201380039848.9 (dated Jun. 8, 2017).
Office Action in U.S. Appl. No. 15/289,544 (dated May 30, 2017).
Crumley et al., Genbank Accession No. 1605206A, acidic fibroblast growth factor (1996).
Office Action in European Patent Application Serial No. 13799858.9 (dated Jul. 31, 2019).
Office Action in U.S. Appl. No. 15/896,469 (dated Jun. 14, 2019).

FIG. 2

```
FGF19 (169)  LPMV EEEPRDLRGH LESDMFSSPL ETDSMDPFGL VTGLEAVRSP SFEK---- ---P
FGF21 (168)  PGLP PALPR--IGP PPGILAPQPP DVGSSDPLSM V-GPSQGRSP SYAS---- ---E LP
FGF23 (163)  ---- EIPLIHFNTP IPRRHTRSAE DDSERDPLN- VLKPRARMTP APASCSQELP

FGF19        ---- --------- ---------- ---------- ---------- -------- ----
FGF21        ---- --------- ---------- ---------- ---------- -------- ----
FGF23 (212)  SAEDNSPMAS DPLGVVRGGR VNTHAGGTGP EGCRPFAKFI
```

CHIMERIC FIBROBLAST GROWTH FACTOR 21 PROTEINS AND METHODS OF USE

This application is a continuation of U.S. patent application Ser. No. 15/289,447, filed Oct. 10, 2016, which is a divisional application of U.S. patent application Ser. No. 13/837,880, filed Mar. 15, 2013, now U.S. Pat. No. 9,464,126, issued Oct. 11, 2016, which claims priority benefit of U.S. Provisional Patent Application No. 61/656,778, filed Jun. 7, 2012, and U.S. Provisional Patent Application No. 61/664,081, filed Jun. 25, 2012, each of which is hereby incorporated by reference in its entirety.

This invention was made with government support under DE13686 awarded by National Institutes of Health. The government has certain rights in the invention.

FIELD OF THE INVENTION

The present invention relates to chimeric fibroblast growth factor ("FGF") proteins and uses thereof.

BACKGROUND OF THE INVENTION

Type 2 diabetes is a chronic progressive disorder, which results from end-organ resistance to the action of insulin in combination with insufficient insulin secretion from the pancreas. The metabolic abnormalities associated with insulin resistance and secretory defects, in particular the hyperglycemia, lead over the course of years to extensive irreversible damage to multiple organs including heart, blood vessels, kidney, and eye. Currently, nearly 200 million or 2.9% of the world population have type 2 diabetes (World Health Organization, Diabetes Fact Sheet No 312, January 2011; Wild et al., "Global Prevalence of Diabetes: Estimates for the Year 2000 and Projections for 2030," *Diabetes Care* 27(5):1047-1053 (2004)), and its prevalence is rising at an alarmingly fast pace in parallel with the rise in the prevalence of overweight and obesity (World Health Organization, Obesity and Overweight Fact Sheet No 311, January 2011). Until the end of the 20$^{th}$ century, type 2 diabetes was observed only in adults but what was once known as "adult-onset diabetes" is now also diagnosed in children and adolescents, and this growing incidence can be related to the increase in overweight and obesity among children and adolescents. The prevalence of pre-diabetes, an intermediate metabolic stage between normal glucose homeostasis and diabetes, is even greater than that of type 2 diabetes. Currently, nearly 80 million or 26% of the population in the United States alone have pre-diabetes (Center for Disease Control and Prevention, National Diabetes Fact Sheet 2011), and as such are at high risk for progressing to type 2 diabetes. Type 2 diabetes ranks among the ten leading causes of death worldwide, and the World Health Organization projects that mortality from diabetes (90% of which is type 2) will more than double within the next decade (World Health Organization, Diabetes Fact Sheet N° 312, January 2011). Type 2 diabetes also is a major cause of disability. As a consequence of diabetic retinopathy, about 10% of all patients with diabetes in the world develop severe visual impairment and 2% become blind 15 years into the disease (World Health Organization, Diabetes Fact Sheet N° 312, January 2011). Diabetic neuropathy, which affects up to half of all patients with diabetes worldwide (World Health Organization, Diabetes Fact Sheet N° 312, January 2011), accounts for the majority of nontraumatic lower-limb amputations. Indeed, in its recently published first worldwide report on non-infectious diseases, the World Health Organization considers diabetes, together with other chronic non-infectious diseases like cancer and heart disease, a global economic and social burden, which exceeds that imposed by infectious diseases such as HIV/AIDS.

The current drug therapy for type 2 diabetes is focused on correcting the hyperglycemia in the patients. Although a number of small molecules and biologics with different mechanisms of anti-hyperglycemic action are available for use as mono-therapy or combination therapy, most, if not all of these have limited efficacy, limited tolerability, and significant adverse effects (Moller, "New Drug Targets for Type 2 Diabetes and the Metabolic Syndrome," *Nature* 414 (6865):821-827 (2001)). For example, treatment with sulfonylureas, glinides, thiazolidinediones, or insulin has been associated with weight gain, which is an undesired effect since overweight is considered a driving force in the pathogenesis of type 2 diabetes. Some of these treatments have also been associated with increased risk of hypoglycemia. A limitation specific to the thiazolidinediones is the potential for adverse cardiovascular effects (DeSouza et al., "Therapeutic Targets to Reduce Cardiovascular Disease in Type 2 Diabetes," *Nat Rev Drug Discov* 8(5):361-367 (2009)). A meta-analysis of clinical data on the thiazolidinedione rosiglitazone (Avandia®), which was widely used for the treatment of type 2 diabetes, found that the drug increased the risk of myocardial infarction in patients with type 2 diabetes (Nissen et al., "Effect of Rosiglitazone on the Risk of Myocardial Infarction and Death from Cardiovascular Causes," *N Engl J Med* 356(24):2457-2471 (2007)). Of all diabetic complications, cardiovascular disease is the main cause of morbidity and mortality in patients with diabetes (World Health Organization, Diabetes Fact Sheet No 312, January 2011; Center for Disease Control and Prevention, National Diabetes Fact Sheet 2011), and hence an aggravation of cardiovascular risk by drug treatment is absolutely unacceptable. In the wake of the debate about the cardiovascular safety of thiazolidinediones, the FDA issued a guidance on evaluating cardiovascular risk in new anti-diabetic therapies to treat type 2 diabetes (Opar A, "Diabetes Drugs Pass Cardiovascular Risk Check," *Nat Rev Drug Discov* 8(5):343-344 (2009)). Meanwhile, thiazolidinediones lost their popularity. Even for glucagon-like peptide-1 agonists, one of the latest class of drugs introduced for the treatment of type 2 diabetes, concerns about safety have been raised, namely the potential for carcinogenicity (Opar A, "Diabetes Drugs Pass Cardiovascular Risk Check," *Nat Rev Drug Discov* 8(5):343-344 (2009)). Therefore, novel therapies that are more effective and safer than existing drugs are needed. Since the currently available drugs do not directly target complications of advanced diabetic disease, especially cardiovascular disease, therapies that are not only effective in lowering blood glucose but also reduce cardiovascular risk factors such as dyslipidemia are particularly desired.

A search conducted by Eli Lilly & Co. for potential novel biotherapeutics to treat type 2 diabetes led to the discovery of fibroblast growth factor (FGF) 21 as a protein that stimulates glucose uptake into adipocytes in an insulin-independent fashion (Kharitonenkov et al., "FGF-21 as a Novel Metabolic Regulator," *J Clin Invest* 115(6):1627-1635 (2005)). FGF21 has since emerged as a key endocrine regulator not only of glucose metabolism but also of lipid metabolism, and has become one of the most promising drug candidates for the treatment of type 2 diabetes, obesity, and metabolic syndrome. In mouse models of diabetes and obesity, pharmacologic doses of FGF21 lower plasma glucose and increase insulin sensitivity (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12): 6018-6027 (2008)). Concurrently, FGF21 lowers plasma triglyceride and cholesterol, enhances lipolysis and suppresses lipogenesis, and accelerates energy expenditure (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12):6018-6027 (2008)). In obese mice, FGF21 causes weight loss, in lean mice, it is weight neutral (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12):6018-6027 (2008)). Thus, FGF21 has some of the most desired characteristics of a drug for the treatment of type 2 diabetes; not only does it improve glycemic control, but also directly affects cardiovascular risk factors, such as hypertriglyceridemia, and reduces obesity, which is considered the single most important promoter of type 2 diabetes. Importantly, FGF21 does not induce hypoglycemia (Kharitonenkov et al., "FGF-21 as a Novel Metabolic Regulator," *J Clin Invest* 115(6):1627-1635 (2005)), a side effect that can occur with several of the current anti-diabetic therapies, including insulin. Moreover, FGF21 does not exhibit any mitogenic activity in mice (Kharitonenkov et al., "FGF-21 as a Novel Metabolic Regulator," *J Clin Invest* 115(6):1627-1635 (2005)), ruling out the possibility of a carcinogenic risk. The findings on FGF21 therapy in mouse models of diabetes have been reproduced in diabetic rhesus monkeys (Kharitonenkov et al., "The Metabolic State of Diabetic Monkeys is Regulated by Fibroblast Growth Factor-21," *Endocrinology* 148(2):774-781 (2007)), and are currently followed up with clinical trials in humans (Kharitonenkov et al., "FGF21 Reloaded: Challenges of a Rapidly Growing Field," *Trends Endocrinol Metab* 22(3):81-86 (2011)). However, there is a need for more effective FGF21 therapeutics.

The present invention overcomes these and other deficiencies in the art.

SUMMARY OF THE INVENTION

One aspect of the present invention relates to a chimeric protein. The chimeric protein includes an N-terminus coupled to a C-terminus, where the N-terminus includes a portion of a paracrine fibroblast growth factor ("FGF") and the C-terminus includes a C-terminal portion of an FGF21 molecule. The portion of the paracrine FGF is modified to decrease binding affinity for heparin and/or heparan sulfate compared to the portion without the modification.

Another aspect of the present invention relates to a method for treating a subject suffering from a disorder. This method involves selecting a subject suffering from the disorder and providing a chimeric FGF protein, where the chimeric FGF protein includes an N-terminus coupled to a C-terminus. The N-terminus includes a portion of a paracrine FGF and the C-terminus includes a C-terminal portion of FGF21. The portion of the paracrine FGF is modified to decrease binding affinity for heparin and/or heparan sulfate compared to the portion without the modification. This method also involves administering a therapeutically effective amount of the chimeric FGF protein to the selected subject under conditions effective to treat the disorder.

Another aspect of the present invention relates to a method of making a chimeric FGF protein possessing enhanced endocrine activity. This method involves introducing one or more modifications to an FGF protein, where the modification decreases the affinity of the FGF protein for heparin and/or heparan sulfate and coupling a Klotho co-receptor binding domain to the modified FGF protein's C-terminus, whereby a chimeric FGF protein possessing enhanced endocrine activity is made.

Yet another aspect of the present invention relates to a method of facilitating fibroblast growth factor receptor ("FGFR")-βKlotho co-receptor complex formation. This method involves providing a cell that includes a βKlotho co-receptor and an FGFR and providing a chimeric FGF protein. The chimeric FGF protein includes a C-terminal portion of FGF21 and a portion of a paracrine FGF, where the portion of the paracrine FGF is modified to decrease binding affinity for heparin and/or heparan sulfate compared to the portion without the modification. This method also involves contacting the cell and the chimeric FGF protein under conditions effective to cause FGFR-βKlotho co-receptor complex formation.

Yet a further aspect of the present invention relates to a method of screening for agents capable of facilitating FGFR-βKlotho complex formation in the treatment of a disorder. This method involves providing a chimeric FGF that includes an N-terminus coupled to a C-terminus, where the N-terminus includes a portion of a paracrine FGF and the C-terminus includes a C-terminal portion of FGF21. The portion of the paracrine FGF is modified to decrease binding affinity for heparin and/or heparan sulfate compared to the portion without the modification. This method also involves providing a binary βKlotho-FGFR complex and providing one or more candidate agents. This method further involves combining the chimeric FGF, the binary βKlotho-FGFR complex, and the one or more candidate agents under conditions permitting the formation of a ternary complex between the chimeric FGF and the binary βKlotho-FGFR complex in the absence of the one or more candidate agents. This method also involves identifying the one or more candidate agents that decrease ternary complex formation between the chimeric FGF and the binary βKlotho-FGFR complex compared to the ternary complex formation in the absence of the one or more candidate agents as suitable for treating the disorder.

Fibroblast growth factors (FGFs) 19, 21, and 23 are hormones that regulate in a Klotho co-receptor-dependent fashion major metabolic processes such as glucose and lipid metabolism (FGF21) and phosphate and vitamin D homeostasis (FGF23). The role of heparan sulfate glycosaminoglycan in the formation of the cell surface signaling complex of endocrine FGFs has remained unclear. To decipher the role of HS in endocrine FGF signaling, we generated FGF19 and FGF23 mutant ligands devoid of HS binding and compared their signaling capacity with that of wild-type ligands. The data presented herein show that the mutated ligands retain full metabolic activity demonstrating that HS does not participate in the formation of the endocrine FGF signaling complex. Here it is shown that heparan sulfate is not a component of the signal transduction unit of FGF19 and FGF23. A paracrine FGF is converted into an endocrine ligand by diminishing heparan sulfate binding affinity of the paracrine FGF and substituting its C-terminal tail for that of an endocrine FGF containing the Klotho co-receptor binding site in order to home the ligand into the target tissue. The ligand conversion provides a novel strategy for engineering endocrine FGF-like molecules for the treatment of metabolic disorders, including global epidemics such as type 2 diabetes and obesity.

BRIEF DESCRIPTION OF THE DRAWINGS

FIG. 1A shows interactions of FGF2 (schematic representation) with a heparin hexasaccharide (shown as sticks) as observed in the crystal structure of the 2:2 FGF2-FGFR1c dimer (PDB ID: 1FQ9; (Schlessinger et al., *Mol. Cell* 6:743-750 (2000), which is hereby incorporated by reference in its entirety)). The heparin hexasaccharide consists of three disaccharide units of 1→4 linked N-sulfated-6-O-sulfated D-glucosamine and 2-O-sulfated L-iduronic acid. Note that the heparin hexasaccharide interacts with both side chain and backbone atoms of residues in the HS-binding site of FGF2. Dashed lines denote hydrogen bonds. K128, R129, and K134, which make the majority of hydrogen bonds with the heparin hexasaccharide, are boxed. The β-strand nomenclature follows the original FGF1 and FGF2 crystal structures (Ago et al., *J. Biochem.* 110:360-363 (1991); Eriksson et al., *Proc. Nat'l. Acad. Sci. U.S.A.* 88:3441-3445 (1991); Zhang et al., *Proc. Nat'l. Acad. Sci. U.S.A.* 88:3446-3450 (1991); Zhu et al., *Science* 251:90-93 (1991), which are hereby incorporated by reference in their entirety). Please note that compared to the prototypical β-trefoil fold seen in soybean trypsin inhibitor (PDB ID: 1TIE; (Onesti et al., *J. Mol. Biol.* 217:153-176 (1991), which is hereby incorporated by reference in its entirety)) and interleukin 1β (PDB ID: 1I1B; (Finzel et al., *J. Mol. Biol.* 209:779-791 (1989), which is hereby incorporated by reference in its entirety)), the β10-β11 strand pairing in FGF2 and other paracrine FGFs is less well defined. FIGS. 1B and 1C show cartoon representation of the crystal structures of FGF19 (PDB ID: 2P23; (Goetz et al., *Mol. Cell Biol.* 27:3417-3428 (2007), which is hereby incorporated by reference in its entirety)) (FIG. 1B) and FGF23 (PDB ID: 2P39; (Goetz et al., *Mol. Cell Biol.* 27:3417-3428 (2007), which is hereby incorporated by reference in its entirety)) (FIG. 1C) shown in the same orientation as the FGF2 structure in FIG. 1A. Side chains of residues that map to the corresponding HS-binding sites of these ligands are shown as sticks. Residues selected for mutagenesis to knock out residual HS binding in FGF19 and FGF23 are boxed. NT and CT indicate N- and C-termini of the FGFs. FIG. 1D is a schematic of two working models for the endocrine FGF-FGFR-Klotho coreceptor signal transduction unit. A recent study on the ternary complex formation between FGF21, FGFR1c, and βKlotho supports the 1:2:1 model rather than the 2:2:2 model (Ming et al., *J. Biol. Chem.* 287:19997-20006 (2012), which is hereby incorporated by reference in its entirety). For comparison, a schematic of the paracrine FGF-FGFR-HS signaling unit is shown, which was made based on the crystal structure of the 2:2:2 FGF2-FGFR1c-HS complex (PDB ID: 1FQ9; (Schlessinger et al., *Mol. Cell* 6:743-750 (2000), which is hereby incorporated by reference in its entirety)). HS engages both paracrine FGF and receptor to enhance binding of FGF to its primary and secondary receptors thus promoting receptor dimerization. A question mark denotes whether or not HS is also a component of the endocrine FGF signaling complex.

FIG. 2 shows a sequence alignment of the endocrine FGFs, FGF1 and FGF2. The amino acid sequences of the mature human FGF19, FGF21, and FGF23 ligands are aligned. Also included in the alignment are the human sequences of FGF1 and FGF2, prototypical paracrine FGFs, which were used in the experiments described herein, in which FGF1 and FGF2 were converted into endocrine FGF ligands. Residue numbers corresponding to the human sequence of FGF1 (SEQ ID NO:1) (GenBank Accession No. AAH32697, which is hereby incorporated by reference in its entirety), FGF2 (SEQ ID NO: 121) (GenBank Accession No. EAX05222, which is hereby incorporated by reference in its entirety), FGF19 (SEQ ID NO:337) (GenBank Accession No. NP 005108, which is hereby incorporated by reference in its entirety), FGF21 (SEQ ID NO: 233) (GenBank Accession No. NP_061986, which is hereby incorporated by reference in its entirety), and FGF23 (SEQ ID NO:351) (GenBank accession no. AAG09917, which is hereby incorporated by reference in its entirety) are in parenthesis to the left of the alignment. Secondary structure elements are labeled, and residues containing these elements for known secondary structures are boxed. Gaps (dashes) were introduced to optimize the sequence alignment. The β-trefoil core domain for known FGF crystal structures is shaded gray. Blue bars on top of the alignment indicate the location of the HS-binding regions. HS-binding residues selected for mutagenesis are shaded blue.

FIG. 3A shows an overlay of SPR sensorgrams illustrating heparin binding of FGF2, FGF19, FGF21, and FGF23 (left panel) and an exploded view of the binding responses for FGF19-, FGF21-, and FGF23-heparin interactions (right panel). Heparin was immobilized on a biosensor chip, and 400 nM of FGF2, FGF19, FGF21, or FGF23 were passed over the chip. Note that FGF19, FGF21, and FGF23 exhibit measurable, residual heparin binding and that differences in heparin binding exist between these three endocrine FGFs. FIGS. 3B-3D show overlays of SPR sensorgrams illustrating binding of FGF19 to heparin (FIG. 3B) and lack of interaction between the FGF19$^{K149A}$ mutant and heparin (FIG. 3C) and between the FGF19$^{K149A,R157A}$ mutant and heparin (FIG. 3D). Heparin was immobilized on a biosensor chip, and increasing concentrations of FGF19 were passed over the chip. Thereafter, FGF19$^{K149A}$ or FGF19$^{K149A, R157A}$ was injected over the heparin chip at the highest concentration tested for the wild-type ligand. FIGS. 3E-3G show overlays of SPR sensorgrams illustrating binding of FGF23 to heparin (FIG. 3E), poor interaction between the FGF23$^{R48A, N49A}$ mutant and heparin (FIG. 3F), and lack of interaction between the FGF23$^{R140A, R143A}$ mutant and heparin (FIG. 3G). Heparin was immobilized on a biosensor chip, and increasing concentrations of FGF23 were passed over the chip. FGF23$^{R48A, N49A}$ or FGF23$^{R140A, R143A}$ was then injected over the heparin chip at the highest concentration tested for the wild-type ligand.

FIG. 4A shows results of an immunoblot analysis of phosphorylation of FRS2α (pFRS2α) and 44/42 MAP kinase (p44/42 MAPK) in H4IIE hepatoma cells following stimulation with the FGF19$^{K149A}$ mutant, the FGF19$^{K149A, R157A}$ mutant, or wild-type FGF19. Numbers above the lanes give the amounts of protein added in ng ml$^{-1}$. Total 44/42 MAPK protein expression was used as a loading control. FIG. 4B shows results of an immunoblot analysis of phosphorylation of FRS2α (pFRS2α) and 44/42 MAP kinase (p44/42 MAPK) in a HEK293-αKlotho cell line following stimulation with the FGF23$^{R48A, N49A}$ mutant, the FGF23$^{R140A, R143A}$ mutant, or wild-type FGF23. Numbers above the lanes give the amounts of protein added in ng ml$^{-1}$. Total 44/42 MAPK and αKlotho protein expression were used as loading controls. FIG. 4C shows graphical results of a quantitative analysis of CYP7A1 and CYP8B1 mRNA expression in liver tissue from mice treated with FGF19$^{K149A}$, FGF19$^{K149A,R157A}$, or vehicle. 1 mg of protein per kg of body weight was given. Data are presented as mean±SEM; ***, P<0.001 by Student's t test. FIG. 4D shows graphical results of analysis of serum phosphate concentrations (serum P$_i$) in mice before and 8 h after intraperitoneal injection of FGF23$^{R48A, N49A}$, FGF23$^{R140A, R143A}$, FGF23, or vehicle. Wild-type mice were given a single dose of protein (0.29 mg kg body weight$^{-1}$), whereas Fgf23 knockout mice received two doses of 0.71 mg kg body weight$^{-1}$ each. Data are presented as mean±SEM; *, P<0.05, and **, P<0.01 by ANOVA.

FIG. 5A is a schematic of human FGF2, FGF19, FGF21, FGF23, and engineered FGF2-FGF19, FGF2-FGF21, and FGF2-FGF23 chimeras. Amino acid boundaries of each ligand and of each component of the chimeras are labeled with residue letter and number. The β-trefoil core domain for the known ligand crystal structures is shaded gray. HS-binding residues mutated in the FGF2 portion of chimeras are labeled with residue letter and number. Also labeled are the arginine residues of the proteolytic cleavage site in the C-terminal region of FGF23 that were mutated to glutamine in both FGF23 and the FGF2-FGF23 chimeras. FIGS. 5B and 5C show overlays of SPR sensorgrams illustrating binding of FGF2$^{WTcore}$-FGF21$^{C\text{-}tail}$ (FIG. 5B) and FGF2$^{\Delta HBScore}$-FGF21$^{C\text{-}tail}$ (FIG. 5C) to heparin, and fitted saturation binding curves. Heparin was immobilized on a biosensor chip, and increasing concentrations of FGF2$^{WTcore}$-FGF21$^{C\text{-}tail}$ or FGF2$^{\Delta HBScore}$-FGF21$^{C\text{-}tail}$ were passed over the chip. Dissociation constants (K$_D$s) were derived from the saturation binding curves. FIGS. 5D and 5E show overlays of SPR sensorgrams illustrating binding of FGF2$^{WTcore}$-FGF23$^{C\text{-}tail}$ (FIG. 5D) and FGF2$^{\Delta HBScore}$-FGF23$^{C\text{-}tail}$ (FIG. 5E) to heparin. Increasing concentrations of FGF2$^{WTcore}$-FGF23$^{C\text{-}tail}$ or FGF2$^{\Delta HBScore}$-FGF23$^{C\text{-}tail}$ were passed over a chip containing immobilized heparin. FIGS. 5F and 5G show results of immunoblot analysis for Egr1 expression in HEK293 cells following stimulation with chimeras or native FGFs as denoted. Numbers above the lanes give the amounts of protein added in nanomolar. GAPDH protein expression was used as a loading control.

FIGS. 7A and 7B show overlays of SPR sensorgrams illustrating inhibition by FGF2$^{\Delta HBScore}$-FGF23$^{C\text{-}tail}$ (FIG. 7A) or FGF23 (FIG. 7B) of αKlotho-FGFR1c binding to FGF23 immobilized on a biosensor chip. Increasing concentrations of FGF2$^{\Delta HBScore}$-FGF23$^{C\text{-}tail}$ or FGF23 were mixed with a fixed concentration of αKlotho-FGFR1c complex, and the mixtures were passed over a FGF23 chip. FIG. 7C shows an overlay of SPR sensorgrams illustrating failure of FGF2 to inhibit αKlotho-FGFR1c binding to FGF23. FGF2 and αKlotho-FGFR1c complex were mixed at a molar ratio of 15:1, and the mixture was passed over a biosensor chip containing immobilized FGF23. FIGS. 7D and 7E show overlays of SPR sensorgrams illustrating no inhibition by FGF2$^{\Delta HBScore}$-FGF23$^{C\text{-}tail}$ (FIG. 7D) or FGF23 (FIG. 7E) of βKlotho-FGFR1c binding to FGF21. FGF2$^{\Delta HBScore}$-FGF23$^{C\text{-}tail}$ or FGF23 were mixed with βKlotho-FGFR1c complex at a molar ratio of 10:1, and the mixtures were passed over a biosensor chip containing immobilized FGF21. FIG. 7F shows analysis of serum phosphate concentrations (serum P$_i$) in mice before and 8 h after intraperitoneal injection of FGF2$^{\Delta HBScore}$-FGF23$^{C\text{-}tail}$, FGF2$^{WTcore}$-FGF23$^{C\text{-}tail}$, FGF23, or vehicle. Wild-type mice and αKlotho knockout mice were given 0.21 mg and 0.51 mg of protein, respectively, per kg of body weight. Data are presented as mean±SEM; , P<0.01; *, P<0.001 by ANOVA. FIG. 7G shows quantitative analysis of CYP27B1 mRNA expression in renal tissue from mice injected with FGF2$^{\Delta HBScore}$-FGF23$^{C\text{-}tail}$, FGF2$^{WTcore}$-FGF23$^{C\text{-}tail}$, FGF23, or vehicle. 0.21 mg of protein per kg of body weight were injected. Data are presented as mean±SEM; ***, P<0.001 by ANOVA.

FIGS. 8A-8B show overlays of SPR sensorgrams illustrating inhibition by FGF2$^{\Delta HBScore}$-FGF21$^{C\text{-}tail}$ (FIG. 8A) or FGF21 (FIG. 8B) of βKlotho-FGFR1c binding to FGF21 immobilized on a biosensor chip. Increasing concentrations of FGF2$^{\Delta HBScore}$-FGF21$^{C\text{-}tail}$ or FGF21 were mixed with a fixed concentration of βKlotho-FGFR1c complex, and the mixtures were passed over a FGF21 chip. FIG. 8C shows an overlay of SPR sensorgrams illustrating failure of FGF2 to inhibit βKlotho-FGFR1c binding to FGF21. FGF2 and βKlotho-FGFR1c complex were mixed at a molar ratio of 15:1, and the mixture was passed over a biosensor chip containing immobilized FGF21. FIGS. 8D-8E show overlays of SPR sensorgrams illustrating no inhibition by FGF2$^{\Delta HBScore}$-FGF21$^{C\text{-}tail}$ (FIG. 8D) or FGF21 (FIG. 8E) of αKlotho-FGFR1c binding to FGF23. FGF2$^{\Delta HBScore}$-FGF21$^{C\text{-}tail}$ or FGF21 were mixed with αKlotho-FGFR1c complex at a molar ratio of 10:1, and the mixtures were passed over a biosensor chip containing immobilized FGF23. FIG. 8F shows results of immunoblot analysis for Egr1 expression in HEK293-βKlotho cells stimulated with FGF2$^{\Delta HBScore}$-FGF21$^{C\text{-}tail}$ or FGF21. Numbers above the lanes give the amounts of protein added in ng ml$^{-1}$. GAPDH protein expression was used as a loading control. Note that the FGF2$^{\Delta HBScore}$-FGF21$^{C\text{-}tail}$ chimera is more potent than native FGF21 at inducing Egr1 expression suggesting that the chimera has agonistic property. This is expected since the core domain of FGF2 has inherently greater binding affinity for FGFR than the core domain of FGF21 (see FIGS. 10A and 10C). FIG. 8G shows graphical results of analysis of blood glucose concentrations in mice before and at the indicated time points after intraperitoneal injection of insulin alone, insulin plus FGF2$^{\Delta HBScore}$-FGF21$^{C\text{-}tail}$ chimera, insulin plus FGF21, or vehicle alone. 0.5 units of insulin per kg of body weight and 0.3 mg of FGF21 ligand per kg of body weight were injected. Blood glucose concentrations are expressed as percent of pre-injection values. Data are presented as mean±SEM.

FIG. 9A shows graphical results of analysis of blood glucose concentrations in ob/ob mice before and at the indicated time points after subcutaneous injection of FGF1 or FGF21.

FIG. 9B shows graphical results of analysis of blood glucose concentrations in ob/ob mice before and at the indicated time points after subcutaneous injection of FGF1, FGF1$^{\Delta NT}$, or FGF1$^{\Delta HBs}$. FIG. 9C shows graphical results of analysis of blood glucose concentrations in ob/ob mice before and at the indicated time points after subcutaneous injection of FGF1 or FGF1$^{\Delta HBScore}$-FGF21$^{C\text{-}tail}$ chimera. For the experiments shown in FIGS. 9A-9C, ob/ob mice were injected with a bolus of 0.5 mg of FGF protein per kg of body weight. Data are presented as mean±SD.

FIGS. 10A-10D show overlays of SPR sensorgrams illustrating binding of FGFR1c to FGF2 (FIG. 10A), FGF19 (FIG. 10B), FGF21 (FIG. 10C), and FGF23 (FIG. 10D), and fitted saturation binding curves. Increasing concentrations of FGFR1c ligand-binding domain were passed over a biosensor chip containing immobilized FGF2, FGF19, FGF21, or FGF23. FIG. 10E shows an overlay of SPR sensorgrams illustrating binding of αKlotho-FGFR1c complex to FGF23. Increasing concentrations of αKlotho-FGFR1c complex were passed over a biosensor chip containing immobilized FGF23. FIG. 10F shows an overlay of SPR sensorgrams showing lack of interaction between the C-terminal tail peptide of FGF23 and FGFR1c. FGF2$^{3C\text{-}tail}$ was immobilized on a biosensor chip and increasing concentrations of FGFR1c ligand-binding domain were passed over the chip. Dissociation constants ($_{K_D}$s) given in FIGS. 10A-10E were derived from the saturation binding curves.

FIG. 11 shows an alignment of the C-terminal tail sequences of human FGF19 (SEQ ID NO:337) (GenBank Accession No. NP_005108, which is hereby incorporated by reference in its entirety), FGF21 (SEQ ID NO:233) (GenBank Accession No. NP_061986, which is hereby incorporated by reference in its entirety), and FGF23 (SEQ ID NO:351) (GenBank accession no. AAG09917, which is hereby incorporated by reference in its entirety). Residue numbers are in parenthesis to the left of the alignment. Gaps (dashes) were introduced to optimize the alignment. Residues that are identical between FGF19 and FGF21 are shaded gray. Note that 40% of these residues map to the most C-terminal sequence.

FIG. 12 shows an alignment of the C-terminal tail sequences of human FGF21 (SEQ ID NO:233) (GenBank Accession No. NP_061986, which is hereby incorporated by reference in its entirety), FGF19 (SEQ ID NO:337) (GenBank Accession No. NP_005108, which is hereby incorporated by reference in its entirety), and variants of FGF21 harboring a single amino acid substitution or insertion for a residue unique to FGF19. Residue numbers for the sequences of native FGF21 and FGF19 are in parenthesis to the left of the alignment. Gaps (dashes) were introduced to optimize the alignment. In the sequence of native FGF19, residues unique to FGF19 are bold and boxed, and in the sequences of the variants of the FGF21 C-terminal tail, introduced FGF19 residues are highlighted in the same manner.

FIG. 13 shows an alignment of the C-terminal tail sequences of human FGF21 (SEQ ID NO:233) (GenBank Accession No. NP_061986, which is hereby incorporated by reference in its entirety), FGF19 (SEQ ID NO:337) (GenBank Accession No. NP_005108, which is hereby incorporated by reference in its entirety), and variants of FGF21 in which residues unique to FGF19 progressively replace the corresponding residues of FGF21 or are inserted into the FGF21 sequence. Residue numbers for the sequences of native FGF21 and FGF19 are in parenthesis to the left of the alignment. Gaps (dashes) were introduced to optimize the alignment. In the sequence of native FGF19, residues unique to FGF19 are bold and boxed, and in the sequences of variants of the FGF21 C-terminal tail, introduced FGF19 residues are highlighted in the same manner.

DETAILED DESCRIPTION OF THE INVENTION

Figures 1A, 1B, 1C, 1D:
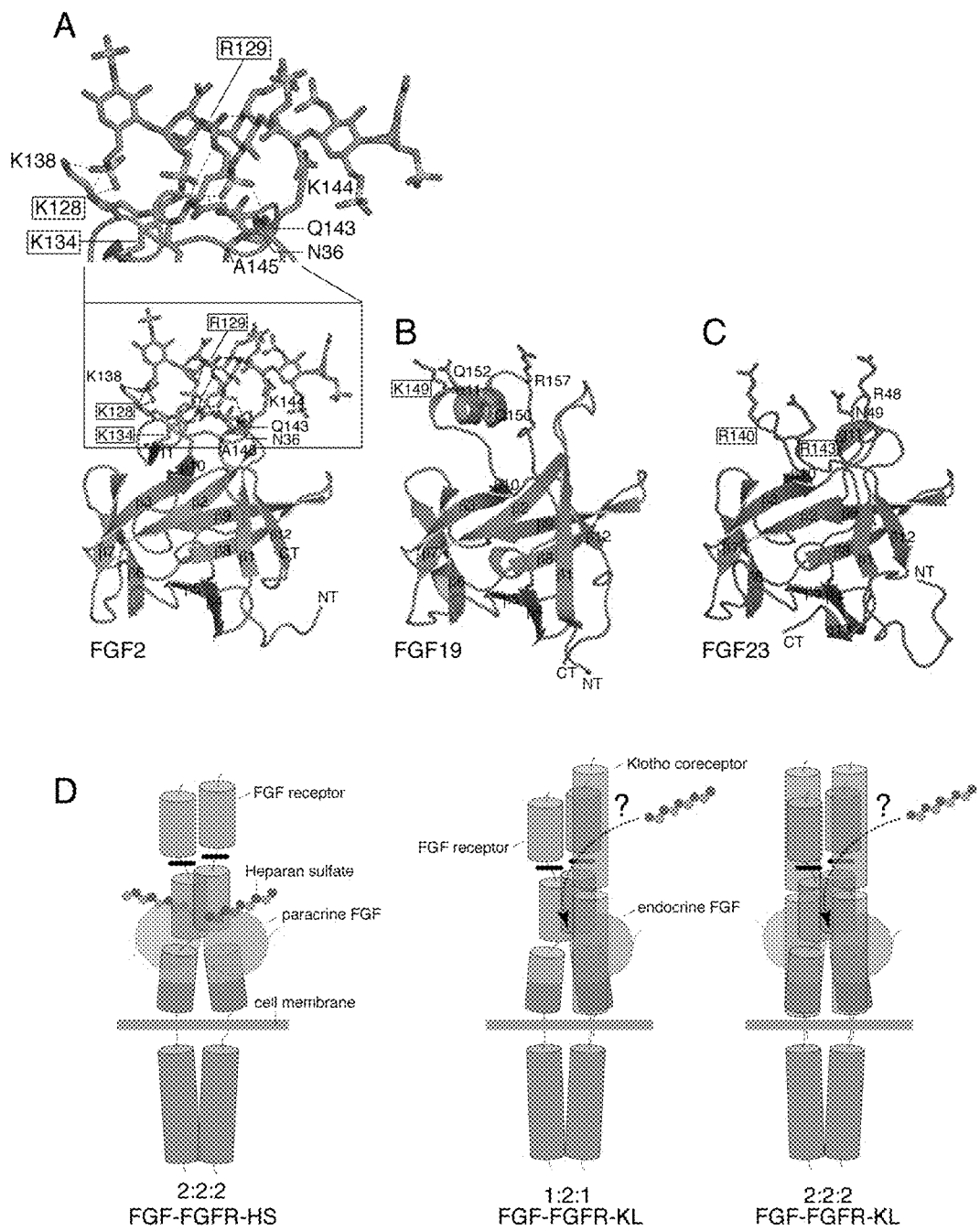
FIGS. 1A-1D are schematic diagrams showing side-by-side comparison of the HS-binding site of FGF2, FGF19, and FGF23, and two working models for the endocrine FGF signaling complex.
Figures 3A, 3B, 3C, 3D, 3E, 3F, 3G:
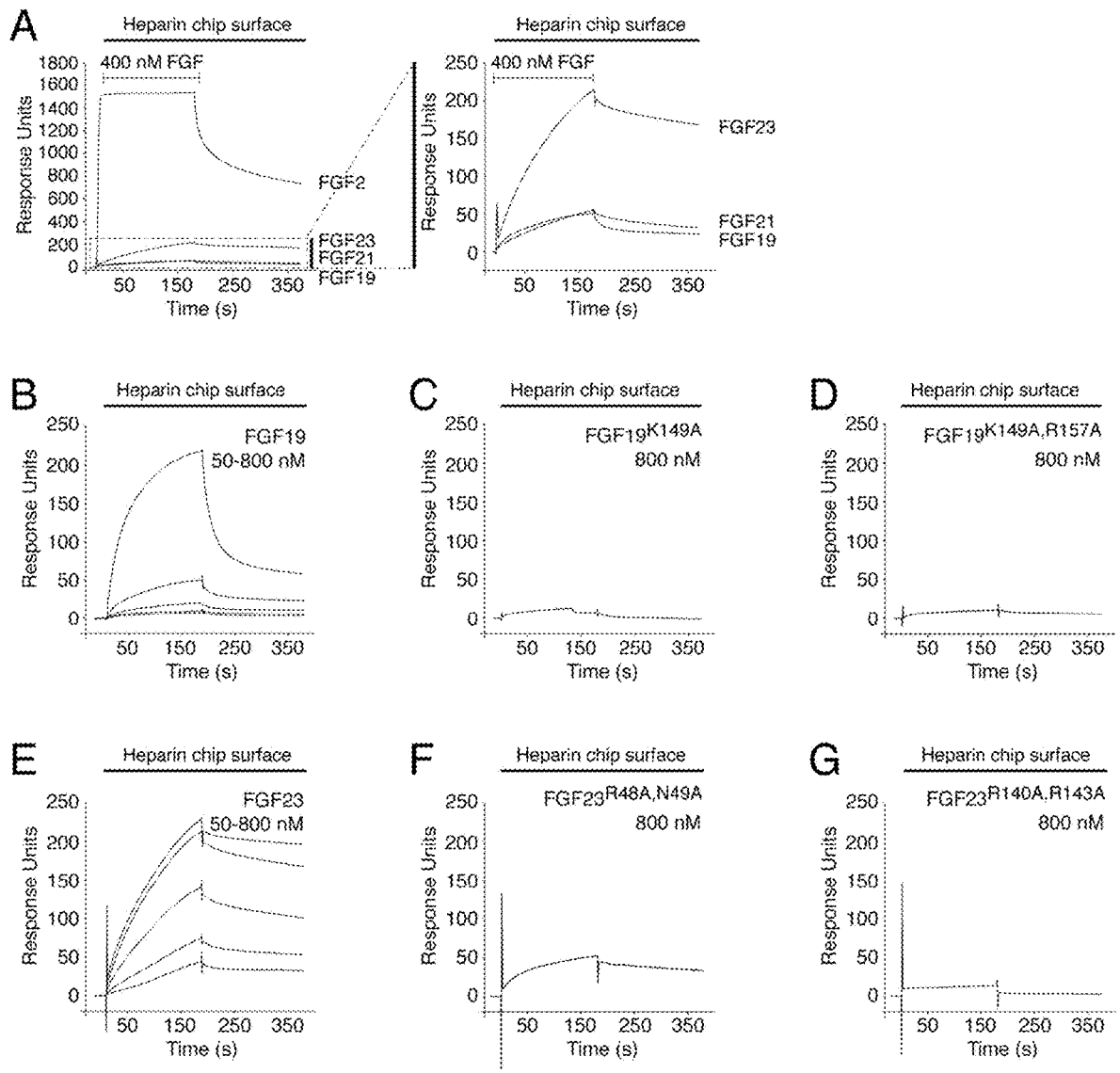
FIGS. 3A-3G show Surface plasmon resonance ("SPR") results relating to knockout of residual heparin binding in FGF19 and FGF23 by site-directed mutagenesis.

One aspect of the present invention relates to a chimeric protein. The chimeric protein includes an N-terminus coupled to a C-terminus, where the N-terminus includes a portion of a paracrine fibroblast growth factor ("FGF") and the C-terminus includes a C-terminal portion of an FGF21 molecule. The portion of the paracrine FGF is modified to decrease binding affinity for heparin and/or heparan sulfate compared to the portion without the modification.

As described by Goetz et al. (Goetz et al., "Molecular Insights into the Klotho-Dependent, Endocrine Mode of Action of Fibroblast Growth Factor 19 Subfamily Members," *Mol Cell Biol* 3417-3428 (2007), which is hereby incorporated by reference in its entirety), the mammalian fibroblast growth factor (FGF) family comprises 18 polypeptides (FGF1 to FGF10 and FGF16 to FGF23), which participate in a myriad of biological processes during embryogenesis, including but not limited to gastrulation, body plan formation, somitogenesis, and morphogenesis of essentially every tissue/organ such as limb, lung, brain, and kidney (Bottcher et al., "Fibroblast Growth Factor Signaling During Early Vertebrate Development," *Endocr Rev* 26:63-77 (2005), and Thisse et al., "Functions and Regulations of Fibroblast Growth Factor Signaling During Embryonic Development," *Dev Biol* 287:390-402 (2005), which are hereby incorporated by reference in their entirety).

FGFs execute their biological actions by binding to, dimerizing, and activating FGFR tyrosine kinases, which are encoded by four distinct genes (Fgfr1 to Fgfr4). Prototypical FGFRs consist of an extracellular domain composed of three immunoglobulin-like domains, a single-pass transmembrane domain, and an intracellular domain responsible for the tyrosine kinase activity (Mohammadi et al., "Structural Basis for Fibroblast Growth Factor Receptor Activation," *Cytokine Growth Factor Rev* 16:107-137 (2005), which is hereby incorporated by reference in its entirety).

The number of principal FGFRs is increased from four to seven due to a major tissue-specific alternative splicing event in the second half of the immunoglobulin-like domain 3 of FGFR1 to FGFR3, which creates epithelial lineage-specific "b" and mesenchymal lineage-specific "c" isoforms (Mohammadi et al., "Structural Basis for Fibroblast Growth Factor Receptor Activation," *Cytokine Growth Factor Rev* 16:107-137 (2005) and Ornitz et al., "Fibroblast Growth Factors," *Genome Biol* 2(3):reviews3005.1-reviews3005.12 (2001), which are hereby incorporated by reference in their entirety). Generally, the receptor-binding specificity of FGFs is divided along this major alternative splicing of receptors whereby FGFRb-interacting FGFs are produced by epithelial cells and FGFRc-interacting FGFs are produced by mesenchymal cells (Ornitz et al., "Fibroblast Growth Factors," *Genome Biol* 2(3):reviews3005.1-reviews3005.12 (2001), which is hereby incorporated by reference in its entirety). These reciprocal expression patterns of FGFs and FGFRs result in the establishment of specific paracrine FGF signaling loops between the epithelium and the mesenchyme, which is essential for proper organogenesis and patterning during embryonic development as well as tissue homeostasis in the adult organism.

Based on sequence homology and phylogenetic and structural considerations, the eighteen mammalian FGFs are grouped into six subfamilies (Itoh et al., "Fibroblast growth factors: from molecular evolution to roles in development, metabolism, and disease," *J Biochem* 149:121-130 (2011); Mohammadi et al., "Structural basis for fibroblast growth factor receptor activation," *Cytokine Growth Factor Rev* 16:107-137 (2005), which are hereby incorporated by reference in its entirety). The FGF core homology domain (approximately 120 amino acids long) is flanked by N- and C-terminal sequences that are highly variable in both length and primary sequence, particularly among different FGF subfamilies. The core region of FGF19 shares the highest sequence identity with FGF21 (38%) and FGF23 (36%), and therefore, these ligands are considered to form a subfamily.

Based on mode of action, the eighteen mammalian FGFs are grouped into paracrine-acting ligands (five FGF subfamilies) and endocrine-acting ligands (one FGF subfamily) comprising FGF19, FGF21 and FGF23 (Itoh and Ornitz, "Fibroblast Growth Factors: From Molecular Evolution to Roles in Development, Metabolism and Disease," *J. Biochem.* 149:121-130 (2011); Mohammadi et al., "Structural Basis for Fibroblast Growth Factor Receptor Activation," *Cytokine Growth Factor Rev.* 16:107-137 (2005), which are hereby incorporated by reference in their entirety).

Paracrine FGFs direct multiple processes during embryogenesis, including gastrulation, somitogenesis, organogenesis, and tissue patterning (Itoh and Ornitz, "Fibroblast Growth Factors: From Molecular Evolution to Roles in Development, Metabolism and Disease," *J. Biochem.* 149: 121-130 (2011); Bottcher and Niehrs, "Fibroblast Growth Factor Signaling During Early Vertebrate Development," *Endocr. Rev.* 26:63-77 (2005); Thisse et al., "Functions and Regulations of Fibroblast Growth Factor Signaling During Embryonic Development," *Dev. Biol.* 287:390-402 (2005), which are hereby incorporated by reference in their entirety), and also regulate tissue homeostasis in the adult (Hart et al., "Attenuation of FGF Signalling in Mouse Beta-cells Leads to Diabetes," *Nature* 408:864-868 (2000); Jonker et al., "A PPARγ-FGF1 Axis is Required for Adaptive Adipose Remodelling and Metabolic Homeostasis," *Nature* 485:391-394 (2012), which is hereby incorporated by reference in its entirety).

Endocrine FGFs control major metabolic processes such as bile acid homeostasis (Inagaki et al., "Fibroblast Growth Factor 15 Functions as an Enterohepatic Signal to Regulate Bile Acid Homeostasis," *Cell Metab.* 2:217-225 (2005), which is hereby incorporated by reference in its entirety), and hepatic glucose and protein metabolism (Kir et al., "FGF19 as a Postprandial, Insulin-Independent Activator of Hepatic Protein and Glycogen Synthesis," *Science* 331: 1621-1624 (2011); Potthoff et al., "FGF15/19 Regulates Hepatic Glucose Metabolism by Inhibiting the CREB-PGC-1α Pathway," *Cell Metab.* 13:729-738 (2011), which are hereby incorporated by reference in their entirety) (FGF19), glucose and lipid metabolism (Badman et al., "Hepatic Fibroblast Growth Factor 21 Is Regulated by PPARα and Is a Key Mediator of Hepatic Lipid Metabolism in Ketotic States," *Cell Metab.* 5:426-437 (2007); Inagaki et al., "Endocrine Regulation of the Fasting Response by PPARalpha-mediated Induction of Fibroblast Growth Factor 21," *Cell Metab.* 5:415-425 (2007); Kharitonenkov et al., "FGF-21 as a Novel Metabolic Regulator," *J. Clin. Invest.* 115: 1627-1635 (2005); Potthoff et al., "FGF21 Induces PGC-1alpha and Regulates Carbohydrate and Fatty Acid Metabolism During the Adaptive Starvation Response," *Proc. Nat'l. Acad. Sci. U.S.A.* 106:10853-10858 (2009), which are hereby incorporated by reference in their entirety) (FGF21), and phosphate and vitamin D homeostasis (White et al., "Autosomal Dominant Hypophosphataemic Rickets is Associated with Mutations in FGF23," *Nat. Genet.* 26:345-348 (2000); Shimada et al., "Targeted Ablation of Fgf23 Demonstrates an Essential Physiological Role of FGF23 in Phosphate and Vitamin D Metabolism," *J. Clin. Invest.* 113:561-568 (2004), which are hereby incorporated by reference in their entirety) (FGF23). Thus, these ligands have attracted much attention as potential drugs for the treatment of various inherited or acquired metabolic disorders (Beenken and Mohammadi, "The FGF Family: Biology, Pathophysiology and Therapy," *Nat. Rev. Drug Discov.* 8:235-253 (2009); Beenken and Mohammadi, "The Structural Biology of the FGF19 Subfamily," in *Endocrine FGFs and Klothos* (Kuro-o, M. ed.), Landes Bioscience. pp 1-24 (2012), which are hereby incorporated by reference in their entirety).

FGFs share a core homology region of about one hundred and twenty amino acids that fold into a β-trefoil (Ago et al., *J. Biochem.* 110:360-363 (1991); Eriksson et al., *Proc. Nat'l. Acad. Sci. U.S.A.* 88:3441-3445 (1991); Zhang et al., *Proc. Nat'l. Acad. Sci. U.S.A.* 88:3446-3450 (1991); Zhu et al., *Science* 251:90-93 (1991), which are hereby incorporated by reference in their entirety) consisting of twelve β strands in paracrine FGFs (β1-β12) and eleven β strands in endocrine FGFs (β1-β10 and β12) (Mohammadi et al., "Structural Basis for Fibroblast Growth Factor Receptor Activation," *Cytokine Growth Factor Rev.* 16:107-137 (2005); Goetz et al., *Mol. Cell Biol.* 27:3417-3428 (2007), which are hereby incorporated by reference in their entirety). The conserved core region is flanked by divergent N- and C-termini, which play a critical role in conferring distinct biological activity on FGFs (Mohammadi et al., "Structural Basis for Fibroblast Growth Factor Receptor Activation," *Cytokine Growth Factor Rev.* 16:107-137 (2005); Olsen et al., *Genes Dev.* 20:185-198 (2006), which are hereby incorporated by reference in their entirety).

All FGFs interact with pericellular heparan sulfate (HS) glycosaminoglycans albeit with different affinities (Asada et al., *Biochim. Biophys. Acta.* 1790:40-48 (2009), which is hereby incorporated by reference in its entirety). The HS-binding site of FGFs is comprised of the β1-β2 loop and the region between β10 and β12 strands (Mohammadi et al., "Structural Basis for Fibroblast Growth Factor Receptor Activation," *Cytokine Growth Factor Rev.* 16:107-137 (2005), which is hereby incorporated by reference in its entirety). HS interacts with both side chain and main chain atoms of the HS-binding site in paracrine FGFs (Schlessinger et al., *Mol. Cell* 6:743-750 (2000), which is hereby incorporated by reference in its entirety). The HS-binding site of endocrine FGFs deviates from the common conformation adopted by paracrine FGFs such that interaction of HS with backbone atoms of the HS-binding site is precluded (Goetz et al., *Mol. Cell Biol.* 27:3417-3428 (2007), which is hereby incorporated by reference in its entirety). As a result, compared to paracrine FGFs, endocrine FGFs exhibit poor affinity for HS (Beenken and Mohammadi, "The FGF Family: Biology, Pathophysiology and Therapy," *Nat. Rev. Drug Discov.* 8:235-253 (2009); Asada et al., *Biochim. Biophys. Acta.* 1790:40-48 (2009), which are hereby incorporated by reference in their entirety). The poor HS affinity enables these ligands to diffuse freely away from the site of their secretion and enter the blood circulation to reach their distant target organs (Goetz et al., *Mol. Cell Biol.* 27:3417-

3428 (2007); Asada et al., *Biochim. Biophys. Acta.* 1790: 40-48 (2009), which are hereby incorporated by reference in their entirety).

By contrast, owing to their high HS affinity (Asada et al., *Biochim. Biophys. Acta.* 1790:40-48 (2009), which is hereby incorporated by reference in its entirety), paracrine FGFs are mostly immobilized in the vicinity of the cells secreting these ligands, and hence can only act within the same organ. There is emerging evidence that differences in HS-binding affinity among paracrine FGFs translate into the formation of ligand-specific gradients in the pericellular matrix (Kalinina et al., *Mol. Cell Biol.* 29:4663-4678 (2009); Makarenkova et al., *Sci. Signal* 2:ra55 (2009), which are hereby incorporated by reference in their entirety), which contribute to the distinct functions of these ligands (Beenken and Mohammadi, "The FGF Family: Biology, Pathophysiology and Therapy," *Nat. Rev. Drug Discov.* 8:235-253 (2009); Itoh and Ornitz, "Fibroblast Growth Factors: From Molecular Evolution to Roles in Development, Metabolism and Disease," *J. Biochem.* 149:121-130 (2011), which are hereby incorporated by reference in their entirety).

Besides controlling ligand diffusion in the extracellular space, HS promotes the formation of the 2:2 paracrine FGF-FGFR signal transduction unit (Schlessinger et al., *Mol. Cell* 6:743-750 (2000); Mohammadi et al., *Curr. Opin. Struct. Biol.* 15:506-516 (2005), which are hereby incorporated by reference in their entirety). HS engages both ligand and receptor to enhance the binding affinity of FGF for receptor and promote dimerization of ligand-bound receptors. Owing to their poor HS-binding affinity, endocrine FGFs rely on Klotho co-receptors to bind their cognate FGFR (Kurosu et al., *J. Biol. Chem.* 282:26687-26695 (2007); Kurosu et al., *J. Biol. Chem.* 281:6120-6123 (2006); Ogawa et al., *Proc. Nat'l. Acad. Sci. U.S.A.* 104:7432-7437 (2007); Urakawa et al., *Nature* 444:770-774 (2006), which are hereby incorporated by reference in their entirety). Klotho co-receptors are single-pass transmembrane proteins with an extracellular domain composed of two type Iβ-glycosidase domains (Ito et al., *Mech. Dev.* 98:115-119 (2000); Kuro-o et al., *Nature* 390:45-51 (1997), which are hereby incorporated by reference in their entirety). Klotho co-receptors constitutively associate with FGFRs to enhance the binding affinity of endocrine FGFs for their cognate FGFRs in target tissues (Kurosu et al., *J. Biol. Chem.* 282:26687-26695 (2007); Kurosu et al., *J. Biol. Chem.* 281:6120-6123 (2006); Ogawa et al., *Proc. Nat'l. Acad. Sci. U.S.A.* 104:7432-7437 (2007); Urakawa et al., *Nature* 444: 770-774 (2006), which are hereby incorporated by reference in their entirety). αKlotho is the co-receptor for FGF23 (Kurosu et al., *J. Biol. Chem.* 281:6120-6123 (2006); Urakawa et al., *Nature* 444:770-774 (2006), which are hereby incorporated by reference in their entirety), and βKlotho is the co-receptor for both FGF19 and FGF21 (Kurosu et al., *J. Biol. Chem.* 282:26687-26695 (2007); Ogawa et al., *Proc. Nat'l. Acad. Sci. U.S.A.* 104:7432-7437 (2007), which are hereby incorporated by reference in their entirety). The C-terminal region of endocrine FGFs mediates binding of these ligands to the FGFR-α/βKlotho co-receptor complex (Goetz et al., *Mol. Cell Biol.* 27:3417-3428 (2007); Goetz et al., *Proc. Nat'l. Acad. Sci. U.S.A* 107:407-412 (2010); Micanovic et al., *J. Cell Physiol.* 219:227-234 (2009); Wu et al., *J. Biol. Chem.* 283:33304-33309 (2008); Yie et al., *FEBS Lett,* 583:19-24 (2009); Goetz et al., *Mol. Cell Biol.* 32:1944-1954 (2012), which are hereby incorporated by reference in their entirety).

βKlotho promotes binding of FGF21 to its cognate FGFR by engaging ligand and receptor simultaneously through two distinct binding sites (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). βKlotho plays the same role in promoting binding of FGF19 to its cognate FGFR (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). The binding site for βKlotho was mapped on FGF21 and FGF19 to the C-terminal region of each ligand that follows the β-trefoil core domain (Goetz et al., "Klotho Coreceptors Inhibit Signaling by Paracrine Fibroblast Growth Factor 8 Subfamily Ligands,"*Mol Cell Biol* 32:1944-1954 (2012), which is hereby incorporated by reference in its entirety). In the course of these studies, it was found that the C-terminal tail peptides of FGF21 and FGF19 share a common binding site on βKlotho, and that the C-terminal tail of FGF19 binds tighter than the C-terminal tail of FGF21 to this site (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety).

Endocrine FGFs still possess residual HS-binding affinity, and moreover, there are differences in this residual binding affinity among the endocrine FGFs (Goetz et al., *Mol. Cell Biol.* 27:3417-3428 (2007), which is hereby incorporated by reference in its entirety). These observations raise the possibility that HS may play a role in endocrine FGF signaling. Indeed, there are several reports showing that HS can promote endocrine FGF signaling in the presence as well as in the absence of Klotho co-receptor. It has been shown that HS augments the mitogenic signal elicited by endocrine FGFs in BaF3 cells over-expressing FGFR and Klotho co-receptor by at least two-fold (Suzuki et al., *Mol. Endocrinol.* 22:1006-1014 (2008), which is hereby incorporated by reference in its entirety). In addition, even in the absence of Klotho co-receptor, HS enables endocrine FGFs to induce proliferation of BaF3 cells over-expressing FGFR (Yu et al., *Endocrinology* 146:4647-4656 (2005); Zhang et al., *J. Biol. Chem.* 281:15694-15700 (2006), which are hereby incorporated by reference in their entirety). Compared to paracrine FGFs, however, significantly higher concentrations of both ligand and HS are needed, and the proliferative response of cells to endocrine FGFs still lags behind that of paracrine FGFs by about one order of magnitude (Zhang et al., *J. Biol. Chem.* 281:15694-15700 (2006), which is hereby incorporated by reference in its entirety).

As used herein, the terms "chimeric polypeptide" and "chimeric protein" encompass a polypeptide having a sequence that includes at least a portion of a full-length sequence of first polypeptide sequence and at least a portion of a full-length sequence of a second polypeptide sequence, where the first and second polypeptides are different polypeptides. A chimeric polypeptide also encompasses polypeptides that include two or more non-contiguous portions derived from the same polypeptide. A chimeric polypeptide or protein also encompasses polypeptides having at least one substitution, wherein the chimeric polypeptide includes a first polypeptide sequence in which a portion of the first polypeptide sequence has been substituted by a portion of a second polypeptide sequence.

As used herein, the term "N-terminal portion" of a given polypeptide sequence is a contiguous stretch of amino acids of the given polypeptide sequence that begins at or near the N-terminal residue of the given polypeptide sequence. An N-terminal portion of the given polypeptide can be defined by a contiguous stretch of amino acids (e.g., a number of amino acid residues). Similarly, the term "C-terminal portion" of a given polypeptide sequence is a contiguous length of the given polypeptide sequence that ends at or near the C-terminal residue of the given polypeptide sequence. A C-terminal portion of the given polypeptide can be defined by a contiguous stretch of amino acids (e.g., a number of amino acid residues).

The term "portion," when used herein with respect to a given polypeptide sequence, refers to a contiguous stretch of amino acids of the given polypeptide's sequence that is shorter than the given polypeptide's full-length sequence. A portion of a given polypeptide may be defined by its first position and its final position, in which the first and final positions each correspond to a position in the sequence of the given full-length polypeptide. The sequence position corresponding to the first position is situated N-terminal to the sequence position corresponding to the final position. The sequence of the portion is the contiguous amino acid sequence or stretch of amino acids in the given polypeptide that begins at the sequence position corresponding to the first position and ending at the sequence position corresponding to the final position. A portion may also be defined by reference to a position in the given polypeptide sequence and a length of residues relative to the referenced position, whereby the sequence of the portion is a contiguous amino acid sequence in the given full-length polypeptide that has the defined length and that is located in the given polypeptide in reference to the defined position.

As noted above, a chimeric protein according to the present invention may include an N-terminus coupled to a C-terminus. N-terminus and C-terminus are used herein to refer to the N-terminal region or portion and the C-terminal region or portion, respectively, of the chimeric protein of the present invention. In some embodiments of the present invention, the C-terminal portion and the N-terminal portion of the chimeric protein of the present invention are contiguously joined. In alternative embodiments, the C-terminal portion and the N-terminal portion of the chimeric protein of the present invention are coupled by an intervening spacer. In one embodiment, the spacer may be a polypeptide sequence of 1, 2, 3, 4, 5, 6, 7, 8, 9, 10, or more amino acid residues. In some embodiments, the C-terminal portion and/or the N-terminal portion of the chimeric protein of the present invention may include additional portion(s) coupled to the C-terminal residue and/or the N-terminal residue of the chimeric protein of the present invention, respectively. In some embodiments, the additional portion(s) may be a polypeptide sequence of 1, 2, 3, 4, 5, 6, 7, 8, 9, 10, or more amino acid residues. In some embodiments, the N-terminal portion and/or the C-terminal portion having such additional portion(s) will maintain the activity of the corresponding naturally occurring N-terminal portion and/or C-terminal portion, respectively. In some embodiments, the N-terminal portion and/or the C-terminal portion having such additional portion(s) will have enhanced and/or prolonged activity compared to the corresponding naturally occurring N-terminal portion and/or C-terminal portion, respectively. In other embodiments, the C-terminal portion and/or the N-terminal portion of the chimeric protein of the present invention do not include any additional portion(s) coupled to the C-terminal residue and/or the N-terminal residue of the chimeric protein of the present invention, respectively.

The portion of the paracrine FGF may be derived from any suitable paracrine FGF. Suitable paracrine FGFs in accordance with the present invention include FGF1, FGF2, and ligands of the FGF4 and FGF9 subfamilies. Certain embodiments of the present invention may include a full-length amino acid sequence of a paracrine FGF, rather than a portion of a paracrine FGF.

In one embodiment, the portion of the paracrine FGF is derived from a mammalian FGF. In one embodiment, the portion of the paracrine FGF is derived from a vertebrate FGF. In one embodiment, the portion of the paracrine FGF is derived from a human FGF. In one embodiment, the paracrine FGF is derived from a non-human mammalian FGF. In one embodiment, the portion of the paracrine FGF is derived from a non-human vertebrate FGF. In one embodiment, the paracrine FGF is derived from an ortholog of human FGF, or a polypeptide or protein obtained from one species that is the functional counterpart of a polypeptide or protein from a different species.

In one embodiment according to the present invention, the portion of the paracrine FGF of the chimeric protein includes an N-terminal portion of the paracrine FGF.

In one embodiment, the paracrine FGF is FGF1. In one embodiment, the portion of the FGF1 is from human FGF1 having the following amino acid sequence (GenBank Accession No. AAH32697, which is hereby incorporated by reference in its entirety) (SEQ ID NO: 1):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

In one embodiment, the portion of the paracrine FGF includes an amino acid sequence beginning at any one of residues 1 to 25 and ending at any one of residues 150 to 155 of SEQ ID NO: 1 (human FGF1). In one embodiment, the portion of the paracrine FGF includes amino acid residues 1-150, 1-151, 1-152, 1-153, 1-154, 1-155, 2-150, 2-151, 2-152, 2-153, 2-154, 2-155, 3-150, 3-151, 3-152, 3-153, 3-154, 3-155, 4-150, 4-151, 4-152, 4-153, 4-154, 4-155, 5-150, 5-151, 5-152, 5-153, 5-154, 5-155, 6-150, 6-151, 6-152, 6-153, 6-154, 6-155, 7-150, 7-151, 7-152, 7-153, 7-154, 7-155, 8-150, 8-151, 8-152, 8-153, 8-154, 8-155, 9-150, 9-151, 9-152, 9-153, 9-154, 9-155, 10-150, 10-151, 10-152, 10-153, 10-154, 10-155, 11-150, 11-151, 11-152, 11-153, 11-154, 11-155, 12-150, 12-151, 12-152, 12-153, 12-154, 12-155, 13-150, 13-151, 13-152, 13-153, 13-154, 13-155, 14-150, 14-151, 14-152, 14-153, 14-154, 14-155, 15-150, 15-151, 15-152, 15-153, 15-154, 15-155, 16-150, 16-151, 16-152, 16-153, 16-154, 16-155, 17-150, 17-151, 17-152, 17-153, 17-154, 17-155, 18-150, 18-151, 18-152, 18-153, 18-154, 18-155, 19-150, 19-151, 19-152, 19-153, 19-154, 19-155, 20-150, 20-151, 20-152, 20-153, 20-154, 20-155, 21-150, 21-151, 21-152, 21-153, 21-154, 21-155, 22-150, 22-151, 22-152, 22-153, 22-154, 22-155, 23-150, 23-151, 23-152, 23-153, 23-154, 23-155, 24-150, 24-151, 24-152, 24-153, 24-154, 24-155, 25-150, 25-151, 25-152, 25-153, 25-154, or 25-155 of FGF1 (SEQ ID NO: 1). In one embodiment, the portion of the paracrine FGF includes amino acid residues 1-150 or 25-150 of SEQ ID NO: 1.

In one embodiment, the portion of the paracrine FGF includes an amino acid sequence that has at least 80%, at least 85%, at least 90%, at least 95%, at least 97% or at least 99% amino acid sequence identity to an amino acid sequence beginning at any one of residues 1 to 25 and ending at any one of residues 150 to 155 of SEQ ID NO: 1 (human FGF1). In one embodiment, the portion of the paracrine FGF includes an amino acid sequence that has at least 80%, at least 85%, at least 90%, at least 95%, at least 97% or at least 99% amino acid sequence homology to an amino acid sequence beginning at any one of residues 1 to 25 and ending at any one of residues 150 to 155 of SEQ ID NO: 1 (human FGF1).

Percent (%) amino acid sequence identity with respect to a given polypeptide sequence identified herein is defined as the percentage of amino acid residues in a candidate sequence that are identical to the amino acid residues in the reference sequence, after aligning the sequences and introducing gaps, if necessary, to achieve the maximum percent sequence identity, and not considering any conservative substitutions as part of the sequence identity. Percent (%) amino acid sequence homology with respect to a given polypeptide sequence identified herein is the percentage of amino acid residues in a candidate sequence that are identical to or strongly similar to the amino acid residues in the reference sequence, after aligning the sequences and introducing gaps, if necessary, to achieve the maximum percent sequence homology. Strongly similar amino acid residues may include, for example, conservative amino acid substitutions known in the art. Alignment for purposes of determining percent amino acid sequence identity and/or homology can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

In one embodiment of the present invention, the portion of the paracrine FGF of the chimeric protein is derived from an ortholog of human FGF1. In one embodiment, the portion of FGF1 is derived from *Papio Anubis, Pongo abelii, Callithrix jacchus, Equus caballus*, Pan troglodytes, Loxodonta *Africana, Canis lupus familiaris, Ailuropoda melanoleuca, Saimiri boliviensis boliviensis, Sus scrofa, Otolemur garnettii, Rhinolophus ferrumequinum, Sorex araneus, Oryctolagus cuniculus, Cricetulus griseus, Sarcophilus harrisii, Mus musculus, Cavia porcellus, Monodelphis domestica, Desmodus rotundus, Bos taurus, Ornithorhynchus anatinus, Taeniopygia guttata, Dasypus novemcinctus, Xenopus Silurana tropicalis, Heterocephalus glaber, Pteropus alecto, Tupaia chinensis, Columba livia, Ovis aries, Gallus gallus, Vicugna pacos, Anolis carolinensis, Otolemur garnettii, Felis catus, Pelodiscus sinensis, Latimeria chalumnae, Tursiops truncates, Mustela putorius furo, Nomascus leucogenys, Gorilla gorilla, Erinaceus europaeus, Procavia capensis, Dipodomys ordii, Petromyzon marinus, Echinops telfairi, Macaca mulatta, Pteropus vampyrus, Myotis lucifugus, Microcebus murinus, Ochotona princeps, Rattus norvegicus, Choloepus hoffmanni, Ictidomys tridecemlineatus, Tarsius syrichta, Tupaia belangeri, Meleagris gallopavo, Macropus eugenii*, or *Danio rerio*. The portions of an ortholog of human paracrine FGF1 include portions corresponding to the above-identified amino acid sequences of human FGF1. Corresponding portions may be determined by, for example, sequence analysis and structural analysis.

In one embodiment, the portion of the FGF1 of the chimeric protein of the present invention is derived from an ortholog of human FGF1 having the amino acid sequence shown in Table 1.

TABLE 1

```
Amino acid sequence of human FGF1 (SEQ ID NO: 1) (GenBank accession
no. AAH32697, which is hereby incorporated by reference in its
entirety):
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD Amino acid sequence of Papio anubis (olive baboon) FGF1 (SEQ ID
NO: 2) (GenBank accession no. NP_001162557, which is hereby
incorporated by reference in its entirety):
  1 MAEGEITTFT ALTEKFNLPP ANYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD Amino acid sequence of Pongo abelii (Sumatran orangutan) FGF1 (SEQ
ID NO: 3) (GenBank accession no. NP_001127073, which is
hereby incorporated by reference in its entirety)
 60                                                                  M
 61 AEGEITTFTA LTEKFNLPPG NYKKPKLLYC SNGGHFLRIL PDGTVDGTRD RSDQHIQLQL
121 SAESVGEVYI KSTETGQYLA MDTDGLLYGS QTPNEECLFL ERLEENHYNT YISKKHAEKN
181 WFVGLKKNGS CKRGPRTHYG QKAILFLPLP VSSD Amino acid sequence of Callithrix jacchus (white-tufted-ear
marmoset) FGF1 (SEQ ID NO: 4) (GenBank accession no.
XP_002744341, which is hereby incorporated by reference
in its entirety):
  1 MAEGEITTFT ALTEKFDLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD Amino acid sequence of Equus caballus (horse) FGF1 (SEQ ID NO: 5)
(GenBank accession no. NP_001157358, which is hereby
incorporated by reference in its entirety):
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

TABLE 1-continued

Amino acid sequence of *Pan troglodytes* (chimpanzee) FGF1 (SEQ ID
NO: 6) (GenBank accession no. JAA29511, which is hereby
incorporated by reference in its entirety):
```
  1MAEGEITTFT ALTEKFNLPS GNYKKPKLLY CSNGGHFLRI LPDGTVDGTR DRSDQHIQLQ
 61LSAESVGEVY IKSTETGQYL AMDTDGLLYG SQTPNEECLF LERLEENHYN TYISKKHAEK
121NWFVGLKKNG SCKRGPRTHY GQKAILFLPL PVSSD
```

Amino acid sequence of *Loxodonta africana* (elephant) FGF1 (SEQ ID
NO: 7) (GenBank accession no. XP_003404621, which is hereby
incorporated by reference in its entirety):
```
  1MAEGEITTFT ALTEKFNLPP GNYKKPKLLY CSNGGHFLRI LPDGTVDGTR DRSDQHIQLQ
 61LSAESVGEVY IKGTETGQYL AMDTDGLLYG SQTPNEECLF LERLEENHYN TYTSKKHAEK
121NWFVGLKKNG SCKRGPRTHY GQKAILFLPL PVSSD
```

Amino acid sequence of *Canis lupus familiaris* (dog) FGF1 (SEQ ID
NO: 8) (GenBank accession no. XP_849274, which is hereby
incorporated by reference in its entirety):
```
  1MAEGEITTFT ALTEKFNLPP GNYMKPKLLY CSNGGHFLRI LPDGTVDGTR DRSDQHIQLQ
 61LSAESVGEVY IKSTETGQYL AMDTDGLLYG SQTPNEECLF LERLEENHYN TYTSKKHAEK
121NWFVGLKKNG SCKRGPRTHY GQKAILFLPL PVSSD
```

Amino acid sequence of *Ailuropoda melanoleuca* (giant panda) FGF1
(SEQ ID NO: 9) (GenBank accession no. XP_002912581,
which is hereby incorporated by reference in its entirety):
```
  1MAEGEITTFT ALTEKFNLPA GNYKKPKLLY CSNGGHFLRI LPDGTVDGTR DRSDQHIQLQ
 61LSAESVGEVY IKSTETGQYL AMDTDGLLYG SQTPNEECLF LERLEENHYN TYTSKKHAEK
121NWFVGLKKNG SCKRGPRTHY GQKAILFLPL PVSSD
```

Amino acid sequence of *Saimiri boliviensis boliviensis* (Bolivian
squirrel monkey) FGF1 (SEQ ID NO: 10) (GenBank accession no.
XP_003920596, which is hereby incorporated by reference in its
entirety):
```
  1MAEGEITTFT ALTEKFDLPP GNYKKPKLLY CSNGGHFLRI LPDGTVDGTR DRSDLHIQLQ
 61LSAESVGEVY IKSTETGQYL AMDTDGLLYG SQTPNEECLF LERLEENHYN TYISKKHAEK
121NWFVGLKKNG SCKRGPRTHY GQKAILFLPL PVSSD
```

Amino acid sequence of *Sus scrofa* (pig) FGF1 (SEQ ID NO: 11)
(GenBank accession no. XP_003124058, which is hereby
incorporated by reference in its entirety):
```
  1MAEGEITTFT ALTEKFNLPP GNYKKPKLLY CSNGGHFLRI LPDGTVDGTR DRSDQHIQLQ
 61LSAESVGEVY IKSTETGQYL AMDTSGLLYG SQTPSEECLF LERLEENHYN TYTSKKHAEK
121NWFVGLKKNG SCKRGPRTHY GQKAILFLPL PVSSD
```

Amino acid sequence of *Otolemur garnettii* (small-eared galago)
FGF1 (SEQ ID NO: 12) (GenBank accession no. XP_003782135, which is
hereby incorporated by reference in its entirety):
```
  1MAEGEITTFT ALTEKFNLPL GNYKKPKLLY CSNGGHFLRI LPDGTVDGTQ DRSDQHIQLQ
 61LSAESVGEVY IKSTQTGQYL AMDSDGLLYG SQTPNEECLF LERLEENHYN TYVSKKHAEK
121NWFVGLKKNG SCKRGPRTHY GQKAILFLPL PVSSD
```

Amino acid sequence of *Rhinolophus ferrumequinum* (greater horseshoe
bat) FGF1 (SEQ ID NO: 13) (GenBank accession no. ACC62496, which is
hereby incorporated by reference in its entirety):
```
  1MAEGEVTTFT ALTEKFNLPT GNYKKPKLLY CSNGGHFLRI LPDGTVDGTR DKSDQHIQLQ
 61LSAESVGEVY IKSTESGQYL AMDSDGLLYG SQTPNEECLF LERLEENHYN TYTSKKHAEK
121NWFVGLKKNG SCKRGPRTHY GQKAILFLPL PVSSD
```

Amino acid sequence of *Sorex araneus* (European shrew) FGF1 (SEQ ID
NO: 14) (GenBank accession no. ACE75805, which is hereby
incorporated by reference in its entirety):
```
  1MAEGEITTFG ALMEKFNLPP GNYKKPKLLY CSNGGHFLRI LPDGTVDGTR DRSDQHIQLQ
 61LSAESVGEVY IKSTETGHYL AMDTDGLLYG SQTPNEECLF LERLEENHYN TYTSKKHAEK
121NWFVGLKKNG SCKRGPRTHY GQKAILFLPL PVSSD
```

Amino acid sequence of *Oryctolagus cuniculus* (rabbit) FGF1 (SEQ ID
NO: 15) (GenBank accession no. NP_001164959, which is hereby
incorporated by reference in its entirety):
```
  1MAEGEVTTFT ALTEKFNLPA GNYKLPKLLY CSNGGHFLRI LPDGTVDGTR DRSDQHIQLQ
 61LSAESVGEVY IKSTETGQYL AMDTDGLLYG SQTPSEECLF LERLEENHYN TYTSKKHAEK
121NWFVGLKKNG SCKRGPRTHY GQKAILFLPL PVSSD
```

Amino acid sequence of *Cricetulus griseus* (Chinese hamster) FGF1
(SEQ ID NO: 16) (GenBank accession no. XP_003502469,
which is hereby incorporated by reference in its entirety):
```
  1MAEGEITTFS ALTERFNLPP GNYKKPKLLY CSNGGHFLRI LPDGTVDGTR DRSDQHIQLQ
 61LSAESAGEVY IKGTETGQYR NMDTDGLLYG SQTPNEECLF LERLEENHYN TYTSKKHAEK
121NWFVGLKKNG SCKRGPRTHY GQKAILFLPL PVSSD
```

TABLE 1-continued

Amino acid sequence of *Sarcophilus harrisii* (Tasmanian devil) FGF1
(SEQ ID NO: 17) (GenBank accession no. XP_003756738,
which is hereby incorporated by reference in its entirety):
```
  1MAEGEITTFT ALTERFNLPL GNYKKPKLLY CSNGGHFLRI LPDGKVDGTR DRNDQHIQLQ
 61LSAESVGEVY IKSTESGQYL AMDTDGLLYG SQTPTEECLF LERLEENHYN TYISKKHAEK
121NWFVGLKKNG SCKRGPRTHY GQKAILFLPL PVSSE
```

Amino acid sequence of *Mus musculus* (house mouse) FGF1 (SEQ ID NO:
18) (GenBank accession no. NP_034327, which is hereby
incorporated by reference in its entirety):
```
  1MAEGEITTFA ALTERFNLPL GNYKKPKLLY CSNGGHFLRI LPDGTVDGTR DRSDQHIQLQ
 61LSAESAGEVY IKGTETGQYL AMDTEGLLYG SQTPNEECLF LERLEENHYN TYTSKKHAEK
121NWFVGLKKNG SCKRGPRTHY GQKAILFLPL PVSSD
```

Amino acid sequence of *Cavia porcellus* (domestic guinea pig) FGF1
(SEQ ID NO: 19) (GenBank accession no. XP_003477242,
which is hereby incorporated by reference in its entirety):
```
  1MAEGITTFA ALTEKFNLPP GNYKKPKLLY CSNGGHFLRI LPDGTVDGTR DRSDQHIQLQ
 61LSAEGVGEVY IQSTETGQYL AMDTDGLLYG SQTPSEECLF LERLEENHYN TYTSKKHVEK
121NWFVGLKKNG SCKRGPRTHY GQKAILFLPL PVSD
```

Amino acid sequence of *Monodelphis domestica* (gray short-tailed
opossum) FGF1 (SEQ ID NO: 20) (GenBank accession no. XP_001368921,
which is hereby incorporated by reference in its entirety):
```
  1MAEGEITTFT ALTERFNLPL GNYKKPKLLY CSNGGHFLRI LPDGKVDGTR DRNDQHIQLQ
 61LSTESVGEVY IKSTESGQYL AMDTDGLLYG SQTPSEECLF LERLEENHYN TYTSKKHAEK
121NWFVGLKKNG SCKKGPRTHY GQKAILFLPL PVSSE
```

Amino acid sequence of *Desmodus rotundus* (common vampire bat) FGF1
(SEQ ID NO: 21) (GenBank accession no. JAA45191, which is hereby
incorporated by reference in its entirety):
```
  1MAEGEVTTFT ALTEKFNLPL ESYKKPKLLY CSNGGHFLRI LPDGTVDGTR DKSDQHIQLQ
 61LSAESVGEVY IKSTGSGQYL AMDSAGLLYG SQTPNEECLF LERLEENHYN TYTSKKHAEK
121NWFVGLKKNG SCKRGPRTHY GQKAILFLPL PVNSD
```

Amino acid sequence of *Bos taurus* (cattle) FGF1 (SEQ ID NO: 22)
(GenBank accession no. NP_776480, which is hereby
incorporated by reference in its entirety):
```
  1MAEGETTTFT ALTEKFNLPL GNYKKPKLLY CSNGGYFLRI LPDGTVDGTK DRSDQHIQLQ
 61LCAESIGEVY IKSTETGQFL AMDTDGLLYG SQTPNEECLF LERLEENHYN TYISKKHAEK
121HWFVGLKKNG RSKLGPRTHF GQKAILFLPL PVSSD
```

Amino acid sequence of *Ornithorhynchus anatinus* (platypus) FGF1 (SEQ
ID NO: 23) (GenBank accession no. XP_001514861, which is hereby
incorporated by reference in its entirety):
```
  1MAEGEITTFT ALMEKFDLPL GNYKKPRLLY CSNGGYFLRI QPDGKVDGTR DRSDQHIQLQ
 61LSAESVGEVY IKSTESGHYL AMDTEGLLYG SQAPSEDCLF LERLEENHYN TYVSKKHAEK
121NWFVGLKKNG SCKRGPRTHY GQKAILFLPL PVASD
```

Amino acid sequence of *Taeniopygia guttata* (zebra finch) FGF1 (SEQ
ID NO: 24) (GenBank accession no. XP_002193287, which is hereby
incorporated by reference in its entirety):
```
  1MAEGEITTFS ALTEKFNLPP GNYKKPKLLY CSNGGHFLRI LPDGTVDGTR DRSDQHIQLQ
 61LSAESVGVVH IQSTQSGQYL AMDTNGLLYG SQLPPGECLF LERLEENHYN TYVSKMHADK
121NWFVGLKKNG TSKLGPRTHY GQKAILFLPL PVAAD
```

Amino acid sequence of *Dasypus novemcinctus* (nine-banded armadillo)
FGF1 (SEQ ID NO: 25) (GenBank accession no. ACO06224, which is
hereby incorporated by reference in its entirety):
```
  1MAEGEITTFM ALMEKFNLPL ENYKHPRLLY CRNGGHFLRI LPDGTVDGTR DRSDQHIQLQ
 61LSAESVGEVY IKSAETGQYL AMDTDGLLYG SETPSEECLF MEKLEENNYN TYISKKHAEK
121KWFVGLKKDG SSKRGPQTHY GQKAILFLPL PVSSD
```

Amino acid sequence of *Xenopus Silurana tropicalis* (western clawed
frog) FGF1 (SEQ ID NO: 26) (GenBank accession no. ACJ50585, which is
hereby incorporated by reference in its entirety):
```
  1MAEGDITTFN PIAESFSLPI GNYKKPKLLY CNNGGYFLRI LPDGVVDGTR DRDDLYITLK
 61LSAQSQGEVH IKSTETGSYL AMDSSGQLYG TLTPNEESLF LETLEENHYN TYKSKKYAEN
121NWFVGIKKNG ASKKGSRTHY GQKAILFLPL PASPD
```

Amino acid sequence of *Heterocephalus glaber* (naked mole-rat) FGF1
(SEQ ID NO: 27) (GenBank accession no. EHA99379, which is hereby
incorporated by reference in its entirety):
```
  1MAEGEITTFT ALTEKFNLPP GNYKKPKLLY CSNGGHFLRI LPDGKVDGTR DRSDQHIQLQ
 61LSAEGVGEVY IKSTETGQYL AMDTDGLLYG SQTASEECLF LERLEENHYN TYISKKHAEK
121NWFVGLKKNG SCKRGPRTHY GQKAILFLPL PVSSD
```

TABLE 1-continued

Amino acid Amino acid sequence of *Pteropus alecto* (black flying fox) FGF1 (SEQ ID NO: 28) (GenBank accession no. ELK02961, which is hereby incorporated by reference in its entirety):
```
  1 MAEGEVTTFT ALTERFNLPP GNYKKPKLLY CSNGGHFLRI LPDGTVDGTR DKSDQHIQLQ
 61 LSAESVGEVY IKSTESGQYL AMDSDGLLYG SQTPDEDCLF LERLEENHYN TYTSKKHAEK
121 NWFVGLKKNG SCKRGPRTHY GQKAILFLPL PVSSD
```

Amino acid Amino acid sequence of *Tupaia chinensis* (Chinese tree shrew) FGF1 (SEQ ID NO: 29) (GenBank accession no. ELW69091, which is hereby incorporated by reference in its entirety):
```
  1 MAEGEITTFA ALTEKFDLPP GNYKKPKLLY CSNGGHFLRI LPDGTVDGTR DRSDQHIQLQ
 61 LTAENVGEVY IKSTETGQYL AMDADGLLYG SQTPNEECLF LERLEENHYN TYISKKHAEK
121 NWFVALKKNG SCKLGPRTHY GQKAILFLPL PVSSD
```

Amino acid Amino acid sequence of *Columba livia* (rock pigeon) FGF1 (SEQ ID NO: 30) (GenBank accession no. EMC79997, which is hereby incorporated by reference in its entirety):
```
  1 MAEGEITTFT ALTEKFNLPP GNYKKPKLLY CSNGGHFLRI LPDGKVDGTR DRSDQHIQLQ
 61 LSAESVGEVY IKSTQSGQYL AMDPTGLLYG SQLLGEECLF LERIEENHYN TYVSKKHADK
121 NWFVGLKKNG NSKLGPRTHY GQKAILFLPL PVSAD
```

Amino acid Amino acid sequence of *Ovis aries* (sheep) FGF1 (SEQ ID NO: 31) (GenBank accession no. XP_004008958, which is hereby incorporated by reference in its entirety):
```
  1 MAEGETTTFR ALTEKFNLPL GNYKKPKLLY CSNGGYFLRI LPDGRVDGTK DRSDQHIQLQ
 61 LYAESIGEVY IKSTETGQFL AMDTNGLLYG SQTPSEECLF LERLEENHYN TYISKKHAEK
121 NWFIGLKKNG SSKLGPRTHF GQKAILFLPL PVSSD
```

Amino acid Amino acid sequence of *Gallus gallus* (chicken) FGF1 (SEQ ID NO: 32) (GenBank accession no. NP_990511, which is hereby incorporated by reference in its entirety):
```
  1 MAEGEITTFT ALTERFGLPL GNYKKPKLLY CSNGGHFLRI LPDGKVDGTR DRSDQHIQLQ
 61 LSAEDVGEVY IKSTASGQYL AMDTNGLLYG SQLPGEECLF LERLEENHYN TYISKKHADK
121 NWFVGLKKNG NSKLGPRTHY GQKAILFLPL PVSAD
```

Amino acid Amino acid sequence of *Vicugna pacos* (alpaca) FGF1 (SEQ ID NO: 33) (Ensembl accession no. ENSVPAP00000007810; partial sequence corresponding to human FGF1 residues 58 to 155, which is hereby incorporated by reference in its entirety):
```
  1 QLQLSAESVG EVYIKSTETG QYLAMDTDGL LHGSQTPNEE CLFLERLEEN HYNTYTSKKH
 61 AEKNWFVGLK KNGSCKRGPR THYGQKAILF LPLPVSSD
```

Amino acid Amino acid sequence of *Anolis carolinensis* (anole lizard) FGF1 (SEQ ID NO: 34) (Ensembl accession no. ENSACAP00000013203, which is hereby incorporated by reference in its entirety):
```
  1 MAEGEITTFT ALTERFALPM ENYKKPKLLY CSNGGHFLRI LPDGKVDGTM DRNDSYIQLL
 61 LTAEDVGVVY IKGTETGQYL AMDANGHLYG SQLPTEECLF VETLEENHYN TYTSKMHGDK
121 KWYVGLKKNG KGKLGPRTHR GQKAILFLPL PVSPD
```

Amino acid Amino acid sequence of *Otolemur garnettii* (bushbaby) FGF1 (SEQ ID NO: 35) (Ensembl accession no. ENSOGAP00000004540, which is hereby incorporated by reference in its entirety):
```
  1 MAEGEITTFT ALTEKFNLPL GNYKKPKLLY CSNGGHFLRI LPDGTVDGTQ DRSDQHIQLQ
 61 LSAESVGEVY IKSTQTGQYL AMDSDGLLYG SQTPNEECLF LERLEENHYN TYVSKKHAEK
121 NWFVGLKKNG SCKRGPRTHY GQKAILFLPL PVSSD
```

Amino acid Amino acid sequence of *Felis catus* (cat) FGF1 (SEQ ID NO: 36) (Ensembl accession no. ENSFCAP00000008457, which is hereby incorporated by reference in its entirety):
```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid Amino acid sequence of *Pelodiscus sinensis* (Chinese softshell turtle) FGF1 (SEQ ID NO: 37) (Ensembl accession no. ENSPSIP00000016356, which is hereby incorporated by reference in its entirety):
```
  1 MAEGEITTFT ALTEKFNLPL GNYKNPKLLY CSNGGYFLRI HPDGKVDGTR DRSDQHIQLQ
 61 LSAESVGEVY IKSTESGQFL AMDANGLLYG SLSPSEECLF LERMEENHYN TYISKKHADK
121 NWFVGLKKNG SCKLGPRTHY GQKAVLFLPL PVSAD
```

Amino acid Amino acid sequence of *Latimeria chalumnae* (coelacanth) FGF1 (SEQ ID NO: 38) (Ensembl accession no. ENSLACP00000015106, which is hereby incorporated by reference in its entirety):
```
  1 MAEDKITTLK ALAEKFNLPM GNYKKAKLLY CSNGGYFLRI PPDGKVEGIR ERSDKYIQLQ
 61 MNAESLGMVS IKGVEAGQYL AMNTNGLLYG SQSLTEECLF MEKMEENHYN TYRSKTHADK
121 NWYVGIRKNG SIKPGPRTHI GQKAVLFLPL PASSD
```

TABLE 1-continued

Amino acid Amino acid sequence of *Tursiops truncatus* (dolphin) FGF1
(SEQ ID NO: 39) (Ensembl accession no. ENSTTRP00000004470,
which is hereby incorporated by reference in its entirety):
```
  1MAEGEITTFT ALTEKFNLPA GNYKKPKLLY CSNGGHFLRI LPDGTVDGTR DRSDQHIQLQ
 61LSAESVGEVY IKSTETGQYL AMDTDGLLYG SQTPNEECLF LERLEENHYN TYASKKHAEK
121NWFVGLKKNG SCKRGPRTHY GQKAILFLPL PVSSD
```

Amino acid Amino acid sequence of *Mustela putorius furo* (ferret)
FGF1 (SEQ ID NO: 40) (Ensembl accession no. ENSMPUP00000007888,
which is hereby incorporated by reference in its entirety):
```
  1MAEGEITTFT ALMEKFNLPA GNYKKPKLLY CSNGGHFLRI LPDGTVDGTR DRSDQHIQLQ
 61LSAESVGEVY IKSTETGQYL AMDTDGLLYG SQTPNEECLF LERLEENHYN TYTSKKHAEK
121NWFVGLKKNG SCKRGPRTHY GQKAILFLPL PVSSD
```

Amino acid Amino acid sequence of *Nomascus leucogenys* (gibbon)
FGF1 (SEQ ID NO: 41) (Ensembl accession no. ENSNLEP00000011873,
which is hereby incorporated by reference in its entirety):
```
  1MAEGEITTFT ALTEKFNLPP GNYKKPKLLY CSNGGHFLRI LPDGTVDGTR DRSDQHIQLQ
 61LSAESVGEVY IKSTETGQYL AMDTDGLLYG SQTPNEECLF LERLEENHYN TYISKKHAEK
121NWFVGLKKNG SCKRGPRTHY GQKAILFLPL PVSSD
```

Amino acid Amino acid sequence of *Gorilla gorilla* (gorilla)
FGF1 (SEQ ID NO: 42) (Ensembl accession no. ENSGGOP00000017663,
which is hereby incorporated by reference in its entirety):
```
  1MAEGEITTFT ALTEKFNLPP GNYKKPKLLY CSNGGHFLRI LPDGTVDGTR DRSDQHIQLQ
 61LSAESVGEVY IKSTETGQYL AMDTDGLLYG SQTPNEECLF LERLEENHYN TYISKKHAEK
121NWFVGLKKNG SCKRGPRTHY GQKAILFLPL PVSSD
```

Amino acid Amino acid sequence of *Erinaceus europaeus* (hedgehog)
FGF1 (SEQ ID NO: 43) (Ensembl accession no. ENSEEUP00000005318,
which is hereby incorporated by reference in its entirety):
```
  1MAEGEITTFT ALTEKFNLPL GNYKKPKLLY CSNGGHFLRI LPDGTVDGTR DRSDQHIQLQ
 61LSAESVGEVY IKSTETGQYL AMDTDGLLYG SQTPNEECLF LERLEENHYN TYTSKKHAEK
121NWFVGLKKNG SCKRGPRTHY GQKAILFLPL PVSSD
```

Amino acid Amino acid sequence of *Procavia capensis* (hyrax) FGF1
(SEQ ID NO: 44) (Ensembl accession no. ENSPCAP00000010969,
which is hereby incorporated by reference in its entirety)
(partial sequence corresponding to human FGF1 residues 1 to 91):
```
  1MAEGEITTFT ALTEKFNLPL ENYKKPKLLY CSNGGHFLRI LPDGTVDGTR DRSDQHIQLQ
 61LSAESVGEVY IKGTETGQYL AMDTDGLLYG S
```

Amino acid Amino acid sequence of *Dipodomys ordii* (kangaroo rat)
FGF1 (SEQ ID NO: 45) (Ensembl accession no. ENSDORP00000006889,
which is hereby incorporated by reference in its entirety)
(partial sequence corresponding to human FGF1 residues 1 to 16
and 58 to 155):
```
  1MAEGEITTFT ALTERF---- ---------- ---------- ---------- -------QLQ
 61LSAESVGEVY IKSTETGQYL AMDADGLLYG SQTPDEECLF LERLEENHYN TYIAKKHAEK
121NWFVGLKKNG SCKRGPRTHY GQKAILFLPL PVSSD
```

Amino acid Amino acid sequence of *Petromyzon marinus* (lamprey) FGF1
(SEQ ID NO: 46) (Ensembl accession no. ENSPMAP00000010683,
which is hereby incorporated by reference in its entirety)
(partial sequence corresponding to human FGF1 residues 1
to 93):
```
  1MEVGHIGTLP VVPAGPVFPG SFKEPRRLYC RSAGHHLQIL GDGTVSGTQD ENEPHAVLQL
 61QAVRRGVVTI RGLCAERFLA MSTEGHLYGA VR
```

Amino acid Amino acid sequence of *Echinops telfairi* (lesser hedgehog
tenrec) FGF1 (SEQ ID NO: 47) (Ensembl accession no.
ENSETEP00000014504, which is hereby incorporated by reference in its
entirety) (partial sequence corresponding to human FGF1 residues 58
to 155)
```
  1QLKLVAESVG VVYIKSIKTG QYLAMNPDGL LYGSETPEEE CLFLETLEEN HYTTFKSKKH
 61VEKNWFVGLR KNGRVKIGPR THQGQKAILF LPLPVSSD
```

Amino acid Amino acid sequence of *Macaca mulatta* (rhesus monkey)
FGF1 (SEQ ID NO: 48) (Ensembl accession no. ENSMMUP00000030943,
which is hereby incorporated by reference in its entirety):
```
  1MAEGEITTFT ALTEKFNLPP GNYKKPKLLY CSNGGHFLRI LPDGTVDGTR DRSDQHIQLQ
 61LSAESVGEVY IKSTETGQYL AMDTDGLLYG SQTPNEECLF LERLEENHYN TYTSKKHAEK
121NWFVGLKKNG SCKRGPRTHY GQKAILFLPL PVSSD
```

Amino acid Amino acid sequence of *Pteropus vampyrus* (megabat)
FGF1 (SEQ ID NO: 49) (Ensembl accession no. ENSPVAP00000004349,
which is hereby incorporated by reference in its entirety):
```
  1MAEGEVTTFT ALTERFNLPP GNYKKPKLLY CSNGGHFLRI LPDGTVDGTR DKSDQHIQLQ
 61LSAESVGEVY IKSTESGQYL AMDSDGLLYG SQTPDEDCLF LERLEENHYN TYTSKKHAEK
121NWFVGLKKNG SCKRGPRTHY GQKAILFLPL PVSSD
```

TABLE 1-continued

Amino acid Amino acid sequence of *Myotis lucifugus* (microbat)
FGF1 (SEQ ID NO: 50) (Ensembl accession no. ENSMLUP00000006481,
which is hereby incorporated by reference in its entirety):
```
  1MAEGEVTTFT ALTERFNLPL ENYKKPKLLY CSNGGHFLRI LPDGTVDGTR DRSDQHIQLQ
 61LSAESVGEVY IKSTESGQYL AMDSDGLLYG SQTPNEECLF LERLEENHYN TYTSKKHAEK
121NWFVGLKKNG SCKRGPRTHY GQKAILFLPL PVSSD
```

Amino acid Amino acid sequence of *Microcebus murinus* (mouse lemur)
FGF1 (SEQ ID NO: 51) (Ensembl accession no. ENSMICP00000008602,
which is hereby incorporated by reference in its entirety):
```
  1MAEGEITTFT ALTEKFNLPP GNYKKPKLLY CSNGGHFLRI LPDGTVDGTR DRSDQHIQLQ
 61LSAESAGEVY IKSTQTGRYL AMDADGLLYG SQTPNEECLF LERLEENHYN TYVSKKHAEK
121NWFVGLKKNG SCKRGPRTHY GQKAILFLPL PVSSD
```

Amino acid Amino acid sequence of *Ochotona princeps* (pika) FGF1
(SEQ ID NO: 52) (Ensembl accession no. ENSOPRP00000011739,
which is hereby incorporated by reference in its entirety):
```
  1MAEGEVTTFS ALTEKFNLPG GNYKLPKLLY CSNGGHFLRI LPDGTVDGTR DRSDLH----
 61-------EVF IKSTETGQYL AMDTDGLLYG SQTPSEECLF LERLEENHYN TYTSKKHAEK
121NWFVGIKKNG SCKRGPRTHY GQKAILFLPL PVSSD
```

Amino acid Amino acid sequence of *Rattus norvegicus* (rat) FGF1
(SEQ ID NO: 53) (Ensembl accession no. ENSRNOP00000018577,
which is hereby incorporated by reference in its entirety):
```
  1MAEGEITTFA ALTERFNLPL GNYKKPKLLY CSNGGHFLRI LPDGTVDGTR DRSDQHIQLQ
 61LSAESAGEVY IKGTETGQYL AMDTEGLLYG SQTPNEECLF LERLEENHYN TYTSKKHAEK
121NWFVGLKKNG SCKRGPRTHY GQKAILFLPL PVSSD
```

Amino acid Amino acid sequence of *Choloepus hoffmanni* (sloth) FGF1
(SEQ ID NO: 54) (Ensembl accession no. ENSCHOP00000010964,
which is hereby incorporated by reference in its entirety):
```
  1MAEGEITTFT ALMEKFNLPP GNYMKPKLLY CSNGGHFLRI LPDGTVDGTR DRSDLHIQLQ
 61LSAESVGEVY IKSAETGQYL AMDTGGLLYG SQTPSEECLF LERLEENHYN TYVSKKHAEK
121NWFVGLKKNG SSKRGPRTHY GQKAILFLPL PVSSD
```

Amino acid Amino acid sequence of *Ictidomys tridecemlineatus*
(squirrel) FGF1 (SEQ ID NO: 55) (Ensembl accession no.
ENSSTOP00000021782, which is hereby incorporated by reference in
its entirety):
```
  1MAEGEITTFT ALTEKFNLPP GNYKKPKLLY CSNGGHFLRI LPDGTVDGTR DRSDQHIQLQ
 61LSAESVGEVY IKSTETGQYL AMDTDGLLYG SQTPNEECLF LERLEENHYN TYTSKKHAEK
121NWFVGLKKNG SCKRGPRTHY GQKAILFLPL PVSSD
```

Amino acid Amino acid sequence of *Tarsius syrichta* (tarsier) FGF1
(SEQ ID NO: 56) (Ensembl accession no. ENSTSYP00000006804,
which is hereby incorporated by reference in its entirety):
```
  1MAEGEITTFT ALTEKFNLPP GNYKKPKLLY CSNGGHFLRI LPDGTVDGTR DRSDQHIQLQ
 61LSAESVGEVY IKSTETGQYL AMDTDGLLYG SQTPNEECLF LERLEENHYN TYVSKKHAEK
121NWFVGLKKNG SCKRGPRTHY GQKAILFLPL PVSSD
```

Amino acid Amino acid sequence of *Tupaia belangeri* (tree shrew) FGF1
(SEQ ID NO: 57) (Ensembl accession no. ENSTBEP00000010264,
which is hereby incorporated by reference in its entirety):
```
  1MAEGEITTFA ALTEKFDLPP GNYKKPKLLY CSNGGHFLRI LPDGTVDGTR DRSDQHIQLQ
 61LTAENVGEVY IKSTETGQYL AMDADGLLYG SQTPNEECLF LERLEENHYN TYISKKHAEK
121NWFVALKKNG SCKLGPRTHY GQKAILFLPL PVSSD
```

Amino acid Amino acid sequence of *Meleagris gallopavo* (turkey) FGF1
(SEQ ID NO: 58) (Ensembl accession no. ENSMGAP00000016398;
partial sequence corresponding to human FGF1 residues 1 to
56, which is hereby incorporated by reference in its entirety):
```
  1MAEGEITTFT ALTERFGLPL GNYKKPKLLY CSNGGHFLRI LPDGKVDGTR DRSDQH
```

Amino acid Amino acid sequence of *Macropus eugenii* (wallaby) FGF1
(SEQ ID NO: 59) (Ensembl accession no. ENSMEUP00000015084,
which is hereby incorporated by reference in its entirety):
```
  1MAEGEITTFT ALTERFNLPL GNYKKPKLLY CSNGGHFLRI LPDGKVDGTR DRNDQHIQLQ
 61LSAESVGEVY IKSTESGQYL AMDTNGLLYG SQTPSEECLF LERLEENHYN TYISKKHAEK
121NWFVGLKKNG SCKRGPRTHY GQKAILFLPL PVSSE
```

Amino acid Amino acid sequence of *Danio rerio* (zebrafish) FGF1
(SEQ ID NO: 60) (Ensembl accession no. ENSDARP00000008825,
which is hereby incorporated by reference in its entirety):
```
  1MTEADIAVKS SPRDYKKLTR LYCMNGGFHL QILADGTVAG AADENTYSIL RIKATSPGVV
 61VIEGSETGLY LSMNEHGKLY ASSLVTDESY FLEKMEENHY NTYQSQKHGE NWYVGIKKNG
121KMKRGPRTHI GQKAIFFLPR QVEQEED
```

As noted above, the portion of the paracrine FGF may be modified to decrease binding affinity for heparin and/or heparan sulfate compared to the portion without the modification. In one embodiment, the modified portion of the paracrine FGF includes one or more substitutions, additions, or deletions.

In one embodiment, the one or more substitutions are located at one or more amino acid residues of SEQ ID NO: 1 selected from N33, K127, K128, N129, K133, R134, R137, Q142, K143, and combinations thereof. In one embodiment, the one or more substitutions are selected from N33T, K127D, K128Q, N129T, K133V, R134L, R137H, Q142M, K143T/L/I, and combinations thereof. In one embodiment, the modification is one or more substitutions which are located at one or more amino acid residues corresponding to residues of SEQ ID NO: 1 selected from N33, K127, K128, N129, K133, R134, R137, Q142, K143, and combinations thereof. In one embodiment, the modification is one or more substitutions which are located at one or more amino acid residues corresponding to residues of SEQ ID NO: 1 selected from N33, K127, K128, N129, K133, R134, R137, Q142, K143, and combinations thereof. Amino acid residues corresponding to those of SEQ ID NO:1 may be determined by, for example, sequence analysis and structural analysis.

Also encompassed within the present invention are portions of paracrine FGFs other than FGF1 (e.g., FGF2, FGF4, FGF5, FGF6, FGF9, FGF16, and FGF20). The portions derived from paracrine FGFs other than FGF1 include portions corresponding to the above-identified amino acid sequences of FGF1. Corresponding portions may be determined by, for example, sequence analysis and structural analysis.

It will be understood that the portion of the paracrine FGF according to the present invention may be derived from a nucleotide sequence that encodes a paracrine FGF protein. For example, in one embodiment, the nucleotide sequence is the nucleotide sequence that encodes human FGF1 (GenBank Accession No. BC032697, which is hereby incorporated by reference in its entirety) (SEQ ID NO: 61), as follows:

```
 91                            ATGGCTGAAG GGGAAATCAC CACCTTCACA
121 GCCCTGACCG AGAAGTTTAA TCTGCCTCCA GGGAATTACA AGAAGCCCAA ACTCCTCTAC
181 TGTAGCAACG GGGCCACTT CCTGAGGATC CTTCCGGATG GCACAGTGGA TGGGACAAGG
241 GACAGGAGCG ACCAGCACAT TCAGCTGCAG CTCAGTGCGG AAAGCGTGGG GGAGGTGTAT
301 ATAAAGAGTA CCGAGACTGG CCAGTACTTG GCCATGGACA CCGACGGGCT TTTATACGGC
361 TCACAGACAC CAAATGAGGA ATGTTTGTTC CTGGAAAGGC TGGAGGAGAA CCATTACAAC
421 ACCTATATAT CCAAGAAGCA TGCAGAGAAG AATTGGTTTG TTGGCCTCAA GAAGAATGGG
481 AGCTGCAAAC GCGGTCCTCG GACTCACTAT GGCCAGAAAG CAATCTTGTT TCTCCCCCTG
541 CCAGTCTCTT CTGATTAA
```

In another embodiment of the present invention, the portion of the paracrine FGF of the chimeric protein may be derived from a nucleotide sequence that encodes an ortholog of human FGF1. Nucleotide sequences that encode FGF1 orthologs are shown in Table 2.

TABLE 2

```
Olive Baboon FGF1 gene coding sequence (1-155) (SEQ ID NO:
62) (GenBank accession no. NM_001169086, which is
hereby incorporated by reference in its entirety):
  1 ATGGCTGAAG GGGAAATCAC CACGTTCACA GCCCTGACCG AGAAGTTTAA TCTGCCTCCA
 61 GCGAATTACA AGAAGCCCAA ACTGCTCTAC TGTAGCAACG GGGACACTT CTTGAGGATC
121 CTTCCGGATG GCACAGTGGA TGGGACAAGG GACAGGAGCG ACCAGCACAT TCAGCTGCAG
181 CTCAGTGCGG AAAGCGTGGG GGAGGTGTAT ATAAAGAGTA CCGAGACTGG CCAGTACTTG
241 GCCATGGACA CCGACGGGCT TTTATACGGC TCACAGACAC CAAATGAGGA ATGTTTGTTC
301 CTGGAAAGGC TGGAGGAGAA CCATTACAAC ACCTACATAT CCAAGAAGCA CGCAGAGAAG
361 AATTGGTTTG TTGGCCTCAA GAAGAATGGA AGCTGCAAAC GTGGTCCTCG GACTCACTAT
421 GGCCAGAAAG CAATCTTGTT TCTTCCCCTG CCAGTCTCTT CTGATTAA Sumatran orangutan FGF1 gene coding sequence (60-214) (SEQ
ID NO: 63) (GenBank accession no. NM_001133601, which
is hereby incorporated by reference in its entirety):
211                            ATGGCTGAAG GGGAAATCAC CACCTTCACA
241 GCCCTGACCG AGAAGTTTAA TCTGCCTCCA GGGAATTACA AGAAGCCCAA ACTCCTCTAC
301 TGTAGCAACG GGGCCACTT CTTGAGGATC CTTCCGGATG GCACAGTGGA TGGGACAAGG
361 GACAGGAGCG ACCAGCACAT TCAGCTGCAG CTCAGTGCGG AAAGCGTGGG GGAGGTGTAT
421 ATAAAGAGTA CCGAGACTGG CCAGTACTTG GCCATGGACA CCGACGGGCT TTTATACGGC
481 TCACAGACAC CAAATGAGGA ATGTTTGTTC CTGGAAAGGC TGGAGGAGAA CCATTACAAC
541 ACCTATATAT CCAAGAAGCA TGCAGAGAAG AATTGGTTTG TTGGCCTCAA GAAGAATGGA
601 AGCTGCAAAC GCGGTCCTCG GACTCACTAT GGCCAGAAAG CAATCTTGTT TCTCCCCCTG
661 CCAGTCTCTT CCGATTAA
```

TABLE 2-continued

White-tufted-ear marmoset FGF1 gene coding sequence (1-155)
(SEQ ID NO: 64) (GenBank accession no. XM_002744295,
which is hereby incorporated by reference in its entirety):

```
130        A TGGCTGAAGG GGAAATCACC ACCTTCACAG CCCTGACCGA GAAGTTTGAT
181CTGCCTCCAG GGAATTACAA GAAGCCCAAA CTCCTCTACT GTAGCAATGG GGGCCACTTC
241TTGAGGATCC TTCCGGATGG CACAGTGGAT GGGACAAGGG ACAGGAGCGA CCAGCACATT
301CAGCTGCAGC TCAGTGCGGA AAGCGTGGGG GAGGTGTATA TAAAGAGTAC CGAGACTGGC
361CAGTACTTGG CCATGGACAC CGACGGGCTT TTATACGGCT CACAGACACC AAATGAGGAA
421TGTTTGTTCC TGGAGAGGCT GGAGGAGAAC CATTACAACA CCTATATATC CAAGAAACAT
481GCAGAGAAGA ATTGGTTTGT CGGCCTCAAG AAGAATGGAA GCTGTAAACG TGGTCCTCGG
541ACTCACTATG GTCAGAAAGC GATCTTGTTT CTCCCCCTGC CAGTTTCTTC TGATTAA
```

Horse FGF1 gene coding sequence (1-155) (SEQ ID NO: 65)
(GenBank accession no. NM_001163886, which is hereby
incorporated by reference in its entirety):

```
 34                         ATGGCTG AAGGAGAAAT CACAACCTTC
 61ACGGCCCTGA CCGAGAAGTT TAATCTGCCT CCAGGGAATT ACAAGAAGCC CAAACTCCTC
121TACTGTAGCA ATGGGGGCCA CTTCCTGAGG ATCCTTCCAG ATGGCACAGT GGATGGGACA
181AGGGACAGGA GCGACCAGCA CATTCAGCTG CAGCTCAGTG CGGAAAGCGT GGGGGAGGTG
241TATATAAAGA GTACCGAGAC TGGCCAGTAC TTGGCCATGG ACACCGACGG GCTGTTGTAC
301GGCTCACAGA CACCCAAACGA GGAATGTTTG TTCCTGGAAA GGCTGGAGGA AAACCATTAC
361AACACCTACA CATCCAAGAA GCATGCAGAG AAGAACTGGT TCGTTGGTCT CAAGAAGAAT
421GGGAGCTGCA AACGCGGTCC TCGGACTCAC TATGGGCAGA AAGCAATCTT GTTTCTTCCC
481CTGCCCGTCT CCTCTGACTA A
```

Chimpanzee FGF1 gene coding sequence (1-155) (SEQ ID NO:
66) (GenBank accession no. GABD01003589, which is hereby
incorporated by reference in its entirety):

```
 80         A TGGCTGAAGG GGAAATCACC ACCTTCACAG CCCTGACCGA
121GAAGTTTAAT CTGCCTTCAG GGAATTACAA GAAGCCCAAA CTCCTCTACT GTAGCAACGG
181GGGCCACTTC CTGAGGATCC TTCCGGATGG CACAGTGGAT GGGACAAGGG ACAGGAGCGA
241CCAGCACATT CAGCTGCAGC TCAGTGCGGA AAGCGTGGGG GAGGTGTATA TAAAGAGTAC
301CGAGACTGGC CAGTACTTGG CCATGGACAC CGACGGGCTT TTATACGGCT CACAGACACC
361AAATGAGGAA TGTTTGTTCC TGGAACGGCT GGAGGAGAAC CATTACAACA CCTATATATC
421CAAGAAGCAT GCAGAGAAGA ATTGGTTTGT TGGCCTCAAG AAGAATGGAA GCTGCAAACG
481CGGTCCTCGG ACTCACTATG GCCAGAAAGC AATCTTGTTT CTCCCCCTGC CAGTCTCTTC
541CGATTAA
```

Elephant FGF1 gene coding sequence (1-155) (SEQ ID NO:
67) (GenBank accession no. XM_003404573, which is
hereby incorporated by reference in its entirety):

```
  1ATGGCCGAAG GGGAAATCAC AACTTTCACA GCCCTGACAG AGAAGTTCAA CCTGCCTCCA
 61GGGAATTACA AGAAGCCCAA ACTCCTCTAC TGTAGCAATG GAGGTCACTT CTTAAGGATC
121CTTCCAGATG GCACAGTGGA TGGCACCAGG GACAGGAGTG ACCAGCACAT TCAGCTGCAG
181CTCAGTGCGG AAAGCGTGGG GGAGGTGTAT ATAAAGGGCA CCGAGACTGG CCAGTACTTG
241GCCATGGACA CCGACGGGCT TTTATACGGC TCACAGACAC CAAATGAGGA ATGTTTGTTC
301CTGGAAAGGC TGGAGGAAAA CCATTACAAC ACCTACACAT CCAAGAAGCA CGCAGAGAAG
361AATTGGTTCG TTGGTCTCAA GAAGAATGGA AGCTGCAAAC GCGGTCCTCG GACTCACTAT
421GGCCAGAAAG CAATCTTGTT TCTCCCCCTG CCAGTCTCCT CTGATTAA
```

Dog FGF1 gene coding sequence (1-155) (SEQ ID NO: 68)
(GenBank accession no. XM_844181, which is hereby
incorporated by reference in its entirety):

```
164                          ATGGCTG AAGGGGAAAT
181CACAACCTTC ACTGCCCTGA CGGAGAAGTT TAATCTGCCT CCGGGGAATT ACATGAAGCC
241CAAACTCCTC TACTGTAGCA ACGGGGGCCA CTTCCTGAGG ATCCTTCCAG ATGGCACAGT
301GGATGGGACA AGGGACAGGA GCGACCAGCA CATTCAGCTG CAGCTCAGTG CGGAAAGCGT
361GGGGGAGGTG TATATAAAGA GCACCGAGAC TGGCCAGTAC TTGGCCATGG ACACCGATGG
421GCTTCTGTAC GGCTCACAGA CACCGAATGA GGAATGTTTG TTCCTGGAAA GGCTGGAGGA
481AAACCATTAC AACACCTACA CATCCAAGAA GCATGCAGAA AAAAATTGGT TTGTTGGTCT
541CAAGAAGAAT GGAAGCTGCA AACGCGGTCC TCGGACTCAC TATGGTCAAA AGCAATTTT
601GTTTCTCCCC CTGCCAGTGT CCTCTGATTA A
```

Giant panda FGF1 gene coding sequence (1-155) (SEQ ID NO:
69) (GenBank accession no. XM_002912535, which is hereby
incorporated by reference in its entirety):

```
146                       ATGGC TGAAGGGGAG ATCACAACCT TCACCGCCCT
181GACGGAGAAG TTTAATCTGC CTGCGGGGAA TTACAAGAAG CCCAAACTCC TCTACTGTAG
241CAACGGGGGC CACTTCCTGA GGATCCTTCC AGATGGCACA GTGGACGGGA CGAGGGACAG
301GAGCGACCAG CACATTCAAC TGCAGCTCAG CGCGGAAAGC GTAGGGGAGG TGTACATAAA
361GAGCACCGAG ACCGCCAGT ACTTGGCCAT GGACACCGAT GGGCTTCTGT ACGGCTCACA
421GACACCAAAT GAGGAATGTT TGTTCCTGGA AAGGCTGGAG GAAACCATT ACAACACCTA
481CACATCCAAG AAGCACGCGG AGAAGAATTG GTTTGTTGGT CTCAAGAAGA ATGGAAGCTG
541CAAACGTGGT CCTCGGACTC ACTATGGCCA GAAAGCAATT CTGTTTCTCC CCTGCCAGT
601CTCCTCTGAT TAA
```

TABLE 2-continued

Bolivian squirrel monkey FGF1 gene coding sequence (1-155)
(SEQ ID NO: 70) (GenBank accession no. XM_003920547,
which is hereby incorporated by reference in its entirety):
```
130                A TGGCTGAAGG GGAAATCACC ACCTTTACAG CCCTGACCGA GAAGTTTGAT
181CTGCCTCCAG GGAATTACAA GAAGCCCAAA CTCCTCTACT GTAGCAACGG GGGCCACTTC
241TTGAGGATCC TTCCGGATGG CACAGTGGAT GGGACCAGGG ACAGGAGCGA TCTTCACATT
301CAGCTGCAGC TCAGTGCGGA AAGCGTGGGG GAGGTGTATA TAAAGAGTAC CGAGACTGGC
361CAGTACTTGG CCATGGACAC CGACGGGCTT TTATACGGCT CACAGACACC AAATGAGGAA
421TGTTTGTTCC TGGAAAGGCT GGAGGAGAAC CATTACAACA CCTATATATC CAAGAAACAC
481GCAGAGAAGA ATTGGTTTGT TGGCCTCAAG AAGAATGGAA GCTGCAAGCC CGGTCCTCGG
541ACTCACTATG GCCAGAAAGC AATCTTGTTT CTCCCCCTGC CAGTCTCTTC TGATTAA
```

Pig FGF1 gene coding sequence (1-155) (SEQ ID NO: 71)
(GenBank accession no. XM_003124010, which is hereby
incorporated by reference in its entirety):
```
 35                                 ATGGCT GAAGGCGAAA TCACAACCTT
 61CACGGCCCTG ACCGAGAAGT TTAATCTGCC TCCAGGAAAT TACAAGAAGC CCAAGCTCCT
121CTACTGCAGC AACGGGGGCC ATTTCCTCAG GATCCTTCCA GATGGCACAG TGGATGGGAC
181CAGGGACAGG AGCGACCAGC ACATTCAGCT GCAGCTCAGT GCGGAAAGCG TGGGGGAGGT
241GTATATAAAG AGTACGGAGA CTGGCCAGTA CTTGGCCATG GACACCAGCG GGCTTTTGTA
301CGGCTCACAG ACACCCAGTG AGGAGTGTTT GTTCCTGGAA AGGCTGGAGG AAAACCATTA
361CAATACCTAC ACATCCAAGA AGCACGCAGA GAAGAACTGG TTCGTTGGCC TCAAGAAGAA
421TGGAAGCTGC AAACGCGGTC CTCGGACTCA CTATGGCCAG AAAGCCATCC TGTTTCTCCC
481CCTGCCAGTA TCCTCGGATT AA
```

Small-eared galago FGF1 gene coding sequence (1-155)
(SEQ ID NO: 72) (GenBank accession no. XM_003782087,
which is hereby incorporated by reference in its entirety):
```
 28                            ATG GCTGAAGGGG AAATCACAAC CTTCACAGCC
 61CTCACAGAGA AGTTTAATCT GCCTCTAGGA AATTACAAGA AGCCCAAGCT CCTCTACTGT
121AGCAACGGGG GTCACTTTCT GAGGATCCTG CCGGATGGCA CCGTGGATGG GACACAAGAC
181AGGAGCGACC AGCACATTCA GCTGCAGCTC AGTGCGGAAA GCGTGGGGGA GGTGTATATA
241AAGAGTACCC AGACTGGCCA GTACTTGGCC ATGGACTCCG ACGGGCTTTT ATACGGCTCA
301CAAACACCAA ATGAGGAATG CCTGTTCCTG GAACGGCTGG AGGAAAACCA TTACAACACC
361TATGTGTCCA AGAAGCACGC CGAGAAGAAT TGGTTTGTCG GTCTCAAGAA GAACGGAAGT
421TGCAAACGTG GTCCTCGGAC TCACTACGGC CAGAAAGCAA TCTTGTTTCT CCCCCTGCCA
481GTCTCCTCTG ATTAA
```

Greater horseshoe bat FGF1 gene coding sequence (1-155)
(SEQ ID NO: 73) (GenBank accession no. DP000705, which is hereby
incorporated by reference in its entirety):
```
190120                                    T TAATCAGAGG AGACTGGCAG
190141GGGGAGAAAC AGGATTGCTT TCTGGCCATA GTGAGTCCGA GGACCGCGCT TGCAGCTTCC
190201ATTCTTCTTG AGCCCAACGA ACCAATTCTT TTCTCGTGTC TTCTTGGACG TGTAGGTGTT
190261GTAATGGTTT TCCTCCAGCC TTTTCCAGGAA CAGACATTCC TCATTTGGTG TCTG
194466     TGAGC CGTACAAAAG CCCGTCGGAG TCCATGGCCA AGTACTGGCC ACTCTCGGTG
194521CTCTTTATAT ACACCTCCCC CACGCTTTCC GCACTGAGCT GCAGCTGAA
208114                                   TGTGCTG GTCACTCTTG TCCCTTGTCC
208141CATCCACTGT GCCATCTGGA AGGATCCTCA GGAAGTGGCC CCCGTTGCTG CAGTAGAGAA
208201GTTTGGGTTT CTTGTAATTC CCTGTAGGCA GATTAAACTT CTCAGTAAGG CTGTGAACG
208261TGGTGACTTC CCCTTCGGCC AT
```

European shrew FGF1 gene coding sequence (1-155) (SEQ
ID NO: 74) (GenBank accession no. DP000767, which is hereby
incorporated by reference in its entirety):
```
138344                                    CTAGTCG GAGGAGACGG
138361GCAGGGGGAG AAACAAGATC GCTTTCTGGC CGTAGTGAGT CCGGGGACCA CGCTTGCAGC
138421TTCCGTTCTT CTTCAGACCA ACAAACCAAT TCTTCTCGGC ATGCTTCTTG GAGGTATAGG
138481TGTTGTAATG GTTTTCCTCC AGCCTTTCCA GAAACAGACA TTCCTCATTC GGTGTTTG
143512                                                 TGAGCCGTA
143521TAAAAGCCCG TCGGTGTCCA TGGCCAAGTA ATGGCCAGTC TCCGTGCTCT TTATATACAC
143581CTCCCCCACG CTTTCCGCAC TGAGCTGCAG CTGAA
157009                                             TG TGCTGGTCGC
157021TGCGGTCCCT GGTCCCATCC ACTGTGCCGT CCGGGAGGAT GCGCAGGAAG TGGCCCCCGT
157081TGCTGCAGTA CAGGAGTTTG GGCTTCTTGT AGTTCCCTGG TGGCAGGTTA AACTTCTCCA
157141TGAGGGCCCC AAAGGTGGTG ATCTCCCCCT CGGCCAT
```

Rabbit FGF1 gene coding sequence (1-155) (SEQ ID NO: 75)
(GenBank accession no. NM_001171488, which is hereby
incorporated by reference in its entirety):
```
  1ATGGCTGAGG GGGAGGTCAC CACCTTCACA GCCCTGACCG AGAAGTTCAA CCTGCCTGCA
 61GGGAACTACA AGTTGCCCAA ACTCCTCTAC TGCAGCAACG GGGGCCACTT CCTGAGGATC
121CTGCCGGACG GCACTGTGGA CGGCACAAGG GACAGGAGCG ACCAGCACAT TCAGCTGCAG
181CTGAGTGCGG AAAGCGTGGG GGAGGTGTAT ATAAAGAGTA CGGAGACCGG CCAGTACTTG
241GCCATGGACA CCGACGGCCT TTTATACGGC TCGCAAACGC CCAGTGAGGA GTGTTTGTTC
301CTGGAACGGC TGGAGGAGAA CCACTACAAC ACCTACACGT CCAAGAAGCA CGCCGAGAAG
361AACTGGTTCG TGGGGCTGAA GAAAAACGGG AGCTGCAAGC GCGGTCCTCG GACTCACTAC
421GGCCAGAAAG CCATCTTGTT CCTCCCCCTG CCGGTCTCCT CCGACTAA
```

TABLE 2-continued

Chinese hamster FGF1 gene coding sequence (1-155) (SEQ ID
NO: 76) (GenBank accession no. XM_003502421, which is
hereby incorporated by reference in its entirety):
```
  1ATGGCTGAAG GAGAAATCAC CACCTTCTCA GCCCTGACAG AGAGATTTAA TCTGCCTCCA
 61GGAAACTACA AGAAGCCCAA ACTGCTCTAC TGCAGCAACG GGGGCCACTT CTTGAGGATC
121CTTCCAGATG GCACAGTGGA TGGGACAAGG GACAGGAGTG ACCAGCACAT TCAGCTGCAG
181CTGAGTGCGG AAAGCGCGGG CGAAGTGTAT ATAAAGGGTA CAGAGACAGG CCAGTACAGG
241AACATGGACA CGGATGGCCT TTTATACGGC TCACAGACAC CAAATGAAGA ATGCCTGTTC
301CTGGAAAGGC TGGAAGAAAA CCATTACAAC ACTTATACAT CCAAGAAGCA CGCAGAGAAG
361AACTGGTTTG TGGGCCTCAA GAAAACGGG AGCTGCAAGC GTGGTCCTCG GACTCACTAT
421GGCCAGAAAG CAATCTTGTT TCTCCCCCTG CCTGTATCTT CTGACTAG
```

Tasmanian devil FGF1 gene coding sequence (1-155) (SEQ ID
NO: 77) (GenBank accession no. XM_003756690, which is
hereby incorporated by reference in its entirety):
```
 24                      ATGGCCG AAGGGGAGAT CACAACCTTC ACAGCCCTGA
 61CCGAAAGATT TAATCTGCCA CTGGGGAATT ACAAGAAGCC CAAGCTTCTC TACTGTAGCA
121ATGGGGGCCA CTTTTTGAGG ATTCTTCCTG ATGGTAAAGT GGATGGGACA AGGGACAGAA
181ATGATCAACA CATTCAACTG CAACTAAGCG CGGAAAGCGT GGGTGAGGTG TATATAAAGA
241GCACTGAGTC TGGCCAGTAT TTGGCTATGG ACACCGATGG ACTTTTATAC GGCTCACAGA
301CACCCACTGA AGAATGCTTG TTCCTGGAGA GATTGGAGGA GAATCATTAC AACACCTACA
361TATCAAAGAA GCATGCGGAG AAAAATTGGT TTGTGGGCCT CAAGAAAAAT GGAAGCTGCA
421AAAGAGGTCC CAGGACTCAC TATGGCCAGA AAGCCATCCT CTTCCTTCCC CTCCCTGTGT
481CCTCTGAGTA A
```

House mouse FGF1 gene coding sequence (1-155) (SEQ ID
NO: 78) (GenBank accession no. NM_010197, which is
hereby incorporated by reference in its entirety):
```
188        ATG GCTGAAGGGG AGATCACAAC CTTCGCAGCC CTGACCGAGA GGTTCAACCT
241GCCTCTAGGA AACTACAAAA AGCCCAAACT GCTCTACTGC AGCAACGGGG GCCACTTCTT
301GAGGATCCTT CCTGATGGCA CCGTGGATGG GACAAGGGAC AGGAGCGACC AGCACATTCA
361GCTGCAGCTC AGTGCGGAAA GTGCGGGCGA AGTGTATATA AAGGGTACGG AGACCGGCCA
421GTACTTGGCC ATGGACACCG AAGGGCTTTT ATACGGCTCG CAGACACCAA ATGAGGAATG
481TCTGTTCCTG GAAAGGCTGG AAGAAAACCA TTATAACACT TACACCTCCA AGAAGCATGC
541GGAGAAGAAC TGGTTTGTGG GCCTCAAGAA GAACGGGAGC TGTAAGCGCG GTCCTCGGAC
601TCACTATGGC CAGAAAGCCA TCTTGTTTCT GCCCCTCCCG GTGTCTTCTG ACTAG
```

Domestic guinea pig FGF1 gene coding sequence (1-154) (SEQ
ID NO: 79) (GenBank accession no. XM_003477194, which
is hereby incorporated by reference in its entirety):
```
  1ATGGCTGAAG GAGAAATCAC AACTTTTGCA GCCCTGACTG AGAAGTTTAA TCTGCCTCCA
 61GGGAATTATA AGAAGCCCAA ACTGCTCTAC TGCAGCAATG GGGGCCACTT CCTGAGGATC
121CTTCCAGACG GCACAGTGGA CGGCACAAGA GACAGGAGCG ACCAGCACAT TCAGCTGCAG
181CTCAGTGCGG AAGGCGTGGG GGAGGTGTAT ATACAGAGCA CCGAGACCGG CCAGTACTTG
241GCCATGGACA CCGACGGGCT TTTATACGGC TCACAGACAC CAAGTGAGGA ATGCTTGTTC
301CTGGAAAGGC TGGAGGAAAA CCATTACAAC ACCTACACAT CCAAGAAGCA TGTGGAGAAG
361AATTGGTTTG TTGGCCTCAA GAAGAACGGA AGCTGCAAGC GTGGTCCTCG GACTCACTAT
421GGCCAGAAAG CAATCTTGTT CCTCCCCTTG CCAGTCTCTG ATTAG
```

Gray short-tailed opossum FGF1 gene coding sequence
(1-155) (SEQ ID NO: 80) (GenBank accession no. XM_001368884,
which is hereby incorporated by reference in its entirety):
```
  1ATGGCCGAAG GGGAGATCAC AACCTTCACA GCCCTGACTG AAAGATTTAA CCTGCCACTG
 61GGGAATTACA AGAAACCCAA GCTTCTCTAC TGTAGCAATG GGGGCCATTT CTTGAGGATC
121CTTCCTGATG GCAAAGTGGA TGGGACACGG GACAGAAATG ATCAACACAT TCAACTGCAG
181CTGAGCACGG AAAGTGTGGG TGAGGTGTAT ATAAAGAGCA CTGAGTCTGG CCAGTATTTG
241GCTATGGACA CCGATGGACT TTTATATGGC TCACAGACAC CCAGTGAAGA ATGCTTGTTT
301CTGGAGAGGT TGGAGGAGAA TCATTACAAC ACCTACACAT CGAAGAAGCA TGCAGAGAAA
361AATTGGTTTG TTGGTCTCAA GAAGAATGGA AGCTGCAAAA AGGGTCCCAG GACTCACTAC
421GGCCAGAAAG CCATCCTGTT CCTTCCCCTC CCTGTGTCCT CTGAGTAA
```

Common vampire bat FGF1 gene coding sequence (1-155) (SEQ
ID NO: 81) (GenBank accession no. GABZ01008334, which is hereby
incorporated by reference in its entirety):
```
  1ATGGCTGAAG GGGAAGTCAC CACGTTCACA GCTCTGACTG AGAAGTTTAA TCTGCCTCTG
 61GAGAGTTACA AGAAGCCCAA ACTTCTCTAC TGCAGCAACG GTGGCCACTT CCTGAGGATC
121CTTCCAGATG GTACAGTGGA TGGGACAAGG GACAAGAGCG ACCAGCACAT TCAGCTGCAG
181CTCAGTGCGG AAAGCGTGGG GGAGGTGTAC ATAAAGAGCA CCGGGAGTGG CCAGTACTTG
241GCCATGGACT CCGCCGGGCT TTTGTATGGC TCACAGACAC CAAATGAGGA ATGTTTGTTC
301CTGGAAAGGC TGGAGGAAAA CCATTACAAC ACCTACACAT CCAAGAAGCA TGCAGAAAAG
361AATTGGTTCG TGGGGCTCAA GAAGAATGGA AGCTGCAAGC GTGGCCCCCG GACTCATTAT
421GGCCAGAAAG CAATCTTGTT TCTCCCCCTG CCAGTCAACT CTGATTAA
```

Cattle FGF1 gene coding sequence (1-155) (SEQ ID NO:
82) (GenBank accession no. NM_174055, which is
hereby incorporated by reference in its entirety):
```
918                 ATG GCTGAAGGAG AAACCACGAC CTTCACGGCC CTGACTGAGA
961AGTTTAACCT GCCTCTAGGC AATTACAAGA AGCCCAAGCT CCTCTACTGC AGCAACGGGG
1021GCTACTTCCT GAGAATCCTC CCAGATGGCA CAGTGGATGG GACGAAGGAC AGGAGCGACC
1081AGCACATTCA GCTGCAGCTC TGTGCGGAAA GCATAGGGGA GGTGTATATT AAGAGTACGG
```

TABLE 2-continued

```
1141AGACTGGCCA GTTCTTGGCC ATGGACACCG ACGGGCTTTT GTACGGCTCA CAGACACCCA
1201ATGAGGAATG TTTGTTCCTG GAAAGGTTGG AGGAAAACCA TTACAACACC TACATATCCA
1261AGAAGCATGC AGAGAAGCAT TGGTTCGTTG GTCTCAAGAA GAACGGAAGG TCTAAACTCG
1321GTCCTCGGAC TCACTTCGGC CAGAAAGCCA TCTTGTTTCT CCCCCTGCCA GTCTCCTCTG
1381ATTAA
```

Platypus FGF1 gene coding sequence (1-155) (SEQ ID
NO: 83) (GenBank accession no. XM_001514811, which
is hereby incorporated by reference in its entirety):
```
  1ATGGCGGAGG GTGAAATCAC CACGTTCACA GCCCTGATGG AGAAGTTCGA CCTACCCCTG
 61GGCAACTACA AAAAGCCTAG GCTGCTCTAC TGCAGCAATG GCGGCTACTT CCTGCGCATC
121CAGCCAGACG GTAAAGTGGA CGGGACCAGG GATCGGAGCG ATCAGCACAT TCAACTGCAG
181CTAAGCGCGG AAAGCGTGGG CGAGGTGTAT ATAAAGAGCA CCGAGTCTGG CCACTATTTG
241GCTATGGACA CCGAAGGACT TTTATATGGC TCACAGGCAC CCAGTGAAGA CTGCTTGTTC
301CTGGAGCGGC TGGAGGAGAA CCACTATAAC ACGTACGTGT CCAAGAAGCA CGCTGAGAAG
361AATTGGTTTG TCGGTCTCAA GAAGAACGGG AGCTGCAAAC GAGGTCCCCG GACTCACTAC
421GGCCAGAAAG CCATCCTCTT CCTCCCGCTC CCCGTGGCAT CCGACTAG
```

Zebra finch FGF1 gene coding sequence (1-155) (SEQ ID NO:
84) (GenBank accession no. XM_002193251, which is
hereby incorporated by reference in its entirety):
```
  1ATGGCCGAGG GGGAGATCAC CACCTTCAGC GCCCTGACGG AGAAGTTCAA CCTGCCCCCG
 61GGGAACTACA AGAAGCCCAA ACTGCTGTAC TGCAGCAACG GGGGCATTT CCTGCGCATC
121CTCCCGGACG GCACCGTGGA TGGCACCAGG GACCGCAGCG ACCAGCACAT TCAGCTCCAG
181CTGAGTGCAG AGAGCGTGGG GGTGGTGCAC ATCCAGAGCA CCCAGTCGGG GCAGTACCTG
241GCCATGGACA CCAACGGGCT GCTCTACGGC TCGCAGCTGC CACCCGGTGA GTGTCTGTTC
301CTGGAAAGGC TGGAGGAGAA CCATTACAAC ACCTACGTCT CCAAAATGCA CGCGGACAAG
361AACTGGTTTG TGGGGCTGAA GAAGAACGGG ACAAGCAAGC TGGGCCCGCG GACTCACTAC
421GGCCAGAAGG CGATCCTGTT CCTGCCGCTG CCCGTGGCGG CCGACTGA
```

Nine-banded armadillo FGF1 gene coding sequence (1-155)
(SEQ ID NO: 85) (GenBank accession no. DP001080, which is
hereby incorporated by reference in its entirety):
```
178389        TT AATCAGAGGA GACTGGCAGG GGAAGAAACA AGATAGCTTT CTGGCCATAG
178441TGAGTCTGAG GACCACGTTT GCTGCTTCCG TCCTTCTTGA GACCAACAAA CCATTTCTTC
178501TCTGCATGCT TCTTGGATAT GTAGGTGTTG TAATTGTTTT CTTCCAGCTT TTCCATGAAC
178561AAGCATTCCT CACTTGGTGT CTC
182873                                                       TGAGCCAT
182881ATAAAAGCCC GTCGGTGTCC ATGGCTAAGT ACTGGCCGGT CTCTGCACTC TTTATATACA
182941CCTCCCCCAC GCTTTCCGCA CTGAGCTGCA GCTGAA
197786                          TGTGT TGGTCGCTCC TGTCCCTTGT CCCATCCACC
197821GTGCCATCTG GAAGGATCCT CAAGAAGTGG CCCCCGTTTC TGCAGTAGAG AGTCTGGGG
197881TGCTTGTAAT TTTCTAGGGG CAGGTTGAAC TTCTCCATCA GGGCCATGAA GGTTGTGATC
197941TCCCCTTCAG CCAT
```

Xenopus Silurana tropicalis FGF1 gene coding sequence
(1-155) (SEQ ID NO: 86) (GenBank accession no. FJ428265, which
is hereby incorporated by reference in its entirety):
```
  1ATGGCAGAGG GAGACATCAC AACATTCAAC CCCATTGCAG AGTCCTTCAG TCTTCCAATT
 61GGCAACTACA AGAAACCAAA ACTTCTGTAC TGTAATAATG GAGGGTATTT TTTGCGCATC
121CTCCCAGATG GGGTTGTGGA TGGAACAAGA GACAGAGATG ACCTTTACAT TACACTGAAG
181TTAAGCGCAC AAAGCCAAGG GGAGGTGCAT ATCAAAAGCA CAGAGACAGG GAGTTACTTA
241GCCATGGACT CCAGTGGACA GTTGTATGGA ACTCTCACAC CAAATGAAGA AGCCTGTTT
301CTGGAGACAT TAGAAGAGAA TCACTATAAC ACATACAAGT CAAAGAAGTA TGCAGAAAAT
361AACTGGTTTG TGGGGATAAA GAAGAACGGG GCAAGCAAAA AGGGATCAAG GACTCACTAT
421GGACAAAAAG CCATCCTTTT TCTGCCGCTG CCAGCATCAC CTGACTAG
```

Heterocephalus glaber FGF1 gene coding sequence (1-155)
(SEQ ID NO: 87) (generated using SMS Reverse Translate tool
on the ExPASy Bioinformatics Resource website (www.expasy.org):
```
  1ATGGCGGAAG GCGAAATTAC CACCTTTACC GCGCTGACCG AAAAATTTAA CCTGCCGCCG
 61GGCAACTATA AAAAACCGAA ACTGCTGTAT TGCAGCAACG GCGGCCATTT TCTGCGCATT
121CTGCCGGATG GCAAAGTGGA TGGCACCCGC GATCGCAGCG ATCAGCATAT TCAGCTGCAG
181CTGAGCGCGG AAGGCGTGGG CGAAGTGTAT ATTAAAAGCA CCGAAAACGG CCAGTATCTG
241GCGATGGATA CCGATGGCCT GCTGTATGGC AGCCAGACCG CGAGCGAAGA ATGCCTGTTT
301CTGGAACGCC TGGAAGAAAA CCATTATAAC ACCTATATTA GCAAAAAACA TGCGGAAAAA
361AACTGGTTTG TGGGCCTGAA AAAAAACGGC AGCTGCAAAC GCGGCCCGCG CACCCATTAT
421GGCCAGAAAG CGATTCTGTT TCTGCCGCTG CCGGTGAGCA GCGAT
```

Black flying fox FGF1 gene coding sequence (1-155) (SEQ
ID NO: 88) (generated using SMS Reverse Translate tool on the
ExPASy Bioinformatics Resource website (www.expasy.org):
```
  1ATGGCGGAAG GCGAAGTGAC CACCTTTACC GCGCTGACCG AACGTTTTAA CCTGCCGCCG
 61GGCAACTATA AAAAACCGAA ACTGCTGTAT TGCAGCAACG GCGGCCATTT TCTGCGCATT
121CTGCCGGATG GCACCGTGGA TGGCACCCGC GATAAAAGCG ATCAGCATAT TCAGCTGCAG
181CTGAGCGCGG AAAGCGTGGG CGAAGTGTAT ATTAAAAGCA CCGAAAGCGG CCAGTATCTG
241GCGATGGATA GCGATGGCCT GCTGTATGGC AGCCAGACCC GGATGAAGA TTGCCTGTTT
301CTGGAACGCC TGGAAGAAAA CCATTATAAC ACCTATACCA GCAAAAAACA TGCGGAAAAA
361AACTGGTTTG TGGGCCTGAA AAAAAACGGC AGCTGCAAAC GCGGCCCGCG CACCCATTAT
421GGCCAGAAAG CGATTCTGTT TCTGCCGCTG CCGGTGAGCA GCGAT
```

TABLE 2-continued

Chinese tree shrew FGF1 gene coding sequence (1-155)
(SEQ ID NO: 89) (generated using SMS Reverse Translate tool
on the ExPASy Bioinformatics Resource website (www.expasy.org):
```
  1ATGGCGGAAG GCGAAATTAC CACCTTTGCG GCGCTGACCG AAAAATTTGA TCTGCCGCCG
 61GGCAACTATA AAAACCGAA ACTGCTGTAT TGCAGCAACG GCGGCCATTT TCTGCGCATT
121CTGCCGGATG GCACCGTGGA TGGCACCCGC GATCGCAGCG ATCAGCATAT TCAGCTGCAG
181CTGACCGCGG AAAACGTGGG CGAAGTGTAT ATTAAAAGCA CCGAAACCGG CCAGTATCTG
241GCGATGGATG CGGATGGCCT GCTGTATGGC AGCCAGACCC CGAACGAAGA ATGCCTGTTT
301CTGGAACGCC TGGAAGAAAA CCATTATAAC ACCTATATTA GCAAAAAACA TGCGGAAAAA
361AACTGGTTTG TGGCGCTGAA AAAAAACGGC AGCTGCAAAC TGGGCCCGCG CACCCATTAT
421GGCCAGAAAG CGATTCTGTT TCTGCCGCTG CCGGTGAGCA GCGAT
```

Rock pigeon FGF1 gene coding sequence (1-155) (SEQ ID
NO: 90) (generated using SMS Reverse Translate tool on the
ExPASy Bioinformatics Resource website (www.expasy.org):
```
  1ATGGCGGAAG GCGAAATTAC CACCTTTACC GCGCTGACCG AAAAATTTAA CCTGCCGCCG
 61GGCAACTATA AAAACCGAA ACTGCTGTAT TGCAGCAACG GCGGCCATTT TCTGCGCATT
121CTGCCGGATG GCAAAGTGGA TGGCACCCGC GATCGCAGCG ATCAGCATAT TCAGCTGCAG
181CTGAGCGCGG AAAGCGTGGG CGAAGTGTAT ATTAAAAGCA CCCAGAGCGG CCAGTATCTG
241GCGATGGATC CGACCGGCCT GCTGTATGGC AGCCAGCTGC TGGGCGAAGA ATGCCTGTTT
301CTGGAACGCA TTGAAGAAAA CCATTATAAC ACCTATGTGA GCAAAAAACA TGCGGATAAA
361AACTGGTTTG TGGGCCTGAA AAAAAACGGC AACAGCAAAC TGGGCCCGCG CACCCATTAT
421GGCCAGAAAG CGATTCTGTT TCTGCCGCTG CCGGTGAGCG CGGAT
```

Sheep FGF1 gene coding sequence (1-155) (SEQ ID NO: 91)
(GenBank accession no. XM_004008909, which is hereby
incorporated by reference in its entirety):
```
361ATGGCTGAAG GAGAAACCAC AACCTTCAGG GCCCTGACTG AGAAGTTTAA CCTGCCTCTA
421GGCAATTACA AGAAGCCCAA GCTCCTCTAT TGCAGCAACG GGGGCTACTT CCTGAGAATC
481CTCCCAGATG GCAGAGTGGA TGGGACGAAG GACAGGAGCG ACCAGCACAT TCAGCTGCAG
541CTCTATGCGG AAAGCATAGG GGAGGTGTAT ATTAAGAGTA CGGAGACTGG CCAGTTCTTG
601GCCATGGACA CCAACGGGCT TTTGTACGGC TCACAAACAC CCAGTGAGGA ATGTTTGTTC
661CTGGAAAGGC TGGAGGAAAA CCATTATAAC ACCTACATAT CCAAGAAGCA TGCAGAGAAG
721AATTGGTTCA TTGGTCTCAA GAAGAACGGA AGCTCCAAAC TCGGTCCTCG GACTCACTTC
781GGCCAGAAAG CCATCTTGTT TCTCCCCCTG CCAGTTTCCT CTGATTAA
```

Chicken FGF1 gene coding sequence (1-155) (SEQ ID NO:
92) (GenBank accession no. NM_205180, which is hereby
incorporated by reference in its entirety):
```
 52                                                      ATGGCCGAG
 61GGGGAGATAA CCACCTTCAC CGCCCTGACC GAGCGCTTCG GCCTGCCGCT GGGCAACTAC
121AAGAAGCCCA AACTCCTGTA CTGCAGCAAC GGGGGCCACT TCCTACGGAT CCTGCCCGAC
181GGCAAGGTGG ACGGGACGCG GGACCGGAGT GACCAGCACA TTCAGCTGCA GCTCAGCGCG
241GAAGATGTGG GCGAGGTCTA TATAAAGAGC ACAGCGTCGG GGCAGTACCT GGCAATGGAC
301ACCAACGGGC TCCTGTATGG CTCGCAGCTA CCAGGCGAGG AGTGCTTGTT CCTTGAGAGG
361CTCGAGGAGA ACCATTACAA CACATACATC TCCAAAAAGC ACGCAGACAA GAACTGGTTC
421GTCGGGCTGA AGAAAAACGG GAACAGCAAG CTGGGGCCGC GGACTCACTA TGGGCAAAAG
481GCGATCCTCT TCCTCCCATT GCCGGTGTCG GCTGACTGA
```

Alpaca FGF1 gene coding sequence (1-155, excluding 1-57)
(SEQ ID NO: 93) (Ensembl accession no. ENSVPAT00000008395, which
is hereby incorporated by reference in its entirety):
```
  1CAGCTGCAGC TCAGTGCGGA AAGCGTGGGG GAGGTGTATA TAAAGAGTAC CGAGACTGGC
 61CAGTACTTGG CCATGGACAC CGACGGGCTT TTGCACGGCT CACAGACACC AAATGAGGAA
121TGTTTGTTCC TGGAAAGGCT GGAGGAGAAC CATTACAACA CCTACACGTC CAAGAAGCAC
181GCCGAAAAGA ATTGGTTTGT TGGTCTCAAG AAGAATGGAA GCTGCAAACG CGGTCCTCGG
241ACTCACTACG GCCAGAAGGC GATCTTGTTT CTCCCCTTGC CAGTCTCCTC TGATTAA
```

Anole lizard FGF1 gene coding sequence (1-155) (SEQ ID NO:
94) (Ensembl accession no. ENSACAT00000013467, which is hereby
incorporated by reference in its entirety):
```
  1ATGGCTGAAG GTGAAATAAC AACATTCACA GCCTTGACCG AGAGGTTTGC TCTCCCAATG
 61GAGAATTACA AGAAGCCCAA ACTCCTGTAT TGCAGCAATG GAGGCCACTT CCTGAGGATC
121CTTCCAGATG GAAAAGTGGA TGGCACCATG GACCGGAATG ACAGCTATAT TCAGTTGCTG
181TTAACAGCAG AAGATGTGGG TGTGGTATAT ATAAAAGGCA CTGAGACCGG CAGTACTTG
241GCCATGGATG CCAATGGACA TTTATATGGC TCGCAGTTGC AACAGAAGA GTGTTTATTT
301GTGGAAACGC TGGAAGAAAA CCATTACAAT ACATATACCT CAAAGATGCA TGGCGATAAG
361AAGTGGTATG TTGGCTTGAA AAAGAATGGG AAAGGCAAAC TGGGGCCACG GACTCATCGC
421GGCCAAAAGG CAATACTTTT CCTTCCACTG CCAGTATCAC CTGATTAG
```

Bushbaby FGF1 gene coding sequence (1-155) (SEQ ID NO:
95) (Ensembl accession no. ENSOGAT00000005081, which is
hereby incorporated by reference in its entirety):
```
  1ATGGCTGAAG GGGAAATCAC AACCTTCACA GCCCTCACAG AGAAGTTTAA TCTGCCTCTA
 61GGAAATTACA AGAAGCCCAA GCTCCTCTAC TGTAGCAACG GGGGTCACTT TCTGAGGATC
121CTGCCGGATG GCACCGTGGA TGGGACACAA GACAGGAGCG ACCAGCACAT TCAGCTGCAG
181CTCAGTGCGG AAAGCGTGGG GGAGGTGTAT ATAAAGAGTA CCCAGACTGG CCAGTACTTG
241GCCATGGACT CCGACGGGCT TTTATACGGC TCACAAACAC CAAATGAGGA ATGCCTGTTC
301CTGGAACGGC TGGAGGAAAA CCATTACAAC ACCTATGTGT CCAAGAAGCA CGCCGAGAAG
```

TABLE 2-continued

```
361AATTGGTTTG TCGGTCTCAA GAAGAACGGA AGTTGCAAAC GTGGTCCTCG GACTCACTAC
421GGCCAGAAAG CAATCTTGTT TCTCCCCCTG CCAGTCTCCT CTGATTAA
```

Cat FGF1 gene coding sequence (1-155) (SEQ ID NO: 96)
(Ensembl accession no. ENSFCAT00000009123, which is hereby
incorporated by reference in its entirety):
```
  1ATGGCTGAAG GGGAAATCAC AACCTTCACG GCCCTGACGG AGAAGTTCAA TCTGCCTCCA
 61GGGAATTACA AGAAACCCAA ACTCCTCTAC TGTAGCAACG GGGGCCACTT CCTGAGGATC
121CTTCCAGATG GCACAGTGGA TGGGACGAGG GACAGGAGCG ACCAGCACAT TCAGCTGCAG
181CTCAGTGCGG AAAGCGTGGG GGAGGTGTAT ATAAAGAGTA CCGAGACTGG CCAGTACTTG
241GCCATGGACA CCGACGGGCT TTTTGTACGGC TCACAGACAC CAATGAGGA ATGCTTGTTC
301CTGGAAAGGC TGGAAGAAAA CCATTACAAC ACCTACACAT CCAAGAAGCA CGCAGAAAAG
361AATTGGTTTG TGGGTCTCAA GAAGAATGGA AGCTGCAAAC GCGGTCCCCG GACTCACTAT
421GGCCAGAAGG CAATTTTGTT TCTCCCCCTG CCAGTCTCCT CTGATTAA
```

Chinese softshell turtle FGF1 gene coding sequence (1-155)
(SEQ ID NO: 97) (Ensembl accession no. ENSPSIT00000016432, which
is hereby incorporated by reference in its entirety):
```
131           ATGGCTGAAG GGGAAATAAC AACGTTCACC GCCCTGACCG AAAAATTCAA
181CCTTCCCCTG GGGAATTACA AGAATCCCAA ACTCTTATAT TGCAGCAATG GAGGCTACTT
241CTTGAGGATA CATCCAGATG GCAAAGTAGA TGGGACAAGG GACCGAAGTG ACCAACACAT
301TCAGCTGCAG CTAAGTGCGG AAAGCGTGGG TGAGGTATAT ATAAAGAGCA CTGAGTCTGG
361ACAGTTTTTG GCTATGGACG CCAATGGACT TTTATATGGA TCACTGTCAC CGAGTGAGGA
291ATGCTTATTC TTGGAAAGAA TGGAAGAAAA TCATTATAAC ACCTACATCT CCAAGAAGCA
351TGCAGACAAG AACTGGTTCG TTGGCTTAAA GAAGAATGGA AGCTGCAAAC TGGGACCGCG
411GACGCACTAC GGCCAAAAGG CCGTCCTTTT CCTTCCACTG CCAGTGTCAG CTGATTAA
```

Coelacanth FGF1 gene coding sequence (1-155) (SEQ ID
NO: 98) (Ensembl accession no. ENSLACT00000015212, which
is hereby incorporated by reference in its entirety):
```
  1ATGGCTGAAG ACAAAATAAC AACACTGAAG GCCTTGGCTG AAAAATTTAA CCTTCCTATG
 61GGAAATTACA AGAAAGCAAA ACTCCTCTAC TGCAGCAACG GAGGGTATTT CCTGCAATA
121CCCCCAGACG GGAAAGTGGA AGGAATTAGA GAACGAAGCG ACAAGTACAT TCAGCTGCAA
181ATGAATGCAG AAAGTTTAGG CATGGTGTCT ATAAAGGGTG TGGAGGCAGG GCAATACCTA
241GCTATGAATA CAAATGGACT CCTGTATGGA TCTCAGTCTC TAACTGAAGA ATGCCTTTTC
301ATGGAAAAGA TGGAAGAAAA CCACTACAAC ACATACAGGT CTAAGACACA TGCAGATAAA
361AACTGGTATG TTGGCATTAG AAAGAACGGT AGCATCAAAC CAGGACCAAG GACTCACATT
421GGCCAAAAGG CTGTTCTTTT TCTCCCTCTG CCTGCCTCGA GTGATTAG
```

Dolphin FGF1 gene coding sequence (1-155) (SEQ ID NO: 99)
(Ensembl accession no. ENSTTRT00000004742, which is hereby
incorporated by reference in its entirety):
```
  1ATGGCTGAAG GGGAAATCAC AACCTTCACA GCCCTGACCG AGAAGTTTAA TCTGCCTCCA
 61GGGAATTACA AGAAGCCCAA ACTCCTCTAC TGTAGCAACG GGGGCCACTT CCTGAGGATC
121CTTCCAGATG GCACAGTGGA TGGGACAAGG GACAGGAGTG ACCAGCACAT TCAGCTGCAG
181CTCAGTGCGG AAAGCGTGGG GGAGGTGTAT ATAAAGAGTA CGGAGACTGG CCAGTACTTG
241GCCATGGACA CCGACGGGCT TTTTGTACGGC TCACAGACAC CAATGAGGA ATGTTTGTTC
301CTGGAAAGGT TGGAGGAAAA CCATTACAAC ACCTACGCAT CCAAGAAGCA TGCAGAAAAG
361AATTGGTTCG TTGGTCTCAA GAAGAACGGA AGCTGCAAAC GCGGTCCTCG GACTCACTAC
421GGCCAGAAAG CAATCTTGTT TCTCCCCCTG CCAGTCTCCT CCGATTAA
```

Ferret FGF1 gene coding sequence (1-155) (SEQ ID NO:
100) (Ensembl accession no. ENSMPUT00000008013, which
is hereby incorporated by reference in its entirety):
```
  1          ATGGCT GAAGGGGAAA TCACAACCTT
 61CACAGCCCTG ATGGAGAAGT TTAATCTGCC TGCGGGGAAT TACAAGAAGC CCAAACTCCT
121CTACTGTAGC AATGGGGGCC ACTTCCTGAG GATCCTTCCA GATGGCACAG TGGACGGCAC
181AAGGGACAGG AGCGACCAGC ACATTCAGCT GCAGCTCAGT GCGGAAAGCG TGGGGGAGGT
241GTACATAAAG AGTACCGAGA CTGGCCAGTA CTTGGCCATG GACACCGATG GCTTTTGTA
301CGGCTCACAA ACACCAAATG AGGAATGTCT GTTCCTGGAA AGGCTGGAGG AAAACCATTA
361CAACACCTAC ACATCCAAGA AGCACGCTGA GAAGAATTGG TTTGTAGGTC TCAAGAAGAA
421CGGAAGCTGC AAACGCGGTC CTCGGACTCA CTATGGCCAG AAAGCAATTC TGTTTCTCCC
481CCTGCCAGTC TCCTCTGATT AA
```

Gibbon FGF1 gene coding sequence (1-155) (SEQ ID NO:
101) (Ensembl accession no. ENSNLET00000012455, which is
hereby incorporated by reference in its entirety):
```
241                                     ATGG CCGAAGGGGA
301AATCACCACC TTCACAGCCC TGACCGAGAA GTTTAATCTG CCTCCAGGGA ATTACAAGAA
361GCCCAAACTC CTCTACTGTA GCAACGGGGG CCACTTCCTG AGGATCCTTC CGGATGGCAC
421AGTGGATGGG ACAAGGGACA GGAGCGACCA GCACATTCAG CTGCAGCTCA GTGCGGAAAG
481CGTGGGGGAG GTGTATATAA AGAGTACCGA GACTGGCCAG TACTTGGCCA TGGACACCGA
541CGGGCTTTTA TACGGCTCAC AGACACCAAA TGAGGAATGT TGTTCCTGG AAAGGCTGGA
601GGAGAACCAT TACAACACCT ATATATCCAA GAAGCATGCA GAGAAGAATT GGTTTGTTGG
661CCTCAAGAAG AATGGAAGCT GCAAACGCGG TCCTCGGACT CACTATGGCC AGAAAGCAAT
721CTTGTTTCTC CCCCTGCCAG TCTCTTCTGA TTAA
```

TABLE 2-continued

Gorilla FGF1 gene coding sequence (1-155) (SEQ ID NO:
102) (Ensembl accession no. ENSGGOT00000025344, which is
hereby incorporated by reference in its entirety):
```
121                                        ATGG CTGAAGGGGA
181AATCACCACC TTCACAGCCC TGACCGAGAA GTTTAATCTG CCTCCAGGGA ATTACAAGAA
241GCCCAAACTC CTCTACTGTA GCAATGGGGG CCACTTCTTG AGGATCCTTC CGGATGGCAC
301AGTGGATGGG ACAAGGGACA GGAGCGACCA GCACATTCAG CTGCAGCTCA GTGCGGAAAG
361CGTGGGGGAG GTGTATATAA AGAGTACCGA GACTGGCCAG TACTTGGCCA TGGACACCGA
421CGGGCTTTTA TACGGCTCAC AGACACCAAA TGAGGAATGT TTGTTCCTGG AAAGGCTGGA
481GGAGAACCAT TACAACACCT ATATATCCAA GAAGCATGCA GAGAAGAATT GGTTTGTTGG
541CCTCAAGAAG AATGGAAGCT GCAAACGCGG TCCTCGGACT CACTATGGCC AGAAAGCAAT
601CTTGTTTCTC CCCCTGCCAG TCTCTTCCGA TTAA
```

Hedgehog FGF1 gene coding sequence (1-155) (SEQ ID NO:
103) (Ensembl accession no. ENSEEUT00000005832, which is
hereby incorporated by reference in its entirety):
```
  1ATGGCTGAAG GAGAAATCAC CACCTTCACG GCCCTGACTG AGAAGTTTAA TCTGCCACTA
 61GGGAATTACA AGAAGCCCAA GCTCCTCTAC TGTAGCAACG GGGGCCACTT CCTGAGGATC
121CTTCCAGATG GCACCGTGGA TGGGACAAGG GACAGGAGCG ACCAGCATAT TCAGCTGCAG
181CTCAGTGCGG AAAGCGTGGG GGAGGTGTAT ATAAAGAGTA CGGAGACTGG CCAGTACTTG
241GCCATGGACA CCGACGGGCT TTTATACGGC TCACAAACAC CAAATGAGGA ATGTCTGTTC
301CTTGAAAGGC TGGAAGAGAA CCATTACAAT ACCTACACAT CCAAGAAGCA TGCCGAGAAG
361AACTGGTTTG TTGGCCTCAA GAAGAATGGA AGCTGCAAGC GTGGTCCTCG GACTCATTAT
421GGCCAGAAAG CTATTTTGTT CTCCCCCTG CCAGTTTCCT CTGATTAA
```

Hyrax FGF1 gene coding sequence (1-155, excluding 1-90)
(SEQ ID NO: 104) (Ensembl accession no. ENSPCAT00000011746,
which is hereby incorporated by reference in its entirety):
```
  1ATGGCTGAAG GCGAAATCAC AACCTTCACA GCCCTGACTG AGAAGTTTAA CCTGCCACTA
 61GAGAATTACA AGAAGCCCAA ACTCCTCTAC TGTAGCAACG GAGGCCACTT CCTGAGGATC
121CTTCCGGACG GCACAGTGGA TGGCACCAGG GACAGGAGTG ACCAGCACAT TCAGCTGCAG
181CTCAGTGCGG AAAGCGTGGG GGAGGTGTAT ATAAAGGGCA CCGAGACTGG CCAGTACTTG
241GCCATGGACA CCGACGGGCT TTTATATGGC TCA
```

Kangaroo rat FGF1 gene coding sequence (1-155, excluding 1-16 and
58-155) (SEQ ID NO: 105) (Ensembl accession no. ENSDORT00000007345,
which is hereby incorporated by reference in its entirety):
```
  1ATGGCTGAAG GGGAAATCAC AACCTTCACA GCCCTGACGG AAAGGTTTAA ----------
   ---------- ---------- ---------- ---------- ---------- ----------
 51---------- ---------- ---------- ---------- ---------T TCAGCTGCAA
 62CTGAGTGCGG AAAGCGTGGG GGAGGTCTAT ATAAAGAGCA CCGAGACTGG CCAATACTTG
122GCCATGGATG CCGACGGGCT TTTATACGGC TCACAGACAC CTGATGAAGA ATGCTTGTTC
182CTGGAGAGGC TGGAAGAAAA TCATTATAAC ACCTACATAG CCAAGAAACA TGCTGAAAAG
242AATTGGTTTG TCGGCCTCAA AAAGAATGGA AGCTGCAAGC GTGGTCCTCG GACTCACTAT
302GGCCAGAAAG CAATCCTGTT CCTCCCCTTG CCTGTCTCCT CTGATTAG
```

Lamprey FGF1 gene coding sequence (1-155, excluding 94-155)
(SEQ ID NO: 106) (Ensembl accession no. ENSPMAT00000010729,
which is hereby incorporated by reference in its entirety):
```
  1ATGGAGGTGG GCCACATCGG CACGCTGCCC GTGGTCCCCG CGGGGCCCGT GTTCCCCGGC
 61AGTTTCAAGG AGCCACGGCG CCTCTACTGC CGCAGCGCGG GCCACCACCT CCAGATCCTG
121GGGGACGGCA CCGTGAGTGG CACCCAGGAC GAGAACGAGC CCACGCCGT TCTGCAGCTG
181CAGGCGGTGC GCCGCGGGGT GGTGACGATC CGTGGGCTCT GCGCCGAGAG GTTCCTCGCC
241ATGAGCACGG AGGGACACCT GTACGGGGCG GTGAGG
```

Lesser hedgehog tenrec FGF1 gene coding sequence (1-155, excluding
1-57) (SEQ ID NO: 107) (Ensembl accession no. ENSETET00000017851,
which is hereby incorporated by reference in its entirety):
```
  1CAGCTGAAGC TCGTTGCCGA AAGCGTGGGG GTGGTGTATA TAAAGAGCAT CAAGACCGGC
 61CAGTACTTGG CCATGAACCC CGACGGGCTT TTATACGGCT CCGAGACCCC AGAGGAAGAA
121TGCTTGTTCC TGGAAACGCT GGAGGAAAAC CACTACACCA CCTTCAAATC TAAGAAGCAC
181GTAGAGAAGA ATTGGTTCGT TGGTCTCCGG AAGAATGGAA GGGTCAAGAT CGGGCCTCGG
241ACTCACCAAG GCCAGAAAGC AATCTTGTTC CTGCCCCTCC CGGTGTCCTC TGATTAA
```

Rhesus monkey FGF1 gene coding sequence (1-155) (SEQ ID
NO: 108) (Ensembl accession no. ENSMMUT00000033070, which is
hereby incorporated by reference in its entirety):
```
 36                                         ATGGC TGAAGGGGAA ATCACCACGT
 61TCACAGCCCT GACCGAGAAG TTTAATCTGC CTCCAGGGAA TTACAAGAAG CCCAAACTGC
121TCTACTGTAG CAATGGGGGC CACTTCTTGA GGATCCTTCC GGATGGCACA GTGGATGGGA
181CAAGGGACAG GAGCGACCAG CACATTCAGC TGCAGCTCAG TGCGGAAAGC GTGGGGGAGG
241TGTATATAAA GAGTACCGAG ACTGGCCAGT ACTTGGCCAT GGACACCGAC GGGCTTTTAT
301ACGGCTCACA GACACCAAAT GAGGAATGTT TGTTCCTGGA AAGGCTGGAG GAGAACCATT
361ACAACACCTA TATATCCAAG AAGCACGCAG AGAAGAATTG GTTTGTTGGC CTCAAGAAGA
421ATGGAAGCTG CAAACGTGGT CCTCGGACTC ACTATGGCCA GAAAGCAATC TTGTTTCTTC
481CCCTGCCAGT CTCTTCTGAT TAA
```

TABLE 2-continued

Megabat FGF1 gene coding sequence (1-155) (SEQ ID NO:
109) (Ensembl accession no. ENSPVAT00000004596, which is
hereby incorporated by reference in its entirety):
```
  1ATGGCCGAGG GGGAAGTCAC GACGTTCACG GCCCTGACCG AGAGGTTTAA CCTGCCTCCA
 61GGGAATTACA AGAAGCCCAA ACTTCTCTAC TGCAGCAACG GGGGCCACTT CCTGAGGATC
121CTCCCAGATG GCACAGTGGA TGGGACAAGG GACAAGAGCG ACCAGCACAT TCAGCTGCAG
181CTCAGTGCGG AAAGTGTGGG GGAGGTGTAT ATAAAGAGCA CCGAGAGTGG CCAGTACTTG
241GCCATGGACT CCGACGGGCT TTTGTACGGC TCACAGACAC CAGATGAGGA CTGTTTGTTC
301CTGGAAAGGC TGGAGGAAAA CCATTACAAC ACCTACACAT CCAAGAAGCA CGCAGAGAAG
361AATTGGTTTG TTGGGCTCAA GAAGAATGGA AGCTGCAAGC GCGGTCCCCG GACTCACTAC
421GGCCAGAAAG CGATCCTGTT TCTCCCCCTG CCAGTCTCCT CTGATTAG
```

Microbat FGF1 gene coding sequence (1-155) (SEQ ID NO:
110) (Ensembl accession no. ENSMLUT00000007098, which is
hereby incorporated by reference in its entirety):
```
 66         ATGGC TGAGGGGGAA GTCACCACAT TCACGGCCCT GACCGAGAGG TTCAATCTGC
121CTCTGGAGAA CTACAAGAAG CCCAAGCTTC TCTACTGCAG CAACGGGGGC CACTTCCTGC
181GGATCCTCCC AGACGGCACC GTGGACGGGA CGAGGGACAG GAGCGACCAG CACATTCAGC
241TGCAGCTCAG TGCGGAAAGC GTGGGGGAGG TGTATATAAA GAGCACCGAG AGTGGCCAGT
301ACTTGGCCAT GGACTCCGAC GGGCTTTTGT ACGGCTCACA AACACCCAAT GAGGAATGTT
361TGTTCCTGGA AAGGCTGGAG GAGAACCACT ACAACACCTA CACGTCCAAG AAGCACGCAG
421AAAAGAATTG GTTCGTTGGG CTCAAGAAGA ACGGAAGCTG CAAGCGTGGT CCTCGGACGC
481ATTATGGCCA GAAAGCAATC TTGTTTCTCC CCCTGCCAGT CTCCTCCGAT TAA
```

Mouse lemur FGF1 gene coding sequence (1-155) (SEQ ID NO:
111) (Ensembl accession no. ENSMICT00000009454, which is
hereby incorporated by reference in its entirety):
```
  1ATGGCCGAAG GGGAGATCAC AACCTTCACG GCCCTCACCG AGAAGTTTAA CCTGCCTCCG
 61GGGAACTACA AGAAGCCCAA GCTCCTCTAC TGCAGCAACG GCGGCCACTT CCTGCGCATC
121CTTCCCGACG GCACCGTGGA TGGCACGAGA GACAGGAGCG ACCAGCACAT TCAGCTGCAG
181CTCAGTGCGG AAAGCGCGGG GGAGGTGTAT ATAAAGAGCA CCCAGACTGG CCGGTACTTG
241GCCATGGACG CCGACGGGCT TTTATACGGC TCACAAACAC CAATGAGGA ATGTTTGTTC
301CTGGAAAGGC TGGAGGAAAA CCATTACAAC ACCTACGTAT CCAAGAAGCA CGCAGAGAAG
361AATTGGTTTG TTGGCCTCAA GAAGAATGGA AGTTGCAAAC GCGGCCCCCG GACTCACTAT
421GGCCAGAAAG CAATCTTGTT TCTGCCCCTG CCAGTCTCCT CTGATTAA
```

Pika FGF1 gene coding sequence (1-155, excluding 57-67)
(SEQ ID NO: 112) (Ensembl accession no. ENSOPRT00000012854,
which is hereby incorporated by reference in its entirety):
```
  1ATGGCCGAGG GAGAAGTCAC CACCTTCTCA GCCCTGACGG AGAAGTTCAA TCTGCCTGGA
 61GGAAACTACA AGTTGCCCAA GCTCCTTTAC TGTAGCAACG GAGGCCACTT CCTGAGGATC
121CTTCCAGATG GCACAGTGGA TGGGACCAGG GACAGGAGCG ACCTGCACA- ----------
170---------- ---------- -GAGGTGTTT ATAAAGAGTA CGGAGACTGG CCAGTACTTG
209GCTATGGACA CCGATGGCCT TTTATATGGC TCGCAGACAC CCAGTGAGGA GTGTTTGTTC
269CTGGAGCGGC TGGAGGAGAA CCACTACAAC ACCTACACAT CCAAGAAGCA TGCCGAGAAG
329AACTGGTTTG TGGGCATCAA GAAGAATGGA AGCTGCAAGC GTGGTCCTCG GACTCACTAC
389GGCCAGAAAG CCATCTTGTT TCTCCCTCTG CCAGTCTCTT CTGACTAA
```

Rat FGF1 gene coding sequence (1-155) (SEQ ID NO: 113)
(Ensembl accession no. ENSRNOT00000018577, which is hereby
incorporated by reference in its entirety):
```
268                      ATG GCCGAAGGGG AGATCACAAC CTTTGCAGCC
301CTGACCGAGA GGTTCAATCT GCCTCTAGGG AACTACAAAA AACCCAAACT GCTCTACTGC
361AGCAACGGGG GCCACTTCTT GAGGATTCTT CCCGATGGCA CCGTGGATGG GACCAGGGAC
421AGGAGCGACC AGCACATTCA GCTGCAGCTC AGTGCGGAAA GCGCGGGCGA AGTGTATATA
481AAGGGTACAG AGACTGGCCA GTACTTGGCC ATGGACACCG AAGGGCTTTT ATACGGCTCG
541CAGACACCAA ATGAAGAATG CCTATTCCTG GAAAGGCTAG AAGAAAACCA TTATAACACT
601TACACATCCA AGAAGCACGC GGGAGAAGAA CTGGTTTGTGG GCCTCAAGAA GAACGGGAGT
661TGTAAGCGCG GTCCTCGGAC TCACTACGGC CAGAAAGCCA TCTTGTTTCT CCCCCTCCCG
721GTATCTTCTG ACTAA
```

Sloth FGF1 gene coding sequence (1-155) (SEQ ID NO: 114)
(Ensembl accession no. ENSCHOT00000012416, which is hereby
incorporated by reference in its entirety):
```
  1ATGGCTGAAG GGAAATCAC AACCTTCACA GCTCTGATGG AGAAGTTTAA CCTGCCACCA
 61GGGAATTACA TGAAGCCCAA ACTCCTCTAC TGTAGCAACG GGGCCACTT CTTGAGGATC
121CTTCCAGACG GCACAGTGGA TGGGACAAGG GACAGGAGCG ACCTGCACAT TCAGCTGCAG
181CTCAGTGCGG AAAGCGTGGG GGAGGTGTAT ATAAAGAGTG CGGAGACCGG CCAGTACTTA
241GCCATGGACA CCGCGGGCT TTTATACGGC TCACAGACAC CAAGTGAGGA ATGCCTGTTC
301CTAGAAAGGC TGGAGGAAAA CCATTACAAC ACCTACGTAT CCAAGAAGCA TGCGGAGAAG
361AACTGGTTCG TTGGCCTAAA GAAGAATGGA AGCAGCAAAC GCGGCCCCCG GACTCACTAT
421GGCCAGAAAG CCATCTTGTT TCTTCCCCTG CCAGTCTCCT CTGATTAA
```

Squirrel FGF1 gene coding sequence (1-155) (SEQ ID NO:
115) (Ensembl accession no. ENSSTOT00000029249, which is
hereby incorporated by reference in its entirety):
```
  1                                                        ATGG
  5CTGAAGGGGA AATCACAACC TTCACAGCCC TGACCGAGAA GTTCAATCTG CCTCCAGGGA
 65ACTACAAGAA GCCCAAACTG CTCTACTGTA GCAACGGAGG CCACTTCTTG AGGATCCTTC
125CTGATGGCAC AGTGGATGGG ACAAGAGACA GGAGCGACCA ACACATTCAG CTGCAGCTCA
```

TABLE 2-continued

```
185 GTGCGGAAAG CGTGGGGGAG GTGTATATAA AGAGTACCGA GACCGGCCAG TACTTGGCCA
245 TGGACACCGA CGGGCTTTTA TATGGCTCAC AGACCCCAAA TGAGGAATGC TTATTCCTGG
305 AAAGGCTGGA GGAAAACCAT TACAACACGT ACACATCCAA GAAGCATGCA GAGAAGAATT
365 GGTTTGTTGG CCTCAAGAAG AACGGAAGCT GCAAGCGCGG TCCCCGGACT CACTATGGCC
425 AGAAAGCGAT CTTGTTTCTC CCACTGCCTG TCTCCTCTGA TTAG
```

Tarsier FGF1 gene coding sequence (1-155) (SEQ ID NO: 116) (Ensembl accession no. ENSTSYT00000007425, which is hereby incorporated by reference in its entirety):

```
  1 ATGGCCGAAG GGGAAATCAC AACCTTCACA GCCCTGACCG AGAAGTTCAA CCTGCCCCCG
 61 GGGAATTACA AGAAGCCCAA ACTCCTCTAC TGCAGCAACG GGGCCACTT  CTTGAGGATC
121 CTTCCGGATG GCACTGTGGA TGGAACGAGG GACAGGAGCG ACCAGCACAT TCAGCTGCAG
181 CTCAGCGCGG AAAAGCGTGG GGAGGTGTAT ATAAAGAGTA CCGAGACCGG CCAGTACTTG
241 GCCATGGACA CCGACGGGCT TTTGTACGGC TCACAGACAC CAAATGAGGA GTGTCTGTTC
301 CTGGAAAGGC TGGAAGAGAA TCATTACAAT ACCTACGTGT CCAAGAAGCA TGCGGAGAAG
361 AATTGGTTTG TCGGCCTCAA GAAGAATGGA AGCTGCAAAC GCGGTCCTCG GACTCACTAT
421 GGCCAGAAAG CAATCTTGTT TCTCCCCCTG CCAGTTTCCT CTGATTAA
```

Tree shrew FGF1 gene coding sequence (1-155) (SEQ ID NO: 117) (Ensembl accession no. ENSTBET00000011861, which is hereby incorporated by reference in its entirety):

```
  1 ATGGCTGAAG GGGAAATCAC GACCTTCGCA GCCCTGACCG AGAAGTTTGA TCTGCCTCCA
 61 GGGAATTACA AGAAGCCCAA ACTTCTCTAC TGTAGCAACG GGGCCATTT  CTTGAGGATT
121 CTTCCAGATG GCACCGTGGA TGGGACAAGA GACAGGAGCG ACCAGCACAT TCAGCTGCAG
181 CTCACTGCGG AAAACGTGGG GGAGGTGTAC ATAAAGATA  CGGAGACTGG CCAGTACTTG
241 GCCATGGACG CCGACGGGCT TTTATATGGC TCACAGACAC CAAACGAGGA ATGTTTGTTC
301 CTGGAAAGGC TGGAGGAGAA CCATTACAAC ACCTACATAT CCAAGAAGCA CGCAGAGAAG
361 AATTGGTTTG TTGCCCTCAA GAAGAACGGA AGCTGCAAAC TCGGTCCTCG GACTCACTAT
421 GGCCAGAAAG CAATCTTGTT TCTCCCCCTG CCAGTCTCCT CTGATTAA
```

Turkey FGF1 gene coding sequence (1-155, excluding 57-155) (SEQ ID NO: 118) (Ensembl accession no. ENSMGAT00000017372, which is hereby incorporated by reference in its entirety):

```
  1 ATGGCCGAGG GGGAGATAAC CACCTTCACA GCCCTGACCG AGCGCTTCGG CCTGCCGCTG
 61 GGCAACTACA AGAAGCCCAA ACTCCTGTAC TGCAGCAACG GGGCCACTT  CCTACGGATC
121 CTGCCGGACG GCAAGGTGGA CGGGACGCGG GACCGGAGCG ACCAGCAC
```

Wallaby FGF1 gene coding sequence (1-155) (SEQ ID NO: 119) (Ensembl accession no. ENSMEUT00000016544, which is hereby incorporated by reference in its entirety):

```
  1 ATGGCCGAAG GGGAGATCAC AACCTTCACA GCCCTGACCG AAAGATTTAA CCTGCCACTG
 61 GGGAATTACA AGAAGCCCAA GCTTCTCTAC TGTAGCAATG GGGCCACTT  TTTGAGGATC
121 CTTCCTGATG GCAAAGTGGA TGGGACAAGG GACAGAAATG ATCAACACAT TCAACTGCAA
181 CTAAGCGCGG AAAGCGTGGG TGAGGTGTAT ATAAAGAGCA CTGAGTCTGG GCAGTATTTG
241 GCCATGGACA CCAATGGACT TTTATATGGC TCACAGACCC CCAGCGAAGA ATGCTTATTC
301 CTGGAGAGGT TGGAGGAGAA TCATTACAAC ACCTACATAT CAAAGAAGCA TGCGGAGAAA
361 AATTGGTTTG TTGGCCTCAA GAAGAACGGA AGTTGCAAAA GAGGTCCCAG GACTCACTAT
421 GGCCAGAAAG CCATCCTATT CCTTCCCCTC CCTGTGTCCT CTGAGTAA
```

Zebrafish FGF1 gene coding sequence (1-147) (SEQ ID NO: 120) (Ensembl accession no. ENSDART00000005842, which is hereby incorporated by reference in its entirety):

```
178                                                                  ATG
181 ACCGAGGCCG ATATTGCGGT AAAGTCCAGC CCGCGCGACT ATAAAAAACT GACGCGGCTG
241 TACTGTATGA ATGGAGGATT TCACCTTCAG ATCCTGGCGG ACGGGACAGT GGCTGGAGCA
124 GCAGACGAAA ACACATACAG CATACTGCGC ATAAAAGCAA CAAGTCCAGG AGTGGTGGTG
184 ATCGAAGGAT CAGAAACAGG TCTTTACCTC TCGATGAATG AACATGGCAA GCTGTACGCT
244 TCATCATTAG TGACGGATGA AAGTTATTTC CTGGAGAGAA TGGAGGAAA  CCACTACAAC
304 ACATATCAGT CTCAAAAGCA CGGTGAAAAC TGGTACGTCG GAATAAAAAA GAACGGGAAA
364 ATGAAACGGG GCCCAAGAAC TCACATCGGA CAAAAGGCCA TTTTCTTTCT TCCACGACAG
424 GTGGAGCAGG AAGAGGACTG A
```

As noted above, also encompassed within the present invention are portions of paracrine FGFs other than FGF1 (e.g., FGF2, FGF4, FGF5, FGF6, FGF9, FGF16, and FGF20). The portions derived from paracrine FGF2 include portions corresponding to the above-identified amino acid sequences of FGF1. Corresponding portions may be determined by, for example, sequence analysis and structural analysis.

In one embodiment, the paracrine FGF is FGF2. In one embodiment, the portion of the FGF2 is derived from human FGF2 having the amino acid sequence of SEQ ID NO: 121 (GenBank Accession No. EAX05222, which is hereby incorporated by reference in its entirety), as follows:

```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 TSWYVALKRT GQYKLGSKTG PGQKAILFLP MSAKS
```

In one embodiment, the portion of the paracrine FGF includes an amino acid sequence beginning at any one of residues 1 to 25 and ending at any one of residues 151 to 155 of SEQ ID NO: 121. In one embodiment, the portion of the paracrine FGF includes amino acid residues 1-151, 1-152, 1-153, 1-154, 1-155, 2-151, 2-152, 2-153, 2-154, 2-155, 3-151, 3-152, 3-153, 3-154, 3-155, 4-151, 4-152, 4-153, 4-154, 4-155, 5-151, 5-152, 5-153, 5-154, 5-155, 6-151, 6-152, 6-153, 6-154, 6-155, 7-151, 7-152, 7-153, 7-154, 7-155, 8-151, 8-152, 8-153, 8-154, 8-155, 9-151, 9-152, 9-153, 9-154, 9-155, 10-151, 10-152, 10-153, 10-154, 10-155, 11-151, 11-152, 11-153, 11-154, 11-155, 12-151, 12-152, 12-153, 12-154, 12-155, 13-151, 13-152, 13-153, 13-154, 13-155, 14-151, 14-152, 14-153, 14-154, 14-155, 15-151, 15-152, 15-153, 15-154, 15-155, 16-151, 16-152, 16-153, 16-154, 16-155, 17-151, 17-152, 17-153, 17-154, 17-155, 18-151, 18-152, 18-153, 18-154, 18-155, 19-151, 19-152, 19-153, 19-154, 19-155, 20-151, 20-152, 20-153, 20-154, 21-155, 21-151, 21-152, 21-153, 21-154, 21-155, 22-151, 22-152, 22-153, 22-154, 22-155, 23-151, 23-152, 23-153, 23-154, 23-155, 24-151, 24-152, 24-153, 24-154, 24-155, 25-151, 25-152, 25-153, 25-154, or 25-155 of FGF2 (SEQ ID NO: 121). In one embodiment, the portion of the paracrine FGF includes amino acid residues 1-151 or 1-152 of SEQ ID NO: 121.

In one embodiment, the portion of the paracrine FGF of the chimeric protein includes an amino acid sequence that has at least 80%, at least 85%, at least 90%, at least 95%, at least 97% or at least 99% amino acid sequence identity to the corresponding amino acid sequence of native paracrine FGF (e.g., SEQ ID NO: 121). In one embodiment, the portion of the paracrine FGF includes an amino acid sequence that has at least 80%, at least 85%, at least 90%, at least 95%, at least 97% or at least 99% amino acid sequence identity to an amino acid sequence beginning at any one of residues 1 to 25 and ending at any one of residues 151 to 155 of SEQ ID NO: 121. In one embodiment, the portion of the paracrine FGF includes an amino acid sequence that has at least 80%, at least 85%, at least 90%, at least 95%, at least 97% or at least 99% amino acid sequence homology to the corresponding amino acid sequence of native paracrine FGF (e.g., SEQ ID NO: 121). In one embodiment, the portion of the paracrine FGF includes an amino acid sequence that has at least 80%, at least 85%, at least 90%, at least 95%, at least 97% or at least 99% amino acid sequence homology to an amino acid sequence beginning at any one of residues 1 to 25 and ending at any one of residues 151 to 155 of SEQ ID NO: 121.

Also encompassed within the present invention are portions of paracrine FGFs other than FGF2 (e.g., FGF1, FGF4, FGF5, FGF6, FGF9, FGF16, and FGF20). The portions derived from paracrine FGFs other than FGF2 include portions corresponding to the above-identified amino acid sequences of FGF2. Corresponding portions may be determined by, for example, sequence analysis and structural analysis.

In one embodiment of the present invention, the portion of the paracrine FGF is derived from an ortholog of a human paracrine FGF. In one embodiment of the present invention, the portion of the paracrine FGF of the chimeric protein is derived from an ortholog of human FGF2. In one embodiment, the portion of the FGF2 is derived from *Gorilla gorilla, Pongo abelii, Macaca mulatta, Pan troglodytes, Pan paniscus, Saimiri boliviensis boliviensis, Nomascus leucogenys, Equus caballus, Bos taurus, Papio Anubis, Vicugna pacos, Ovis aries, Capreolus capreolus, Loxodonta Africana, Sus scrofa, Ailuropoda melanoleuca, Choloepus hoffmanni, Bubalus bubalis, Canis lupus familiaris, Rattus norvegicus, Heterocephalus glaber, Otolemur garnettii, Mus musculus, Ictidomys tridecemlineatus, Felis catus, Cavia porcellus, Sarcophilus harrisii, Monodelphis domestica, Oryctolagus cuniculus, Meleagris gallopavo, Gallus gallus, Taeniopygia guttata, Cynops pyrrhogaster, Xenopus laevis, Didelphis albiventris, Myotis lucifugus, Anolis carolinensis, Dasypus novemcinctus, Tupaia belangeri, Xenopus silurana tropicalis, Latimeria chalumnae, Tetraodon nigroviridis, Gasterosteus aculeatus, Takifugu rubripes, Oncorhynchus mykiss, Salmo salar, Danio rerio, Oreochromis niloticus,* or *Oryzias latipes*. The portions of an ortholog of human paracrine FGF include portions corresponding to the above-identified amino acid sequences of FGF2. Corresponding portions may be determined by, for example, sequence analysis and structural analysis.

In one embodiment, the portion of the FGF2 of the chimeric protein of the present invention is derived from an ortholog of human FGF2 having the amino acid sequence shown in Table 3.

TABLE 3

```
Amino acid sequence of Gorilla gorilla (gorilla) FGF2 (SEQ ID NO: 122)
(Ensembl accession no. ENSGGOP00000004720, which is hereby
incorporated by reference in its entirety):
104                                               MAAGSI TTLPALPEDG
120 GSGAFPPGHF KDPKRLYCKN GGFFLRIHPD GRVDGVREKS DPHIKLQLQA EERGVVSIKG
180 VCANRYLAMK EDGRLLASKC VTDECFFFER LESNNYNTYR SRKYTSWYVA LKRTGQYKLG
240 SKTGPGQKAI LFLPMSAKS Amino acid sequence of Pongo abelii (sumatran orangutan) FGF2 (SEQ ID
NO: 123) (GenBank accession no. XP_002815172, which is hereby
incorporated by reference in its entirety):
168                                                 MAA GSITTLPALP
181 EDGGSGAFPP GHFKDPKRLY CKNGGFFLRI HPDGRVDGVR EKSDPHIKLQ LQAEERGVVS
241 IKGVCANRYL AMKEDGRLLA SKCVTDECFF FERLESNNYN TYRSRKYTSW YVALKRTGQY
301 KLGSKTGPGQ KAILFLPMSA KS Amino acid sequence of Macaca mulatta (rhesus monkey) FGF2 (SEQ ID
NO: 124) (GenBank accession no. XP_001099284, which is hereby
incorporated by reference in its entirety):
83                           MAAGSITT LPALPEDGGS GAFPPGHFKD PKRLYCKNGG
121 FFLRIHPDGR VDGVREKSDP HIKLQLQAEE RGVVSIKGVC ANRYLAMKED GRLLASKCVT
181 DECFFFERLE SNNYNTYRSR KYTSWYVALK RTGQYKLGSK TGPGQKAILF LPMSAKS
```

TABLE 3-continued

Amino acid sequence of *Pan troglodytes* (chimpanzee) FGF2 (SEQ ID
NO: 125) (GenBank accession no. NP_001103711, which is hereby
incorporated by reference in its entirety):
```
134             MAAGSIT TLPALPEDGG SGAFPPGHFK DPKRLYCKNG GFFLRIHPDG
181 RVDGVREKSD PHIKLQLQAE ERGVVSIKGV CANRYLAMKE DGRLLASKCV TDECFFFERL
241 ESNNYNTYRS RKYTSWYVAL KRTGQYKLGS KTGPGQKAIL FLPMSAKS
```

Amino acid sequence of *Pan paniscus* (Pygmy chimpanzee) FGF (SEQ ID
NO: 126) (GenBank accession no. XP_003816481, which is hereby
incorporated by reference in its entirety):
```
112                                                      MAAGSITTL
121 PALPEDGGSG AFPPGHFKDP KRLYCKNGGF FLRIHPDGRV DGVREKSDPH IKLQLQAEER
181 GVVSIKGVCA NRYLAMKEDG RLLASKCVTD ECFFFERLES NNYNTYRSRK YTSWYVALKR
241 TGQYKLGSKT GPGQKAILFL PMSAKS
```

Amino acid sequence of *Saimiri boliviensis boliviensis* (Bolivian
squirrel monkey) FGF2 (SEQ ID NO: 127) (GenBank accession no.
XP_003936290, which is hereby incorporated by reference in its
entirety):
```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 TSWYVALKRT GQYKLGSKTG PGQKAILFLP MSAKS
```

Amino acid sequence of *Nomascus leucogenys* (Northern white-cheeked
gibbon) FGF2 (SEQ ID NO: 128) (GenBank accession no. XP_003271404,
which is hereby incorporated by reference in its entirety):
```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 TSWYVALKRT GQYKLGSKTG PGQKAILFLP MSAKS
```

Amino acid sequence of *Equus caballus* (horse) FGF2 (SEQ ID NO: 129)
(GenBank accession no. NP_001182150, which is hereby incorporated by
reference in its entirety):
```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 SSWYVALKRT GQYKLGPKTG PGQKAILFLP MSAKS
```

Amino acid sequence of *Bos taurus* (cattle) FGF2 (SEQ ID NO: 130)
(GenBank accession no. NP_776481, which is hereby incorporated by
reference in its entirety):
```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 SSWYVALKRT GQYKLGPKTG PGQKAILFLP MASKS
```

Amino acid sequence of *Papio anubis* (Olive baboon) FGF (SEQ ID
NO: 131) (GenBank accession no. XP_003899210, which is hereby
incorporated by reference in its entirety):
```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 TSWYVALKRT GQYKLGSKTG PGQKAILFLP MSAKS
```

Amino acid sequence of *Vicugna pacos* (alpaca) FGF2 (SEQ ID NO: 132)
(Ensembl accession no. ENSVPAP00000009804, which is hereby
incorporated by reference in its entirety):
```
111                                                      MAAGSITTLP
121 ALPEDGGSGA FPPGHFKDPK RLYCKNGGFF LRIHPDGRVD GVREKSDPHI KLQLQAEERG
181 VVSIKGVCAN RYLAMKEDGR LLASKCVTDE CFFFERLESN NYNTYRSRKY SSWYVALKRT
241 GQYKLGPKTG PGQKAILFLP MSAKS
```

Amino acid sequence of *Ovis aries* (sheep) FGF2 (SEQ ID NO: 133)
(GenBank accession no. NP_001009769, which is hereby incorporated by
reference in its entirety):
```
  1 MAAGSITTLP ALPEDGGSSA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 SSWYVALKRT GQYKLGPKTG PGQKAILFLP MSAKS
```

Amino acid sequence of *Capreolus capreolus* (Western roe deer) FGF2
(partial amino acid sequence corresponding to human FGF2 residues 42
to 149) (SEQ ID NO: 134) (GenBank accession no. AAF73226, which is
hereby incorporated by reference in its entirety):
```
  1 RIHPDGRVDG VREKSDPHIK LQLQAEERGV VSIKGVCANR YLAMKEDGRL LASKCVTDEC
 61 FFFERLESNN YNTYRSRKYS SWYVALKRTG QYKLGPKTGP GQKAILFL
```

Amino acid sequence of *Loxodonta africana* (elephant) FGF2 (partial
amino acid sequence corresponding to human FGF2 residues 60 to 155)
(SEQ ID NO: 135) (Ensembl accession no. ENSLAFP00000008249, which is
hereby incorporated by reference in its entirety):
```
  1 VKLQLQAEER GVVSIKGVCA NRYLAMKEDG RLLASRCVTD ECFFFERLES NNYNTYRSRK
 61 YTSWYVALKR TGQYKLGSKT GPGQKAILFL PMSAKS
```

TABLE 3-continued

Amino acid sequence of *Sus scrofa* (pig) FGF2 (partial amino acid
sequence corresponding to human FGF2 residues 36 to 155) (SEQ ID
NO: 136) (GenBank accession no. CAE11791 and Ensembl accession no.
ENSSSCP00000009695, which is hereby incorporated by reference in its
entirety):
    1 NGGFFLRIHP DGRVDGVREK SDPHIKLQLQ AEERGVVSIK GVCANRYLAM KEDGRLLASK
   61 CVTDECFFFE RLESNNYNTY RSRKYSSWYV ALKRTGQYKL GPKTGPGQKA ILFLPMSAKS Amino acid sequence of *Ailuropoda melanoleuca* (panda) FGF2 (partial
amino acid sequence corresponding to human FGF2 residues 60 to
155) (SEQ ID NO: 137) (Ensembl accession no. ENSAMEP00000018489, which
is hereby incorporated by reference in its entirety):
    1 VKLQLQAEER GVVSIKGVCA NRYLAMKEDG RLLASKCVTD ECFFFERLES NNYNTYRSRK
   61 YSSWYVALKR TGQYKLGPKT GPGQKAILFL PMSAKS Amino acid sequence of *Choloepus hoffmanni* (sloth) FGF2 (SEQ ID
NO: 138) (Ensembl accession no. ENSCHOP00000010051, which is hereby
incorporated by reference in its entirety):
   14                                                          MAAGSIT
   21 TLPALPEDGG SGALPPGHFK DPKRLYCKNG GFFLRIHPDG RVDGVREKSD PHIKLQLQAE
   81 ERGVVSIKGV CANRYLAMKE DGRLQASKCV TDECFFFERL ESNNYNTYRS RKYSSWYVAL
  141 KRTGQYKLGP KTGPGQKAIL FLPMSAKS Amino acid sequence of *Bubalus bubalis* (water buffalo) FGF2 (SEQ ID
NO: 139) (GenBank accession no. AFH66795, which is hereby incorporated
by reference in its entirety):
    1 MAAGSITTLP PLPEDGGSGA FPPGHFKDPK RLYCKNGGFF LRIHPDGRVD GVREKSDPHI
   61 KLQLQAEERG VVSIKGVCAN RYLAMKEDGR LLASKCVTDE CFFFERLESS NYNTYRSRKY
  121 SSWYVALKRT GQYKLGPKTG PGQKAILFLP MSAKS Amino acid sequence of *Canis lupus familiaris* (dog) FGF2 (SEQ ID
NO: 140) (GenBank accession no. XP_003432529, which is hereby
incorporated by reference in its entirety):
   40                                                        M AAGSITTLPA LPEDGGSGAF
   61 PPGHFKDPKR LYCKKGGFFL RIHPDGRVDG VREKSDPHVK LQLQAEERGV VSIKGVCANR
  121 YLAMKEDGRL LASKCVTDEC FFFERLESNN YNTYRSRKYS SWYVALKRTG QYKLGPKTGP
  181 GQKAILFLPM SAKS Amino acid sequence of *Rattus norvegicus* (Norway rat) FGF2 (SEQ ID
NO: 141) (GenBank accession no. NP_062178, which is hereby incorporated
by reference in its entirety):
    1 MAAGSITSLP ALPEDGGGAF PPGHFKDPKR LYCKNGGFFL RIHPDGRVDG VREKSDPHVK
   61 LQLQAEERGV VSIKGVCANR YLAMKEDGRL LASKCVTEEC FFFERLESNN YNTYRSRKYS
  121 SWYVALKRTG QYKLGSKTGP GQKAILFLPM SAKS Amino acid sequence of *Heterocephalus glaber* (naked mole-rat) FGF2
(partial amino acid sequence corresponding to human FGF2 residues 22
to 155) (SEQ ID NO: 142) (GenBank accession no. EHB17407, which is
hereby incorporated by reference in its entirety):
    1 ppghfkdpkr lycknggffl rihpdgrvdg vreksdphvk lqlqaeergv vsikgvcanr
   61 ylamkedgrl laskcvtdec ffferlesnn yntyrsrkys swyvalkrtg qyklgsktgp
  121 gqkailflpm saks Amino acid sequence of *Otolemur garnettii* (bushbaby) FGF2 (SEQ ID
NO: 143) (Ensembl accession no. ENSOGAP00000021960, which is hereby
incorporated by reference in its entirety):
   52                                                         MAAGSITTL
   61 PSLPEDGGSD AFPPGHFKDP KRLYCKNGGF FLRIHPDGRV DGVREKSDPY IKLQLQAEER
  121 GVVSIKGVCA NRYLAMKEDG RLLASKLITD ECFFFERLES NNYNTYRSRK YSSWYVALKR
  181 TGQYKLGSKT GPGQKAILFL PMSAKS Amino acid sequence of *Mus musculus* (house mouse) FGF2 (SEQ ID NO: 144)
(GenBank accession no. NP_032032, which is hereby incorporated by
reference in its entirety):
    1 MAASGITSLP ALPEDGGAAF PPGHFKDPKR LYCKNGGFFL RIHPDGRVDG VREKSDPHVK
   61 LQLQAEERGV VSIKGVCANR YLAMKEDGRL LASKCVTEEC FFFERLESNN YNTYRSRKYS
  121 SWYVALKRTG QYKLGSKTGP GQKAILFLPM SAKS Amino acid sequence of *Ictidomys tridecemlineatus* (squirrel) FGF2
(partial amino acid sequence corresponding to human FGF2 residues 12
to 155) (SEQ ID NO: 145) (Ensembl accession no. ENSSTOP00000015653,
which is hereby incorporated by reference in its entirety):
    1 LPEDGGGAF PPGHFKDPKR LYCKNGGFFL RIHPDGRVDG VREKSDPHIK LQLQAEDRGV
   61 VSIKGVCANR YLAMKEDGRL LASKCVTDEC FFFERLESNN YNTYRSRKYS SWYVALKRTG
  121 QYKLGSKTGP GQKAILFLPM SAKS

TABLE 3-continued

Amino acid sequence of *Felis catus* (domestic cat) FGF2 (partial amino acid sequence corresponding to human FGF2 residues 25 to 130) (SEQ ID NO: 146) (GenBank accession no. ABY47638, which is hereby incorporated by reference in its entirety):
```
  1 HFKDPKRLYC KNGGFFLRIH PDGRVDGVRE KSDPHIKLQL QAEERGVVSI KGVCANRYLA
 61 MKEDGRLLAS KCVTDECFFF ERLESNNYNT YRSRKYSSWY VALKRT
```

Amino acid sequence of *Cavia porcellus* (guinea pig) FGF (partial amino acid sequence corresponding to human FGF2 residues 60 to 155) (SEQ ID NO: 147) (Ensembl accession no. ENSCPOP00000004847, which is hereby incorporated by reference in its entirety):
```
  1 VKLQLQAEDR GVVSIKGVCA NRYLAMKEDG RLLASKCVTD ECFFFERLES NNYNTYRSRK
 61 YSSWYVALKR TGQYKLGSKT GPGQKAILFL PMSAKS
```

Amino acid sequence of *Sarcophilus harrisii* (Tasmanian devil) FGF2 (SEQ ID NO: 148) (Ensembl accession no. ENSSHAP00000012215, which is hereby incorporated by reference in its entirety):
```
 48                                             MAA GSITTLPALA
 61 GDGASGGAFP PGHFQDPKRL YCKNGGFFLR IHPDGHVDGI REKSDPHIKL QLQAEERGVV
121 SIKGVCANRY LAMKEDGRLL ALKCVTEECF FFERLESNNY NTYRSRKYSN WYVALKRTGQ
181 YKLGSKTGPG QKAILFLPMS AKS
```

Amino acid sequence of *Monodelphis domestica* (gray short-tailed opossum) FGF2 (SEQ ID NO: 149) (GenBank accession no. NP_001029148, which is hereby incorporated by reference in its entirety):
```
  1 MAAGSITTLP ALSGDGGGGG AFPPGHFKDP KRLYCKNGGF FLRIHPDGRV DGIREKSDPN
 61 IKLQLQAEER GVVSIKGVCA NRYLAMKEDG RLLALKYVTE ECFFFERLES NNYNTYRSRK
121 YSNWYVALKR TGQYKLGSKT GPGQKAILFL PMSAKS
```

Amino acid sequence of *Oryctolagus cuniculus* (rabbit) FGF2 (SEQ ID NO: 150) (GenBank accession no. XP_002717284, which is hereby incorporated by reference in its entirety):
```
  1 MAAESITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 SSWYVALKRT GQYKLGSKTG PGQKAILFLP MSAKS
```

Amino acid sequence of *Meleagris gallopavo* (turkey) FGF2 (partial amino acid sequence corresponding to human FGF2 residues 31 to 155) (SEQ ID NO: 151) (Ensembl accession no. ENSMGAP00000010977, which is hereby incorporated by reference in its entirety):
```
  1 RLYCKNGGFF LRINPDGRVD GVREKSDPHI KLQLQAEERG VVSIKGVSAN RFLAMKEDGR
 61 LLALKCATEE CFFFERLESN NYNTYRSRKY SDWYVALKRT GQYKPGPKTG PGQKAILFLP
121 MSAKS
```

Amino acid sequence of *Gallus gallus* (chicken) FGF (SEQ ID NO: 152) (GenBank accession no. NP_990764
```
  1 maagaagsit tlpalpddgg ggafppghfk dpkrlyckng gfflrinpdg rvdgvreksd
 61 PHIKLQLQAE ERGVVSIKGV SANRFLAMKE DGRLLALKCA TEECFFFERL ESNNYNTYRS
121 RKYSDWYVAL KRTGQYKPGP KTGPGQKAIL FLPMSAKS
```

Amino acid sequence of *Taeniopygia guttata* (zebra finch) FGF2 (SEQ ID NO: 153) (GenBank accession no. XP_002188397, which is hereby incorporated by reference in its entirety):
```
  1 MAAAGGIATL PDDGGSGAFP PGHFKDPKRL YCKNGGFFLR INPDGKVDGV REKSDPHIKL
 61 QLQAEERGVV SIKGVSANRF LAMKEDGRLL ALKYATEECF FFERLESNNY NTYRSRKYSD
121 WYVALKRTGQ YKPGPKTGPG QKAILFLPMS AKS
```

Amino acid sequence of *Cynops pyrrhogaster* (Japanese firebelly newt) FGF2 (SEQ ID NO: 154) (GenBank accession no. BAB63249, which is hereby incorporated by reference in its entirety):
```
  1 MAAGSITSLP ALPEDGNGGT FTPGGFKEPK RLYCKNGGFF LRINSDGKVD GAREKSDSYI
 61 KLQLQAEERG VVSIKGVCAN RYLAMKDDGR LMALKWITDE CFFFERLESN NYNTYRSRKY
121 SDWYVALKRT GQYKNGSKTG AGQKAILFLP MSAKS
```

Amino acid sequence of *Xenopus laevis* (African clawed frog) FGF2 (SEQ ID NO: 155) (GenBank accession no. NP_001093341, which is hereby incorporated by reference in its entirety):
```
  1 MAAGSITTLP TESEDGGNTP FSPGSFKDPK RLYCKNGGFF LRINSDGRVD GSRDKSDSHI
 61 KLQLQAVERG VVSIKGITAN RYLAMKEDGR LTSLRCITDE CFFFERLEAN NYNTYRSRKY
121 SSWYVALKRT GQYKNGSSTG PGQKAILFLP MSAKS
```

Amino acid sequence of *Didelphis albiventris* (white-eared opossum) FGF2 (SEQ ID NO: 156) (GenBank accession no. ABL77404, which is hereby incorporated by reference in its entirety):
```
  1 MAAGSITTLP ALSGDGGGGG AFPPGHFKDP KRLYCKNGGF FLRIHPDGRV DGIREKSDPN
 61 IKLQLQAEER GVVSIKGVCA NRYLAMKEDG RLLALKYVTE ECFFFERLES NNYNTYRSRK
121 YSNWYVALKR TGQYKLGSKT GPGQKAILFS PCLLRC
```

TABLE 3-continued

Amino acid sequence of *Myotis lucifugus* (microbat) FGF2 (partial amino acid sequence corresponding to human FGF2 residues 60 to 155) (SEQ ID NO: 157) (Ensembl accession no. ENSMLUP00000017859, which is hereby incorporated by reference in its entirety):
```
  1 VKLQLQAEER GVVSIKGVCA NRYLAMKEDG RLQASKCVTD ECFFFERLES NNYNTYRSRK
 61 YSSWYVALKR NGQYKLGPKT GPGQKAILFL PMSAKS
```

Amino acid sequence of *Anolis carolinensis* (anole lizard) FGF2 (partial amino acid sequence corresponding to human FGF2 residues 16 to 155) (SEQ ID NO: 158) (Ensembl accession no. ENSACAP00000011657, which is hereby incorporated by reference in its entirety):
```
  1 AAAASFPPGP FKDPKRLYCK NGGFFLRINP DGGVDGVREK SDPNIKLLLQ AEERGVVSIK
 61 GVCANRFLAM NEDGRLLALK YVTDECFFFE RLESNNYNTY RSRKYRDWYI ALKRTGQYKL
121 GPKTGRGQKA ILFLPMSAKS
```

Amino acid sequence of *Dasypus novemcinctus* (armadillo) FGF2 (partial amino acid sequence corresponding to human FGF2 residues 1 to 94) (SEQ ID NO: 159) (Ensembl accession no. ENSDNOP00000011351, which is hereby incorporated by reference in its entirety):
```
124      MAAGSIT TLPALPEDGG SGAFPPGHFK DPKRLYCKNG GFFLRIHPDG RVDGVREKSD
181 PNIKLQLQAE ERGVVSIKGV CANRYLAMRE DGRLQAS
```

Amino acid sequence of *Tupaia belangeri* (tree shrew) FGF2 (SEQ ID NO: 160) (Ensembl accession no. ENSTBEP00000000985, which is hereby incorporated by reference in its entirety):
```
  1 AGVRAEREEA PGSGDSRGTD PAARSLIRRP DAAAREALLG ARSRVQGSST SWPASSRTGI
 61 KLPDDSGQGM GGYPLDRPSR STGRGLGGAP DPAVKLQLQA EERGVVSIKG VCANRYLAMK
121 EDGRLLASKC VTDECFFFER LESNNYNTYR SRKYSSWYVA LKRTGQYKLG SKTGPGQKAI
181 LFLPMSAKS
```

Amino acid sequence of *Xenopus silurana tropicalis* (western clawed frog) FGF2 (SEQ ID NO: 161) (GenBank accession no. NP_001017333, which is hereby incorporated by reference in its entirety):
```
  1 MAAGSITTLP TESEDGNTPF PPGNFKDPKR LYCKNGGYFL RINSDGRVDG SRDKSDLHIK
 61 LQLQAVERGV VSIKGITANR YLAMKEDGRL TSLKCITDEC FFYERLEANN YNTYRSRKNN
121 SWYVALKRTG QYKNGSTTGP GQKAILFLPM SAKS
```

Amino acid sequence of *Latimeria chalumnae* (coelacanth) FGF2 (SEQ ID NO: 162) (Ensembl accession no. ENSLACP00000019200, which is hereby incorporated by reference in its entirety):
```
  1 MAAGGITTLP AVPEDGGSST FPPGNFKEPK RLYCKNGGYF LRINPDGRVD GTREKNDPYI
 61 KLQLQAESIG VVSIKGVCSN RYLAMNEDCR LFGLKYPTDE CFFHERLESN NYNTYRSKKY
121 SDWYVALKRT GQYKPGPKTG LGQKAILFLP MSAKS
```

Amino acid sequence of *Tetraodon nigroviridis* (spotted green pufferfish) FGF2 (SEQ ID NO: 163) (GenBank accession no. CAG04681, which is hereby incorporated by reference in its entirety):
```
 34                              MATGGIT TLPSTPEDGG SSGFPPGSFK
 61 DPKRLYCKNG GFFLRIKSDG VVDGIREKSD PHIKLQLQAT SVGEVVIKGV CANRYLAMNR
121 DGRLFGTKRA TDECHFLERL ESNNYNTYRS RKYPTMFVGL TRTGQYKSGS KTGPGQKAIL
181 FLPMSAKC
```

Amino acid sequence of *Gasterosteus aculeatus* (stickleback) FGF2 (SEQ ID NO: 164) (Ensembl accession no. ENSGACP00000022078, which is hereby incorporated by reference in its entirety):
```
  1 MATAGFATLP STPEDGGSGG FTPGGFKDPK RLYCKNGGFF LRIRSDGGVD GIREKSDAHI
 61 KLQIQATSVG EVVIKGVCAN RYLAMNRDGR LFGVRRATDE CYFLERLESN NYNTYRSRKY
121 PGMYVALKRT GQYKSGSKTG PGQKAILFLP MSAKC
```

Amino acid sequence of *Takifugu rubripes* (fugu *rubripes*) FGF2 (SEQ ID NO: 165) (GenBank accession no. CAD19830, which is hereby incorporated by reference in its entirety):
```
  1 MATGGITTLP STPEDGGSGG FPPGSFKDPK RLYCKNGGFF LRIRSDGAVD GTREKTDPHI
 61 KLQLQATSVG EVVIKGVCAN RYLAMNRDGR LFGMKRATDE CHFLERLESN NYNTYRSRKY
121 PNMFVGLTRT GNYKSGTKTG PCQKAILFLP MSAKY
```

Amino acid sequence of *Oncorhynchus mykiss* (rainbow trout) FGF2 (SEQ ID NO: 166) (GenBank accession no. NP_001118008, which is hereby incorporated by reference in its entirety):
```
  1 MATGEITTLP ATPEDGGSGG FLPGNFKEPK RLYCKNGGYF LRINSNGSVD GIRDKNDPHN
 61 KLQLQATSVG EVVIKGVSAN RYLAMNADGR LFGPRRTTDE CYFMERLESN NYNTYRSRKY
121 PEMYVALKRT GQYKSGSKTG PGQKAILFLP MSARR
```

Amino acid sequence of *Salmo salar* (salmon) FGF2 (SEQ ID NO: 167) (GenBank accession no. ACJ02099, which is hereby incorporated by reference in its entirety):
```
  1 MATGEITTLP ATPEDGGSGG FPPGNFKDPK RLYCKNGGYF LRINSNGSVD GIREKNDPHK
 61 QPQFVRAWTL QGVKRSTGML AHVDSNASHN CVKVAGCSLG EFGSMSNRPH NRRPRVATPA
121 QDLHIRLLHL RDRLKPATRT ADKTEEYFCL
```

TABLE 3-continued

Amino acid sequence of *Danio rerio* (zebrafish) FGF2 (SEQ ID NO: 168) (GenBank accession no. AAP32155, which is hereby incorporated by reference in its entirety):

```
  1 MATGGITTLP AAPDAENSSF PAGSFRDPKR LYCKNGGFFL RINADGRVDG ARDKSDPHIR
 61 LQLQATAVGE VLIKGICTNR FLAMNADGRL FGTKRTTDEC YFLERLESNN YNTYRSRKYP
121 DWYVALKRTG QYKSGSKTSP GQKAILFLPM SAKC
```

Amino acid sequence of *Oreochromis niloticus* (Nile tilapia) FGF2 (SEQ ID NO: 169) (GenBank accession no. XP_003443412, which is hereby incorporated by reference in its entirety):

```
  1 MATGGITTLP ATPEDGGSSG FPPGNFKDPK RLYCKNGGFF LRIKSDGGVD GIREKNDPHI
 61 KLQLQATSVG EVVIKGICAN RYLAMNRDGR LFGARRATDE CYFLERLESN NYNTYRSRKY
121 PNMYVALKRT GQYKSGSKTG PGQKAILFLP MSAKC
```

Amino acid sequence of *Oryzias latipes* (medaka) FGF2 (SEQ ID NO: 170) (Ensembl accession no. ENSORLP00000025834, which is hereby incorporated by reference in its entirety):

```
  1 MATGEITTLP SPAENSRSDG FPPGNYKDPK RLYCKNGGLF LRIKPDGGVD GIREKKDPHV
 61 KLRLQATSAG EVVIKGVCSN RYLAMHGDGR LFGVRQATEE CYFLERLESN NYNTYRSKKY
121 PNMYVALKRT GQYKPGNKTG PGQKAILFLP MSAKY
```

As noted above, the portion of the paracrine FGF may be modified to decrease binding affinity for heparin and/or heparan sulfate compared to the portion without the modification. In one embodiment, the modification of the paracrine FGF includes one or more substitutions, additions, or deletions.

In one embodiment, the modification is one or more substitutions located at one or more amino acid residues of SEQ ID NO: 121 selected from N36, K128, R129, K134, K138, Q143, K144, C78, C96, and combinations thereof. In one embodiment, the one or more substitutions are selected from N36T, K128D, R129Q, K134V, K138H, Q143M, K144T/L/I, C78S, C96S, and combinations thereof. In one embodiment, the modification is one or more substitutions which are located at one or more amino acid residues corresponding to residues of SEQ ID NO: 121 selected from N36, K128, R129, K134, K138, Q143, K144, C78, C96, and combinations thereof. In one embodiment, the modification is one or more substitutions which are located at one or more amino acid residues corresponding to residues of SEQ ID NO: 121 selected from N36, K128, R129, K134, K138, Q143, K144, C78, C96, and combinations thereof. Amino acid residues corresponding to those of SEQ ID NO: 121 may be determined by, for example, sequence analysis and structural analysis.

It will be understood that the portion of the paracrine FGF according to the present invention may be derived from a nucleotide sequence that encodes a paracrine FGF protein. For example, in one embodiment, nucleotide sequence is the nucleotide sequence that encodes human FGF2 (GenBank Accession No. NM_002006, which is hereby incorporated by reference in its entirety) (SEQ ID NO: 171), as follows:

```
468                                                       ATG GCAGCCGGGA
481 GCATCACCAC GCTGCCCGCC TTGCCCGAGG ATGGCGGCAG CGGCGCCTTC CCGCCCGGCC
541 ACTTCAAGGA CCCCAAGCGG CTGTACTGCA AAAACGGGGG CTTCTTCCTG CGCATCCACC
601 CCGACGGCCG AGTTGACGGG GTCCGGGAGA AGAGCGACCC TCACATCAAG CTACAACTTC
661 AAGCAGAAGA GAGAGGAGTT GTGTCTATCA AAGGAGTGTG TGCTAACCGT TACCTGGCTA
721 TGAAGGAAGA TGGAAGATTA CTGGCTTCTA AATGTGTTAC GGATGAGTGT TTCTTTTTTG
781 AACGATTGGA ATCTAATAAC TACAATACTT ACCGGTCAAG GAAATACACC AGTTGGTATG
841 TGGCACTGAA ACGAACTGGG CAGTATAAAC TTGGATCCAA AACAGGACCT GGGCAGAAAG
901 CTATACTTTT TCTTCCAATG TCTGCTAAGA GCTGA
```

In another embodiment of the present invention, the portion of the paracrine FGF of the chimeric protein may be derived from a nucleotide sequence that encodes an ortholog of human FGF2. Nucleotide sequences that encode FGF2 orthologs are shown in Table 4.

TABLE 4

*Gorilla* FGF2 gene coding sequence (amino acids ("aa") 104-258) (SEQ ID NO: 172) (Ensembl accession no. ENSGGOT00000004842, which is hereby incorporated by reference in its entirety):

```
310              ATGGCAGCC GGGAGCATCA CCACGCTGCC CGCCTTGCCC GAGGATGGCG
359 GCAGCGGCGC CTTCCCGCCC GGCCACTTCA AGGACCCCAA GCGGCTGTAC TGCAAAAACG
419 GGGGCTTCTT CCTGCGCATC CACCCCGACG GCCGAGTTGA CGGGGTCCGG GAGAAGAGCG
479 ACCCTCACAT CAAGCTACAA CTTCAAGCAG AAGAGAGAGG AGTTGTGTCT ATCAAAGGAG
```

TABLE 4-continued

```
539  TGTGTGCTAA CCGTTACCTT GCTATGAAGG AAGATGGAAG ATTACTGGCT TCTAAATGTG
599  TTACGGATGA GTGTTTCTTT TTTGAACGAT TGGAATCTAA TAACTACAAT ACTTACCGGT
659  CAAGGAAATA CACCAGTTGG TATGTGGCAC TGAAACGAAC TGGGCAGTAT AAACTTGGAT
719  CCAAAACAGG ACCTGGGCAG AAAGCTATAC TTTTTCTTCC AATGTCTGCT AAGAGCTGA
```

Sumatran orangutan FGF2 gene coding sequence (aa 168-322) (SEQ ID NO: 173)
(GenBank accession no. XM_002815126, which is hereby incorporated by
reference in its entirety):
```
504                       ATGGCAG CCGGGAGCAT CACCACGCTG CCCGCCTTGC
541  CCGAGGATGG CGGCAGCGGC GCCTTCCCGC CGGGCCACTT CAAGGACCCC AAGCGGCTGT
601  ACTGCAAAAA CGGGGGCTTC TTCCTGCGCA TCCACCCCGA CGGCCGAGTT GACGGGGTCC
661  GAGAGAAGAG CGACCCTCAC ATCAAACTAC AACTTCAAGC AGAAGAAAGA GGAGTTGTGT
721  CTATCAAAGG AGTGTGTGCT AACCGCTACC TTGCTATGAA GGAAGATGGA AGATTACTGG
781  CTTCTAAATG TGTTACGGAT GAGTGTTTCT TTTTTGAACG ATTGGAATCT AATAACTACA
841  ATACTTACCG GTCAAGGAAA TACACCAGTT GGTATGTGGC ACTGAAACGA ACTGGGCAGT
901  ATAAACTTGG ATCCAAAACA GGACCTGGGC AGAAAGCTAT ACTTTTTCTT CCAATGTCTG
961  CTAAGAGCTG A
```

Rhesus monkey FGF2 gene coding sequence (aa 83-237) (SEQ ID NO: 174)
(GenBank accession no. XM_001099284, which is hereby incorporated by
reference in its entirety):
```
247       ATGG CAGCCGGGAG CATCACCACG CTGCCCGCCT TGCCCGAGGA TGGCGGCAGC
301  GGCGCCTTCC CGCCTGGCCA CTTCAAGGAC CCCAAGCGGC TGTACTGCAA AAACGGGGGC
361  TTCTTCCTGC GCATTCACCC CGACGGCCGA GTTGACGGGG TCCGGGAGAA GAGCGACCCT
421  CACATCAAAT ACACTTCA AGCAGAAGAG AGAGGAGTTG TGTCTATCAA AGGAGTGTGT
481  GCTAACCGTT ACCTTGCTAT GAAGGAAGAT GGAAGATTAC TGGCTTCTAA ATGTGTTACA
541  GATGAGTGTT TCTTTTTTGA ACGATTGGAA TCTAATAACT ACAATACTTA CCGGTCAAGG
601  AAATACACCA GTTGGTATGT GGCACTGAAA CGAACTGGGC AATATAAACT TGGATCCAAA
661  ACAGGACCTG GGCAGAAAGC TATACTTTTT CTTCCAATGT CTGCTAAGAG CTGA
```

Chimpanzee FGF2 gene coding sequence (aa 134-288) (SEQ ID NO: 175)
(GenBank accession no. NM_001110241, which is hereby incorporated by
reference in its entirety):
```
400                           A TGGCAGCCGG GAGCATCACC
421  ACGCTGCCCG CCTTGCCCGA GGATGGCGGC AGCGGCGCCT TCCCGCCCGG CCACTTCAAG
481  GACCCCAAGC GGCTGTACTG CAAAAACGGG GGCTTCTTCC TGCGCATCCA CCCCGACGGC
541  CGAGTTGACG GGGTCCGGGA AGAGCGAC CCTCACATCA AGCTACAACT TCAAGCAGAA
601  GAGAGGAGGAG TTGTGTCTAT CAAAGGAGTG TGTGCTAACC GTTACCTTGC TATGAAGGAA
661  GATGGAAGAT TACTGGCTTC TAAATGTGTT ACGGATGAGT GTTTCTTTTT TGAACGATTG
721  GAATCTAATA ACTACAATAC TTACCGGTCA AGGAAATACA CCAGTTGTA TGTGGCACTG
781  AAACGAACTG GGCAGTATAA ACTTGGATCC AAAACAGGAC TGGGCAGAA AGCTATACTT
841  TTTCTTCCAA TGTCTGCTAA GAGCTGA
```

Pygmy chimpanzee FGF2 gene coding sequence (112-266) (SEQ ID NO: 176)
(GenBank accession no. XM_003816433, which is hereby incorporated by
reference in its entirety):
```
334                       ATGGCAG CCGGGAGCAT CACCACGCTG
361  CCCGCCTTGC CCGAGGATGG CGGCAGCGGC GCCTTCCCGC CCGGCCACTT CAAGGACCCC
421  AAGCGGCTGT ACTGCAAAAA CGGGGGCTTC TTCCTGCGCA TCCACCCCGA CGGCCGAGTT
481  GACGGGGTCC GGGAGAAGAG CGACCCTCAC ATCAAGCTAC AACTTCAAGC AGAAGAAGAA
541  GGAGTTGTGT CTATCAAAGG AGTGTGTGCT AACCGTTACC TTGCTATGAA GGAAGATGGA
601  AGATTACTGG CTTCTAAATG TGTTACGGAT GAGTGTTTCT TTTTGAACG ATTGGAATCT
661  AATAACTACA ATACTTACCG GTCAAGGAAA TACACCAGTT GGTATGTGGC ACTGAAACGA
721  ACTGGGCAGT ATAAACTTGG ATCCAAAACA GGACCTGGGC AGAAAGCTAT ACTTTTTCTT
781  CCAATGTCTG CTAAGAGCTG A
```

Bolivian squirrel monkey FGF2 gene coding sequence (1-155) (SEQ ID
NO: 177) (GenBank accession no. XM_003936241, which is hereby incorporated
by reference in its entirety):
```
23                        ATGGCAGC CGGGAGCATC ACCACGCTGC CCGCCCTGCC
61   CGAAGACGGC GGCAGCGGCG CCTTCCCGCC CGGCCACTTC AAAGACCCCA AGCGGCTGTA
121  CTGCAAAAAC GGGGGCTTCT TCCTGCGAAT CCACCCCGAC GGCCGAGTGG ACGGGGTCCG
181  GGAGAAGAGC GACCCTCACA TCAAACTACA ACTTCAAGCA GAAGAAGAGA GAGGTTGTAT C
241  TATCAAAGGA GTGTGTGCTA ACCGTTACCT TGCTATGAAG GAAGATGGAA GATTACTGGC
301  TTCTAAATGT GTTACGGACG AGTGTTTCTT TTTTGAACGA TTGGAATCTA ATAACTACAA
361  TACTTACCGA TCAAGGAAAT ACACCAGTTG GTATGTGGCA CTGAAACGAA CTGGGCAGTA
421  TAAACTTGGA TCCAAAACAG GACCTGGGCA GAAAGCTATA CTTTTTCTTC AATGTCTGC
481  TAAGAGCTGA
```

Northern white-cheeked gibbon FGF2 gene coding sequence (aa 1-155) (SEQ
ID NO: 178) (GenBank accession no. XM_003271356, which is hereby
incorporated by reference in its entirety):
```
435                                           ATG GCAGCCGGGA
481  GCATCACCAC GCTGCCCGCC TTGCCGGAGG ATGGCGGCAG CGGCGCCTTC CCGCCCGGCC
541  ACTTCAAGGA CCCCAAGCGG CTGTACTGCA AAAACGGGGG TTTCTTCCTG CGCATCCACC
601  CCGACGGTCG AGTTGACGGG TCCGGGAGA AGAGCGACCC TCACATCAAA CTACAACTTC
661  AAGCAGAAGA GAGAGGAGTT GTGTCTATCA AGGAGTGTG TGCTAACCGT TACCTTGCTA
721  TGAAGGAAGA TGGAAGATTA CTGGCTTCTA AATGTGTTAC GGATGAGTGT TTCTTTTTTG
781  AACGATTGGA ATCTAATAAC TACAATACTT ACCGGTCAAG GAAATACACC AGTTGGTATG
```

TABLE 4-continued

```
841  TGGCACTGAA ACGAACTGGG CAGTATAAAC TTGGATCCAA AACAGGACCT GGGCAGAAAG
901  CTATACTTTT TCTTCCAATG TCTGCTAAGA GCTGA
```

Horse FGF2 gene coding sequence (aa 1-155) (SEQ ID NO: 179) (GenBank accession no. NM_001195221, which is hereby incorporated by reference in its entirety):

```
 54                                                              ATGGCAG
 61  CCGGGAGCAT CACCACGCTG CCCGCCCTGC CCGAGGACGG CGGCAGCGGC GCCTTCCCGC
121  CCGGCCACTT CAAGGACCCC AAGCGGCTCT ACTGCAAAAA CGGGGGCTTC TTCCTGCGCA
181  TCCACCCCGA CGGCCGAGTG GACGGGGTCC GGGAGAAGAG CGACCCTCAC ATCAAACTAC
241  AACTTCAAGC AGAAGAGAGA GGGGTTGTGT CTATCAAAGG AGTGTGTGCG AACCGTTATC
301  TTGCTATGAA GGAAGATGGA AGGTTACTGG CTTCTAAATG TGTTACGGAC GAGTGTTTCT
361  TTTTTGAACG ATTGGAATCT AATAACTACA ATACTTACCG GTCAAGGAAA TACTCCAGTT
421  GGTATGTGGC CCTGAAACGA ACGGGGCAGT ATAAACTTGG ACCCAAAACA GGACCTGGAC
481  AGAAAGCTAT ACTTTTTCTT CCAATGTCTG CTAAGAGCTG A
```

Cattle FGF2 gene coding sequence (aa 1-155) (SEQ ID NO: 180) (GenBank accession no. NM_174056, which is hereby incorporated by reference in its entirety):

```
104                                                     ATGGCCG CCGGGAGCAT
121  CACCACGCTG CCAGCCCTGC CGGAGGACGG CGGCAGCGGC GCTTTCCCGC CGGGCCACTT
181  CAAGGACCCC AAGCGGCTGT ACTGCAAGAA CGGGGGCTTC TTCCTGCGCA TCCACCCCGA
241  CGGCCGAGTG GACGGGGTCC GCGAGAAGAG CGACCCACAC ATCAAACTAC AACTTCAAGC
301  AGAAGAGAGA GGGGTTGTGT CTATCAAAGG AGTGTGTGCA AACCGTTACC TTGCTATGAA
361  AGAAGATGGA AGATTACTAG CTTCTAAATG TGTTACGGAC GAGTGTTTCT TTTTTGAACG
421  ATTGGAGTCT AATAACTACA ATACTTACCG GTCAAGGAAA TACTCCAGTT GGTATGTGGC
481  ACTGAAACGA ACTGGGCAGT ATAAACTTGG ACCCAAAACA GGACCTGGGC AGAAAGCTAT
541  ACTTTTTCTT CCAATGTCTG CTAAGAGCTG A
```

Olive baboon FGF2 gene coding sequence (1-155) (SEQ ID NO: 181) (GenBank accession no. XM_003899161, which is hereby incorporated by reference in its entirety):

```
467                                                        ATGG CAGCCGGGAG
481  CATCACCACG CTGCCCGCCT TGCCCGAGGA TGGCGGCAGC GGCGCCTTCC CGCCCGGCCA
541  CTTCAAGGAC CCCAAGCGGC TGTACTGCAA AAACGGGGGC TTCTTCCTGC GCATTCACCC
601  CGACGGCCGA GTTGACGGGG TCCGGGAGAA GAGCGACCCT CACATCAAAT TACAACTTCA
661  AGCAGAAGAG AGAGGAGTTG TGTCTATCAA AGGAGTGTGT GCTAACCGTT ACCTTGCTAT
721  GAAGGAAGAT GGAAGATTAC TGGCTTCTAA ATGTGTTACG GATGAGTGTT TCTTTTTTGA
781  ACGATTGGAA TCTAATAACT ACAATACTTA CCGGTCAAGG AAATACACCA GTTGGTATGT
841  GGCACTGAAA CGAACTGGGC AGTATAAACT TGGATCCAAA ACAGGACCTG GCAGAAAGC
901  TATACTTTTT CTTCCAATGT CTGCTAAGAG CTGA
```

Alpaca FGF2 gene coding sequence (aa 111-265) (SEQ ID NO: 182) (Ensembl accession no. ENSVPAT00000010536, which is hereby incorporated by reference in its entirety):

```
341                                  ATGGCAGCTG GGAGCATCAC CACGCTGCCC
361  GCCCTGCCGG AGGACGGCGG CAGCGGCGCC TTCCCGCCCG GCCACTTCAA GGACCCCAAG
421  CGGTTGTACT GCAAAAACGG GGGCTTCTTC CTGCGCATCC ACCCCGACGG CCGAGTGGAC
481  GGGGTCCGGG AGAAGAGCGA CCCTCACATC AAACTACAAC TTCAAGCAGA GAGAGAGGG
541  GTCGTGTCTA TCAAAGGAGT GTGTGCAAAC CGTTACCTTG CTATGAAGGA AGATGGAAGA
601  TTACTGGCTT CTAAATGTGT CACAGACGAG TGTTTCTTTT TTGAACGATT GGAATCTAAT
661  AACTACAATA CTTACCGGTC AAGGAAATAC TCCAGTTGGT ATGTGGCACT GAAACGAACT
721  GGGCAGTACA AACTTGGACC CAAAACAGGA CCTGGGCAGA AAGCTATACT TTTCCTTCCA
781  ATGTCTGCTA AGAGCTGA
```

Sheep FGF2 gene coding sequence (aa 1-155) (SEQ ID NO: 183) (GenBank accession no. NM_001009769, which is hereby incorporated by reference in its entirety):

```
  1  ATGGCCGCCG GGAGCATCAC CACGCTGCCA GCCCTGCCGG AGGACGGCGG CAGCAGCGCT
 61  TTCCCGCCCG GCCACTTTAA GGACCCCAAG CGGCTGTACT GCAAGAACGG GGGCTTCTTC
121  CTGCGCATCC ACCCCGACGG CCGAGTGGAC GGGGTCCGGG AGAAGAGCGA CCCTCACATC
181  AAACTACAAC TTCAAGCAGA AGAGAGAGGG GTTGTGTCTA TCAAAGGAGT GTGTGCAAAC
241  CGTTACCTTG CTATGAAAGA AGATGGAAGA TTACTAGCTT CTAAATGTGT TACAGACGAG
301  TGTTTCTTTT TTGAACGATT GGAGTCTAAT AACTACAATA CTTACCGGTC AAGGAAATAC
361  TCCAGTTGGT ATGTGGCACT GAAACGAACT GGGCAGTATA ACTTGGACC CAAAACAGGA
421  CCTGGGCAGA AAGCTATACT TTTTCTTCCA ATGTCTGCTA AGAGCTGA
```

Western roe deer FGF2 gene coding sequence (1-108; partial amino acid sequence corresponding to human FGF2 residues 42 to 149) (SEQ ID NO: 184) (GenBank accession no. AF152587, which is hereby incorporated by reference in its entirety):

```
  1  GCGCATCCAC CCCGACGGCC GAGTGGACGG GGTCCGCGAG AAGAGTGACC CTCACATCAA
 61  ACTACAACTT CAAGCAGAAG AGAGAGGGGT TGTGTCTATC AAAGGAGTGT GTGCGAACCG
121  TTATCTTGCT ATGAAAGAAG ACGGAAGATT ATTGGCTTCA AATGTGTTA CAGACGAATG
181  TTTCTTTTTT GAACGATTGG AGTCTAATAA CTACAATACT TACCGGTCAA GGAAATACTC
241  CAGTTGGTAT GTGGCACTGA ACGAACTGG GCAGTATAAA CTTGGACCCA AAACAGGACC
301  TGGGCAGAAA GCTATACTTT TTCTT
```

TABLE 4-continued

Elephant FGF2 gene coding sequence (1-96; partial amino acid sequence corresponding to human FGF2 residues 60 to 155) (SEQ ID NO: 185) (Ensembl accession no. ENSLAFT00000008249, which is hereby incorporated by reference in its entirety):

```
  1 GTTAAACTAC AGCTTCAAGC AGAAGAGAGA GGTGTTGTGT CTATCAAAGG AGTGTGTGCC
 61 AACCGTTATC TGGCTATGAA GGAAGATGGA AGATTGCTGG CTTCTAGATG TGTGACAGAT
121 GAATGTTTCT TCTTTGAACG ACTGGAATCT AATAACTACA ATACTTACCG GTCAAGGAAA
181 TACACCAGTT GGTATGTGGC ACTGAAACGA ACGGGGCAGT ATAAACTTGG ATCCAAAACA
241 GGACCTGGAC AGAAAGCTAT ACTTTTTCTT CCCATGTCTG CTAAGAGC
```

Pig FGF2 gene coding sequence (1-120; partial amino acid sequence corresponding to human FGF2 residues 36 to 155) (SEQ ID NO: 186) (GenBank accession no. AJ577089 and Ensembl accession no. ENSSSCT00000009952, which is hereby incorporated by reference in its entirety):

```
  1 GAACGGGGGC TTCTTCCTGC GCATCCACCC CGACGGCCGA GTGGATGGGG TCCGGGAGAA
 61 GAGCGACCCT CACATCAAAC TACAACTTCA AGCAGAAGAG AGAGGGGTTG TGTCTATCAA
121 AGGAGTGTGT GCAAACCGTT ATCTTGCTAT GAAGGAAGAT GGAAGATTAC TGGCTTCTAA
181 ATGTGTTACA GACGAGTGTT TCTTTTTTGA ACGACTGGAA TCTAATAACT ACAATACTTA
241 CCGGTCGAGG AAATACTCCA GTTGGTATGT GGCACTGAAA CGAACTGGGC AGTATAAACT
301 TGGACCCAAA ACAGGACCTG GGCAGAAAGC TATACTTTTT CTTCCAATGT CTGCTAAGAG
361 C
```

Panda FGF2 gene coding sequence (1-96; partial amino acid sequence corresponding to human FGF2 residues 60 to 155) (SEQ ID NO: 187) (Ensembl accession no. ENSAMET00000019232, which is hereby incorporated by reference in its entirety):

```
  1 GTCAAACTGC AACTTCAAGC GGAAGAGAGA GGGGGTTGTAT CCATCAAAGG AGTATGTGCA
 61 AATCGCTATC TTGCCATGAA GGAAGATGGA AGATTACTGG CTTCTAAATG TGTTACCGAT
121 GAGTGTTTCT TTTTTGAGCG ACTGGAATCT AATAACTACA ATACTTACCG GTCAAGGAAA
181 TACTCCAGTT GGTATGTGGC ACTGAAACGA ACTGGGCAGT ATAAACTTGG ACCCAAAACA
241 GGACCTGGGC AGAAAGCTAT ACTTTTTCTT CCAATGTCTG CTAAGAGC
```

Sloth FGF2 gene coding sequence (aa 14-168) (SEQ ID NO: 188) (Ensembl accession no. ENSCHOT00000011394, which is hereby incorporated by reference in its entirety):

```
 40                                              A TGGCAGCCGG GAGCATCACC
 61 ACGCTGCCCG CCCTGCCCGA GGACGGAGGC AGCGGCGCCT TACCGCCCGG CCACTTCAAA
121 GATCCCAAGC GGCTCTACTG CAAAAACGGG GGCTTCTTCC TGCGTATCCA TCCCGACGGC
181 AGAGTGGACG GGGTCCGGGA AGAGCGAC CCCCACATCA AACTACAACT TCAAGCAGAA
241 GAGAGAGGGG TTGTGTCTAT CAAAGGTGTG TGTGCAAACC GATATCTTGC TATGAAGGAA
301 GATGGAAGAT TACAGGCTTC TAAATGTGTA ACGGACGAGT GTTTCTTTTT TGAACGATTG
361 GAATCTAATA ACTACAATAC GTACCGATCA AGGAAATACT CCAGTTGGTA TGTGGCACTG
421 AAACGAACTG GGCAATATAA ACTTGGACCC AAAACAGGAC CTGGGCAGAA AGCCATACTT
481 TTTCTTCCAA TGTCTGCTAA GAGCTGA
```

Water buffalo FGF2 gene coding sequence (aa 1-155) (SEQ ID NO: 189) (GenBank accession no. JQ326277, which is hereby incorporated by reference in its entirety):

```
  1 ATGGCCGCCG GGAGCATCAC CACGCTGCCA CCCCTGCCGG AGGACGGCGG CAGCGGCGCT
 61 TTCCCGCCCG GCCACTTCAA GGACCCCAAG CGGCTGTACT GCAAGAACGG GGGCTTCTTC
121 CTGCGCATCC ACCCCGACGG CCGAGTGGAC GGGGTCCGCG AAGAGCGCA CCCACACATC
181 AAACTACAAC TTCAAGCAGA AGAGAGAGGG GTTGTGTCTA TCAAAGGAGT GTGTGCAAAC
241 CGTTACCTTG CTATGAAAGA AGATGGAAGA TTACTAGCTT CCAAATGTGT TACAGACGAG
301 TGTTTCTTTT TTGAACGATT GGAGTCTAGT AACTACAATA CTTACCGGTC AAGGAAATAC
361 TCCAGTTGGT ATGTGGCACT GAAACGAACT GGGCAGTATA AACTTGGACC CAAAACAGGA
421 CCTGGGCAGA AAGCTATACT TTTTCTTCCA ATGTCTGCTA AGAGCTGA
```

Dog FGF2 gene coding sequence (aa 40-194) (SEQ ID NO: 190) (GenBank accession no. XM_003432481, which is hereby incorporated by reference in its entirety):

```
118                                                                ATG
121 GCAGCCGGGA GCATCACCAC GCTGCCCGCC CTGCCGGAGG ACGGCGGCAG CGGCGCCTTC
181 CCGCCCGGCC ACTTCAAGGA CCCCAAGAGG CTGTACTGCA AAAAGGGGG CTTCTTCCTG
241 CGGATCCACC CCGACGGCCG GGTGGACGGG GTCCGGGAGA AGAGCGATCC CCACGTCAAA
301 TTGCAACTTC AAGCAGAAGA GAGAGGCGTT GTGTCCATCA AGGAGTATG TGCAAATCGC
361 TATCTTGCTA TGAAGGAAGA TGGAAGATTA CTGGCTTCTA AATGTGTTAC TGACGAGTGC
421 TTCTTTTTTG AACGATTGGA ATCTAATAAC TACAATACT ACCGGTCAA GAAATACTCC
481 AGTTGGTATG TGGCACTGAA ACGAACTGGG CAGTATAAAC TTGGACCAAA AACAGGACCT
541 GGGCAGAAAG CTATACTTTT TCTTCCAATG TCTGCTAAGA GCTGA
```

Norway rat FGF2 gene coding sequence (aa 1-154) (SEQ ID NO: 191) (GenBank accession no. NM_019305, which is hereby incorporated by reference in its entirety):

```
533                                                            ATGGCTGC
541 CGGCAGCATC ACTTCGCTTC CCGCACTGCC GGAGGACGGC GGCGGCGCCT TCCCACCCGG
601 CCACTTCAAG GATCCCAAGC GGCTCTACTG CAAGAACGGC GGCTTCTTCC TGCGCATCCA
661 TCCAGACGGC CGCGTGGACG GCGTCCGGGA GAAGAGCGAC CCACACGTCA AACTACAGCT
721 CCAAGCAGAA GAGAGAGGAG TTGTGTCCAT CAAGGGAGTG TGTGCGAACC GGTACCTGGC
781 TATGAAGGAA GATGGACGGC TGCTGGCTTC TAAGTGTGTT ACAGAAGAGT GTTTCTTCTT
841 TGAACGCCTG GAGTCCAATA ACTACAACAC TTACCGGTCA CGGAAATACT CCAGTTGGTA
```

TABLE 4-continued

```
    901 TGTGGCACTG AAACGAACTG GGCAGTATAA ACTCGGATCC AAAACGGGGC CTGGACAGAA
    961 GGCCATACTG TTTCTTCCAA TGTCTGCTAA GAGCTGA
```

Naked mole-rat FGF2 gene coding sequence (1-134; partial amino acid
sequence corresponding to human FGF2 residues 22 to 155) (SEQ ID NO: 192)
(GenBank accession no. JH173674, which is hereby incorporated by
reference in its entirety):
```
 378500          C CACCCGGCCA CTTCAAGGAC CCAAAGCGGC
 378531 TGTACTGCAA AAACGGGGGC TTCTTCCTGC GCATCCACCC CGACGGCCGC
 378581 GTGGACGGGG TCCGGGAGAA GAGCGACCCT CACG
 418784    TCAAACT ACAACTTCAA GCAGAAGAGA GAGGAGTTGT GTCTATTAAG
 418831 GGAGTGTGTG CGAACCGTTA CCTTGCTATG AAGGAAGATG GAAGATTACT
 418881 GGCTTCT
 433983    AAATGTGT TACAGATGAG TGTTTCTTTT TTGAACGATT GGAATCTAAT
 434031 AACTACAATA CTTATCGGTC AAGGAAATAC TCCAGTTGGT ATGTGGCACT
 434081 GAAACGAACT GGACAATATA AACTTGGATC CAAAACAGGA CCGGGGCAGA
 434131 AAGCTATACT TTTTCTTCCA ATGTCTGCTA AGAGCTGA
```

Bushbaby FGF2 gene coding sequence (aa 52-206) (SEQ ID NO: 193) (Ensembl
accession no. ENSOGAT00000025228, which is hereby incorporated by
reference in its entirety):
```
    154                    ATGGCAG CCGGGAGCAT CACCACGCTG
    181 CCCTCCCTGC CCGAGGACGG CGGCAGCGAC GCCTTTCCGC CCGGCCACTT CAAGGACCCC
    241 AAGCGACTGT ACTGCAAAAA CGGGGGCTTC TTCCTGCGCA TCCACCCCGA CGGCCGAGTG
    301 GACGGGGTCC GGGAGAAGAG CGACCCTTAC ATCAAACTAC AACTTCAAGC AGAAGAGAGA
    361 GGAGTTGTGT CTATCAAAGG AGTGTGTGCG AACCGTTACC TTGCTATGAA GGAAGACGGA
    421 AGATTGCTGG CTTCTAAATT GATTACAGAC GAGTGCTTCT TTTTTGAACA CTGGAATCT
    481 AATAACTACA ATACTTACCG GTCAAGAAAA TACTCCAGTT GGTATGTGGC ACTGAAACGA
    541 ACTGGACAGT ATAAACTTGG ATCCAAAACA GGACCTGGGC AGAAAGCTAT ACTTTTTCTT
    601 CCAATGTCTG CTAAGAGCTG A
```

House mouse FGF2 gene coding sequence (aa 1-154) (SEQ ID NO: 194) (GenBank
accession no. NM_008006, which is hereby incorporated by reference in its
entirety):
```
    198               ATG GCTGCCAGCG GCATCACCTC GCTTCCCGCA CTGCCGGAGG
    241 ACGGCGGCGC CGCCTTCCCA CCAGGCCACT TCAAGGACCC CAAGCGGCTC TACTGCAAGA
    301 ACGGCGGCTT CTTCCTGCGC ATCCATCCCG ACGGCCGCGT GGATGCGTC CGCGAGAAGA
    361 GCGACCCACA CGTCAAACTA CAACTCCAAG CAGAAGAGAG AGGAGTTGTG TCTATCAAGG
    421 GAGTGTGTGC CAACCGGTAC CTTGCTATGA AGGAAGATGG ACGGCTGCTG GCTTCTAAGT
    481 GTGTTACAGA AGAGTGTTTC TTCTTTGAAC GACTGGAATC TAATAACTAC AATACTTACC
    541 GGTCACGGAA ATACTCCAGT TGGTATGTGG CACTGAAACG AACTGGGCAG TATAAACTCG
    601 GATCCAAAAC GGGACCTGGA CAGAAGGCCA TACTGTTTCT TCCAATGTCT GCTAAGAGCT
    661 GA
```

Squirrel FGF2 gene coding sequence (1-144; partial amino acid sequence
corresponding to human FGF2 residues 12 to 155) (SEQ ID NO: 195) (Ensembl
accession no. ENSSTOT00000022105, which is hereby incorporated by
reference in its entirety):
```
      1 CTGCCCGAGG ACGGCGGCGG CGGCGCCTTC CCGCCCGGCC ACTTTAAGGA CCCCAAGCGG
     61 CTCTACTGCA AAAACGGAGG CTTCTTCCTG CGCATCCACC CCGACGGCCG AGTGGACGGG
    121 GTCCGGGAGA AGAGCGACCC CCACATCAAG CTCCAGCTTC AAGCCGAAGA CCGAGGGGTT
    181 GTGTCCATCA AGGGAGTGTG TGCAAACCGA TACCTGGCCA TGAAGGAGGA CGGGAGGCTC
    241 CTGGCTTCTA AATGTGTTAC GGACGAGTGT TTCTTTTTTG AACGACTGGA ATCAAATAAC
    301 TACAATACTT ACCGGTCAAG GAAATACTCC AGTTGGTATG TGGCCCTGAA CGAACAGGG
    361 CAGTATAAAC TTGGATCCAA ACAGGACCT GGGCAGAAAG CTATACTTTT TCTTCCAATG
    421 TCTGCTAAGA GC
```

Domestic cat FGF2 gene coding sequence (1-106; partial amino acid
sequence corresponding to human FGF2 residues 25 to 130) (SEQ ID NO: 196)
(GenBank accession no. EU314952, which is hereby incorporated by
reference in its entirety):
```
      1 CCACTTCAAG GACCCCAAGC GTCTGTACTG CAAAAACGGG GCTTCTTCC TGCGCATCCA
     61 CCCCGACGGC CGAGTGGATG GGGTCCGGGA GAAGAGCGAC CCTCACATCA AACTGCAACT
    121 TCAGGCAGAA GAGAGAGGGG TTGTGTCCAT CAAAGGAGTC TGTGCAAACC GCTATCTTGC
    181 CATGAAGGAA GATGGAAGAT TACTGGCTTC TAAATGTGTT ACGGACGAGT GTTTCTTTTT
    241 TGAACGATTG GAATCTAATA ACTACAATAC TTATCGGTCA AGGAAATACT CCAGCTGGTA
    301 TGTGGCACTG AAACGAAC
```

Guinea pig FGF2 gene coding sequence (1-96; partial amino acid sequence
corresponding to human FGF2 residues 60 to 155) (SEQ ID NO: 197) (Ensembl
accession no. ENSCPOT00000005443, which is hereby incorporated by
reference in its entirety):
```
      1 GTTAAACTAC AACTTCAAGC CGAAGACAGA GGAGTTGTGT CTATCAAGGG AGTCTGTGCG
     61 AACCGTTACC TTGCTATGAA GGAAGACGGA AGATTATTGG CTTCAAATG TGTTACAGAT
    121 GAATGTTTCT TTTTTGAACG ACTGGAATCT AATAACTACA ACACTTACCG GTCAAGGAAA
    181 TACTCCAGTT GGTATGTGGC ACTGAAACGA ACTGGACAAT ATAAACTTGG GTCCAAAACA
    241 GGACCAGGGC AGAAAGCCAT ACTTTTTCTT CCAATGTCTG CGAAGAGC
```

TABLE 4-continued

Tasmanian devil FGF2 gene coding sequence (aa 48-203) (SEQ ID NO: 198)
(Ensembl accession no. ENSSHAP00000012215, which is hereby incorporated
by reference in its entirety):
```
142                   ATGGCCGCG GGCAGCATCA CCACGTTGCC GGCCCTGGCC
181    GGGGATGGAG CCAGCGGGGG CGCCTTTCCC CCGGGCCACT TCCAGGACCC CAAGCGGCTG
241    TACTGCAAGA ACGGAGGCTT CTTCTTGCGC ATCCATCCCG ACGGTCACGT GGACGGCATC
301    CGCGAGAAGA GCGATCCGCA CATTAAACTT CAGCTTCAGG CAGAAGAGAG AGGAGTAGTG
361    TCTATTAAAG GAGTTTGTGC CAACCGCTAT CTTGCCATGA AAGGATGG CAGATTACTG
421    GCTCTGAAAT GTGTGACTGA AGAGTGTTTC TTCTTTGAAC GTCTAGAGTC CAACAATTAC
481    AACACTTATC GCTCAAGGAA ATACTCCAAT TGGTATGTGG CATTGAAACG CACAGGCCAG
541    TATAAGCTTG GATCCAAGAC TGGACCAGGG CAGAAAGCCA TCCTTTTCCT TCCCATGTCT
601    GCTAAGAGCT GA
```

Gray short-tailed opossum FGF2 gene coding sequence (aa 1-155) (SEQ ID
NO: 199) (GenBank accession no. NM_001033976, which is hereby incorporated
by reference in its entirety):
```
 29                          AT GGCCGCAGGC AGCATCACCA CGCTGCCAGC
 61    CCTGTCCGGG GACGGAGGCG GCGGGGGCGC CTTTCCCCCG GCCCACTTCA AGGACCCCAA
121    GCGGCTGTAC TGCAAGAACG GAGGCTTCTT CCTGCGCATC CACCCCGACG GCCGTGTGGA
181    CGGCATCCGC GAGAAGAGCG ACCCGAACAT TAAACTACAA CTTCAGGCAG AAGAGAGAGG
241    AGTGGTGTCT ATTAAAGGAG TATGTGCCAA TCGCTATCTT GCCATGAAGG AAGATGGAAG
301    ATTATTGGCT TTGAAATATG TGACCGAAGA GTGTTTCTTT TTCGAACGCT TGGAGTCCAA
361    CAACTACAAC ACTTATCGCT CGAGGAAATA TTCCAATTGG TACGTGGCAC TGAAACGAAC
421    GGGGCAGTAC AAGCTTGGAT CCAAGACTGG CCCGGGGCAG AAAGCCATCC TTTTCCTCCC
481    CATGTCTGCT AAGAGCTGA
```

Rabbit FGF2 gene coding sequence (aa 1-155) (SEQ ID NO: 200) (GenBank
accession no. XM_002717238, which is hereby incorporated by reference in
its entirety):
```
  1    ATGGCAGCCG AGAGCATCAC CACGCTGCCC GCCCTGCCGG AGGATGGAGG CAGCGGCGCC
 61    TTCCCGCCCG GCCACTTCAA GGACCCCAAG CGGCTGTACT GCAAAAACGG GGGTTTCTTC
121    CTGCGTATCC ACCCCGACGG CCGCGTGGAC GGGGTCCGGG AGAAGAGCGA CCCACACATC
181    AAATTACAAC TTCAAGCAGA AGAGAGAGGA GTTGTATCCA TCAAAGGTGT GTGTGCAAAC
241    CGTTACCTTG CTATGAAGGA AGATGGAAGA CTGCTGGCTT CTAAATGTGT TACAGACGAG
301    TGCTTCTTTT TTGAACGACT GGAGTCTAAT AACTACAATA CTTACCGGTC AAGGAAATAT
361    TCCAGCTGGT ATGTGGCACT GAAACGAACT GGGCAGTATA ACTTGGATC CAAAACAGGA
421    CCTGGGCAGA AGGCTATACT TTTTCTTCCA ATGTCTGCTA AGAGCTGA
```

Turkey FGF2 gene coding sequence (1-125; partial amino acid sequence
corresponding to human FGF2 residues 31 to 155) (SEQ ID NO: 201) (Ensembl
accession no. ENSMGAT00000011845, which is hereby incorporated by
reference in its entirety):
```
  1    CGGCTCTACT GTAAGAACGG CGGCTTCTTC CTGCGCATCA ATCCCGACGG CAGAGTGGAC
 61    GGCGTCCGCG AGAAGAGCGA TCCGCACATC AAACTGCAGC TTCAGGCAGA AGAAAGAGGA
121    GTGGTATCAA TCAAAGGTGT AAGTGCAAAC CGCTTTCTGG CTATGAAGGA GGATGGCAGA
181    TTGCTGGCAC TGAAATGTGC AACAGAAGAA TGTTTCTTTT TTGAGCGTTT GGAATCTAAT
241    AATTATAACA CTTACCGGTC ACGGAAGTAC TCTGATTGGT ATGTGGCACT GAAAAGAACT
301    GGACAGTACA AGCCCGGACC AAAAACTGGA CCTGGACAGA AAGCTATCCT TTTTCTTCCA
361    ATGTCTGCTA AAAGC
```

*Gallus gallus* FGF2 gene coding sequence (aa 1-158) (SEQ ID NO: 202)
(GenBank accession no. NM_205433, which is hereby incorporated by
reference in its entirety):
```
 98                          ATG GCGGCGGGGG CGGCGGGGAG
121    CATCACCACG CTGCCGGCGC TGCCCGACGA CGGGGGCGGC GGCGCTTTTC CCCCCGGGCA
181    CTTCAAGGAC CCCAAGCGGC TCTACTGCAA GAACGGCGGC TTCTTCCTGC GCATCAACCC
241    CGACGGCAGG GTGGACGGCG TCCGCGAGAA GAGCGATCCG CACATCAAAC TGCAGCTTCA
301    AGCAGAAGAA AGAGGAGTAG TATCAATCAA AGGCGTAAGT GCAAACCGTT TTCTGGCTAT
361    GAAGGAGGAT GGCAGATTGC TGGCACTGAA ATGTGCAACA GAGGAATGTT TCTTTTTCGA
421    GCGCTTGGAA TCTAATAACT ATAACACTTA CCGGTCACGG AAGTACTCTG ATTGGTATGT
481    GGCACTGAAA AGGACTGGAC AGTACAAGCC CGGACCAAAA ACTGGACCTG GACAGAAAGC
541    TATCCTTTTT CTTCCAATGT CTGCTAAAAG CTGA
```

Zebra finch FGF2 gene coding sequence (aa 1-153) (SEQ ID NO: 203) (GenBank
accession no. XM_002188361, which is hereby incorporated by reference in
its entirety):
```
  1    ATGGCGGCGG CGGGGGGCAT CGCTACGCTG CCCGACGACG GCGGCAGCGG CGCCTTTCCC
 61    CCGGGGCACT TCAAGGACCC CAAGCGCCTG TACTGCAAGA ACGGCGGCTT CTTCCTGCGC
121    ATCAACCCCG ACGGGAAGGT GGACGGCGTC CGCGAGAAGA GCGACCCGCA CATCAAGCTG
181    CAGCTTCAGG CGGAGGAACG AGGAGTGGTG TCCATCAAAG GTGTCAGTGC AATCGCTTC
241    CTGGCCATGA AAGAGGATGG CAGATTGCTG GCCTTGAAAT ATGCAACAGA AGAATGTTTC
301    TTTTTTGAAC GTTTGGAATC CAATAACTAT AACACTTACC GGTCACGGAA ATACTCGGAT
361    TGGTATGTGG CACTGAAAAG AACTGGACAG TACAAACCTG ACCAAAAAC TGGACCTGGA
421    CAGAAAGCTA TCCTTTTCCT TCCTATGTCT GCTAAAAGCT GA
```

Japanese firebelly newt FGF2 gene coding sequence (aa 1-155) (SEQ ID
NO: 204) (GenBank accession no. AB064664, which is hereby incorporated by
reference in its entirety):
```
384                        ATGGCTG CTGGGAGCAT CACCAGTCTC CCTGCCCTAC
421    CCGAGGACGG GAATGGCGGC ACCTTCACAC CCGGCGGATT CAAAGAGCCG AAGAGGCTGT
```

TABLE 4-continued

```
481  ACTGCAAGAA CGGGGGCTTC TTTCTCCGGA TCAACTCCGA CGGCAAGGTG GACGGAGCCC
541  GGGAGAAGAG CGACTCCTAC ATTAAACTGC AGCTTCAAGC AGAAGAGCGC GGTGTGGTGT
601  CCATCAAGGG AGTATGTGCA AACCGCTATC TCGCTATGAA GGATGATGGC AGGCTGATGG
661  CGCTGAAATG GATAACCGAT GAATGCTTCT TTTTCGAGTG ACTGAGTCC AACAACTATA
721  ACACGTATCG ATCACGGAAA TATTCCGATT GGTATGTGGC GCTGAAAAGA ACTGGGCAAT
781  ACAAAAATGG ATCAAAAACC GGAGCAGGAC AGAAAGCAAT CCTTTTTCTA CCCATGTCGG
841  CCAAGAGTTG A
```

African clawed frog FGF2 gene coding sequence (aa 1-155) (SEQ ID NO: 205)
(GenBank accession no. NM_001099871, which is hereby incorporated by
reference in its entirety):

```
335                               ATGGCG GCAGGGAGCA TCACAACTCT
361  GCCAACTGAA TCCGAGGATG GGGGAAACAC TCCTTTTTCA CCAGGGAGTT TTAAAGACCC
421  CAAGAGGCTC TACTGCAAGA ACGGGGGCTT CTTCCTCAGG ATAAACTCAG ACGGGAGAGT
481  GGACGGGTCA AGGGACAAAA GTGACTCGCA CATAAAATTA CAGCTACAAG CTGTAGAGCG
541  GGGAGTGGTA TCAATAAAGG GAATCACTGC AAATCGCTAC CTTGCCATGA AGGAAGATGG
601  GAGATTAACA TCGCTGAGGT GTATAACAGA TGAATGCTTC TTTTTTGAAC GACTGGAAGC
661  TAATAACTAC AACACTTACC GGTCTCGGAA ATACAGCAGC TGGTATGTGG CACTCAAAGCG
721  AACCGGGCAG TACAAAAATG GATCGAGCAC TGGACCGGGA CAAAAAGCTA TTTTATTTCT
781  CCCAATGTCC GCAAAGAGCT GA
```

White-eared opossum FGF2 gene coding sequence (aa 1-156) (SEQ ID NO: 206)
(GenBank accession no. EF057322, which is hereby incorporated by
reference in its entirety):

```
  1  ATGGCAGCAG GCAGCATCAC CACATTGCCG GCCCTGTCCG GGGACGGAGG CGGCGGGGGA
 61  GCCTTTCCTC CAGGCCACTT CAAGGACCCC AAGCGGCTGT ACTGCAAGAA CGGAGGCTTC
121  TTCCTGCGCA TCCACCCCGA CGGCCGCGTG GACGGCATCC GCGAGAAGAG CGACCCGAAC
181  ATTAAACTAC AACTTCAGGC AGAAGAGAGA GGAGTAGTGT CTATTAAAGG AGTATGTGCC
241  AACCGATATC TTGCCATGAA GGAGGATGGC AGATTATTGG CTTTGAAATA TGTGACCGAA
301  GAGTGTTTCT TTTTTGAACG TTTGGAGTCC AACAACTACA ACACTTATCG CTCAAGAAAA
361  TATTCCAATT GGTATGTGGC ACTGAAACGA ACGGGGCAGT ATAAGCTTGG ATCCAAGACT
421  GGCCCGGGGC AGAAAGCCAT CCTTTTCTCC CCATGTCGC TAAGATGCTG A
```

Microbat FGF2 gene coding sequence (1-96; partial amino acid sequence
corresponding to human FGF2 residues 60 to 155) (SEQ ID NO: 207) (Ensembl
accession no. ENSMLUT00000027717, which is hereby incorporated by
reference in its entirety):

```
  1  GTCAAACTCC AACTTCAAGC AGAAGAGAGA GGGGTCGTGT CTATCAAAGG AGTGTGTGCC
 61  AACCGCTATC TCGCTATGAA GGAGGACGGC CGGTTACAGG CTTCTAAATG TGTTACGGAT
121  GAGTGTTTCT TTTTTGAACG GTTGGAATCC AATAACTACA ACACTTACCG GTCAAGAAAG
181  TACTCCAGTT GGTATGTGGC ATTGAAGCGA ATGGGCAGT ATAAACTTGG ACCCAAAACA
241  GGACCTGGCC AGAAAGCCAT ACTTTTTCTT CCCATGTCTG CTAAGAGC
```

Anole lizard FGF2 gene coding sequence (1-140; partial amino acid
sequence corresponding to human FGF2 residues 16 to 155) (SEQ ID NO: 208)
(Ensembl accession no. ENSACAT00000011897, which is hereby incorporated
by reference in its entirety):

```
  1  GCGGCGGCGG CCTCTTTCCC CCCGGGCCCC TTCAAGGACC CCAAGCGCCT CTACTGCAAG
 61  AACGGGGGCT TCTTCCTGCG GATCAACCCC GACGGCGGCG TGGACGGCGT CCGAGAGAAG
121  AGCGACCCCA ACATCAAATT GCTGCTCCAG GCAGAGGAGA GAGGTGTAGT GTCCATCAAA
181  GGTGTATGCG CAAACCGTTT CCTGGCTATG AATGAAGACG GTCGATTGTT AGCACTGAAA
241  TACGTAACAG ATGAATGCTT CTTTTTTGAA CGCTTGGAAT CTAATAATTA CAATACTTAT
301  CGGTCTCGTA AATACCGTGA TTGGTACATT GCACTGAAAC GAACTGGTCA GTACAAACTT
361  GGACCAAAAA CTGGACGAGG CCAGAAAGCT ATCCTTTTCC TTCCAATGTC TGCCAAAAGT
```

Armadillo FGF2 gene coding sequence (124-217; partial amino acid sequence
corresponding to human FGF2 residues 1 to 94) (SEQ ID NO: 209) (Ensembl
accession no. ENSDNOT00000014647, which is hereby incorporated by
reference in its entirety):

```
361           A TGGCAGCCGG GAGCATCACC ACGCTGCCCG CTCTGCCCGA GGACGGCGGC
421  AGCGGCGCCT TCCCGCCGGG CCACTTCAAG GACCCCAAGC GGCTGTACTG CAAAAACGGG
481  GGCTTCTTCC TGCGCATCCA TCCCGACGGC CGAGTGGACG GCGTCCGGGA GAAGAGCGAC
541  CCTAACATCA AACTACAACT TCAAGCAGAA GAGAGAGGGG TCGTGTCTAT CAAAGGCGTG
601  TGTGCGAACC GTTACCTTGC TATGCGGGAA GACGGAAGAC TCCAGGCGTC T
```

Tree shrew FGF2 gene coding sequence (1-189) (SEQ ID NO: 210) (Ensembl
accession no. ENSTBET00000001143, which is hereby incorporated by
reference in its entirety):

```
  1  GCGGGGGTTA GAGCTGAGAG GGAGGAGGCA CCGGGGAGCG GTGACAGCCG GGGGACCGAT
 61  CCCGCCGCGC GTTCGCTCAT CAGGAGGCCG GATGCTGCAG CGCGAGAGGC GCTTCTTGGA
121  GCCAGGAGCC GGGTTCAGGG CAGCTCCACC TCCTGGCCAG CCTCGTCACG AACCGGGATC
181  AAGTTGCCGG ACGACTCAGG TCAAGGAATG GGCGGCTATC TCTGGACCG CCCGAGCCGG
241  AGCACAGGGC GAGGGCTGGG CGGTGCCCCG GACCCTGCCG TAAAACTACA GCTTCAAGCG
301  GAAGAGAGAG GGGTCGTGTC TATCAAAGGA GTGTGTGCAA ACCGTTACCT GGCCATGAAG
361  GAGGATGGGC GACTGCTGGC TTCTAAATGT GTTACAGATG AGTGTTTCTT TTTTGAACGA
421  CTGGAATCTA ATAACTACAA TACTTACCGG TCCCGAAAGT ACTCCAGCTG GTATGTGGCA
481  CTGAAACGAA CTGGGCAGTA TAAACTTGGA TCCAAAACAG GACCTGGGCA GAAAGCTATA
541  CTTTTTCTTC CAATGTCTGC TAAAAGC
```

TABLE 4-continued

Western clawed frog FGF2 gene coding sequence (aa 1-154) (SEQ ID NO: 211)
(GenBank accession no. NM_001017333, which is hereby incorporated by
reference in its entirety):
```
171                                              ATGGCAGCAG
181   GAAGCATCAC AACCCTACCA ACCGAATCTG AGGATGGAAA CACTCCTTTC CCACCGGGGA
241   ACTTTAAGGA CCCCAAGAGG CTCTACTGCA AGAATGGGGG CTACTTCCTC AGGATTAACT
301   CAGACGGGAG AGTGGACGGA TCAAGGGATA AAAGTGACTT ACACATAAAA TTACAGCTAC
361   AAGCAGTAGA GCGGGGAGTG GTATCAATAA AGGGAATCAC TGCAAATCGC TACCTTGCCA
421   TGAAGGAAGA TGGGAGATTA ACATCGCTGA AGTGTATAAC AGATGAATGC TTCTTTTATG
481   AACGATTGGA AGCTAATAAC TACAACACTT ACCGGTCTCG GAAAAACAAC AGCTGGTATG
541   TGGCACTAAA GCGAACTGGG CAGTATAAAA ATGGATCGAC CACTGGACCA GGACAAAAAG
601   CTATTTTGTT TCTCCCAATG TCAGCAAAAA GCTGA
```

Coelacanth FGF2 gene coding sequence (aa 1-155) (SEQ ID NO: 212) (Ensembl
accession no. ENSLACT00000019333, which is hereby incorporated by
reference in its entirety):
```
  1                      ATGGCTGCGG GAGGAATCAC TACCCTGCCG GCGGTACCTG
 41   AGGATGGAGG CAGCAGCACC TTCCCTCCAG GAAACTTCAA GGAGCCCAAG AGACTTTACT
101   GTAAGAATGG AGGCTATTTC TTAAGGATAA ACCCCGATGG AAGAGTGGAT GGAACAAGGG
161   AGAAAAATGA TCCTTATATA AAATTACAAC TGCAAGCTGA ATCTATAGGA GTGGTGTCGA
221   TAAAGGGAGT TTGTTCAAAC CGTTACCTAG CGATGAATGA AGACTGTAGA CTTTTTGGAT
281   TGAAATATCC AACGGATGAA TGTTTCTTCC ATGAGAGGCT GGAGTCCAAC AACTACAATA
341   CTTATCGTTC AAAGAAGTAT TCGGATTGGT ATGTGGCGCT GAAACGGACT GGTCAGTACA
401   AACCTGGGCC AAAAACTGGA CTGGGACAAA AAGCAATCCT TTTCCTTCCG ATGTCTGCCA
461   AGAGTTGA
```

Spotted green pufferfish FGF2 gene coding sequence (aa 34-188) (SEQ ID
NO: 213) (Ensembl accession no. ENSTNIT00000016254, which is hereby
incorporated by reference in its entirety):
```
  1   ATGGCCACGG GAGGGATCAC GACGCTTCCA TCCACACCTG AAGACGGCGG CAGCAGCGGC
 61   TTTCCTCCCG GCAGCTTCAA GGATCCCAAA AGGCTCTACT GTAAAAACGG AGGTTTCTTC
121   CTGAGGATCA AGTCCGACGG GGTCGTGGAC GGAATCCTGG AGAAGAGTGA CCCCCACATA
181   AAGCTTCAGC TCCAGGCGAC CTCTGTGGGG GAGGTGGTCA TCAAGGGGGT GTGCGCTAAC
241   CGCTATCTGG CCATGAACAG AGATGGACGG CTGTTCGGAA CGAAACGAGC CACGGACGAA
301   TGCCATTTCT TAGAGCGGCT TGAGAGCAAC AACTACAACA CTTACCGCTC CAGGAAGTAC
361   CCAACCATGT TTGTGGGACT GACGCGGACG GGCCAGTACA AGTCTGGGAG CAAAACTGGA
421   CCGGGCCAAA AGGCCATCCT TTTTCTTCCG ATGTCCGCCA AATGCTAA
```

Stickleback FGF2 gene coding sequence (aa 1-155) (SEQ ID NO: 214) (Ensembl
accession no. ENSGACT00000022120, which is hereby incorporated by
reference in its entirety):
```
  1                   AT GGCCACGGCA GGCTTCGCGA CGCTTCCCTC CACGCCCGAA
 43   GACGGCGGCA GCGGCGGCTT CACCCCCGGG GGATTCAAGG ATCCCAAGAG GCTGTACTGC
103   AAAAACGGGG GCTTCTTCTT GAGGATCAGG TCCGACGGAG GTGTAGATGG AATCAGGGAG
163   AAGAGCGACG CCCACATAAA GCTCCAAATC CAGGCGACGT CGGTGGGGGA GGTGGTCATC
223   AAAGGAGTCT GTGCCAACCG CTATCTGGCC ATGAACAGAG ACGGCCGGCT GTTCGGAGTG
283   AGACGGGCGA CGGACGAATG CTACTTCCTG GAGCGGCTGG AGAGTAACAA CTACAACACC
343   TACCGCTCCA GGAAGTACCC CGGCATGTAC GTGGCTCTGA AGCGGACCGG CCAGTACAAG
403   TCCGGGAGCA AAACCGGACC CGGTCAAAAG GCCATTCTGT TCCTCCCCAT GTCGGCTAAG
463   TGCTAA
```

Fugu rubripes FGF2 gene coding sequence (aa 1-155) (SEQ ID NO: 215)
(Ensembl accession no. ENSTRUT00000022363, which is hereby incorporated
by reference in its entirety):
```
127          ATGG CCACGGGAGG GATCACAACA CTTCCATCCA CACCTGAAGA CGGCGGCAGC
181   GGCGGTTTTC CTCCCGGGAG CTTCAAGGAT CCCAAAAGGC TGTACTGTAA AAACGGCGGC
241   TTCTTCCTGA GGATCAGGTC CGACGGGGCC GTGGACGGAA CCCGGGAGAA GACTGACCCC
301   CACATAAAGC TTCAGCTCCA GGCGACCTCT GTGGGGGAGG TGGTCATCAA GGGGGTTTGT
361   GCTAATCGTT ATCTGGCCAT GAACAGAGAT GGACGACTGT TTGGAATGAA ACGAGCGACG
421   GATGAATGCC ACTTCTTAGA GCGGCTCGAG AGCAACAACT ACAACACCTA CCGCTCCAGG
481   AAGTACCCCA ACATGTTTGT GGGACTGACG CGAACTGGCA ACTACAAGTC TGGGACTAAA
541   ACTGGACCGG GCCAAAAGGC CATCCTCTTT CTTCCGATGT CGGCCAAATA CTAA
```

Rainbow trout FGF2 gene coding sequence (aa 1-155) (SEQ ID NO: 216)
(GenBank accession no. NM_001124536, which is hereby incorporated by
reference in its entirety):
```
390                                                A TGGCCACAGG AGAAATCACC ACTCTACCCG
421   CCACACCTGA AGATGGAGGC AGTGGCGGCT TCCTTCCAGG AAACTTTAAG GAGCCCAAGA
481   GGTTGTACTG TAAAAATGGA GGCTACTTCT TGAGGATAAA CTCTAACGGA AGCGTGGACG
541   GGATCAGAGA TAAGAACGAC CCCCACAATA AGCTTCAACT CCAGGCGACC TCAGTGGGGG
601   AAGTAGTAAT CAAGGGGGTC TCAGCCAACC GCTATCTGGC CATGAATGCA GATGGAAGAC
661   TGTTTGGACC GAGACGGACA ACAGATGAAT GCTACTTCAT GGAGAGGCTG GAGAGTAACA
721   ACTACAACAC CTACCGCTCT CGAAAGTACC CTGAAATGTA TGTGGCACTG AAAAGGACTG
781   GCCAGTACAA GTCAGGATCC AAAACTGGAC CCGGCCAAAA AGCCATCCTC TTCCTCCCCA
841   TGTCAGCCAG ACGCTGA
```

TABLE 4-continued

Salmon FGF2 gene coding sequence (1-150) (SEQ ID NO: 217) (GenBank
accession no. EU816603, which is hereby incorporated by reference in its
entirety):
```
    99402                                              ATGGCCACA GGAGAAATCA
    99421 CCACTCTACC CGCCACACCT GAAGATGGAG GCAGTGGCGG CTTCCCTCCA GGAAACTTTA
    99481 AGGATCCCAA GAGGCTGTAC TGTAAAAACG GGGGCTACTT CTTGAGAATA AACTCTAATG
    99541 GAAGCGTGGA CGGGATCCGA GAGAAGAACC ACCCCCACA
   100968                                                   AAC AGCCTCAATT
   100981 TGTCAGGGCA TGGACTCTTC AAGGTGTCAA ACGTTCCACA GGGATGCTGG CCCATGTTGA
   101041 CTCCAACGCT TCCCACAATT GTGTCAAGGT GGCTGGATGT TCTTTGGGAG
   101845                       AATTTG GCAGTATGTC AACCGGCCT CATAACCGCA
   101881 GACCACGTGT AGCTACACCA GCCCAGGACC TCCACATCCG GCTTCTTCAT CTACGGGATC
   101941 GTCTGAAACC AGCCACCCGA ACAGCTGATA AACTGAGGA GTATTTCTGT CTGTAA
```

Zebrafish FGF2 gene coding sequence (aa 1-154) (SEQ ID NO: 218) (GenBank
accession no. AY269790, which is hereby incorporated by reference in its
entirety):
```
     43                                             ATGGCCAC CGGAGGGATC
     61 ACCACACTCC CGGCCGCTCC GGACGCCGAA AACAGCAGCT TTCCCGCGGG CAGCTTCAGG
    121 GATCCCAAGC GCCTGTACTG CAAAAACGGA GGATTCTTCC TGCGGATCAA CGCGGACGGC
    181 CGAGTGGACG GAGCCCGAGA CAAGAGCGAC CCGCACATTC GTCTGCAGCT GCAGGCGACG
    241 GCAGTGGGTG AAGTACTCAT TAAAGGCATC TGTACCAACC GTTTCCTTGC CATGAACGCA
    301 GACGGACGAC TGTTCGGGAC GAAAAGGACC ACAGATGAAT GTTATTTCCT GGAGCGCCTG
    361 GAGTCCAACA ACTACAACAC ATACAGATCC CGCAAGTATC CCGACTGGTA CGTGGCTCTG
    421 AAGAGAACCG GCCAGTATAA AAGCGGCTCT AAAACCAGCC CGGGACAGAA GGCCATCCTG
    481 TTTCTGCCCA TGTCGGCCAA ATGCTGA
```

Nile tilapia FGF2 gene coding sequence (aa 1-155) (SEQ ID NO: 219)
(GenBank accession no. XM_003443364, which is hereby incorporated by
reference in its entirety):
```
      1 ATGGCCACGG GAGGAATCAC AACACTTCCC GCTACACCTG AAGACGGCGG CAGCAGCGGC
     61 TTTCCTCCTG GAACTTCAA GGACCCTAAA AGGCTGTACT GTAAAAATG TGGCTTCTTC
    121 TTGAGGATAA AATCTGATGG AGGAGTGGAT GGAATACGGA AGAAAACGA CCCCCACATA
    181 AAGCTTCAAC TCCAGGCGAC CTCAGTGGGA GAAGTGGTCA TCAAAGGGAT TTGTGCAAAC
    241 CGATATCTGG CAATGAACAG AGATGGACGA CTGTTTGGAG CGAGAAGAGC AACAGATGAG
    301 TGCTACTTCT TAGAGCGGCT CGAGAGCAAC AACTACAACA CCTACCGCTC CAGGAAGTAC
    361 CCAAACATGT ACGTGGCGCT GAAGCGGACT GGCCAGTACA AGTCTGGAAG CAAAACTGGA
    421 CCGGGTCAAA AGGCAATTCT CTTTCTCCCA ATGTCTGCTA AATGCTAA
```

Medaka FGF2 gene coding sequence (aa 1-155) (SEQ ID NO: 220) (Ensembl
accession no. ENSORLT00000025835, which is hereby incorporated by
reference in its entirety):
```
      1 ATGGCTACGG GAGAAATCAC AACACTTCCC TCCCCAGCTG AAAACAGCAG AAGCGATGGC
     61 TTTCCTCCAG GAACTACAA GGATCCTAAG AGGCTCTACT GTAAAAATG AGGTTTGTTT
    121 TTGAGGATTA AACCTGATGG AGGAGTGGAT GGAATCCGGG AAAAAAAGA TCCCCACGTT
    181 AAGCTTCGCC TTCAGGCTAC CTCAGCGGGA GAGGTGGTGA TCAAAGGAGT TTGTTCAAAC
    241 AGATATCTGG CGATGCATGG AGATGGACGT CTATTTGGAG TGAGACAAGC AACAGAGGAA
    301 TGCTACTTCT TGGAGCGACT AGAGAGCAAC AACTATAACA CCTATCGCTC TAAAAAGTAC
    361 CCAAACATGT ACGTGGCACT GAAGCGGACA GGCCAGTACA AACCTGGAAA CAAAACTGGA
    421 CCAGGTCAAA AGGCCATTCT CTTTCTGCCT ATGTCTGCCA AGTACTAA
```

As noted above, also encompassed within the present invention are portions of paracrine FGFs other than FGF1 and/or FGF2 (e.g., FGF4, FGF5, FGF6, FGF9, FGF16, and FGF20). The portion of the paracrine FGF may be from human FGF4, FGF5, FGF6, FGF9, FGF16, and/or FGF20 having the amino acid sequences shown in Table 5, or orthologs thereof.

TABLE 5

Amino acid sequence of human FGF4 (SEQ ID NO: 221) (GenBank
accession no. NP_001998, which is hereby incorporated by reference
in its entirety):
```
  1 MSGPGTAAVA LLPAVLLALL APWAGRGGAA APTAPNGTLE AELERRWESL VALSLARLPV
 61 AAQPKEAAVQ SGAGDYLLGI KRLRRLYCNV GIGFHLQALP DGRIGGAHAD TRDSLLELSP
121 VERGVVSIFG VASRFFVAMS SKGKLYGSPF FTDECTFKEI LLPNNYNAYE SYKYPGMFIA
181 LSKNGKTKKG NRVSPTMKVT HFLPRL
```

Amino acid sequence of human FGF5 (SEQ ID NO: 222) (GenBank
Accession No. NP_004455, which is hereby incorporated by reference
in its entirety):
```
  1 MSLSFLLLLF FSHLILSAWA HGEKRLAPKG QPGPAATDRN PRGSSSRQSS SSAMSSSSAS
 61 SSPAASLGSQ GSGLEQSSFQ WSPSGRRTGS LYCRVGIGFH LQIYPDGKVN GSHEANMLSV
121 LEIFAVSQGI VGIRGVFSNK FLAMSKKGKL HASAKFTDDC KFRERFQENS YNTYASAIHR
```

TABLE 5-continued

```
181 TEKTGREWYV ALNKRGKAKR GCSPRVKPQH ISTHFLPRFK QSEQPELSFT VTVPEKKKPP
241 SPIKPKIPLS APRKNTNSVK YRLKFRFG
```

Amino acid sequence of human FGF6 (SEQ ID NO: 223) (NP_066276, which is hereby incorporated by reference in its entirety):
```
  1 MALGQKLFIT MSRGAGRLQG TLWALVFLGI LVGMVVPSPA GTRANNTLLD SRGWGTLLSR
 61 SRAGLAGEIA GVNWESGYLV GIKRQRRLYC NVGIGFHLQV LPDGRISGTH EENPYSLLEI
121 STVERGVVSL FGVRSALFVA MNSKGRLYAT PSFQEECKFR ETLLPNNYNA YESDLYQGTY
181 IALSKYGRVK RGSKVSPIMT VTHFLPRI
```

Amino acid sequence of human FGF9 (SEQ ID NO: 224) (GenBank accession no. NP_002001, which is hereby incorporated by reference in its entirety):
```
  1 MAPLGEVGNY FGVQDAVPFG NVPVLPVDSP VLLSDHLGQS EAGGLPRGPA VTDLDHLKGI
 61 LRRRQLYCRT GFHLEIFPNG TIQGTRKDHS RFGILEFISI AVGLVSIRGV DSGLYLGMNE
121 KGELYGSEKL TQECVFREQF EENWYNTYSS NLYKHVDTGR RYYVALNKDG TPREGTRTKR
181 HQKFTHFLPR PVDPDKVPEL YKDILSQS
```

Amino acid sequence of human FGF16 (SEQ ID NO: 225) (GenBank accession no. NP_003859, which is hereby incorporated by reference in its entirety):
```
  1 MAEVGGVFAS LDWDLHGFSS SLGNVPLADS PGFLNERLGQ IEGKLQRGSP TDFAHLKGIL
 61 RRRQLYCRTG FHLEIFPNGT VHGTRHDHSR FGILEFISLA VGLISIRGVD SGLYLGMNER
121 GELYGSKKLT RECVFREQFE ENWYNTYAST LYKHSDSERQ YYVALNKDGS PREGYRTKRH
181 QKFTHFLPRP VDPSKLPSMS RDLFHYR
```

Amino acid sequence of human FGF20 (SEQ ID NO: 226) (GenBank accession no. NP_062825, which is hereby incorporated by reference in its entirety):
```
  1 MAPLAEVGGF LGGLEGLGQQ VGSHFLLPPA GERPPLLGER RSAAERSARG GPGAAQLAHL
 61 HGILRRRQLY CRTGFHLQIL PDGSVQGTRQ DHSLFGILEF ISVAVGLVSI RGVDSGLYLG
121 MNDKGELYGS EKLTSECIFR EQFEENWYNT YSSNIYKHGD TGRRYFVALN KDGTPRDGAR
181 SKRHQKFTHF LPRPVDPERV PELYKDLLMY T
```

It will be understood that the portion of the paracrine FGF according to the present invention may be derived from a nucleotide sequence that encodes human FGF4, FGF5, FGF6, FGF9, FGF16, and/or FGF20 having the nucleotide sequences shown in Table 6, or orthologs thereof.

TABLE 6

Human FGF4 gene coding sequence (1-206) (SEQ ID NO: 227) (GenBank accession no. NM_002007, which is hereby incorporated by reference in its entirety):
```
 320                        A TGTCGGGGCC CGGGACGGCC GCGGTAGCGC TGCTCCCGGC
 361 GGTCCTGCTG GCCTTGCTGG CGCCCTGGGC GGGCCGAGGG GGCGCCGCCG CACCCACTGC
 421 ACCCAACGGC ACGCTGGAGG CCGAGCTGGA GCGCGCCTGG AGAGCCTGG TGGCGCTCTC
 481 GTTGGCGCGC CTGCCGGTGG CAGCGCAGCC CAAGGAGGCG GCCGTCCAGA GCGGCGCCGG
 541 CGACTACCTG CTGGGCATCA AGCGGCTGCG GCGGCTCTAC TGCAACGTGG GCATCGGCTT
 601 CCACCTCCAG GCGCTCCCCG ACGGCCGCAT CGGCGGCGCG CACGCGGACA CCCGCGACAG
 661 CCTGCTGGAG CTCTCGCCCG TGGAGCGGGG CGTGGTGAGC ATCTTCGGCG TGGCCAGCCG
 721 GTTCTTCGTG GCCATGAGCA GCAAGGGCAA GCTCTATGGC TCGCCCTTCT TCACCGATGA
 781 GTGCACGTTC AAGGAGATTC TCCTTCCCAA CAACTACAAC GCCTACGAGT CCTACAAGTA
 841 CCCCGGCATG TTCATCGCCC TGAGCAAGAA TGGGAAGACC AAGAAGGGGA ACCGAGTGTC
 901 GCCCACCATG AAGGTCACCC ACTTCCTCCC CAGGCTGTGA
```

Human FGF5 gene coding sequence (1-268) (SEQ ID NO: 228) (GenBank Accession No. NM_004464, which is hereby incorporated by reference in its entirety):
```
 238                                                                  ATG
 241 AGCTTGTCCT TCCTCCTCCT CCTCTTCTTC AGCCACCTGA TCCTCAGCGC CTGGGCTCAC
 301 GGGGAGAAGC GTCTCGCCCC CAAAGGGCAA CCCGGACCCG CTGCCACTGA TAGGAACCCT
 361 AGAGGCTCCA GCAGCAGACA GAGCAGCAGT AGCGCTATGT CTTCCTCTTC TGCCTCCTCC
 421 TCCCCCGCAG CTTCTCTGGG CAGCCAAGGA AGTGGCTTGG AGCAGAGCAG TTTCCAGTGG
 481 AGCCCCTCGG GGCGCCGGAC CGGCAGCCTC TACTGCAGAG TGGGCATCGG TTTCCATCTG
 541 CAGATCTACC CGGATGGCAA AGTCAATGGA TCCCACGAAG CCAATATGTT AAGTGTTTTG
 601 GAAATATTTG CTGTGTCTCA GGGGATTGTA GGAATACGAG GAGTTTTCAG CAACAAATTT
 661 TTAGCGATGT CAAAAAAAGG AAAACTCCAT GCAAGTGCCA AGTTCACAGA TGACTGCAAG
 721 TTCAGGGAGC GTTTTCAAGA AAATAGCTAT AATACCTATG CCTCAGCAAT ACATAGAACT
 781 GAAAAAACAG GGCGGAGTG GTATGTGGCC CTGAATAAAA GAGGAAAAGC CAAACGAGGG
 841 TGCAGCCCCC GGGTTAAACC CCAGCATATC TCTACCCATT TTCTGCCAAG ATTCAAGCAG
 901 TCGGAGCAGC CAGAACTTTC TTTCACGGTT ACTGTTCCTG AAAAGAAAAA GCCACCTAGC
 961 CCTATCAAGC CAAAGATTCC CCTTTCTGCA CCTCGGAAAA ATACCAACTC AGTGAAATAC
1021 AGACTCAAGT TTCGCTTTGG ATAA
```

TABLE 6-continued

```
Human FGF6 gene coding sequence (1-208) (SEQ ID NO: 229) (NM_020996,
which is hereby incorporated by reference in its entirety):
    45                                                       ATGGCC CTGGGACAGA
    61 AACTGTTCAT CACTATGTCC CGGGGAGCAG GACGTCTGCA GGGCACGCTG TGGGCTCTCG
   121 TCTTCCTAGG CATCCTAGTG GGCATGGTGG TGCCCTCGCC TGCAGGCACC CGTGCCAACA
   181 ACACGCTGCT GGACTCGAGG GGCTGGGGCA CCCTGCTGTC CAGGTCTCGC GCGGGGCTAG
   241 CTGGAGAGAT TGCCGGGGTG AACTGGGAAA GTGGCTATTT GGTGGGGATC AAGCGGCAGC
   301 GGAGGCTCTA CTGCAACGTG GGCATCGGCT TTCACCTCCA GGTGCTCCCC GACGGCCGGA
   361 TCAGCGGGAC CCACGAGGAG AACCCCTACA GCCTGCTGGA AATTTCCACT GTGGAGCGAG
   421 GCGTGGTGAG TCTCTTTGGA GTGAGAAGTG CCCTCTTCGT TGCCATGAAC AGTAAAGGAA
   481 GATTGTACGC AACGCCCAGC TTCCAAGAAG AATGCAAGTT CAGAGAAACC CTCCTGCCCA
   541 ACAATTACAA TGCCTACGAG TCAGACTTGT ACCAAGGGAC CTACATTGCC CTGAGCAAAT
   601 ACGGACGGGT AAAGCGGGGC AGCAAGGTGT CCCCGATCAT GACTGTCACT CATTTCCTTC
   661 CCAGGATCTA A Human FGF9 gene coding sequence (1-208) (SEQ ID NO: 230) (GenBank
accession no. NM_002010, which is hereby incorporated by reference in
its entirety):
   838                                                                      ATG
   841 GCTCCCTTAG GTGAAGTTGG GAACTATTTC GGTGTGCAGG ATGCGGTACC GTTTGGGAAT
   901 GTGCCCGTGT TGCCGGTGGA CAGCCCGGTT TTGTTAAGTG ACCACCTGGG TCAGTCCGAA
   961 GCAGGGGGGC TCCCCAGGGG ACCCGCAGTC ACGGACTTGG ATCATTTAAA GGGGATTCTC
  1021 AGGCGGAGGC AGCTATACTG CAGGACTGGA TTTCACTTAG AAATCTTCCC CAATGGTACT
  1081 ATCCAGGGAA CCAGGAAAGA CCACAGCCGA TTTGGCATTC TGGAATTTAT CAGTATAGCA
  1141 GTGGGCCTGG TCAGCATTCG AGGCGTGGAC AGTGGACTCT ACCTCGGGAT GAATGAGAAG
  1201 GGGGAGCTGT ATGGATCAGA AAAACTAACC CAAGAGTGTG TATTCAGAGA ACAGTTCGAA
  1261 GAAAACTGGT ATAATACGTA CTCATCAAAC CTATATAAGC ACGTGGACAC TGGAAGGCGA
  1321 TACTATGTTG CATTAAATAA AGATGGGACC CCGAGAGAAG GGACTAGGAC TAAACGGCAC
  1381 CAGAAATTCA CACATTTTTT ACCTAGACCA GTGGACCCCG ACAAGTACC TGAACTGTAT
  1441 AAGGATATTC TAAGCCAAAG TTGA Human FGF16 gene coding sequence (1-207) (SEQ ID NO: 231) (GenBank
accession no. NM_003868, which is hereby incorporated by reference in
its entirety):
     1 ATGGCAGAGG TGGGGGGCGT CTTCGCCTCC TTGGACTGGG ATCTACACGG CTTCTCCTCG
    61 TCTCTGGGGA ACGTGCCCTT AGCTGACTCC CCAGGTTTCC TGAACGAGCG CCTGGGCCAA
   121 ATCGAGGGGA AGCTGCAGCG TGGCTCACCC ACAGACTTCG CCCACCTGAA GGGGATCCTG
   181 CGGCGCCGCC AGCTCTACTG CCGCACCGGC TTCCACCTGG AGATCTTCCC CAACGGCACG
   241 GTCCACGGGA CCCGCCACGA CCACAGCCGC TTCGGAATCC TGGAGTTTAT CAGCCTGGCT
   301 GTGGGGCTGA TCAGCATCCG GGGAGTGGAC TCTGGCCTGT ACCTAGGAAT GAATGAGCGA
   361 GGAGAACTCT ATGGGTCGAA GAAACTCACA CGTGAATGTG TTTTCCGGGA ACAGTTTGAA
   421 GAAAACTGGT ACAACACCTA TGCCTCAACC TTGTACAAAC ATTCGGACTC AGAGAGACAG
   481 TATTACGTGG CCCTGAACAA AGATGGCTCA CCCCGGGAGG GATACAGGAC TAAACGACAC
   541 CAGAAATTCA CTCACTTTTT ACCCAGGCCT GTAGATCCTT CTAAGTTGCC CTCCATGTCC
   601 AGAGACCTCT TCACTATAG GTAA Human FGF20 gene coding sequence (1-211) (SEQ ID NO: 232) (GenBank
accession no. NM_019851, which is hereby incorporated by reference in
its entirety):
   134           ATGGCTC CCTTAGCCGA AGTCGGGGGC TTTCTGGGCG GCCTGGAGGG
   181 CTTGGGCCAG CAGGTGGGTT CGCATTTCCT GTTGCCTCCT GCCGGGGAGC GGCCGCCGCT
   241 GCTGGGCGAG CGCAGGAGCG CGGCGGAGCG GAGCGCGCGC GGCGGGCCGG GGGCTGCGCA
   301 GCTGGCGCAC CTGCACGGCA TCCTGCGCCG CCGGCAGCTC TATTGCCGCA CCGGCTTCCA
   361 CCTGCAGATC CTGCCCGACG GCAGCGTGCA GGGCACCCGG CAGGACCACA GCCTCTTCGG
   421 TATCTTGGAA TTCATCAGTG TGGCAGTGGG ACTGGTCAGT ATTAGAGGTG TGGACAGTGG
   481 TCTCTATCTT GGAATGAATG ACAAAGGAGA ACTCTATGGA TCAGAGAAAC TTACTTCCGA
   541 ATGCATCTTT AGGGAGCAGT TTGAAGAGAA CTGGTATAAC ACCTATTCAT CTAACATATA
   601 TAAACATGGA GACACTGGCC GCAGGTATTT TGTGGCACTT AACAAAGACG GAACTCCAAG
   661 AGATGGCGCC AGGTCCAAGA GGCATCAGAA ATTTACACAT TTCTTACCTA GACCAGTGGA
   721 TCCAGAAAGA GTTCCAGAAT TGTACAAGGA CCTACTGATG TACACTTGA
```

As noted above, the chimeric protein includes a portion of a paracrine FGF coupled to a C-terminal region derived from an FGF21 molecule. FGF21 is an endocrine FGF expressed primarily by the pancreas (Fon Tacer et al., "Research Resource: Comprehensive Expression Atlas of the Fibroblast Growth Factor System in Adult Mouse," *Mol Endocrinol* 24(10):2050-2063 (2010), which is hereby incorporated by reference in its entirety) and has metabolic effects similar to that of FGF19, such as increased energy metabolism, weight loss, lowered blood glucose levels, and resistance to obesity and diabetes (Kharitonenkov et al., "FGF-21 as a Novel Metabolic Regulator," *J Clin Invest* 115(6), 1627-1635 (2005); Coskun et al., "Fibroblast growth factor 21 corrects obesity in mice," *Endocrinology* 149(12): 6018-6027 (2008), which are hereby incorporated by reference in their entirety). Transgenic mice overexpressing FGF21 are also resistant to diet-induced obesity (Kharitonenkov et al., "FGF-21 as a Novel Metabolic Regulator," *J Clin Invest* 115(6), 1627-1635 (2005), which is hereby incorporated by reference in its entirety). Moreover, in diabetic rodent models, FGF21 administration lowers blood glucose and triglyceride levels (Kharitonenkov et al., "FGF-21 as a Novel Metabolic Regulator," *J Clin Invest* 115(6), 1627-1635 (2005), which is hereby incorporated by reference in its entirety).

In one embodiment, the C-terminal portion of FGF21 of the chimeric protein of the present invention is from human FGF21 having the amino acid sequence of SEQ ID NO: 233 (GenBank Accession No. NP_061986, which is hereby incorporated by reference in its entirety), as follows:

```
  1 MDSDETGFEH SGLWVSVLAG LLLGACQAHP IPDSSPLLQF
    GGQVRQRYLY TDDAQQTEAH

61 LEIREDGTVG GAADQSPESL LQLKALKPGV IQILGVKTSR
    FLCQRPDGAL YGSLHFDPEA

121 CSFRELLLED GYNVYQSEAH GLPLHLPGNK SPHRDPAPRG
    PARFLPLPGL PPALPEPPGI

181 LAPQPPDVGS SDPLSMVGPS QGRSPSYAS.
```

In one embodiment, the C-terminal portion of FGF21 of the chimeric protein of the present invention includes a β-Klotho co-receptor binding domain.

In one embodiment, the C-terminal portion of FGF21 of the chimeric protein of the present invention includes amino acid residues 168-209 of SEQ ID NO: 233.

In one embodiment, the C-terminal portion of FGF21 of the chimeric protein further includes one or more substitutions, deletions, or additions. In one embodiment, the C-terminal portion of FGF21 of the chimeric protein further includes one or more substitutions, deletions, or additions while retaining the ability to bind β-Klotho. In one embodiment, the C-terminal portion of FGF21 of the chimeric protein further includes one or more substitutions, deletions, or additions while retaining the ability to selectively bind β-Klotho. In one embodiment, the C-terminal portion of FGF21 of the chimeric protein further includes one or more substitutions, additions, or deletions to enhance binding affinity for β-Klotho.

In one embodiment of the present invention, the C-terminal portion of the chimeric protein according to the present invention is or is derived from a mammalian FGF21. In one embodiment of the present invention, the C-terminal portion of the chimeric protein according to the present invention is or is derived from a vertebrate FGF21. In one embodiment, the C-terminal portion of the chimeric protein according to the present invention is derived from a non-human vertebrate FGF21. It will be understood that this includes orthologs of human FGF21, or a polypeptide or protein obtained from one species that is the functional counterpart of a polypeptide or protein from a different species. In one embodiment of the present invention, the C-terminal portion of FGF21 of the chimeric protein according to the present invention is derived from human, *Pongo abelii*, *Pan troglodytes*, *Canis lupus familiaris*, *Bos taurus*, *Equus caballus*, *Ailuropoda melanoleuca*, *Oryctolagus cuniculus*, *Gorilla gorilla*, *Nomascus leucogenys*, *Procavia capensis*, *Cavia porcellus*, *Tupaia belangeri*, *Sorex araneus*, *Ictidomys tridecemlineatus*, *Loxodonta africana*, *Sus scrofa*, *Felis catus*, *Otolemur garnettii*, *Rattus norvegicus*, *Mus musculus*, *Vicugna pacos*, *Anolis carolinensis*, *Gadus morhua*, *Latimeria chalumnae*, *Tursiops truncatus*, *Mustela putorius furo*, *Takifugu rubripes*, *Dipodomys ordii*, *Echinops telfairi*, *Macaca mulatta*, *Microcebus murinus*, *Ochotona princeps*, *Xiphophorus maculatus*, *Gasterosteus aculeatus*, *Sarcophilus harrisii*, *Macropus eugenii*, *Xenopus tropicalis*, *Danio rerio*, *Bos grunniens mutus*, *Saimiri boliviensis boliviensis*, *Callithrix jacchus*, *Tupaia chinensis*, *Papio anubis*, *Pteropus alecto*, *Heterocephalus glaber*, *Cricetulus griseus*, *Ovies aries*, *Pan paniscus*, *Macaca fascicularis*, *Mesocricetus auratus*, or *Oreochromis niloticus*.

In one embodiment of the present invention, the portion of FGF21 of the chimeric protein of the present invention is from an ortholog of human FGF21 having an amino acid sequence as shown in Table 7. The portions of an ortholog of human FGF21 of a chimeric protein according to the present invention include portions corresponding to the above-identified amino acid sequences of human FGF21. Corresponding portions may be determined by, for example, sequence analysis and structural analysis.

TABLE 7

```
Pongo abelii (Sumatran orangutan) FGF21 (GenBank Accession No.
XP_002829565, which is hereby incorporated by reference in its
entirety) (SEQ ID NO: 234)
    1 MDSDETGFEH SGLWVPVLAG LLLGACQAHP IPDSSPLLQF GGQVRQRYLY TDDAQQTEAH
   61 LEIREDGTVG GAADQSPESL LQLKALKPGV IQILGVKTSR FLCQRPDGAL YGSLHFDPEA
  121 CSFRELLLED GYNVYQSEAH GLPLHLPGNK SPHRDPAPRG PARFLPLPGL PPAPPEPPGI
  181 LAPQPPDVGS SDPLSMVGPS QGRSPSYAS Pan troglodytes (chimpanzee) FGF21 (GenBank Accession No. XP_524333,
which is hereby incorporated by reference in its entirety)
(SEQ ID NO: 235)
    1 MDSDETGFEH SGLWVSVLAG LLLGACQAHP IPDSSPLLQF GGQVRQRYLY TDDAQQTEAH
   61 LEIREDGTVG GAADQSPESL LQLKALKPGV IQILGVKTSR FLCQRPDGAL YGSLHFDPEA
  121 CSFRELLLED GYNVYQSEAH GLPLHLPGNK SPHRDPAPRG PARFLPLPGL PPAPPEPPGI
  181 LAPQPPDVGS SDPLSMVGPS QGRSPSYTS Canis lupus familiaris (dog) FGF21 (GenBank Accession No. XP_541510,
which is hereby incorporated by reference in its entirety)
(SEQ ID NO: 236)
    1 MGWAEAGFEH LGLWVPVLAV LLLEACRAHP IPDSSPLLQF GGQVRQRYLY TDDAQETEAH
   61 LEIRADGTVV GAARQSPESL LELKALKPGV IQILGVKTSR FLCQGPDGTL YGSLHFDPVA
  121 CSFRELLLED GYNIYHSETL GLPLRLRPHN SAYRDLAPRG PARFLPLPGL LPAPPEPPGI
  181 LAPEPPDVGS SDPLSMVGPS QGRSPSYAS Bos taurus (bovine) FGF21 (GenBank Accession No. XP_001789639, which
is hereby incorporated by reference in its entirety)
(SEQ ID NO: 237)
    1 MGWDEAKFKH LGLWVPVLAV LLLGTCRAHP IPDSSPLLQF GGQVRQRYLY TDDAQETEAH
   61 LEIRADGTVV GAARQSPESL LELKALKPGV IQILGVKTSR FLCQGPDGKL YGSLHFDPKA
  121 CSFRELLLED GYNVYQSETL GLPLRLPPQR SSNRDPAPRG PARFLPLPGL PAAPPDPPGI
  181 LAPEPPDVGS SDPLSMVGPS YGRSPSYTS Equus caballus (horse) FGF21 (GenBank Accession No. XP_001489202,
which is hereby incorporated by reference in its entirety)
(SEQ ID NO: 238)
    1 MDWDKTGFKY QGLWVPVLAV LLLGACQSHP IPDSSPLLQF GGQVRQRHLY TDDAQETEAH
   61 LEIRADGTVA GAVHRSPESL LELKALKPGV IQILGVKTSR FLCQGPDGTL YGSLHFDPVA
```

TABLE 7-continued

```
121 CSFRELLLED GYNVYQSETL GLPLRLPHHS SPYQDPAPRA PARFLPLPGF PPAPPEPPGI
181 PAPEPPPDVGS SDPLSMVGPS RSRSPSYTS
```

*Ailuropoda melanoleuca* (giant panda) FGF21 (GenBank Accession No. XP_002917910, which is hereby incorporated by reference in its entirety) (SEQ ID NO: 239)
```
  1 MGWDEARSEQ LGLWVPVLAV LLLEACQAHP IPDSSPLLQF GGQVRQRYLY TDDAQETEAH
 61 LAIRADGTVV GAASRSPESL LELKALKPGV IQILGVKTSR FLCQGPDGTL YGSVRFDPVA
121 CSFRELLLED GYNIYHSETL GLPLRLPAHN SPYRDSAPRG PARFLPLPGL LPVPPDPPGI
181 LGPEPPDVGS SDPLSMVGPS QGRSPSYAS
```

*Oryctolagus cuniculus* (rabbit) FGF21 (GenBank Accession No. XP_002723745, which is hereby incorporated by reference in its entirety) (SEQ ID NO: 240)
```
  1 MDWGKAKCRP PGLWVPALAA LLLGACQAHP IPDSSPLLQF GDQVRQQHLY TDDAQETEAH
 61 LEIRADGTVV GAARRSPESL LQMKALQPGI IQILGVQTSR FLCQRPDGTL YGSLHFDREA
121 CSFRELLRED GYNVYLSEAL GLPLRLSPGS SPRRAPAPRG PARFLPLPGL PPDLPEPPGL
181 LAAAPPDVDS PDPLSMVQPA LDQSPSYTS
```

*Gorilla gorilla* (gorilla) FGF21 (Ensembl Accession No. ENSGGOP00000001229, which is hereby incorporated by reference in its entirety) (SEQ ID NO: 241)
```
  1 MDSDETGFEH SGLWVSVLAG LLLGACQAHP IPDSSPLLQF GGQVRQRYLY TDDAQQTEAH
 61 LEIREDGTVG GAADQSPESL LQLKALKPGV IQILGVKTSR FLCQRPDGAL YGSLHFDPEA
121 CSFRELLLED GYNVYQSEAH GLPHLPGNK SPHRDPAPRG PARFLPLPGL PPAPPEPPGI
181 LAPQPPDVGS SDPLSMVGPS QGRSPSYAS
```

*Nomascus leucogenys* (Northern white-cheeked gibbon) FGF21 (Ensembl Accession No. ENSNLEP00000005639, which is hereby incorporated by reference in its entirety) (SEQ ID NO: 242)
```
  1 MDSDETGFEH SGLWVPVLAG LLLGACQAHP IPDSSPLLQF GGQVRQRYLY TDDAQQTEAH
 61 LEIREDGTVG GAADQSPESL LQLKALKPGV IQILGVKTSR FLCQRPDGAL YGSLHFDPEA
121 CSFRELLLED GYNVYQSEAH GLPHLPGNK SPHRDPAPRG PARFLPLPGL PPAPPEPPGI
181 LAPQPPDVGS SDPLSMVGPS QGRSPSYAS
```

*Procavia capensis* (hyrax) FGF21 (Ensembl Accession No. ENSOGAG00000001210, which is hereby incorporated by reference in its entirety) (SEQ ID NO: 243)
```
  1 MDWAKFGIEH PGLWVPVMAV LLLGACQGYP IPDSSPLLQF GGQVRQRYLY TDDAQETEAH
 61 LEIRADGTVV GAAHRSPESL LELKALKPGI IQILGVKTSR FLCQGPDGVL YGSLRFDPVA
121 CSFRELLLED GYNVYQSEAH GLPLRLPSHN SPQRDLASRV PARFLPLPGR LTVLPEPSGV
181 LGPEPPDVDS SDPLSMVGPS QGRSPSYAS
```

*Cavia porcellus* (guinea pig) FGF21 (Ensembl Accession No. ENSCPOP00000000237, which is hereby incorporated by reference in its entirety) (SEQ ID NO: 244)
```
  1 MDWARTECER PRLWVSMLAI LLVGACQAHP IPDSSPLLQF GGQVRQRYLY TDDAQDTEVH
 61 LEIRADGSVR GIAHRSPESL LELKALKPGV IQILGIRTSR FLCQRPDGSL YGSLHFDPEA
121 CSFRELLLAD GYNVYKSEAH GLPLHLLRGD SLSQEPAPPG PARFLPLPGL PATPPEPPRM
181 LPPGPPDVGS SDPLSMVGPL WDRSPSYTS
```

*Tupaia belangeri* (tree shrew) FGF21 (Ensembl Accession No. ENSTBEP00000013946, which is hereby incorporated by reference in its entirety) (SEQ ID NO: 245)
```
  1 MGWDKARFEH LGAWAPVLAV LLLGACQAYP IPDSSPLLQF GGQVRQRYLY TDDTQDTEAH
 61 LEIRADGTVV GAAHQSPESL LELKALKPGV IQILGVKTSR FLCQRPDGAL YGSLHFDPEA
121 CSFRELLLED GYNIYQSEAR GLPLRLPPHD SPHRDRTPRG PARFLPLPGL PLVPPELPGV
181 LALEPPDVGS SDPLSMMGPS QGQSPSYAS
```

*Sorex araneus* (shrew) FGF21 (Ensembl Accession No. ENSSARP00000002784, which is hereby incorporated by reference in its entirety) (SEQ ID NO: 246)
```
  1 MVWDKARGQQ LGLWAPMLLG LLLGACQAHP LPDSSPLLQF GGQVRLRFLY TDDAQRTGAH
 61 LEIRADGTVQ GAAHRTPECL LELKALKPGV IQILGVSTSR FLCQRPDGVL YGSLRFDPEA
121 CSFRELLLQD GYNVYQSEAL GLPLYLHPPS APVSQEPASR GAVRFLPLPG LPPASLEPPR
181 PPAPVPPDVG SSDPLSMVGP PERHSPSYTS
```

*Ictidomys tridecemlineatus* (squirrel) FGF21 (SEQ ID NO: 247)
```
  1 MDWVKAKLEP LGLWVLVLAA LVLGACQAYP IPDSSPLLQF GGQVRQRYLY TDDAQETEAH
 61 LEIRADGTVV GAAHQSPESL LELKALKPGV IQILGVKTSR FLCQRPDGVL YGSLHFDPEA
121 CSFREQLLED GYNVYQSESH GLPVRLPPNS PYRDPAPPGP ARFLPLPGLP PAALEPPGIL
181 GPEPPDVGSS DPLSMVGPLQ GRSPSYAS
```

*Loxodonta africana* (elephant) FGF21 (Ensembl Accession No. ENSLAFP00000016854, which is hereby incorporated by reference in its entirety) (SEQ ID NO: 248)
```
  1 MDWAKFGLE HPGLWVPVMA VLLLGACQGH PIPDSSPLLQ FGGQVRQRYL YTDDQETEAH
 60 LEIRADGTVA GAAHRSSESL LELKALKPGI IQILGVKTSR FLCQGPDGVL YGSLHFDPAA
120 CSFRELLLED GYNVYWSEAH GLPIRLPSHN SPYRDPASRV PARFLPLPGL LPMLQEPPGV
180 LAPEPPDVDS SDPLSMVGPS QGRSPSYAS
```

TABLE 7-continued

*Sus scrofa* (pig) FGF21 (GenBank Accession No. NP_001156882, which is hereby incorporated by reference in its entirety) (SEQ ID NO: 249)
```
  1 MGWAEAKFER LGLWVPVLAV LLGACQARPI PDSSPLLQFG GQVRQRYLYT DDAQETEAHL
 61 EIRADGTVAG VARQSPESLL ELKALKPGVI QILGVQTSRF LCQGPDGRLY GSLHFDPEAC
121 SFRELLLEDG YNVYQSEALG LPLRLPPHRS SNRDLAPRGA ARFLPLPGLP PAPPEPPGIL
181 APEPPDVGSS DPLSMVGPSH GRSPSYTS
```

*Felis catus* (cat) FGF21 (Ensembl Accession No. ENSFCAP00000006832, which is hereby incorporated by reference in its entirety) (SEQ ID NO: 250)
```
  1 MDWDEAGSQ RLGLWVVLGV LLPEACQAHP IPDSSPLLQF GGQVRQRFLY TDDAQETEVH
 60 LEIKADGTVV GTARRSPESL LELKALKPGV IQILGVKTSR FLCQGPDGTL YGSLRFDPAA
120 CSFRELLLED GYNIYHSETL GLPLRLPPHN SPYRDLAPRA PARFLPLPGL LPAPPEPPGI
180 LAPEPPDVGS SDPLSMVGPS QGRSPSYAS
```

*Otolemur garnettii* (bushbaby) FGF21 (Ensembl Accession No. ENSOGAG00000003581, which is hereby incorporated by reference in its entirety) (SEQ ID NO: 251)
```
  1 DKARTGFKH PGPWFPLLAV LLLGACQAHP IPDSSPLLQF GGQVRQRYLY TDDAQETEAH
 60 LEIREDGTVV GAAQQSPESL LELKALKPGV IQILGVKTSR FLCQRPDGGL YGSLYFDPKA
120 CSFRELLLED GYNVYWSETY GLPLHLPPAN SPYWGPSLRS PARFLPLPGP PAASPELPGI
180 LALEPPDVGS SDPLSMVGPS QGRSPSYAS
```

*Rattus norvegicus* (Norway rat) FGF21 (GenBank Accession No. NP_570108, which is hereby incorporated by reference in its entirety) (SEQ ID NO: 252)
```
  1 MDWMKSRVGA PGLWVCLLLP VFLLGVCEAY PISDSSPLLQ FGGQVRQRYL YTDDDQDTEA
 61 HLEIREDGTV VGTAHRSPES LLELKALKPG VIQILGVKAS RFLCQQPDGT LYGSPHFDPE
121 ACSFRELLLK DGYNVYQSEA HGLPLRLPQK DSQDPATRGP VRFLPMPGLP HEPQEQPGVL
181 PPEPPDVGSS DPLSMVEPLQ GRSPSYAS
```

*Mus musculus* (house mouse) FGF21 (GenBank Accession No. NP_064397, which is hereby incorporated by reference in its entirety) (SEQ ID NO: 253)
```
  1 MEWMRSRVGT LGLWVRLLLA VFLLGVYQAY PIPDSSPLLQ FGGQVRQRYL YTDDDQDTEA
 61 HLEIREDGTV VGAAHRSPES LLELKALKPG VIQILGVKAS RFLCQQPDGA LYGSPHFDPE
121 ACSFRELLLE DGYNVYQSEA HGLPLRLPQK DSPNQDATSW GPVRFLPMPG LLHEPQDQAG
181 FLPPEPPDVG SSDPLSMVEP LQGRSPSYAS
```

*Vicugna pacos* (alpaca) FGF21 (Ensembl Accession No. ENSVPAP00000005562, which is hereby incorporated by reference in its entirety) (SEQ ID NO: 254); partial sequence corresponding to human FGF21 residues 1 to 78, 169 to 171, and 183 to 209
```
  1 MDWDEAKFEH RGLWVPVLTV LLLGACQARP IPDSSPLLQF GGQVRQRYLY TDDAQETEAH
 61 LEIRADGTVV GVARQPE--- ---------- ---------- ---------- ----------
121 ---------- ---------- ---------- ---------- --------GI P---------
181 --PEPPDVGS SDPLSMVGPS YSRSPSYTS
```

*Anolis carolinensis* (anole lizard) FGF21 (Ensembl Accession No. ENSACAP00000016895, which is hereby incorporated by reference in its entirety) (SEQ ID NO: 255)
```
  1 CKSKGGGKGG ERMWVDLVFW AALLRTAPAL PLRNSNPIYQ FDGQVRLRHL YTADEQTHLH
 61 LEILPDGTVG GSRFQNPFSL MEIKAVKPGV IRMQAKKTSR FLCMKPNGRL YGSLFYSEEA
121 CNFHEKVLSD GYNLYYSENY NIPVSLSSAG NLGQSRQLPP FSQFLPLVNK IPLEPVLEDF
181 DFYGHQLDVE SADPLSILGQ NPGFMSPSYV F
```

*Gadus morhua* (cod) FGF21 (Ensembl Accession No. ENSGMOP00000013789, which is hereby incorporated by reference in its entirety) (SEQ ID NO: 256)
```
  1 LLLATLLHIG LSFYVPDSGP LLWLGDQVRE RHLYTAESHR RGLFLEMSPD GQVTGSAAQT
 61 PLSVLELRSV RAGDTVIRAR LSSLYLCVDR AGHLTGQRQY TESDCTFREV ILEDGYTHFL
121 SVHHGLPISL APRHSPGRQG LRFSRFLPLR SSLSEDRVAE PPDSPLNLDS EDPLGMGLGS
181 LLSPAFSM
```

*Latimeria chalumnae* (coelacanth) FGF21 (Ensembl Accession No. ENSLACP00000003781, which is hereby incorporated by reference in its entirety) (SEQ ID NO: 257)
```
  1 MLCQSFVILS QKFIFGLFLT GLGLTGLAWT RPFQDSNPIL QYSDSIRLRH LYTASESRHL
 61 HLQINSDGQV GGTTKQSPYS LLEMKAVKTG FVVIRGKKSA RYLCMERSGR LYGSLQYTEK
121 DCTFKEVVLA DGYNLYVSEE HQATVTLSPM RARIAQGKKI PPFSHFLPMV NKVPVEDVAA
181 EMEFVQVLRE MTADVDSPDP FGMTWEESVH SPSFFA
```

Tursiops truncatus (dolphin) FGF21 (Ensembl Accession No. ENSTTRP00000013808, which is hereby incorporated by reference in its entirety) (SEQ ID NO: 258)
```
  1 MGWDKTKLEH LGLWVPVLAV LLGPCQAHPI PDSSPLLQFG GQVRQRYLYT DDAQETEAHL
 61 EIRADGTVVG TARRSPEGVK TSRFLCQGPE GRLYGSLHFN PQACSFRELL LEDGYNVYQS
121 EALGIPLRLP PHRSSNWDLA PRGPARFLPL PGFLPPPLEP PGILAPEPPN VGSSDPLSMV
181 GPSHGRSPSY TS
```

TABLE 7-continued

*Mustela putorius furo* (ferret) FGF21 (Ensembl Accession No.
ENSMPUP00000003687, which is hereby incorporated by reference in its
entirety) (SEQ ID NO: 259)
```
  1 MGWEEARSEH LGLWVPVLAV LLLGACQAYP IPDSSPLLQF GGVRQRYLY TDDAQETEAH
 61 LEIRADGTVV GAARRSPESL LELKALKPGV IQILGVKTSR FLCQGPNGTL YGSFHFDPVA
121 CSFREVLLED GYNIYHSETL GLPLRLPPHN SPHRDLAPRG PARFLPLPGL LPATPESRGI
181 PAPEPPNVGS SDPLSMVGPL QGQSPSYTS
```

*Takifugu rubripes* (fugu) FGF21 (Ensembl Accession No.
ENSTRUP00000033950, which is hereby incorporated by reference in its
entirety) (SEQ ID NO: 260)
```
  1 FIYLFIQTAL FSPSKWFNFY LPDSNPLLSF DSHGRGIHLY TDNQRRGMYL QMSTDGSVSG
 61 SDVQTANSVL ELKSVRNGHV VIRGKSSSLF LCMDSRGRLW GQRHPTEADC TFREVLLADG
121 YTRFLSLHNG TPVSLAPKQS PDQHTVPFTR FLPLRNTLAE ESMSEPPSNQ QRYFNIDSDD
181 LLGMDLNAMV SPQFSGDK
```

*Dipodomys ordii* (kangaroo rat) FGF21 (Ensembl Accession No.
ENSDORP00000001155, which is hereby incorporated by reference in its
entirety) (SEQ ID NO: 261)
```
  1 MDQAKTRVGA RGLGGLVLAV IILGACKARP IPDSSPLLQF GGVRLRHLY TDDTQETEAH
 61 LEIRADGTVV GTAHRSPESL LELKALKPGV IQILGIKTSR FLCQRPDGTL YGSLHFDPEV
121 CSFQELLLED GYNIYRSEAL GLPLRLSPDP APWGPARFLP LPGVPPAPPE PPGILAPEPP
181 DVGSSDPLSM VGLLQGRSPS YAS
```

*Echinops telfairi* (lesser hedgehog tenrec) FGF21 (Ensembl Accession
No. ENSETEP00000008707, which is hereby incorporated by reference in
its entirety) (SEQ ID NO: 262)
```
  1 MGCTKSGWKS PGLWVPVLAS LLLGGCGAHP IPDSSPLLQF GGVRQRYLY TDDAQTTEAH
 61 LEIRADGTVG GVAHQSPEKF LSQWREKPLR SLHFDPAACS FREKLLEDGY NLYHSETHGL
121 PLRLPPRGGD PSSQPGARFP PLPGQLPQLQ ETPGVLAPEP PDVGSSDPLS MVGPWRGQSP
181 SYAS
```

*Macaca mulatta* (rhesus monkey) FGF21 (Ensembl Accession No.
ENSMMUP00000031540, which is hereby incorporated by reference in its
entirety) (SEQ ID NO: 263)
```
  1 MDSDETGFEH SGLWVPVLAG LLLGACQAHP IPDSSPLLQF GGVRQRYLY TDDAQQTEAH
 61 LEIREDGTVG GAAHQSPESE CGPEPGSEGG GAVGGAEGPG LLGLREAGLG PGSWLHFDPE
121 ACSFRELLLE NGYNVYQSEA HGLPLHLPGN KSPHRDPASQ GPARFLPLPG LPPAPPEPPG
181 ILAPQPPDVG SSDPLSMVGP SQARSPSYAS
```

*Microcebus murinus* (mouse lemur) FGF21 (Ensembl Accession No.
ENSMICP00000012089, which is hereby incorporated by reference in its
entirety) (SEQ ID NO: 264)
```
  1 MGWDEAGAGF EHPGLWFPML GVLLLGACQA YPIPDSSPLL QFGGVRQRH LYTDDIQETE
 61 AHLEIRADGT VVGAARQSPE LELKALKPGV IQILGVKTSR FLCQRPDGAL YGSLHFDPEC
121 SFRELLLEDG YNVYCPYLPL HLSPRIELAG SRSALPLPPA PERRILAPEP PDGSSDPLSM
181 VGPSQGRSPS YAS
```

*Ochotona princeps* (pika) FGF21 (Ensembl Accession No.
ENSOPRP00000006754, which is hereby incorporated by reference in its
entirety) (SEQ ID NO: 265)
```
  1 KDMDGLQPPG LRVPVLAALL LGVGQARPIP DSSPLLQFGG QVRQRHLYTD DAQESEVHLE
 61 IRADGTVAGT ARRSPESLLE MKALKPGVIQ ILGVHTSRFL CQRPDGTLYG SLHFDHKACS
121 FREQLLEDGY NVYHSETHGL PLRLSPDRAP RGPARFLPLP GPPPDLLVPP LPPDVLAPEP
181 PDVDSPDPLS MVGPLQGQSP SYTS
```

*Xiphophorus maculatus* (platyfish) FGF21 (Ensembl Accession No.
ENSXMAP00000001576, which is hereby incorporated by reference in its
entirety) (SEQ ID NO: 266)
```
  1 CPFPFLFLIL SLPFFSSSFY IPESNPIFAF RNQLREVHLY TENHRRGLYV EIHLDGRVTG
 61 SDAQSPYSVL QIKSVKPGHV VIKGQTSSLF LCMDDSGNLR GQTTYDEADC SFRELLLADG
121 YTRFLNSQHG VPLSLASRNS PDRHSVPFTR FLPLRNTLTV SEESTKTQRD FNLDSDDLLG
181 MG
```

*Gasterosteus aculeatus* (stickleback) FGF21 (Ensembl Accession No.
ENSGACP00000010703, which is hereby incorporated by reference in its
entirety) (SEQ ID NO: 267)
```
  1 SLLLMVPLPF CSSFYLTDSS PLLPFNNQVK EVHLYTAENH RRAMYLQIAL DGSVSGSDAR
 61 STYSVLQLKS IQPGHVVIRG KASSMFLCVD SGGRLRGQGP YSEADCSFRE LLLGDGYTRF
121 LSSQHGSPLS LASRPSPDPN SVPFTRFLPI RTAPEAESVI EEPPSNQRYV NVDSEDLLGM
181 GLNTVVSPQF SA
```

*Sarcophilus harrisii* (tasmanian devil) FGF21 (Ensembl Accession No.
ENSSHAP00000005963, which is hereby incorporated by reference in its
entirety) (SEQ ID NO: 268); partial sequence corresponding to human
FGF21 residues 3 to 172
```
  1 VSAMGLRERA PRYLAPLLSL LLACRASGHP LPDSSPMLLF GGVRLRHLY TDVGQEAEAH
 61 VELASDGTVR AAARRSPNSL LELKAVKPGI VRILAVHSSR FLCMRPNGEL YGAIHYDPSA
121 CNFRERLLGD GYNVYESEAH GRTLRLPPKA APGPAGPSRF LPLPG
```

TABLE 7-continued

*Macropus eugenii* (wallaby) FGF21 (Ensembl Accession No. ENSMEUP00000013936, which is hereby incorporated by reference in its entirety) (SEQ ID NO: 269)

```
  1 TEEPSTGSRH LGQWAPGLPG PLLSLLLAYR GWGSPIPDSS PMLLFGGQVR LRHLYTDDGQ
 61 DTEAHVELGP DGVVRAVAER SPNSLLELKA VKPGVIRILA VQSSRFLCMR PNGELYGAVH
121 YDPSACNFRE HLLGDGYNVY ESETHRRTLR LSPSLGQAGP SRFLPLPGDW LPGPDPPWAQ
181 GPEPPDVGSA DPLSMVGAVQ GLSPSYSS
```

*Xenopus tropicalis* (Western clawed frog) FGF21 (Ensembl Accession No. ENSXETP00000009917, which is hereby incorporated by reference in its entirety) (SEQ ID NO: 270); partial sequence corresponding to human FGF21 residues 1 to 169

```
  1 RGGRTKKKTL LRKWLCLLAI MLSRSRFSLA NPIQNSNPIL SNDNQVRTQY LYTDNNNMHL
 61 YLQITHNGVV TGTEEKNDYG VLEIKAVKAG VVVIKGIRSN LYLCMDSRHQ LYASAYDKDD
121 CHFHEKITPD NYNMYSSEKH SEYVSLAPLK GSQMARFLPI
```

*Danio rerio* (zebrafish) FGF21 (Ensembl Accession No. ENSDARP00000094287, which is hereby incorporated by reference in its entirety) (SEQ ID NO: 271)

```
  1 MLLACFFIFF ALFPHLRWCM YVPAQNVLLQ FGTQVRERLL YTDGLFLEMN PDGSVKGSPE
 61 KNLNCVLELR SVKAGETVIQ SAATSLYLCV DDQDKLKGQH HYSALDCTFQ ELLLDGYSFF
121 LSPHTNLPVS LLSKRQKHGN PLSRFLPVSR AEDSRTQEVK QYIQDINLDS DDPLGMGHRS
181 HLQTVFSPSL HTKK
```

*Bos grunniens mutus* (yak) FGF21 (GenBank Accession No. ELR56628, which is hereby incorporated by reference in its entirety) (SEQ ID NO: 272)

```
  1 MGWDEAKFKH LGLWVPVLAV LLLGTCRAHP IPDSSPLLQF GGVRQRYLY TDDAQETEAH
 61 LEIRADGTVV GAARQSPESL LELKALKPGV IQILGVKTSR FLCQGPDGKL YGSLHFDPKA
121 CSFRELLLED GYNVYQSETL GLPLRLPPQR SSNRDPAPRG PARFLPLPGL PAEPPDPPGI
181 LAPEPPDVGS SDPLSMVGPS YGRSPSYTS
```

*Saimiri boliviensis boliviensis* (Bolivian squirrel monkey) FGF21 (GenBank Accession No. XP_003940375, which is hereby incorporated by reference in its entirety) (SEQ ID NO: 273)

```
  1 MGSEEVALER PALWVSVLAG LLLGTCQAYP IPDSSPLLQF GGVRQRYLY TDDAQQTEAH
 61 LEIREDGTVA GAAHQSPESL LQLKALKPGV IQILGVKTSR FLCQRPDGAL YGSLYFDPEA
121 CSFRELLLED GYNVYQSVAH SLPHLPGGR SPPWDPAPRG PARFLPLPGL PPEPPEAPGI
181 LAPEPPDVGS SDPLSMVGPS QGQSPSYTS
```

*Callithrix jacchus* (white-tufted-ear marmoset) FGF21 (GenBank Accession No. XP_003735669, which is hereby incorporated by reference in its entirety) (SEQ ID NO: 274)

```
  1 MGSEEVGLEH PALWVSVLAG LLLGTCQAHP IPDSSPLLQF GGVRQRYLY TDDAQQKEAH
 61 LEIXEDGTVA GAATKVPKVS LLQLKALKPG VIQILGVKTS RFLCQRPDGA LYGSLHFDPE
121 ACSFRELLLE DGYNVYQSVA HGLPLHLPES RSPPRDPAPR GPARFLPLPG LPPEPPEPPG
181 ILAPEPPDVG SSDPLSMVGP SQGQSPSYAS
```

*Tupaia chinensis* (Chinese tree shrew) FGF21 (GenBank Accession No. ELW47159, which is hereby incorporated by reference in its entirety) (SEQ ID NO: 275)

```
  1 MGWDKARFEH LGAWAPVLAV LLLGACQAYP IPDSSPLLQF GGVRQRYLY TDDTQDTEAH
 61 LEIRADGTVV GAAHQSPESL LELKALKPGV IQILGVKTSR FLCQRPDGAL YGSLHFDPEA
121 CSFRELLLED GYNIYQSEAR GLPLRLPPHD SPHRDRTPQG PARFLPLPGL PLVPPELPGV
181 LALEPPDVGS SDPLSMMGPS QGQSPSYAS
```

*Papio anubis* (olive baboon) FGF21 (GenBank Accession No. XP_003915900, which is hereby incorporated by reference in its entirety) (SEQ ID NO: 276)

```
  1 MDSDETGFEH SGLWVPVLAG LLLGACQAHP IPDSSPLLQF GGVRQRYLY TDDAQQTEAH
 61 LEIREDGTVG GAAHQSPESK CGPEPGSEGG GALHFDPEAC SFRELLLENG YNVYQSEAHG
121 LPLHLPGNKS PHRDPASRGP ARFLPLPGLP PAPPEPPGIL APQPPDVGSS DPLSMVGPSQ
181 ARSPSYAS
```

*Pteropus alecto* (black flying fox) FGF21 (GenBank Accession No. ELK18566, which is hereby incorporated by reference in its entirety) (SEQ ID NO: 277)

```
  1 MGWGKARLQH PGLWGPVLAV LLGACQAHPI LDSSPLFQFG SQVRRRYLYT DDAQDTEAHL
 61 EIRADGTVAG AARRSPESLL ELKALKPGVI QVLGVKTSRF LCQRPDGTLY GSLHFDPAAC
121 SFRELLLKDG YNVYQSEALA RPLRLPPYSS PSSDPARRGP ARFLPLPGPP PEPPQPPGRL
181 APEPPDVGSS DPLSMVWPSR GRSPSYTS
```

*Heterocephalus glaber* (naked mole-rat) FGF21 (GenBank Accession No. EHB06286, which is hereby incorporated by reference in its entirety) (SEQ ID NO: 278)

```
  1 MDWARAESER PGLWVPAVLA VLLLGACQAH PIPDSSPLLQ FGGQVRQRHL YTDDAQDTEV
 61 HLEIRADGSV GGAAHRSPES LLELKALKPG VIQILGVRTS RFLCQRPDGT LYGSLHFDPE
121 ACSFRELLLA DGYNIYQSEA YGLPLRMLPS DSASRDPVPP GPARFLPLPG LHPPPLEPPG
181 MLPPEPPDVG SSDPLSMVGP LQGRSPSYAF
```

TABLE 7-continued

```
Cricetulus griseus (Chinese hamster) FGF21 (GenBank Accession No.
XP_003508726, which is hereby incorporated by reference in its
entirety) (SEQ ID NO: 279)
    1 MDWMKSGVGV PGLWVPLLPI FLLGVSQAHP IPDSSPLLQF GGQVRHRHLY TDDNQETEVH
   61 LEIRQDGTVI GTTHRSPESL LELKALKPEV IPVLGVKASR FLCQQPDGTL YGSPHFDPEA
  121 CSFRELLLED GYNVYQSEVH GLPLRLPQRD SPNQAPASWG PVPPLPVPGL LHQPQELPGF
  181 LAPEPPDVGS SDPLSMVGPL QGRSPSYAS Ovis aries (sheep) FGF21 (GenBank Accession No. XP_004015845, which is
hereby incorporated by reference in its entirety) (SEQ ID NO: 280)
    1 MGWDEAKFKH LGLWVPVLAV LLLGTCRAHP IPDSSPLLQF GGQVRQRYLY TDDAQETEAH
   61 LEIRADGTVV GAARQSPESL LELKALKPGV IQIFGVKTSR FLCQGPDGKL YGSLHFDPKA
  121 CSFRELLLED GYNVYQSETL GLPLRLPPQR SSNRDPAPRG PPKPQLHFLK TSAVQYWPRY
  181 EKVPAFLHPF PG Pan paniscus (pygmy chimpanzee) FGF21 (GenBank Accession No.
XP_003814163, which is hereby incorporated by reference in its
entirety) (SEQ ID NO: 281); partial sequence corresponding to human
FGF21 residues 1 to 116 and 195 to 201
    1 MDSDETGFEH SGLWVSVLAG LLLGACQAHP IPDSSPLLQF GGQVRQRYLY TDDAQQTEAH
   61 LEIREDGTVG GAADQSPESL LQLKALKPGV IQILGVKTSR FLCQRPDGAL YGSVSF----
  121 ---------- ---------- ---------- ----Q----- ---------- -----DPP--
  181 --HHPP---C S---SYMSPS Q---PG---

Macaca fascicularis (crab-eating macaque) FGF21 (GenBank Accession No.
EHH59757, which is hereby incorporated by reference in its entirety)
(SEQ ID NO: 282); partial sequence corresponding to human FGF21
residues 1 to 116
    1 MDSDETGFEH SGLWVPVLAG LLLGACQAHP IPDSSPLLQF GGQVRQRYLY TDDAQQTEAH
   61 LEIREDGTVG GAAHQSPESL LQLKALKPGV IQILGVKTSR FLCQKPDGAL YGSVSF Mesocricetus auratus (golden hamster) FGF21 (GenBank Accession No.
ACB30542, which is hereby incorporated by reference in its entirety)
(SEQ ID NO: 283); partial sequence corresponding to human FGF21
residues 90 to 193
    1 VIQILGVKAA RFPCQQPDGS LYGSPHFDPE ACSFRELLLE DGYNVYQSEA HGLPLRLPQR
   61 DAPSQPPASW GPVRFLPVPG LFQPPHDLPG RPAPEPPDVG SSDP Oreochromis niloticus (Nile tilapia) FGF21 (GenBank Accession No.
XP_003438516, which is hereby incorporated by reference in its
entirety) (SEQ ID NO: 284); partial sequence corresponding to human
FGF21 residues 59 to 209
    1 MYLQMNMDGR VTGSDAQTPY SLMQLKSVKP GHVIIKGPSS SLFLCVDSEG NLRGQSHYSE
   61 TSCTFREMLL ADGYTRFISS QYGFPMSLAS RHSPDRHALP FTRFLPLRNN LKTDSVSEQL
  121 PNNQRLFNVD SDDLLGMGLN SMGSPQFSMD K
```

In certain embodiments according to the present invention, the C-terminal portion of FGF21 of the chimeric protein of the present invention includes a polypeptide sequence that has at least 80%, at least 85%, at least 90%, at least 95%, at least 97%, or at least 99% amino acid sequence identity to amino acid residues 168-209 of SEQ ID NO: 233. In certain embodiments according to the present invention, the C-terminal portion of FGF21 of the chimeric protein of the present invention includes a polypeptide sequence that has at least 80%, at least 85%, at least 90%, at least 95%, at least 97%, or at least 99% amino acid sequence homology to amino acid residues 168-209 of SEQ ID NO: 233.

It will be understood that the portion of FGF21 of the chimeric protein of the present invention may be derived from a nucleotide sequence that encodes a vertebrate or a non-vertebrate FGF21 protein. In one embodiment, the portion of FGF21 of the chimeric protein of the present invention may be derived from a nucleotide sequence that encodes a mammalian FGF21 protein. Nucleotide sequences encoding a vertebrate FGF21 protein according to the present invention may include, but are not limited to, those shown in Table 8. The portion of FGF21 of the chimeric protein of the present invention derived from an ortholog of human FGF21 include portions corresponding to the above-identified amino acid sequences of FGF21. Corresponding portions may be determined by, for example, sequence analysis and structural analysis.

TABLE 8

```
Human FGF21 gene coding sequence (SEQ ID NO: 285) (GenBank Accession
No. NM_019113, which is hereby incorporated by reference in its
entirety)
  151 ATGGACTCGG ACGAGACCGG GTTCGAGCAC TCAGGACTGT GGGTTTCTGT GCTGGCTGGT
  211 CTTCTGCTGG GAGCCTGCCA GGCACACCCC ATCCCTGACT CCAGTCCTCT CCTGCAATTC
  271 GGGGGCCAAG TCCGGCAGCG GTACCTCTAC ACAGATGATG CCCAGCAGAC AGAAGCCCAC
  331 CTGGAGATCA GGGAGGATGG GACGGTGGGG GGCGCTGCTG ACCAGAGCCC CGAAAGTCTC
  391 CTGCAGCTGA AAGCCTTGAA GCCGGGAGTT ATTCAAATCT TGGGAGTCAA GACATCCAGG
  451 TTCCTGTGCC AGCGGCCAGA TGGGGCCCTG TATGGATCGC TCCACTTTGA CCCTGAGGCC
  511 TGCAGCTTCC GGGAGCTGCT TCTTGAGGAC GGATACAATG TTTACCAGTC CGAAGCCCAC
  571 GGCCTCCCGC TGCACCTGCC AGGGAACAAG TCCCCACACC GGGACCCTGC ACCCCGAGGA
```

TABLE 8-continued

```
631 CCAGCTCGCT TCCTGCCACT ACCAGGCCTG CCCCCCGCAC TCCCGGAGCC ACCCGGAATC
691 CTGGCCCCCC AGCCCCCCGA TGTGGGCTCC TCGGACCCTC TGAGCATGGT GGGACCTTCC
751 CAGGGCCGAA GCCCCAGCTA CGCTTCCTGA
```

*Pongo abelii* (Sumatran orangutan) FGF21 gene coding sequence (SEQ ID NO: 286) (GenBank Accession No. XM_002829519, which is hereby incorporated by reference in its entirety)

```
165      ATGGAC TCGGACGAGA CCGGGTTCGA GCACTCAGGA CTGTGGGTTC CTGTGCTGGC
221 TGGTCTTCTG CTGGGAGCCT GCCAGGCACA CCCCATCCCT GACTCCAGTC CTCTCCTGCA
281 ATTCGGGGGC CAAGTCCGGC AGCGGTACCT CTACACAGAT GATGCCAGC AGACAGAAGC
341 CCACCTGGAG ATCAGGGAGG ATGGGACGGT GGGGGGCGCT GCTGACCAGA GCCCCGAAAG
401 TCTCCTGCAG CTGAAAGCCT TGAAGCCGGG AGTTATTCAA ATCTTGGGAG TCAAGACATC
461 CAGGTTCCTG TGCCAGAGGC CAGATGGGGC CCTGTATGGA TCGCTCCACT TTGACCCTGA
521 GGCCTGCAGC TTCCGGGAGC TGCTTCTTGA GGACGGATAC AATGTTTATC AGTCCGAGGC
581 CCATGGCCTC CCGCTGCACC TGCCGGGAAA CAAGTCCCCA CACCGGGACC CTGCACCCCG
641 AGGACCAGCT CGCTTCCTGC CACTACCAGG CCTGCCCCCC GCACCCCAG AGCCGCCCGG
701 AATCCTGGCC CCCCAGCCCC CCGATGTGGG CTCCTGGAC CCTCTGAGCA TGGTGGGACC
761 TTCCCAGGGC CGAAGCCCCA GCTATGCTTC CTGA
```

*Pan troglodytes* (chimpanzee) FGF21 gene coding sequence (SEQ ID NO: 287) (GenBank Accession No. XM_524333, which is hereby incorporated by reference in its entirety)

```
573    ATGGACTC GGACGAGACC GGGTTCGAGC ACTCAGGACT GTGGGTTTCT GTGCTGGCTG
631 GTCTTCTGCT AGGAGCCTGC CAGGCACACC CCATCCCTGA CTCCAGTCCT CTCCTGCAAT
691 TCGGGGGCCA AGTCCGGCAG CGGTACCTCT ACAGATGA TGCCCAGCAG ACAGAAGCCC
751 ACCTGGAGAT CAGGGAGGAT GGGACGGTGG GGGCGCTGG TGACCAGAGC CCCGAAAGTC
811 TCCTGCAGCT GAAAGCCTTG AAGCCGGGAG TTATTCAAAT CTTGGGAGTC AAGACATCCA
871 GGTTCCTGTG CCAGAGGCCA GATGGGGCCC TGTATGGATC GCTCCACTTT GACCCTGAGG
931 CCTGCAGCTT CCGGGAGCTG CTTCTTGAGG ACGGATACAA TGTTTACCAG TCCGAGGCCC
991 ACGGCCTCCC GCTGCACCTG CCGGGGAACA AGTCCCCACA CCGGGACCCT GCACCCCGAG
1051 GACCAGCTCG CTTCCTGCCA CTACCAGGCC TGCCCCCCGC ACCCCGGAG CCACCCGGAA
1111 TCCTGGCCCC CCAGCCCCCC GATGTGGGCT CCTCAGACCC TCTGAGCATG GTGGGACCTT
1171 CCCAGGGCCG AAGCCCCAGC TACACTTCCT GA
```

*Canis lupus familiaris* (dog) FGF21 gene coding sequence (SEQ ID NO: 288) (GenBank Accession No. XM_541510, which is hereby incorporated by reference in its entirety)

```
1 ATGGGCTGGG CCGAGGCCGG GTTCGAGCAC CTGGGACTGT GGGTCCCTGT GCTGGCTGTG
61 CTTTTGCTGG AAGCCTGCCG GGCACATCCG ATCCCTGACT CCAGCCCCCT CCTACAATTT
121 GGAGGTCAAG TTCGACAGCG GTACCTCTAC ACCGACGATG CCCAGGAGAC AGAGGCCCAC
181 CTAGAGATCA GGGCCGATGG CACAGTGGTG GGGGCTGCCC GCCAGAGCCC TGAAAGTCTC
241 CTGGAGCTGA AAGCCCTAAA GCCAGGGGTC ATTCAAATCT TGGGAGTCAA AACATCCAGG
301 TTCCTGTGCC AGGGCCCAGA TGGGACACTA TATGGCTCGC TCCATTTCGA CCCTGTGGCC
361 TGCAGTTTCC GAGAACTGCT TCTTGAGGAT GGGTACAACA TCTACCACTC CGAGACCCTT
421 GGTCTCCCGC TTCGCCTGCG CCCCCACAAC TCCGCATACC GGGACTTGGC ACCCCGCGGG
481 CCTGCCCCGCT TCCTGCCACT GCCAGGCCTG CTTCCAGCAC CCCCAGAGCC TCCAGGGATC
541 CTGGCCCCGG AGCCTCCTGA CGTGGGCTCC TCGGACCCTC TGAGCATGGT GGGGCCTTCA
601 CAGGGCCGGA GTCCCAGCTA TGCTTCCTAA
```

*Bos taurus* (bovine) FGF21 gene coding sequence (SEQ ID NO: 289) (GenBank Accession No. XP_001789587, which is hereby incorporated by reference in its entirety)

```
1 ATGGGCTGGG ACGAGGCCAA GTTCAAGCAC TTGGGACTGT GGGTCCCTGT GCTGGCTGTC
61 CTCCTGCTAG AACCTGCCG GCGCATCCC ATTCCAGACT CCAGCCCCCT CCTCCAGTTT
121 GGGGGCCAAG TCCGCCAGCG GTACCTCTAC ACGGATGATG CCCAGGAGAC AGAGGCCCAC
181 CTGGAGATCA GGGCCGATGG CACAGTGGTG GGGGCAGCCC GCCAGAGCCC CGAAAGTCTC
241 TTGGAGCTGA AAGCCCTGAA GCCAGGCGTC ATTCAGATCT TGGGAGTTAA AACATCCAGG
301 TTTCTCTGCC AGGGGCCAGA TGGGAAGCTG TACGGATCGC TGCACTTTGA CCCCAAAGCC
361 TGCAGCTTTC GGGAGCTGCT TCTTGAAGAT GGATACAACG TCTACCAGTC GGAGACCCTG
421 GGCCTTCCAC TCCGCCTGCC CCCCCAGCGC TCGTCCAACC GGGACCCGGC CCCGCGGGGA
481 CCTGCTCGCT TCCTTCCACT GCCGGGCCTG CCCGCGGCGC CCCCGGATCC TCCAGGGATC
541 TTGGCCCCCG AGCCTCCCGA CGTGGGCTCC TCGGATCCCC TGAGTATGGT GGGACCCTCG
601 TATGGCCGAA GCCCCAGCTA CACTTCTTGA
```

*Equus caballus* (horse) FGF21 gene coding sequence (SEQ ID NO: 290) (GenBank Accession No. XM_001489152, which is hereby incorporated by reference in its entirety)

```
1 ATGGACTGGG ACAAGACGGG GTTCAAGTAC CAGGGACTGT GGGTCCCTGT GCTGGCTGTC
61 CTTCTGCTGG GAGCCTGCCA GTCACACCCC ATCCCTGACT CCAGTCCCCT CCTCCAATTC
121 GGGGGCCAAG TCAGGCAGCG CCACCTCTAC ACAGATGATG CCCAGGAGAC AGAGGCGCAC
181 CTGGAGATCA GGGCTGACGG CACTGTGGCA GGGGCTGTCC ACCGGAGCCC AGAAAGTCTC
241 TTGGAGCTGA AAGCCCTGAA GCCAGGGGTA ATTCAAATCT TGGGAGTCAA GACATCCAGG
301 TTTCTGTGCC AGGGGCCAGA CGGGACGCTG TACGGATCGC TCCACTTCGA CCCCGTGGCC
361 TGCAGCTTCC GGGAGCTGCT TCTCGAAGAC GGCTACAACG TTTACCAGTC TGAGACCCTT
421 GGCCTCCCAC TCCGCCTGCC CCACCACAGC TCCCCATACC AGGATCCGGC CCCTCGGGCA
481 CCCGCCCGCT TCCTGCCGCT GCCAGGCTTT CCCCCAGCAC CCCCGGAGCC TCCAGGGATC
541 CCGGCCCCCG AGCCCCCGGA CGTGGGCTCC TCGGACCCCC TGAGCATGGT GGGGCCTTCA
601 CGCAGCCGGA GCCCCAGCTA CACTTCCTGA
```

TABLE 8-continued

*Ailuropoda melanoleuca* (giant panda) FGF21 gene coding sequence (SEQ
ID NO: 291) (GenBank Accession No. XM_002917864, which is hereby
incorporated by reference in its entirety)

```
  1 ATGGGCTGGG ACGAGGCCAG GTCCGAGCAG CTGGGGCTGT GGGTCCCTGT GCTGGCTGTC
 61 CTTTTGCTGG AAGCTTGCCA GGCACACCCT ATCCCTGACT CCAGCCCCCT CCTCCAATTC
121 GGAGGCCAAG TTCGACAGCG GTACCTCTAC ACGGACGATG CCCAGGAGAC AGAGGCCCAC
181 CTAGCGATCA GGGCTGATGG CACAGTGGTG GGGGCTGCCA GCCGGAGCCC AGAAAGTCTC
241 TTGGAGCTGA AAGCCCTGAA ACCGGGGGTC ATTCAAATCT GGGGAGTGAA AACATCTAGG
301 TTCCTGTGCC AGGGCCCAGA TGGGACACTG TACGGATCGG TCCGCTTCGA CCCCGTAGCC
361 TGCAGCTTCC GGGAACTGCT CCTGGAGGAT GGGTACAACA TCTACCACTC TGAGACCCTC
421 GGCCTCCCAC TTCGCCTGCC CGCCCACAAC TCTCCATACC GGGACTCGGC GCCCCGGGGG
481 CCTGCCCGCT TCCTGCCCCT GCCAGGCCTG CTTCCGGTCC CCCCGGACCC CCCAGGGATC
541 CTGGGCCCCG AGCCTCCCGA CGTGGGCTCC TCGGACCCCC TGAGCATGGT GGGGCCTTCA
601 CAGGGCCGAA GTCCCAGCTA CGCTTCCTGA
```

*Oryctolagus cuniculus* (rabbit) FGF21 gene coding sequence (SEQ ID NO:
292) (GenBank Accession No. XM_002723699, which is hereby incorporated
by reference in its entirety)

```
  1 ATGGACTGGG GCAAGGCCAA GTGCCGGCCC CCGGGGCTGT GGGTCCCCGC GCTCGCTGCC
 61 CTGCTGCTGG GGGCCTGCCA GGCACACCCC ATCCCCGACT CCAGCCCCCT CCTCCAGTTT
121 GGGGACCAAG TGCGGCAGCA GCACCTGTAC ACGGACGATG CGCAGGAAAC AGAAGCCCAC
181 CTGGAGATCA GGGCGGATGG CACGGTGGTG GGGGCTGCCC GGAGGAGCCC AGAAAGTCTC
241 TTGCAGATGA AAGCCTTACA ACCGGGGATC ATTCAGATCT GGGGGTCCA GACGTCCAGG
301 TTCCTCTGCC AGAGGCCGGA TGGCACGCTC TACGGCTCGC TCCACTTCGA CCGCGAGGCC
361 TGCAGCTTCC GGGAGCTGCT GCGTGAGGAT GGGTACAACA TTTACCTCTC GGAGGCCCTG
421 GGCCTGCCCC TGCGCCTGTC CCCCGGCAGC TCCCCACGCA GGGCGCCGGC CCCCCGGGGA
481 CCAGCCCGCT TCCTGCCGCT GCCCGCCCTG CCGCCAGACC TTCCGGAACC GCCAGGCCTC
541 CTGGCCGCCG CGCCCCCCGA TGTCGACTCC CCGGACCCCC TGAGCATGGT GCAGCCTGCG
601 CTGGACCAGA GCCCCAGCTA CACCTCCTGA
```

*Gorilla gorilla* (gorilla) FGF21 gene coding sequence (SEQ ID NO: 293)
(Ensembl Accession No. ENSGGOT00000001253, which is hereby
incorporated by reference in its entirety)

```
151 ATGGACTCGG ACGAGACCGG GTTCGAGCAC TCAGGACTGT GGGTTTCTGT GCTGGCTGGT
211 CTTCTGCTGG GAGCCTGCCA GGCACACCCC ATCCCTGACT CCAGTCCTCT CCTGCAATTC
271 GGGGGCCAAG TCCGGCAGCG GTACCTCTAC ACAGATGATG CCCAGCAGAC AGAAGCCCAC
331 CTGGAGATCA GGGAGGATGG GACGGTGGGG GGTGCTGCTG ACCAGAGCCC TGAAAGTCTC
391 CTGCAGCTGA AAGCCTTGAA GCCGGGAGTT ATTCAAATCT TGGGAGTCAA GACATCCAGG
451 TTCCTGTGCC AGAGGCCAGA TGGGGCCCTG TATGGATCGC TCCACTTTGA CCCTGAGGCC
511 TGCAGCTTCC GGGAGCTGCT TCTTGAGGAC GGATACAATG TTTACCAGTC CGAGGCCCAC
571 GGCCTCCCGC TGCACCTGCC GGGGAACAAG TCCCCACACC GGGACCCTGC ACCCCGAGGA
631 CCAGCTCGCT TCCTGCCACT ACCAGGCCTG CCCCCCGCAC CCCCGGAGCC ACCCGGAATC
691 CTGGCCCCCC AGCCCCCCGA TGTGGGCTCC TCGGACCCTC TGAGCATGGT GGGACCTTCC
751 CAGGGCCGAA GCCCCAGCTA CGCTTCCTGA
```

*Nomascus leucogenys* (Northern white-cheeked gibbon) FGF21 gene coding
sequence (SEQ ID NO: 294) (Ensembl Accession No. ENSNLET00000005931,
which is hereby incorporated by reference in its entirety)

```
587      ATGG ACTCGGACGA GACCGGGTTC GAGCACTCAG GACTGTGGGT TCCTGTGCTG
647 GCTGGTCTTC TGCTGGGAGC CTGCCAGGCA CACCCCATCC CTGACTCCAG TCCTCTCCTG
707 CAATTCGGGG GCCAAGTCCG GCAGCGGTAC CTCTACACAG ATGATGCCCA GCAGACAGAA
767 GCCCACCTGG AGATCAGGGA GGATGGGACG GTGGGGGCGC TGCTGACCA GAGCCCTGAA
831 AGTCTCCTGC AGCTGAAAGC CTTGAAGCCG GGAGTTATTC AAATCTTGGG AGTCAAGACA
891 TCCAGGTTCC TATGCCAGAG GCCAGATGGG GCCCTGTATG GATCGCTCCA CTTTGACCCT
951 GAGGCCTGCA GCTTCCGGGA GCTGCTTCTT GAGGACGGAT ACAATGTTTA CCAGTCCGAG
1011 GCCCATGGCC TCCCGCTGCA CCTGCCGGGG AACAAGTCCC CACACCGGGA CCCTGCACCC
1071 CGAGGACCAG CTCGCTTCCT GCCACTACCA GGCCTGCCCC CTGCACCCCC AGAGCCGCCC
1131 GGAATCCTGG CCCCCCAGCC CCCCGATGTG GGCTCCTCGG ACCCTCTGAG CATGGTGGGA
1191 CCTTCCCAGG GCCGAAGCCC CAGCTACGCT TCCTGA
```

*Procavia capensis* (hyrax) FGF21 gene coding sequence (SEQ ID NO: 295)
(Ensembl Accession No. ENSPCAT00000001288, which is hereby
incorporated by reference in its entirety)

```
  1 ATGGACTGGG CCAAGTTTGG GATCGAGCAC CCGGGACTGT GGGTCCCGGT GATGGCAGTA
 61 CTTCTGCTGG GAGCCTGCCA AGGATACCCT ATTCCTGACT CCAGCCCCCT TCTCCAATTC
121 GGAGGCCAGG TCCGGCAACG TTACCTCTAC ACAGATGACG CGCAGGAGAC CGAGGCCCAC
181 CTGGAGATCC GAGCAGACGG CACGGTGGTG GGGGCTGCCC ACCGGAGCCC CGGAGAGTCTC
241 TTGGAGCTGA AAGCTTTGAA GCCCGGCATA ATTCAGATCT TGGGAGTCAA GACATCCAGA
301 TTCCTCTGCC AGGGTCCTGA TGGGGTGCTG TATGGATCGC TCCGTTTTGA CCCAGTGGCC
361 TGCAGCTTCC GGGAGCTGCT TCTTGAAGAT GGATACAATG TTTACCAGTC TGAGGCCCAC
421 GGCCTCCCGC TTCGCCTACC ATCCCACAAT TCCCCACAGA GGGACCTGGC GTCCCGGGTG
481 CCAGCCCGCT TCCTGCCACT GCCAGGCCGG CTCACGGTGC TCCCAGAACC TTCGGGGGTC
541 CTGGGCCCTG AGCCCCCCGA TGTGGACTCC TCAGACCCCC TGAGCATGGT GGGGCCTTCG
601 CAGGGCCGAA GCCCCAGTTA CGCCTCCTGA
```

*Cavia porcellus* (guinea pig) FGF21 gene coding sequence (SEQ ID
NO: 296) (Ensembl Accession No. ENSCPOT00000000273, which is hereby
incorporated by reference in its entirety)

```
  1 ATGGACTGGG CCCGGACTGA GTGTGAGCGC CAAGGCTGTG GGTCTCCAT GCTGGCCATC
 61 CTTCTGGTGG GAGCCTGCCA GGCACACCCT ATCCCTGACT CCAGCCCCCT CCTCCAGTTT
```

TABLE 8-continued

```
121 GGGGGCCAGG TCCGGCAGCG GTACCTCTAC ACAGATGATG CTCAGGACAC TGAAGTGCAC
181 CTGGAGATCA GGGCCGATGG CTCAGTACGG GGCATTGCCC ACAGGAGCCC TGAAAGTCTC
241 CTGGAGCTGA AAGCCTTGAA GCCAGGAGTC ATTCAGATCT TGGGAATCAG GACTTCCAGG
301 TTCCTGTGCC AGAGGCCCGA TGGGAGTCTG TATGGATCAC TCCACTTTGA TCCTGAGGCC
361 TGCAGCTTCC GGGAGCTGCT GCTTGCTGAT GGCTACAATG TCTACAAGTC TGAAGCCCAC
421 GGCCTCCCTC TGCACCTGCT GCGCGGTGAC TCTCTATCGC AGGAACCAGC ACCCCCAGGA
481 CCAGCCCGAT TTCTGCCACT ACCAGGCCTG CCCGCAACAC CCCCGGAGCC ACCCAGGATG
541 CTGCCCCCAG GCCCCCAGA TGTGGGCTCC TCGGACCCTT TGAGCATGGT GGGGCCTTTA
601 TGGGACCGAA GCCCCAGCTA TACTTCCTGA
```

*Tupaia belangeri* (tree shrew) FGF21 gene coding sequence (SEQ ID
NO: 297) (Ensembl Accession No. ENSTBET00000016056, which is hereby
incorporated by reference in its entirety)

```
  1 ATGGGCTGGG ACAAGGCCCG GTTCGAGCAC CTGGGAGCGT GGGCTCCTGT GCTGGCTGTC
 61 CTCCTCCTGG GAGCCTGCCA GGCATACCCC ATCCCTGACT CCAGCCCCCT CCTACAATTC
121 GGGGGCCAGG TCCGGCAGCG GTACCTCTAC ACGGACGACA CGCAGGACAC AGAAGCCCAC
181 CTTGAGATCA GGGCCGACGG CACCGTGGTG GGGGCCGACC ACCAAAGCCC GGAAAGTCTC
241 CTGGAGCTGA AAGCCTTGAA GCCGGGGGTC ATTCAAATCC TGGGGAGTCAA GACCTCCAGG
301 TTCCTGTGCC AGAGGCCAGA CGGGGCCCTG TACGGGTCGC TTCACTTCGA CCCCGAGGCC
361 TGCAGCTTCC GGGAGCTGCT TCTCGAGGAT GGATACAACA TTTACCAGTC TGAGGCTCGT
421 GGCCTCCCCC TGCGCCTGCC GCCCCACGAC TCCCCACATC GGGACCGGAC CCCTCGGGGA
481 CCAGCTCGTT TCCTGCCGCT GCCTGGCCTG CCCCTGGTTC CTCCAGAGCT GCCAGGGGTC
541 CTGGCCCTTG AGCCCCCGA CGTGGGCTCC TCAGACCCGC TGA
```

*Sorex araneus* (shrew) FGF21 gene coding sequence (SEQ ID NO: 298)
(Ensembl Accession No. ENSSART00000003074, which is hereby
incorporated by reference in its entirety)

```
  1 ATGGTCTGGG ACAAGGCCAG GGGGCAGCAG TTGGGACTGT GGGCCCCCAT GCTGCTGGGC
 61 TTGCTGCTGG GTGCCTGCCA GGCACACCCC CTCCCTGACT CCAGCCCCT CCTCCAATTC
121 GGGGGCCAAG TCCGACTGAG GTTCCTGTAC ACCGACGATG CCCAGAGGAC AGGGGCGCAC
181 CTGGAGATCA GGGCCGACGG CACAGTGCAG GGTGCGGCCC ACAGGACCCC AGAATGTCTC
241 CTGGAGCTGA AAGCCTTGAA GCCAGGCGTA ATTCAAATCC TTGGGGTCAG CACATCCAGA
301 TTCCTGTGCC AGCGGCCCGA TGGGGTCCTG TATGGATCGC TTCGCTTTGA CCCAGAGGCC
361 TGCAGTTTCC GGGAACTTCT TCTCCAGGAT GGATATAACG TTTACCAGTC TGAGGCCCTG
421 GGTCTCCCGC TCTACCTACA CCCGCCCAGT GCCCCAGTGT CCCAGGAACC AGCCTCACGG
481 GGCGCCGTCC GCTTCCTGCC ACTGCCAGGA CTGCCACCTG CCTCCCTGGA GCCCCCCAGG
541 CCCCCCGCCC GGTGCCTCC AGACGTGGGT TCCTCAGACC CCCTGA
```

*Ictidomys tridecemlineatus* (squirrel) FGF21 gene coding sequence (SEQ
ID NO: 299)

```
  1 ATGTACCCCA TCCCTGACTC AAGCCCCCTC CTCCAATTTG GGGGCCAAGT CCGGCAGCGG
 61 TACCTGTACA CAGATGATGC CCAGGAGACT GAGGCCCACC TGGAGATCAG GGCTGATGGC
121 ACCGTGGTGG GGGCTGCCCA TCAAAGCCCG GAAAGTCTCT TGGAACTGAA AGCCTTGAAG
181 CCTGGGGTCA TTCAAATCTT GGGGGTCAAA ACATCCAGGT TCCTGTGCCA GAGGCCAGAT
241 GGAGTGCTGT ATGGATCGCT CCACTTTGAC CCTGAGGCCT GCAGCTTCCG GGAGCAGCTT
301 CTGGAGGACG GGTACAACGT TTACCAGTCA GAATCCCACG GCCTCCCCGT GCGCCTGCCC
361 CCTAACTCAC CATACCGGGA CCCAGCGCCG CCAGGACCAG CCCGCTTCCT TCCACTGCCA
421 GGCCTGCCCC CAGCAGCCCT GGAGCCGCCA GGGATCCTGG GCCCTGAGCC CCTGATGTG
481 GGCTCCTCCG ACCCACTCAG CATGGTGGGG CCTTTGCAGG GCCGAAGCCC CAGTTACGCT
541 TCCTGA
```

*Loxodonta africana* (elephant) FGF21 gene coding sequence (SEQ ID
NO: 300) (Ensembl Accession No. ENSLAFT00000022429, which is hereby
incorporated by reference in its entirety)

```
  1 ATGGACTGGG CCAAGTTTGG GTTGGAGCAC CCAGGACTGT GGGTCCCTGT GATGGCTGTC
 61 CTTCTGCTGG GAGCCTGCCA GGGACACCCC ATCCCTGACT CCAGCCCCCT CCTCCAATTC
121 GGGGGCCAGG TCCGGCAACG TTACCTCTAC ACAGATGATC AGGAGACCGA GGCCCACCTG
181 GAGATCAGAG CAGATGGCAC AGTGGCGGGA GCCGCTCACA GGACGTCTGA GAGTCTCTTG
241 GAGCTGAAAG CTTTGAAGCC TGGAATAATT CAGATCTTGG GGGTCAAGAC ATCCCGGTTC
301 CTGTGCCAGG GCCTGATGG GGTGCTGTAC GGATCGCTCC ATTTCGACCC AGCCGCCTGC
361 AGCTTCCGGG AGCTGCTTCT TGAAGATGGA TACAATGTTT ACTGGTCCGA GGCCCATGGA
421 CTCCCAATCC GCCTGCCCTC CCACAACTCC CCATATAGGG ACCCAGCATC CCGGGTACCA
481 GCCCGCTTCC TGCCACTGCC AGGCCTGCTC CCAATGCTCC AAGAACCTCC AGGGGTCCTG
541 GCCCCTGAGC CCCCTGATGT GGACTCCTCA GACCCCCTGA GCATGGTGGG GCCTTCACAG
601 GGCCGAAGCC CCAGCTATGC CTCCTGA
```

*Sus scrofa* (pig) FGF21 gene coding sequence (SEQ ID NO: 301) (GenBank
Accession No. NM_001163410, which is hereby incorporated by reference
in its entirety

```
131 ATGGGCTGGG CCGAGGCCAA GTTCGAGCGC TTGGGACTGT GGGTCCCTGT GCTGGCTGTC
191 CTGCTGGGAG CCTGCCAGGC ACGTCCCATT CCTGACTCCA GCCCCCTCCT CCAATTTGGG
251 GGCCAAGTGC GCCAACGATA CCTCTACACG GATGATGCCC AGGAAACTGA AGCCCACCTG
311 GAGATCAGAG CTGATGGCAC CGTGGCAGGG GTAGCCCGCC AGAGCCCTGA AAGTCTCTTG
371 GAGCTGAAAG CCCTGAAGCC AGGGGTCATT CAAATTTTGG GAGTCCAGAC ATCCCGGTTC
431 CTGTGCCAGG GGCCAGACGG GAGACTGTAC GGATCGCTCC ACTTCGACCC TGAGGCCTGC
491 AGCTTCCGGG AGCTGCTTCT TGAGGATGGC TACAACGTTT ACCAGTCTGA GGCCCTTGGC
551 CTCCCACTCC GGCTGCCTCC GCACCGCTCC TCCAACCGGG ACCTGGCCCC CCGGGGACCT
611 GCTCGCTTCC TGCCACTGCC AGGCCTGCCC CGGCACCCC GGAGCCGCC AGGGATCTTG
671 GCCCCTGAAC CTCCCGACGT GGGCTCCTCG ACCCCCTGA GCATGGTGGG GCCTTCACAC
731 GGCCGGAGCC CCAGCTACAC TTCTTGA
```

TABLE 8-continued

*Felis catus* (cat) FGF21 gene coding sequence (SEQ ID NO: 302) (Ensembl Accession No. ENSFCAT00000007367, which is hereby incorporated by reference in its entirety)

```
  1  ATGGGCTGGG ACGAGGCCGG GTCCCAGCGC CTGGGACTGT GGGTCGTGCT GGGGGTCCTT
 61  TTGCCGGAAG CCTGCCAGGC ACACCCTATC CCTGACTCCA GCCCCTCCT CCAATTCGGG
121  GGCCAAGTTC GACAGCGGTT CCTCTACACG GACGACGCCC AGGAGACAGA GGTCCACCTC
181  GAGATCAAGG CTGATGGCAC AGTGGTGGGG ACCGCTCGCC GGAGCCCTGA GAGTCTCTTG
241  GAGCTAAAAG CCCTGAAGCC GGGGGTAATT CAAATCTTGG GGGTCAAAAC GTCCAGGTTC
301  CTGTGCCAGG GCCCAGATGG GACACTGTAT GGATCGCTCC GCTTTGACCC CGCAGCCTGC
361  AGCTTCCGGG AACTGCTCCT GGAGGACGGA TACAACATCT ACCACTCGGA GACCCTCGGG
421  CTCCCACTCC GCCTGCCCCC CCACAACTCC CCATACCGGG ACTTGGCCCC CCGGGCACCT
481  GCCCGCTTCC TGCCGCTGCC AGGCCTGCTT CCGGCACCCC CGGAGCCTCC AGGGATCCTG
541  GCCCCCGAGC CCCCGGACGT GGGCTCCTCG GACCCTCTGA GCATGGTGGG GCCTTCCCAG
601  GGCCGAAGTC CCAGCTACGC TTCCTGA
```

*Otolemur garnettii* (bushbaby) FGF21 gene coding sequence (SEQ ID NO: 303) (Ensembl Accession No. ENSOGAT00000003585, which is hereby incorporated by reference in its entirety)

```
  1  GACAAGGCCA GGACTGGGTT CAAGCACCCA GGACCATGGT TTCCCCTGCT GGCTGTACTT
 61  TTGTTGGGAG CCTGCCAGGC ACACCCTATC CCTGACTCCA GCCCCCTACT CCAGTTTGGT
121  GGCCAAGTCC GGCAGCGGTA CCTCTACACA GATGATGCCC AGGAGACAGA AGCCCACCTG
181  GAGATCAGGG AAGATGGCAC AGTGGTGGGG GCTGCACAAC AGAGCCCTGA AAGTCTCTTG
241  GAGCTGAAAG CTTTAAAGCC AGGGGTCATT CAAATCTTGG GAGTCAAGAC ATCCAGGTTC
301  CTGTGCCAGA GGCCAGATGG GGGCCTATAT GGATCGCTCT ACTTTGACCC CAAGGCCTGC
361  AGTTTCCGGG AGCTGCTTCT TGAGGATGGA TACAACGTTT ACTGGTCTGA GACCTATGGC
421  CTCCCACTGC ACCTGCCTCC TGCCAATTCC CCATACTGGG GCCCATCCCT TCGGAGCCCA
481  GCCCGCTTCC TGCCACTGCC AGGCCCTCCT GCAGCATCCC CAGAGCTGCC GGGGATCTTG
541  GCCCTGGAAC CCCCCGATGT GGGCTCCTCG GACCCTCTGA GCATGGTGGG GCCTTCGCAG
601  GGCCGAAGCC CCAGCTATGC TTCCTGA
```

*Rattus norvegicus* (Norway rat) FGF21 gene coding sequence (SEQ ID NO: 304) (GenBank Accession No. NM_130752, which is hereby incorporated by reference in its entirety)

```
  1  ATGGACTGGA TGAAATCTAG AGTTGGGGCC CCGGGACTGT GGGTCTGTCT CCTGCTGCCT
 61  GTCTTCCTGC TGGGGGTGTG CGAGGCATAC CCCATCTCTG ACTCCAGCCC CCTCCTCCAG
121  TTTGGGGGTC AAGTCCGACA GAGGTATCTC TACACAGATG ACGACCAGGA CACCGAAGCC
181  CACCTGGAGA TCAGGGAGGA CGGAACAGTG GTGGGCACAG CACACCGCAG TCCAGAAAGT
241  CTCCTGGAGC TCAAAGCCTT GAAGCCAGGG GTCATTCAAA TCCTGGGTGT CAAAGCCTCT
301  AGGTTTCTTT GCCAACAACC AGATGGAACT CTCTATGGAT CGCCTCACTT TGATCCTGAG
361  GCCTGCAGTT TCAGAGAGCT GCTGCTTAAG GACGGATACA ATGTGTACCA GTCTGAGGCC
421  CATGGCCTGC CCCTGCGTCT GCCCCAGAAG GACTCCCAGG ATCCAGCAAC CCGGGGACCT
481  GTGCGCTTCC TGCCCATGCC AGGCCTGCCC CACGAGCCCC AAGAGCAACC AGGAGTCCTT
541  CCCCCAGAGC CCCCAGATGT GGGTTCCTCC GACCCCCTGA GCATGGTAGA GCCTTTGCAA
601  GGCCGAAGCC CCAGCTATGC ATCTTGA
```

*Mus musculus* (house mouse) FGF21 gene coding sequence (SEQ ID NO: 305) (GenBank Accession No. NM_020013, which is hereby incorporated by reference in its entirety)

```
185       ATGGAA TGGATGAGAT CTAGAGTTGG GACCCTGGGA CTGTGGGTCC GACTGCTGCT
241  GGCTGTCTTC CTGCTGGGGG TCTACCAAGC ATACCCCATC CCTGACTCCA GCCCCCTCCT
301  CCAGTTTGGG GGTCAAGTCC GGCAGAGGTA CCTCTACACA GATGACGACC AAGACACTGA
361  AGCCCACCTG GAGATCAGGG AGGATGGAAC AGTGGTAGGC GCAGCACACC GCAGTCCAGA
421  AAGTCTCCTG GAGCTCAAAG CCTTGAAGCC AGGGGTCATT CAAATCCTGG GTGTCAAAGC
481  CTCTAGGTTT CTTTGCCAAC AGCCAGATGG AGCTCTCTAT GGATCGCCTC ACTTTGATCC
541  TGAGGCCTGC AGCTTCAGAG AACTGCTGCT GGAGGACGGT TACAATGTGT ACCAGTCTGA
601  AGCCCATGGC CTGCCCCTGC GTCTGCCTCA GAAGGACTCC CCAAACCAGG ATGCAACATC
661  CTGGGGACCT GTGCGCTTCC TGCCCATGCC AGGCCTGCTC CACGAGCCCC AAGACCAAGC
721  AGGATTCCTG CCCCCAGAGC CCCCAGATGT GGGCTCCTCT GACCCCCTGA GCATGGTAGA
781  GCCTTTACAG GGCCGAAGCC CCAGCTATGC GTCCTGA
```

*Vicugna pacos* (alpaca) FGF21 gene coding sequence (SEQ ID NO: 306) (Ensembl accession no. ENSVPAT00000005993, which is hereby incorporated by reference in its entirety) (1-209, excluding 79-168 and 172-182)

```
  1  ATGGACTGGG ACGAGGCCAA GTTCGAGCAT CGGGGACTGT GGGTCCCAGT GCTCACTGTC
 61  CTTCTGCTGG GAGCCTGCCA GGCACGCCCC ATTCCTGACT CCAGCCCCCT CCTCCAATTC
121  GGGGGCCAAG TCCGGCAGCG GTACCTCTAC ACGGATGACG CCCAGGAGAC AGAAGCCCAC
181  CTGGAGATCA GGGCTGATGG CACAGTGGTG GGGGTGGCCC GCCAG---CC CGAA------
241  ---------- ---------- ---------- ---------- ---------- ----------
301  ---------- ---------- ---------- ---------- ---------- ----------
361  ---------- ---------- ---------- ---------- ---------- ----------
421  ---------- ---------- ---------- ---------- ---------- ----------
481  ---------- ---------- ----GGAATT CCT------- ---------- ----------
541  ------CCCG AGCCTCCTGA CGTGGGCTCC TCAGACCCCC TGAGCATGGT GGGGCCTTCA
601  TACAGCAGAA GCCCCAGCTA CACTTCCTGA
```

TABLE 8-continued

*Anolis carolinensis* (anole lizard) FGF21 gene coding sequence (SEQ ID
NO: 307) (Ensembl accession no. ENSACAT00000017230, which is hereby
incorporated by reference in its entirety)

```
  1  TGTAAAAGCA AGGGAGGAGG GAAGGGGGGA GAGAGGATGT GGGTAGACCT AGTTTTCTGG
 61  GCTGCCTTGC TCCGCACAGC TCCTGCTCTT CCCTTGCGGA ATTCCAACCC CATCTACCAA
121  TTTGATGGGC AGGTCCGGCT TCGGCACCTC TACACAGCAG ATGAACAGAC GCACCTCCAC
181  TTGGAGATCT TGCCAGACGG TACCGTGGGT GGATCCAGGT TTCAGAATCC CTTCAGTTTG
241  ATGGAGATCA AAGCTGTGAA GCCAGGAGTC ATTCGCATGC AGGCCAAGAA GACCTCTAGA
301  TTTCTCTGTA TGAAACCCAA TGGACGACTG TATGCTCGC TGTTCTACTC TGAGGAGGCA
361  TGCAACTTCC ATGAGAAGGT TCTCAGCGAT GGCTACAACC TCTACTATTC TGAAAACTAC
421  AACATACCTG TCAGCCTCAG CTCGGCAGGG AACCTGGGTC AGAGCCGTCA GTTGCCTCCC
481  TTCTCCCAAT TCCTGCCGTT AGTCAACAAA ATTCCTCTTG AGCCTGTGCT TGAAGACTTT
541  GACTTCTATG GACATCAATT GGATGTTGAA TCAGCTGATC CTTTGAGCAT TTTAGGACAA
601  AACCCTGGTT TCATGAGTCC GAGCTATGTC TTC
```

*Gadus morhua* (cod) FGF21 gene coding sequence (SEQ ID NO: 308) (Ensembl
accession no. ENSGMOT00000014151, which is hereby incorporated by
reference in its entirety)

```
  1  CTCCTCCTCG CCACCCTCCT CCACATCGGC CTCTCCTTCT ACGTCCCCGA CTCCGGCCCC
 61  CTGCTGTGGC TGGGCGACCA GGTCAGGGAG AGACACCTCT ACACAGCAGA GAGCCACCGG
121  AGGGGGCTGT TCCTGGAGAT GAGCCCGGAC GGTCAGGTGA CAGGAAGTGC TGCTCAGACG
181  CCGCTCAGTG TTCTGGAGCT GAGGTCGGTC AGAGCAGGAG ATACGGTCAT CAGAGCGCGC
241  CTCTCCTCTC TCTACCTGTG TGTGGACAGG GCAGGTCACC TGACAGGACA GAGACAGTAC
301  ACAGAGTCCG ACTGCACCTT CAGAGAGGTC ATCCTTGAGG ACGGCTACAC CCACTTCCTG
361  TCCGTGCACC ACGGACTTCC TATTTCGCTG GCGCCGAGAC ACTCCCCAGG GAGACAGGGG
421  CTGCGCTTCA GCAGGTTCCT CCCGCTGAGG AGCAGTCTGT CAGAGGATAG GGTCGCCGAG
481  CCCCCAGACA GCCCACTGAA CCTGGACTCT GAAGACCCCC TGGGGATGGG TCTGGGTTCG
541  CTCCTCAGCC CGGCCTTCTC CATG
```

*Latimeria chalumnae* (coelacanth) FGF21 gene coding sequence (SEQ ID
NO: 309) (Ensembl accession no. ENSLACT00000003815, which is hereby
incorporated by reference in its entirety)

```
  1  ATGTTATGCC AGAGTTTTGT GATATTAAGT CAGAAATTCA TTTTTGGGCT CTTTTTGACT
 61  GGATTGGGGC TAACAGGATT GGCTTGGACA AGGCCCTTCC AGGATTCCAA TCCCATCCTG
121  CAGTATTCCG ATTCCATCCG GCTCCGACAT CTGTACACTG CCAGTGAGAG TCGGCACCTT
181  CACCTACAAA TCAACTCGGA TGGACAGGTG GGAGGGACAA CCAAGCAAAG CCCTTACAGT
241  CTGTTGGAGA TGAAGGCGGT GAAGACAGGT TTTGTGGTCA TCAGGGGCAA GAAAAGCGCC
301  CGTTACCTCT GTATGGAACG TAGTGGACGG CTCTATGGAT CGCTGCAGTA TACAGAAAAA
361  GACTGCACCT TCAAAGAGGT TGTGTTGGCA GATGGATACA ACCTGTATGT CTCAGAGGAA
421  CACCAGGCCA CAGTGACGCT GAGCCCCATG AGGGCGAGGA TAGCGCAAGG GAAAAAGATC
481  CCACCCTTTT CCCATTTCCT TCCAATGGTG AACAAGGTGC TGTGGAGGA TGTTGCCGCT
541  GAGATGGAGT TTGTCCAGGT GCTGCGGGAA ATGACGGCCG ACGTGGACTC TCCGGATCCC
601  TTTGGAATGA CCTGGGAAGA ATCGGTTCAC AGTCCGAGCT TTTTTGCC
```

*Tursiops truncatus* (dolphin) FGF21 gene coding sequence (SEQ ID
NO: 310) (Ensembl accession no. ENSTTRT00000014561, which is hereby
incorporated by reference in its entirety)

```
  1  ATGGGCTGGG ACAAGACCAA ACTCGAGCAC CTGGGACTGT GGGTCCCTGT GCTAGCTGTC
 61  CTGCTGGGAC CCTGCCAGGC ACATCCCATT CCTGACTCCA GCCCCTCCT CCAATTTGGG
121  GGCCAAGTCC GCCAGCGATA CCTCTACACG GATGACGCCC AGGAGACGGA GGCCCACCTG
181  GAGATCAGGG CTGATGGCAC AGTGGTGGGG ACGGCCCGCC GGAGCCCCGA AGGAGTTAAA
241  ACATCCAGGT TCCTGTGCCA GGGGCAGAG GGGAGGCTGT ATGGATCGCT CCACTTCAAC
301  CCCCAGGCCT GCAGCTTCCG GGAGCTGCTT CTTGAGGATG GATACAACGT TTACCAGTCT
361  GAGGCTCTTG GCATTCCCCT CCGCCTGCCC CCGCACCGCT CCTCCAACTG GGACCTGGCC
421  CCCCGGGGAC CTGCTCGCTT CCTGCCGCTG CCAGGCTTCC TCCCGCCACC CCTGGAGCCT
481  CCAGGGATCT TGGCCCCCGA GCCTCCCAAC GTAGGTTCCT CGGACCCCTT GAGCATGGTG
541  GGACCTTCAC ATGGCCGAAG CCCCAGCTAC ACTTCCTGA
```

*Mustela putorius furo* (ferret) FGF21 gene coding sequence (SEQ ID
NO: 311) (Ensembl accession no. ENSMPUT00000003755, which is hereby
incorporated by reference in its entirety)

```
188         ATG GGCTGGGAAG AGGCCAGGTC CGAGCACCTG GGGCTGTGGG TCCCTGTGCT
241  GGCGGTCCTT TTGCTGGGAG CCTGCCAGGC ATACCCTATT CCTGACTCCA GCCCCTCCT
301  CCAATTTGGA GGCCAAGTTC GACAGCGGTA CCTCTACACA GACGACGCTC AGGAGACGGA
361  GGCCCACCTA GAGATCAGGG CTGATGGCAC GGTGGTGGGG CTGCCCGCC GGAGCCCCGA
421  AAGTCTCTTG GAGCTGAAAG CCCTGAAGCC AGGGGTCATT CAGATCTTGG GAGTGAAAAC
481  ATCCAGGTTC CTGTGCCAGG GCCCGAATGG GACACTGTAC GGATCGTTCC ACTTCGACCC
541  CGTAGCCTGC AGCTTCCGGG AAGTGCTTCT GGAAGATGGA TACAACATCT ACCACTCTGA
601  GACCCTGGGC CTCCCACTGC GCCTGCCCCC CACAACTCC CCACACAGGG ACCTGGCGCC
661  CCGGGGGCCT GCCCGCTTCC TGCCCCTGCC AGGCCTGCTT CCGGCCACCC CGGAGTCCCG
721  GGGGATCCCA GCCCCGAGC CTCCCAACGT GGGCTCCTCA GACCCCCTGA GCATGGTGGG
781  GCCTTTGCAG GGTCAAAGTC CCAGCTACAC TTCCTGA
```

*Takifugu rubripes* (fugu) FGF21 gene coding sequence (SEQ ID NO: 312)
(Ensembl accession no. ENSTRUT00000034076, which is hereby
incorporated by reference in its entirety)

```
  1  TTTATTTATT TATTTATTCA AACTGCACTT TTTTCCCCTT CCAAATGGTT CAACTTTTAT
 61  CTCCCTGACT CCAACCCGCT CTTATCCTTT GACAGTCATG GCAGAGGCAT CCACCTCTAC
121  ACAGATAATC AAAGGCGAGG GATGTATCTG CAGATGAGCA CAGATGGAAG CGTTTCCGGG
181  AGTGATGTCC AGACGGCGAA CAGTGTGCTG GAACTGAAGT CAGTCAGAAA CGGCCACGTC
```

TABLE 8-continued

```
241 GTCATCCGAG GAAAATCGTC TTCTCTGTTT CTCTGTATGG ACAGCAGAGG CCGTTTATGG
301 GGGCAGAGGC ACCCCACTGA GGCCGACTGC ACTTTCAGGG AAGTGTTGCT GGCAGATGGA
361 TACACTGCTT CCTGTCCCT GCACAACGGA ACTCCTGTGT CTCTGGCACC TAAACAATCT
421 CCAGACCAGC ACACAGTCCC CTTCACTCGT TTCCTGCCGC TCAGGAATAC ACTGGCAGAG
481 GAGAGCATGT CTGAACCACC ATCAAACCAA CAGAGATATT TTAACATTGA CTCTGATGAT
541 CTTCTTGGAA TGGATTTAAA TGCGATGGTC AGTCCTCAGT TTTCAGGGGA CAAGTGA
```

*Dipodomys ordii* (kangaroo rat) FGF21 gene coding sequence (SEQ ID NO: 313) (Ensembl accession no. ENSDORT00000001234, which is hereby incorporated by reference in its entirety)

```
  1 ATGGACCAGG CAAAGACCAG GGTTGGGGCC CGGGGGCTGG GGGGCCTTGT GCTGGCTGTC
 61 ATAATTCTGG GAGCATGCAA GGCACGGCCT ATCCCTGACT CCAGCCCCCT CCTCCAATTT
121 GGGGGTCAAG TTCGGCTTCG GCACCTCTAC ACAGATGACA CTCAGGAGAC GGAAGCCCAT
181 CTGGAGATCA GGGCAGATGG CACGGTAGTG GGGACTGCCC ACCGGAGCCC TGAAAGTCTC
241 TTGGAGCTGA AGCCTTGAA GCCAGGAGTC ATTCAAATCT TAGGGATCAA GACATCCAGA
301 TTCTTATGCC AGAGACCAGA CGGGACACTG TATGGATCAC TCCACTTTGA CCCTGAGGTT
361 TGCAGCTTCC AGGAGCTGCT TCTGGAAGAT GGATACAACA TTTACCGTTC TGAAGCCCTG
421 GGTCTCCCCC TGCGCCTGTC CCCAGATCCA GCACCCTGGG GGCCAGCCCG CTTCCTGCCC
481 CTGCCTGGTG TGCCCCCCGC ACCGCCGGAG CCCCCCGGGA TCCTGGCTCC CGAACCCCCT
541 GATGTCGGCT CCTCCGACCC TCTGAGTATG GTGGGACTGT TGCAGGGCCG AAGCCCCAGC
601 TATGCATCCT GA
```

*Echinops telfairi* (lesser hedgehog tenrec) FGF21 gene coding sequence (SEQ ID NO: 314) (Ensembl accession no. ENSETET00000010721, which is hereby incorporated by reference in its entirety)

```
  1 ATGGGTTGCA CCAAATCTGG GTGGAAGTCC CCGGGACTGT GGGTCCCTGT GCTGGCCAGC
 61 CTTCTGCTGG GAGGCTGCGG AGCACACCCC ATCCCTGACT CCAGCCCCCT CCTCCAATTC
121 GGGGGCCAAG TCCGGCAGCG ATACCTCTAT ACGGATGACG CCCAGACCAC CGAGGCCCAC
181 CTGGAGATCA GAGCGGATGG CACAGTGGGG GGCGTCGCCC ACCAGAGCCC AGAGAAGTTC
241 CTGAGTCAAT GGCGTGAAAA GCCCCTGAGA TCACTCCATT TCGACCCAGC CGCCTGCAGC
301 TTCCGGGAGA AGCTTCTAGA AGACGGATAC AACTTGTACC ACTCTGAGAC CCACGGCCTC
361 CCCCTCCGCC TCCCACCCCG TGGGGCGAC CCCTCTTCTC AGCCTGGGGC CCGCTTCCCA
421 CCGCTGCCGG GCCAGCTCCC ACAACTCCAA GAGACGCCAG GGGTCCTCGC CCCCGAACCC
481 CCCGACGTGG GCTCTTCAGA CCCCCTGAGC ATGGTGGGGC CTTGGCGAGG GCAAAGTCCC
541 AGTTATGCCT CCTGA
```

*Macaca mulatta* (rhesus monkey) FGF21 gene coding sequence (SEQ ID NO: 315) (Ensembl accession no. ENSMMUT00000038440, which is hereby incorporated by reference in its entirety)

```
  1 ATGGACTCGG ACGAGACCGG GTTCGAGCAC TCAGGACTGT GGGTTCCTGT GCTGGCTGGT
 61 CTTCTGCTGG AGCCTGCCA GGCACACCCC ATCCCTGACT CCAGTCCTCT CCTGCAATTC
121 GGGGGCCAAG TCCGGCAACG GTACCTCTAC ACAGATGACG CCCAGCAGAC AGAAGCCCAC
181 CTGGAGATCA GGGAGGATGG GACAGTGGGG GGCGCTGCTC ACCAGAGCCC CGAAAGTGAG
241 TGTGGGCCAG AGCCTGGGTC TGAGGGAGGA GGGGCTGTGG GAGGTGCTGA GGGACCTGGA
301 CTCCTGGGTC TGAGGGAGGC AGGGCTGGGG CCTGGATCCT GGCTCCACTT TGACCCTGAG
361 GCCTGCAGCT TCCGGGAGCT GCTTCTTGAG AACGGATACA ATGTTTACCA GTCCGAGGCC
421 CACGGCCTCC CACTGCACCT GCCGGGAAAC AAGTCCCCAC ACCGGGACCC TGCATCCCAA
481 GGACCAGCTC GCTTCCTGCC ACTACCAGGC CTGCCCCCCG CACCCCCGGA GCCGCCAGGA
541 ATCCTCGCCC CCAGCCCCC CGATGTGGGC TCCTCGGACC CTCTGAGCAT GGTGGGACCT
601 TCCCAGGCCC GAAGCCCCAG CTATGCTTCC TGA
```

*Microcebus murinus* (mouse lemur) FGF21 gene coding sequence (SEQ ID NO: 316) (Ensembl accession no. ENSMICT00000013258, which is hereby incorporated by reference in its entirety)

```
  1 ATGGGCTGGG ACGAGGCCGG CGCCGGGTTC GAGCACCCAG GACTGTGGTT TCCCATGCTG
 61 GGTGTCCTGC TGCTGGGAGC CTGCCAGGCG TACCCCATCC CTGACTCCAG CCCCCTCCTC
121 CAATTTGGCG GCCAAGTCCG GCAGCGGCAC CTCTACACAG ACGATATCCA GGAGACAGAA
181 GCCCACCTGG AGATCAGGGC GGACGGCACA GTGGTGGGGG CCGCCCGACA GAGCCCTGAG
241 TTGGAGCTGA AGCCTTAAA GCCAGGGGTC ATTCAAATCT TGGGAGTCAA GACCTCCAGG
301 TTCCTGTGCC AGAGGCCAGA CGGGGCCCTG TACGGATCGC TCCACTTTGA CCCCGAGTGC
361 AGCTTCCGGG AGCTGCTTCT TGAGGATGGA TACAACGTCT ACTGTCCCTA CCTCCCGCTG
421 CACCTGTCCC CACGCATCGA ACTGGCCGGA TCACGCTCTG CGCTGCCACT GCCCCCAGCA
481 CCTGAACGCA GGATTTTGGC CCCGGAGCCC CCGGATGGCT CCTCGGACCC TCTGAGCATG
541 GTGGGGCCTT CGCAGGGCCG AAGTCCCAGC TATGCTTCCT GA
```

*Ochotona princeps* (pika) FGF21 gene coding sequence (SEQ ID NO: 317) (Ensembl accession no. ENSOPRT00000007373, which is hereby incorporated by reference in its entirety)

```
  1 AAAGACATGG ACGGGCTCCA GCCTCCGGGG CTGCGGGTTC CTGTGCTGGC TGCCCTGCTT
 61 TTGGGAGTTG GCCAGGCACG CCCCATCCCT GATTCTAGCC CTCTCCTCCA ATTCGGGGGC
121 CAGGTCCGGC AGAGGCACCT CTACACGGAT GACGCCCAGG AATCGGAAGT ACACCTGGAG
181 ATCCGGGCAG ACGGCACCGT GGCAGGGACT GCCGCCGGA GCCCTGAAAG TCTCTTAGAA
241 ATGAAAGCGT TGAAGCCAGG CGTCATTCAG ATCCTGGGGG TCCACACATC CAGGTTCCTG
301 TGCCAGAGAC CAGACGGGAC GCTGTACGGC TCGCTCCACT TCGACACACA GGCCTGCAGC
361 TTCCGGGAGC AGCTGCTGGA GGATGGGTAC AACGTGTACC ACTCAGAGAC ACACGGCCTC
421 CCGCTGCGCC TGTCTCCAGA CCGAGCCCCC CGGGGCCCAG CCCGCTTCCT GCCACTGCCA
481 GGCCCTCCTC CTGACCTCCT GGTGCCACCC CTGCCACCGG ACGTCCTAGC CCCTGAGCCC
541 CCCGACGTGG ACTCCCCAGA CCCCCTGAGC ATGGTGGGGC CCTTGCAGGG CCAAAGCCCC
601 AGCTACACTT CCTGA
```

TABLE 8-continued

*Xiphophorus maculatus* (platyfish) FGF21 gene coding sequence (SEQ ID NO: 318) (Ensembl accession no. ENSXMAT00000001579, which is hereby incorporated by reference in its entirety)
```
  1 TGCCCGTTCC CCTTCCTTTT CTTAATCCTC TCTCTTCCCT TTTTCTCTTC CTCGTTTTAC
 61 ATCCCAGAAT CCAACCCAAT CTTTGCCTTC AGGAATCAGC TCAGAGAGGT GCATCTCTAC
121 ACAGAAAATC ACAGACGGGG TTTGTATGTG GAGATACATC TGGATGGGAG AGTGACTGGA
181 AGTGATGCTC AGAGTCCTTA TAGTGTGTTG CAGATAAAGT CTGTTAAACC GGGTCATGTG
241 GTCATAAAGG GACAGACATC GTCCCTGTTC CTCTGCATGG ACGACTCCGG GAATCTAAGA
301 GGACAGACAA CCTATGACGA GGCTGACTGC TCCTTCAGGG AACTGCTGCT GGCCGATGGC
361 TACACCCGTT TCCTGAACTC ACAACATGGC GTTCCTTTAT CACTGGCATC CAGAAACTCT
421 CCAGATCGAC ACTCCGTTCC TTTCACAAGA TTTTTACCTC TCAGGAATAC TTTAACGGTT
481 TCAGAAGAAT CAACAAAAAC TCAGAGGGAC TTCAACCTGG ACTCGGACGA CCTTCTCGGG
541 ATGGGA
```

*Gasterosteus aculeatus* (stickleback) FGF21 gene coding sequence (SEQ ID NO: 319) (Ensembl accession no. ENSGACT00000010725, which is hereby incorporated by reference in its entirety)
```
  1 TCTCTCCTCC TCATGGTCCC ACTTCCTTTC TGTTCATCCT TTTATCTCAC TGACTCCAGC
 61 CCACTTCTAC CCTTCAATAA TCAAGTCAAA GAGGTGCACC TCTACACAGC AGAGAATCAC
121 AGAAGAGCGA TGTACCTGCA GATCGCTCTG GACGGGAGCG TGTCGGAAG CGACGCTCGG
181 TCCACTTACA GTGTGCTGCA GCTGAAATCT ATCCAGCCGG GCCACGTGGT CATCAGAGGG
241 AAGGCCTCCT CCATGTTCCT CTGCGTGGAC AGCGGGGGCC GTTTGAGAGG ACAGGGGCCG
301 TACTCAGAGG CCGACTGCAG CTTCAGGGAG CTGCTGCTGG GGATGGCTA CACCCGGTTC
361 CTGTCCTCGC AGCACGGGTC CCCGCTGTCT CTGGCGTCGA GGCCTTCCCC GGATCCCAAC
421 TCGGTGCCCT TCACTCGATT CCTACCCATC CGGACCGCCC CCGAGGCTGA GAGCGTGATC
481 GAAGAGCCAC CGAGCAATCA GAGATACGTC AACGTGGACT CCGAGGATCT TCTTGGAATG
541 GGCCTGAACA CTGTGGTCAG TCCTCAGTTC TCGGCG
```

*Sarcophilus harrisii* (Tasmanian devil) FGF21 gene coding sequence (SEQ ID NO: 320) (Ensembl accession no. ENSSHAT00000006017, which is hereby incorporated by reference in its entirety) (1-209, excluding 1-2 and 173-209)
```
132           GTGTCTGCC ATGGGCCTGA GGGAGCGAGC TCCCAGGTAC CTGGCCCCGC
181 TGCTGTCCTT GCTCTTGGCC TGCAGGGCCT CGGGTCACCC CCTCCCGGAT TCCAGCCCCA
241 TGCTCCTGTT TGGGGGGCAG GTCCGCCTCC GGCACCTCTA CACGGATGTG GGCCAGGAGG
301 CCGAGGCCCA CGTGGAACTG GCGTCCGACG GCACAGTCCG GGCGGCAGCG CGGAGGAGTC
361 CCAACAGTCT CCTGGAGCTG AAGGCTGTGA AGCCGGGCAT CGTCCGAATC CTGGCCGTCC
421 ACAGCTCTCG GTTTCTGTGT ATGAGGCCCA ACGGGGAGCT GTACGGAGCG ATACACTACG
481 ACCCTTCCGC CTGCAACTTT CGGGAGCGCC TGCTGGGGA CGGCTACAAC GTGTACGAGT
541 CCGAGGCTCA CGGGAGGACC CTCCGCCTGC CCCCCAAGGC CGCACCGGGA CCCGCCGGAC
601 CTTCTCGCTT CCTGCCGCTC CCCGGC
```

*Macropus eugenii* (wallaby) FGF21 gene coding sequence (SEQ ID NO: 321) (Ensembl accession no. ENSMEUT00000015309, which is hereby incorporated by reference in its entirety)
```
  1 ACAGAGGAGC CTTCTACTGG GTCCAGGCAC CTGGACAAT GGGCTCCCGG GCTGCCTGGT
 61 CCTCTGCTGT CCTTGCTCCT GGCCTACAGG GGCTGGGGCT CCCCCATCCC TGATTCCAGC
121 CCCATGCTCC TGTTTGGTGG CCAGGTCCGC CTCCGACACC TGTACACAGA TGATGGCCAG
181 GACACGGAGG CCCATGTGGA GCTGGGGCCA GATGGAGTGG TTCGAGCTGT GGCTGAGAGG
241 AGCCCCAACA GTCTTCTGGA ACTGAAGGCG GTGAAGCCTG GAGTCATCCG AATCCTCGCT
301 GTCCAGAGCT CTCGGTTTCT GTGTATGAGG CCCAACGGGG AACTGTATGG AGCGGTACAC
361 TATGACCCTT CTGCCTGCAA CTTTCGGGAA CATCTGCTGG GGGATGGTTA TAATGTGTAT
421 GAATCAGAGA CTCACAGAAG GACCCTCCGT CTGTCCCCAT CCCTGGGTCA GGCTGGCCCC
481 TCTCGCTTCC TGCCACTTCC AGGCGACTGG CTGCCCGGCC CTGATCCACC TTGGGCACAG
541 GGCCCTGAGC CCCCAGACGT GGGCTCTGCA GACCCCCTGA GCATGGTGGG GGCCGTGCAG
601 GGCCTCAGCC CCAGCTACTC CTCCTGA
```

*Xenopus tropicalis* (Western clawed frog) FGF21 gene coding sequence (SEQ ID NO: 322) (Ensembl accession no. ENSXETT00000009917, which is hereby incorporated by reference in its entirety) (1-209, excluding 170-209)
```
  1 AGAGGGGGTA GGACCAAAAA AAAAGACGTTA CTCAGGAAAT GGCTTTGCCT TTTAGCCATT
 61 ATGTTGAGTA GGTCAAGGTT TTCTTTAGCA AATCCTATCC AGAATTCGAA CCCAATCTTA
121 TCCAACGACA ACCAAGTACG GACTCAGTAT TTATACACAG ATAACAATAA CATGCACCTG
181 TATCTTCAGA TCACCCACAA TGGAGTAGTA ACTGGTACCG AAGAAAAGAA TGACTATGGT
241 GTGCTGGAAA TAAAGGCAGT AAAAGCTGGG GTTGTAGTTA TAAAGGAAT TCGAAGCAAT
301 CTCTACCTAT GCATGGATTC TAGACACCAA TTGTATGCGT CGGCATATGA TAAAGATGAC
361 TGCCATTTCC ATGAAAAGAT CACACCAGAT AATTACAACA TGTATAGCTC AGAGAAGCAT
421 TCAGAATACG TGTCCTTAGC TCCATTAAAA GGAAGCCAGA TGGCTCGTTT TCTACCTATA
```

*Danio rerio* (zebrafish) FGF21 gene coding sequence (SEQ ID NO: 323) (Ensembl accession no. ENSDART00000103511, which is hereby incorporated by reference in its entirety)
```
 30                    A TGCTTCTTGC CTGCTTTTTT ATATTTTTTG
 61 CTCTTTTTCC TCATCTTCGG TGGTGTATGT ATGTTCCTGC ACAGAACGTG CTTCTGCAGT
121 TTGGCACACA AGTCAGGGAA CGCCTGCTTT ACACAGATGG GTTGTTTCTT GAAATGAATC
181 CAGATGGCTC CGTCAAAGGC TCTCCTGAAA AGAATCTAAA TTGTGTGCTG GAGCTGCGTT
241 CAGTCAAAGC GGGTGAAACC GTCATCCAGA GTGCAGCTAC ATCTCTCTAC CTCTGCGTCG
301 ATGATCAAGA CAAGCTGAAA GGACAGCATC ATTACTCTGC ACTAGACTGC ACCTTTCAGG
361 AATTGCTACT GGATGGATAT TCGTTTTTCC TTTCTCCACA CACTAATCTT CCCGTATCGC
```

TABLE 8-continued

```
421 TCCTCTCGAA ACGTCAGAAA CACGGCAATC CTCTTTCTCG CTTCCTCCCT GTTAGCAGAG
481 CAGAGGACAG CCGGACACAG GAGGTGAAAC AGTATATTCA GGATATAAAC CTGGACTCTG
541 ACGACCCACT AGGAATGGGA CATCGGTCAC ACTTACAGAC CGTCTTCAGT CCCAGTCTGC
572 ATACTAAAAA ATGA
```

*Bos grunniens mutus* (yak) FGF21 gene coding sequence (SEQ ID NO: 324) (generated using SMS Reverse Translate tool on the ExPASy Bioinformatics Resource website (www.expasy.org))

```
  1 ATGGGCTGGG ATGAAGCGAA ATTTAAACAT CTGGGCCTGT GGGTGCCGGT GCTGGCGGTG
 61 CTGCTGCTGG GCACCTGCCG CGCGCATCCG ATTCCGGATA GCAGCCCGCT GCTGCAGTTT
121 GGCGGCCAGG TGCGCCAGCG CTATCTGTAT ACCGATGATG CGCAGGAAAC CGAAGCGCAT
181 CTGGAAATTC GCGCGGATGG CACCGTGGTG GGCGCGGCGC GCCAGAGCCC GGAAAGCCTG
241 CTGGAACTGA AAGCGCTGAA ACCGGGCGTG ATTCAGATTC TGGGCGTGAA AACCAGCCGC
301 TTTCTGTGCC AGGGCCCGGA TGGCAAACTG TATGGCAGCC TGCATTTTGA TCCGAAAGCG
361 TGCAGCTTTC GCGAACTGCT GCTGGAAGAT GGCTATAACG TGTATCAGAG CGAAACCCTG
421 GGCCTGCCGC TGCGCCTGCC GCCGCAGCGC AGCAGCAACC GCGATCCGGC GCCGCGCGGC
481 CCGGCGCGCT TTCTGCCGCT GCCGGGCCTG CCGGCGGAAC CGCCGGATCC GCCGGGCATT
541 CTGGCGCCGG AACCGCCGGA TGTGGGCAGC AGCGATCCGC TGAGCATGGT GGGCCCGAGC
601 TATGGCCGCA GCCCGAGCTA TACCAGCTAA
```

*Saimiri boliviensis boliviensis* (Bolivian squirrel monkey) FGF21 gene coding sequence (SEQ ID NO: 325) (GenBank accession no. XM_003940326, which is hereby incorporated by reference in its entirety)

```
163                                          atgggctc ggaggaggtc
181 GCGTTGGAGC GCCCTGCACT GTGGGTCTCT GTGTTGGCTG GGGAACCTGC
241 CAGGCATACC CCATCCCTGA CTCTAGTCCC CTCCTGCAAT TTGGAGGCCA AGTCCGGCAG
301 CGGTACCTCT ACACAGATGA CGCTCAGCAG ACAGAAGCCC ACCTGGAGAT CAGGGAAGAT
361 GGCACGGTGG CGGGGGCTGC CCACCAGAGC CCCGAAAGTC TCTTGCAGCT GAAAGCCTTA
421 AAGCCAGGGG TTATTCAAAT CTTGGGAGTC AAGACCTCCA GGTTCCTGTG CCAGAGGCCG
481 GACGGGGCCC TGTACGGATC GCTCTACTTT GACCCCGAGG CCTGCAGCTT CCGGGAGCTG
541 CTTCTTGAGG ACGGATACAA TGTGTACCAG TCCGTGGCCC ACAGCCTCCC GCTGCACCTG
601 CCAGGGGGCA GGTCCCCACC CTGGGACCCT GCACCTCGAG GACCAGCTCG CTTCCTGCCG
661 CTACCAGGCC TGCCCCCCGA ACCCCCGAG GCGCCAGGAA TCCTGGCCCC CGAGCCCCCC
721 GATGTGGGCT CCTCAGACCC TCTGAGCATG GTGGGGCCTT CCCAAGGCCA AAGCCCCAGC
781 TACACTTCCT GA
```

*Callithrix jacchus* (white-tufted-ear marmoset) FGF21 gene coding sequence (SEQ ID NO: 326) (GenBank accession no. XM_003735621, which is hereby incorporated by reference in its entirety)

```
  1 ATGGGCTCGG AGGAGGTCGG GTTGGAGCAC CCTGCACTGT GGGTTTCTGT GCTGGCTGGT
 61 CTCCTGCTGG GAACCTGCCA GGCGCACCCC ATCCCTGACT CCAGTCCCCT CCTGCAATTT
121 GGAGGCCAAG TCCGGCAGCG GTACCTCTAC ACAGATGATG CCCAGCAGAA AGAAGCCCAC
181 CTGGAGATCN AGGAAGATGG CACAGTGGCC GGGGCTGCCA CCAAAGTCCC GAAAGTGAGT
241 CTCTTGCAGC TGAAAGCCTT AAAGCCAGGG GTTATTCAAA TCTTGGGAGT CAAGACATCC
301 AGGTTCCTGT GCCAGAGGCC AGACGGGGCG CTGTATGGAT CGCTCCACTT TGACCCCGAG
361 GCCTGCAGCT TCCGGGAGCT GCTTCTTGAG GACGGATACA ATGTGTACCA GTCCTGTGCC
421 CACGCCTCC CGCTGCACCT GCCAGAGAGC AGGTCACCAC CCCGGGACCC TGCACCCCGA
481 GGACCAGCTC GCTTCCTGCC ACTACCAGGC CTGCCCCCTG AACCCCCAGA GCCGCCAGGA
541 ATCCTGGCCC CTGAGCCCCC CGACGTGGGC TCCTCAGACC CTCTGAGCAT GGTGGGGCCT
601 TCCCAAGGCC AAAGCCCCAG CTACGCTTCC TGA
```

*Tupaia chinensis* (Chinese tree shrew) FGF21 gene coding sequence (SEQ ID NO: 327)(generated using SMS Reverse Translate tool on the ExPASy Bioinformatics Resource website (www.expasy.org))

```
  1 ATGGGCTGGG ATAAAGCGCG CTTTGAACAT CTGGGCGCGT GGGCGCCGGT GCTGGCGGTG
 61 CTGCTGCTGG GCGCGTGCCA GGCGTATCCG ATTCCGGATA GCAGCCCGCT GCTGCAGTTT
121 GGCGGCCAGG TGCGCCAGCG CTATCTGTAT ACCGATGATA CCCAGGATAC CGAAGCGCAT
181 CTGGAAATTC GCGCGGATGG CACCGTGGTG GGCGCGGCGC ATCAGAGCCC GGAAAGCCTG
241 CTGGAACTGA AAGCGCTGAA ACCGGGCGTG ATTCAGATTC TGGGCGTGAA AACCAGCCGC
301 TTTCTGTGCC AGCGCCCGGA TGGCGCGCTG TATGGCAGCC TGCATTTTGA TCCGGAAGCG
361 TGCAGCTTTC GCGAACTGCT GCTGGAAGAT GGCTATAACA TTTATCAGAG CGAAGCGCGC
421 GGCCTGCCGC TGCGCCTGCC GCCGCATGAT AGCCCGCATC GCGATCGCAC CCCGCAGGGC
481 CCGGCGCGCT TTCTGCCGCT GCCGGGCCTG CCGCTGGTGC CGCCGGAACT GCCGGGCGTG
541 CTGGCGCTGG AACCGCCGGA TGTGGGCAGC AGCGATCCGC TGAGCATGAT GGGCCCGAGC
601 CAGGGCCAGA GCCCGAGCTA TGCGAGCTAA
```

*Papio anubis* (olive baboon) FGF21 gene coding sequence (SEQ ID NO: 328) (GenBank accession no. XM_003915851, which is hereby incorporated by reference in its entirety)

```
  1 ATGGACTCGG ACGAGACCGG GTTCGAGCAC TCAGGACTGT GGGTTCCTGT GCTGGCTGGT
 61 CTTCTGCTGG GAGCCTGCCA GGCACACCCC ATCCCTGACT CCAGTCCTCT CCTGCAATTC
121 GGGGGCCAAG TCCGGCAACG GTACCTCTAC ACAGATGATG CCCAGCAGAC AGAAGCCCAC
181 CTGGAGATCA GGGAGGATGG GACAGTGGGG GGCGCTGCTC ACCAGAGCCC CGAAAGTAAG
241 TGTGGGCCAA AGCCTGGGTC TGAGGGAGGA GGGGCTCTCC ACTTTGACCC TGAGGCCTGC
301 AGCTTCCGCG AGCTGCTTCT TGAGAACGGA TACAATGTTT ACCAGTCCGA GGCCCACGGC
361 CTCCCACTGC ACCTGCCGGG AAACAAGTCC CCACACCGGG ACCCTGCATC CCGAGGACCA
421 GCTCGCTTCC TGCCACTACC AGGCCTGCCC CCGCACCCC CAGAGCCACC AGGAATCCTC
481 GCCCCCCAGC CCCCCGATGT GGGCTCCTCG GACCCTCTGA GCATGGTGGG ACCTTCCCAG
541 GCCCGAAGCC CTAGCTACGC TTCCTGA
```

TABLE 8-continued

*Pteropus alecto* (black flying fox) FGF21 gene coding sequence (SEQ ID NO: 329) (generated using SMS Reverse Translate tool on the ExPASy Bioinformatics Resource website (www.expasy.org))
```
  1  ATGGGCTGGG GCAAAGCGCG CCTGCAGCAT CCGGGCCTGT GGGGCCCGGT GCTGGCGGTG
 61  CTGCTGGGCG CGTGCCAGGC GCATCCGATT CTGGATAGCA GCCCGCTGTT TCAGTTTGGC
121  AGCCAGGTGC GCCGCCGCTA TCTGTATACC GATGATGCGC AGGATACCGA AGCGCATCTG
181  GAAATTCGCG CGGATGGCAC CGTGGCGGGC GCGGCGCGCC GCAGCCCGGA AAGCCTGCTG
241  GAACTGAAAG CGCTGAAACC GGGCGTGATT CAGGTGCTGG GCGTGAAAAC CAGCCGCTTT
301  CTGTGCCAGC GCCCGGATGG CACCCTGTAT GGCAGCCTGC ATTTTGATCC GGCGGCGTGC
361  AGCTTTCGCG AACTGCTGCT GAAAGATGGC TATAACGTGT ATCAGAGCGA AGCGCTGGCG
421  CGCCCGCTGC GCCTGCCGCC GTATAGCAGC CCGAGCAGCG ATCCGGCGCG CCGCGGCCCG
481  GCGCGCTTTC TGCCGCTGCC GGGCCCGCCG CCGGAACCGC CGCAGCCGCC GGGCCGCCTG
541  GCGCCGGAAC CGCCGGATGT GGGCAGCAGC GATCCGCTGA GCATGGTGTG GCCGAGCCGC
601  GGCCGCAGCC CGAGCTATAC CAGCTAA
```

*Heterocephalus glaber* (naked mole-rat) FGF21 gene coding sequence (SEQ ID NO: 330) (generated using SMS Reverse Translate tool on the ExPASy Bioinformatics Resource website (www.expasy.org))
```
  1  ATGGATTGGG CGCGCGCGGA AAGCGAACGC CCGGGCCTGT GGGTGCCGGC GGTGCTGGCG
 61  GTGCTGCTGC TGGGCGCGTG CCAGGCGCAT CCGATTCCGG ATAGCAGCCC GCTGCTGCAG
121  TTTGGCGGCC AGGTGCGCCA GCGCCATCTG TATACCGATG ATGCGCAGGA TACCGAAGTG
181  CATCTGGAAA TTCGCGCGGA TGGCAGCGTG GGCGGCGCGG CGCATCGCAG CCCGGAAAGC
241  CTGCTGGAAC TGAAAGCGCT GAAACCGGGC GTGATTCAGA TTCTGGGCGT GCGCACCAGC
301  CGCTTTCTGT GCCAGCGCCC GGATGGCACC CTGTATGGCA GCCTGCATTT TGATCCGGAA
361  GCGTGCAGCT TTCGCGAACT GCTGCTGGCG GATGGCTATA ACATTTATCA GAGCGAAGCG
421  TATGGCCTGC CGCTGCGCAT GCTGCCGAGC GATAGCGCGA GCCGCGATCC GGTGCCGCCG
481  GGCCCGGCGC GCTTTCTGCC GCTGCCGGGC CTGCATCCGC CGCCGCTGGA ACCGCCGGGC
541  ATGCTGCCGC CGGAACCGCC GGATGTGGGC AGCAGCGATC CGCTGAGCAT GGTGGGCCCG
601  CTGCAGGGCC GCAGCCCGAG CTATGCGTTT TAA
```

*Cricetulus griseus* (Chinese hamster) FGF21 gene coding sequence (SEQ ID NO: 331) (GenBank accession no. XM_003508678, which is hereby incorporated by reference in its entirety)
```
  1  ATGGACTGGA TGAAATCTGG AGTTGGGGTC CCGGGACTGT GGGTCCCTCT GCTGCCTATC
 61  TTCCTGCTGG GGGTCTCCCA GGCACACCCC ATCCCTGACT CCAGCCCCCT CCTCCAGTTT
121  GGGGGTCAAG TCCGGCACAG GCACCTCTAC ACAGATGACA ACCAGGAAAC TGAAGTCCAC
181  CTGGAGATTA GGCAGGATGG CACGGTGATA GGGACCACAC ACCGCAGCCC AGAAAGTCTC
241  CTGGAGCTCA AAGCCTTGAA GCCAGAGGTC ATCCCAGTGC TGGGTGTCAA GGCCTCCAGG
301  TTTCTTTGCC AACAACCAGA CGGAACCCTG TATGGATCGC CTCACTTTGA TCCTGAGGCC
361  TGCAGTTTCA GGGAGCTCTT GCTTGAGGAT GGATACAATG TGTACCAATC TGAAGTCCAT
421  GGCCTGCCCC TGCGCCTGCC CAGAGGGAC TCTCCAAACC AGGCCCAGC ATCCTGGGGA
481  CCTGTGCCCC CCCTGCCAGT GCCAGGACTG CTCCACCAGC CCAGGAGCT ACCAGGGTTC
541  CTGGCCCCAG AACCTCCAGA TGTGGGCTCC TCTGACCCAC TGAGCATGGT GGGACCTTTG
601  CAGGGCCGAA GCCCCAGCTA TGCTTCCTGA
```

*Ovis aries* (sheep) FGF21 gene coding sequence (SEQ ID NO: 332) (GenBank accession no. XM_004015796, which is hereby incorporated by reference in its entirety)
```
  1  ATGGGCTGGG ACGAGGCCAA GTTCAAGCAC TTGGGACTGT GGGTCCCTGT GCTGGCTGTC
 61  CTCCTGCTAG GAACCTGCCG GGCGCATCCA ATTCCAGACT CCAGCCCCCT CCTCCAGTTT
121  GGGGGCCAAG TCCGCCAGCG GTACCTCTAC ACGGATGATG CCCAGGAGAC AGAGGCCCAC
181  CTGGAGATCA GGGCCGATGG CACAGTGGTG GGGGCGGCCC GCCAGAGTCC CGAAAGTCTC
241  TTGGAGCTGA AAGCCCTGAA GCCAGGAGTC ATTCAGATCT TTGGAGTTAA AACATCCAGG
301  TTCCTGTGCC AGGGGCCAGA TGGGAAGCTG TATGATGTGC TGCACTTTGA CCCCAAAGCC
361  TGCAGCTTCC GGGAGCTGCT TCTTGAAGAT GGGTACAATG TCTACCAGTC GGAGACCCTG
421  GGCCTTCCAC TCCGCCTGCC GCCGCAGCGC TCATCCAACC GGGACCCGGC CCCGCGGGGA
481  CCTCCGAAGC CCCAGCTACA CTTCTTGAAG ACGTCCGCTG TGCAGTACTG GCCACGTTAT
541  GAGAAGGTCC CAGCTTTTCT GCACCCCTTC CCCGGCTGA
```

*Pan paniscus* (pygmy chimpanzee) FGF21 gene coding sequence (SEQ ID NO: 333) (GenBank accession no. XM_003814115, which is hereby incorporated by reference in its entirety) (1-209, excluding 117-194 and 202-209)
```
573                                         ATGGACTC GGACGAGACC GGGTTCGAGC
601  ACTCAGGACT GTGGGTTTCT GTGCTGGCTG GTCTTCTGCT GGGAGCCTGC CAGGCACACC
661  CCATCCCTGA CTCCAGTCCT CTCCTGCAAT TCGGGGGCCA AGTCCGGCAG CGGTACCTCT
721  ACACAGATGA TGCCCAGCAG ACAGAAGCCC ACCTGGAGAT CAGGGAGGAT GGGACGGTGG
781  GGGGCGCTGC TGACCAGAGC CCCGAAAGTC TCCTGCAGCT GAAAGCCTTG AAGCCGGGAG
841  TTATTCAAAT CTTGGGAGTC AAGACATCCA GGTTCCTGTG CCAGAGGCCA GATGGGGCCC
901  TGTATGGATC GGTGAGTTTC ---------- ---------- ---------- ----------
     ---------- ---------- ---------- ---------- ---------- ----------
921  ---------- ----CAG--- ---------- ---------- ---------- ----------
924  ---------- -------GAC CCTCCT---- --------CA CCACCCACCA ---------T
946  GCTCC----- ----TCCTAT ATGTCGCCCT CACAG------ ---CCTGGG
```

*Macaca fascicularis* (crab-eating macaque) FGF21 gene coding sequence (SEQ ID NO: 334) (generated using SMS Reverse Translate tool on the ExPASy Bioinformatics Resource website (www.expasy.org)) (1-209, excluding 117-209)
```
  1  ATGGATAGCG ATGAAACCGG CTTTGAACAT AGCGGCCTGT GGGTGCCGGT GCTGGCGGGC
 61  CTGCTGCTGG GCGCGTGCCA GGCGCATCCG ATTCCGGATA GCAGCCCGCT GCTGCAGTTT
```

TABLE 8-continued

```
121  GGCGGCCAGG TGCGCCAGCG CTATCTGTAT ACCGATGATG CGCAGCAGAC CGAAGCGCAT
181  CTGGAAATTC GCGAAGATGG CACCGTGGGC GGCGCGGCGC ATCAGAGCCC GGAAAGCCTG
241  CTGCAGCTGA AAGCGCTGAA ACCGGGCGTG ATTCAGATTC TGGGCGTGAA AACCAGCCGC
301  TTTCTGTGCC AGAAACCGGA TGGCGCGCTG TATGGCAGCG TGAGCTTTTA A
```

Mesocricetus auratus (golden hamster) FGF21 gene coding sequence (SEQ ID NO: 335) (GenBank accession no. EU497769, which is hereby incorporated by reference in its entirety) (1-209, excluding 1-89 and 194-209)

```
  1  GGTCATCCAA ATCCTGGGTG TCAAGGCTGC TAGGTTTCCT TGCCAGCAAC CAGACGGAAG
 61  CCTGTACGGA TCGCCTCACT TCGATCCCGA GGCCTGCAGT TTCCGGGAGC TCCTGCTTGA
121  GGATGGATAC AATGTGTACC AGTCGGAAGC CCACGGCCTG CCCCTGCGCC TGCCCCAGAG
181  GGACGCTCCG AGCCAGCCCC CAGCATCCTG GGGACCGGTG CGCTTCCTGC CAGTGCCCGG
241  ACTGTTCCAG CCGCCCCACG ACCTCCCAGG GCGCCCGGCC CCAGAGCCTC CGGACGTGGG
301  CTCCTCCGAC CCAC
```

Nile tilapia FGF21 gene coding sequence (SEQ ID NO: 336) (GenBank accession no. XM_003438468, which is hereby incorporated by reference in its entirety) (1-209, excluding 1-58)

```
  1  ATGTATTTGC AGATGAACAT GGATGGGAGA GTCACAGGAA GTGATGCTCA GACACCTTAC
 61  AGTTTGATGC AGCTGAAATC AGTTAAACCA GGCCATGTAA TCATTAAAGG ACCATCATCA
121  TCTCTTTTTC TCTGTGTGGA CAGCGAAGGC AATCTGAGAG GGCAGAGTCA CTACTCAGAA
181  ACCAGCTGCA CCTTCAGAGA AATGCTGCTG GCTGACGGAT ACACCCGTTT CATTTCCTCA
241  CAATATGGAT TTCCCATGTC ACTGGCATCA AGACATTCCC CAGATCGACA CGCGCTTCCC
301  TTTACGCGGT TCCTACCACT GAGGAATAAC TTGAAAACGG ATAGCGTATC AGAGCAGCTG
361  CCAAACAATC AGAGACTCTT CAACGTGGAC TCTGATGACC TTCTTGGAAT GGGTCTAAAT
421  TCTATGGGCA GTCCTCAGTT TTCTATGGAC AAATAA
```

In one embodiment of the present invention, the chimeric protein may include one or more substitutions for or additions of amino acids from another FGF. In one embodiment, the C-terminal portion from FGF21 includes a modification that includes a substitution for or addition of amino acid residues from an FGF19 (including a human FGF19 and orthologs of human FGF19). In one embodiment the FGF19 is a human FGF19 protein having an amino acid sequence of SEQ ID NO: 337 (GenBank Accession No. NP_005108, which is hereby incorporated by reference in its entirety) or a portion or ortholog thereof, as follows:

```
  1 MRSGCVVVHV WILAGLWLAV AGRPLAFSDA GPHVHYGWGD PIRLRHLYTS GPHGLSSCFL

61 RIRADGVVDC ARGQSAHSLL EIKAVALRTV AIKGVHSVRY LCMGADGKMQ GLLQYSEEDC

121 AFEEEIRPDG YNVYRSEKHR LPVSLSSAKQ RQLYKNRGFL PLSHFLPMLP MVPEEPEDLR

181 GHLESDMFSS PLETDSMDPF GLVTGLEAVR SPSFEK
```

Figure 12:
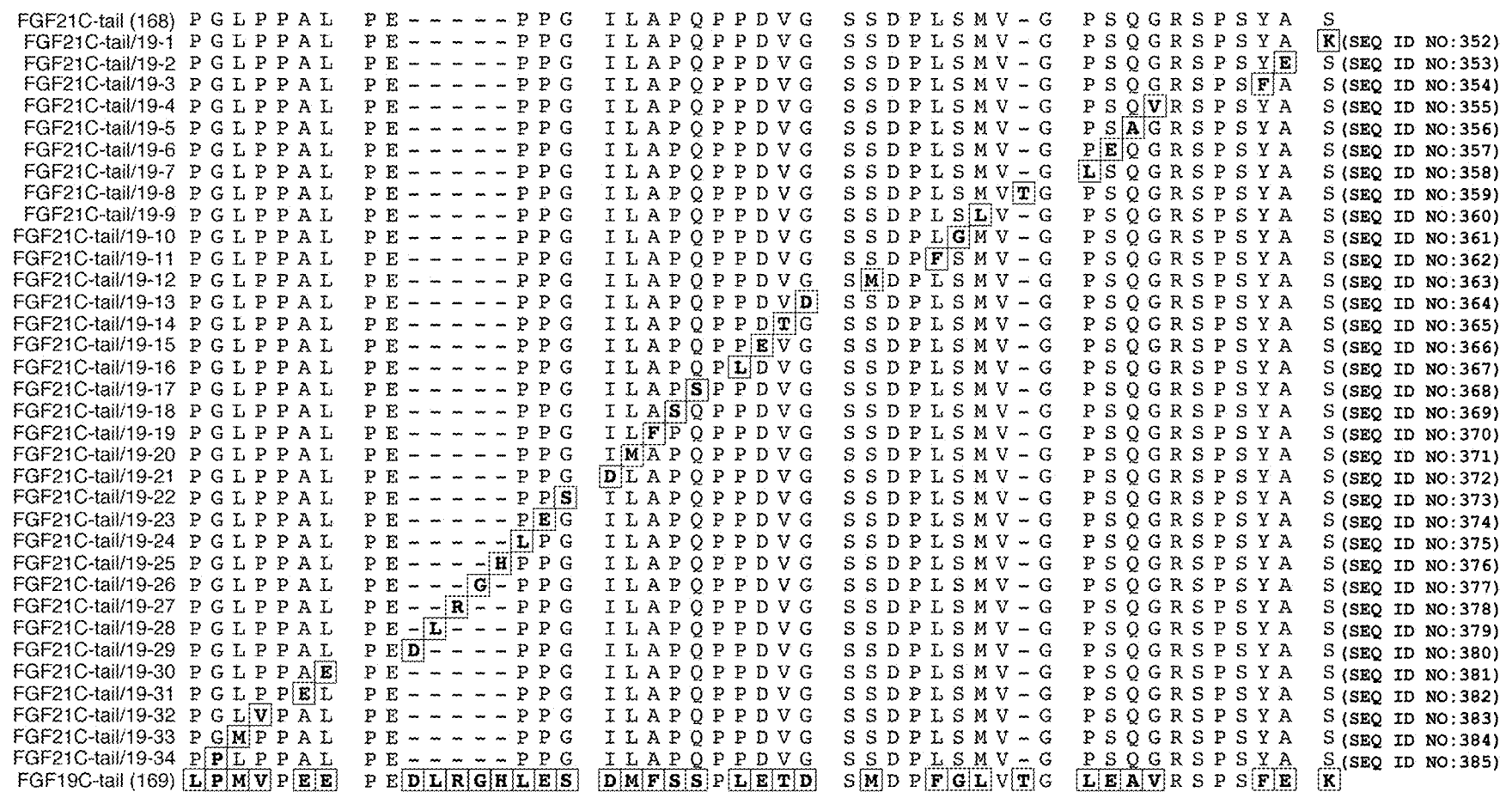
Figure 13:
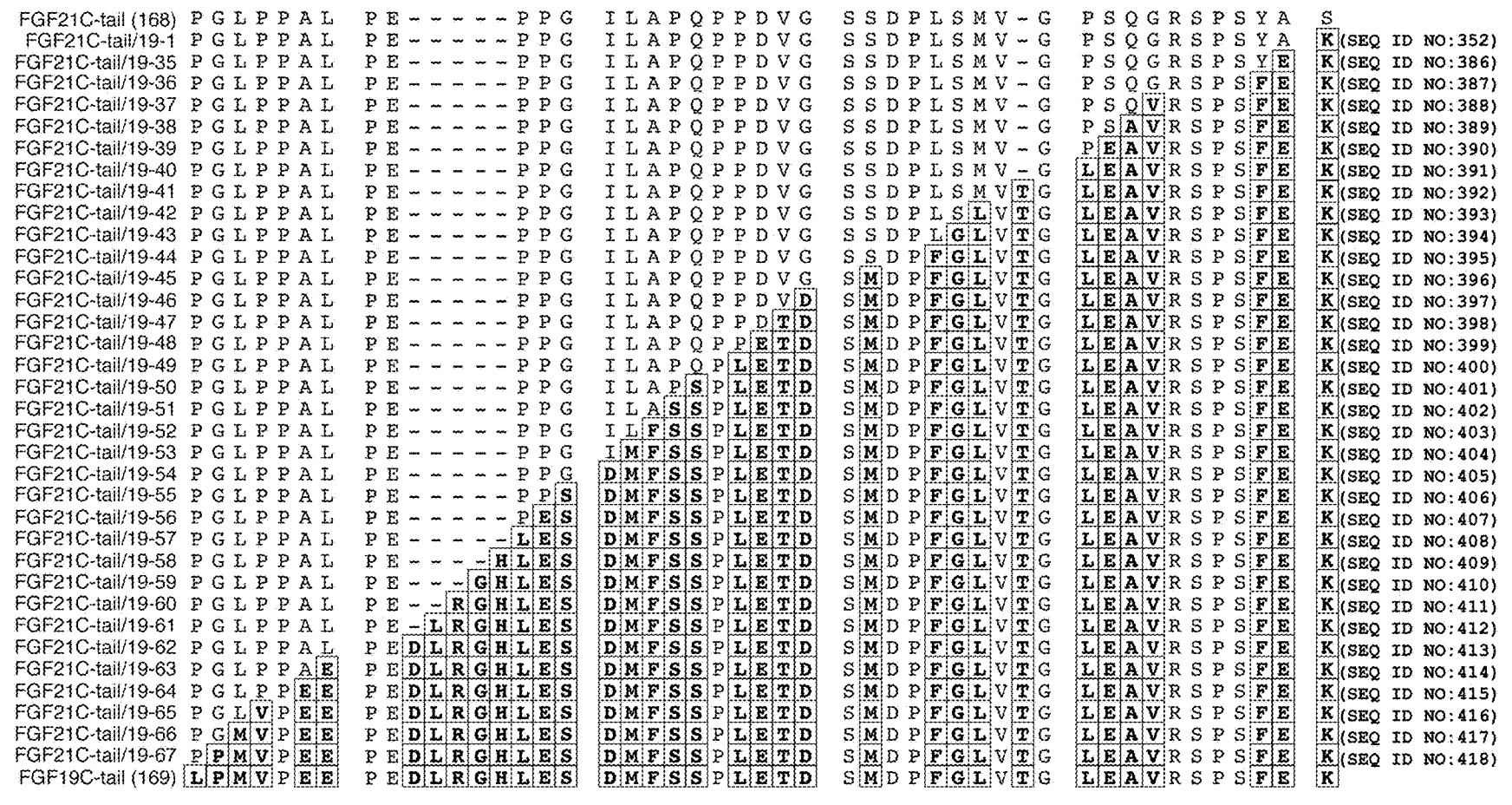

Exemplary substitutions and additions of such residues are shown in FIGS. 12 and 13.

In one embodiment, the C-terminal portion from FGF21 includes a modification that includes a substitution of amino acid residues from an FGF19 molecule. In one embodiment, the modification includes a substitution for or addition of amino acid residues 169 to 216 of SEQ ID NO: 337 (FGF19). In one embodiment, the modification is a substitution of amino acid residues from SEQ ID NO: 337 (FGF19) for corresponding amino acid residues of SEQ ID NO: 233 (FGF21). The corresponding residues of FGFs may be identified by sequence analysis and/or structural analysis. See FIGS. 2, 11, 12, and 13. In one embodiment, the modification includes a substitution of a contiguous stretch of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 amino acid residues 169 to 216 of SEQ ID NO: 337 (FGF19) for the corresponding contiguous stretch of amino acid residues of SEQ ID NO: 233 (FGF21). In one embodiment, amino acid residues 168 to 209, 191 to 209, or 198 to 209 of SEQ ID NO: 233 (FGF21) are substituted with the corresponding amino acid residues selected from the sequence including amino acid residues 169 to 216 of SEQ ID NO: 337 (FGF19).

In one embodiment, the modification includes a substitution of one or more individual amino acid residues from residues 169 to 216 of SEQ ID NO: 337 (FGF19) for the corresponding amino acid residues of SEQ ID NO: 233 (FGF21). In one embodiment, the C-terminal portion includes substitutions of one or more of amino acid residues 168, 169, 170, 171, 173, 174, 177, 178, 179, 180, 181, 182, 183, 184, 186, 187, 188, 189, 191, 194, 195, 196, 199, 200, 201, 202, 207, 208, or 209 of SEQ ID NO: 233 (FGF21) for the corresponding amino acid residues of SEQ ID NO:337 (FGF19).

In one embodiment of the present invention, the C-terminal portion from FGF21 includes a modification that includes an addition of amino acid residues that are present in the corresponding C-terminal portion from FGF19. As shown in FIGS. 11, 12, and 13, FGF19 residues that are absent in the corresponding C-terminal portion of FGF21 may be identified by sequence analysis and/or structural analysis. In one embodiment, the modification includes an addition of amino acid residues selected from residues 204 to 216, 197 to 216, 174 to 216, or 169 to 216 of SEQ ID NO: 337 (FGF19). In one embodiment, the modification includes an addition of amino acid residue 204 of SEQ ID NO: 337 (FGF19). In one embodiment, the modification includes an addition of amino acid residues 178, 179, 180, 181, and/or 182 of SEQ ID NO: 337 (FGF19) individually or in combination.

It will be understood that the C-terminal portion from FGF21 that includes a substitution of amino acid residues from an FGF19 molecule may be derived using a nucleotide sequence that encodes a human FGF19 protein having a nucleotide sequence of SEQ ID NO: 338 (Human FGF19 gene coding sequence (1-216); GenBank Accession No. NM_005117, which is hereby incorporated by reference in its entirety) or a portion or ortholog thereof, as follows:

```
 464 ATGCGGA GCGGGTGTGT GGTGGTCCAC GTATGGATCC TGGCCGGCCT CTGGCTGGCC

521 GTGGCCGGGC GCCCCCTCGC CTTCTCGGAC GCGGGGCCCC ACGTGCACTA CGGCTGGGGC

581 GACCCCATCC GCCTGCGGCA CCTGTACACC TCCGGCCCCC ACGGGCTCTC CAGCTGCTTC

641 CTGCGCATCC GTGCCGACGG CGTCGTGGAC TGCGCGCGGG GCCAGAGCGC GCACAGTTTG

701 CTGGAGATCA AGGCAGTCGC TCTGCGGACC GTGGCCATCA AGGGCGTGCA CAGCGTGCGG

761 TACCTCTGCA TGGGCGCCGA CGGCAAGATG CAGGGGCTGC TTCAGTACTC GGAGGAAGAC

821 TGTGCTTTCG AGGAGGAGAT CCGCCCAGAT GGCTACAATG TGTACCGATC CGAGAAGCAC

881 CGCCTCCCGG TCTCCCTGAG CAGTGCCAAA CAGCGGCAGC TGTACAAGAA CAGAGGCTTT

941 CTTCCACTCT CTCATTTCCT GCCCATGCTG CCCATGGTCC CAGAGGAGCC TGAGGACCTC

1001 AGGGGCCACT TGGAATCTGA CATGTTCTCT TCGCCCCTGG AGACCGACAG CATGGACCCA

1061 TTTGGGCTTG TCACCGGACT GGAGGCCGTG AGGAGTCCCA GCTTTGAGAA GTAA
```

In one embodiment, the chimeric protein of the present invention includes the amino acid sequence of SEQ ID NO: 339, SEQ ID NO: 340, SEQ ID NO: 341, or SEQ ID NO: 342, as shown in Table 9.

TABLE 9

| Description of Chimeric Protein | Sequence |
|---|---|
| Amino acid sequence of a FGF1/FGF21 chimera composed of residues M1 to L150 of human FGF1 harboring K127D/K128Q/K133V triple mutation (bold) and residues P168 to S209 of human FGF21 (bold) | SEQ ID NO: 339<br>MAEGEITTFT ALTEKFNLPP GNYKKPKLLY CSNGGHFLRI LPDGTVDGTR DRSDQHIQLQ LSAESVGEVY IKSTETGQYL AMDTDGLLYG SQTPNEECLF LERLEENHYN TYISKKHAEK NWFVGLDQNG SCVRGPRTHY GQKAILFLPL PGLPPALPEP PGILAPQPPD VGSSDPLSMV GPSQGRSPSY AS |
| Amino acid sequence of a FGF1/FGF21 chimera composed of residues K25 to L150 of human FGF1 harboring K127D/K128Q/K133V triple mutation (bold) and residues P168 to S209 of human FGF21 (bold) | SEQ ID NO: 340<br>KPKLLY CSNGGHFLRI LPDGTVDGTR DRSDQHIQLQ LSAESVGEVY IKSTETGQYL AMDTDGLLYG SQTPNEECLF LERLEENHYN TYISKKHAEK NWFVGLDQNG SCVRGPRTHY GQKAILFLPL PGLPPALPEP PGILAPQPPD VGSSDPLSMV GPSQGRSPSY AS |
| Amino acid sequence of a FGF2/FGF21 chimera composed of residues M1 to M151 of human FGF2 harboring K128D/R129Q/K134V triple mutation (bold) and residues P168 to S209 of human FGF21 (bold) | SEQ ID NO: 341<br>MAAGSITTLP ALPEDGGSGA FPPGHFKDPK RLYCKNGGFF LRIHPDGRVD GVREKSDPHI KLQLQAEERG VVSIKGVCAN RYLAMKEDGR LLASKCVTDE CFFFERLESN NYNTYRSRKY TSWYVALDQT GQYVLGSKTG PGQKAILFLP MPGLPPALPE PPGILAPQPP DVGSSDPLSM VGPSQGRSPS YAS |
| Amino acid sequence of a FGF2/FGF21 chimera composed of residues H25 to M151 of human FGF2 harboring K128D/R129Q/K134V triple mutation (bold) and residues P168 to S209 of human FGF21 (bold) | SEQ ID NO: 342<br>HFKDPK RLYCKNGGFF LRIHPDGRVD GVREKSDPHI KLQLQAEERG VVSIKGVCAN RYLAMKEDGR LLASKCVTDE CFFFERLESN NYNTYRSRKY TSWYVALDQT GQYVLGSKTG PGQKAILFLP MPGLPPALPE PPGILAPQPP DVGSSDPLSM VGPSQGRSPS YAS |

Chimeric proteins according to the present invention may be isolated proteins or polypeptides. The isolated chimeric proteins of the present invention may be prepared for use in accordance with the present invention using standard methods of synthesis known in the art, including solid phase peptide synthesis (Fmoc or Boc strategies) or solution phase peptide synthesis. Alternatively, peptides of the present invention may be prepared using recombinant expression systems.

Accordingly, another aspect of the present invention relates to an isolated nucleic acid molecule encoding a chimeric protein according to the present invention. In one embodiment, the nucleic acid molecule includes the nucleotide sequence of SEQ ID NO: 343, SEQ ID NO: 344, SEQ ID NO: 345, or SEQ ID NO: 346 (as shown in Table 10).

TABLE 10

| Description of Chimeric Protein | Sequence |
| --- | --- |
| Nucleotide sequence of a FGF1/FGF21 chimera composed of residues M1 to L150 of human FGF1 harboring K127D/K128Q/K133V triple mutation (bold) and residues P168 to S209 of human FGF21 (bold) | SEQ ID NO: 343<br>ATGGCTGAAG GGGAAATCAC CACCTTCACA<br>GCCCTGACCG AGAAGTTTAA TCTGCCTCCA<br>GGGAATTACA AGAAGCCCAA ACTCCTCTAC<br>TGTAGCAACG GGGGCCACTT CCTGAGGATC<br>CTTCCGGATG GCACAGTGGA TGGGACAAGG<br>GACAGGAGCG ACCAGCACAT TCAGCTGCAG<br>CTCAGTGCGG AAAGCGTGGG GGAGGTGTAT<br>ATAAAGAGTA CCGAGACTGG CCAGTACTTG<br>GCCATGGACA CCGACGGGCT TTTATACGGC<br>TCACAGACAC CAAATGAGGA ATGTTTGTTC<br>CTGGAAAGGC TGGAGGAGAA CCATTACAAC<br>ACCTATATAT CCAAGAAGCA TGCAGAGAAG<br>AATTGGTTTG TTGGCCTCGA TCAGAATGGG<br>AGCTGCGTTC GCGGTCCTCG GACTCACTAT<br>GGCCAGAAAG CAATCTTGTT TCTCCCCCTG<br>CCAGGCCTGC CCCCGCACT CCCGGAGCCA<br>CCCGGAATCC TGGCCCCCCA GCCCCCCGAT<br>GTGGGCTCCT CGGACCCTCT GAGCATGGTG<br>GGACCTTCCC AGGGCCGAAG CCCCAGCTAC<br>GCTTCC |
| Nucleotide sequence of a FGF1/FGF21 chimera composed of residues K25 to L150 of human FGF1 harboring K127D/K128Q/K133V triple mutation (bold) and residues P168 to S209 of human FGF21 (bold) | SEQ ID NO: 344<br>AAGCCCAA ACTCCTCTAC<br>TGTAGCAACG GGGGCCACTT CCTGAGGATC<br>CTTCCGGATG GCACAGTGGA TGGGACAAGG<br>GACAGGAGCG ACCAGCACAT TCAGCTGCAG<br>CTCAGTGCGG AAAGCGTGGG GGAGGTGTAT<br>ATAAAGAGTA CCGAGACTGG CCAGTACTTG<br>GCCATGGACA CCGACGGGCT TTTATACGGC<br>TCACAGACAC CAAATGAGGA ATGTTTGTTC<br>CTGGAAAGGC TGGAGGAGAA CCATTACAAC<br>ACCTATATAT CCAAGAAGCA TGCAGAGAAG<br>AATTGGTTTG TTGGCCTCGA TCAGAATGGG<br>AGCTGCGTTC GCGGTCCTCG GACTCACTAT<br>GGCCAGAAAG CAATCTTGTT TCTCCCCCTG<br>CCAGGCCTGC CCCCGCACT CCCGGAGCCA<br>CCCGGAATCC TGGCCCCCCA GCCCCCCGAT<br>GTGGGCTCCT CGGACCCTCT GAGCATGGTG<br>GGACCTTCCC AGGGCCGAAG CCCCAGCTAC<br>GCTTCC |
| Nucleotide sequence of a FGF2/FGF21 chimera composed of residues M1 to M151 of human FGF2 harboring K128D/R129Q/K134V triple mutation (bold) and residues P168 to S209 of human FGF21 (bold) | SEQ ID NO: 345<br>ATG GCAGCCGGGA<br>GCATCACCAC GCTGCCCGCC TTGCCCGAGG<br>ATGGCGGCAG CGGCGCCTTC CCGCCCGGCC<br>ACTTCAAGGA CCCCAAGCGG CTGTACTGCA<br>AAAACGGGGG CTTCTTCCTG CGCATCCACC<br>CCGACGGCCG AGTTGACGGG GTCCGGGAGA<br>AGAGCGACCC TCACATCAAG CTACAACTTC<br>AAGCAGAAGA GAGAGGAGTT GTGTCTATCA<br>AAGGAGTGTG TGCTAACCGT TACCTGGCTA<br>TGAAGGAAGA TGGAAGATTA CTGGCTTCTA<br>AATGTGTTAC GGATGAGTGT TTCTTTTTTG<br>AACGATTGGA ATCTAATAAC TACAATACTT<br>ACCGGTCAAG GAAATACACC AGTTGGTATG<br>TGGCACTGGA TCAGACTGGG CAGTATGTTC<br>TTGGATCCAA AACAGGACCT GGGCAGAAAG<br>CTATACTTTT TCTTCCAATG CCAGGCCTGC<br>CCCCCGCACT CCCGGAGCCA CCCGGAATCC<br>TGGCCCCCCA GCCCCCCGAT GTGGGCTCCT<br>CGGACCCTCT GAGCATGGTG GGACCTTCCC<br>AGGGCCGAAG CCCCAGCTAC GCTTCC |

TABLE 10-continued

| Description of Chimeric Protein | Sequence |
|---|---|
| Nucleotide sequence of a FGF2/FGF21 chimera composed of residues H25 to M151 of human FGF2 harboring K128D/R129Q/K134V triple mutation (bold) and residues P168 to S209 of human FGF21 (bold) | SEQ ID NO: 346<br>                                                                  C<br>ACTTCAAGGA CCCCAAGCGG CTGTACTGCA<br>AAAACGGGGG CTTCTTCCTG CGCATCCACC<br>CCGACGGCCG AGTTGACGGG GTCCGGGAGA<br>AGAGCGACCC TCACATCAAG CTACAACTTC<br>AAGCAGAAGA GAGAGGAGTT GTGTCTATCA<br>AAGGAGTGTG TGCTAACCGT TACCTGGCTA<br>TGAAGGAAGA TGGAAGATTA CTGGCTTCTA<br>AATGTGTTAC GGATGAGTGT TTCTTTTTTG<br>AACGATTGGA ATCTAATAAC TACAATACTT<br>ACCGGTCAAG GAAATACACC AGTTGGTATG<br>TGGCACTGGA TCAGACTGGG CAGTATGTTC<br>TTGGATCCAA AACAGGACCT GGGCAGAAAG<br>CTATACTTTT TCTTCCAATG CCAGGCCTGC<br>CCCCCGCACT CCCGGAGCCA CCCGGAATCC<br>TGGCCCCCCA GCCCCCCGAT GTGGGCTCCT<br>CGGACCCTCT GAGCATGGTG GGACCTTCCC<br>AGGGCCGAAG CCCCAGCTAC GCTTCC |

Another aspect of the present invention relates to a nucleic acid construct including a nucleic acid molecule encoding a chimeric protein according to the present invention, a 5' DNA promoter sequence, and a 3' terminator sequence. The nucleic acid molecule, the promoter, and the terminator are operatively coupled to permit transcription of the nucleic acid molecule.

Also encompassed are vectors or expression vectors including such nucleic acid molecules and host cells including such nucleic acid molecules. Nucleic acid molecules according to the present invention can be expressed in a host cell, and the encoded polynucleotides isolated, according to techniques that are known in the art.

Generally, the use of recombinant expression systems involves inserting the nucleic acid molecule encoding the amino acid sequence of the desired peptide into an expression system to which the molecule is heterologous (i.e., not normally present). One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., MOLECULAR CLONING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize protein production. For the purposes of expressing a cloned nucleic acid sequence encoding a desired protein, it is advantageous to use strong promoters to obtain a high level of transcription. Depending upon the host system utilized, any one of a number of suitable promoters may be used. For instance, when cloning in E. coli, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other E. coli promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR.

There are other specific initiation signals required for efficient gene transcription and translation in prokaryotic cells that can be included in the nucleic acid construct to maximize protein production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination In Vitro," *Methods in Enzymology* 68:473-82 (1979), which is hereby incorporated by reference in its entirety.

A nucleic acid molecule encoding an isolated protein of the present invention, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999); and U.S. Pat. No. 4,237,224 to Cohen and Boyer, which are hereby incorporated by reference in their entirety.

Once the nucleic acid molecule encoding the protein has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by JOSEPH SAMBROOK et al., MOLECULAR CLONING: A LABORATORY MANUAL (Cold Springs Harbor 1989), which is hereby incorporated by reference in its entirety.

A variety of suitable host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Purified proteins may be obtained by several methods readily known in the art, including ion exchange chromatography, hydrophobic interaction chromatography, affinity chromatography, gel filtration, and reverse phase chromatography. The protein is preferably produced in purified form (preferably at least about 80% or 85% pure, more preferably at least about 90% or 95% pure) by conventional techniques. Depending on whether the recombinant host cell is made to secrete the protein into growth medium (see U.S. Pat. No. 6,596,509 to Bauer et al., which is hereby incorporated by reference in its entirety), the protein can be isolated and purified by centrifugation (to separate cellular components from supernatant containing the secreted protein) followed by sequential ammonium sulfate precipitation of the supernatant. The fraction containing the protein is subjected to gel filtration in an appropriately sized dextran or polyacrylamide column to separate the protein of interest from other proteins. If necessary, the protein fraction may be further purified by HPLC.

Another aspect of the present invention relates to a pharmaceutical composition that includes a chimeric protein according to the present invention and a pharmaceutically acceptable carrier.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "pharmaceutically acceptable" means it is, within the scope of sound medical judgment, suitable for use in contact with the cells of humans and lower animals without undue toxicity, irritation, allergic response, and the like, and is commensurate with a reasonable benefit/risk ratio.

In one embodiment, the pharmaceutical composition includes an organotropic targeting agent. In one embodiment, the targeting agent is covalently linked to the chimeric protein via a linker that is cleaved under physiological conditions.

Chimeric and/or modified proteins according to the present invention may also be modified using one or more additional or alternative strategies for prolonging the in vivo half-life of the protein. One such strategy involves the generation of D-peptide chimeric proteins, which consist of unnatural amino acids that are not cleaved by endogenous proteases. Alternatively, the chimeric and/or modified proteins may be fused to a protein partner that confers a longer half-life to the protein upon in vivo administration. Suitable fusion partners include, without limitation, immunoglobulins (e.g., the Fc portion of an IgG), human serum albumin (HAS) (linked directly or by addition of the albumin binding domain of streptococcal protein G), fetuin, or a fragment of any of these. The chimeric and/or modified proteins may also be fused to a macromolecule other than protein that confers a longer half-life to the protein upon in vivo administration. Suitable macromolecules include, without limitation, polyethylene glycols (PEGs). Methods of conjugating proteins or peptides to polymers to enhance stability for therapeutic administration are described in U.S. Pat. No. 5,681,811 to Ekwuribe, which is hereby incorporated by reference in its entirety. Nucleic acid conjugates are described in U.S. Pat. No. 6,528,631 to Cook et al., U.S. Pat. No. 6,335,434 to Guzaev et al., U.S. Pat. No. 6,235,886 to Manoharan et al., U.S. Pat. No. 6,153,737 to Manoharan et al., U.S. Pat. No. 5,214,136 to Lin et al., or U.S. Pat. No. 5,138,045 to Cook et al., which are hereby incorporated by reference in their entirety.

The pharmaceutical composition according to the present invention can be formulated for administration orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The formulations may conveniently be presented in unit dosage form and may be prepared by any of the methods well known in the art of pharmacy.

Another aspect of the present invention relates to a method for treating a subject suffering from a disorder. This method involves selecting a subject suffering from the disorder and administering the pharmaceutical composition according to the present invention to the selected subject under conditions effective to treat the disorder. In one embodiment the disorder is diabetes, obesity, or metabolic syndrome.

Another aspect of the present invention relates to a method for treating a subject suffering from a disorder. This method involves selecting a subject suffering from the disorder and providing a chimeric FGF protein, where the chimeric FGF protein includes an N-terminus coupled to a C-terminus. The N-terminus includes a portion of a paracrine FGF and the C-terminus includes a C-terminal portion of FGF21. The portion of the paracrine FGF is modified to decrease binding affinity for heparin and/or heparan sulfate compared to the portion without the modification. This method also involves administering a therapeutically effective amount of the chimeric FGF protein to the selected subject under conditions effective to treat the disorder.

Suitable chimeric proteins for use in accordance with this aspect of the present invention are described above and throughout the present application.

In one embodiment, the selected subject is a mammal. In one embodiment, the selected subject is a human. In another embodiment, the selected subject is a rodent.

In one embodiment, the selected subject is in need of increased FGF21-βKlotho-FGF receptor ("FGFR") complex formation.

In one embodiment, the disorder is a selected from diabetes, obesity, and metabolic syndrome. As used herein, diabetes includes type I diabetes, type II diabetes, gestational diabetes, and drug-induced diabetes. In yet another embodiment, the subject has obesity. In yet another embodiment, the subject has metabolic syndrome.

The chimeric protein of the present invention or pharmaceutical composition thereof can be used to treat a number of conditions. In one embodiment, the condition is one which the therapeutic outcome includes a decrease in blood glucose, a decrease in blood fructosamine, an increase in energy expenditure, an increase in fat utilization, a decrease in body weight, a decrease in body fat, a decrease in triglycerides, a decrease in free fatty acids, an increase in fat excretion, an improvement, or even a preservation, of pancreatic β-cell function and mass, a decrease in total blood cholesterol, a decrease in blood low-density lipoprotein cholesterol, an increase in blood high-density lipoprotein cholesterol, an increase in blood adiponectin, an increase in insulin sensitivity, an increase in leptin sensitivity, a decrease in blood insulin, a decrease in blood leptin, a decrease in blood glucagon, an increase in glucose uptake by adipocytes, a decrease in fat accumulation in hepatocytes, and/or an increase in fat oxidation in hepatocytes. Each of these parameters can be measured by standard methods, for example, by measuring oxygen consumption to determine metabolic rate, using scales to determine weight, and measuring lean body mass composition or mass to determine fat. Moreover, the presence and amount of triglycerides, free fatty acids, glucose and leptin can be determined by standard methods (e.g., blood test).

Additional conditions that are treatable in accordance with the present invention include one or more of type 1 diabetes, type 2 diabetes, gestational diabetes, drug-induced diabetes, high blood glucose, metabolic syndrome, lipodystrophy syndrome, dyslipidemia, insulin resistance, leptin resistance, atherosclerosis, vascular disease, inflammatory disease, fibrotic disease, hypercholesterolemia, hypertriglyceridemia, non-alcoholic fatty liver disease, overweight, and obesity.

In one embodiment, the chimeric protein of the present invention or pharmaceutical composition thereof is administered with a pharmaceutically-acceptable carrier.

The chimeric protein according to the present invention or pharmaceutical composition thereof can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The most suitable route may depend on the condition and disorder of the recipient. Formulations including chimeric proteins according to the present invention may conveniently be presented in unit dosage form and may be prepared by any of the methods well known in the art of pharmacy.

Dosages and desired drug concentrations of pharmaceutical compositions of the present invention may vary depending on the particular use envisioned. The determination of the appropriate dosage or route of administration is well within the skill of an ordinary physician. Those skilled in the art can readily optimize pharmaceutically effective dosages and administration regimens for therapeutic compositions including the chimeric protein according to the present invention, as determined by good medical practice and the clinical condition of the individual patient.

When in vivo administration of a chimeric protein of the present invention or is employed, normal dosage amounts may vary from, for example, about 10 ng/kg to up to 100 mg/kg of mammal body weight or more per day. In one embodiment, the dosage may be from about 1 µg/kg/day to 10 mg/kg/day, depending upon the route of administration. In one embodiment, the chimeric protein according to the present invention is administered at a dose of about 0.1 to 10 mg/kg once or twice daily. In one embodiment, the chimeric protein according to the present invention is administered at a dose of about 1 to 9, 1 to 8, 1 to 7, 1 to 6, 1 to 5, 1 to 4, 1 to 3, or 1 to 2 mg/kg. In one embodiment, the dosage is the same as that of a native FGF21 therapeutic. In one embodiment, the dosage is less than that of a native FGF21 therapeutic, but has the same effect as a higher dosage of a native FGF21 therapeutic. Guidance as to particular dosages and methods of delivery of proteins is provided in the literature; see, for example, U.S. Pat. No. 4,657,760; 5,206,344; or 5,225,212, which are hereby incorporated by reference in their entirety. It is anticipated that different formulations will be effective for different treatment compounds and different disorders, that administration targeting one organ or tissue, for example, may necessitate delivery in a manner different from that to another organ or tissue.

Where sustained-release administration of a chimeric protein of the present invention is desired in a formulation with release characteristics suitable for the treatment of any disease or disorder requiring administration of the chimeric protein of the present invention, microencapsulation is contemplated. Microencapsulation of recombinant proteins for sustained release has been successfully performed with human growth hormone (rhGH), interferon-(rhIFN-), interleukin-2, and MN rgp120. Johnson et al., "Preparation and Characterization of Poly(D,L-lactide-co-glycolide) Microspheres for Controlled Release of Human Growth Hormone," Nat. Med. 2:795-799 (1996); Yasuda, "Sustained Release Formulation of Interferon," Biomed. Ther. 27:1221-1223 (1993); Hora et al., "Controlled Release of Interleukin-2 from Biodegradable Microspheres," Nat. Biotechnol. 8:755-758 (1990); Cleland, "Design and Production of Single Immunization Vaccines Using Polylactide Polyglycolide Microsphere Systems," in VACCINE DESIGN: THE SUBUNIT AND ADJUVANT APPROACH 439-462 (Powell and Newman, eds. 1995); WO 97/03692; WO 96/40072; WO 96/07399; and U.S. Pat. No. 5,654,010, which are hereby incorporated by reference in their entirety. The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/ glycolide polymer," in: BIODEGRADABLE POLYMERS AS DRUG DELIVERY SYSTEMS 1-41 (M. Chasin and R. Langer eds. 1990), which is hereby incorporated by reference in its entirety.

The chimeric protein of the present invention or pharmaceutical composition thereof may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. For other patients, it will be necessary to prescribe not more than one or two doses per day.

In some embodiments, the chimeric protein of the present invention or a pharmaceutical composition thereof is administered in a therapeutically effective amount in combination with a therapeutically effective amount of a second agent. In one embodiment, the chimeric protein of the present invention or pharmaceutical composition thereof is administered in conjunction with the second agent, i.e., the respective periods of administration are part of a single administrative regimen. In one embodiment, the chimeric protein of the present invention or pharmaceutical composition thereof and the second agent are administered concurrently, i.e., the respective periods of administration overlap each other. In one embodiment, the chimeric protein of the present invention or pharmaceutical composition thereof and the second agent are administered non-concurrently, i.e., the respective periods of administration do not overlap each other. In one embodiment, the chimeric protein of the present invention or pharmaceutical composition thereof and the second agent are administered sequentially, i.e., the chimeric protein of the present invention or pharmaceutical composition thereof is administered prior to and/or after the administration of the second agent. In one embodiment, the chimeric protein of the present invention or pharmaceutical composition thereof and the second agent are administered simultaneously as separate compositions. In one embodiment, the chimeric protein of the present invention or pharmaceutical composition thereof and the second agent are administered simultaneously as part of the same compositions.

In one embodiment, the second agent is an anti-inflammatory agent, an antifibrotic agent, an antihypertensive agent, an anti-diabetic agent, a triglyceride-lowering agent, and/or cholesterol-lowering drug such as a drug of the "statin" class. In one embodiment, the second agent is insulin. In one embodiment, the insulin is rapid acting, short acting, regular acting, intermediate acting, or long acting insulin. In one embodiment, the insulin is and/or comprises Humalog®, Lispro, Novolog®, Apidra®, Humulin®, Aspart, regular insulin, NPH, Lente, Ultralente, Lantus®, Glargine, Levemir®, or Detemir. In one embodiment, the second agent is a statin. In one embodiment, the statin is and/or comprises Atorvastatin (e.g., Lipitor® or Torvast®), Cerivastatin (e.g., Lipobay® or Baycol®), Fluvastatin (e.g., Lescol® or LescolXL®), Lovastatin (e.g., Mevacor®, Altocor®, or) Altoprev® Mevastatin, Pitavastatin (e.g., Livalo® or Pitava®), Pravastatin (e.g., Pravachol®, Selektine, or Lipostat®) Rosuvastatin (e.g., Crestor®), Simvastatin (e.g., Zocor® or Lipex®), Vytorin®, Advicor®, Besylate Caduet® or Simcor®.

In one embodiment of the present invention, the chimeric protein according to the present invention or the pharmaceutical composition thereof is administered with an anti-inflammatory agent, an antifibrotic agent, an antihypertensive agent, an antidiabetic agent, a triglyceride-lowering agent, and/or a cholesterol-lowering agent.

Another aspect of the present invention relates to a method of making a chimeric FGF protein possessing enhanced endocrine activity. This method involves introducing one or more modifications to an FGF protein, where the modification decreases the affinity of the FGF protein for heparin and/or heparan sulfate and coupling a Klotho co-receptor binding domain to the modified FGF protein's C-terminus, whereby a chimeric FGF protein possessing enhanced endocrine activity is made.

In one embodiment, the method includes selecting a Klotho co-receptor binding domain, where the Klotho co-receptor binding domain is selected to target an endocrine FGF target tissue. In one embodiment, the Klotho co-receptor binding domain is selected to home the chimeric FGF protein into a target tissue of endocrine FGF. In one embodiment, the Klotho co-receptor binding domain is selected to target white adipose tissue, brown adipose tissue, skeletal muscle, pancreas, and/or liver.

In one embodiment, the Klotho co-receptor binding domain includes a β-Klotho co-receptor binding domain. In one embodiment, the β-Klotho co-receptor binding domain includes a C-terminal portion from FGF21. In one embodiment, the C-terminal portion from the FGF21 includes amino acid residues 168-209 of SEQ ID NO: 233. In one embodiment, the C-terminal portion derived from FGF21 further includes one or more substitutions while retaining the ability to bind β-Klotho. In one embodiment, the C-terminal portion derived from FGF21 further includes one or more substitutions to enhance its binding affinity for β-Klotho. In one embodiment, the C-terminal portion from FGF21 is derived from a mammalian FGF21. In one embodiment, the C-terminal portion derived from FGF21 is from a vertebrate FGF21. Suitable FGF21 molecules, C-terminal portions therof, and modifications thereto, are described above.

In one embodiment, the chimeric FGF protein has greater binding affinity for FGFR than native endocrine FGF ligand having the Klotho co-receptor binding domain. In one embodiment, the chimeric FGF protein possesses enhanced endocrine activity compared to the chimeric FGF protein in the absence of the modification or the Klotho co-receptor binding domain. In one embodiment, the native endocrine FGF ligand having the Klotho co-receptor binding domain is native FGF21. In one embodiment, the FGFR is FGFR1c, FGFR2c, or FGFR4.

In one embodiment, the chimeric FGF protein has greater stability than a native endocrine FGF ligand possessing the Klotho co-receptor binding domain. In one embodiment, increasing the stability includes an increase in thermal stability of the protein as compared to either wild type protein or native endocrine FGF ligand. In one embodiment, increasing the stability includes increasing the half-life of the protein in the blood circulation as compared to wild type protein or native endocrine FGF ligand.

In one embodiment, the method involves introducing one or more modifications to the FGF protein, where the modification alters the receptor-binding specificity of the FGF protein. In one embodiment, the method involves introducing one or more modifications to the FGF protein, where the modification alters the receptor-binding affinity of the FGF protein.

In one embodiment, the FGF is derived from a mammalian FGF. In one embodiment, the FGF is derived from a vertebrate FGF. In one embodiment, the FGF protein is a paracrine FGF molecule. In one embodiment the FGF molecule is FGF1 or FGF2. In one embodiment, the FGF protein is an FGF protein that possesses intrinsically greater binding affinity for FGF receptor than a native endocrine FGF ligand. In one embodiment, the FGF protein is an FGF protein that possesses intrinsically greater thermal stability than a native endocrine FGF ligand. In one embodiment, the method involves introducing one or more modifications to the FGF protein, where the modification alters receptor-binding specificity and/or receptor-binding affinity of the FGF protein. In one embodiment, the method involves introducing one or more modifications to the FGF protein, where the modification alters the stability of the FGF protein. For example, receptor-binding specificity of FGF1, which by nature binds to all the seven principal FGFRs, may be altered to, for example, reduce any risk for adverse effects (e.g., mitogenicity). Paracrine FGFs, portions of paracrine FGFs, and modifications thereto are described above.

In one embodiment, the chimeric FGF protein is effective to treat diabetes, obesity, and/or metabolic syndrome.

Suitable methods of generating chimeric proteins according to the present invention include standard methods of synthesis known in the art, as described above.

Yet another aspect of the present invention relates to a method of facilitating fibroblast growth factor receptor ("FGFR")-βKlotho co-receptor complex formation. This method involves providing a cell that includes a βKlotho co-receptor and an FGFR and providing a chimeric FGF protein. The chimeric FGF protein includes a C-terminal portion of FGF21 and a portion of a paracrine FGF, where the portion of the paracrine FGF is modified to decrease binding affinity for heparin and/or heparan sulfate compared to the portion without the modification. This method also involves contacting the cell and the chimeric FGF protein under conditions effective to cause FGFR-βKlotho co-receptor complex formation.

The portion of the paracrine FGF may also be modified to alter receptor-binding specificity and/or receptor-binding affinity of the FGF, as noted above. Suitable portions of the paracrine FGFs for use in accordance with the present invention, as well as modifications to alter receptor-binding specificity and/or receptor-binding affinity of the FGF, are described above. Suitable modifications to the paracrine FGFs for use in accordance with the present invention are also described above. Suitable C-terminal portions from FGF21 are described above and throughout the present application.

In one embodiment according to the present invention, βKlotho is mammalian βKlotho. In one embodiment, βKlotho is human or mouse βKlotho. In one particular embodiment of the present invention, βKlotho is human or mouse βKlotho having the amino acid sequence of SEQ ID NO: 347 (i.e., GenBank Accession No. NP_783864, which is hereby incorporated by reference in its entirety) or SEQ ID NO: 348 (i.e., GenBank Accession No. NP_112457, which is hereby incorporated by reference in its entirety), respectively, as follows:

```
SEQ ID NO: 347:
   1 MKPGCAAGSP GNEWIFFSTD EITTRYRNTM SNGGLQRSVI LSALILLRAV TGFSGDGRAI

61 WSKNPNFTPV NESQLFLYDT FPKNFFWGIG TGALQVEGSW KKDGKGPSIW DHFIHTHLKN

121 VSSTNGSSDS YIFLEKDLSA LDFIGVSFYQ FSISWPRLFP DGIVTVANAK GLQYYSTLLD

181 ALVLRNIEPI VTLYHWDLPL ALQEKYGGWK NDTIIDIFND YATYCFQMFG DRVKYWITIH

241 NPYLVAWHGY GTGMHAPGEK GNLAAVYTVG HNLIKAHSKV WHNYNTHFRP HQKGWLSITL

301 GSHWIEPNRS ENTMDIFKCQ QSMVSVLGWF ANPIHGDGDY PEGMRKKLFS VLPIFSEAEK

361 HEMRGTADFF AFSFGPNNFK PLNTMAKMGQ NVSLNLREAL NWIKLEYNNP RILIAENGWF

421 TDSRVKTEDT TAIYMMKNFL SQVLQAIRLD EIRVFGYTAW SLLDGFEWQD AYTIRRGLFY

481 VDFNSKQKER KPKSSAHYYK QIIRENGFSL KESTPDVQGQ FPCDFSWGVT ESVLKPESVA

541 SSPQFSDPHL YVWNATGNRL LHRVEGVRLK TRPAQCTDFV NIKKQLEMLA RMKVTHYRFA

601 LDWASVLPTG NLSAVNRQAL RYYRCVVSEG LKLGISAMVT LYYPTHAHLG LPEPLLHADG

661 WLNPSTAEAF QAYAGLCFQE LGDLVKLWIT INEPNRLSDI YNRSGNDTYG AAHNLLVAHA

721 LAWRLYDRQF RPSQRGAVSL SLHADWAEPA NPYADSHWRA AERFLQFEIA WFAEPLFKTG

781 DYPAAMREYI ASKHRRGLSS SALPRLTEAE RRLLKGTVDF CALNHFTTRF VMHEQLAGSR

841 YDSDRDIQFL QDITRLSSPT RLAVIPWGVR KLLRWVRRNY GDMDIYITAS GIDDQALEDD

901 RLRKYYLGKY LQEVLKAYLI DKVRIKGYYA FKLAEEKSKP RFGFFTSDFK AKSSIQFYNK

961 VISSRGFPFE NSSSRCSQTQ ENTECTVCLF LVQKKPLIFL GCCFFSTLVL LLSIAIFQRQ

1021 KRRKFWKAKN LQHIPLKKGK RVVS

SEQ ID NO: 348:
   1 MKTGCAAGSP GNEWIFFSSD ERNTRSRKTM SNRALQRSAV LSAFVLLRAV TGFSGDGKAI

61 WDKKQYVSPV NPSQLFLYDT FPKNFSWGVG TGAFQVEGSW KTDGRGPSIW DRYVYSHLRG

121 VNGTDRSTDS YIFLEKDLLA LDFLGVSFYQ FSISWPRLFP NGTVAAVNAQ GLRYYRALLD

181 SLVLRNIEPI VTLYHWDLPL TLQEEYGGWK NATMIDLFND YATYCFQTFG DRVKYWITIH

241 NPYLVAWHGF GTGMHAPGEK GNLTAVYTVG HNLIKAHSKV WHNYDKNFRP HQKGWLSITL

301 GSHWIEPNRT DNMEDVINCQ HSMSSVLGWF ANPIHGDGDY PEFMKTGAMI PEFSEAEKEE

361 VRGTADFFAF SFGPNNFRPS NTVVKMGQNV SLNLRQVLNW IKLEYDDPQI LISENGWFTD

421 SYIKTEDTTA IYMMKNFLNQ VLQAIKFDEI RVFGYTAWTL LDGFEWQDAY TTRRGLFYVD
```

```
 481 FNSEQKERKP KSSAHYYKQI IQDNGFPLKE STPDMKGRFP CDFSWGVTES VLKPEFTVSS

541 PQFTDPHLYV WNVTGNRLLY RVEGVRLKTR PSQCTDYVSI KKRVEMLAKM KVTHYQFALD

601 WTSILPTGNL SKVNRQVLRY YRCVVSEGLK LGVFPMVTLY HPTHSHLGLP LPLLSSGGWL

661 NMNTAKAFQD YAELCFRELG DLVKLWITIN EPNRLSDMYN RTSNDTYRAA HNLMIAHAQV

721 WHLYDRQYRP VQHGAVSLSL HCDWAEPANP FVDSHWKAAE RFLQFEIAWF ADPLFKTGDY

781 PSVMKEYIAS KNQRGLSSSV LPRFTAKESR LVKGTVDFYA LNHFTTRFVI HKQLNTNRSV

841 ADRDVQFLQD ITRLSSPSRL AVTPWGVRKL LAWIRRNYRD RDIYITANGI DDLALEDDQI

901 RKYYLEKYVQ EALKAYLIDK VKIKGYYAFK LTEEKSKPRF GFFTSDFRAK SSVQFYSKLI

961 SSSGLPAENR SPACGQPAED TDCTICSFLV EKKPLIFFGC CFISTLAVLL SITVFHHQKR

1021 RKFQKARNLQ NIPLKKGHSR VFS
```

In one particular embodiment of the present invention, βKlotho is human or mouse βKlotho encoded by a nucleotide sequence having the nucleotide sequences of SEQ ID NO: 349 (GenBank Accession No. NM_175737, which is hereby incorporated by reference in its entirety) and SEQ ID NO: 350 (GenBank Accession No. NM_031180, which is hereby incorporated by reference in its entirety), as follows:

```
SEQ ID NO: 349 (Human βKlotho gene coding sequence):
  98        ATG AAGCCAGGCT GTGCGGCAGG ATCTCCAGGG AATGAATGGA TTTTCTTCAG

151 CACTGATGAA ATAACCACAC GCTATAGGAA TACAATGTCC AACGGGGAT TGCAAAGATC

211 TGTCATCCTG TCAGCACTTA TTCTGCTACG AGCTGTTACT GGATTCTCTG GAGATGGAAG

271 AGCTATATGG TCTAAAAATC CTAATTTTAC TCCGGTAAAT GAAAGTCAGC TGTTTCTCTA

331 TGACACTTTC CCTAAAAACT TTTTCTGGGG TATTGGGACT GGAGCATTGC AAGTGGAAGG

391 GAGTTGGAAG AAGGATGGAA AAGGACCTTC TATATGGGAT CATTTCATCC ACACACACCT

451 TAAAAATGTC AGCAGCACGA ATGGTTCCAG TGACAGTTAT ATTTTTCTGG AAAAAGACTT

511 ATCAGCCCTG GATTTTATAG GAGTTTCTTT TTATCAATTT TCAATTTCCT GGCCAAGGCT

571 TTTCCCCGAT GGAATAGTAA CAGTTGCCAA CGCAAAAGGT CTGCAGTACT ACAGTACTCT

631 TCTGGACGCT CTAGTGCTTA GAAACATTGA ACCTATAGTT ACTTTATACC ACTGGGATTT

691 GCCTTTGGCA CTACAAGAAA ATATGGGGG GTGGAAAAAT GATACCATAA TAGATATCTT

751 CAATGACTAT GCCACATACT GTTTCCAGAT GTTTGGGGAC CGTGTCAAAT ATTGGATTAC

811 AATTCACAAC CCATATCTAG TGGCTTGGCA TGGGTATGGG ACAGGTATGC ATGCCCCTGG

871 AGAGAAGGGA AATTTAGCAG CTGTCTACAC TGTGGGACAC AACTTGATCA AGGCTCACTC

931 GAAAGTTTGG CATAACTACA ACACACATTT CCGCCCACAT CAGAAGGGTT GGTTATCGAT

991 CACGTTGGGA TCTCATTGGA TCGAGCCAAA CCGGTCGGAA AACACGATGG ATATATTCAA

1051 ATGTCAACAA TCCATGGTTT CTGTGCTTGG ATGGTTTGCC AACCCTATCC ATGGGGATGG

1111 CGACTATCCA GAGGGGATGA GAAAGAAGTT GTTCTCCGTT CTACCCATTT TCTCTGAAGC

1171 AGAGAAGCAT GAGATGAGAG GCACAGCTGA TTTCTTTGCC TTTTCTTTTG GACCCAACAA

1231 CTTCAAGCCC CTAAACACCA TGGCTAAAAT GGGACAAAAT GTTTCACTTA ATTTAAGAGA

1291 AGCGCTGAAC TGGATTAAAC TGGAATACAA CAACCCTCGA ATCTTGATTG CTGAGAATGG

1351 CTGGTTCACA GACAGTCGTG TGAAAACAGA AGACACCACG GCCATCTACA TGATGAAGAA

1411 TTTCCTCAGC CAGGTGCTTC AAGCAATAAG GTTAGATGAA ATACGAGTGT TTGGTTATAC

1471 TGCCTGGTCT CTCCTGGATG GCTTTGAATG GCAGGATGCT TACACCATCC GCCGAGGATT
```

```
1531 ATTTTATGTG GATTTTAACA GTAAACAGAA AGAGCGGAAA CCTAAGTCTT CAGCACACTA

1591 CTACAAACAG ATCATACGAG AAAATGGTTT TTCTTTAAAA GAGTCCACGC CAGATGTGCA

1651 GGGCCAGTTT CCCTGTGACT TCTCCTGGGG TGTCACTGAA TCTGTTCTTA AGCCCGAGTC

1711 TGTGGCTTCG TCCCCACAGT TCAGCGATCC TCATCTGTAC GTGTGGAACG CCACTGGCAA

1771 CAGACTGTTG CACCGAGTGG AAGGGGTGAG GCTGAAAACA CGACCCGCTC AATGCACAGA

1831 TTTTGTAAAC ATCAAAAAAC AACTTGAGAT GTTGGCAAGA ATGAAAGTCA CCCACTACCG

1891 GTTTGCTCTG GATTGGGCCT CGGTCCTTCC CACTGGCAAC CTGTCCGCGG TGAACCGACA

1951 GGCCCTGAGG TACTACAGGT GCGTGGTCAG TGAGGGGCTG AAGCTTGGCA TCTCCGCGAT

2011 GGTCACCCTG TATTATCCGA CCCACGCCCA CCTAGGCCTC CCCGAGCCTC TGTTGCATGC

2071 CGACGGGTGG CTGAACCCAT CGACGGCCGA GGCCTTCCAG GCCTACGCTG GCTGTGCTT

2131 CCAGGAGCTG GGGGACCTGG TGAAGCTCTG GATCACCATC AACGAGCCTA ACCGGCTAAG

2191 TGACATCTAC AACCGCTCTG GCAACGACAC CTACGGGCG GCGCACAACC TGCTGGTGGC

2251 CCACGCCCTG GCCTGGCGCC TCTACGACCG GCAGTTCAGG CCCTCACAGC GCGGGGCCGT

2311 GTCGCTGTCG CTGCACGCGG ACTGGGCGGA ACCCGCCAAC CCCTATGCTG ACTCGCACTG

2371 GAGGGCGGCC GAGCGCTTCC TGCAGTTCGA GATCGCCTGG TTCGCCGAGC CGCTCTTCAA

2431 GACCGGGGAC TACCCCGCGG CCATGAGGGA ATACATTGCC TCCAAGCACC GACGGGGCT

2491 TTCCAGCTCG GCCCTGCCGC GCCTCACCGA GGCCGAAAGG AGGCTGCTCA AGGGCACGGT

2551 CGACTTCTGC GCGCTCAACC ACTTCACCAC TAGGTTCGTG ATGCACGAGC AGCTGGCCGG

2611 CAGCCGCTAC GACTCGGACA GGGACATCCA GTTTCTGCAG GACATCACCC GCCTGAGCTC

2671 CCCCACGCGC CTGGCTGTGA TTCCCTGGGG GGTGCGCAAG CTGCTGCGGT GGGTCCGGAG

2731 GAACTACGGC GACATGGACA TTTACATCAC CGCCAGTGGC ATCGACGACC AGGCTCTGGA

2791 GGATGACCGG CTCCGGAAGT ACTACCTAGG GAAGTACCTT CAGGAGGTGC TGAAAGCATA

2851 CCTGATTGAT AAAGTCAGAA TCAAAGGCTA TTATGCATTC AAACTGGCTG AAGAGAAATC

2911 TAAACCCAGA TTTGGATTCT TCACATCTGA TTTTAAAGCT AAATCCTCAA TACAATTTTA

2971 CAACAAAGTG ATCAGCAGCA GGGGCTTCCC TTTTGAGAAC AGTAGTTCTA GATGCAGTCA

3031 GACCCAAGAA AATACAGAGT GCACTGTCTG CTTATTCCTT GTGCAGAAGA AACCACTGAT

3091 ATTCCTGGGT TGTTGCTTCT TCTCCACCCT GGTTCTACTC TTATCAATTG CCATTTTTCA

3151 AAGGCAGAAG AGAAGAAAGT TTTGGAAAGC AAAAAACTTA CAACACATAC CATTAAAGAA

3211 AGGCAAGAGA GTTGTTAGCT AA
```

SEQ ID NO: 350 (House mouse βKlotho gene coding sequence):

```
  2 ATGAAGACA GGCTGTGCAG CAGGGTCTCC GGGGAATGAA TGGATTTTCT TCAGCTCTGA

61 TGAAAGAAAC ACACGCTCTA GGAAAACAAT GTCCAACAGG GCACTGCAAA GATCTGCCGT

121 GCTGTCTGCG TTTGTTCTGC TGCGAGCTGT TACCGGCTTC TCCGGAGACG GGAAAGCAAT

181 ATGGGATAAA AAACAGTACG TGAGTCCGGT AAACCCAAGT CAGCTGTTCC TCTATGACAC

241 TTTCCCTAAA AACTTTTCCT GGGGCGTTGG GACCGGAGCA TTTCAAGTGG AAGGGAGTTG

301 GAAGACAGAT GGAAGAGGAC CCTCGATCTG GATCGGTAC GTCTACTCAC ACCTGAGAGG

361 TGTCAACGGC ACAGACAGAT CCACTGACAG TTACATCTTT CTGGAAAAAG ACTTGTTGGC

421 TCTGGATTTT TTAGGAGTTT CTTTTTATCA GTTCTCAATC TCCTGGCCAC GGTTGTTTCC

481 CAATGGAACA GTAGCAGCAG TGAATGCGCA AGGTCTCCGG TACTACCGTG CACTTCTGGA

541 CTCGCTGGTA CTTAGGAATA TCGAGCCCAT TGTTACCTTG TACCATTGGG ATTTGCCTCT

601 GACGCTCCAG GAAGAATATG GGGGCTGGAA AAATGCAACT ATGATAGATC TCTTCAACGA
```

```
-continued
 661 CTATGCCACA TACTGCTTCC AGACCTTTGG AGACCGTGTC AAATATTGGA TTACAATTCA

721 CAACCCTTAC CTTGTTGCTT GGCATGGGTT TGGCACAGGT ATGCATGCAC CAGGAGAGAA

781 GGGAAATTTA ACAGCTGTCT ACACTGTGGG ACACAACCTG ATCAAGGCAC ATTCGAAAGT

841 GTGGCATAAC TACGACAAAA ACTTCCGCCC TCATCAGAAG GGTTGGCTCT CCATCACCTT

901 GGGGTCCCAT TGGATAGAGC CAAACAGAAC AGACAACATG GAGGACGTGA TCAACTGCCA

961 GCACTCCATG TCCTCTGTGC TTGGATGGTT CGCCAACCCC ATCCACGGGG ACGGCGACTA

1021 CCCTGAGTTC ATGAAGACGG GCGCCATGAT CCCCGAGTTC TCTGAGGCAG AGAAGGAGGA

1081 GGTGAGGGGC ACGGCTGATT TCTTTGCCTT TTCCTTCGGG CCCAACAACT TCAGGCCCTC

1141 AAACACCGTG GTGAAAATGG GACAAAATGT ATCACTCAAC TTAAGGCAGG TGCTGAACTG

1201 GATTAAACTG GAATACGATG ACCCTCAAAT CTTGATTTCG GAGAACGGCT GGTTCACAGA

1261 TAGCTATATA AAGACAGAGG ACACCACGGC CATCTACATG ATGAAGAATT TCCTAAACCA

1321 GGTTCTTCAA GCAATAAAAT TTGATGAAAT CCGCGTGTTT GGTTATACGG CCTGGACTCT

1381 CCTGGATGGC TTTGAGTGGC AGGATGCCTA TACGACCCGA CGAGGGCTGT TTTATGTGGA

1441 CTTTAACAGT GAGCAGAAAG AGAGGAAACC CAAGTCCTCG GCTCATTACT ACAAGCAGAT

1501 CATACAAGAC AACGGCTTCC CTTTGAAAGA GTCCACGCCA GACATGAAGG GTCGGTTCCC

1561 CTGTGATTTC TCTTGGGGAG TCACTGAGTC TGTTCTTAAG CCCGAGTTTA CGGTCTCCTC

1621 CCCGCAGTTT ACCGATCCTC ACCTGTATGT GTGGAATGTC ACTGGCAACA GATTGCTCTA

1681 CCGAGTGGAA GGGGTAAGGC TGAAAACAAG ACCATCCCAG TGCACAGATT ATGTGAGCAT

1741 CAAAAAACGA GTTGAAATGT TGGCAAAAAT GAAAGTCACC CACTACCAGT TTGCTCTGGA

1801 CTGGACCTCT ATCCTTCCCA CTGGCAATCT GTCCAAAGTT AACAGACAAG TGTTAAGGTA

1861 CTATAGGTGT GTGGTGAGCG AAGGACTGAA GCTGGGCGTC TTCCCCATGG TGACGTTGTA

1921 CCACCCAACC CACTCCCATC TCGGCCTCCC CCTGCCACTT CTGAGCAGTG GGGGTGGCT

1981 AAACATGAAC ACAGCCAAGG CCTTCCAGGA CTACGCTGAG CTGTGCTTCC GGGAGTTGGG

2041 GGACTTGGTG AAGCTCTGGA TCACCATCAA TGAGCCTAAC AGGCTGAGTG ACATGTACAA

2101 CCGCACGAGT AATGACACCT ACCGTGCAGC CCACAACCTG ATGATCGCCC ATGCCCAGGT

2161 CTGGCACCTC TATGATAGGC AGTATAGGCC GGTCCAGCAT GGGGCTGTGT CGCTGTCCTT

2221 ACATTGCGAC TGGGCAGAAC CTGCCAACCC CTTTGTGGAT TCACACTGGA AGGCAGCCGA

2281 GCGCTTCCTC CAGTTTGAGA TCGCCTGGTT TGCAGATCCG CTCTTCAAGA CTGGCGACTA

2341 TCCATCGGTT ATGAAGGAAT ACATCGCCTC CAAGAACCAG CGAGGGCTGT CTAGCTCAGT

2401 CCTGCCGCGC TTCACCGCGA AGGAGAGCAG GCTGGTGAAG GGTACCGTCG ACTTCTACGC

2461 ACTGAACCAC TTCACTACGA GGTTCGTGAT ACACAAGCAG CTGAACACCA ACCGCTCAGT

2521 TGCAGACAGG GACGTCCAGT TCCTGCAGGA CATCACCCGC TAAGCTCGC CCAGCCGCCT

2581 GGCTGTAACA CCCTGGGGAG TGCGCAAGCT CCTTGCGTGG ATCCGGAGGA ACTACAGAGA

2641 CAGGGATATC TACATCACAG CCAATGGCAT CGATGACCTG GCTCTAGAGG ATGATCAGAT

2701 CCGAAAGTAC TACTTGGAGA AGTATGTCCA GGAGGCTCTG AAAGCATATC TCATTGACAA

2761 GGTCAAAATC AAAGGCTACT ATGCATTCAA ACTGACTGAA GAGAAATCTA AGCCTAGATT

2821 TGGATTTTTC ACCTCTGACT TCAGAGCTAA GTCCTCTGTC CAGTTTTACA GCAAGCTGAT

2881 CAGCAGCAGT GGCCTCCCCG CTGAGAACAG AAGTCCTGCG TGTGGTCAGC CTGCGGAAGA

2941 CACAGACTGC ACCATTTGCT CATTTCTCGT GGAGAAGAAA CCACTCATCT TCTTCGGTTG

3001 CTGCTTCATC TCCACTCTGG CTGTACTGCT ATCCATCACC GTTTTTCATC ATCAAAAGAG
```

```
-continued
3061 AAGAAAATTC CAGAAAGCAA GGAACTTACA AAATATACCA TTGAAGAAAG GCCACAGCAG

3121 AGTTTTCAGC TAA
```

In one embodiment, the FGFR is FGFR1c, FGFR2c, or FGFR4. In one embodiment of the present invention, the FGF receptor is FGFR1c receptor. In one particular embodiment, the FGFR1c receptor is the human FGFR1c receptor (GenBank Accession No. NP_075598, which is hereby incorporated by reference in its entirety). In another embodiment, the FGF receptor is FGFR2c receptor. In one particular embodiment, the FGFR2c receptor is the human FGFR2c receptor (GenBank Accession No. NP_000132, which is hereby incorporated by reference in its entirety). In another embodiment, the FGF receptor is FGFR4 receptor. In one particular embodiment, the FGFR4 receptor is the human FGFR4 receptor (GenBank Accession No. NP_002002, which is hereby incorporated by reference in its entirety).

In one embodiment, the method of facilitating FGFR-βKlotho co-receptor complex formation is carried out in vitro. In one embodiment, the method is carried out in an adipocyte. In another embodiment, the method is carried out in a skeletal muscle cell, a pancreatic β cell, or a hepatocyte.

In one embodiment, the method of facilitating FGFR-βKlotho co-receptor complex formation is carried out in vivo. In one embodiment, the method is carried out in a mammal. In one particular embodiment, the mammal is a mouse.

Yet a further aspect of the present invention relates to a method of screening for agents capable of facilitating FGFR-βKlotho complex formation in the treatment of a disorder. This method involves providing a chimeric FGF that includes an N-terminus coupled to a C-terminus, where the N-terminus includes a portion of a paracrine FGF and the C-terminus includes a C-terminal portion of FGF21. The portion of the paracrine FGF is modified to decrease binding affinity for heparin and/or heparan sulfate compared to the portion without the modification. This method also involves providing binary βKlotho-FGFR complex and providing one or more candidate agents. This method further involves combining the chimeric FGF, the binary βKlotho-FGFR complex, and the one or more candidate agents under conditions permitting the formation of a ternary complex between the chimeric FGF and the binary βKlotho-FGFR complex in the absence of the one or more candidate agents. This method also involves identifying the one or more candidate agents that decrease ternary complex formation between the chimeric FGF and the binary βKlotho-FGFR complex compared to the ternary complex formation in the absence of the one or more candidate agents as suitable for treating the disorder.

The portion of the paracrine FGF may also be modified to alter receptor-binding specificity and/or reduce receptor-binding affinity compared to the portion without the modification.

Suitable chimeric proteins for use in accordance with this aspect of the present invention are described above and throughout the present application. Suitable paracrine FGFs, as well as suitable modifications to decrease binding affinity for heparin and/or heparan sulfate, to alter receptor-binding specificity and/or to reduce receptor-binding affinity compared to the portion without the modification, are also described above.

In one embodiment, the modulation is a competitive interaction between the chimeric FGF molecule and the one or more candidate agents for binding to the binary βKlotho-FGFR complex.

In one embodiment, the FGFR is FGFR1c, FGFR2c, or FGFR4.

In one embodiment, the disorder is a selected from diabetes, obesity, and metabolic syndrome. In one embodiment, the disorder is diabetes selected from type II diabetes, gestational diabetes, or drug-induced diabetes. In one embodiment, the disorder is type I diabetes. In one embodiment, the disorder is obesity. In one embodiment, the disorder is metabolic syndrome.

In one embodiment of the screening aspects of the present invention, a plurality of compounds or agents is tested. Candidate agents may include small molecule compounds or larger molecules (e.g., proteins or fragments thereof). In one embodiment, the candidate compounds are biomolecules. In one embodiment, the biomolecules are proteins.

In one embodiment, the biomolecules are peptides. In one embodiment, the candidates are peptides or peptide mimetics having similar structural features to native FGF ligand. In one embodiment, the candidate agent is a second chimeric FGF molecule. In one particular embodiment, the peptides are synthetic peptides. In one embodiment, the compounds are small organic molecules.

In one embodiment of the screening aspects of the present invention, the method is carried out using a cell-based assay. In one embodiment, the identifying is carried out using a cell-based assay.

In one embodiment of the screening aspects of the present invention, the method is carried out using a binding assay. In one embodiment, the binding assay is a direct binding assay. In one embodiment, the binding assay is a competition-binding assay. In one embodiment, the modulation stabilizes the ternary complex between the chimeric FGF molecule and the binary βKlotho-FGFR complex. In one embodiment, the stabilization is compared to the native ternary complex.

In one embodiment, the modulation is an allosteric or kinetic modulation. In one embodiment, the allosteric or kinetic modulation is compared to the native ternary complex. Such stabilization or allosteric or kinetic modulation can be measured using methods known in the art (e.g., by use of surface plasmon resonance (SPR) spectroscopy experiments as described in the Examples infra).

In one embodiment, the binding assay is carried out using surface plasmon resonance spectroscopy. In one embodiment, the identifying is carried out using a binding assay. In one embodiment, the identifying is carried out using surface plasmon resonance spectroscopy.

In one embodiment of the screening aspects of the present invention, the cell-based assay is carried out with adipocytes. In one embodiment, the cell-based assay is carried out with skeletal muscle cells. In one embodiment, the cell-based assay is carried out with pancreatic β cells. In one embodiment, the cell-based assay is carried out with hepatocytes. In one embodiment, stimulation of glucose uptake is the assay readout. In one embodiment, induction of glucose transporter 1 gene expression is the assay readout. In one embodiment, a dose-response curve is generated for the stimulation of glucose uptake by a candidate compound to determine potency and efficacy of the candidate compound. In one embodiment, a dose-response curve is generated for the induction of glucose transporter 1 gene expression by a candidate compound to determine potency and efficacy of the candidate compound. For example, if the dose-response curve is shifted to the left compared to that obtained for the chimeric FGF protein, the candidate compound has greater potency than the chimeric FGF protein and/or native FGF21. In one embodiment, an $IC_{50}$ value is derived from the dose-response curve of a candidate compound to determine potency of the candidate compound. An $IC_{50}$ value smaller than that obtained for the chimeric FGF protein identifies a candidate compound as more potent than the chimeric FGF protein and/or native FGF21.

In one embodiment of the screening aspects of the present invention, the cell-based assay is carried out with mammalian cells ectopically expressing βKlotho. In one particular embodiment, the cells are HEK293 cells. In one embodiment, activation of FGF receptor is the assay readout. In one embodiment, tyrosine phosphorylation of an FGF receptor substrate is used as readout for FGF receptor activation. In one particular embodiment, the FGF receptor substrate is FGF receptor substrate 2α. In one embodiment, activation of downstream mediators of FGF signaling is used as readout for (or an indicator of) FGF receptor activation. In one particular embodiment, the downstream mediator of FGF signaling is 44/42 mitogen-activated protein kinase. In one embodiment, the downstream mediator of FGF signaling is a transcription factor. In one particular embodiment, the transcription factor is early growth response 1. In one embodiment, a dose-response curve is generated for βKlotho-dependent activation of FGF receptor by a candidate compound to determine potency and efficacy of the candidate compound. For example, if the dose-response curve is shifted to the left compared to that obtained for the chimeric FGF protein, the candidate compound is more potent than the chimeric FGF protein and/or native FGF21. In one embodiment, an $IC_{50}$ value is derived from the dose-response curve of a candidate compound to determine potency of the candidate compound. An $IC_{50}$ value smaller than that obtained for the chimeric FGF protein identifies a candidate compound as more potent than the chimeric FGF protein and/or native FGF21.

In one embodiment of the screening aspects of the present invention, the surface plasmon resonance spectroscopy-based assay is carried out using the chimeric FGF protein as ligand coupled to a biosensor chip. In one embodiment, mixtures of βKlotho ectodomain with increasing concentrations of a candidate compound are passed over a biosensor chip containing chimeric FGF protein. In one embodiment, mixtures of the binary complex of FGFR ligand-binding domain and βKlotho ectodomain with increasing concentrations of a candidate compound are passed over a biosensor chip containing chimeric FGF protein. In one particular embodiment, the FGFR ligand-binding domain is the FGFR1c ligand-binding domain. In one embodiment, an inhibition-binding curve is plotted for a candidate compound to determine potency of the candidate compound. For example, if the inhibition-binding curve is shifted to the left compared to that obtained for the chimeric FGF protein, the candidate compound has greater potency than the chimeric FGF protein and/or native FGF21. In one embodiment, an $IC_{50}$ value is derived from the inhibition-binding curve of a candidate compound to determine potency of the candidate compound. An $IC_{50}$ value smaller than that obtained for containing chimeric FGF protein identifies a candidate compound as more potent than the chimeric FGF protein and/or native FGF21. In one embodiment, the inhibition constant $K_i$ is determined for a candidate compound to determine potency of the candidate compound. A $K_i$ value smaller than that obtained for native FGF21 identifies a candidate compound as more potent than the chimeric FGF protein and/or native FGF21.

In one embodiment of the screening aspects of the present invention, the method is carried out in vivo. In one embodiment, the method is carried out in a mammal. In one particular embodiment, the mammal is a mouse. In one embodiment, the mammal has obesity, diabetes, or a related metabolic disorder. In one embodiment, the ability of a candidate compound to potentiate the hypoglycemic effect of insulin is used as readout for FGF21-like metabolic activity. This involves fasting the mammal for a period of time prior to insulin injection and measuring fasting blood glucose levels. The mammal is then injected with insulin alone or co-injected with insulin plus a candidate compound. Blood glucose levels are measured at several time points after the injection. If a candidate compound potentiates the hypoglycemic effect of insulin to a greater degree than the chimeric FGF protein and/or native FGF21 does, the candidate compound exhibits enhanced efficacy. Likewise, if a candidate compound potentiates the hypoglycemic effect of insulin to a similar degree than the chimeric FGF protein and/or native FGF21 does but at a lower dose compared to that of the chimeric FGF protein and/or native FGF21 and/or for a longer period of time compared to the chimeric FGF protein and/or native FGF21, the candidate compound has enhanced agonistic properties. In one embodiment, the ability of a candidate compound to elicit a hypoglycemic effect in a mammal with diabetes, obesity, or a related metabolic disorder is used as readout for FGF21-like metabolic activity. This involves injecting a mammal suffering from diabetes, obesity, or a related metabolic disorder with the candidate compound. Blood glucose levels are measured before the injection and at several time points thereafter. If a candidate compound has a greater hypoglycemic effect than the chimeric FGF protein and/or native FGF21 does, the candidate compound exhibits enhanced efficacy. Likewise, if a candidate compound shows a similar hypoglycemic effect than the chimeric FGF protein and/or native FGF21 does but at a lower dose compared to that of the chimeric FGF protein and/or native FGF21 and/or for a longer period of time compared to the chimeric FGF protein and/or native FGF21, the candidate compound has enhanced agonistic properties.

EXAMPLES

Example 1—Purification of FGF, FGFR, and Klotho Proteins

Figures 5A, 5B, 5C, 5D, 5E, 5F, 5G:
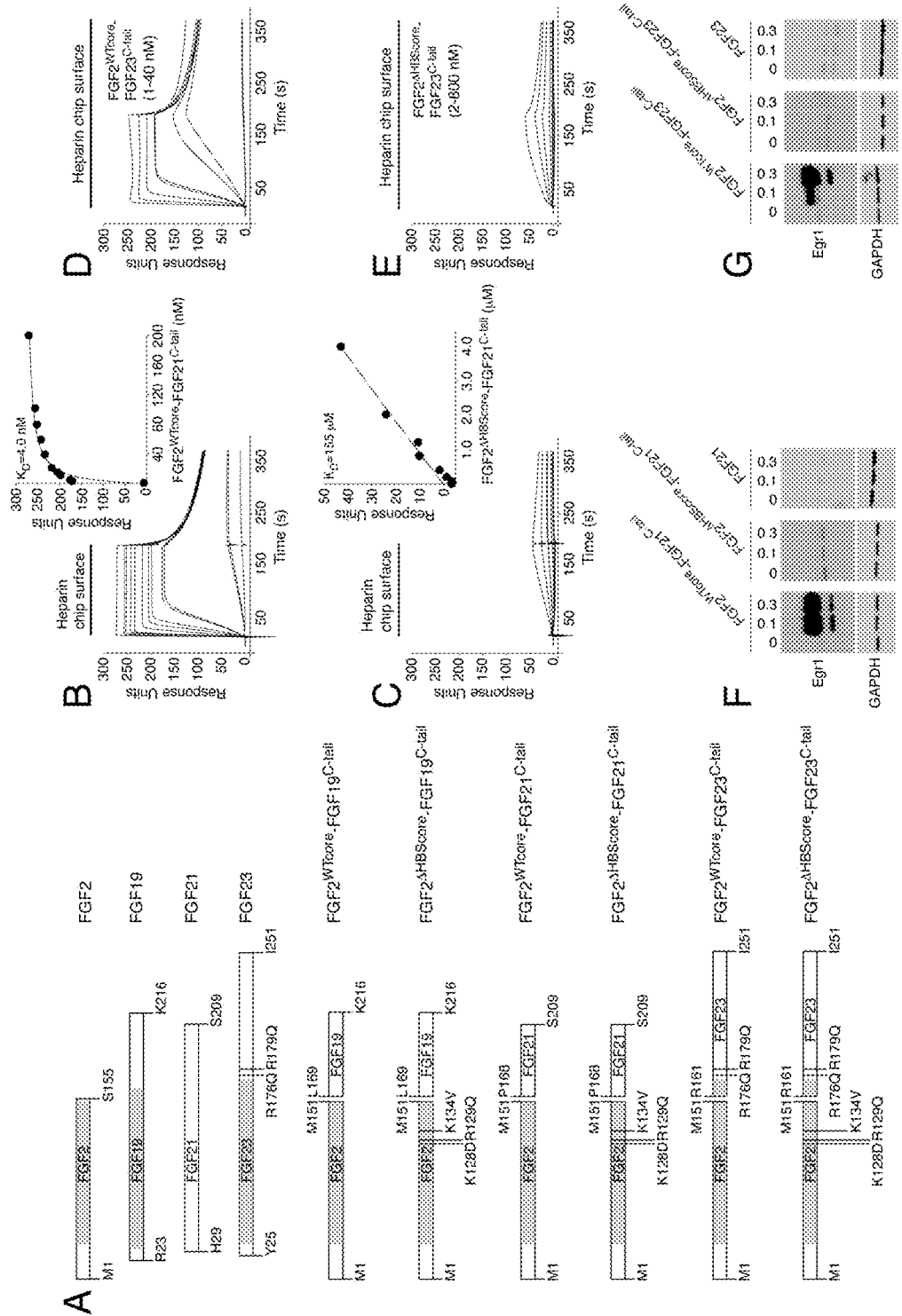
FIGS. 5A-5G show design and results relating to the conversion of FGF2 into an endocrine ligand.

The N-terminally hexahistidine-tagged, mature form of human FGF19 (SEQ ID NO: 337) (R23 to K216), human FGF21 (SEQ ID NO:233) (H29 to S209; FIG. 5A), and human FGF23 (SEQ ID NO: 351) (Y25 to I251; FIG. 5A) was refolded in vitro from bacterial inclusion bodies, and purified by published protocols (Ibrahimi et al., *Hum. Mol. Genet.* 13:2313-2324 (2004); Plotnikov et al., *Cell* 101:413-424 (2000), which is hereby incorporated by reference in its entirety). The amino acid sequence of human FGF23 (SEQ ID NO:351) (GenBank accession no. AAG09917, which is hereby incorporated by reference in its entirety) is as follows:

```
1 MLGARLRLWV CALCSVCSMS VLRAYPNASP LLGSSWGGLI HLYTATARNS YHLQIHKNGH

61 VDGAPHQTIY SALMIRSEDA GFVVITGVMS RRYLCMDFRG NIFGSHYFDP ENCRFQHQTL
```

```
-continued
121 ENGYDVYHSP QYHFLVSLGR AKRAFLPGMN PPPYSQFLSR RNEIPLIHFN TPIPRRHTRS

181 AEDDSERDPL NVLKPRARMT PAPASCSQEL PSAEDNSPMA SDPLGVVRGG RVNTHAGGTG

241 PEGCRPFAKF I
```

Figure 6:
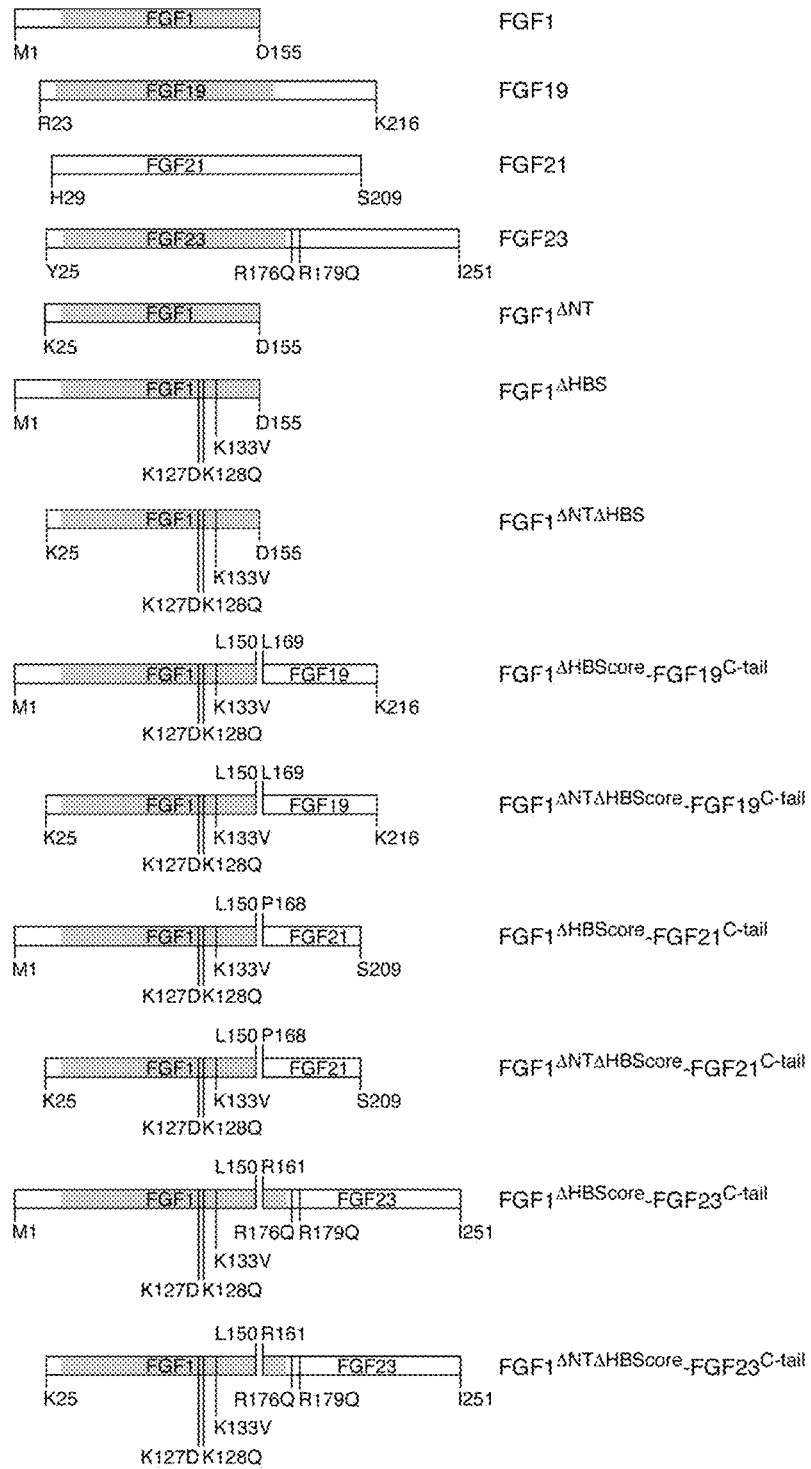
FIG. 6 is a schematic illustrating the conversion of FGF1 into an endocrine ligand. Shown are schematic drawings of human FGF1, FGF19, FGF21, FGF23, and exemplary FGF1-FGF19, FGF1-FGF21, and FGF1-FGF23 chimeras according to the present invention. Amino acid boundaries of each ligand and of each component of the chimeras are labeled with residue letter and number. The β-trefoil core domain for the known ligand crystal structures is shaded gray. HS-binding residues mutated in the FGF1 portion of chimeras are labeled with residue letter and number. Also labeled are the arginine residues of the proteolytic cleavage site in the C-terminal region of FGF23 that were mutated to glutamine in both FGF23 and the FGF1-FGF23 chimeras.

HS-binding site mutants of FGF19 (K149A) and FGF23 (R140A/R143A) were purified from bacterial inclusion bodies by similar protocols as the wild-type proteins. In order to minimize proteolysis of FGF23 wild-type and mutant proteins, arginine residues 176 and 179 of the proteolytic cleavage site $^{176}$RXXR$^{179}$ were replaced with glutamine as it occurs in the phosphate wasting disorder "autosomal dominant hypophosphatemic rickets" (ADHR) (White et al., Nat. Genet. 26:345-348 (2000); White et al., Kidney Int. 60:2079-2086 (2001), which are hereby incorporated by reference in their entirety). Human FGF1 (SEQ ID NO:1) (M1 to D155; FIG. 6), N-terminally truncated human FGF1 (K25 to D155, termed FGF1$^{ΔNT}$; FIG. 6), human FGF2 (SEQ ID NO: 121) (M1 to S155; FIG. 5A), and human FGF homologous factor 1B (FHF1B; M1 to T181) were purified by published protocols (Plotnikov et al., Cell 101:413-424 (2000); Olsen et al., J. Biol. Chem. 278:34226-34236 (2003), which are hereby incorporated by reference in their entirety).

Chimeras composed of the core domain of FGF2 (M1 to M151) and the C-terminal region of either FGF21 (P168 to S209) or FGF23 (R161 to I251) (termed FGF2$^{WTcore}$-FGF21$^{C-tail}$ and FGF2$^{WTcore}$-FGF23$^{C-tail}$, respectively; FIG. 5A) were purified by the same protocol as that for native FGF2 (Plotnikov et al., Cell 101:413-424 (2000), which is hereby incorporated by reference in its entirety). Analogous chimeras containing three mutations in the HS-binding site of the FGF2 core (K128D/R129Q/K134V) (termed FGF2$^{ΔHBScore}$-FGF21$^{C-tail}$ and FGF2$^{ΔHBScore}$-FGF23$^{C-tail}$, respectively, FIG. 5A) were purified from the soluble bacterial cell lysate fraction by ion-exchange and size-exclusion chromatographies. In order to minimize proteolysis of the chimeras containing the C-terminal sequence from R161 to I251 of FGF23, arginine residues 176 and 179 of the proteolytic cleavage site $^{176}$RXXR$^{179}$ located within this sequence were replaced with glutamine as it occurs in ADHR (White et al., Nat. Genet. 26:345-348 (2000); White et al., Kidney Int. 60:2079-2086 (2001), which are hereby incorporated by reference in their entirety). In addition, in order to prevent disulfide-mediated dimerization of FGF2 and chimeric FGF2 proteins, cysteine residues 78 and 96 were mutated to serine. An HS-binding site mutant of FGF1 (K127D/K128Q/K133V) (termed FGF1$^{ΔHBScore}$; FIG. 6) and chimeras composed of the core domain of the HS-binding site mutant of FGF1 (M1 to L150, K127D/K128Q/K133V) and the C-terminal region of either FGF19 (L169 to K216) or FGF21 (P168 to S209) (termed FGF1$^{ΔHBScore}$-FGF19$^{C-tail}$ and FGF1$^{ΔHBScore}$-FGF2 respectively; FIG. 6) were purified from the soluble bacterial cell lysate fraction by ion-exchange and size-exclusion chromatographies. The N-terminally hexahistidine-tagged C-terminal tail peptide of FGF23 (S180 to I251, termed FGF23$^{C-tail}$) was purified by a published protocol (Goetz et al., Proc. Nat'l. Acad. Sci. U.S.A 107:407-412 (2010), which is hereby incorporated by reference in its entirety). The ligand-binding domain of human FGFR1c (D142 to R365) was refolded in vitro from bacterial inclusion bodies, and purified by published protocols (Ibrahimi et al., Hum. Mol. Genet. 13:2313-2324 (2004); Plotnikov et al., Cell 101:413-424 (2000), which are hereby incorporated by reference in their entirety). The ectodomain of murine αKlotho (A35 to K982) and the ectodomain of murine βKlotho (F53 to L995) were expressed in HEK293 cells as fusion proteins with a C-terminal FLAG tag (Kurosu et al., J. Biol. Chem. 281:6120-6123 (2006); Kurosu et al., Science 309:1829-1833 (2005), which are hereby incorporated by reference in their entirety). The binary complex of FGFR1c ligand-binding domain with αKlotho ectodomain (referred to as αKlotho-FGFR1c complex) was prepared by a published protocol (Goetz et al., Proc. Nat'l. Acad. Sci. U.S.A 107:407-412 (2010), which is hereby incorporated by reference in its entirety). The binary complex of FGFR1c ligand-binding domain with βKlotho ectodomain (referred to as βKlotho-FGFR1c complex) was prepared in the same fashion as the αKlotho-FGFR1c complex.

Example 2—Analysis of FGF-Heparin and FGF-FGFR-α/βKlotho Interactions by Surface Plasmon Resonance Spectroscopy Surface plasmon resonance (SPR) experiments were performed on a Biacore 2000 instrument (Biacore AB), and the interactions were studied at 25° C. in HBS-EP buffer (10 mM HEPES-NaOH, pH 7.4, 150 mM NaCl, 3 mM EDTA, 0.005% (v/v) polysorbate 20). To study endocrine FGF-heparin interactions, a heparin chip was prepared by immobilizing biotinylated heparin (Sigma-Aldrich) on flow channels of a research-grade streptavidin chip (Biacore AB). The coupling density was ~5 fmol mm$^{-2}$ of flow channel. To measure binding of chimeric FGF2 proteins to heparin, biotinylated heparin was coupled to a streptavidin chip at an approximately 4-fold lower density as judged based on the binding responses obtained for FGF1. To study FGF-FGFR-α/βKlotho interactions, FGF chips were prepared by covalent coupling of FGF proteins through their free amino groups on flow channels of research grade CMS chips (Biacore AB). Proteins were injected over a chip at a flow rate of 50 μl min$^{-1}$, and at the end of each protein injection (180 and 300 s, respectively), HBS-EP buffer (50 μl min$^{-1}$) was flowed over the chip to monitor dissociation for 180 or 240 s. The heparin chip surface was regenerated by injecting 50 μl of 2.0 M NaCl in 10 mM sodium acetate, pH 4.5. For FGF chips, regeneration was achieved by injecting 2.0 M NaCl in 10 mM sodium/potassium phosphate, pH 6.5. To control for nonspecific binding in experiments where an FGF ligand was immobilized on the chip, FHF1B, which shares structural similarity with FGFs but does not exhibit any FGFR binding (Olsen et al., J. Biol. Chem. 278:34226-34236 (2003), which is hereby incorporated by reference in its entirety), was coupled to the control flow channel of the chip (~15-30 fmol mm$^{-2}$). In experiments where heparin was immobilized on the chip, the control flow channel was left blank. The data were processed with BiaEvaluation software (Biacore AB). For each protein injection over the heparin chip, the nonspecific responses from the control flow channel were subtracted from the responses recorded for the heparin flow channel. Similarly, for each protein injection over a FGF chip, the nonspecific responses from the FHF1B control flow channel were subtracted from the responses recorded for the FGF flow channel. Where possible, equilibrium dissociation constants ($K_D$s) were calculated from fitted saturation binding curves. Fitted binding curves were judged to be accurate based on the distribution of the residuals (even and near zero) and $\chi^2$ (<10% of $R_{max}$).

To examine whether the K149A mutation abrogates residual heparin binding of FGF19, increasing concentrations of wild-type FGF19 were passed over a heparin chip. Thereafter, the FGF19$^{K149A}$ mutant was injected over the heparin chip at the highest concentration tested for the wild-type ligand. The effect of the R140A/R143A double mutation in the HS-binding site of FGF23 on residual heparin binding of FGF23 was examined in the same fashion as was the effect of the HS-binding site mutation in FGF19.

To verify that the K128D/R129Q/K134V triple mutation in the HS-binding site of the FGF2 core domain diminishes heparin-binding affinity of the FGF2 core, increasing concentrations of FGF2$^{\Delta HBScore}$-FGF21$^{C\text{-}tail}$ and FGF2$^{\Delta HBScore}$-FGF23$^{C\text{-}tail}$ were passed over a heparin chip. As a control, binding of FGF2$^{WTcore}$-FGF21$^{C\text{-}tail}$ and FGF2$^{WTcore}$-FGF23$^{C\text{-}tail}$ to heparin was studied.

To examine whether the FGF2$^{\Delta HBScore}$-FGF23$^{C\text{-}tail}$ chimera can compete with FGF23 for binding to the αKlotho-FGFR1c complex, FGF23 was immobilized on a chip (~16 fmol mm$^{-2}$ of flow channel). Increasing concentrations of FGF2$^{\Delta HBScore}$-FGF23$^{C\text{-}tail}$ were mixed with a fixed concentration of αKlotho-FGFR1c complex in HBS-EP buffer, and the mixtures were injected over the FGF23 chip. As controls, the binding competition was carried out with FGF23 or FGF2 as the competitor in solution. As an additional specificity control, competition of the FGF2$^{\Delta HBScore}$-FGF23$^{C\text{-}tail}$ chimera with FGF21 for binding to the αKlotho-FGFR1c complex was studied. αKlotho-FGFR1c complex was mixed with FGF2$^{\Delta HBScore}$-FGF23$^{C\text{-}tail}$ or FGF23 at a molar ratio of 1:10, and the mixture was injected over a chip containing immobilized FGF21 (~12 fmol mm$^{-2}$ of flow channel).

To test whether the FGF2$^{\Delta HBScore}$-FGF21$^{C\text{-}tail}$ chimera can compete with FGF21 for binding to the βKlotho-FGFR1c complex, increasing concentrations of FGF2$^{\Delta HBScore}$-FGF21$^{C\text{-}tail}$ were mixed with a fixed concentration of βKlotho-FGFR1c complex in HBS-EP buffer, and the mixtures were passed over a chip containing immobilized FGF21 (~19 fmol mm$^{-2}$ of flow channel). As controls, the binding competition was carried out with FGF21 or FGF2 as the competitor in solution. As an additional specificity control, competition of the FGF2$^{\Delta HBScore}$-FGF21$^{C\text{-}tail}$ chimera with FGF23 for binding to the αKlotho-FGFR1c complex was studied. αKlotho-FGFR1c complex was mixed with FGF2$^{\Delta HBScore}$-FGF21$^{C\text{-}tail}$ or FGF21 at a molar ratio of 1:10, and the mixture was injected over a chip containing immobilized FGF23 (~12 fmol mm$^{-2}$ of flow channel).

To measure binding of FGFR1c to each of the three endocrine FGFs, increasing concentrations of FGFR1c ligand-binding domain were injected over a chip containing immobilized FGF19, FGF21, and FGF23 (~30 fmol mm$^{-2}$ of flow channel). As a control, binding of FGFR1c to FGF2 immobilized on a chip was studied. As additional controls, binding of the αKlotho-FGFR1c complex to FGF23 and binding of FGFR1c to the C-terminal tail peptide of FGF23 was measured.

Example 3—Analysis of Phosphorylation of FRS2α and 44/42 MAP Kinase in Hepatoma and Epithelial Cell Lines To examine whether the FGF19$^{K149A}$ and FGF23$^{R140A/R143A}$ mutants can activate FGFR in a α/βKlotho-dependent fashion, induction of tyrosine phosphorylation of FGFR substrate 2α (FRS2α) and downstream activation of MAP kinase cascade was used as readout for FGFR activation. Subconfluent cells of the H4IIE rat hepatoma cell line, which endogenously expresses βKlotho (Kurosu et al., J. Biol. Chem. 282:26687-26695 (2007), which is hereby incorporated by reference in its entirety), were serum starved for 16 h and then stimulated for 10 min with the FGF19$^{K149A}$ mutant or wild-type FGF19 (0.2 ng ml$^{-1}$ to 2.0 µg ml$^{-1}$). Similarly, subconfluent cells of a HEK293 cell line ectopically expressing the transmembrane isoform of murine αKlotho (Kurosu et al., J. Biol. Chem. 281:6120-6123 (2006), which is hereby incorporated by reference in its entirety) were treated with the FGF23$^{R140A/R143A}$ mutant or wild-type FGF23 (0.1 to 100 ng ml$^{-1}$). After stimulation, the cells were lysed (Kurosu et al., Science 309:1829-1833 (2005), which is hereby incorporated by reference in its entirety), and cellular proteins were resolved on SDS-polyacrylamide gels and transferred to nitrocellulose membranes. The protein blots were probed with antibodies to phosphorylated FRS2α, phosphorylated 44/42 MAP kinase, total (phosphorylated and nonphosphorylated) 44/42 MAP kinase, and αKlotho. Except for the anti-αKlotho antibody (KM2119) (Kato et al., Biochem. Biophys. Res. Commun. 267:597-602 (2000), which is hereby incorporated by reference in its entirety), all antibodies were from Cell Signaling Technology.

Example 4—Analysis of Egr1 Protein Expression in an Epithelial Cell Line

To examine whether the FGF2$^{\Delta HBScore}$-FGF21$^{C\text{-}tail}$ and FGF2$^{\Delta HBScore}$-FGF23$^{C\text{-}tail}$ chimeras can activate FGFR in a HS-dependent fashion, induction of protein expression of the transcription factor early growth response 1 (Egr1), a known downstream mediator of FGF signaling, was used as readout for FGFR activation. HEK293 cells were serum starved overnight and then stimulated for 90 min with FGF2$^{\Delta HBScore}$-FGF21$^{C\text{-}tail}$ or FGF2$^{\Delta HBScore}$-FGF23$^{C\text{-}tail}$ (0.1 and 0.3 nM). Cell stimulation with FGF2$^{WTcore}$-FGF21$^{C\text{-}tail}$, FGF2$^{WTcore}$-FGF23$^{C\text{-}tail}$, FGF21, and FGF23 served as controls. To test whether the FGF2$^{\Delta HBScore}$-FGF21$^{C\text{-}tail}$ chimera can activate FGFR in a βKlotho-dependent fashion, HEK293 cells transfected with murine βKlotho were serum starved overnight and then stimulated for 90 min with FGF2$^{\Delta HBScore}$-FGF21$^{C\text{-}tail}$ or FGF21 (3 to 300 ng ml$^{-1}$). After stimulation, the cells were lysed (Kurosu et al., Science 309:1829-1833 (2005), which is hereby incorporated by reference in its entirety), and cellular proteins were resolved on SDS-polyacrylamide gels and transferred to nitrocellulose membranes. The protein blots were probed with antibodies to Egr1 and glyceraldehyde 3-phosphate dehydrogenase (GAPDH). The anti-Egr1 antibody was from Cell Signaling Technology and the anti-GAPDH antibody was from Abcam.

Example 5—Analysis of CYP7A1 and CYP8B1 mRNA Expression in Murine Liver Tissue

To examine the metabolic activity of the FGF19$^{K149A}$ mutant in vivo, 6- to 8-week old C57BL/6 mice were fasted overnight and then given intraperitoneally a single dose (1 mg kg body weight$^{-1}$) of FGF19$^{K149A}$ or FGF19 as a control. 6 h after the injection, the mice were sacrificed, and liver tissue was excised and frozen. Total RNA was isolated from liver tissue, and mRNA levels of cholesterol 7α-hydroxylase (CYP7A1) and sterol 12α-hydroxylase (CYP8B1) were measured using quantitative real time RT-PCR as described previously (Inagaki et al., *Cell Metab.* 2:217-225 (2005); Kim et al., *J. Lipid Res.* 48:2664-2672 (2007), which are hereby incorporated by reference in their entirety). The Institutional Animal Care and Use Committee at the University of Texas Southwestern Medical Center at Dallas had approved the experiments.

Example 6—Measurement of Serum Phosphate in Mice

The metabolic activity of the $FGF23^{R140A/R143A}$ mutant was examined both in normal mice and in Fgf23 knockout mice. 4- to 5-week old C57BL/6 mice were given intraperitoneally a single dose (0.29 mg kg body weight$^{-1}$) of $FGF23^{R140A/R143A}$ or FGF23 as a control. Before the injection and 8 h after the injection, blood was drawn from the cheek pouch and spun at 3,000×g for 10 min to obtain serum. Phosphate concentration in serum was measured using the Phosphorus Liqui-UV Test (Stanbio Laboratory). 6- to 8-week old Fgf23 knockout mice (Sitara et al., *Matrix Biol.* 23:421-432 (2004), which is hereby incorporated by reference in its entirety) (56) were given two injections of $FGF23^{R140A/R143A}$ or FGF23 at 8 h intervals (0.71 mg kg body weight$^{-1}$ each), and blood samples were collected for phosphate analysis before the first injection and 8 h after the second injection.

To test whether the $FGF2^{\Delta HBScore}$-$FGF23^{C\text{-}tail}$ chimera exhibits FGF23-like metabolic activity, 5- to 6-week old C57BL/6 mice were given a single injection of $FGF2^{\Delta HBScore}$-$FGF23^{C\text{-}tail}$ (0.21 mg kg body weight$^{-1}$). As controls, mice were injected with $FGF2^{WTcore}$-$FGF23^{C\text{-}tail}$ or FGF23. Before the injection and 8 h after the injection, blood samples were collected for measurement of serum phosphate. To confirm that αKlotho is required for the metabolic activity of the $FGF2^{\Delta HBScore}$-$FGF23^{C\text{-}tail}$ chimera, 7- to 8-week old αKlotho knockout mice (Lexicon Genetics) were injected once with $FGF2^{\Delta HBScore}$-$FGF23^{C\text{-}tail}$ or FGF23 as a control (0.51 mg kg body weight$^{-1}$). Before the injection and 8 h after the injection, blood samples were collected for phosphate analysis. The Harvard University Animal Care and Research committee board had approved all the experiments.

Example 7—Analysis of CYP27B1 mRNA Expression in Murine Renal Tissue

The ability of the $FGF2^{\Delta HBScore}$-$FGF23^{C\text{-}tail}$ chimera to reduce renal expression of 25-hydroxyvitamin D$_3$ 1α-hydroxylase (CYP27B1) was used as another readout for FGF23-like metabolic activity. C57BL/6 mice injected with $FGF2^{\Delta HBScore}$-$FGF23^{C\text{-}tail}$, $FGF2^{WTcore}$-$FGF23^{C\text{-}tail}$, or FGF23 were sacrificed 8 h after the protein injection, and renal tissue was excised and frozen. CYP27B1 mRNA levels in total renal tissue RNA were measured using real time quantitative PCR as described previously (Nakatani et al., *FASEB J.* 23:3702-3711 (2009); Ohnishi et al., *Kidney Int.* 75:1166-1172 (2009), which are hereby incorporated by reference in their entirety). The Harvard University Animal Care and Research committee board had approved the experiments.

Example 8—Insulin Tolerance Test in Mice

The ability of the $FGF2^{\Delta HBScore}$-$FGF21^{C\text{-}tail}$ chimera to potentiate the hypoglycemic effect of insulin was used as readout for FGF21-like metabolic activity (Ohnishi et al., *FASEB J.* 25:2031-2039 (2011), which is hereby incorporated by reference in its entirety). 8- to 12-week old C57BL/6 mice were kept on normal chow. On the day of the insulin tolerance test, mice were fasted for 4 h and then bled from the cheek pouch for measuring fasting blood glucose levels. Thereafter, mice were administered intraperitoneally insulin (0.5 units kg body weight$^-$) alone or insulin (0.5 units·kg body weight$^-$) plus $FGF2^{\Delta HBScore}$-$FGF21^{C\text{-}tail}$ chimera (0.3 mg kg body weight$^{-1}$). As a control, mice were co-injected with insulin plus FGF21. At the indicated time points after the injection (FIG. 7G), blood was drawn from the tail vein. Glucose concentrations in the blood samples were determined using Bayer Contour® blood glucose test strips (Bayer Corp.). The Harvard University Animal Care and Research committee board had approved the experiments.

Example 9—Analysis of Blood Glucose in Ob/Ob Mice ob/ob mice were injected subcutaneously with $FGF1^{\Delta NT}$, $FGF1^{\Delta HBS}$, or $FGF1^{\Delta HBScore}$-$FGF21^{C\text{-}tail}$ chimera. Injection of native FGF1 or native FGF21 served as controls. A single bolus of 0.5 mg of protein per kg of body weight was injected. This dose was chosen on the basis that maximal efficacy of the hypoglycemic effect of native FGF1 is seen at this dose. Before the protein injection and at the indicated time points after the injection (FIGS. 9A-9C), blood glucose concentrations were measured using an OneTouch Ultra glucometer (Lifescan). The Institutional Animal Care and Use Committee at the Salk Institute for Biological Sciences at La Jolla had approved the experiments.

Example 10—Statistical Analysis

Data are expressed as mean±SEM. A Student's t test or analysis of variance (ANOVA) was used as appropriate to make statistical comparisons. A value of P<0.05 was considered significant.

Example 11—HS is Dispensable for the Metabolic Activity of FGF19 and FGF23

Figure 2:
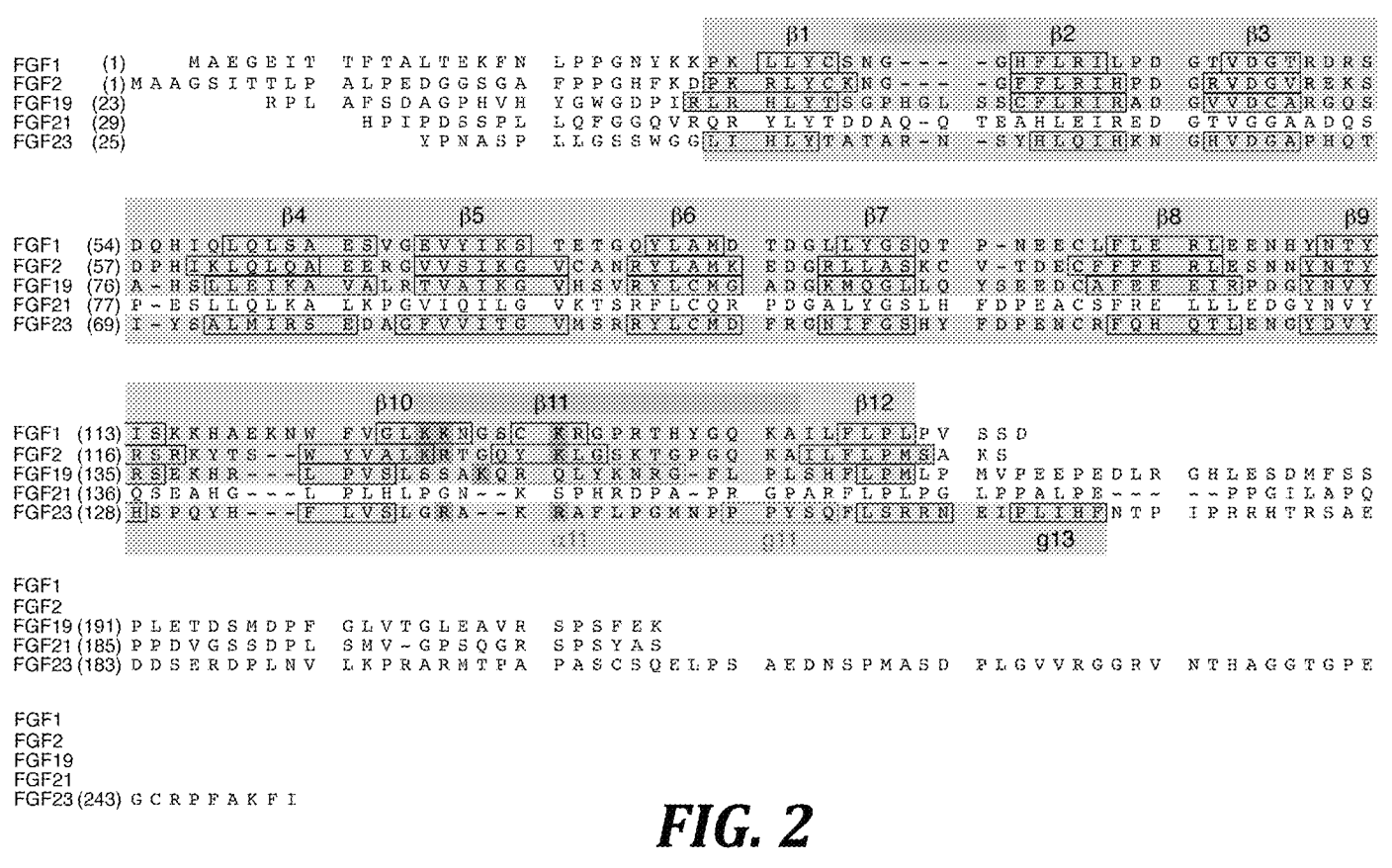

In order to engineer endocrine FGFs devoid of HS binding, the FGF19 crystal structure (PDB ID: 2P23; (Goetz et al., *Mol. Cell Biol.* 27:3417-3428 (2007), which is hereby incorporated by reference in its entirety) was compared with that of FGF2 bound to a heparin hexasaccharide (PDB ID: 1FQ9; (Schlessinger et al., *Mol. Cell* 6:743-750 (2000), which is hereby incorporated by reference in its entirety)). This analysis shows that solvent-exposed residues K149, Q150, Q152, and R157 of FGF19 lie at the corresponding HS-binding site of this ligand, and hence could account for the residual HS binding of FGF19 (FIGS. 1A, 1B, and 2). Likewise, comparative analysis of the FGF23 crystal structure (PDB ID: 2P39; (Goetz et al., *Mol. Cell Biol.* 27:3417-3428 (2007), which is hereby incorporated by reference in its entirety) (29)) with that of heparin-bound FGF2 (PDB ID: 1FQ9; (Schlessinger et al., *Mol. Cell* 6:743-750 (2000), which is hereby incorporated by reference in its entirety)) points to R48, N49, R140, and R143 as candidates mediating the residual HS binding of this ligand (FIGS. 1A, 1C, and 2). In agreement with the structural predictions, replacement of K149 alone in FGF19 with alanine and combined substitution of R140 and R143 in FGF23 for alanine were sufficient to abolish residual HS binding of these ligands (FIGS. 3B-3G).

Figures 4A, 4B, 4C, 4D:
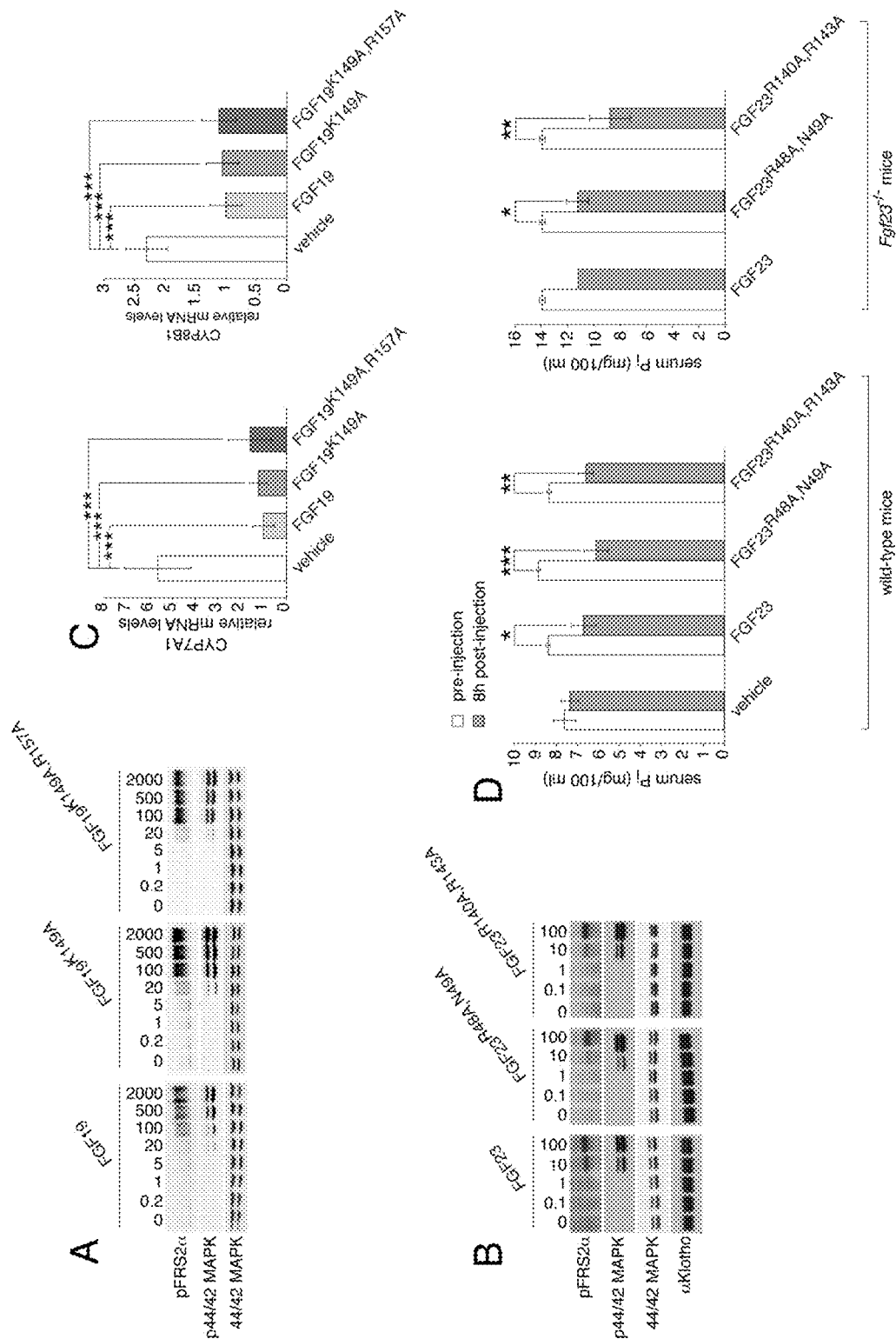
FIGS. 4A-4D show results demonstrating that HS is dispensable for the metabolic activity of FGF19 and FGF23.

To test the impact of knocking out residual HS binding of FGF19 on the signaling by this ligand, H4IIE hepatoma cells were stimulated with the FGF19$^{K149A}$ mutant or wild-type FGF19. H4IIE cells endogenously express FGFR4 and βKlotho (Kurosu et al., *J. Biol. Chem.* 282:26687-26695 (2007), which is hereby incorporated by reference in its entirety), the cognate receptor and co-receptor, respectively, for FGF19. The FGF19$^{K149A}$ mutant was as effective as wild-type FGF19 in inducing tyrosine phosphorylation of FRS2α and downstream activation of MAP kinase cascade (FIG. 4A). These data show that elimination of residual HS binding has no impact on the ability of FGF19 to signal in cultured cells. To test whether the same holds true for FGF23 signaling, HEK293 cells, which naturally express two of the three cognate receptors of FGF23, namely FGFR1c and FGFR3c (Kurosu et al., *J. Biol. Chem.* 281:6120-6123 (2006), which is hereby incorporated by reference in its entirety) were transfected with the transmembrane isoform of αKlotho, the co-receptor of FGF23. These cells were treated with the FGF23$^{R140A/R143A}$ double mutant or wild-type FGF23. The FGF23$^{R140A/R143A}$ mutant had the same capacity as wild-type FGF23 in inducing phosphorylation of FRS2α and downstream activation of MAP kinase cascade (FIG. 4B). These data show that similar to FGF19, FGF23 does not need to bind HS in order to activate FGFR in cultured cells.

To substantiate the findings in cells, the metabolic activity of wild-type and mutated ligands in vivo were compared. Mice were injected with the FGF19$^{K149A}$ mutant or wild-type FGF19 and liver gene expression of CYP7A1 and CYP8B1, which are key enzymes in the major bile acid biosynthetic pathway (Russell, D. W., *Annu. Rev. Biochem.* 72:137-174 (2003), which is hereby incorporated by reference in its entirety), was analyzed. Like wild-type FGF19, the FGF19$^{K149A}$ mutant markedly decreased CYP7A1 and CYP8B1 mRNA levels (FIG. 4C), demonstrating that knockout of residual HS binding does not affect the metabolic activity of FGF19. To examine whether residual HS binding is also dispensable for the metabolic activity of FGF23, mice were injected with the FGF23$^{R140A/R143A}$ mutant or wild-type FGF23 and serum phosphate concentrations were measured. The FGF23$^{R140A/R143A}$ mutant reduced serum phosphate as effectively as wild-type FGF23 (FIG. 4D). Moreover, when injected into Fgf23 knockout mice, the FGF23$^{R140A/R143A}$ mutant exhibited as much of phosphate-lowering activity as wild-type FGF23 (FIG. 4D). These data show that, as in the case of FGF19, abolishment of residual HS binding does not impact the metabolic activity of FGF23 leading to the conclusion that HS is not a component of the endocrine FGF signal transduction unit (FIG. 1D).

Example 12—Conversion of a Paracrine FGF into an Endocrine Ligand Confirms that HS is Dispensable for the Metabolic Activity of Endocrine FGFs If HS is dispensable for the metabolic activity of endocrine FGFs, then it should be feasible to convert a paracrine FGF into an endocrine FGF by eliminating HS-binding affinity of the paracrine FGF and substituting its C-terminal tail for that of an endocrine FGF containing the Klotho co-receptor binding site. Reducing HS-binding affinity will allow the ligand to freely diffuse and enter the blood circulation while attaching the C-terminal tail of an endocrine FGF will home the ligand into its target tissues. FGF2, a prototypical paracrine FGF, was chosen for conversion into FGF23-like and FGF21-like ligands, respectively. FGF2 was selected as paracrine ligand for this protein engineering exercise because it preferentially binds to the "c" isoform of FGFR1, the principal receptor mediating the metabolic activity of FGF23 (Gattineni et al., *Am. J. Physiol. Renal Physiol.* 297:F282-291 (2009); Liu et al., *J. Am. Soc. Nephrol.* 19:2342-2350 (2008), which are hereby incorporated by reference in their entirety) and FGF21 (Kurosu et al., *J. Biol. Chem.* 282:26687-26695 (2007), which is hereby incorporated by reference in its entirety), respectively. In the crystal structure of heparin-bound FGF2 (PDB ID: 1FQ9; (Schlessinger et al., *Mol. Cell* 6:743-750 (2000), which is hereby incorporated by reference in its entirety)), K128, R129, and K134 mediate the majority of hydrogen bonds with heparin and hence mutation of these residues was predicted to cause a major reduction in HS-binding affinity of FGF2 (FIGS. 1A, 2, and 5A). Accordingly, these three residues were mutated and then the short C-terminal tail of the mutated FGF2 was replaced with the C-terminal tail of FGF23 (R161 to I251) or the C-terminal tail of FGF21 (P168 to S209) (FIG. 5A). The resulting chimeras were termed FGF2$^{\Delta HBScore}$-FGF23$^{C\text{-}tail}$ and FGF2$^{\Delta HBScore}$-FGF21$^{C\text{-}tail}$ (FIG. 5A). To demonstrate that reduction in HS-binding affinity is required for converting FGF2 into an endocrine ligand, two control chimeras were made in which the HS-binding site of the FGF2 core was left intact (FGF2$^{WTcore}$-FGF23$^{C\text{-}tail}$ and FGF2$^{WTcore}$-FGF21$^{C\text{-}tail}$; FIG. 5A).

Consistent with the structural prediction, FGF2$^{\Delta HBScore}$-FGF23$^{C\text{-}tail}$ and FGF2$^{\Delta HBScore}$-FGF21$^{C\text{-}tail}$ exhibited poor binding affinity for HS compared to the corresponding control chimeras with intact HS-binding site (FIGS. 5B-5E). Since HS is an obligatory cofactor in paracrine FGF signaling, the FGF2$^{\Delta HBScore}$-FGF23$^{C\text{-}tail}$ and FGF2$^{\Delta HBScore}$-FGF21$^{C\text{-}tail}$ chimeras were predicted to lose the ability to activate FGFR1c in an HS-dependent fashion. To test this, HEK293 cells, which endogenously express FGFR1c, were stimulated with FGF2$^{\Delta HBScore}$-FGF23$^{C\text{-}tail}$ or FGF2$^{WTcore}$-FGF23$^{C\text{-}tail}$. Induction of protein expression of the transcription factor Egr1, a known downstream mediator of FGF signaling, was used as readout for FGFR activation. As shown in FIG. 5G, the FGF2$^{\Delta HBScore}$-FGF23$^{C\text{-}tail}$ chimera, like native FGF23, was ineffective in inducing Egr1 expression at concentrations at which the FGF2$^{WTcore}$-FGF23$^{C\text{-}tail}$ chimera elicited a near maximal effect. The same observations were made for the FGF2$^{\Delta HBScore}$-FGF21$^{C\text{-}tail}$ chimera (FIG. 5F). These data show that, similar to native FGF23 and FGF21, the FGF2$^{\Delta HBScore}$-FGF23$^{C\text{-}tail}$ and FGF2$^{\Delta HBScore}$-FGF21$^{C\text{-}tail}$ chimeras lost the ability to activate FGFR in an HS-dependent, paracrine fashion.

Figures 7A, 7B, 7C, 7D, 7E, 7F, 7G:
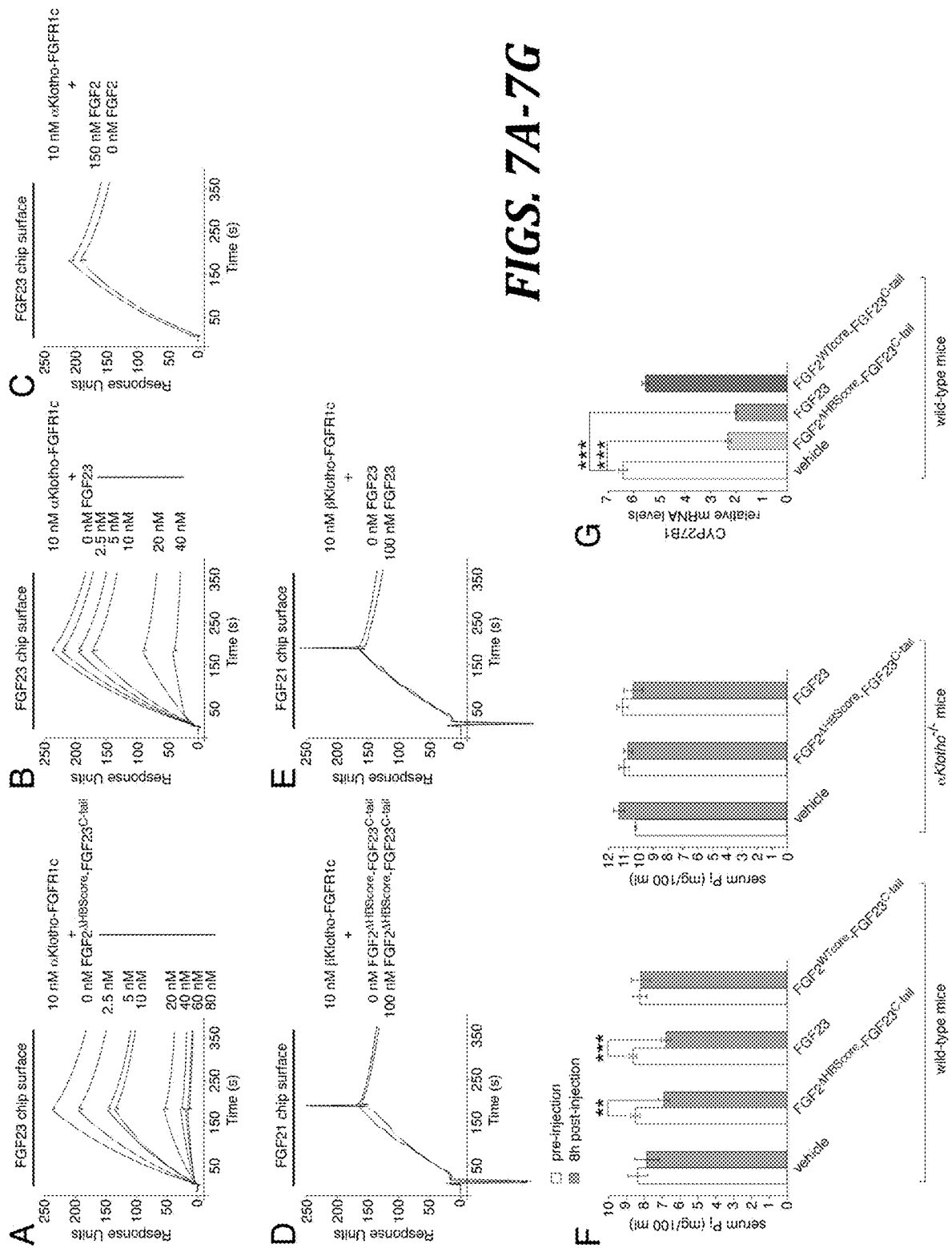
FIGS. 7A-7G show results demonstrating that the FGF2$^{\Delta HBScore}$-FGF23$^{C\text{-}tail}$ chimera exhibits FGF23-like activity.
Figures 8A, 8B, 8C, 8D, 8E, 8F, 8G:
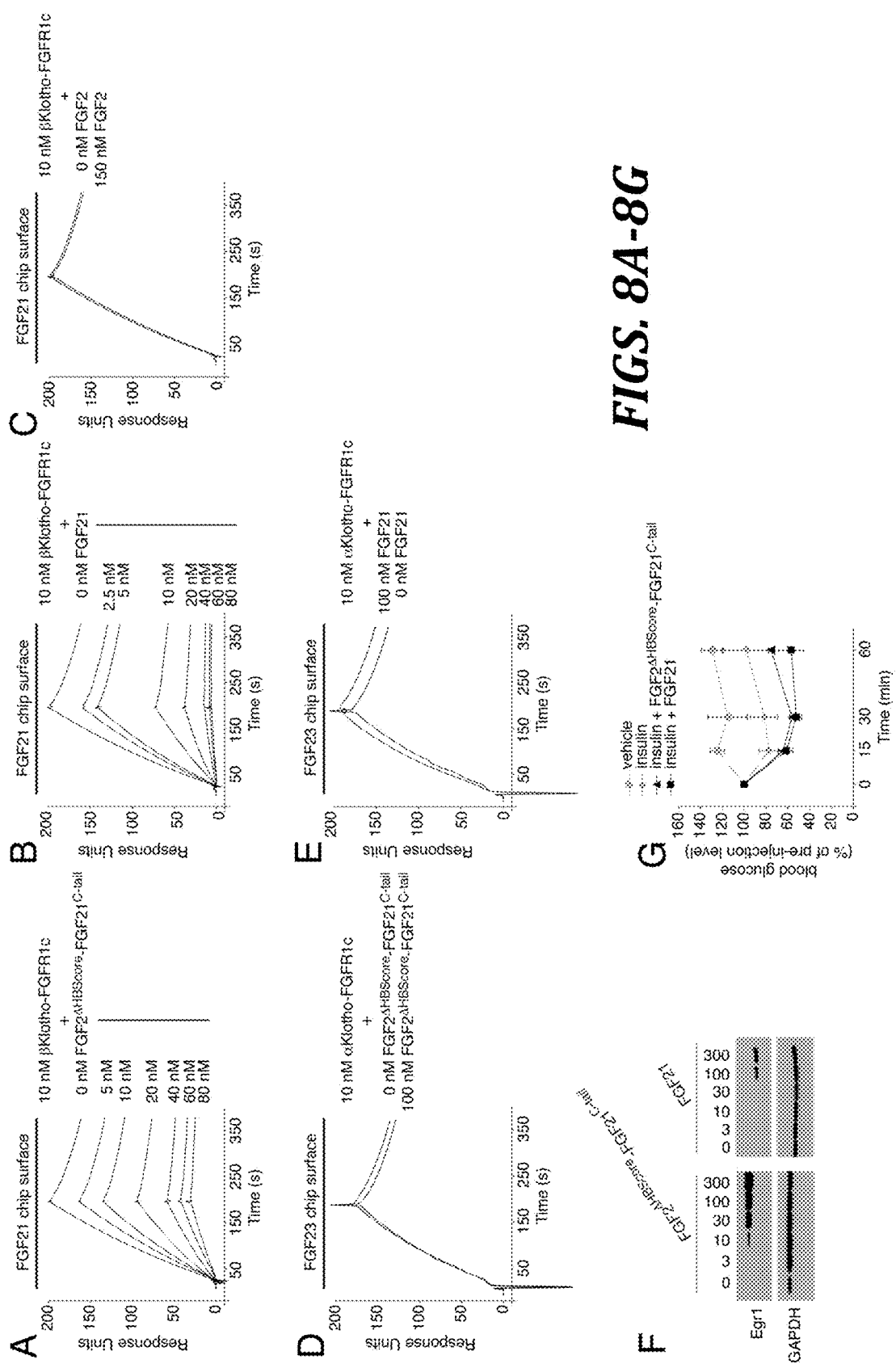
FIGS. 8A-8G show results demonstrating that the FGF2$^{\Delta HBScore}$-FGF21$^{C\text{-}tail}$ chimera exhibits FGF21-like activity.

To determine whether the FGF2$^{\Delta HBScore}$-FGF23$^{C\text{-}tail}$ and FGF2$^{\Delta HBScore}$-FGF21$^{C\text{-}tail}$ chimeras gained the ability to signal in a Klotho co-receptor-dependent, endocrine fashion, it was first analyzed whether these chimeras can form ternary complexes with FGFR1c and Klotho co-receptor. To this end, a SPR-based binding competition assay was employed. FGF23 was immobilized onto a SPR biosensor chip, and mixtures of a fixed concentration of binary αKlotho-FGFR1c complex with increasing concentrations of FGF2$^{\Delta HBScore}$-FGF23$^{C\text{-}tail}$ chimera were passed over the chip. FGF2$^{\Delta HBScore}$-FGF23$^{C\text{-}tail}$ competed, in a dose-dependent fashion, with immobilized FGF23 for binding to the αKlotho-FGFR1c complex (FIG. 7A), demonstrating that the chimera, like native FGF23 (FIG. 7B), is able to form a ternary complex with FGFR1c and αKlotho. To test whether the FGF2$^{\Delta HBScore}$-FGF21$^{C\text{-}tail}$ chimera can likewise form a ternary complex with FGFR1c and βKlotho, FGF21 was coupled to a SPR biosensor chip, and mixtures of the binary βKlotho-FGFR1c complex with FGF2$^{\Delta HBScore}$-FGF21$^{C\text{-}tail}$ were passed over the chip. FGF2$^{\Delta HBScore}$-FGF21$^{C\text{-}tail}$ effectively competed with immobilized FGF21 for binding to the βKlotho-FGFR1c complex (FIG. 8A), demonstrating that the chimera, like native FGF21 (FIG. 8B), is capable of binding to the binary complex of FGFR1c and βKlotho. Notably, native FGF2 failed to compete with FGF23 for binding to the αKlotho-FGFR1c complex (FIG. 7C), and with FGF21 for binding to the βKlotho-FGFR1c complex (FIG. 8C) since it lacks the Klotho co-receptor binding domain. To further confirm the binding specificity of the FGF2$^{\Delta HBScore}$-FGF23$^{C\text{-}tail}$ chimera for the αKlotho-FGFR1c complex, FGF2$^{\Delta HBScore}$-FGF23$^{C\text{-}tail}$ and βKlotho-FGFR1c complex were mixed at a molar ratio of 10:1, and the mixture was injected over a chip containing immobilized FGF21. FGF2$^{\Delta HBScore}$-FGF23$^{C\text{-}tail}$, like native FGF23, failed to compete with FGF21 for binding to the βKlotho-FGFR1c complex (FIGS. 7D and 7E). Similarly, the FGF2$^{\Delta HBScore}$-FGF21$^{C\text{-}tail}$ chimera, like native FGF21, failed to compete with FGF23 for binding to the αKlotho-FGFR1c complex (FIGS. 8D and 8E). For the FGF2$^{\Delta HBScore}$-FGF21$^{C\text{-}tail}$ chimera, we investigated whether it is able to activate FGFR1c in a βKlotho-dependent fashion in cells. HEK293 cells were transfected with βKlotho and then stimulated with FGF2$^{\Delta HBScore}$-FGF21$^{C\text{-}tail}$ or FGF21. Similar to native FGF21, the FGF2$^{\Delta HBScore}$-FGF21$^{C\text{-}tail}$ chimera induced Egr1 protein expression in HEK293-βKlotho cells (FIG. 8F), indicating that the chimera is capable of activating FGFR1c in the presence of βKlotho.

To provide definite proof for the ligand conversion, the metabolic activity of the chimeras in vivo was tested. Specifically, the ability of the FGF2$^{\Delta HBScore}$-FGF23$^{C\text{-}tail}$ chimera to lower serum phosphate and to reduce renal gene expression of CYP27B1, which catalyzes the conversion of vitamin D into its bioactive form, was examined. Mice were injected with FGF2$^{\Delta HBScore}$-FGF23$^{C\text{-}tail}$ or as controls, FGF23 or FGF2$^{WTcore}$-FGF23$^{C\text{-}tail}$, and serum phosphate concentrations and renal CYP27B1 mRNA levels were measured. Similar to native FGF23, the FGF2$^{\Delta HBScore}$-FGF23$_{C\text{-}tail}$ chimera caused a decrease in serum phosphate in wild-type mice (FIG. 7F). The chimera also induced a marked decrease in CYP27B1 mRNA levels, just like the native FGF23 ligand (FIG. 7G). These data show that the FGF2$^{\Delta HBScore}$-FGF23$^{C\text{-}tail}$ chimera acts as an FGF23-like hormone. Importantly, the FGF2$^{WTcore}$-FGF23$^{C\text{-}tail}$ chimera failed to decrease serum phosphate or CYP27B1 mRNA levels (FIGS. 7F and 7G). This is expected because, owing to its high affinity for HS, this chimera should be trapped in the vicinity of the injection site and hence not be able to enter the blood circulation. Moreover, these data show that adding the Klotho co-receptor binding site is not sufficient to convert a paracrine FGF into an endocrine ligand. To confirm that the metabolic activity of the FGF2$^{\Delta HBScore}$-FGF23$^{C\text{-}tail}$ chimera is dependent on αKlotho, αKlotho knockout mice were injected with FGF2$^{\Delta HBScore}$-FGF23$^{C\text{-}tail}$ or FGF23 as a control, and serum concentrations of phosphate were measured. As shown in FIG. 7F, FGF2$^{\Delta HBScore}$-FGF23$^{C\text{-}tail}$ failed to lower serum phosphate, demonstrating that the chimera, like native FGF23 (FIG. 7F), requires αKlotho for metabolic activity.

To determine whether the FGF2$^{\Delta HBScore}$-FGF21$^{C\text{-}tail}$ chimera exhibits FGF21-like metabolic activity, its ability to potentiate the hypoglycemic effect of insulin was examined (Ohnishi et al., *FASEB J.* 25:2031-2039 (2011), which is hereby incorporated by reference in its entirety). Mice were injected with insulin plus FGF2$^{\Delta HBScore}$-FGF21$^{C\text{-}tail}$, insulin plus FGF21, or insulin alone, and blood glucose concentrations were monitored for up to one hour after the injection. Similar to FGF21, the FGF2$^{\Delta HBScore}$-FGF21$^{C\text{-}tail}$ chimera enhanced the hypoglycemic effect of insulin (FIG. 8G), demonstrating that the chimera acts as an FGF21-like hormone.

Figures 9A, 9B, 9C:
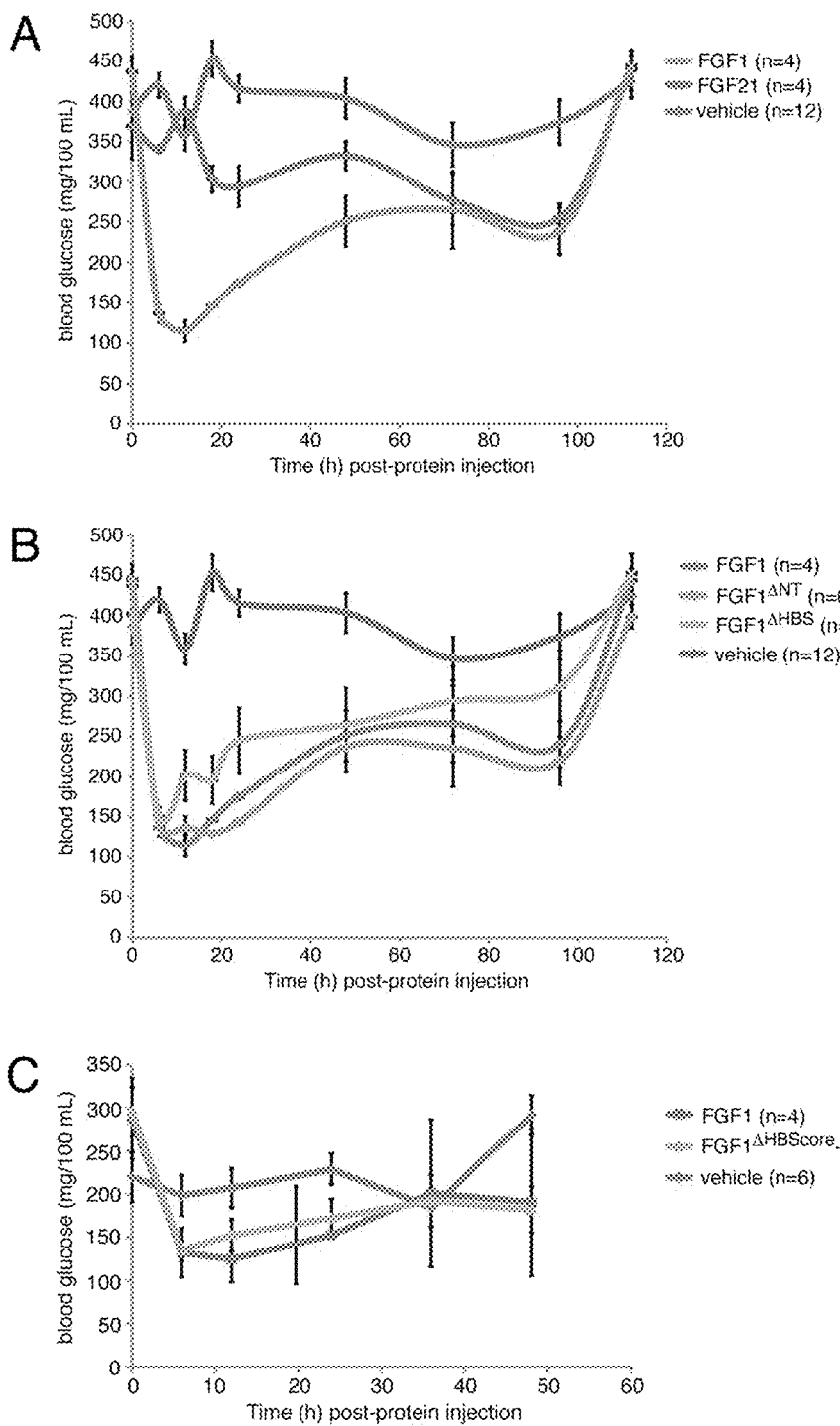
FIGS. 9A-9C show the glucose-lowering effects in ob/ob mice of FGF1 variants according to the present invention.

To substantiate further the concept of FGF ligand conversion, another FGF21-like ligand was engineered using FGF1 as paracrine FGF, and the metabolic activity of the engineered protein was tested in vivo in a mouse model of diabetes and obesity. Besides serving as an additional proof-of-concept, the use of FGF1 for this particular ligand conversion was appealing because FGF1 on its own plays an essential role in glucose metabolism (Jonker et al., "A PPARγ-FGF1 Axis is Required for Adaptive Adipose Remodelling and Metabolic Homeostasis," *Nature* 485:391-394 (2012), which is hereby incorporated by reference in its entirety). Notably, similar to FGF21, FGF1 is induced postprandially in gonadal white adipose tissue by the nuclear hormone receptor PPARγ (peroxisome proliferator activated receptor-γ) (Jonker et al., "A PPARγ-FGF1 Axis is Required for Adaptive Adipose Remodelling and Metabolic Homeostasis," *Nature* 485:391-394 (2012); Dutchak et al., "Fibroblast Growth Factor-21 Regulates PPARγ Activity and the Antidiabetic Actions of Thiazolidinediones," *Cell* 148:556-567 (2012), which are hereby incorporated by reference in their entirety). FGF1 is required for the remodeling of adipose tissue to adjust to fluctuations in nutrient availability (Jonker et al., "A PPARγ-FGF1 Axis is Required for Adaptive Adipose Remodelling and Metabolic Homeostasis," *Nature* 485:391-394 (2012), which is hereby incorporated by reference in its entirety), and this process is influenced by FGF21 (Hotta et al., "Fibroblast Growth Factor 21 Regulates Lipolysis in White Adipose Tissue But is Not Required for Ketogenesis and Triglyceride Clearance in Liver," *Endocrinology* 150:4625-4633 (2009); Dutchak et al., "Fibroblast Growth Factor-21 Regulates PPARγ Activity and the Antidiabetic Actions of Thiazolidinediones," *Cell* 148:556-567 (2012), which are hereby incorporated by reference in their entirety). As part of a positive feedback loop, FGF21 stimulates PPARγ activity in adipocytes (Dutchak et al., "Fibroblast Growth Factor-21 Regulates PPARγ Activity and the Antidiabetic Actions of Thiazolidinediones," *Cell* 148:556-567 (2012), which is hereby incorporated by reference in its entirety), raising the intriguing possibility that FGF21 regulates FGF1 signaling in adipose tissue through PPARγ. An FGF1$^{\Delta HBScore}$-FGF21$^{C\text{-}tail}$ chimera was generated in the same manner as the FGF2$^{\Delta HBScore}$-FGF21$^{C\text{-}tail}$ chimera (FIGS. 5 and 6). Specifically, K127, K128, and K133 of FGF1, which correspond to the key HS-binding residues identified in the crystal structure of heparin-bound FGF2 (PDB ID: 1FQ9; (Schlessinger et al., *Mol. Cell* 6:743-750 (2000), which is hereby incorporated by reference in its entirety)), were mutated and then the short C-terminal tail of the mutated FGF1 was replaced with the C-terminal tail of FGF21 (P168 to S209) (FIG. 6). A full-length FGF1 protein harboring the HS-binding site mutations was used as a control (FIG. 6). Consistent with the structural prediction, this protein exhibited poor binding affinity for HS compared to wild-type FGF1 as evidenced by the fact that, unlike the wild-type ligand, the mutant protein did not bind to a Heparin sepharose column. A subcutaneous bolus injection of the FGF1$^{\Delta HBScore}$-FGF21$^{C\text{-}tail}$ chimera elicited a hypoglycemic effect in ob/ob mice (FIG. 9C), demonstrating that the chimera has metabolic activity. The effect was of similar magnitude as that observed for native FGF1 (FIG. 9C), which itself has a much greater hypoglycemic effect in ob/ob mice than native FGF21 (FIG. 9A). The HS-binding site mutant of FGF1, which was included as a control in these experiments, showed a similar hypoglycemic effect as the wild-type ligand (FIG. 9B), indicating that the loss in HS-binding affinity had no impact on the metabolic activity of FGF1. To alter the receptor-binding specificity of FGF1 such that FGF1 selectively binds to the "c" splice isoform of FGFR1, the principal receptor mediating the metabolic activity of FGF21, an N-terminally truncated FGF1 protein was made (FIG. 6). The truncated FGF1 ligand lacked twenty four residues from the N-terminus including the nine residues that are critical for the promiscuous binding of FGF1 to both splice isoforms of FGFR1-3 (Beenken et al., "Plasticity in Interactions of Fibroblast Growth Factor 1 (FGF1) N Terminus with FGF Receptors Underlies Promiscuity of FGF1," *J Biol Chem* 287(5):3067-3078 (2012), which is hereby incorporated by reference in its entirety). Based on the crystal structures of FGF1-FGFR complexes, the truncation was also predicted to reduce the receptor-binding affinity of FGF1, and hence the ligand's mitogenicity. The truncated FGF1 protein induced a similar hypoglycemic effect in ob/ob mice as native FGF1 did, indicating that the metabolic activity of FGF1 is mediated through the "c" splice isoform of FGFR. Together, these findings provide a starting point for engineering FGF1 ligands that have no mitogenicity but the same or enhanced metabolic activity compared to native FGF1.

The demonstrated ability to convert a paracrine FGF into an endocrine ligand by means of reducing HS-binding affinity of the paracrine FGF and adding the Klotho co-receptor binding site substantiates that HS does not participate in the formation of the endocrine FGF signal transduction unit. The dispensability of HS for the metabolic activity of endocrine FGFs has an intriguing implication as to how these FGFs have evolved to become hormones. It appears that these ligands have lost the requirement to bind HS in order to signal, while acquiring the ability to bind Klotho co-receptors, which is necessary to direct these ligands to their target organs.

Figures 10A, 10B, 10C, 10D, 10E, 10F:
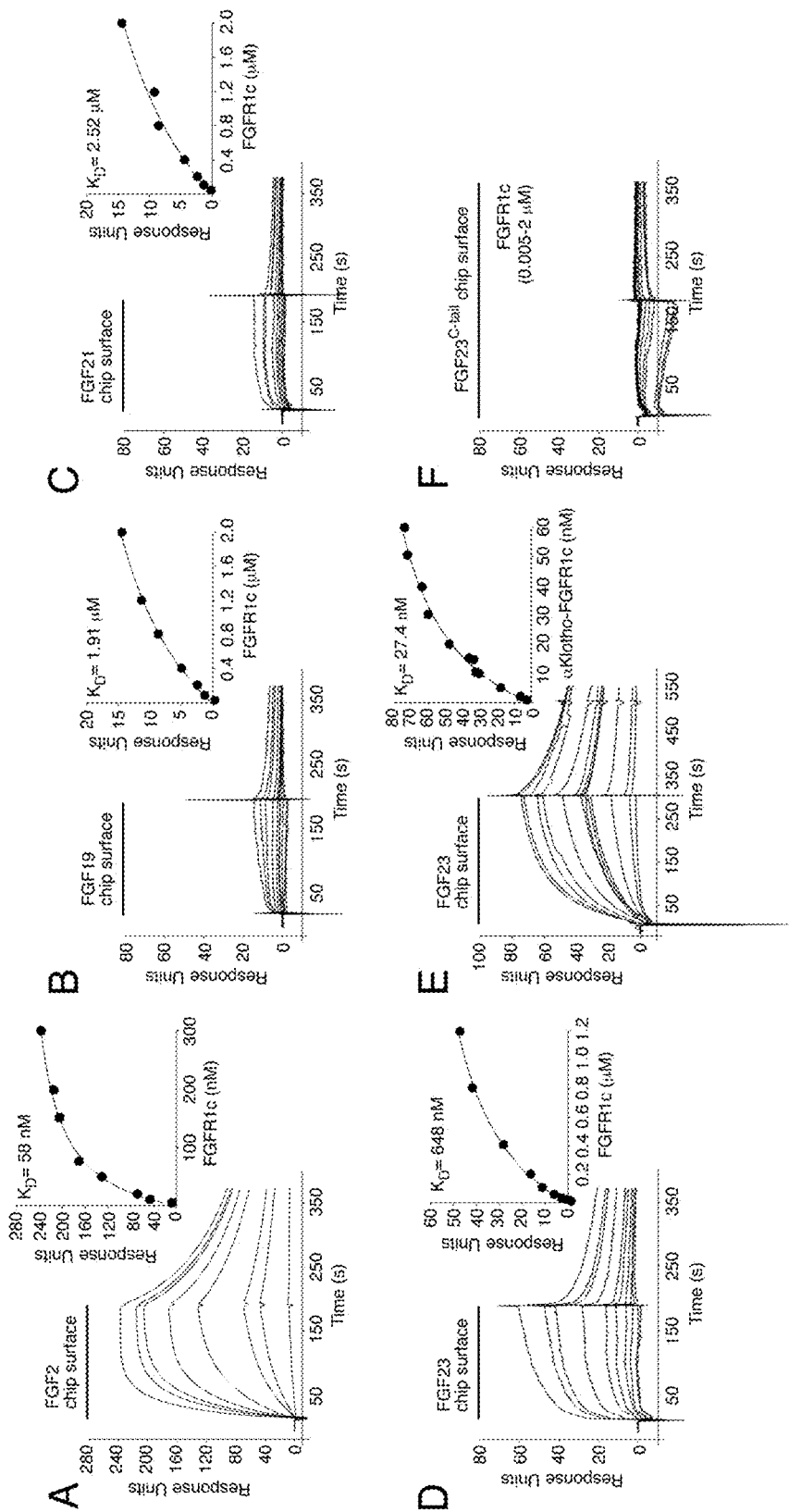
FIGS. 10A-10F show results demonstrating that endocrine FGFs have low binding affinity for FGFR1c compared to FGF2.

In the target tissue, Klotho co-receptors constitutively associate with cognate receptors of endocrine FGFs to offset the inherently low receptor-binding affinity of endocrine FGFs (FIGS. 10B-10D; Kurosu et al., *J Biol. Chem.* 282:26687-26695 (2007); Kurosu et al., *J. Biol. Chem.* 281: 6120-6123 (2006); Ogawa et al., *Proc. Nat'l. Acad. Sci. U.S.A.* 104:7432-7437 (2007); Urakawa et al., *Nature* 444:770-774 (2006), which are hereby incorporated by reference in their entirety). This low binding affinity is due to the fact that key receptor-binding residues in the β-trefoil core of endocrine FGFs are replaced by residues that are suboptimal for receptor binding (Goetz et al., *Mol. Cell Biol.* 27:3417-3428 (2007), which is hereby incorporated by reference in its entirety). To measure the degree to which Klotho co-receptors enhance the receptor-binding affinity of endocrine FGFs, SPR experiments were conducted using FGF23 and FGFR1c and αKlotho co-receptor as an example (see FIGS. 10A-10F). The SPR data show that αKlotho enhances the affinity of FGF23 for FGFR1c by over 20-fold (FIGS. 10D and 10E). The affinity of FGF23 for FGFR1c in the presence of αKlotho is comparable to that of FGF2 for FGFR1c in the absence of its HS cofactor (FIGS. 10A and 10E). It should be noted, however, that HS further increases the binding affinity of FGF2 for FGFR1c by at least an order of magnitude (Pantoliano et al., *Biochemistry* 33:10229-10248 (1994); Roghani et al., *J. Biol. Chem.* 269:3976-3984 (1994), which are hereby incorporated by reference in their entirety). Hence, the receptor-binding affinity of FGF23 in the presence of αKlotho co-receptor still is lower than that of FGF2 in the presence of HS cofactor. These observations imply that the signaling capacity of the endocrine FGF signal transduction unit should be weaker than that of the paracrine FGF signaling unit. Indeed, cell-based studies show that even in the presence of their Klotho co-receptor, endocrine FGFs are inferior to paracrine FGFs at activating FGFR-induced intracellular signaling pathways (Kurosu et al., *J. Biol. Chem.* 282:26687-26695 (2007); Urakawa et al., *Nature* 444:770-774 (2006), which are hereby incorporated by reference in their entirety).

The finding that endocrine FGFs do not need to rely on HS for signaling has another important implication in regard to the role of Klotho co-receptors. Since FGFR dimerization is a prerequisite for FGF signaling in general, it is proposed that Klotho co-receptors not only enhance the binding affinity of endocrine ligand for receptor but also promote receptor dimerization upon ligand binding. In other words, Klotho co-receptors must fulfill the same dual role that HS plays in signaling by paracrine FGFs (FIG. 1D). The ligand conversion also provides the framework for the rational design of endocrine FGF-like molecules for the treatment of metabolic disorders. An FGF23-like molecule, for example, will be useful for the treatment of inherited or acquired hyperphosphatemia, and an FGF21-like molecule, for example, for the treatment of type 2 diabetes, obesity, and related metabolic disorders.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for decreasing blood glucose level in a subject suffering from diabetes, the method comprising:

selecting a subject suffering from diabetes;

providing a chimeric fibroblast growth factor (FGF) protein, wherein the chimeric FGF protein comprises an N-terminus coupled to a C-terminus, wherein the N-terminus comprises an FGF2 portion beginning at any one of residues 1 to 25 and ending at any one of residues 151 to 155 of SEQ ID NO: 121, wherein the FGF2 amino acid positions corresponding to those selected from the group consisting of N36, K128, R129, K134, K138, Q143, K144, and combinations thereof are substituted to decrease binding affinity for heparin and/or heparan sulfate compared to FGF2 without the substitution, and wherein the C-terminus comprises a portion of an FGF21 comprising amino acid residues 168 to 209 of SEQ ID NO: 233; and administering to said selected subject an effective amount of the chimeric FGF protein to decrease blood glucose level in the selected subject.

2. The method according to claim 1, wherein the FGF2 portion is amino acid residues 1-151 of SEQ ID NO: 121.

3. The method according to claim 1, wherein the FGF2 portion is amino acid residues 25-151 of SEQ ID NO: 121.

4. The method according to claim 1, wherein the FGF2 portion is amino acid residues 1-152, 1-153, 1-154, 1-155, 2-151, 2-152, 2-153, 2-154, 2-155, 3-151, 3-152, 3-153, 3-154, 3-155, 4-151, 4-152, 4-153, 4-154, 4-155, 5-151, 5-152, 5-153, 5-154, 5-155, 6-151, 6-152, 6-153, 6-154, 6-155, 7-151, 7-152, 7-153, 7-154, 7-155, 8-151, 8-152, 8-153, 8-154, 8-155, 9-151, 9-152, 9-153, 9-154, 9-155, 10-151, 10-152, 10-153, 10-154, 10-155, 11-151, 11-152, 11-153, 11-154, 11-155, 12-151, 12-152, 12-153, 12-154, 12-155, 13-151, 13-152, 13-153, 13-154, 13-155, 14-151, 14-152, 14-153, 14-154, 14-155, 15-151, 15-152, 15-153, 15-154, 15-155, 16-151, 16-152, 16-153, 16-154, 16-155, 17-151, 17-152, 17-153, 17-154, 17-155, 18-151, 18-152, 18-153, 18-154, 18-155, 19-151, 19-152, 19-153, 19-154, 19-155, 20-151, 20-152, 20-153, 20-154, 20-155, 21-151, 21-152, 21-153, 21-154, 21-155, 22-151, 22-152, 22-153, 22-154, 22-155, 23-151, 23-152, 23-153, 23-154, 23-155, 24-151, 24-152, 24-153, 24-154, 24-155, 25-152, 25-153, 25-154, or 25-155 of SEQ ID NO: 121.

5. The method according to claim 1, wherein the one or more substitutions are selected from the group consisting of N36T; K128D; R129Q; K134V; K138H; Q143M; K144T, K144L, or K144I; and combinations thereof.

6. The method according to claim 1, wherein the subject has type II diabetes, gestational diabetes, or drug-induced diabetes.

7. The method according to claim 1, wherein the subject has type I diabetes.

8. The method according to claim 1, wherein the subject is obese.

9. The method according to claim 1, wherein the subject has metabolic syndrome.

10. The method according to claim 1, wherein said administering is carried out parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

11. The method according to claim 1, wherein the chimeric FGF protein is administered with a pharmaceutically-acceptable carrier.

12. The method according to claim 1, wherein the selected subject is a mammal.

13. The method according to claim 1, wherein the selected subject is a human.

14. The method according to claim 1, wherein the chimeric FGF protein is co-administered with one or more agents selected from the group consisting of an anti-inflammatory agent, an antifibrotic agent, an antihypertensive agent, an antidiabetic agent, a triglyceride-lowering agent, and a cholesterol-lowering agent.

15. The method according to claim 1, wherein the chimeric FGF protein comprises the amino acid sequence of SEQ ID NO:341 or SEQ ID NO:342.

16. The method according to claim 1, wherein the one or more amino acid substitutions comprises a substitution at amino acid residue N36.

17. The method according to claim 16, wherein the substitution is N36T.

18. The method according to claim 1, wherein the one or more amino acid substitutions comprises a substitution at amino acid residue K128.

19. The method according to claim 18, wherein the substitution is K128D.

20. The method according to claim 1, wherein the one or more amino acid substitutions comprises a substitution at amino acid residue R129.

21. The method according to claim 20, wherein the substitution is R129Q.

22. The method according to claim 1, wherein the one or more amino acid substitutions comprises a substitution at amino acid residue K134.

23. The method according to claim 22, wherein the substitution is K134V.

24. The method according to claim 1, wherein the one or more amino acid substitutions comprises a substitution at amino acid residue K138.

25. The method according to claim 24, wherein the substitution is K138H.

26. The method according to claim 1, wherein the one or more amino acid substitutions comprises a substitution at amino acid residue Q143.

27. The method according to claim 26, wherein the substitution is Q143M.

28. The method according to claim 1, wherein the one or more amino acid substitutions comprises a substitution at amino acid residue K144.

29. The method according to claim 28, wherein the substitution is K144T.

30. The method according to claim 28, wherein the substitution is K144L.

31. The method according to claim 28, wherein the substitution is K144I.

32. The method according to claim 1, wherein the one or more amino acid substitutions comprises substitutions at amino acid residues K128, R129, and K134.

33. The method according to claim 32, wherein the substitutions are K128D, R129Q, and K134V.

* * * * *

SEQUENCE LISTING

<160> NUMBER OF SEQ ID NOS: 418

<210> SEQ ID NO 1
<211> LENGTH: 155
<212> TYPE: PRT
<213> ORGANISM: Homo sapiens

<400> SEQUENCE: 1

Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
            20                  25                  30

```
Asn Gly Gly His Phe Leu Arg Ile Leu Pro Asp Gly Thr Val Asp Gly
             35                  40                  45

Thr Arg Asp Arg Ser Asp Gln His Ile Gln Leu Gln Leu Ser Ala Glu
 50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
                130                 135                 140

Ile Leu Phe Leu Pro Leu Pro Val Ser Ser Asp
145                 150                 155

<210> SEQ ID NO 2
<211> LENGTH: 155
<212> TYPE: PRT
<213> ORGANISM: Papio anubis

<400> SEQUENCE: 2

Met Ala Glu Gly Glu Ile Thr Thr Phe Thr Ala Leu Thr Glu Lys Phe
 1               5                  10                  15

Asn Leu Pro Pro Ala Asn Tyr Lys Lys Pro Lys Leu Leu Tyr Cys Ser
                 20                  25                  30

Asn Gly Gly His Phe Leu Arg Ile Leu Pro Asp Gly Thr Val Asp Gly
             35                  40                  45

Thr Arg Asp Arg Ser Asp Gln His Ile Gln Leu Gln Leu Ser Ala Glu
 50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
                130                 135                 140

Ile Leu Phe Leu Pro Leu Pro Val Ser Ser Asp
145                 150                 155

<210> SEQ ID NO 3
<211> LENGTH: 155
<212> TYPE: PRT
<213> ORGANISM: Pongo abelii

<400> SEQUENCE: 3

Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
                 20                  25                  30

Asn Gly Gly His Phe Leu Arg Ile Leu Pro Asp Gly Thr Val Asp Gly
             35                  40                  45
```

```
Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 4
<211> LENGTH: 155
<212> TYPE: PRT
<213> ORGANISM: Callithrix jacchus

<400> SEQUENCE: 4

Met Ala Glu Gly Glu Ile Thr Thr Phe Thr Ala Leu Thr Glu Lys Phe
1               5                   10                  15

Asp Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 5
<211> LENGTH: 155
<212> TYPE: PRT
<213> ORGANISM: Equus caballus

<400> SEQUENCE: 5

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60
```

```
Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 6
<211> LENGTH: 155
<212> TYPE: PRT
<213> ORGANISM: Pan troglodytes

<400> SEQUENCE: 6

Met Ala Glu Gly Glu Ile Thr Thr Phe Thr Ala Leu Thr Glu Lys Phe
  1               5                  10                  15

Asn Leu Pro Ser Gly Asn Tyr Lys Lys Pro Lys Leu Leu Tyr Cys Ser
                 20                  25                  30

Asn Gly Gly His Phe Leu Arg Ile Leu Pro Asp Gly Thr Val Asp Gly
             35                  40                  45

Thr Arg Asp Arg Ser Asp Gln His Ile Gln Leu Gln Leu Ser Ala Glu
     50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 7
<211> LENGTH: 155
<212> TYPE: PRT
<213> ORGANISM: Loxodonta Africana

<400> SEQUENCE: 7

Met Ala Glu Gly Glu Ile Thr Thr Phe Thr Ala Leu Thr Glu Lys Phe
  1               5                  10                  15

Asn Leu Pro Pro Gly Asn Tyr Lys Lys Pro Lys Leu Leu Tyr Cys Ser
                 20                  25                  30

Asn Gly Gly His Phe Leu Arg Ile Leu Pro Asp Gly Thr Val Asp Gly
             35                  40                  45

Thr Arg Asp Arg Ser Asp Gln His Ile Gln Leu Gln Leu Ser Ala Glu
     50                  55                  60

Ser Val Gly Glu Val Tyr Ile Lys Gly Thr Glu Thr Gly Gln Tyr Leu
 65                  70                  75                  80
```

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 8
<211> LENGTH: 155
<212> TYPE: PRT
<213> ORGANISM: Canis lupus familiaris

<400> SEQUENCE: 8

Met Ala Glu Gly Glu Ile Thr Thr Phe Thr Ala Leu Thr Glu Lys Phe
1               5                   10                  15

Asn Leu Pro Pro Gly Asn Tyr Met Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 9
<211> LENGTH: 155
<212> TYPE: PRT
<213> ORGANISM: Ailuropoda melanoleuca

<400> SEQUENCE: 9

Met Ala Glu Gly Glu Ile Thr Thr Phe Thr Ala Leu Thr Glu Lys Phe
1               5                   10                  15

Asn Leu Pro Ala Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Tyr Gly Ser Gln Thr Pro Asn Glu
                85                  90                  95

Glu Cys Leu Phe Leu Glu Arg Leu Glu Asn His Tyr Asn Thr Tyr
                100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 10
<211> LENGTH: 155
<212> TYPE: PRT
<213> ORGANISM: Saimiri boliviensis boliviensis

<400> SEQUENCE: 10

Met Ala Glu Gly Glu Ile Thr Thr Phe Thr Ala Leu Thr Glu Lys Phe
1               5                   10                  15

Asp Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Leu His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 11
<211> LENGTH: 155
<212> TYPE: PRT
<213> ORGANISM: Sus scrofa

<400> SEQUENCE: 11

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Ser Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 12
<211> LENGTH: 155
<212> TYPE: PRT
<213> ORGANISM: Otolemur garnettii

<400> SEQUENCE: 12

Met Ala Glu Gly Glu Ile Thr Thr Phe Thr Ala Leu Thr Glu Lys Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Gln Asp Arg Ser Asp Gln His Ile Gln Leu Gln Leu Ser Ala Glu
    50                  55                  60

Ser Val Gly Glu Val Tyr Ile Lys Ser Thr Gln Thr Gly Gln Tyr Leu
65                  70                  75                  80

Ala Met Asp Ser Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 13
<211> LENGTH: 155
<212> TYPE: PRT
<213> ORGANISM: Rhinolophus ferrumequinum

<400> SEQUENCE: 13

Met Ala Glu Gly Glu Val Thr Thr Phe Thr Ala Leu Thr Glu Lys Phe
1               5                   10                  15

Asn Leu Pro Thr Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Lys Ser Asp Gln His Ile Gln Leu Gln Leu Ser Ala Glu
    50                  55                  60

Ser Val Gly Glu Val Tyr Ile Lys Ser Thr Glu Ser Gly Gln Tyr Leu
65                  70                  75                  80

Ala Met Asp Ser Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 14
<211> LENGTH: 155
<212> TYPE: PRT
<213> ORGANISM: Sorex araneus

<400> SEQUENCE: 14

Met Ala Glu Gly Glu Ile Thr Thr Phe Gly Ala Leu Met Glu Lys Phe
1               5                   10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly His Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 15
<211> LENGTH: 155
<212> TYPE: PRT
<213> ORGANISM: Oryctolagus cuniculus

<400> SEQUENCE: 15

Met Ala Glu Gly Glu Val Thr Thr Phe Thr Ala Leu Thr Glu Lys Phe
1               5                   10                  15

Asn Leu Pro Ala Gly Asn Tyr Lys Leu Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

```
Ile Leu Phe Leu Pro Leu Pro Val Ser Ser Asp
145                 150                 155
```

<210> SEQ ID NO 16
<211> LENGTH: 155
<212> TYPE: PRT
<213> ORGANISM: Cricetulus griseus

<400> SEQUENCE: 16

```
Met Ala Glu Gly Glu Ile Thr Thr Phe Ser Ala Leu Thr Glu Arg Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Ala Gly Glu Val Tyr Ile Lys Gly Thr Glu Thr Gly Gln Tyr Arg
65                  70                  75                  80

Asn Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 17
<211> LENGTH: 155
<212> TYPE: PRT
<213> ORGANISM: Sarcophilus harrisii

<400> SEQUENCE: 17

```
Met Ala Glu Gly Glu Ile Thr Thr Phe Thr Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Asn Asp Gln His Ile Gln Leu Gln Leu Ser Ala Glu
    50                  55                  60

Ser Val Gly Glu Val Tyr Ile Lys Ser Thr Glu Ser Gly Gln Tyr Leu
65                  70                  75                  80

Ala Met Asp Thr Asp Gly Leu Leu Tyr Gly Ser Gln Thr Pro Thr Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Glu
145                 150                 155
```

<210> SEQ ID NO 18
<211> LENGTH: 155
<212> TYPE: PRT
<213> ORGANISM: Mus musculus

<400> SEQUENCE: 18

Met Ala Glu Gly Glu Ile Thr Thr Phe Ala Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Ala Gly Glu Val Tyr Ile Lys Gly Thr Glu Thr Gly Gln Tyr Leu
65                  70                  75                  80

Ala Met Asp Thr Glu Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 19
<211> LENGTH: 154
<212> TYPE: PRT
<213> ORGANISM: Cavia porcellus

<400> SEQUENCE: 19

Met Ala Glu Gly Glu Ile Thr Thr Phe Ala Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Gly Val Gly Glu Val Tyr Ile Gln Ser Thr Glu Thr Gly Gln Tyr Leu
65                  70                  75                  80

Ala Met Asp Thr Asp Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Thr Ser Lys Lys His Val Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Asp
145                 150

<210> SEQ ID NO 20
<211> LENGTH: 155

<212> TYPE: PRT
<213> ORGANISM: Monodelphis domestica

<400> SEQUENCE: 20

Met Ala Glu Gly Glu Ile Thr Thr Phe Thr Ala Leu Thr Glu Arg Phe
1               5                   10                  15

Asn Leu Pro Leu Gly Asn Tyr Lys Pro Lys Leu Leu Tyr Cys Ser
            20                  25                  30

Asn Gly Gly His Phe Leu Arg Ile Leu Pro Asp Gly Lys Val Asp Gly
            35                  40                  45

Thr Arg Asp Arg Asn Asp Gln His Ile Gln Leu Gln Leu Ser Thr Glu
        50                  55                  60

Ser Val Gly Glu Val Tyr Ile Lys Ser Thr Glu Ser Gly Gln Tyr Leu
65                  70                  75                  80

Ala Met Asp Thr Asp Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Lys Gly Pro Arg Thr His Tyr Gly Gln Lys Ala
130                 135                 140

Ile Leu Phe Leu Pro Leu Pro Val Ser Ser Glu
145                 150                 155

<210> SEQ ID NO 21
<211> LENGTH: 155
<212> TYPE: PRT
<213> ORGANISM: Desmodus rotundus

<400> SEQUENCE: 21

Met Ala Glu Gly Glu Val Thr Thr Phe Thr Ala Leu Thr Glu Lys Phe
1               5                   10                  15

Asn Leu Pro Leu Glu Ser Tyr Lys Lys Pro Lys Leu Leu Tyr Cys Ser
            20                  25                  30

Asn Gly Gly His Phe Leu Arg Ile Leu Pro Asp Gly Thr Val Asp Gly
            35                  40                  45

Thr Arg Asp Lys Ser Asp Gln His Ile Gln Leu Gln Leu Ser Ala Glu
        50                  55                  60

Ser Val Gly Glu Val Tyr Ile Lys Ser Thr Gly Ser Gly Gln Tyr Leu
65                  70                  75                  80

Ala Met Asp Ser Ala Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
130                 135                 140

Ile Leu Phe Leu Pro Leu Pro Val Asn Ser Asp
145                 150                 155

<210> SEQ ID NO 22
<211> LENGTH: 155
<212> TYPE: PRT
<213> ORGANISM: Bos taurus

<400> SEQUENCE: 22

Met Ala Glu Gly Glu Thr Thr Thr Phe Thr Ala Leu Thr Glu Lys Phe
1               5                   10                  15

Asn Leu Pro Leu Gly Asn Tyr Lys Lys Pro Lys Leu Leu Tyr Cys Ser
            20                  25                  30

Asn Gly Gly Tyr Phe Leu Arg Ile Leu Pro Asp Gly Thr Val Asp Gly
        35                  40                  45

Thr Lys Asp Arg Ser Asp Gln His Ile Gln Leu Gln Leu Cys Ala Glu
    50                  55                  60

Ser Ile Gly Glu Val Tyr Ile Lys Ser Thr Glu Thr Gly Gln Phe Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys His Trp Phe Val Gly Leu Lys Lys
        115                 120                 125

Asn Gly Arg Ser Lys Leu Gly Pro Arg Thr His Phe Gly Gln Lys Ala
    130                 135                 140

Ile Leu Phe Leu Pro Leu Pro Val Ser Ser Asp
145                 150                 155

<210> SEQ ID NO 23
<211> LENGTH: 155
<212> TYPE: PRT
<213> ORGANISM: Ornithorhynchus anatinus

<400> SEQUENCE: 23

Met Ala Glu Gly Glu Ile Thr Thr Phe Thr Ala Leu Met Glu Lys Phe
1               5                   10                  15

Asp Leu Pro Leu Gly Asn Tyr Lys Lys Pro Arg Leu Leu Tyr Cys Ser
            20                  25                  30

Asn Gly Gly Tyr Phe Leu Arg Ile Gln Pro Asp Gly Lys Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Ser Gly His Tyr Leu
65                  70                  75                  80

Ala Met Asp Thr Glu Gly Leu Leu Tyr Gly Ser Gln Ala Pro Ser Glu
                85                  90                  95

Asp Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ala Ser Asp
145                 150                 155

<210> SEQ ID NO 24
<211> LENGTH: 155
<212> TYPE: PRT
<213> ORGANISM: Taeniopygia guttata

<400> SEQUENCE: 24

Met Ala Glu Gly Glu Ile Thr Thr Phe Ser Ala Leu Thr Glu Lys Phe

```
                1               5                  10                  15
Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Val Val His Ile Gln Ser Thr Gln Ser Gly Gln Tyr Leu
65                  70                  75                  80

Ala Met Asp Thr Asn Gly Leu Leu Tyr Gly Ser Gln Leu Pro Pro Gly
                85                  90                  95

Glu Cys Leu Phe Leu Glu Arg Leu Glu Glu Asn His Tyr Asn Thr Tyr
            100                 105                 110

Val Ser Lys Met His Ala Asp Lys Asn Trp Phe Val Gly Leu Lys Lys
        115                 120                 125

Asn Gly Thr Ser Lys Leu Gly Pro Arg Thr His Tyr Gly Gln Lys Ala
    130                 135                 140

Ile Leu Phe Leu Pro Leu Pro Val Ala Ala Asp
145                 150                 155

<210> SEQ ID NO 25
<211> LENGTH: 155
<212> TYPE: PRT
<213> ORGANISM: Dasypus novemcinctus

<400> SEQUENCE: 25

Met Ala Glu Gly Glu Ile Thr Thr Phe Met Ala Leu Met Glu Lys Phe
1               5                   10                  15

Asn Leu Pro Leu Glu Asn Tyr Lys His Pro Arg Leu Leu Tyr Cys Arg
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Glu Val Tyr Ile Lys Ser Ala Glu Thr Gly Gln Tyr Leu
65                  70                  75                  80

Ala Met Asp Thr Asp Gly Leu Leu Tyr Gly Ser Glu Thr Pro Ser Glu
                85                  90                  95

Glu Cys Leu Phe Met Glu Lys Leu Glu Glu Asn Asn Tyr Asn Thr Tyr
            100                 105                 110

Ile Ser Lys Lys His Ala Glu Lys Lys Trp Phe Val Gly Leu Lys Lys
        115                 120                 125

Asp Gly Ser Ser Lys Arg Gly Pro Gln Thr His Tyr Gly Gln Lys Ala
    130                 135                 140

Ile Leu Phe Leu Pro Leu Pro Val Ser Ser Asp
145                 150                 155

<210> SEQ ID NO 26
<211> LENGTH: 155
<212> TYPE: PRT
<213> ORGANISM: Xenopus Silurana tropicalis

<400> SEQUENCE: 26

Met Ala Glu Gly Asp Ile Thr Thr Phe Asn Pro Ile Ala Glu Ser Phe
1               5                   10                  15

Ser Leu Pro Ile Gly Asn Tyr Lys Lys Pro Lys Leu Leu Tyr Cys Asn
```

```
                20                  25                  30

Asn Gly Gly Tyr Phe Leu Arg Ile Leu Pro Asp Gly Val Asp Gly
                35                  40                  45

Thr Arg Asp Arg Asp Asp Leu Tyr Ile Thr Leu Lys Leu Ser Ala Gln
 50                  55                  60

Ser Gln Gly Glu Val His Ile Lys Ser Thr Glu Thr Gly Ser Tyr Leu
 65                  70                  75                  80

Ala Met Asp Ser Ser Gly Gln Leu Tyr Gly Thr Leu Thr Pro Asn Glu
                85                  90                  95

Glu Ser Leu Phe Leu Glu Thr Leu Glu Glu Asn His Tyr Asn Thr Tyr
                100                 105                 110

Lys Ser Lys Lys Tyr Ala Glu Asn Asn Trp Phe Val Gly Ile Lys Lys
            115                 120                 125

Asn Gly Ala Ser Lys Lys Gly Ser Arg Thr His Tyr Gly Gln Lys Ala
            130                 135                 140

Ile Leu Phe Leu Pro Leu Pro Ala Ser Pro Asp
145                 150                 155

<210> SEQ ID NO 27
<211> LENGTH: 155
<212> TYPE: PRT
<213> ORGANISM: Heterocephalus glaber

<400> SEQUENCE: 27

Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Lys Val Asp Gly
                35                  40                  45

Thr Arg Asp Arg Ser Asp Gln His Ile Gln Leu Gln Leu Ser Ala Glu
 50                  55                  60

Gly Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Ala Ser Glu
                85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 28
<211> LENGTH: 155
<212> TYPE: PRT
<213> ORGANISM: Pteropus alecto

<400> SEQUENCE: 28

Met Ala Glu Gly Glu Val Thr Thr Phe Thr Ala Leu Thr Glu Arg Phe
 1               5                  10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
```

```
                    35                  40                  45
Thr Arg Asp Lys Ser Asp Gln His Ile Gln Leu Gln Leu Ser Ala Glu
 50                  55                  60

Ser Val Gly Glu Val Tyr Ile Lys Ser Thr Glu Ser Gly Gln Tyr Leu
 65                  70                  75                  80

Ala Met Asp Ser Asp Gly Leu Leu Tyr Gly Ser Gln Thr Pro Asp Glu
                 85                  90                  95

Asp Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
130                 135                 140

Ile Leu Phe Leu Pro Leu Pro Val Ser Ser Asp
145                 150                 155

<210> SEQ ID NO 29
<211> LENGTH: 155
<212> TYPE: PRT
<213> ORGANISM: Tupaia chinensis

<400> SEQUENCE: 29

Met Ala Glu Gly Glu Ile Thr Thr Phe Ala Ala Leu Thr Glu Lys Phe
 1               5                  10                  15

Asp Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Thr Ala Glu
 50                  55                  60

Asn Val Gly Glu Val Tyr Ile Lys Ser Thr Glu Thr Gly Gln Tyr Leu
 65                  70                  75                  80

Ala Met Asp Ala Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Ala Leu Lys Lys
            115                 120                 125

Asn Gly Ser Cys Lys Leu Gly Pro Arg Thr His Tyr Gly Gln Lys Ala
130                 135                 140

Ile Leu Phe Leu Pro Leu Pro Val Ser Ser Asp
145                 150                 155

<210> SEQ ID NO 30
<211> LENGTH: 155
<212> TYPE: PRT
<213> ORGANISM: Columba livia

<400> SEQUENCE: 30

Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Lys Val Asp Gly
            35                  40                  45

Thr Arg Asp Arg Ser Asp Gln His Ile Gln Leu Gln Leu Ser Ala Glu
```

```
            50                  55                  60
Ser Val Gly Glu Val Tyr Ile Lys Ser Thr Gln Ser Gly Gln Tyr Leu
 65                  70                  75                  80

Ala Met Asp Pro Thr Gly Leu Leu Tyr Gly Ser Gln Leu Leu Gly Glu
                 85                  90                  95

Glu Cys Leu Phe Leu Glu Arg Ile Glu Asn His Tyr Asn Thr Tyr
                100                 105                 110

Val Ser Lys Lys His Ala Asp Lys Asn Trp Phe Val Gly Leu Lys Lys
            115                 120                 125

Asn Gly Asn Ser Lys Leu Gly Pro Arg Thr His Tyr Gly Gln Lys Ala
        130                 135                 140

Ile Leu Phe Leu Pro Leu Pro Val Ser Ala Asp
145                 150                 155

<210> SEQ ID NO 31
<211> LENGTH: 155
<212> TYPE: PRT
<213> ORGANISM: Ovis aries

<400> SEQUENCE: 31

Met Ala Glu Gly Glu Thr Thr Thr Phe Arg Ala Leu Thr Glu Lys Phe
 1               5                  10                  15

Asn Leu Pro Leu Gly Asn Tyr Lys Lys Pro Lys Leu Leu Tyr Cys Ser
                20                  25                  30

Asn Gly Gly Tyr Phe Leu Arg Ile Leu Pro Asp Gly Arg Val Asp Gly
            35                  40                  45

Thr Lys Asp Arg Ser Asp Gln His Ile Gln Leu Gln Leu Tyr Ala Glu
        50                  55                  60

Ser Ile Gly Glu Val Tyr Ile Lys Ser Thr Glu Thr Gly Gln Phe Leu
 65                  70                  75                  80

Ala Met Asp Thr Asn Gly Leu Leu Tyr Gly Ser Gln Thr Pro Ser Glu
                 85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Ile Gly Leu Lys Lys
            115                 120                 125

Asn Gly Ser Ser Lys Leu Gly Pro Arg Thr His Phe Gly Gln Lys Ala
        130                 135                 140

Ile Leu Phe Leu Pro Leu Pro Val Ser Ser Asp
145                 150                 155

<210> SEQ ID NO 32
<211> LENGTH: 155
<212> TYPE: PRT
<213> ORGANISM: Gallus gallus

<400> SEQUENCE: 32

Met Ala Glu Gly Glu Ile Thr Thr Phe Thr Ala Leu Thr Glu Arg Phe
 1               5                  10                  15

Gly Leu Pro Leu Gly Asn Tyr Lys Lys Pro Lys Leu Leu Tyr Cys Ser
                20                  25                  30

Asn Gly Gly His Phe Leu Arg Ile Leu Pro Asp Gly Lys Val Asp Gly
            35                  40                  45

Thr Arg Asp Arg Ser Asp Gln His Ile Gln Leu Gln Leu Ser Ala Glu
        50                  55                  60

Asp Val Gly Glu Val Tyr Ile Lys Ser Thr Ala Ser Gly Gln Tyr Leu
```

```
                65                  70                  75                  80
Ala Met Asp Thr Asn Gly Leu Leu Tyr Gly Ser Gln Leu Pro Gly Glu
                    85                  90                  95

Glu Cys Leu Phe Leu Glu Arg Leu Glu Glu Asn His Tyr Asn Thr Tyr
                100                 105                 110

Ile Ser Lys Lys His Ala Asp Lys Asn Trp Phe Val Gly Leu Lys Lys
                115                 120                 125

Asn Gly Asn Ser Lys Leu Gly Pro Arg Thr His Tyr Gly Gln Lys Ala
            130                 135                 140

Ile Leu Phe Leu Pro Leu Pro Val Ser Ala Asp
145                 150                 155

<210> SEQ ID NO 33
<211> LENGTH: 98
<212> TYPE: PRT
<213> ORGANISM: Vicugna pacos

<400> SEQUENCE: 33

Gln Leu Gln Leu Ser Ala Glu Ser Val Gly Glu Val Tyr Ile Lys Ser
1               5                   10                  15

Thr Glu Thr Gly Gln Tyr Leu Ala Met Asp Thr Asp Gly Leu Leu His
                20                  25                  30

Gly Ser Gln Thr Pro Asn Glu Glu Cys Leu Phe Leu Glu Arg Leu Glu
            35                  40                  45

Glu Asn His Tyr Asn Thr Tyr Thr Ser Lys Lys His Ala Glu Lys Asn
        50                  55                  60

Trp Phe Val Gly Leu Lys Lys Asn Gly Ser Cys Lys Arg Gly Pro Arg
65                  70                  75                  80

Thr His Tyr Gly Gln Lys Ala Ile Leu Phe Leu Pro Leu Pro Val Ser
                85                  90                  95

Ser Asp

<210> SEQ ID NO 34
<211> LENGTH: 155
<212> TYPE: PRT
<213> ORGANISM: Anolis carolinensis

<400> SEQUENCE: 34

Met Ala Glu Gly Glu Ile Thr Thr Phe Thr Ala Leu Thr Glu Arg Phe
1               5                   10                  15

Ala Leu Pro Met Glu Asn Tyr Lys Lys Pro Lys Leu Leu Tyr Cys Ser
                20                  25                  30

Asn Gly Gly His Phe Leu Arg Ile Leu Pro Asp Gly Lys Val Asp Gly
            35                  40                  45

Thr Met Asp Arg Asn Asp Ser Tyr Ile Gln Leu Leu Leu Thr Ala Glu
        50                  55                  60

Asp Val Gly Val Val Tyr Ile Lys Gly Thr Glu Thr Gly Gln Tyr Leu
65                  70                  75                  80

Ala Met Asp Ala Asn Gly His Leu Tyr Gly Ser Gln Leu Pro Thr Glu
                85                  90                  95

Glu Cys Leu Phe Val Glu Thr Leu Glu Glu Asn His Tyr Asn Thr Tyr
                100                 105                 110

Thr Ser Lys Met His Gly Asp Lys Lys Trp Tyr Val Gly Leu Lys Lys
                115                 120                 125

Asn Gly Lys Gly Lys Leu Gly Pro Arg Thr His Arg Gly Gln Lys Ala
            130                 135                 140
```

```
Ile Leu Phe Leu Pro Leu Pro Val Ser Pro Asp
145                 150                 155

<210> SEQ ID NO 35
<211> LENGTH: 155
<212> TYPE: PRT
<213> ORGANISM: Otolemur garnettii

<400> SEQUENCE: 35

Met Ala Glu Gly Glu Ile Thr Thr Phe Thr Ala Leu Thr Glu Lys Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Gln Asp Arg Ser Asp Gln His Ile Gln Leu Gln Leu Ser Ala Glu
    50                  55                  60

Ser Val Gly Glu Val Tyr Ile Lys Ser Thr Gln Thr Gly Gln Tyr Leu
65                  70                  75                  80

Ala Met Asp Ser Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 36
<211> LENGTH: 155
<212> TYPE: PRT
<213> ORGANISM: Felis catus

<400> SEQUENCE: 36

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 37
<211> LENGTH: 155
<212> TYPE: PRT
<213> ORGANISM: Pelodiscus sinensis

<400> SEQUENCE: 37

Met Ala Glu Gly Glu Ile Thr Thr Phe Thr Ala Leu Thr Glu Lys Phe
1               5                   10                  15

Asn Leu Pro Leu Gly Asn Tyr Lys Asn Pro Lys Leu Leu Tyr Cys Ser
            20                  25                  30

Asn Gly Gly Tyr Phe Leu Arg Ile His Pro Asp Gly Lys Val Asp Gly
        35                  40                  45

Thr Arg Asp Arg Ser Asp Gln His Ile Gln Leu Gln Leu Ser Ala Glu
50                  55                  60

Ser Val Gly Glu Val Tyr Ile Lys Ser Thr Glu Ser Gly Gln Phe Leu
65                  70                  75                  80

Ala Met Asp Ala Asn Gly Leu Leu Tyr Gly Ser Leu Ser Pro Ser Glu
                85                  90                  95

Glu Cys Leu Phe Leu Glu Arg Met Glu Glu Asn His Tyr Asn Thr Tyr
            100                 105                 110

Ile Ser Lys Lys His Ala Asp Lys Asn Trp Phe Val Gly Leu Lys Lys
        115                 120                 125

Asn Gly Ser Cys Lys Leu Gly Pro Arg Thr His Tyr Gly Gln Lys Ala
    130                 135                 140

Val Leu Phe Leu Pro Leu Pro Val Ser Ala Asp
145                 150                 155

<210> SEQ ID NO 38
<211> LENGTH: 155
<212> TYPE: PRT
<213> ORGANISM: Latimeria chalumnae

<400> SEQUENCE: 38

Met Ala Glu Asp Lys Ile Thr Thr Leu Lys Ala Leu Ala Glu Lys Phe
1               5                   10                  15

Asn Leu Pro Met Gly Asn Tyr Lys Lys Ala Lys Leu Leu Tyr Cys Ser
            20                  25                  30

Asn Gly Gly Tyr Phe Leu Arg Ile Pro Pro Asp Gly Lys Val Glu Gly
        35                  40                  45

Ile Arg Glu Arg Ser Asp Lys Tyr Ile Gln Leu Gln Met Asn Ala Glu
50                  55                  60

Ser Leu Gly Met Val Ser Ile Lys Gly Val Glu Ala Gly Gln Tyr Leu
65                  70                  75                  80

Ala Met Asn Thr Asn Gly Leu Leu Tyr Gly Ser Gln Ser Leu Thr Glu
                85                  90                  95

Glu Cys Leu Phe Met Glu Lys Met Glu Glu Asn His Tyr Asn Thr Tyr
            100                 105                 110

Arg Ser Lys Thr His Ala Asp Lys Asn Trp Tyr Val Gly Ile Arg Lys
        115                 120                 125

Asn Gly Ser Ile Lys Pro Gly Pro Arg Thr His Ile Gly Gln Lys Ala
    130                 135                 140

Val Leu Phe Leu Pro Leu Pro Ala Ser Ser Asp
145                 150                 155

<210> SEQ ID NO 39

<211> LENGTH: 155
<212> TYPE: PRT
<213> ORGANISM: Tursiops truncatus

<400> SEQUENCE: 39

```
Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ala Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 40
<211> LENGTH: 155
<212> TYPE: PRT
<213> ORGANISM: Mustela putorius furo

<400> SEQUENCE: 40

```
Met Ala Glu Gly Glu Ile Thr Thr Phe Thr Ala Leu Met Glu Lys Phe
1               5                   10                  15

Asn Leu Pro Ala Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 41
<211> LENGTH: 155
<212> TYPE: PRT
<213> ORGANISM: Nomascus leucogenys

<400> SEQUENCE: 41

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 42
<211> LENGTH: 155
<212> TYPE: PRT
<213> ORGANISM: Gorilla gorilla

<400> SEQUENCE: 42

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 43
<211> LENGTH: 155
<212> TYPE: PRT
<213> ORGANISM: Erinaceus europaeus

<400> SEQUENCE: 43

Met Ala Glu Gly Glu Ile Thr Thr Phe Thr Ala Leu Thr Glu Lys Phe
1               5                   10                  15

Asn Leu Pro Leu Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 44
<211> LENGTH: 91
<212> TYPE: PRT
<213> ORGANISM: Procavia capensis

<400> SEQUENCE: 44

Met Ala Glu Gly Glu Ile Thr Thr Phe Thr Ala Leu Thr Glu Lys Phe
1               5                   10                  15

Asn Leu Pro Leu Glu Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
    50                  55                  60

Ser Val Gly Glu Val Tyr Ile Lys Gly Thr Glu Thr Gly Gln Tyr Leu
65                  70                  75                  80

Ala Met Asp Thr Asp Gly Leu Leu Tyr Gly Ser
                85                  90

<210> SEQ ID NO 45
<211> LENGTH: 114
<212> TYPE: PRT
<213> ORGANISM: Dipodomys ordii

<400> SEQUENCE: 45

Met Ala Glu Gly Glu Ile Thr Thr Phe Thr Ala Leu Thr Glu Arg Phe
1               5                   10                  15

Gln Leu Gln Leu Ser Ala Glu Ser Val Gly Glu Val Tyr Ile Lys Ser
                20                  25                  30

Thr Glu Thr Gly Gln Tyr Leu Ala Met Asp Ala Asp Gly Leu Leu Tyr
            35                  40                  45

Gly Ser Gln Thr Pro Asp Glu Glu Cys Leu Phe Leu Glu Arg Leu Glu
    50                  55                  60

Glu Asn His Tyr Asn Thr Tyr Ile Ala Lys Lys His Ala Glu Lys Asn
65                  70                  75                  80

```
Trp Phe Val Gly Leu Lys Lys Asn Gly Ser Cys Lys Arg Gly Pro Arg
                85                  90                  95
Thr His Tyr Gly Gln Lys Ala Ile Leu Phe Leu Pro Leu Pro Val Ser
            100                 105                 110
Ser Asp

<210> SEQ ID NO 46
<211> LENGTH: 92
<212> TYPE: PRT
<213> ORGANISM: Petromyzon marinus

<400> SEQUENCE: 46

Met Glu Val Gly His Ile Gly Thr Leu Pro Val Val Pro Ala Gly Pro
 1               5                  10                  15
Val Phe Pro Gly Ser Phe Lys Glu Pro Arg Arg Leu Tyr Cys Arg Ser
                20                  25                  30
Ala Gly His His Leu Gln Ile Leu Gly Asp Gly Thr Val Ser Gly Thr
            35                  40                  45
Gln Asp Glu Asn Glu Pro His Ala Val Leu Gln Leu Gln Ala Val Arg
        50                  55                  60
Arg Gly Val Val Thr Ile Arg Gly Leu Cys Ala Glu Arg Phe Leu Ala
65                  70                  75                  80
Met Ser Thr Glu Gly His Leu Tyr Gly Ala Val Arg
                85                  90

<210> SEQ ID NO 47
<211> LENGTH: 98
<212> TYPE: PRT
<213> ORGANISM: Echinops telfairi

<400> SEQUENCE: 47

Gln Leu Lys Leu Val Ala Glu Ser Val Gly Val Val Tyr Ile Lys Ser
 1               5                  10                  15
Ile Lys Thr Gly Gln Tyr Leu Ala Met Asn Pro Asp Gly Leu Leu Tyr
                20                  25                  30
Gly Ser Glu Thr Pro Glu Glu Glu Cys Leu Phe Leu Glu Thr Leu Glu
            35                  40                  45
Glu Asn His Tyr Thr Thr Phe Lys Ser Lys Lys His Val Glu Lys Asn
        50                  55                  60
Trp Phe Val Gly Leu Arg Lys Asn Gly Arg Val Lys Ile Gly Pro Arg
65                  70                  75                  80
Thr His Gln Gly Gln Lys Ala Ile Leu Phe Leu Pro Leu Pro Val Ser
                85                  90                  95
Ser Asp

<210> SEQ ID NO 48
<211> LENGTH: 155
<212> TYPE: PRT
<213> ORGANISM: Macaca mulatta

<400> SEQUENCE: 48

Met Ala Glu Gly Glu Ile Thr Thr Phe Thr Ala Leu Thr Glu Lys Phe
 1               5                  10                  15
Asn Leu Pro Pro Gly Asn Tyr Lys Lys Pro Lys Leu Leu Tyr Cys Ser
                20                  25                  30
Asn Gly Gly His Phe Leu Arg Ile Leu Pro Asp Gly Thr Val Asp Gly
            35                  40                  45
```

```
Thr Arg Asp Arg Ser Asp Gln His Ile Gln Leu Gln Leu Ser Ala Glu
 50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
                130                 135                 140

Ile Leu Phe Leu Pro Leu Pro Val Ser Ser Asp
145                 150                 155

<210> SEQ ID NO 49
<211> LENGTH: 155
<212> TYPE: PRT
<213> ORGANISM: Pteropus vampyrus

<400> SEQUENCE: 49

Met Ala Glu Gly Glu Val Thr Thr Phe Thr Ala Leu Thr Glu Arg Phe
  1               5                  10                  15

Asn Leu Pro Pro Gly Asn Tyr Lys Lys Pro Lys Leu Leu Tyr Cys Ser
                 20                  25                  30

Asn Gly Gly His Phe Leu Arg Ile Leu Pro Asp Gly Thr Val Asp Gly
                 35                  40                  45

Thr Arg Asp Lys Ser Asp Gln His Ile Gln Leu Gln Leu Ser Ala Glu
 50                  55                  60

Ser Val Gly Glu Val Tyr Ile Lys Ser Thr Glu Ser Gly Gln Tyr Leu
 65                  70                  75                  80

Ala Met Asp Ser Asp Gly Leu Leu Tyr Gly Ser Gln Thr Pro Asp Glu
                 85                  90                  95

Asp Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
                130                 135                 140

Ile Leu Phe Leu Pro Leu Pro Val Ser Ser Asp
145                 150                 155

<210> SEQ ID NO 50
<211> LENGTH: 155
<212> TYPE: PRT
<213> ORGANISM: Myotis lucifugus

<400> SEQUENCE: 50

Met Ala Glu Gly Glu Val Thr Thr Phe Thr Ala Leu Thr Glu Arg Phe
  1               5                  10                  15

Asn Leu Pro Leu Glu Asn Tyr Lys Lys Pro Lys Leu Leu Tyr Cys Ser
                 20                  25                  30

Asn Gly Gly His Phe Leu Arg Ile Leu Pro Asp Gly Thr Val Asp Gly
                 35                  40                  45

Thr Arg Asp Arg Ser Asp Gln His Ile Gln Leu Gln Leu Ser Ala Glu
 50                  55                  60
```

```
Ser Val Gly Glu Val Tyr Ile Lys Ser Thr Glu Ser Gly Gln Tyr Leu
 65                  70                  75                  80

Ala Met Asp Ser Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 51
<211> LENGTH: 155
<212> TYPE: PRT
<213> ORGANISM: Microcebus murinus

<400> SEQUENCE: 51

Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
                 20                  25                  30

Asn Gly Gly His Phe Leu Arg Ile Leu Pro Asp Gly Thr Val Asp Gly
             35                  40                  45

Thr Arg Asp Arg Ser Asp Gln His Ile Gln Leu Gln Leu Ser Ala Glu
         50                  55                  60

Ser Ala Gly Glu Val Tyr Ile Lys Ser Thr Gln Thr Gly Arg Tyr Leu
 65                  70                  75                  80

Ala Met Asp Ala Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
                100                 105                 110

Val Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 52
<211> LENGTH: 144
<212> TYPE: PRT
<213> ORGANISM: Ochotona princeps

<400> SEQUENCE: 52

Met Ala Glu Gly Glu Val Thr Thr Phe Ser Ala Leu Thr Glu Lys Phe
 1               5                  10                  15

Asn Leu Pro Gly Gly Asn Tyr Lys Leu Pro Lys Leu Leu Tyr Cys Ser
                 20                  25                  30

Asn Gly Gly His Phe Leu Arg Ile Leu Pro Asp Gly Thr Val Asp Gly
             35                  40                  45

Thr Arg Asp Arg Ser Asp Leu His Glu Val Phe Ile Lys Ser Thr Glu
         50                  55                  60

Thr Gly Gln Tyr Leu Ala Met Asp Thr Asp Gly Leu Leu Tyr Gly Ser
 65                  70                  75                  80
```

```
Gln Thr Pro Ser Glu Glu Cys Leu Phe Leu Glu Arg Leu Glu Glu Asn
                85                  90                  95

His Tyr Asn Thr Tyr Thr Ser Lys Lys His Ala Glu Lys Asn Trp Phe
            100                 105                 110

Val Gly Ile Lys Lys Asn Gly Ser Cys Lys Arg Gly Pro Arg Thr His
        115                 120                 125

Tyr Gly Gln Lys Ala Ile Leu Phe Leu Pro Leu Pro Val Ser Ser Asp
    130                 135                 140
```

<210> SEQ ID NO 53
<211> LENGTH: 155
<212> TYPE: PRT
<213> ORGANISM: Rattus norvegicus

<400> SEQUENCE: 53

```
Met Ala Glu Gly Glu Ile Thr Thr Phe Ala Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Ala Gly Glu Val Tyr Ile Lys Gly Thr Glu Thr Gly Gln Tyr Leu
65                  70                  75                  80

Ala Met Asp Thr Glu Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 54
<211> LENGTH: 155
<212> TYPE: PRT
<213> ORGANISM: Choloepus hoffmanni

<400> SEQUENCE: 54

```
Met Ala Glu Gly Glu Ile Thr Thr Phe Thr Ala Leu Met Glu Lys Phe
1               5                   10                  15

Asn Leu Pro Pro Gly Asn Tyr Met Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Leu His Ile Gln Leu Gln Leu Ser Ala Glu
    50                  55                  60

Ser Val Gly Glu Val Tyr Ile Lys Ser Ala Glu Thr Gly Gln Tyr Leu
65                  70                  75                  80

Ala Met Asp Thr Gly Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110
```

Val Ser Lys Lys His Ala Glu Lys Asn Trp Phe Val Gly Leu Lys Lys
            115                 120                 125

Asn Gly Ser Ser Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 55
<211> LENGTH: 155
<212> TYPE: PRT
<213> ORGANISM: Ictidomys tridecemlineatus

<400> SEQUENCE: 55

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 56
<211> LENGTH: 155
<212> TYPE: PRT
<213> ORGANISM: Tarsius syrichta

<400> SEQUENCE: 56

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
            115                 120                 125

```
Asn Gly Ser Cys Lys Arg Gly Pro Arg Thr His Tyr Gly Gln Lys Ala
        130                 135                 140
Ile Leu Phe Leu Pro Leu Pro Val Ser Ser Asp
145                 150                 155

<210> SEQ ID NO 57
<211> LENGTH: 155
<212> TYPE: PRT
<213> ORGANISM: Tupaia belangeri

<400> SEQUENCE: 57

Met Ala Glu Gly Glu Ile Thr Thr Phe Ala Ala Leu Thr Glu Lys Phe
1               5                   10                  15
Asp Leu Pro Pro Gly Asn Tyr Lys Lys Pro Lys Leu Leu Tyr Cys Ser
                20                  25                  30
Asn Gly Gly His Phe Leu Arg Ile Leu Pro Asp Gly Thr Val Asp Gly
            35                  40                  45
Thr Arg Asp Arg Ser Asp Gln His Ile Gln Leu Gln Leu Thr Ala Glu
        50                  55                  60
Asn Val Gly Glu Val Tyr Ile Lys Ser Thr Glu Thr Gly Gln Tyr Leu
65                  70                  75                  80
Ala Met Asp Ala Asp Gly Leu Leu Tyr Gly Ser Gln Thr Pro Asn Glu
                85                  90                  95
Glu Cys Leu Phe Leu Glu Arg Leu Glu Glu Asn His Tyr Asn Thr Tyr
                100                 105                 110
Ile Ser Lys Lys His Ala Glu Lys Asn Trp Phe Val Ala Leu Lys Lys
            115                 120                 125
Asn Gly Ser Cys Lys Leu Gly Pro Arg Thr His Tyr Gly Gln Lys Ala
        130                 135                 140
Ile Leu Phe Leu Pro Leu Pro Val Ser Ser Asp
145                 150                 155

<210> SEQ ID NO 58
<211> LENGTH: 56
<212> TYPE: PRT
<213> ORGANISM: Meleagris gallopavo

<400> SEQUENCE: 58

Met Ala Glu Gly Glu Ile Thr Thr Phe Thr Ala Leu Thr Glu Arg Phe
1               5                   10                  15
Gly Leu Pro Leu Gly Asn Tyr Lys Lys Pro Lys Leu Leu Tyr Cys Ser
                20                  25                  30
Asn Gly Gly His Phe Leu Arg Ile Leu Pro Asp Gly Lys Val Asp Gly
            35                  40                  45
Thr Arg Asp Arg Ser Asp Gln His
        50                  55

<210> SEQ ID NO 59
<211> LENGTH: 155
<212> TYPE: PRT
<213> ORGANISM: Macropus eugenii

<400> SEQUENCE: 59

Met Ala Glu Gly Glu Ile Thr Thr Phe Thr Ala Leu Thr Glu Arg Phe
1               5                   10                  15
Asn Leu Pro Leu Gly Asn Tyr Lys Lys Pro Lys Leu Leu Tyr Cys Ser
                20                  25                  30
Asn Gly Gly His Phe Leu Arg Ile Leu Pro Asp Gly Lys Val Asp Gly
```

```
                   35                  40                  45

Thr Arg Asp Arg Asn Asp Gln His Ile Gln Leu Gln Leu Ser Ala Glu
             50                  55                  60

Ser Val Gly Glu Val Tyr Ile Lys Ser Thr Glu Ser Gly Gln Tyr Leu
 65                  70                  75                  80

Ala Met Asp Thr Asn Gly Leu Leu Tyr Gly Ser Gln Thr Pro Ser Glu
                 85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Glu
145                 150                 155

<210> SEQ ID NO 60
<211> LENGTH: 147
<212> TYPE: PRT
<213> ORGANISM: Danio rerio

<400> SEQUENCE: 60

Met Thr Glu Ala Asp Ile Ala Val Lys Ser Ser Pro Arg Asp Tyr Lys
  1               5                  10                  15

Lys Leu Thr Arg Leu Tyr Cys Met Asn Gly Gly Phe His Leu Gln Ile
                 20                  25                  30

Leu Ala Asp Gly Thr Val Ala Gly Ala Ala Asp Glu Asn Thr Tyr Ser
             35                  40                  45

Ile Leu Arg Ile Lys Ala Thr Ser Pro Gly Val Val Ile Glu Gly
 50                  55                  60

Ser Glu Thr Gly Leu Tyr Leu Ser Met Asn Glu His Gly Lys Leu Tyr
 65                  70                  75                  80

Ala Ser Ser Leu Val Thr Asp Glu Ser Tyr Phe Leu Glu Lys Met Glu
                 85                  90                  95

Glu Asn His Tyr Asn Thr Tyr Gln Ser Gln Lys His Gly Glu Asn Trp
            100                 105                 110

Tyr Val Gly Ile Lys Lys Asn Gly Lys Met Lys Arg Gly Pro Arg Thr
        115                 120                 125

His Ile Gly Gln Lys Ala Ile Phe Phe Leu Pro Arg Gln Val Glu Gln
    130                 135                 140

Glu Glu Asp
145

<210> SEQ ID NO 61
<211> LENGTH: 468
<212> TYPE: DNA
<213> ORGANISM: Homo sapiens

<400> SEQUENCE: 61
atggctgaag gggaaatcac caccttcaca gccctgaccg agaagtttaa tctgcctcca      60
gggaattaca agaagcccaa actcctctac tgtagcaacg ggggccactt cctgaggatc     120
cttccggatg gcacagtgga tgggacaagg gacaggagcg accagcacat tcagctgcag     180
ctcagtgcgg aaagcgtggg ggaggtgtat ataaagagta ccgagactgg ccagtacttg     240
gccatggaca ccgacgggct tttatacggc tcacagacac aaatgagga atgtttgttc     300
```

```
ctggaaaggc tggaggagaa ccattacaac acctatatat ccaagaagca tgcagagaag    360
aattggtttg ttggcctcaa gaagaatggg agctgcaaac gcggtcctcg gactcactat    420
ggccagaaag caatcttgtt tctccccctg ccagtctctt ctgattaa                 468
```

```
<210> SEQ ID NO 62
<211> LENGTH: 468
<212> TYPE: DNA
<213> ORGANISM: Olive Baboon

<400> SEQUENCE: 62
atggctgaag gggaaatcac cacgttcaca gccctgaccg agaagtttaa tctgcctcca     60
gcgaattaca agaagcccaa actgctctac tgtagcaacg ggggacactt cttgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctacatat ccaagaagca cgcagagaag    360
aattggtttg ttggcctcaa gaagaatgga agctgcaaac gtggtcctcg gactcactat    420
ggccagaaag caatcttgtt tcttcccctg ccagtctctt ctgattaa                 468
```

```
<210> SEQ ID NO 63
<211> LENGTH: 468
<212> TYPE: DNA
<213> ORGANISM: Sumatran orangutan

<400> SEQUENCE: 63
atggctgaag gggaaatcac caccttcaca gccctgaccg agaagtttaa tctgcctcca     60
gggaattaca agaagcccaa actcctctac tgtagcaacg ggggccactt cttgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
aattggtttg ttggcctcaa gaagaatgga agctgcaaac gcggtcctcg gactcactat    420
ggccagaaag caatcttgtt tctccccctg ccagtctctt ccgattaa                 468
```

```
<210> SEQ ID NO 64
<211> LENGTH: 468
<212> TYPE: DNA
<213> ORGANISM: White-tufted-ear marmoset

<400> SEQUENCE: 64
atggctgaag gggaaatcac caccttcaca gccctgaccg agaagtttga tctgcctcca     60
gggaattaca agaagcccaa actcctctac tgtagcaatg ggggccactt cttgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggagaggc tggaggagaa ccattacaac acctatatat ccaagaaaca tgcagagaag    360
aattggtttg tcggcctcaa gaagaatgga agctgtaaac gtggtcctcg gactcactat    420
ggtcagaaag cgatcttgtt tctccccctg ccagtttctt ctgattaa                 468
```

```
<210> SEQ ID NO 65
<211> LENGTH: 468
<212> TYPE: DNA
<213> ORGANISM: Horse

<400> SEQUENCE: 65
atggctgaag gagaaatcac aaccttcacg gccctgaccg agaagtttaa tctgcctcca      60
gggaattaca agaagcccaa actcctctac tgtagcaatg ggggccactt cctgaggatc     120
cttccagatg gcacagtgga tgggacaagg gacaggagcg accagcacat tcagctgcag     180
ctcagtgcgg aaagcgtggg ggaggtgtat ataaagagta ccgagactgg ccagtacttg     240
gccatggaca ccgacgggct gttgtacggc tcacagacac aaacgagga atgtttgttc      300
ctggaaaggc tggaggaaaa ccattacaac acctacacat ccaagaagca tgcagagaag     360
aactggttcg ttggtctcaa gaagaatggg agctgcaaac gcggtcctcg gactcactat     420
gggcagaaag caatcttgtt tcttcccctg cccgtctcct ctgactaa                  468

<210> SEQ ID NO 66
<211> LENGTH: 468
<212> TYPE: DNA
<213> ORGANISM: Chimpanzee

<400> SEQUENCE: 66
atggctgaag gggaaatcac caccttcaca gccctgaccg agaagtttaa tctgccttca      60
gggaattaca agaagcccaa actcctctac tgtagcaacg ggggccactt cctgaggatc     120
cttccggatg gcacagtgga tgggacaagg gacaggagcg accagcacat tcagctgcag     180
ctcagtgcgg aaagcgtggg ggaggtgtat ataaagagta ccgagactgg ccagtacttg     240
gccatggaca ccgacgggct tttatacggc tcacagacac aaatgagga atgtttgttc      300
ctggaacggc tggaggagaa ccattacaac acctatatat ccaagaagca tgcagagaag     360
aattggtttg ttggcctcaa gaagaatgga agctgcaaac gcggtcctcg gactcactat     420
ggccagaaag caatcttgtt tctccccctg ccagtctctt ccgattaa                  468

<210> SEQ ID NO 67
<211> LENGTH: 468
<212> TYPE: DNA
<213> ORGANISM: Elephant

<400> SEQUENCE: 67
atggccgaag gggaaatcac aactttcaca gccctgacag agaagttcaa cctgcctcca      60
gggaattaca agaagcccaa actcctctac tgtagcaatg gaggtcactt cttaaggatc     120
cttccagatg gcacagtgga tggcaccagg gacaggagtg accagcacat tcagctgcag     180
ctcagtgcgg aaagcgtggg ggaggtgtat ataaagggca ccgagactgg ccagtacttg     240
gccatggaca ccgacgggct tttatacggc tcacagacac aaatgagga atgtttgttc      300
ctggaaaggc tggaggaaaa ccattacaac acctacacat ccaagaagca cgcagagaag     360
aattggttcg ttggtctcaa gaagaatgga agctgcaaac gcggtcctcg gactcactat     420
ggccagaaag caatcttgtt tctccccctg ccagtctcct ctgattaa                  468

<210> SEQ ID NO 68
<211> LENGTH: 468
<212> TYPE: DNA
<213> ORGANISM: Dog

<400> SEQUENCE: 68
```

```
atggctgaag gggaaatcac aaccttcact gccctgacgg agaagtttaa tctgcctccg    60
gggaattaca tgaagcccaa actcctctac tgtagcaacg ggggccactt cctgaggatc   120
cttccagatg gcacagtgga tgggacaagg gacaggagcg accagcacat tcagctgcag   180
ctcagcgcgg aaagcgtggg ggaggtgtat ataaagagca ccgagactgg ccagtacttg   240
gccatggaca ccgatgggct tctgtacggc tcacagacac cgaatgagga atgtttgttc   300
ctggaaaggc tggaggaaaa ccattacaac acctacacat ccaagaagca tgcagaaaaa   360
aattggtttg ttggtctcaa gaagaatgga agctgcaaac gcggtcctcg gactcactat   420
ggtcaaaaag caattttgtt ctccccctg ccagtgtcct ctgattaa                  468
```

<210> SEQ ID NO 69
<211> LENGTH: 468
<212> TYPE: DNA
<213> ORGANISM: Giant panda

<400> SEQUENCE: 69

```
atggctgaag gggagatcac aaccttcacc gccctgacgg agaagtttaa tctgcctgcg    60
gggaattaca agaagcccaa actcctctac tgtagcaacg ggggccactt cctgaggatc   120
cttccagatg gcacagtgga cgggacgagg gacaggagcg accagcacat tcaactgcag   180
ctcagcgcgg aaagcgtagg ggaggtgtac ataaagagca ccgagaccgg ccagtacttg   240
gccatggaca ccgatgggct tctgtacggc tcacagacac caaatgagga atgtttgttc   300
ctggaaaggc tggaggaaaa ccattacaac acctacacat ccaagaagca cgcggagaag   360
aattggtttg ttggtctcaa gaagaatgga agctgcaaac gtggtcctcg gactcactat   420
ggccagaaag caattctgtt ctccccctg ccagtctcct ctgattaa                  468
```

<210> SEQ ID NO 70
<211> LENGTH: 468
<212> TYPE: DNA
<213> ORGANISM: Bolivian squirrel monkey

<400> SEQUENCE: 70

```
atggctgaag gggaaatcac caccttaca gccctgaccg agaagtttga tctgcctcca     60
gggaattaca agaagcccaa actcctctac tgtagcaacg ggggccactt cttgaggatc   120
cttccggatg gcacagtgga tgggaccagg gacaggagcg atcttcacat tcagctgcag   180
ctcagtgcgg aaagcgtggg ggaggtgtat ataaagagta ccgagactgg ccagtacttg   240
gccatggaca ccgacgggct tttatacggc tcacagacac caaatgagga atgtttgttc   300
ctggaaaggc tggaggagaa ccattacaac acctatatat ccaagaaaca cgcagagaag   360
aattggtttg ttggcctcaa gaagaatgga agctgcaagc gcggtcctcg gactcactat   420
ggccagaaag caatcttgtt ctccccctg ccagtctctt ctgattaa                  468
```

<210> SEQ ID NO 71
<211> LENGTH: 468
<212> TYPE: DNA
<213> ORGANISM: Pig

<400> SEQUENCE: 71

```
atggctgaag gcgaaatcac aaccttcacg gccctgaccg agaagtttaa tctgcctcca    60
ggaaattaca agaagcccaa gctcctctac tgcagcaacg ggggccattt cctcaggatc   120
cttccagatg gcacagtgga tgggaccagg gacaggagcg accagcacat tcagctgcag   180
ctcagtgcgg aaagcgtggg ggaggtgtat ataaagagta cggagactgg ccagtacttg   240
```

```
gccatggaca ccagcgggct tttgtacggc tcacagacac ccagtgagga gtgtttgttc    300
ctggagaggc tggaggaaaa ccattacaat acctacacat ccaagaagca cgcagagaag    360
aactggttcg ttggcctcaa gaagaatgga agctgcaaac gcggtcctcg gactcactat    420
ggccagaaag ccatcctgtt tctcccctg ccagtatcct cggattaa                  468
```

<210> SEQ ID NO 72
<211> LENGTH: 468
<212> TYPE: DNA
<213> ORGANISM: Small-eared galago

<400> SEQUENCE: 72

```
atggctgaag ggaaatcac aaccttcaca gccctcacag agaagtttaa tctgcctcta    60
ggaaattaca agaagcccaa gctcctctac tgtagcaacg ggggtcactt tctgaggatc   120
ctgccggatg gcaccgtgga tgggacacaa gacaggagcg accagcacat tcagctgcag   180
ctcagtgcgg aaagcgtggg ggaggtgtat ataaagagta cccagactgg ccagtacttg   240
gccatggact ccgacgggct tttatacggc tcacaaacac caaatgagga atgcctgttc   300
ctggaacggc tggaggaaaa ccattacaac acctatgtgt ccaagaagca cgccgagaag   360
aattggtttg tcggtctcaa gaagaacgga agttgcaaac gtggtcctcg gactcactac   420
ggccagaaag caatcttgtt tctcccctg ccagtctcct ctgattaa                  468
```

<210> SEQ ID NO 73
<211> LENGTH: 468
<212> TYPE: DNA
<213> ORGANISM: Greater horseshoe bat

<400> SEQUENCE: 73

```
ttaatcagag gagactggca gggggagaaa caggattgct ttctggccat agtgagtccg    60
aggaccgcgc ttgcagcttc cattcttctt gagcccaacg aaccaattct tttctgcgtg   120
cttcttggac gtgtaggtgt tgtaatggtt ttcctccagc ctttccagga acagacattc   180
ctcatttggt gtctgtgagc cgtacaaaag cccgtcggag tccatggcca agtactggcc   240
actctcggtg ctctttatat acacctcccc cacgctttcc gcactgagct gcagctgaat   300
gtgctggtca ctcttgtccc ttgtcccatc cactgtgcca tctggaagga tcctcaggaa   360
gtggcccccg ttgctgcagt agagaagttt gggtttcttg taattccctg taggcagatt   420
aaacttctca gtaagggctg tgaacgtggt gacttcccct tcggccat                 468
```

<210> SEQ ID NO 74
<211> LENGTH: 468
<212> TYPE: DNA
<213> ORGANISM: European shrew

<400> SEQUENCE: 74

```
ctagtcggag gagacgggca gggggagaaa caagatcgct ttctggccgt agtgagtccg    60
gggaccacgc ttgcagcttc cgttcttctt cagaccaaca accaattct tctcggcatg   120 cttcttggag gtataggtgt tgtaatggtt ttcctccagc ctttccagaa acagacattc   180
ctcattcggt gtttgtgagc cgtataaaag cccgtcggtg tccatggcca agtaatggcc   240
agtctccgtg ctctttatat acacctcccc cacgctttcc gcactgagct gcagctgaat   300
gtgctggtcg ctgcggtccc tggtcccatc cactgtgccg tccggagga tgcgcaggaa   360 gtggcccccg ttgctgcagt acaggagttt gggcttcttg tagttccctg gtggcaggtt   420
```
aaacttctcc atgagggccc caaaggtggt gatctccccc tcggccat        468

<210> SEQ ID NO 75
<211> LENGTH: 468
<212> TYPE: DNA
<213> ORGANISM: Rabbit

<400> SEQUENCE: 75
atggctgagg gggaggtcac caccttcaca gccctgaccg agaagttcaa cctgcctgca        60
gggaactaca agttgcccaa actcctctac tgcagcaacg ggggccactt cctgaggatc        120
ctgccggacg gcactgtgga cggcacaagg gacaggagcg accagcacat tcagctgcag        180
ctgagtgcgg aaagcgtggg ggaggtgtat ataaagagta cggagaccgg ccagtacttg        240
gccatggaca ccgacggcct tttatacggc tcgcaaacgc ccagtgagga gtgtttgttc        300
ctggaacggc tggaggagaa ccactacaac acctacacgt ccaagaagca cgccgagaag        360
aactggttcg tggggctgaa gaaaaacggg agctgcaagc gcggtcctcg gactcactac        420
ggccagaaag ccatcttgtt cctcccctg ccggtctcct ccgactaa                     468

<210> SEQ ID NO 76
<211> LENGTH: 468
<212> TYPE: DNA
<213> ORGANISM: Chinese hamster

<400> SEQUENCE: 76
atggctgaag gagaaatcac caccttctca gccctgacag agagatttaa tctgcctcca        60
ggaaactaca agaagcccaa actgctctac tgcagcaacg ggggccactt cttgaggatc        120
cttccagatg gcacagtgga tggacaagg acaggagtg accagcacat tcagctgcag         180
ctgagtgcgg aaagcgcggg cgaagtgtat ataagggta cagagacagg ccagtacagg         240
aacatggaca cggatggcct tttatacggc tcacagacac caaatgaaga atgcctgttc        300
ctggaaaggc tggaagaaaa ccattacaac acttatacat ccaagaagca cgcagagaag        360
aactggtttg tgggcctcaa gaaaaacggg agctgcaagc gtggtcctcg gactcactat        420
ggccagaaag caatcttgtt tctcccctg cctgtatctt ctgactag                     468

<210> SEQ ID NO 77
<211> LENGTH: 468
<212> TYPE: DNA
<213> ORGANISM: Tasmanian devil

<400> SEQUENCE: 77
atggccgaag gggagatcac aaccttcaca gccctgaccg aaagatttaa tctgccactg        60
gggaattaca agaagcccaa gcttctctac tgtagcaatg ggggccactt tttgaggatt        120
cttcctgatg gtaaagtgga tggacaagg acagaaatg atcaacacat tcaactgcaa         180
ctaagcgcgg aaagcgtggg tgaggtgtat ataagagca ctgagtctgg ccagtatttg         240
gctatggaca ccgatggact tttatacggc tcacagacac ccactgaaga atgcttgttc        300
ctggagagat tggaggagaa tcattacaac acctacatat caaagaagca tgcggagaaa        360
aattggtttg tgggcctcaa gaaaaatgga agctgcaaaa gaggtcccag gactcactat        420
ggccagaaag ccatcctctt ccttcccctc cctgtgtcct ctgagtaa                    468

<210> SEQ ID NO 78
<211> LENGTH: 468
<212> TYPE: DNA
<213> ORGANISM: House mouse

<400> SEQUENCE: 78

```
atggctgaag gggagatcac aaccttcgca gccctgaccg agaggttcaa cctgcctcta      60
ggaaactaca aaaagcccaa actgctctac tgcagcaacg ggggccactt cttgaggatc     120
cttcctgatg gcaccgtgga tgggacaagg gacaggagcg accagcacat tcagctgcag     180
ctcagtgcgg aaagtgcggg cgaagtgtat ataaagggta cggagaccgg ccagtacttg     240
gccatggaca ccgaagggct tttatacggc tcgcagacac caaatgagga atgtctgttc     300
ctggaaaggc tggaagaaaa accattataa cttacacct ccaagaagca tgcggagaag      360
aactggtttg tggcctcaa gaagaacggg agctgtaagc gcggtcctcg gactcactat      420
ggccagaaag ccatcttgtt tctgcccctc ccggtgtctt ctgactag                   468
```

<210> SEQ ID NO 79
<211> LENGTH: 465
<212> TYPE: DNA
<213> ORGANISM: Domestic guinea pig

<400> SEQUENCE: 79

```
atggctgaag gagaaatcac aacttttgca gccctgactg agaagtttaa tctgcctcca      60
gggaattata agaagcccaa actgctctac tgcagcaatg ggggccactt cctgaggatc     120
cttccagacg gcacagtgga cggcacaaga gacaggagcg accagcacat tcagctgcag     180
ctcagtgcgg aaggcgtggg ggaggtgtat atacagagca ccgagaccgg ccagtacttg     240
gccatggaca ccgacgggct tttatacggc tcacagacac caagtgagga atgcttgttc     300
ctggaaaggc tggaggaaaa ccattacaac acctacacat ccaagaagca tgtggagaag     360
aattggtttg ttggcctcaa gaagaacgga agctgcaagc gtggtcctcg gactcactat     420
ggccagaaag caatcttgtt cctccccttg ccagtctctg attag                      465
```

<210> SEQ ID NO 80
<211> LENGTH: 468
<212> TYPE: DNA
<213> ORGANISM: Gray short-tailed opossum

<400> SEQUENCE: 80

```
atggccgaag gggagatcac aaccttcaca gccctgactg aaagatttaa cctgccactg      60
gggaattaca agaaacccaa gcttctctac tgtagcaatg ggggccattt cttgaggatc     120
cttcctgatg gcaaagtgga tgggacacgg gacagaaatg atcaacacat tcaactgcag     180
ctgagcacgg aaagtgtggg tgaggtgtat ataagagca ctgagtctgg ccagtatttg       240
gctatggaca ccgatggact tttatatggc tcacagacac ccagtgaaga atgcttgttt     300
ctggagaggt tggaggagaa tcattacaac acctacacat cgaagaagca tgcagagaaa     360
aattggtttg ttggtctcaa gaagaatgga agctgcaaaa agggtcccag gactcactac     420
ggccagaaag ccatcctgtt ccttcccctc cctgtgtcct ctgagtaa                   468
```

<210> SEQ ID NO 81
<211> LENGTH: 468
<212> TYPE: DNA
<213> ORGANISM: Common vampire bat

<400> SEQUENCE: 81

```
atggctgaag gggaagtcac cacgttcaca gctctgactg agaagtttaa tctgcctctg      60
gagagttaca agaagcccaa acttctctac tgcagcaacg gtggccactt cctgaggatc     120
```

```
cttccagatg gtacagtgga tgggacaagg gacaagagcg accagcacat tcagctgcag    180
ctcagtgcgg aaagcgtggg ggaggtgtac ataaagagca ccgggagtgg ccagtacttg    240
gccatggact ccgccgggct tttgtatggc tcacagacac caaatgagga atgtttgttc    300
ctggaaaggc tggaggaaaa ccattacaac acctacacat ccaagaagca tgcagaaaag    360
aattggttcg tggggctcaa gaagaatgga agctgcaagc gtggcccccg gactcattat    420
ggccagaaag caatcttgtt tctcccccctg ccagtcaact ctgattaa               468
```

<210> SEQ ID NO 82  
<211> LENGTH: 468  
<212> TYPE: DNA  
<213> ORGANISM: Cattle

<400> SEQUENCE: 82

```
atggctgaag gagaaaccac gaccttcacg gccctgactg agaagtttaa cctgcctcta     60
ggcaattaca gaagcccaa gctcctctac tgcagcaacg ggggctactt cctgagaatc    120
ctcccagatg gcacagtgga tgggacgaag gacaggagcg accagcacat tcagctgcag    180
ctctgtgcgg aaagcatagg ggaggtgtat attaagagta cggagactgg ccagttcttg    240
gccatggaca ccgacgggct tttgtacggc tcacagacac ccaatgagga atgtttgttc    300
ctggaaaggt tggaggaaaa ccattacaac acctacatat ccaagaagca tgcagagaag    360
cattggttcg ttggtctcaa gaagaacgga aggtctaaac tcggtcctcg gactcacttc    420
ggccagaaag ccatcttgtt tctcccccctg ccagtctcct ctgattaa               468
```

<210> SEQ ID NO 83  
<211> LENGTH: 468  
<212> TYPE: DNA  
<213> ORGANISM: Platypus

<400> SEQUENCE: 83

```
atggcggagg gtgaaatcac cacgttcaca gccctgatgg agaagttcga cctacccctg     60
ggcaactaca aaaagcctag gctgctctac tgcagcaatg gcggctactt cctgcgcatc    120
cagccagacg gtaaagtgga cgggaccagg gatcggagcg atcagcacat tcaactgcag    180
ctaagcgcgg aaagcgtggg cgaggtgtat ataaagagca ccgagtctgg ccactatttg    240
gctatggaca ccgaaggact tttatatggc tcacaggcac ccagtgaaga ctgcttgttc    300
ctggagcggc tggaggagaa ccactataac acgtacgtgt ccaagaagca cgctgagaag    360
aattggtttg tcggtctcaa gaagaacggg agctgcaaac gaggtccccg gactcactac    420
ggccagaaag ccatcctctt cctcccgctc cccgtggcat ccgactag                468
```

<210> SEQ ID NO 84  
<211> LENGTH: 468  
<212> TYPE: DNA  
<213> ORGANISM: Zebra finch

<400> SEQUENCE: 84

```
atggccgagg gggagatcac caccttcagc gccctgacgg agaagttcaa cctgcccccg     60
gggaactaca gaagcccaa actgctgtac tgcagcaacg gggggcattt cctgcgcatc    120
ctcccggacg gcaccgtgga tggcaccagg gaccgcagcg accagcacat tcagctccag    180
ctgagtgcag agagcgtggg ggtggtgcac atccagagca cccagtcggg gcagtacctg    240
gccatggaca ccaacgggct gctctacggc tcgcagctgc cacccggtga gtgtctgttc    300
ctggaaaggc tggaggagaa ccattacaac acctacgtct ccaaaatgca cgcggacaag    360
```

```
aactggtttg tggggctgaa gaagaacggg acaagcaagc tgggcccgcg gactcactac    420
ggccagaagg cgatcctgtt cctgccgctg cccgtggcgg ccgactga               468

<210> SEQ ID NO 85
<211> LENGTH: 468
<212> TYPE: DNA
<213> ORGANISM: Nine-banded armadillo

<400> SEQUENCE: 85
ttaatcagag gagactggca ggggaagaaa caagatagct ttctggccat agtgagtctg    60
aggaccacgt ttgctgcttc cgtccttctt gagaccaaca aaccatttct tctctgcatg   120
cttcttggat atgtaggtgt tgtaattgtt ttcttccagc ttttccatga acaagcattc   180
ctcacttggt gtctctgagc catataaaag cccgtcggtg tccatggcta agtactggcc   240
ggtctctgca ctctttatat acacctcccc cacgctttcc gcactgagct gcagctgaat   300
gtgttggtcg ctcctgtccc ttgtcccatc caccgtgcca tctggaagga tcctcaagaa   360
gtggcccccg tttctgcagt agaggagtct ggggtgcttg taattttcta ggggcaggtt   420
gaacttctcc atcagggcca tgaaggttgt gatctcccct tcagccat               468

<210> SEQ ID NO 86
<211> LENGTH: 468
<212> TYPE: DNA
<213> ORGANISM: Xenopus Silurana tropicalis

<400> SEQUENCE: 86
atggcagagg gagacatcac aacattcaac cccattgcag agtccttcag tcttccaatt    60
ggcaactaca agaaaccaaa acttctgtac tgtaataatg gagggtattt tttgcgcatc   120
ctcccagatg gggttgtgga tggaacaaga gacagagatg acctttacat tacactgaag   180
ttaagcgcac aaagccaagg ggaggtgcat atcaaaagca cagagacagg gagttactta   240
gccatggact ccagtggaca gttgtatgga actctcacac caaatgaaga aagcctgttt   300
ctggagacat tagaagagaa tcactataac acatacaagt caaagaagta tgcagaaaat   360
aactggtttg tggggataaa gaagaacggg gcaagcaaaa agggatcaag gactcactat   420
ggacaaaaag ccatccttt tctgccgctg ccagcatcac ctgactag                468

<210> SEQ ID NO 87
<211> LENGTH: 465
<212> TYPE: DNA
<213> ORGANISM: Heterocephalus glaber

<400> SEQUENCE: 87
atggcggaag gcgaaattac cacctttacc gcgctgaccg aaaaatttaa cctgccgccg    60
ggcaactata aaaaaccgaa actgctgtat tgcagcaacg gcggccattt tctgcgcatt   120
ctgccggatg gcaaagtgga tggcacccgc gatcgcagcg atcagcatat tcagctgcag   180
ctgagcgcgg aaggcgtggg cgaagtgtat attaaaagca ccgaaaccgg ccagtatctg   240
gcgatggata ccgatggcct gctgtatggc agccagaccg cgagcgaaga atgcctgttt   300
ctggaacgcc tggaagaaaa ccattataac acctatatta gcaaaaaaca tgcggaaaaa   360
aactggtttg tgggcctgaa aaaaaacggc agctgcaaac gcggcccgcg cacccattat   420
ggccagaaag cgattctgtt tctgccgctg ccggtgagca gcgat                  465

<210> SEQ ID NO 88
```

```
<211> LENGTH: 465
<212> TYPE: DNA
<213> ORGANISM: Black flying fox

<400> SEQUENCE: 88
atggcggaag gcgaagtgac cacctttacc gcgctgaccg aacgctttaa cctgccgccg      60
ggcaactata aaaaaccgaa actgctgtat tgcagcaacg gcggccattt tctgcgcatt     120
ctgccggatg gcaccgtgga tggcacccgc gataaaagcg atcagcatat tcagctgcag     180
ctgagcgcgg aaagcgtggg cgaagtgtat attaaaagca ccgaaagcgg ccagtatctg     240
gcgatggata cgatggcct gctgtatggc agccagaccc cggatgaaga ttgcctgttt      300
ctggaacgcc tggaagaaaa ccattataac acctatacca gcaaaaaaca tgcggaaaaa     360
aactggtttg tgggcctgaa aaaaaacggc agctgcaaac gcggcccgcg cacccattat     420
ggccagaaag cgattctgtt tctgccgctg ccggtgagca gcgat                      465

<210> SEQ ID NO 89
<211> LENGTH: 465
<212> TYPE: DNA
<213> ORGANISM: Chinese tree shrew

<400> SEQUENCE: 89
atggcggaag gcgaaattac cacctttgcg gcgctgaccg aaaaatttga tctgccgccg      60
ggcaactata aaaaaccgaa actgctgtat tgcagcaacg gcggccattt tctgcgcatt     120
ctgccggatg gcaccgtgga tggcacccgc gatcgcagcg atcagcatat tcagctgcag     180
ctgaccgcgg aaaacgtggg cgaagtgtat attaaaagca ccgaaaccgg ccagtatctg     240
gcgatggatg cggatggcct gctgtatggc agccagaccc cgaacgaaga tgcctgttt      300 ctggaacgcc tggaagaaaa ccattataac acctatatta gcaaaaaaca tgcggaaaaa     360
aactggtttg tggcgctgaa aaaaaacggc agctgcaaac tgggcccgcg cacccattat     420
ggccagaaag cgattctgtt tctgccgctg ccggtgagca gcgat                      465

<210> SEQ ID NO 90
<211> LENGTH: 465
<212> TYPE: DNA
<213> ORGANISM: Rock pigeon

<400> SEQUENCE: 90
atggcggaag gcgaaattac cacctttacc gcgctgaccg aaaaatttaa cctgccgccg      60
ggcaactata aaaaaccgaa actgctgtat tgcagcaacg gcggccattt tctgcgcatt     120
ctgccggatg gcaaagtgga tggcacccgc gatcgcagcg atcagcatat tcagctgcag     180
ctgagcgcgg aaagcgtggg cgaagtgtat attaaaagca cccagagcgg ccagtatctg     240
gcgatggatc cgaccggcct gctgtatggc agccagctgc tgggcgaaga tgcctgttt      300 ctggaacgca ttgaagaaaa ccattataac acctatgtga gcaaaaaaca tgcggataaa     360
aactggtttg tgggcctgaa aaaaaacggc aacagcaaac tgggcccgcg cacccattat     420
ggccagaaag cgattctgtt tctgccgctg ccggtgagcg cggat                      465

<210> SEQ ID NO 91
<211> LENGTH: 468
<212> TYPE: DNA
<213> ORGANISM: Sheep

<400> SEQUENCE: 91
atggctgaag gagaaaccac aaccttcagg gccctgactg agaagtttaa cctgcctcta      60
```

```
ggcaattaca agaagcccaa gctcctctat tgcagcaacg ggggctactt cctgagaatc    120
ctcccagatg gcagagtgga tgggacgaag gacaggagcg accagcacat tcagctgcag    180
ctctatgcgg aaagcatagg ggaggtgtat attaagagta cggagactgg ccagttcttg    240
gccatggaca ccaacgggct tttgtacggc tcacaaacac ccagtgagga atgtttgttc    300
ctggaaaggc tggaggaaaa ccattataac acctacatat ccaagaagca tgcagagaag    360
aattggttca ttggtctcaa gaagaacgga agctccaaac tcggtcctcg gactcacttc    420
ggccagaaag ccatcttgtt tctcccctg ccagtttcct ctgattaa                  468
```

<210> SEQ ID NO 92
<211> LENGTH: 468
<212> TYPE: DNA
<213> ORGANISM: Chicken

<400> SEQUENCE: 92

```
atggccgagg gggagataac caccttcacc gccctgaccg agcgcttcgg cctgccgctg     60
ggcaactaca agaagcccaa actcctgtac tgcagcaacg ggccactt cctacggatc     120 ctgccggacg gcaaggtgga cgggacgcgg gaccggagtg accagcacat tcagctgcag    180
ctcagcgcgg aagatgtggg cgaggtctat ataaagagca cagcgtcggg gcagtacctg    240
gcaatggaca ccaacgggct cctgtatggc tcgcagctac caggcgagga gtgcttgttc    300
cttgagaggc tcgaggagaa ccattacaac acatacatct ccaaaaagca cgcagacaag    360
aactggttcg tcgggctgaa gaaaaacggg aacagcaagc tggggccgcg gactcactat    420
gggcaaaagg cgatcctctt cctcccattg ccggtgtcgg ctgactga                 468
```

<210> SEQ ID NO 93
<211> LENGTH: 297
<212> TYPE: DNA
<213> ORGANISM: Alpaca

<400> SEQUENCE: 93

```
cagctgcagc tcagtgcgga aagcgtgggg gaggtgtata taaagagtac cgagactggc     60
cagtacttgg ccatggacac cgacgggctt ttgcacggct cacagacacc aaatgaggaa    120
tgtttgttcc tggaaaggct ggaggagaac cattacaaca cctacacgtc caagaagcac    180
gccgaaaaga attggtttgt tggtctcaag aagaatggaa gctgcaaacg cggtcctcgg    240
actcactacg gccagaaggc gatcttgttt ctccccttgc cagtctcctc tgattaa      297
```

<210> SEQ ID NO 94
<211> LENGTH: 468
<212> TYPE: DNA
<213> ORGANISM: Anole lizard

<400> SEQUENCE: 94

```
atggctgaag gtgaaataac aacattcaca gccttgaccg agaggtttgc tctcccaatg     60
gagaattaca agaagcccaa actcctgtat tgcagcaatg gaggccactt cctgaggatc    120
cttccagatg gaaaagtgga tgcaccatg gaccggaatg acagctatat tcagttgctg    180
ttaacagcag aagatgtggg tgtggtatat ataaaaggca ctgagaccgg gcagtacttg    240
gccatggatg ccaatggaca tttatatggc tcgcagttgc caacagaaga gtgtttattt    300
gtggaaacgc tggaagaaaa ccattacaat acatatacct caaagatgca tgcgataag    360 aagtggtatg ttggcttgaa aaagaatggg aaaggcaaac tggggccacg gactcatcgc    420
```

| | |
|---|---|
| ggccaaaagg caatactttt ccttccactg ccagtatcac ctgattag | 468 |

<210> SEQ ID NO 95
<211> LENGTH: 468
<212> TYPE: DNA
<213> ORGANISM: Bushbaby

<400> SEQUENCE: 95

| | |
|---|---|
| atggctgaag gggaaatcac aaccttcaca gccctcacag agaagtttaa tctgcctcta | 60 |
| ggaaattaca agaagcccaa gctcctctac tgtagcaacg ggggtcactt tctgaggatc | 120 |
| ctgccggatg gcaccgtgga tgggacacaa gacaggagcg accagcacat tcagctgcag | 180 |
| ctcagtgcgg aaagcgtggg ggaggtgtat ataaagagta cccagactgg ccagtacttg | 240 |
| gccatggact ccgacgggct tttatacggc tcacaaacac caaatgagga atgcctgttc | 300 |
| ctggaacggc tggaggaaaa ccattacaac acctatgtgt ccaagaagca cgccgagaag | 360 |
| aattggtttg tcggtctcaa gaagaacgga agttgcaaac gtggtcctcg gactcactac | 420 |
| ggccagaaag caatcttgtt tctcccccctg ccagtctcct ctgattaa | 468 |

<210> SEQ ID NO 96
<211> LENGTH: 468
<212> TYPE: DNA
<213> ORGANISM: Cat

<400> SEQUENCE: 96

| | |
|---|---|
| atggctgaag gggaaatcac aaccttcacg gccctgacgg agaagttcaa tctgcctcca | 60 |
| gggaattaca agaaacccaa actcctctac tgtagcaacg ggggccactt cctgaggatc | 120 |
| cttccagatg gcacagtgga tgggacgagg acaggagcg accagcacat tcagctgcag | 180 |
| ctcagtgcgg aaagcgtggg ggaggtgtat ataaagagta ccgagactgg ccagtacttg | 240 |
| gccatggaca ccgacgggct tttgtacggc tcacagacac caaatgagga atgcttgttc | 300 |
| ctggaaaggc tggaagaaaa ccattacaac acctacacat ccaagaagca cgcagaaaag | 360 |
| aattggtttg tgggtctcaa gaagaatgga agctgcaaac gcggtccccg gactcactat | 420 |
| ggccagaagg caattttgtt tctcccccctg ccagtctcct ctgattaa | 468 |

<210> SEQ ID NO 97
<211> LENGTH: 468
<212> TYPE: DNA
<213> ORGANISM: Chinese softshell turtle

<400> SEQUENCE: 97

| | |
|---|---|
| atggctgaag gggaaataac aacgttcacc gccctgaccg aaaaattcaa ccttcccctg | 60 |
| gggaattaca agaatcccaa actcttatat tgcagcaatg gaggctactt cttgaggata | 120 |
| catccagatg gcaaagtaga tgggacaagg gaccgaagtg accaacacat tcagctgcag | 180 |
| ctaagtgcgg aaagcgtggg tgaggtatat ataaagagca ctgagtctgg acagttttg | 240 |
| gctatggacg ccaatggact tttatatgga tcactgtcac cgagtgagga atgcttattc | 300 |
| ttggaaagaa tggaagaaaa tcattataac acctacatct ccaagaagca tgcagacaag | 360 |
| aactggttcg ttggcttaaa gaagaatgga agctgcaaac tggaccgcg gacgcactac | 420 |
| ggccaaaagg ccgtcctttt ccttccactg ccagtgtcag ctgattaa | 468 |

<210> SEQ ID NO 98
<211> LENGTH: 468
<212> TYPE: DNA
<213> ORGANISM: Coelacanth

<400> SEQUENCE: 98

```
atggctgaag acaaaataac aacactgaag gccttggctg aaaaatttaa ccttcctatg    60
ggaaattaca agaaagcaaa actcctctac tgcagcaacg agggtatttt cctgcgaata   120
cccccagacg ggaaagtgga aggaattaga gaacgaagcg acaagtacat tcagctgcaa   180
atgaatgcag aaagtttagg catggtgtct ataaagggtg tggaggcagg caataccta    240
gctatgaata caaatggact cctgtatgga tctcagtctc taactgaaga atgccttttc   300
atggaaaaga tggaagaaaa ccactacaac acatacaggt ctaagacaca tgcagataaa   360
aactggtatg ttggcattag aaagaacggt agcatcaaac caggaccaag gactcacatt   420
ggccaaaagg ctgttctttt tctccctctg cctgcctcga gtgattag               468
```

<210> SEQ ID NO 99
<211> LENGTH: 468
<212> TYPE: DNA
<213> ORGANISM: Dolphin

<400> SEQUENCE: 99

```
atggctgaag gggaaatcac aaccttcaca gccctgaccg agaagtttaa tctgcctcca    60
gggaattaca agaagcccaa actcctctac tgtagcaacg ggggccactt cctgaggatc   120
cttccagatg gcacagtgga tgggacaagg gacaggagtg accagcacat tcagctgcag   180
ctcagtgcgg aaagcgtggg ggaggtgtat ataaagagta cggagactgg ccagtacttg   240
gccatggaca ccgacgggct tttgtacggc tcacagacac ccaatgagga atgtttgttc   300
ctggaaaggt tggaggaaaa ccattacaac acctacgcat ccaagaagca tgcagaaaag   360
aattggttcg ttggtctcaa gaagaacgga agctgcaaac gcggtcctcg gactcactac   420
ggccagaaag caatcttgtt tctcccccctg ccagtctcct ccgattaa                468
```

<210> SEQ ID NO 100
<211> LENGTH: 468
<212> TYPE: DNA
<213> ORGANISM: Ferret

<400> SEQUENCE: 100

```
atggctgaag gggaaatcac aaccttcaca gccctgatgg agaagtttaa tctgcctgcg    60
gggaattaca agaagcccaa actcctctac tgtagcaatg ggggccactt cctgaggatc   120
cttccagatg gcacagtgga cggcacaagg gacaggagcg accagcacat tcagctgcag   180
ctcagtgcgg aaagcgtggg ggaggtgtac ataaagagta ccgagactgg ccagtacttg   240
gccatggaca ccgatgggct tttgtacggc tcacaaacac caaatgagga atgtctgttc   300
ctggaaaggc tggaggaaaa ccattacaac acctacacat ccaagaagca cgctgagaag   360
aattggtttg taggtctcaa gaagaacgga agctgcaaac gcggtcctcg gactcactat   420
ggccagaaag caattctgtt tctcccccctg ccagtctcct ctgattaa                468
```

<210> SEQ ID NO 101
<211> LENGTH: 468
<212> TYPE: DNA
<213> ORGANISM: Gibbon

<400> SEQUENCE: 101

```
atggccgaag gggaaatcac caccttcaca gccctgaccg agaagtttaa tctgcctcca    60
gggaattaca agaagcccaa actcctctac tgtagcaacg ggggccactt cttgaggatc   120
```

```
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
aattggtttg ttggcctcaa gaagaatgga agctgcaaac gcggtcctcg gactcactat    420
ggccagaaag caatcttgtt tctccccctg ccagtctctt ctgattaa                 468
```

<210> SEQ ID NO 102
<211> LENGTH: 468
<212> TYPE: DNA
<213> ORGANISM: Gorilla

<400> SEQUENCE: 102

```
atggctgaag gggaaatcac caccttcaca gccctgaccg agaagtttaa tctgcctcca    60
gggaattaca agaagcccaa actcctctac tgtagcaatg ggggccactt cttgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
aattggtttg ttggcctcaa gaagaatgga agctgcaaac gcggtcctcg gactcactat    420
ggccagaaag caatcttgtt tctccccctg ccagtctctt ccgattaa                 468
```

<210> SEQ ID NO 103
<211> LENGTH: 468
<212> TYPE: DNA
<213> ORGANISM: Hedgehog

<400> SEQUENCE: 103

```
atggctgaag gagaaatcac caccttcacg gccctgactg agaagtttaa tctgccacta    60
gggaattaca agaagcccaa gctcctctac tgtagcaacg ggggccactt cctgaggatc    120
cttccagatg gcaccgtgga tgggacaagg gacaggagcg accagcatat tcagctgcag    180
ctcagtgcgg aaagcgtggg ggaggtgtat ataaagagta cggagactgg ccagtacttg    240
gccatggaca ccgacgggct tttatacggc tcacaaacac caaatgagga atgtctgttc    300
cttgaaaggc tggaagagaa ccattacaat acctacacat ccaagaagca tgccgagaag    360
aactggtttg ttggcctcaa gaagaatgga agctgcaagc gtggtcctcg gactcattat    420
ggccagaaag ctatttttgtt tctccccctg ccagtttcct ctgattaa                468
```

<210> SEQ ID NO 104
<211> LENGTH: 273
<212> TYPE: DNA
<213> ORGANISM: Hyrax

<400> SEQUENCE: 104

```
atggctgaag gcgaaatcac aaccttcaca gccctgactg agaagtttaa cctgccacta    60
gagaattaca agaagcccaa actcctctac tgtagcaacg gaggccactt cctgaggatc    120
cttccggacg gcacagtgga tggcaccagg gacaggagtg accagcacat tcagctgcag    180
ctcagtgcgg aaagcgtggg ggaggtgtat ataagggca ccgagactgg ccagtacttg    240
gccatggaca ccgacgggct tttatatggc tca                                  273
```

```
<210> SEQ ID NO 105
<211> LENGTH: 349
<212> TYPE: DNA
<213> ORGANISM: Kangaroo rat

<400> SEQUENCE: 105
atggctgaag gggaaatcac aaccttcaca gccctgacgg aaaggtttaa ttcagctgca    60
actgagtgcg gaaagcgtgg gggaggtcta tataaagagc accgagactg gccaatactt   120
ggccatggat gccgacgggc ttttatacgg ctcacagaca cctgatgaag aatgcttgtt   180
cctggagagg ctggaagaaa atcattataa cacctacata gccaagaaac atgctgaaaa   240
gaattggttt gtcggcctca aaagaatgg aagctgcaag cgtggcctc ggactcacta    300 tggccagaaa gcaatcctgt tcctcccctt gcctgtctcc tctgattag              349

<210> SEQ ID NO 106
<211> LENGTH: 276
<212> TYPE: DNA
<213> ORGANISM: Lamprey

<400> SEQUENCE: 106
atggaggtgg ccacatcgg cacgctgccc gtggtccccg cggggcccgt gttccccggc     60
agtttcaagg agccacggcg cctctactgc cgcagcgcgg gccaccacct ccagatcctg   120
ggggacggca ccgtgagtgg cacccaggac gagaacgagc cccacgccgt tctgcagctg   180
caggcggtgc gccgcggggt ggtgacgatc cgtgggctct gcgccgagag gttcctcgcc   240
atgagcacgg agggacacct gtacgggggcg gtgagg                           276

<210> SEQ ID NO 107
<211> LENGTH: 297
<212> TYPE: DNA
<213> ORGANISM: Lesser hedgehog tenrec

<400> SEQUENCE: 107
cagctgaagc tcgttgccga aagcgtgggg gtggtgtata taaagagcat caagaccggc     60
cagtacttgg ccatgaaccc cgacgggctt ttatacggct ccgagacccc agaggaagaa   120
tgcttgttcc tggaaacgct ggaggaaaac cactacacca ccttcaaatc taagaagcac   180
gtagagaaga attggttcgt tggtctccgg aagaatggaa gggtcaagat cgggcctcgg   240
actcaccaag gccagaaagc aatcttgttc ctgccccctcc ggtgtcctc tgattaa      297

<210> SEQ ID NO 108
<211> LENGTH: 468
<212> TYPE: DNA
<213> ORGANISM: Rhesus monkey

<400> SEQUENCE: 108
atggctgaag gggaaatcac cacgttcaca gccctgaccg agaagtttaa tctgcctcca    60
gggaattaca gaagcccaa actgctctac tgtagcaatg gggccacttc ttgaggatc    120 cttccggatg gcacagtgga tgggacaagg acaggagcg accagcacat tcagctgcag   180
ctcagtgcgg aaagcgtggg ggaggtgtat ataaagagta ccgagactgg ccagtacttg   240
gccatggaca ccgacgggct tttatacggc tcacagacac caaatgagga atgtttgttc   300
ctggaaaggc tggaggagaa ccattacaac acctatacat ccaagaagca cgcagagaag   360
aattggtttg ttggcctcaa gaagaatgga agctgcaaac gtggtcctcg gactcactat   420
ggccagaaag caatcttgtt tcttcccctg ccagtctctt ctgattaa                468
```

<210> SEQ ID NO 109
<211> LENGTH: 468
<212> TYPE: DNA
<213> ORGANISM: Megabat

<400> SEQUENCE: 109

```
atggccgagg gggaagtcac gacgttcacg gccctgaccg agaggtttaa cctgcctcca      60
gggaattaca agaagcccaa acttctctac tgcagcaacg ggggccactt cctgaggatc     120
ctcccagatg gcacagtgga tgggacaagg acaagagcc accagcacat tcagctgcag     180
ctcagtgcgg aaagtgtggg ggaggtgtat ataaagagca ccgagagtgg ccagtacttg     240
gccatggact ccgacgggct tttgtacggc tcacagacac cagatgagga ctgtttgttc     300
ctggaaaggc tggaggaaaa ccattacaac acctacacat ccaagaagca cgcagagaag     360
aattggtttg ttgggctcaa gaagaatgga agctgcaagc gcggtccccg gactcactac     420
ggccagaaag cgatcctgtt tctccccctg ccagtctcct ctgattag               468
```

<210> SEQ ID NO 110
<211> LENGTH: 468
<212> TYPE: DNA
<213> ORGANISM: Microbat

<400> SEQUENCE: 110

```
atggctgagg gggaagtcac cacattcacg gccctgaccg agaggttcaa tctgcctctg      60
gagaactaca agaagcccaa gcttctctac tgcagcaacg ggggccactt cctgcggatc     120
ctcccagacg gcaccgtgga cgggacgagg acaggagcg accagcacat tcagctgcag     180
ctcagtgcgg aaagcgtggg ggaggtgtat ataaagagca ccgagagtgg ccagtacttg     240
gccatggact ccgacgggct tttgtacggc tcacaaacac ccaatgagga atgtttgttc     300
ctggaaaggc tggaggagaa ccactacaac acctacacgt ccaagaagca cgcagaaaag     360
aattggttcg ttgggctcaa gaagaacgga agctgcaagc gtggtcctcg gacgcattat     420
ggccagaaag caatcttgtt tctccccctg ccagtctcct ccgattaa               468
```

<210> SEQ ID NO 111
<211> LENGTH: 468
<212> TYPE: DNA
<213> ORGANISM: Mouse lemur

<400> SEQUENCE: 111

```
atggccgaag gggagatcac aaccttcacg gccctcaccg agaagtttaa cctgcctccg      60
gggaactaca agaagcccaa gctcctctac tgcagcaacg gcggccactt cctgcgcatc     120
cttcccgacg gcaccgtgga tggcacgaga gacaggagcg accagcacat tcagctgcag     180
ctcagtgcgg aaagcgcggg ggaggtgtat ataaagagca cccagactgg ccggtacttg     240
gccatggacg ccgacgggct tttatacggc tcacaaacac caaatgagga atgtttgttc     300
ctggaaaggc tggaggaaaa ccattacaac acctacgtat ccaagaagca cgcagagaag     360
aattggtttg ttggcctcaa gaagaatgga agttgcaaac gcggccccg gactcactat     420
ggccagaaag caatcttgtt tctgcccctg ccagtctcct ctgattaa               468
```

<210> SEQ ID NO 112
<211> LENGTH: 436
<212> TYPE: DNA
<213> ORGANISM: Pika

<400> SEQUENCE: 112

```
atggccgagg gagaagtcac caccttctca gccctgacgg agaagttcaa tctgcctgga    60
ggaaactaca agttgcccaa gctcctttac tgtagcaacg gaggccactt cctgaggatc   120
cttccagatg gcacagtgga tgggaccagg acaggagcg acctgcacag aggtgtttat    180
aaagagtacg gagactggcc agtacttggc tatggacacc gatggccttt tatatggctc   240
gcagacaccc agtgaggagt gtttgttcct ggagcggctg gaggagaacc actacaacac   300
ctacacatcc aagaagcatg ccgagaagaa ctggtttgtg gcatcaaga agaatggaag   360 ctgcaagcgt ggtcctcgga ctcactacgg ccagaaagcc atcttgtttc tccctctgcc   420
agtctcttct gactaa                                                   436
```

<210> SEQ ID NO 113
<211> LENGTH: 468
<212> TYPE: DNA
<213> ORGANISM: Rat

<400> SEQUENCE: 113

```
atggccgaag gggagatcac aacctttgca gccctgaccg agaggttcaa tctgcctcta    60
gggaactaca aaaaacccaa actgctctac tgcagcaacg gggccacctt cttgaggatt   120
cttcccgatg gcaccgtgga tgggaccagg acaggagcg accagcacat tcagctgcag    180
ctcagtgcgg aaagcgcggg cgaagtgtat ataaagggta cagagactgg ccagtacttg   240
gccatggaca ccgaagggct tttatacggc tcgcagacac caaatgaaga tgcctattc    300 ctggaaaggc tagaagaaaa ccattataac acttacacat ccaagaagca cgcggagaag   360
aactggtttg tgggcctcaa gaagaacggg agttgtaagc gcggtcctcg gactcactac   420
ggccagaaag ccatcttgtt tctccccctc ccggtatctt ctgactaa                468
```

<210> SEQ ID NO 114
<211> LENGTH: 468
<212> TYPE: DNA
<213> ORGANISM: Sloth

<400> SEQUENCE: 114

```
atggctgaag gggaaatcac aaccttcaca gctctgatgg agaagtttaa cctgccacca    60
gggaattaca tgaagcccaa actcctctac tgtagcaacg gggccacttt cttgaggatc   120
cttccagacg gcacagtgga tgggacaagg acaggagcg acctgcacat tcagctgcag    180
ctcagtgcgg aaagcgtggg ggaggtgtat ataagagtg cggagaccgg ccagtactta    240
gccatggaca ccggcgggct tttatacggc tcacagacac caagtgagga tgcctgttc    300 ctagaaaggc tggaggaaaa ccattacaac acctacgtat ccaagaagca tgcggagaag   360
aactggttcg ttggcctaaa gaagaatgga agcagcaaac gcggccccg gactcactat    420 ggccagaaag ccatcttgtt tcttcccctg ccagtctcct ctgattaa                468
```

<210> SEQ ID NO 115
<211> LENGTH: 468
<212> TYPE: DNA
<213> ORGANISM: Squirrel

<400> SEQUENCE: 115

```
atggctgaag gggaaatcac aaccttcaca gccctgaccg agaagttcaa tctgcctcca    60
gggaactaca agaagcccaa actgctctac tgtagcaacg gaggccactt cttgaggatc   120
cttcctgatg gcacagtgga tgggacaaga gacaggagcg accaacacat tcagctgcag   180
```

```
ctcagtgcgg aaagcgtggg ggaggtgtat ataaagagta ccgagaccgg ccagtacttg    240
gccatggaca ccgacgggct tttatatggc tcacagaccc caaatgagga atgcttattc    300
ctggaaaggc tggaggaaaa ccattacaac acgtacacat ccaagaagca tgcagagaag    360
aattggtttg ttggcctcaa gaagaacgga agctgcaagc gcggtccccg gactcactat    420
ggccagaaag cgatcttgtt tctcccactg cctgtctcct ctgattag                 468

<210> SEQ ID NO 116
<211> LENGTH: 468
<212> TYPE: DNA
<213> ORGANISM: Tarsier

<400> SEQUENCE: 116
atggccgaag gggaaatcac aaccttcaca gccctgaccg agaagttcaa cctgcccccg     60
gggaattaca agaagcccaa actcctctac tgcagcaacg ggggccactt cttgaggatc    120
cttccggatg gcactgtgga tggaacgagg gacaggagcg accagcacat tcagctgcag    180
ctcagcgcgg aaagcgtggg ggaggtgtat ataaagagta ccgagaccgg ccagtacttg    240
gccatggaca ccgacgggct tttgtacggc tcacagacac caaatgagga gtgtctgttc    300
ctggaaaggc tggaagagaa tcattacaat acctacgtgt ccaagaagca tgcggagaag    360
aattggtttg tcggcctcaa gaagaatgga agctgcaaac gcggtcctcg gactcactat    420
ggccagaaag caatcttgtt tctcccctg ccagtttcct ctgattaa                  468

<210> SEQ ID NO 117
<211> LENGTH: 468
<212> TYPE: DNA
<213> ORGANISM: Tree shrew

<400> SEQUENCE: 117
atggctgaag gggaaatcac gaccttcgca gccctgaccg agaagtttga tctgcctcca     60
gggaattaca agaagcccaa acttctctac tgtagcaacg ggggccattt cttgaggatt    120
cttccagatg gcaccgtgga tgggacaaga gacaggagcg accagcacat tcagctgcag    180
ctcactgcgg aaaacgtggg ggaggtgtac ataaagagta cggagactgg ccagtacttg    240
gccatggacg ccgacgggct tttatatggc tcacagacac caaacgagga tgtttgttc    300 ctggaaaggc tggaggagaa ccattacaac acctacatat ccaagaagca cgcagagaag    360
aattggtttg ttgccctcaa gaagaacgga agctgcaaac tcggtcctcg gactcactat    420
ggccagaaag caatcttgtt tctcccccctg ccagtctcct ctgattaa                 468

<210> SEQ ID NO 118
<211> LENGTH: 168
<212> TYPE: DNA
<213> ORGANISM: Turkey

<400> SEQUENCE: 118
atggccgagg gggagataac caccttcaca gccctgaccg agcgcttcgg cctgccgctg     60
ggcaactaca agaagcccaa actcctgtac tgcagcaacg ggggccactt cctacggatc    120
ctgccggacg gcaaggtgga cgggacgcgg gaccggagcg accagcac                 168

<210> SEQ ID NO 119
<211> LENGTH: 468
<212> TYPE: DNA
<213> ORGANISM: Wallaby

<400> SEQUENCE: 119
```

```
atggccgaag ggagatcac aaccttcaca gccctgaccg aaagatttaa cctgccactg      60
gggaattaca agaagcccaa gcttctctac tgtagcaatg ggggccactt tttgaggatc    120
cttcctgatg gcaaagtgga tgggacaagg acagaaatg atcaacacat tcaactgcaa     180
ctaagcgcgg aaagcgtggg tgaggtgtat ataaagagca ctgagtctgg gcagtatttg    240
gccatggaca ccaatggact tttatatggc tcacagaccc ccagcgaaga atgcttattc    300
ctggagaggt tggaggagaa tcattacaac acctacatat caagaagca tgcggagaaa     360 aattggtttg ttggcctcaa gaagaacgga agttgcaaaa gaggtcccag gactcactat    420
ggccagaaag ccatcctatt ccttcccctc cctgtgtcct ctgagtaa                 468
```

<210> SEQ ID NO 120
<211> LENGTH: 444
<212> TYPE: DNA
<213> ORGANISM: Zebrafish

<400> SEQUENCE: 120

```
atgaccgagg ccgatattgc ggtaaagtcc agcccgcgcg actataaaaa actgacgcgg      60
ctgtactgta tgaatggagg atttcacctt cagatcctgg cggacgggac agtggctgga    120
gcagcagacg aaaacacata cagcatactg cgcataaaag caacaagtcc aggagtggtg    180
gtgatcgaag gatcagaaac aggtctttac ctctcgatga atgaacatgg caagctgtac    240
gcttcatcat tagtgacgga tgaaagttat ttcctggaga agatggagga aaaccactac    300
aacacatatc agtctcaaaa gcacggtgaa aactggtacg tcggaataaa aaagaacggg    360
aaaatgaaac ggggcccaag aactcacatc ggacaaaagg ccattttctt tcttccacga    420
caggtggagc aggaagagga ctga                                            444
```

<210> SEQ ID NO 121
<211> LENGTH: 155
<212> TYPE: PRT
<213> ORGANISM: Homo sapiens

<400> SEQUENCE: 121

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

-continued

```
<210> SEQ ID NO 122
<211> LENGTH: 155
<212> TYPE: PRT
<213> ORGANISM: Gorilla gorilla

<400> SEQUENCE: 122

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 123
<211> LENGTH: 155
<212> TYPE: PRT
<213> ORGANISM: Pongo abelii

<400> SEQUENCE: 123

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 124
<211> LENGTH: 155
```

```
<212> TYPE: PRT
<213> ORGANISM: Macaca mulatta

<400> SEQUENCE: 124

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 125
<211> LENGTH: 155
<212> TYPE: PRT
<213> ORGANISM: Pan troglodytes

<400> SEQUENCE: 125

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 126
<211> LENGTH: 155
<212> TYPE: PRT
<213> ORGANISM: Pan paniscus
```

```
<400> SEQUENCE: 126

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 127
<211> LENGTH: 155
<212> TYPE: PRT
<213> ORGANISM: Saimiri boliviensis boliviensis

<400> SEQUENCE: 127

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 128
<211> LENGTH: 155
<212> TYPE: PRT
<213> ORGANISM: Nomascus leucogenys

<400> SEQUENCE: 128

Met Ala Ala Gly Ser Ile Thr Thr Leu Pro Ala Leu Pro Glu Asp Gly
```

```
1               5                  10                 15
Gly Ser Gly Ala Phe Pro Pro Gly His Phe Lys Asp Pro Lys Arg Leu
            20                 25                 30

Tyr Cys Lys Asn Gly Gly Phe Phe Leu Arg Ile His Pro Asp Gly Arg
            35                 40                 45

Val Asp Gly Val Arg Glu Lys Ser Asp Pro His Ile Lys Leu Gln Leu
        50                 55                 60

Gln Ala Glu Glu Arg Gly Val Val Ser Ile Lys Gly Val Cys Ala Asn
65                     70                 75                 80

Arg Tyr Leu Ala Met Lys Glu Asp Gly Arg Leu Leu Ala Ser Lys Cys
                    85                 90                 95

Val Thr Asp Glu Cys Phe Phe Phe Glu Arg Leu Glu Ser Asn Asn Tyr
                100                105                110

Asn Thr Tyr Arg Ser Arg Lys Tyr Thr Ser Trp Tyr Val Ala Leu Lys
                115                120                125

Arg Thr Gly Gln Tyr Lys Leu Gly Ser Lys Thr Gly Pro Gly Gln Lys
            130                135                140

Ala Ile Leu Phe Leu Pro Met Ser Ala Lys Ser
145                 150                155

<210> SEQ ID NO 129
<211> LENGTH: 155
<212> TYPE: PRT
<213> ORGANISM: Equus caballus

<400> SEQUENCE: 129

Met Ala Ala Gly Ser Ile Thr Thr Leu Pro Ala Leu Pro Glu Asp Gly
1               5                  10                 15

Gly Ser Gly Ala Phe Pro Pro Gly His Phe Lys Asp Pro Lys Arg Leu
            20                 25                 30

Tyr Cys Lys Asn Gly Gly Phe Phe Leu Arg Ile His Pro Asp Gly Arg
            35                 40                 45

Val Asp Gly Val Arg Glu Lys Ser Asp Pro His Ile Lys Leu Gln Leu
        50                 55                 60

Gln Ala Glu Glu Arg Gly Val Val Ser Ile Lys Gly Val Cys Ala Asn
65                     70                 75                 80

Arg Tyr Leu Ala Met Lys Glu Asp Gly Arg Leu Leu Ala Ser Lys Cys
                    85                 90                 95

Val Thr Asp Glu Cys Phe Phe Phe Glu Arg Leu Glu Ser Asn Asn Tyr
                100                105                110

Asn Thr Tyr Arg Ser Arg Lys Tyr Ser Ser Trp Tyr Val Ala Leu Lys
                115                120                125

Arg Thr Gly Gln Tyr Lys Leu Gly Pro Lys Thr Gly Pro Gly Gln Lys
            130                135                140

Ala Ile Leu Phe Leu Pro Met Ser Ala Lys Ser
145                 150                155

<210> SEQ ID NO 130
<211> LENGTH: 155
<212> TYPE: PRT
<213> ORGANISM: Bos Taurus

<400> SEQUENCE: 130

Met Ala Ala Gly Ser Ile Thr Thr Leu Pro Ala Leu Pro Glu Asp Gly
1               5                  10                 15

Gly Ser Gly Ala Phe Pro Pro Gly His Phe Lys Asp Pro Lys Arg Leu
```

```
            20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
        50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
            115                 120                 125

Arg Thr Gly Gln Tyr Lys Leu Gly Pro Lys Thr Gly Pro Gly Gln Lys
        130                 135                 140

Ala Ile Leu Phe Leu Pro Met Ala Ser Lys Ser
145                 150                 155

<210> SEQ ID NO 131
<211> LENGTH: 155
<212> TYPE: PRT
<213> ORGANISM: Papio Anubis

<400> SEQUENCE: 131

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
        50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155

<210> SEQ ID NO 132
<211> LENGTH: 155
<212> TYPE: PRT
<213> ORGANISM: Vicugna pacos

<400> SEQUENCE: 132

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
```

```
                35                  40                  45
Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Ser Ser Trp Tyr Val Ala Leu Lys
                115                 120                 125

Arg Thr Gly Gln Tyr Lys Leu Gly Pro Lys Thr Gly Pro Gly Gln Lys
                130                 135                 140

Ala Ile Leu Phe Leu Pro Met Ser Ala Lys Ser
145                 150                 155

<210> SEQ ID NO 133
<211> LENGTH: 155
<212> TYPE: PRT
<213> ORGANISM: Ovis aries

<400> SEQUENCE: 133

Met Ala Ala Gly Ser Ile Thr Thr Leu Pro Ala Leu Pro Glu Asp Gly
  1               5                  10                  15

Gly Ser Ser Ala Phe Pro Pro Gly His Phe Lys Asp Pro Lys Arg Leu
                 20                  25                  30

Tyr Cys Lys Asn Gly Gly Phe Phe Leu Arg Ile His Pro Asp Gly Arg
                 35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Ser Ser Trp Tyr Val Ala Leu Lys
                115                 120                 125

Arg Thr Gly Gln Tyr Lys Leu Gly Pro Lys Thr Gly Pro Gly Gln Lys
                130                 135                 140

Ala Ile Leu Phe Leu Pro Met Ser Ala Lys Ser
145                 150                 155

<210> SEQ ID NO 134
<211> LENGTH: 108
<212> TYPE: PRT
<213> ORGANISM: Capreolus capreolus

<400> SEQUENCE: 134

Arg Ile His Pro Asp Gly Arg Val Asp Gly Val Arg Glu Lys Ser Asp
  1               5                  10                  15

Pro His Ile Lys Leu Gln Leu Gln Ala Glu Glu Arg Gly Val Val Ser
                 20                  25                  30

Ile Lys Gly Val Cys Ala Asn Arg Tyr Leu Ala Met Lys Glu Asp Gly
                 35                  40                  45

Arg Leu Leu Ala Ser Lys Cys Val Thr Asp Glu Cys Phe Phe Phe Glu
```

```
                    50                  55                  60

Arg Leu Glu Ser Asn Asn Tyr Asn Thr Tyr Arg Ser Arg Lys Tyr Ser
 65                  70                  75                  80

Ser Trp Tyr Val Ala Leu Lys Arg Thr Gly Gln Tyr Lys Leu Gly Pro
                    85                  90                  95

Lys Thr Gly Pro Gly Gln Lys Ala Ile Leu Phe Leu
                100                 105
```

<210> SEQ ID NO 135
<211> LENGTH: 96
<212> TYPE: PRT
<213> ORGANISM: Loxodonta Africana

<400> SEQUENCE: 135

```
Val Lys Leu Gln Leu Gln Ala Glu Glu Arg Gly Val Val Ser Ile Lys
  1               5                  10                  15

Gly Val Cys Ala Asn Arg Tyr Leu Ala Met Lys Glu Asp Gly Arg Leu
                 20                  25                  30

Leu Ala Ser Arg Cys Val Thr Asp Glu Cys Phe Phe Phe Glu Arg Leu
                 35                  40                  45

Glu Ser Asn Asn Tyr Asn Thr Tyr Arg Ser Arg Lys Tyr Thr Ser Trp
 50                  55                  60

Tyr Val Ala Leu Lys Arg Thr Gly Gln Tyr Lys Leu Gly Ser Lys Thr
 65                  70                  75                  80

Gly Pro Gly Gln Lys Ala Ile Leu Phe Leu Pro Met Ser Ala Lys Ser
                 85                  90                  95
```

<210> SEQ ID NO 136
<211> LENGTH: 120
<212> TYPE: PRT
<213> ORGANISM: Sus scrofa

<400> SEQUENCE: 136

```
Asn Gly Gly Phe Phe Leu Arg Ile His Pro Asp Gly Arg Val Asp Gly
  1               5                  10                  15

Val Arg Glu Lys Ser Asp Pro His Ile Lys Leu Gln Leu Gln Ala Glu
                 20                  25                  30

Glu Arg Gly Val Val Ser Ile Lys Gly Val Cys Ala Asn Arg Tyr Leu
                 35                  40                  45

Ala Met Lys Glu Asp Gly Arg Leu Leu Ala Ser Lys Cys Val Thr Asp
 50                  55                  60

Glu Cys Phe Phe Phe Glu Arg Leu Glu Ser Asn Asn Tyr Asn Thr Tyr
 65                  70                  75                  80

Arg Ser Arg Lys Tyr Ser Ser Trp Tyr Val Ala Leu Lys Arg Thr Gly
                 85                  90                  95

Gln Tyr Lys Leu Gly Pro Lys Thr Gly Pro Gly Gln Lys Ala Ile Leu
                100                 105                 110

Phe Leu Pro Met Ser Ala Lys Ser
                115                 120
```

<210> SEQ ID NO 137
<211> LENGTH: 96
<212> TYPE: PRT
<213> ORGANISM: Ailuropoda melanoleuca

<400> SEQUENCE: 137

```
Val Lys Leu Gln Leu Gln Ala Glu Glu Arg Gly Val Val Ser Ile Lys
  1               5                  10                  15
```

```
Gly Val Cys Ala Asn Arg Tyr Leu Ala Met Lys Glu Asp Gly Arg Leu
            20                  25                  30

Leu Ala Ser Lys Cys Val Thr Asp Glu Cys Phe Phe Phe Glu Arg Leu
        35                  40                  45

Glu Ser Asn Asn Tyr Asn Thr Tyr Arg Ser Arg Lys Tyr Ser Ser Trp
    50                  55                  60

Tyr Val Ala Leu Lys Arg Thr Gly Gln Tyr Lys Leu Gly Pro Lys Thr
65                  70                  75                  80

Gly Pro Gly Gln Lys Ala Ile Leu Phe Leu Pro Met Ser Ala Lys Ser
                85                  90                  95

<210> SEQ ID NO 138
<211> LENGTH: 155
<212> TYPE: PRT
<213> ORGANISM: Choloepus hoffmanni

<400> SEQUENCE: 138

Met Ala Ala Gly Ser Ile Thr Thr Leu Pro Ala Leu Pro Glu Asp Gly
1               5                   10                  15

Gly Ser Gly Ala Leu Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Gln Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155

<210> SEQ ID NO 139
<211> LENGTH: 155
<212> TYPE: PRT
<213> ORGANISM: Bubalus bubalis

<400> SEQUENCE: 139

Met Ala Ala Gly Ser Ile Thr Thr Leu Pro Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95
```

```
Val Thr Asp Glu Cys Phe Phe Phe Glu Arg Leu Glu Ser Ser Asn Tyr
            100                 105                 110

Asn Thr Tyr Arg Ser Arg Lys Tyr Ser Ser Trp Tyr Val Ala Leu Lys
            115                 120                 125

Arg Thr Gly Gln Tyr Lys Leu Gly Pro Lys Thr Gly Pro Gly Gln Lys
        130                 135                 140

Ala Ile Leu Phe Leu Pro Met Ser Ala Lys Ser
145                 150                 155

<210> SEQ ID NO 140
<211> LENGTH: 155
<212> TYPE: PRT
<213> ORGANISM: Canis lupus familiaris

<400> SEQUENCE: 140

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Lys Gly Gly Phe Phe Leu Arg Ile His Pro Asp Gly Arg
        35                  40                  45

Val Asp Gly Val Arg Glu Lys Ser Asp Pro His Val Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
            115                 120                 125

Arg Thr Gly Gln Tyr Lys Leu Gly Pro Lys Thr Gly Pro Gly Gln Lys
        130                 135                 140

Ala Ile Leu Phe Leu Pro Met Ser Ala Lys Ser
145                 150                 155

<210> SEQ ID NO 141
<211> LENGTH: 154
<212> TYPE: PRT
<213> ORGANISM: Rattus norvegicus

<400> SEQUENCE: 141

Met Ala Ala Gly Ser Ile Thr Ser Leu Pro Ala Leu Pro Glu Asp Gly
1               5                   10                  15

Gly Gly Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Val Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110
```

```
Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150

<210> SEQ ID NO 142
<211> LENGTH: 134
<212> TYPE: PRT
<213> ORGANISM: Heterocephalus glaber

<400> SEQUENCE: 142

Pro Pro Gly His Phe Lys Asp Pro Lys Arg Leu Tyr Cys Lys Asn Gly
1               5                   10                  15

Gly Phe Phe Leu Arg Ile His Pro Asp Gly Arg Val Asp Gly Val Arg
            20                  25                  30

Glu Lys Ser Asp Pro His Val Lys Leu Gln Leu Gln Ala Glu Glu Arg
        35                  40                  45

Gly Val Val Ser Ile Lys Gly Val Cys Ala Asn Arg Tyr Leu Ala Met
    50                  55                  60

Lys Glu Asp Gly Arg Leu Leu Ala Ser Lys Cys Val Thr Asp Glu Cys
65                  70                  75                  80

Phe Phe Phe Glu Arg Leu Glu Ser Asn Asn Tyr Asn Thr Tyr Arg Ser
                85                  90                  95

Arg Lys Tyr Ser Ser Trp Tyr Val Ala Leu Lys Arg Thr Gly Gln Tyr
            100                 105                 110

Lys Leu Gly Ser Lys Thr Gly Pro Gly Gln Lys Ala Ile Leu Phe Leu
        115                 120                 125

Pro Met Ser Ala Lys Ser
    130

<210> SEQ ID NO 143
<211> LENGTH: 155
<212> TYPE: PRT
<213> ORGANISM: Otolemur garnettii

<400> SEQUENCE: 143

Met Ala Ala Gly Ser Ile Thr Thr Leu Pro Ser Leu Pro Glu Asp Gly
1               5                   10                  15

Gly Ser Asp Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro Tyr Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Leu
                85                  90                  95

Ile Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Ser Lys Thr Gly Pro Gly Gln Lys
    130                 135                 140
```

```
Ala Ile Leu Phe Leu Pro Met Ser Ala Lys Ser
145                 150                 155

<210> SEQ ID NO 144
<211> LENGTH: 154
<212> TYPE: PRT
<213> ORGANISM: Mus musculus

<400> SEQUENCE: 144

Met Ala Ala Ser Gly Ile Thr Ser Leu Pro Ala Leu Pro Glu Asp Gly
1               5                   10                  15

Gly Ala Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
            35                  40                  45

Asp Gly Val Arg Glu Lys Ser Asp Pro His Val Lys Leu Gln Leu Gln
        50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150

<210> SEQ ID NO 145
<211> LENGTH: 144
<212> TYPE: PRT
<213> ORGANISM: Ictidomys tridecemlineatus

<400> SEQUENCE: 145

Leu Pro Glu Asp Gly Gly Gly Ala Phe Pro Pro Gly His Phe Lys
1               5                   10                  15

Asp Pro Lys Arg Leu Tyr Cys Lys Asn Gly Gly Phe Phe Leu Arg Ile
            20                  25                  30

His Pro Asp Gly Arg Val Asp Gly Val Arg Glu Lys Ser Asp Pro His
        35                  40                  45

Ile Lys Leu Gln Leu Gln Ala Glu Asp Arg Gly Val Val Ser Ile Lys
    50                  55                  60

Gly Val Cys Ala Asn Arg Tyr Leu Ala Met Lys Glu Asp Gly Arg Leu
65                  70                  75                  80

Leu Ala Ser Lys Cys Val Thr Asp Glu Cys Phe Phe Phe Glu Arg Leu
                85                  90                  95

Glu Ser Asn Asn Tyr Asn Thr Tyr Arg Ser Arg Lys Tyr Ser Ser Trp
            100                 105                 110

Tyr Val Ala Leu Lys Arg Thr Gly Gln Tyr Lys Leu Gly Ser Lys Thr
        115                 120                 125

Gly Pro Gly Gln Lys Ala Ile Leu Phe Leu Pro Met Ser Ala Lys Ser
    130                 135                 140

<210> SEQ ID NO 146
```

```
<211> LENGTH: 106
<212> TYPE: PRT
<213> ORGANISM: Felis catus

<400> SEQUENCE: 146

His Phe Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Ser Ser Trp Tyr Val Ala Leu Lys Arg Thr
            100                 105

<210> SEQ ID NO 147
<211> LENGTH: 96
<212> TYPE: PRT
<213> ORGANISM: Cavia porcellus

<400> SEQUENCE: 147

Val Lys Leu Gln Leu Gln Ala Glu Asp Arg Gly Val Val Ser Ile Lys
1               5                   10                  15

Gly Val Cys Ala Asn Arg Tyr Leu Ala Met Lys Glu Asp Gly Arg Leu
            20                  25                  30

Leu Ala Ser Lys Cys Val Thr Asp Glu Cys Phe Phe Phe Glu Arg Leu
        35                  40                  45

Glu Ser Asn Asn Tyr Asn Thr Tyr Arg Ser Arg Lys Tyr Ser Ser Trp
    50                  55                  60

Tyr Val Ala Leu Lys Arg Thr Gly Gln Tyr Lys Leu Gly Ser Lys Thr
65                  70                  75                  80

Gly Pro Gly Gln Lys Ala Ile Leu Phe Leu Pro Met Ser Ala Lys Ser
                85                  90                  95

<210> SEQ ID NO 148
<211> LENGTH: 156
<212> TYPE: PRT
<213> ORGANISM: Sarcophilus harrisii

<400> SEQUENCE: 148

Met Ala Ala Gly Ser Ile Thr Thr Leu Pro Ala Leu Ala Gly Asp Gly
1               5                   10                  15

Ala Ser Gly Gly Ala Phe Pro Pro Gly His Phe Gln Asp Pro Lys Arg
            20                  25                  30

Leu Tyr Cys Lys Asn Gly Gly Phe Phe Leu Arg Ile His Pro Asp Gly
        35                  40                  45

His Val Asp Gly Ile Arg Glu Lys Ser Asp Pro His Ile Lys Leu Gln
    50                  55                  60

Leu Gln Ala Glu Glu Arg Gly Val Val Ser Ile Lys Gly Val Cys Ala
65                  70                  75                  80

Asn Arg Tyr Leu Ala Met Lys Glu Asp Gly Arg Leu Leu Ala Leu Lys
                85                  90                  95
```

Cys Val Thr Glu Glu Cys Phe Phe Phe Glu Arg Leu Glu Ser Asn Asn
                100                 105                 110

Tyr Asn Thr Tyr Arg Ser Arg Lys Tyr Ser Asn Trp Tyr Val Ala Leu
            115                 120                 125

Lys Arg Thr Gly Gln Tyr Lys Leu Gly Ser Lys Thr Gly Pro Gly Gln
130                 135                 140

Lys Ala Ile Leu Phe Leu Pro Met Ser Ala Lys Ser
145                 150                 155

<210> SEQ ID NO 149
<211> LENGTH: 156
<212> TYPE: PRT
<213> ORGANISM: Monodelphis domestica

<400> SEQUENCE: 149

Met Ala Ala Gly Ser Ile Thr Thr Leu Pro Ala Leu Ser Gly Asp Gly
1               5                   10                  15

Gly Gly Gly Gly Ala Phe Pro Pro Gly His Phe Lys Asp Pro Lys Arg
                20                  25                  30

Leu Tyr Cys Lys Asn Gly Gly Phe Phe Leu Arg Ile His Pro Asp Gly
            35                  40                  45

Arg Val Asp Gly Ile Arg Glu Lys Ser Asp Pro Asn Ile Lys Leu Gln
        50                  55                  60

Leu Gln Ala Glu Glu Arg Gly Val Val Ser Ile Lys Gly Val Cys Ala
65                  70                  75                  80

Asn Arg Tyr Leu Ala Met Lys Glu Asp Gly Arg Leu Leu Ala Leu Lys
                85                  90                  95

Tyr Val Thr Glu Glu Cys Phe Phe Phe Glu Arg Leu Glu Ser Asn Asn
                100                 105                 110

Tyr Asn Thr Tyr Arg Ser Arg Lys Tyr Ser Asn Trp Tyr Val Ala Leu
            115                 120                 125

Lys Arg Thr Gly Gln Tyr Lys Leu Gly Ser Lys Thr Gly Pro Gly Gln
130                 135                 140

Lys Ala Ile Leu Phe Leu Pro Met Ser Ala Lys Ser
145                 150                 155

<210> SEQ ID NO 150
<211> LENGTH: 155
<212> TYPE: PRT
<213> ORGANISM: Oryctolagus cuniculus

<400> SEQUENCE: 150

Met Ala Ala Glu Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
        50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Ser Ser Trp Tyr Val Ala Leu Lys
            115                 120                 125

Arg Thr Gly Gln Tyr Lys Leu Gly Ser Lys Thr Gly Pro Gly Gln Lys
130                 135                 140

Ala Ile Leu Phe Leu Pro Met Ser Ala Lys Ser
145                 150                 155

<210> SEQ ID NO 151
<211> LENGTH: 125
<212> TYPE: PRT
<213> ORGANISM: Meleagris gallopavo

<400> SEQUENCE: 151

Arg Leu Tyr Cys Lys Asn Gly Gly Phe Phe Leu Arg Ile Asn Pro Asp
1               5                   10                  15

Gly Arg Val Asp Gly Val Arg Glu Lys Ser Asp Pro His Ile Lys Leu
                20                  25                  30

Gln Leu Gln Ala Glu Glu Arg Gly Val Val Ser Ile Lys Gly Val Ser
            35                  40                  45

Ala Asn Arg Phe Leu Ala Met Lys Glu Asp Gly Arg Leu Leu Ala Leu
        50                  55                  60

Lys Cys Ala Thr Glu Glu Cys Phe Phe Phe Glu Arg Leu Glu Ser Asn
65                  70                  75                  80

Asn Tyr Asn Thr Tyr Arg Ser Arg Lys Tyr Ser Asp Trp Tyr Val Ala
                85                  90                  95

Leu Lys Arg Thr Gly Gln Tyr Lys Pro Gly Pro Lys Thr Gly Pro Gly
                100                 105                 110

Gln Lys Ala Ile Leu Phe Leu Pro Met Ser Ala Lys Ser
            115                 120                 125

<210> SEQ ID NO 152
<211> LENGTH: 158
<212> TYPE: PRT
<213> ORGANISM: Gallus gallus

<400> SEQUENCE: 152

Met Ala Ala Gly Ala Ala Gly Ser Ile Thr Thr Leu Pro Ala Leu Pro
1               5                   10                  15

Asp Asp Gly Gly Gly Gly Ala Phe Pro Pro Gly His Phe Lys Asp Pro
                20                  25                  30

Lys Arg Leu Tyr Cys Lys Asn Gly Gly Phe Phe Leu Arg Ile Asn Pro
            35                  40                  45

Asp Gly Arg Val Asp Gly Val Arg Glu Lys Ser Asp Pro His Ile Lys
        50                  55                  60

Leu Gln Leu Gln Ala Glu Glu Arg Gly Val Val Ser Ile Lys Gly Val
65                  70                  75                  80

Ser Ala Asn Arg Phe Leu Ala Met Lys Glu Asp Gly Arg Leu Leu Ala
                85                  90                  95

Leu Lys Cys Ala Thr Glu Glu Cys Phe Phe Phe Glu Arg Leu Glu Ser
                100                 105                 110

Asn Asn Tyr Asn Thr Tyr Arg Ser Arg Lys Tyr Ser Asp Trp Tyr Val
            115                 120                 125

Ala Leu Lys Arg Thr Gly Gln Tyr Lys Pro Gly Pro Lys Thr Gly Pro
        130                 135                 140

Gly Gln Lys Ala Ile Leu Phe Leu Pro Met Ser Ala Lys Ser
145                 150                 155

<210> SEQ ID NO 153
<211> LENGTH: 153
<212> TYPE: PRT
<213> ORGANISM: Taeniopygia guttata

<400> SEQUENCE: 153

Met Ala Ala Gly Gly Ile Ala Thr Leu Pro Asp Asp Gly Gly Ser
1               5                   10                  15

Gly Ala Phe Pro Pro Gly His Phe Lys Asp Pro Lys Arg Leu Tyr Cys
            20                  25                  30

Lys Asn Gly Gly Phe Phe Leu Arg Ile Asn Pro Asp Gly Lys Val Asp
        35                  40                  45

Gly Val Arg Glu Lys Ser Asp Pro His Ile Lys Leu Gln Leu Gln Ala
    50                  55                  60

Glu Glu Arg Gly Val Val Ser Ile Lys Gly Val Ser Ala Asn Arg Phe
65                  70                  75                  80

Leu Ala Met Lys Glu Asp Gly Arg Leu Leu Ala Leu Lys Tyr Ala Thr
                85                  90                  95

Glu Glu Cys Phe Phe Phe Glu Arg Leu Glu Ser Asn Asn Tyr Asn Thr
            100                 105                 110

Tyr Arg Ser Arg Lys Tyr Ser Asp Trp Tyr Val Ala Leu Lys Arg Thr
        115                 120                 125

Gly Gln Tyr Lys Pro Gly Pro Lys Thr Gly Pro Gly Gln Lys Ala Ile
    130                 135                 140

Leu Phe Leu Pro Met Ser Ala Lys Ser
145                 150

<210> SEQ ID NO 154
<211> LENGTH: 155
<212> TYPE: PRT
<213> ORGANISM: Cynops pyrrhogaster

<400> SEQUENCE: 154

Met Ala Ala Gly Ser Ile Thr Ser Leu Pro Ala Leu Pro Glu Asp Gly
1               5                   10                  15

Asn Gly Gly Thr Phe Thr Pro Gly Gly Phe Lys Glu Pro Lys Arg Leu
            20                  25                  30

Tyr Cys Lys Asn Gly Gly Phe Phe Leu Arg Ile Asn Ser Asp Gly Lys
        35                  40                  45

Val Asp Gly Ala Arg Glu Lys Ser Asp Ser Tyr Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Asp Asp Gly Arg Leu Met Ala Leu Lys Trp
                85                  90                  95

Ile Thr Asp Glu Cys Phe Phe Phe Glu Arg Leu Glu Ser Asn Asn Tyr
            100                 105                 110

Asn Thr Tyr Arg Ser Arg Lys Tyr Ser Asp Trp Tyr Val Ala Leu Lys
        115                 120                 125

Arg Thr Gly Gln Tyr Lys Asn Gly Ser Lys Thr Gly Ala Gly Gln Lys
    130                 135                 140

Ala Ile Leu Phe Leu Pro Met Ser Ala Lys Ser
145                 150                 155

<210> SEQ ID NO 155
<211> LENGTH: 155

-continued

<212> TYPE: PRT
<213> ORGANISM: Xenopus laevis

<400> SEQUENCE: 155

Met Ala Ala Gly Ser Ile Thr Thr Leu Pro Thr Glu Ser Glu Asp Gly
1               5                   10                  15

Gly Asn Thr Pro Phe Ser Pro Gly Ser Phe Lys Asp Pro Lys Arg Leu
            20                  25                  30

Tyr Cys Lys Asn Gly Gly Phe Phe Leu Arg Ile Asn Ser Asp Gly Arg
        35                  40                  45

Val Asp Gly Ser Arg Asp Lys Ser Asp Ser His Ile Lys Leu Gln Leu
    50                  55                  60

Gln Ala Val Glu Arg Gly Val Val Ser Ile Lys Gly Ile Thr Ala Asn
65                  70                  75                  80

Arg Tyr Leu Ala Met Lys Glu Asp Gly Arg Leu Thr Ser Leu Arg Cys
                85                  90                  95

Ile Thr Asp Glu Cys Phe Phe Phe Glu Arg Leu Glu Ala Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Asn Gly Ser Ser Thr Gly Pro Gly Gln Lys
    130                 135                 140

Ala Ile Leu Phe Leu Pro Met Ser Ala Lys Ser
145                 150                 155

<210> SEQ ID NO 156
<211> LENGTH: 156
<212> TYPE: PRT
<213> ORGANISM: Didelphis albiventris

<400> SEQUENCE: 156

Met Ala Ala Gly Ser Ile Thr Thr Leu Pro Ala Leu Ser Gly Asp Gly
1               5                   10                  15

Gly Gly Gly Gly Ala Phe Pro Pro Gly His Phe Lys Asp Pro Lys Arg
            20                  25                  30

Leu Tyr Cys Lys Asn Gly Gly Phe Phe Leu Arg Ile His Pro Asp Gly
        35                  40                  45

Arg Val Asp Gly Ile Arg Glu Lys Ser Asp Pro Asn Ile Lys Leu Gln
    50                  55                  60

Leu Gln Ala Glu Glu Arg Gly Val Val Ser Ile Lys Gly Val Cys Ala
65                  70                  75                  80

Asn Arg Tyr Leu Ala Met Lys Glu Asp Gly Arg Leu Leu Ala Leu Lys
                85                  90                  95

Tyr Val Thr Glu Glu Cys Phe Phe Phe Glu Arg Leu Glu Ser Asn Asn
            100                 105                 110

Tyr Asn Thr Tyr Arg Ser Arg Lys Tyr Ser Asn Trp Tyr Val Ala Leu
        115                 120                 125

Lys Arg Thr Gly Gln Tyr Lys Leu Gly Ser Lys Thr Gly Pro Gly Gln
    130                 135                 140

Lys Ala Ile Leu Phe Ser Pro Cys Leu Leu Arg Cys
145                 150                 155

<210> SEQ ID NO 157
<211> LENGTH: 96
<212> TYPE: PRT
<213> ORGANISM: Myotis lucifugus

<400> SEQUENCE: 157

Val Lys Leu Gln Leu Gln Ala Glu Glu Arg Gly Val Val Ser Ile Lys
1               5                   10                  15

Gly Val Cys Ala Asn Arg Tyr Leu Ala Met Lys Glu Asp Gly Arg Leu
            20                  25                  30

Gln Ala Ser Lys Cys Val Thr Asp Glu Cys Phe Phe Phe Glu Arg Leu
        35                  40                  45

Glu Ser Asn Asn Tyr Asn Thr Tyr Arg Ser Arg Lys Tyr Ser Ser Trp
    50                  55                  60

Tyr Val Ala Leu Lys Arg Asn Gly Gln Tyr Lys Leu Gly Pro Lys Thr
65                  70                  75                  80

Gly Pro Gly Gln Lys Ala Ile Leu Phe Leu Pro Met Ser Ala Lys Ser
                85                  90                  95

<210> SEQ ID NO 158
<211> LENGTH: 140
<212> TYPE: PRT
<213> ORGANISM: Anolis carolinensis

<400> SEQUENCE: 158

Ala Ala Ala Ala Ser Phe Pro Pro Gly Pro Phe Lys Asp Pro Lys Arg
1               5                   10                  15

Leu Tyr Cys Lys Asn Gly Gly Phe Phe Leu Arg Ile Asn Pro Asp Gly
            20                  25                  30

Gly Val Asp Gly Val Arg Glu Lys Ser Asp Pro Asn Ile Lys Leu Leu
        35                  40                  45

Leu Gln Ala Glu Glu Arg Gly Val Val Ser Ile Lys Gly Val Cys Ala
    50                  55                  60

Asn Arg Phe Leu Ala Met Asn Glu Asp Gly Arg Leu Leu Ala Leu Lys
65                  70                  75                  80

Tyr Val Thr Asp Glu Cys Phe Phe Glu Arg Leu Glu Ser Asn Asn
                85                  90                  95

Tyr Asn Thr Tyr Arg Ser Arg Lys Tyr Arg Asp Trp Tyr Ile Ala Leu
            100                 105                 110

Lys Arg Thr Gly Gln Tyr Lys Leu Gly Pro Lys Thr Gly Arg Gly Gln
        115                 120                 125

Lys Ala Ile Leu Phe Leu Pro Met Ser Ala Lys Ser
    130                 135                 140

<210> SEQ ID NO 159
<211> LENGTH: 94
<212> TYPE: PRT
<213> ORGANISM: Dasypus novemcinctus

<400> SEQUENCE: 159

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro Asn Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Arg Glu Asp Gly Arg Leu Gln Ala Ser
                85                  90

<210> SEQ ID NO 160
<211> LENGTH: 189
<212> TYPE: PRT
<213> ORGANISM: Tupaia belangeri

<400> SEQUENCE: 160

Ala Gly Val Arg Ala Glu Arg Glu Ala Pro Gly Ser Gly Asp Ser
1               5                   10                  15

Arg Gly Thr Asp Pro Ala Ala Arg Ser Leu Ile Arg Arg Pro Asp Ala
                20                  25                  30

Ala Ala Arg Glu Ala Leu Leu Gly Ala Arg Ser Arg Val Gln Gly Ser
            35                  40                  45

Ser Thr Ser Trp Pro Ala Ser Ser Arg Thr Gly Ile Lys Leu Pro Asp
50                  55                  60

Asp Ser Gly Gln Gly Met Gly Gly Tyr Pro Leu Asp Arg Pro Ser Arg
65                  70                  75                  80

Ser Thr Gly Arg Gly Leu Gly Gly Ala Pro Asp Pro Ala Val Lys Leu
                85                  90                  95

Gln Leu Gln Ala Glu Glu Arg Gly Val Val Ser Ile Lys Gly Val Cys
            100                 105                 110

Ala Asn Arg Tyr Leu Ala Met Lys Glu Asp Gly Arg Leu Leu Ala Ser
        115                 120                 125

Lys Cys Val Thr Asp Glu Cys Phe Phe Glu Arg Leu Glu Ser Asn
    130                 135                 140

Asn Tyr Asn Thr Tyr Arg Ser Arg Lys Tyr Ser Ser Trp Tyr Val Ala
145                 150                 155                 160

Leu Lys Arg Thr Gly Gln Tyr Lys Leu Gly Ser Lys Thr Gly Pro Gly
                165                 170                 175

Gln Lys Ala Ile Leu Phe Leu Pro Met Ser Ala Lys Ser
            180                 185

<210> SEQ ID NO 161
<211> LENGTH: 154
<212> TYPE: PRT
<213> ORGANISM: Xenopus silurana tropicalis

<400> SEQUENCE: 161

Met Ala Ala Gly Ser Ile Thr Thr Leu Pro Thr Glu Ser Glu Asp Gly
1               5                   10                  15

Asn Thr Pro Phe Pro Pro Gly Asn Phe Lys Asp Pro Lys Arg Leu Tyr
                20                  25                  30

Cys Lys Asn Gly Gly Tyr Phe Leu Arg Ile Asn Ser Asp Gly Arg Val
            35                  40                  45

Asp Gly Ser Arg Asp Lys Ser Asp Leu His Ile Lys Leu Gln Leu Gln
50                  55                  60

Ala Val Glu Arg Gly Val Val Ser Ile Lys Gly Ile Thr Ala Asn Arg
65                  70                  75                  80

Tyr Leu Ala Met Lys Glu Asp Gly Arg Leu Thr Ser Leu Lys Cys Ile
                85                  90                  95

Thr Asp Glu Cys Phe Phe Tyr Glu Arg Leu Glu Ala Asn Asn Tyr Asn
            100                 105                 110

Thr Tyr Arg Ser Arg Lys Asn Asn Ser Trp Tyr Val Ala Leu Lys Arg
        115                 120                 125

Thr Gly Gln Tyr Lys Asn Gly Ser Thr Thr Gly Pro Gly Gln Lys Ala

```
                130                 135                 140
Ile Leu Phe Leu Pro Met Ser Ala Lys Ser
145                 150

<210> SEQ ID NO 162
<211> LENGTH: 155
<212> TYPE: PRT
<213> ORGANISM: Latimeria chalumnae

<400> SEQUENCE: 162

Met Ala Ala Gly Gly Ile Thr Thr Leu Pro Ala Val Pro Glu Asp Gly
1               5                   10                  15

Gly Ser Ser Thr Phe Pro Pro Gly Asn Phe Lys Glu Pro Lys Arg Leu
            20                  25                  30

Tyr Cys Lys Asn Gly Gly Tyr Phe Leu Arg Ile Asn Pro Asp Gly Arg
        35                  40                  45

Val Asp Gly Thr Arg Glu Lys Asn Asp Pro Tyr Ile Lys Leu Gln Leu
    50                  55                  60

Gln Ala Glu Ser Ile Gly Val Val Ser Ile Lys Gly Val Cys Ser Asn
65                  70                  75                  80

Arg Tyr Leu Ala Met Asn Glu Asp Cys Arg Leu Phe Gly Leu Lys Tyr
                85                  90                  95

Pro Thr Asp Glu Cys Phe Phe His Glu Arg Leu Glu Ser Asn Asn Tyr
            100                 105                 110

Asn Thr Tyr Arg Ser Lys Lys Tyr Ser Asp Trp Tyr Val Ala Leu Lys
        115                 120                 125

Arg Thr Gly Gln Tyr Lys Pro Gly Pro Lys Thr Gly Leu Gly Gln Lys
    130                 135                 140

Ala Ile Leu Phe Leu Pro Met Ser Ala Lys Ser
145                 150                 155

<210> SEQ ID NO 163
<211> LENGTH: 155
<212> TYPE: PRT
<213> ORGANISM: Tetraodon nigroviridis

<400> SEQUENCE: 163

Met Ala Thr Gly Gly Ile Thr Thr Leu Pro Ser Thr Pro Glu Asp Gly
1               5                   10                  15

Gly Ser Ser Gly Phe Pro Pro Gly Ser Phe Lys Asp Pro Lys Arg Leu
            20                  25                  30

Tyr Cys Lys Asn Gly Gly Phe Phe Leu Arg Ile Lys Ser Asp Gly Val
        35                  40                  45

Val Asp Gly Ile Arg Glu Lys Ser Asp Pro His Ile Lys Leu Gln Leu
    50                  55                  60

Gln Ala Thr Ser Val Gly Glu Val Val Ile Lys Gly Val Cys Ala Asn
65                  70                  75                  80

Arg Tyr Leu Ala Met Asn Arg Asp Gly Arg Leu Phe Gly Thr Lys Arg
                85                  90                  95

Ala Thr Asp Glu Cys His Phe Leu Glu Arg Leu Glu Ser Asn Asn Tyr
            100                 105                 110

Asn Thr Tyr Arg Ser Arg Lys Tyr Pro Thr Met Phe Val Gly Leu Thr
        115                 120                 125

Arg Thr Gly Gln Tyr Lys Ser Gly Ser Lys Thr Gly Pro Gly Gln Lys
    130                 135                 140

Ala Ile Leu Phe Leu Pro Met Ser Ala Lys Cys
```

145              150              155

<210> SEQ ID NO 164
<211> LENGTH: 155
<212> TYPE: PRT
<213> ORGANISM: Gasterosteus aculeatus

<400> SEQUENCE: 164

Met Ala Thr Ala Gly Phe Ala Thr Leu Pro Ser Thr Pro Glu Asp Gly
1               5                   10                  15

Gly Ser Gly Gly Phe Thr Pro Gly Gly Phe Lys Asp Pro Lys Arg Leu
                20                  25                  30

Tyr Cys Lys Asn Gly Gly Phe Phe Leu Arg Ile Arg Ser Asp Gly Gly
                35                  40                  45

Val Asp Gly Ile Arg Glu Lys Ser Asp Ala His Ile Lys Leu Gln Ile
50                  55                  60

Gln Ala Thr Ser Val Gly Glu Val Val Ile Lys Gly Val Cys Ala Asn
65                  70                  75                  80

Arg Tyr Leu Ala Met Asn Arg Asp Gly Arg Leu Phe Gly Val Arg Arg
                85                  90                  95

Ala Thr Asp Glu Cys Tyr Phe Leu Glu Arg Leu Glu Ser Asn Asn Tyr
                100                 105                 110

Asn Thr Tyr Arg Ser Arg Lys Tyr Pro Gly Met Tyr Val Ala Leu Lys
                115                 120                 125

Arg Thr Gly Gln Tyr Lys Ser Gly Ser Lys Thr Gly Pro Gly Gln Lys
                130                 135                 140

Ala Ile Leu Phe Leu Pro Met Ser Ala Lys Cys
145                 150                 155

<210> SEQ ID NO 165
<211> LENGTH: 155
<212> TYPE: PRT
<213> ORGANISM: Takifugu rubripes

<400> SEQUENCE: 165

Met Ala Thr Gly Gly Ile Thr Thr Leu Pro Ser Thr Pro Glu Asp Gly
1               5                   10                  15

Gly Ser Gly Gly Phe Pro Pro Gly Ser Phe Lys Asp Pro Lys Arg Leu
                20                  25                  30

Tyr Cys Lys Asn Gly Gly Phe Phe Leu Arg Ile Arg Ser Asp Gly Ala
                35                  40                  45

Val Asp Gly Thr Arg Glu Lys Thr Asp Pro His Ile Lys Leu Gln Leu
50                  55                  60

Gln Ala Thr Ser Val Gly Glu Val Val Ile Lys Gly Val Cys Ala Asn
65                  70                  75                  80

Arg Tyr Leu Ala Met Asn Arg Asp Gly Arg Leu Phe Gly Met Lys Arg
                85                  90                  95

Ala Thr Asp Glu Cys His Phe Leu Glu Arg Leu Glu Ser Asn Asn Tyr
                100                 105                 110

Asn Thr Tyr Arg Ser Arg Lys Tyr Pro Asn Met Phe Val Gly Leu Thr
                115                 120                 125

Arg Thr Gly Asn Tyr Lys Ser Gly Thr Lys Thr Gly Pro Cys Gln Lys
                130                 135                 140

Ala Ile Leu Phe Leu Pro Met Ser Ala Lys Tyr
145                 150                 155

<210> SEQ ID NO 166
<211> LENGTH: 155
<212> TYPE: PRT
<213> ORGANISM: Oncorhynchus mykiss

<400> SEQUENCE: 166

Met Ala Thr Gly Glu Ile Thr Thr Leu Pro Ala Thr Pro Glu Asp Gly
1               5                   10                  15

Gly Ser Gly Gly Phe Leu Pro Gly Asn Phe Lys Glu Pro Lys Arg Leu
            20                  25                  30

Tyr Cys Lys Asn Gly Gly Tyr Phe Leu Arg Ile Asn Ser Asn Gly Ser
        35                  40                  45

Val Asp Gly Ile Arg Asp Lys Asn Asp Pro His Asn Lys Leu Gln Leu
    50                  55                  60

Gln Ala Thr Ser Val Gly Glu Val Val Ile Lys Gly Val Ser Ala Asn
65                  70                  75                  80

Arg Tyr Leu Ala Met Asn Ala Asp Gly Arg Leu Phe Gly Pro Arg Arg
                85                  90                  95

Thr Thr Asp Glu Cys Tyr Phe Met Glu Arg Leu Glu Ser Asn Asn Tyr
            100                 105                 110

Asn Thr Tyr Arg Ser Arg Lys Tyr Pro Glu Met Tyr Val Ala Leu Lys
        115                 120                 125

Arg Thr Gly Gln Tyr Lys Ser Gly Ser Lys Thr Gly Pro Gly Gln Lys
    130                 135                 140

Ala Ile Leu Phe Leu Pro Met Ser Ala Arg Arg
145                 150                 155

<210> SEQ ID NO 167
<211> LENGTH: 150
<212> TYPE: PRT
<213> ORGANISM: Salmo salar

<400> SEQUENCE: 167

Met Ala Thr Gly Glu Ile Thr Thr Leu Pro Ala Thr Pro Glu Asp Gly
1               5                   10                  15

Gly Ser Gly Gly Phe Pro Pro Gly Asn Phe Lys Asp Pro Lys Arg Leu
            20                  25                  30

Tyr Cys Lys Asn Gly Gly Tyr Phe Leu Arg Ile Asn Ser Asn Gly Ser
        35                  40                  45

Val Asp Gly Ile Arg Glu Lys Asn Asp Pro His Lys Gln Pro Gln Phe
    50                  55                  60

Val Arg Ala Trp Thr Leu Gln Gly Val Lys Arg Ser Thr Gly Met Leu
65                  70                  75                  80

Ala His Val Asp Ser Asn Ala Ser His Asn Cys Val Lys Val Ala Gly
                85                  90                  95

Cys Ser Leu Gly Glu Phe Gly Ser Met Ser Asn Arg Pro His Asn Arg
            100                 105                 110

Arg Pro Arg Val Ala Thr Pro Ala Gln Asp Leu His Ile Arg Leu Leu
        115                 120                 125

His Leu Arg Asp Arg Leu Lys Pro Ala Thr Arg Thr Ala Asp Lys Thr
    130                 135                 140

Glu Glu Tyr Phe Cys Leu
145                 150

<210> SEQ ID NO 168
<211> LENGTH: 154
<212> TYPE: PRT

<213> ORGANISM: Danio rerio

<400> SEQUENCE: 168

Met Ala Thr Gly Gly Ile Thr Thr Leu Pro Ala Ala Pro Asp Ala Glu
1               5                   10                  15

Asn Ser Ser Phe Pro Ala Gly Ser Phe Arg Asp Pro Lys Arg Leu Tyr
            20                  25                  30

Cys Lys Asn Gly Gly Phe Phe Leu Arg Ile Asn Ala Asp Gly Arg Val
        35                  40                  45

Asp Gly Ala Arg Asp Lys Ser Asp Pro His Ile Arg Leu Gln Leu Gln
    50                  55                  60

Ala Thr Ala Val Gly Glu Val Leu Ile Lys Gly Ile Cys Thr Asn Arg
65                  70                  75                  80

Phe Leu Ala Met Asn Ala Asp Gly Arg Leu Phe Gly Thr Lys Arg Thr
                85                  90                  95

Thr Asp Glu Cys Tyr Phe Leu Glu Arg Leu Glu Ser Asn Asn Tyr Asn
            100                 105                 110

Thr Tyr Arg Ser Arg Lys Tyr Pro Asp Trp Tyr Val Ala Leu Lys Arg
        115                 120                 125

Thr Gly Gln Tyr Lys Ser Gly Ser Lys Thr Ser Pro Gly Gln Lys Ala
    130                 135                 140

Ile Leu Phe Leu Pro Met Ser Ala Lys Cys
145                 150

<210> SEQ ID NO 169
<211> LENGTH: 155
<212> TYPE: PRT
<213> ORGANISM: Oreochromis niloticus

<400> SEQUENCE: 169

Met Ala Thr Gly Gly Ile Thr Thr Leu Pro Ala Thr Pro Glu Asp Gly
1               5                   10                  15

Gly Ser Ser Gly Phe Pro Pro Gly Asn Phe Lys Asp Pro Lys Arg Leu
            20                  25                  30

Tyr Cys Lys Asn Gly Gly Phe Phe Leu Arg Ile Lys Ser Asp Gly Gly
        35                  40                  45

Val Asp Gly Ile Arg Glu Lys Asn Asp Pro His Ile Lys Leu Gln Leu
    50                  55                  60

Gln Ala Thr Ser Val Gly Glu Val Val Ile Lys Gly Ile Cys Ala Asn
65                  70                  75                  80

Arg Tyr Leu Ala Met Asn Arg Asp Gly Arg Leu Phe Gly Ala Arg Arg
                85                  90                  95

Ala Thr Asp Glu Cys Tyr Phe Leu Glu Arg Leu Glu Ser Asn Asn Tyr
            100                 105                 110

Asn Thr Tyr Arg Ser Arg Lys Tyr Pro Asn Met Tyr Val Ala Leu Lys
        115                 120                 125

Arg Thr Gly Gln Tyr Lys Ser Gly Ser Lys Thr Gly Pro Gly Gln Lys
    130                 135                 140

Ala Ile Leu Phe Leu Pro Met Ser Ala Lys Cys
145                 150                 155

<210> SEQ ID NO 170
<211> LENGTH: 155
<212> TYPE: PRT
<213> ORGANISM: Oryzias latipes

<400> SEQUENCE: 170

```
Met Ala Thr Gly Glu Ile Thr Thr Leu Pro Ser Pro Ala Glu Asn Ser
1               5                   10                  15

Arg Ser Asp Gly Phe Pro Pro Gly Asn Tyr Lys Asp Pro Lys Arg Leu
            20                  25                  30

Tyr Cys Lys Asn Gly Gly Leu Phe Leu Arg Ile Lys Pro Asp Gly Gly
                35                  40                  45

Val Asp Gly Ile Arg Glu Lys Lys Asp Pro His Val Lys Leu Arg Leu
    50                  55                  60

Gln Ala Thr Ser Ala Gly Glu Val Val Ile Lys Gly Val Cys Ser Asn
65                  70                  75                  80

Arg Tyr Leu Ala Met His Gly Asp Gly Arg Leu Phe Gly Val Arg Gln
                85                  90                  95

Ala Thr Glu Glu Cys Tyr Phe Leu Glu Arg Leu Glu Ser Asn Asn Tyr
            100                 105                 110

Asn Thr Tyr Arg Ser Lys Lys Tyr Pro Asn Met Tyr Val Ala Leu Lys
                115                 120                 125

Arg Thr Gly Gln Tyr Lys Pro Gly Asn Lys Thr Gly Pro Gly Gln Lys
    130                 135                 140

Ala Ile Leu Phe Leu Pro Met Ser Ala Lys Tyr
145                 150                 155

<210> SEQ ID NO 171
<211> LENGTH: 468
<212> TYPE: DNA
<213> ORGANISM: Homo sapiens

<400> SEQUENCE: 171
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttacctgg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata acttggatc caaaacagga     420 cctgggcaga aagctatact ttttcttcca atgtctgcta agagctga                 468

<210> SEQ ID NO 172
<211> LENGTH: 468
<212> TYPE: DNA
<213> ORGANISM: Gorilla

<400> SEQUENCE: 172
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttaccttg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata acttggatc caaaacagga     420 cctgggcaga aagctatact ttttcttcca atgtctgcta agagctga                 468
```

<210> SEQ ID NO 173
<211> LENGTH: 468
<212> TYPE: DNA
<213> ORGANISM: Sumatran orangutan

<400> SEQUENCE: 173

```
atggcagccg ggagcatcac cacgctgccc gccttgcccg aggatggcgg cagcggcgcc      60
ttcccgccgg gccacttcaa ggaccccaag cggctgtact gcaaaaacgg gggcttcttc     120
ctgcgcatcc accccgacgg ccgagttgac ggggtccgag agaagagcga ccctcacatc     180
aaactacaac ttcaagcaga agaaagagga gttgtgtcta tcaaaggagt gtgtgctaac     240
cgctaccttg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctga                  468
```

<210> SEQ ID NO 174
<211> LENGTH: 468
<212> TYPE: DNA
<213> ORGANISM: Rhesus monkey

<400> SEQUENCE: 174

```
atggcagccg ggagcatcac cacgctgccc gccttgcccg aggatggcgg cagcggcgcc      60
ttcccgcctg gccacttcaa ggaccccaag cggctgtact gcaaaaacgg gggcttcttc     120
ctgcgcattc accccgacgg ccgagttgac ggggtccggg agaagagcga ccctcacatc     180
aaattacaac ttcaagcaga agagagagga gttgtgtcta tcaaaggagt gtgtgctaac     240
cgttaccttg ctatgaagga agatggaaga ttactggctt ctaaatgtgt tacagatgag     300
tgtttctttt ttgaacgatt ggaatctaat aactacaata cttaccggtc aaggaaatac     360
accagttggt atgtggcact gaaacgaact gggcaatata aacttggatc caaaacagga     420
cctgggcaga aagctatact ttttcttcca atgtctgcta agagctga                  468
```

<210> SEQ ID NO 175
<211> LENGTH: 468
<212> TYPE: DNA
<213> ORGANISM: Chimpanzee

<400> SEQUENCE: 175

```
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttaccttg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctga                  468
```

<210> SEQ ID NO 176
<211> LENGTH: 468
<212> TYPE: DNA
<213> ORGANISM: Pygmy chimpanzee

<400> SEQUENCE: 176

```
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttaccttg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctga                  468
```

<210> SEQ ID NO 177
<211> LENGTH: 468
<212> TYPE: DNA
<213> ORGANISM: Bolivian squirrel monkey

<400> SEQUENCE: 177

```
atggcagccg ggagcatcac cacgctgccc gccctgcccg agacggcgg cagcggcgcc       60 ttcccgcccg gccacttcaa agaccccaag cggctgtact gcaaaaacgg gggcttcttc     120
ctgcgaatcc accccgacgg ccgagtggac ggggtccggg agaagagcga ccctcacatc     180
aaactacaac ttcaagcaga agagagagga gttgtatcta tcaaaggagt gtgtgctaac     240
cgttaccttg ctatgaagga agatggaaga ttactggctt ctaaatgtgt tacggacgag     300
tgtttctttt ttgaacgatt ggaatctaat aactacaata cttaccgatc aaggaaatac     360
accagttggt atgtggcact gaaacgaact gggcagtata aacttggatc caaaacagga     420
cctgggcaga aagctatact ttttcttcca atgtctgcta agagctga                  468
```

<210> SEQ ID NO 178
<211> LENGTH: 468
<212> TYPE: DNA
<213> ORGANISM: Northern white-cheeked gibbon

<400> SEQUENCE: 178

```
atggcagccg ggagcatcac cacgctgccc gccttgccgg aggatggcgg cagcggcgcc      60
ttcccgcccg gccacttcaa ggaccccaag cggctgtact gcaaaaacgg gggtttcttc     120
ctgcgcatcc accccgacgg tcgagttgac ggggtccggg agaagagcga ccctcacatc     180
aaactacaac ttcaagcaga agagagagga gttgtgtcta tcaaaggagt gtgtgctaac     240
cgttaccttg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctga                  468
```

<210> SEQ ID NO 179
<211> LENGTH: 468
<212> TYPE: DNA
<213> ORGANISM: Horse

<400> SEQUENCE: 179

```
atggcagccg ggagcatcac cacgctgccc gccctgcccg aggacggcgg cagcggcgcc      60
ttcccgcccg gccacttcaa ggaccccaag cggctctact gcaaaaacgg gggcttcttc     120
ctgcgcatcc accccgacgg ccgagtggac ggggtccggg agaagagcga ccctcacatc     180
```

```
aaactacaac ttcaagcaga agagagaggg gttgtgtcta tcaaaggagt gtgtgcgaac    240
cgttatcttg ctatgaagga agatggaagg ttactggctt ctaaatgtgt tacggacgag    300
tgtttctttt ttgaacgatt ggaatctaat aactacaata cttaccggtc aaggaaatac    360
tccagttggt atgtggccct gaaacgaacg gggcagtata aacttggacc caaaacagga    420
cctggacaga aagctatact ttttcttcca atgtctgcta agagctga                 468
```

<210> SEQ ID NO 180
<211> LENGTH: 468
<212> TYPE: DNA
<213> ORGANISM: Cattle

<400> SEQUENCE: 180

```
atggccgccg ggagcatcac cacgctgcca gccctgccgg aggacggcgg cagcggcgct    60
ttcccgccgg gccacttcaa ggaccccaag cggctgtact gcaagaacgg gggcttcttc    120
ctgcgcatcc accccgacgg ccgagtggac ggggtccgcg agaagagcga cccacacatc    180
aaactacaac ttcaagcaga agagagaggg gttgtgtcta tcaaaggagt gtgtgcaaac    240
cgttaccttg ctatgaaaga agatggaaga ttactagctt ctaaatgtgt tacagacgag    300
tgtttctttt ttgaacgatt ggagtctaat aactacaata cttaccggtc aaggaaatac    360
tccagttggt atgtggcact gaaacgaact gggcagtata aacttggacc caaaacagga    420
cctgggcaga aagctatact ttttcttcca atgtctgcta agagctga                 468
```

<210> SEQ ID NO 181
<211> LENGTH: 468
<212> TYPE: DNA
<213> ORGANISM: Olive baboon

<400> SEQUENCE: 181

```
atggcagccg ggagcatcac cacgctgccc gccttgcccg aggatggcgg cagcggcgcc    60
ttcccgcccg gccacttcaa ggaccccaag cggctgtact gcaaaaacgg gggcttcttc    120
ctgcgcattc accccgacgg ccgagttgac ggggtccggg agaagagcga ccctcacatc    180
aaattacaac ttcaagcaga agagagagga gttgtgtcta tcaaaggagt gtgtgctaac    240
cgttaccttg ctatgaagga agatggaaga ttactggctt ctaaatgtgt tacggatgag    300
tgtttctttt ttgaacgatt ggaatctaat aactacaata cttaccggtc aaggaaatac    360
accagttggt atgtggcact gaaacgaact gggcagtata aacttggatc caaaacagga    420
cctgggcaga aagctatact ttttcttcca atgtctgcta agagctga                 468
```

<210> SEQ ID NO 182
<211> LENGTH: 468
<212> TYPE: DNA
<213> ORGANISM: Alpaca

<400> SEQUENCE: 182

```
atggcagctg ggagcatcac cacgctgccc gccctgccgg aggacggcgg cagcggcgcc    60
ttcccgcccg gccacttcaa ggaccccaag cggttgtact gcaaaaacgg gggcttcttc    120
ctgcgcatcc accccgacgg ccgagtggac ggggtccggg agaagagcga ccctcacatc    180
aaactacaac ttcaagcaga agagagaggg gtcgtgtcta tcaaaggagt gtgtgcaaac    240
cgttaccttg ctatgaagga agatggaaga ttactggctt ctaaatgtgt cacagacgag    300
tgtttctttt ttgaacgatt ggaatctaat aactacaata cttaccggtc aaggaaatac    360
tccagttggt atgtggcact gaaacgaact gggcagtaca aacttggacc caaaacagga    420
```

```
cctgggcaga aagctatact tttccttcca atgtctgcta agagctga              468
```

<210> SEQ ID NO 183
<211> LENGTH: 468
<212> TYPE: DNA
<213> ORGANISM: Sheep

<400> SEQUENCE: 183

```
atggccgccg ggagcatcac cacgctgcca gccctgccgg aggacggcgg cagcagcgct    60
ttcccgcccg gccactttaa ggaccccaag cggctgtact gcaagaacgg gggcttcttc   120
ctgcgcatcc accccgacgg ccgagtggac ggggtccgcg agaagagcga ccctcacatc   180
aaactacaac ttcaagcaga agagagaggg gttgtgtcta tcaaaggagt gtgtgcaaac   240
cgttaccttg ctatgaaaga gatggaaga ttactagctt ctaaatgtgt tacagacgag    300
tgtttctttt ttgaacgatt ggagtctaat aactacaata cttaccggtc aaggaaatac   360
tccagttggt atgtggcact gaaacgaact gggcagtata aacttggacc caaaacagga   420
cctgggcaga agctatact ttttcttcca atgtctgcta agagctga                468
```

<210> SEQ ID NO 184
<211> LENGTH: 325
<212> TYPE: DNA
<213> ORGANISM: Western roe deer

<400> SEQUENCE: 184

```
gcgcatccac cccgacggcc gagtggacgg ggtccgcgag aagagtgacc ctcacatcaa    60
actacaactt caagcagaag agaggggt tgtgtctatc aaaggagtgt gtgcgaaccg    120
ttatcttgct atgaaagaag acggaagatt attggcttca aaatgtgtta cagacgaatg   180
tttctttttt gaacgattgg agtctaataa ctacaatact taccggtcaa ggaaatactc   240
cagttggtat gtggcactga acgaactgg gcagtataaa cttggaccca aacaggacc    300
tgggcagaaa gctatacttt ttctt                                         325
```

<210> SEQ ID NO 185
<211> LENGTH: 288
<212> TYPE: DNA
<213> ORGANISM: Elephant

<400> SEQUENCE: 185

```
gttaaactac agcttcaagc agaagagaga ggtgttgtgt ctatcaaagg agtgtgtgcc    60
aaccgttatc tggctatgaa ggaagatgga agattgctgg cttctagatg tgtgacagat   120
gaatgtttct ctttgaacg actggaatct aataactaca atacttaccg gtcaaggaaa   180
tacaccagtt ggtatgtggc actgaaacga acggggcagt ataaacttgg atccaaaaca   240
ggacctggac agaaagctat acttttttctt cccatgtctg ctaagagc              288
```

<210> SEQ ID NO 186
<211> LENGTH: 361
<212> TYPE: DNA
<213> ORGANISM: Pig

<400> SEQUENCE: 186

```
gaacgggggc ttcttcctgc gcatccaccc cgacggccga gtggatgggg tccgggagaa    60
gagcgaccct cacatcaaac tacaacttca agcagaagag agggggttg tgtctatcaa   120
aggagtgtgt gcaaaccgtt atcttgctat gaaggaagat ggaagattac tggcttctaa   180
```

```
atgtgttaca gacgagtgtt tcttttttga acgactggaa tctaataact acaatactta      240
ccggtcgagg aaatactcca gttggtatgt ggcactgaaa cgaactgggc agtataaact      300
tggacccaaa acaggacctg ggcagaaagc tatactttt cttccaatgt ctgctaagag       360
c                                                                     361
```

<210> SEQ ID NO 187
<211> LENGTH: 288
<212> TYPE: DNA
<213> ORGANISM: Panda

<400> SEQUENCE: 187

```
gtcaaactgc aacttcaagc ggaagagaga ggggttgtat ccatcaaagg agtatgtgca       60
aatcgctatc ttgccatgaa ggaagatgga agattactgg cttctaaatg tgttaccgat      120
gagtgtttct tttttgagcg actggaatct aataactaca atacttaccg gtcaaggaaa      180
tactccagtt ggtatgtggc actgaaacga actgggcagt ataaacttgg acccaaaaca      240
ggacctgggc agaaagctat acttttctt ccaatgtctg ctaagagc                    288
```

<210> SEQ ID NO 188
<211> LENGTH: 468
<212> TYPE: DNA
<213> ORGANISM: Sloth

<400> SEQUENCE: 188

```
atggcagccg ggagcatcac cacgctgccc gccctgcccg aggacggagg cagcggcgcc       60
ttaccgcccg gccacttcaa agatcccaag cggctctact gcaaaaacgg ggcttcttc      120
ctgcgtatcc atcccgacgg cagagtggac ggggtccggg agaagagcga cccccacatc      180
aaactacaac ttcaagcaga agagagaggg gttgtgtcta tcaaaggtgt gtgtgcaaac      240
cgatatcttg ctatgaagga agatggaaga ttacaggctt ctaaatgtgt aacggacgag      300
tgtttctttt tgaacgatt ggaatctaat aactacaata cgtaccgatc aaggaaatac      360
tccagttggt atgtggcact gaaacgaact gggcaatata aacttggacc caaaacagga      420
cctgggcaga aagccatact ttttcttcca atgtctgcta agagctga                   468
```

<210> SEQ ID NO 189
<211> LENGTH: 468
<212> TYPE: DNA
<213> ORGANISM: Water buffalo

<400> SEQUENCE: 189

```
atggccgccg ggagcatcac cacgctgcca ccctgccgg aggacggcgg cagcggcgct        60
ttcccgcccg gccacttcaa ggaccccaag cggctgtact gcaagaacgg ggcttcttc      120
ctgcgcatcc accccgacgg ccgagtggac ggggtccgcg agaagagcga cccacacatc      180
aaactacaac ttcaagcaga agagagaggg gttgtgtcta tcaaaggagt gtgtgcaaac      240
cgttaccttg ctatgaaaga agatggaaga ttactagctt ccaaatgtgt tacagacgag      300
tgtttctttt tgaacgatt ggagtctagt aactacaata cttaccggtc aaggaaatac      360
tccagttggt atgtggcact gaaacgaact gggcagtata aacttggacc caaaacagga      420
cctgggcaga aagctatact ttttcttcca atgtctgcta agagctga                   468
```

<210> SEQ ID NO 190
<211> LENGTH: 468
<212> TYPE: DNA
<213> ORGANISM: Dog

```
<400> SEQUENCE: 190
atggcagccg ggagcatcac cacgctgccc gccctgccgg aggacggcgg cagcggcgcc    60
ttcccgcccg gccacttcaa ggaccccaag aggctgtact gcaaaaaagg gggcttcttc   120
ctgcggatcc accccgacgg ccgggtggac ggggtccggg agaagagcga tccccacgtc   180
aaattgcaac ttcaagcaga agagagaggc gttgtgtcca tcaaaggagt atgtgcaaat   240
cgctatcttg ctatgaagga agatggaaga ttactggctt ctaaatgtgt tactgacgag   300
tgcttctttt ttgaacgatt ggaatctaat aactacaata cttaccggtc aaggaaatac   360
tccagttggt atgtggcact gaaacgaact gggcagtata aacttggacc aaaaacagga   420
cctgggcaga aagctatact ttttcttcca atgtctgcta agagctga                468

<210> SEQ ID NO 191
<211> LENGTH: 465
<212> TYPE: DNA
<213> ORGANISM: Norway rat

<400> SEQUENCE: 191
atggctgccg gcagcatcac ttcgcttccc gcactgccgg aggacggcgg cggcgccttc    60
ccacccggcc acttcaagga tcccaagcgg ctctactgca gaacggcgg cttcttcctg   120 cgcatccatc cagacggccg cgtgacggc gtccggagag agagcgaccc acacgtcaaa   180
ctacagctcc aagcagaaga gagaggagtt gtgtccatca agggagtgtg tgcgaaccgg   240
tacctggcta tgaaggaaga tggacggctg ctggcttcta agtgtgttac agaagagtgt   300
ttcttctttg aacgcctgga gtccaataac tacaacactt accggtcacg gaaatactcc   360
agttggtatg tggcactgaa acgaactggg cagtataaac tcggatccaa aacggggcct   420
ggacagaagg ccatactgtt tcttccaatg tctgctaaga gctga                  465

<210> SEQ ID NO 192
<211> LENGTH: 405
<212> TYPE: DNA
<213> ORGANISM: Naked mole-rat

<400> SEQUENCE: 192
ccacccggcc acttcaagga cccaaagcgg ctgtactgca aaaacggggg cttcttcctg    60
cgcatccacc ccgacggccg cgtggacggg gtccggagag agagcgaccc tcacgtcaaa   120
ctacaacttc aagcagaaga gagaggagtt gtgtctatta agggagtgtg tgcgaaccgt   180
taccttgcta tgaaggaaga tggaagatta ctggcttcta aatgtgttac agatgagtgt   240
ttcttttttg aacgattgga atctaataac tacaatactt atcggtcaag gaaatactcc   300
agttggtatg tggcactgaa acgaactgga caatataaac ttggatccaa aacaggaccg   360
gggcagaaag ctatactttt tcttccaatg tctgctaaga gctga                  405

<210> SEQ ID NO 193
<211> LENGTH: 468
<212> TYPE: DNA
<213> ORGANISM: Bushbaby

<400> SEQUENCE: 193
atggcagccg ggagcatcac cacgctgccc tccctgcccg aggacggcgg cagcgacgcc    60
tttccgcccg gccacttcaa ggaccccaag cgactgtact gcaaaaacgg gggcttcttc   120
ctgcgcatcc accccgacgg ccgagtggac ggggtccggg agaagagcga cccttacatc   180
```

| | |
|---|---|
| aaactacaac ttcaagcaga agagagagga gttgtgtcta tcaaaggagt gtgtgcgaac | 240 |
| cgttaccttg ctatgaagga agacggaaga ttgctggctt ctaaattgat tacagacgag | 300 |
| tgcttctttt ttgaacgact ggaatctaat aactacaata cttaccggtc aagaaaatac | 360 |
| tccagttggt atgtggcact gaaacgaact ggacagtata aacttggatc caaaacagga | 420 |
| cctgggcaga aagctatact ttttcttcca atgtctgcta agagctga | 468 |

<210> SEQ ID NO 194
<211> LENGTH: 465
<212> TYPE: DNA
<213> ORGANISM: House mouse

<400> SEQUENCE: 194

| | |
|---|---|
| atggctgcca gcggcatcac ctcgcttccc gcactgccgg aggacggcgg cgccgccttc | 60 |
| ccaccaggcc acttcaagga ccccaagcgg ctctactgca agaacggcgg cttcttcctg | 120 |
| cgcatccatc ccgacggccg cgtggatggc gtccgcgaga gagcgaccc acacgtcaaa | 180 |
| ctacaactcc aagcagaaga gagaggagtt gtgtctatca agggagtgtg tgccaaccgg | 240 |
| taccttgcta tgaaggaaga tggacggctg ctggcttcta agtgtgttac agaagagtgt | 300 |
| ttcttctttg aacgactgga atctaataac tacaatactt accggtcacg gaaatactcc | 360 |
| agttggtatg tggcactgaa acgaactggg cagtataaac tcggatccaa acgggacct | 420 |
| ggacagaagg ccatactgtt tcttccaatg tctgctaaga gctga | 465 |

<210> SEQ ID NO 195
<211> LENGTH: 432
<212> TYPE: DNA
<213> ORGANISM: Squirrel

<400> SEQUENCE: 195

| | |
|---|---|
| ctgcccgagg acggcggcgg cggcgccttc ccgcccggcc actttaagga ccccaagcgg | 60 |
| ctctactgca aaaacggagg cttcttcctg cgcatccacc ccgacggccg agtggacggg | 120 |
| gtccgggaga agagcgaccc ccacatcaag ctccagcttc aagccgaaga ccgaggggtt | 180 |
| gtgtccatca agggagtgtg tgcaaaccga tacctggcca tgaaggagga cgggaggctc | 240 |
| ctggcttcta aatgtgttac ggacgagtgt ttctttttg aacgactgga atcaaataac | 300 |
| tacaatactt accggtcaag gaaatactcc agttggtatg tggccctgaa acgaacaggg | 360 |
| cagtataaac ttggatccaa acaggacct gggcagaaag ctatactttt tcttccaatg | 420 |
| tctgctaaga gc | 432 |

<210> SEQ ID NO 196
<211> LENGTH: 318
<212> TYPE: DNA
<213> ORGANISM: Domestic cat

<400> SEQUENCE: 196

| | |
|---|---|
| ccacttcaag gaccccaagc gtctgtactg caaaaacggg ggcttcttcc tgcgcatcca | 60 |
| ccccgacggc cgagtggatg gggtccggga agagcgac cctcacatca aactgcaact | 120 |
| tcaggcagaa gagagagggg ttgtgtccat caaaggagtc tgtgcaaacc gctatcttgc | 180 |
| catgaaggaa gatggaagat tactggcttc taaatgtgtt acggacgagt gtttcttttt | 240 |
| tgaacgattg gaatctaata actacaaatac ttatcggtca aggaaatact ccagctggta | 300 |
| tgtggcactg aaacgaac | 318 |

```
<210> SEQ ID NO 197
<211> LENGTH: 288
<212> TYPE: DNA
<213> ORGANISM: Guinea pig

<400> SEQUENCE: 197
gttaaactac aacttcaagc cgaagacaga ggagttgtgt ctatcaaggg agtctgtgcg      60
aaccgttacc ttgctatgaa ggaagacgga agattattgg cttccaaatg tgttacagat    120
gaatgtttct tttttgaacg actggaatct aataactaca acacttaccg gtcaaggaaa    180
tactccagtt ggtatgtggc actgaaacga actggacaat ataaacttgg gtccaaaaca    240
ggaccagggc agaaagccat acttttttctt ccaatgtctg cgaagagc                288

<210> SEQ ID NO 198
<211> LENGTH: 471
<212> TYPE: DNA
<213> ORGANISM: Tasmanian devil

<400> SEQUENCE: 198
atggccgcgg gcagcatcac cacgttgccg gccctggccg gggatggagc cagcggggc      60 gccttttcccc cgggccactt ccaggacccc aagcggctgt actgcaagaa cggaggcttc    120
ttcttgcgca tccatcccga cggtcacgtg acggcatcc gcgagaagag cgatccgcac     180
attaaacttc agcttcaggc agaagagaga ggagtagtgt ctattaaagg agtttgtgcc    240
aaccgctatc ttgccatgaa agaggatggc agattactgg ctctgaaatg tgtgactgaa    300
gagtgtttct tctttgaacg tctagagtcc aacaattaca acacttatcg ctcaaggaaa    360
tactccaatt ggtatgtggc attgaaacgc acaggccagt ataagcttgg atccaagact    420
ggaccagggc agaaagccat ccttttcctt cccatgtctg ctaagagctg a              471

<210> SEQ ID NO 199
<211> LENGTH: 471
<212> TYPE: DNA
<213> ORGANISM: Gray short-tailed opossum

<400> SEQUENCE: 199
atggccgcag gcagcatcac cacgctgcca gccctgtccg ggacggagg cggcggggc       60 gccttttcccc cgggccactt caaggacccc aagcggctgt actgcaagaa cggaggcttc    120
ttcctgcgca tccaccccga cggccgtgtg acggcatcc gcgagaagag cgacccgaac     180
attaaactac aacttcaggc agaagagaga ggagtggtgt ctattaaagg agtatgtgcc    240
aatcgctatc ttgccatgaa ggaagatgga agattattgg ctttgaaata tgtgaccgaa    300
gagtgtttct ttttcgaacg cttggagtcc aacaactaca acacttatcg ctcgaggaaa    360
tattccaatt ggtacgtggc actgaaacga acggggcagt acaagcttgg atccaagact    420
ggcccggggc agaaagccat ccttttcctc cccatgtctg ctaagagctg a              471

<210> SEQ ID NO 200
<211> LENGTH: 468
<212> TYPE: DNA
<213> ORGANISM: Rabbit

<400> SEQUENCE: 200
atggcagccg agagcatcac cacgctgccc gccctgccgg aggatggagg cagcggcgcc     60
ttcccgcccg ccacttcaa ggaccccaag cggctgtact gcaaaaacgg ggtttcttc     120 ctgcgtatcc accccgacgg ccgcgtggac gggtccggg agaagagcga cccacacatc    180
```

| | |
|---|---|
| aaattacaac ttcaagcaga agagagagga gttgtatcca tcaaggtgtg tgtgcaaac | 240 |
| cgttaccttg ctatgaagga agatggaaga ctgctggctt ctaaatgtgt tacagacgag | 300 |
| tgcttctttt ttgaacgact ggagtctaat aactacaata cttaccggtc aaggaaatat | 360 |
| tccagctggt atgtggcact gaaacgaact gggcagtata aacttggatc caaaacagga | 420 |
| cctgggcaga aggctatact ttttcttcca atgtctgcta agagctga | 468 |

<210> SEQ ID NO 201
<211> LENGTH: 375
<212> TYPE: DNA
<213> ORGANISM: Turkey

<400> SEQUENCE: 201

| | |
|---|---|
| cggctctact gtaagaacgg cggcttcttc ctgcgcatca atcccgacgg cagagtggac | 60 |
| ggcgtccgcg agaagagcga tccgcacatc aaactgcagc ttcaggcaga agaaagagga | 120 |
| gtggtatcaa tcaaaggtgt aagtgcaaac cgctttctgg ctatgaagga ggatggcaga | 180 |
| ttgctggcac tgaaatgtgc aacagaagaa tgtttctttt tgagcgtttt ggaatctaat | 240 |
| aattataaca cttaccggtc acggaagtac tctgattggt atgtggcact gaaaagaact | 300 |
| ggacagtaca agcccggacc aaaaactgga cctggacaga agctatcctt ttttcttcca | 360 |
| atgtctgcta aaagc | 375 |

<210> SEQ ID NO 202
<211> LENGTH: 477
<212> TYPE: DNA
<213> ORGANISM: Gallus gallus

<400> SEQUENCE: 202

| | |
|---|---|
| atggcggcgg gggcggcggg gagcatcacc acgctgccgg cgctgcccga cgacgggggc | 60 |
| ggcggcgctt ttcccccgg gcacttcaag gaccccaagc ggctctactg caagaacggc | 120 |
| ggcttcttcc tgcgcatcaa ccccgacggc agggtggacg gcgtccgcga gaagagcgat | 180 |
| ccgcacatca aactgcagct tcaagcagaa gaaagaggag tagtatcaat caaaggcgta | 240 |
| agtgcaaacc gctttctggc tatgaaggag gatggcagat tgctggcact gaaatgtgca | 300 |
| acagaggaat gtttcttttt cgagcgcttg gaatctaata actataacac ttaccggtca | 360 |
| cggaagtact ctgattggta tgtggcactg aaaaggactg gacagtacaa gcccggacca | 420 |
| aaaactggac ctggacagaa agctatcctt tttcttccaa tgtctgctaa aagctga | 477 |

<210> SEQ ID NO 203
<211> LENGTH: 462
<212> TYPE: DNA
<213> ORGANISM: Zebra finch

<400> SEQUENCE: 203

| | |
|---|---|
| atggcggcgg cggggggcat cgctacgctg cccgacgacg gcggcagcgg cgcctttccc | 60 |
| ccggggcact tcaaggaccc caagcgcctg tactgcaaga acggcggctt cttcctgcgc | 120 |
| atcaaccccg acgggaaggt ggacggcgtc cgcgagaaga gcgacccgca catcaagctg | 180 |
| cagcttcagg cggaggaacg aggagtggtg tccatcaaag tgtcagtgc caatcgcttc | 240 |
| ctggccatga agaggatgg cagattgctg gccttgaaat atgcaacaga agaatgtttc | 300 |
| ttttttgaac gtttggaatc caataactat aacacttacc ggtcacggaa atactcggat | 360 |
| tggtatgtgg cactgaaaag aactggacag tacaaacctg gaccaaaaac tggacctgga | 420 |
| cagaaagcta tccttttcct tccatgtctct gctaaaagct ga | 462 |

<210> SEQ ID NO 204
<211> LENGTH: 468
<212> TYPE: DNA
<213> ORGANISM: Japanese firebelly newt

<400> SEQUENCE: 204

```
atggctgctg ggagcatcac cagtctccct gccctacccg aggacgggaa tggcggcacc      60
ttcacacccg gcggattcaa agagccgaag aggctgtact gcaagaacgg gggcttcttt     120
ctccggatca actccgacgg caaggtggac ggagcccggg agaagagcga ctcctacatt     180
aaactgcagc ttcaagcaga gagcgcggt gtggtgtcca tcaagggagt atgtgcaaac     240
cgctatctcg ctatgaagga tgatggcagg ctgatggcgc tgaaatggat aaccgatgaa     300
tgcttctttt tcgagcgact ggagtccaac aactataaca cgtatcgatc acggaaatat     360
tccgattggt atgtggcgct gaaaagaact gggcaataca aaaatggatc aaaaaccgga     420
gcaggacaga aagcaatcct ttttctaccc atgtcggcca agagttga                 468
```

<210> SEQ ID NO 205
<211> LENGTH: 468
<212> TYPE: DNA
<213> ORGANISM: African clawed frog

<400> SEQUENCE: 205

```
atggcggcag ggagcatcac aactctgcca actgaatccg aggatggggg aaacactcct      60
ttttcaccag ggagttttaa agaccccaag aggctctact gcaagaacgg gggcttcttc     120
ctcaggataa actcagacgg gagagtggac gggtcaaggg acaaaagtga ctcgcacata     180
aaattacagc tacaagctgt agagcgggga gtggtatcaa taagggaat cactgcaaat     240
cgctaccttg ccatgaagga agatgggaga ttaacatcgc tgaggtgtat aacagatgaa     300
tgcttctttt ttgaacgact ggaagctaat aactacaaca cttaccggtc tcggaaatac     360
agcagctggt atgtggcact aaagcgaacc gggcagtaca aaaatggatc gagcactgga     420
ccgggacaaa aagctatttt atttctccca atgtccgcaa agagctga                 468
```

<210> SEQ ID NO 206
<211> LENGTH: 471
<212> TYPE: DNA
<213> ORGANISM: White-eared opossum

<400> SEQUENCE: 206

```
atggcagcag gcagcatcac cacattgccg gccctgtccg gggacggagg cggcggggga      60
gcctttcctc caggccactt caaggacccc aagcggctgt actgcaagaa cggaggcttc     120
ttcctgcgca tccaccccga cggccgcgtg acggcatcc gcgagaagag cgacccgaac     180
attaaactac aacttcaggc agaagagaga ggagtagtgt ctattaaagg agtatgtgcc     240
aaccgatatc ttgccatgaa ggaggatggc agattattgg ctttgaaata tgtgaccgaa     300
gagtgtttct tttttgaacg tttggagtcc aacaactaca cacttatcg ctcaagaaaa     360
tattccaatt ggtatgtggc actgaaacga acggggcagt ataagcttgg atccaagact     420
ggccccgggc agaaagccat cctttttctcc ccatgtctgc taagatgctg a             471
```

<210> SEQ ID NO 207
<211> LENGTH: 288
<212> TYPE: DNA
<213> ORGANISM: Microbat

<400> SEQUENCE: 207

```
gtcaaactcc aacttcaagc agaagagaga ggggtcgtgt ctatcaaagg agtgtgtgcc    60
aaccgctatc tcgctatgaa ggaggacggc cggttacagg cttctaaatg tgttacggat   120
gagtgtttct tttttgaacg gttggaatcc aataactaca acacttaccg gtcaagaaag   180
tactccagtt ggtatgtggc attgaagcgg aatgggcagt ataaacttgg acccaaaaca   240
ggacctggcc agaaagccat acttttttctt cccatgtctg ctaagagc               288
```

<210> SEQ ID NO 208
<211> LENGTH: 420
<212> TYPE: DNA
<213> ORGANISM: Anole lizard

<400> SEQUENCE: 208

```
gcggcggcgg cctctttccc cccgggcccc ttcaaggacc ccaagcgcct ctactgcaag    60
aacgggggct tcttcctgcg gatcaacccc gacggcggcg tggacggcgt ccgagagaag   120
agcgacccca acatcaaatt gctgctccag gcagaggaga gaggtgtagt gtccatcaaa   180
ggtgtatgcg caaaccgttt cctggctatg aatgaagacg tcgattgtt agcactgaaa    240
tacgtaacag atgaatgctt ctttttttgaa cgcttggaat ctaataatta caatacttat   300
cggtctcgta ataccgtga ttggtacatt gcactgaaac gaactggtca gtacaaactt    360
ggaccaaaaa ctggacgagg ccagaaagct atccttttcc ttccaatgtc tgccaaaagt   420
```

<210> SEQ ID NO 209
<211> LENGTH: 282
<212> TYPE: DNA
<213> ORGANISM: Armadillo

<400> SEQUENCE: 209

```
atggcagccg ggagcatcac cacgctgccc gctctgcccg aggacggcgg cagcggcgcc    60
ttcccgccgg gccacttcaa ggaccccaag cggctgtact gcaaaaacgg ggcttcttc    120
ctgcgcatcc atcccgacgg ccgagtggac ggggtccggg agaagagcga ccctaacatc   180
aaactacaac ttcaagcaga agagagaggg gtcgtgtcta tcaaaggcgt gtgtgcgaac   240
cgttaccttg ctatgcggga agacggaaga ctccaggcgt ct                     282
```

<210> SEQ ID NO 210
<211> LENGTH: 567
<212> TYPE: DNA
<213> ORGANISM: Tree shrew

<400> SEQUENCE: 210

```
gcggggtta gagctgagag ggaggaggca ccggggagcg gtgacagccg ggggaccgat     60
cccgccgcgc gttcgctcat caggaggccg gatgctgcag cgcgagaggc gcttcttgga   120
gccaggagcc gggttcaggg cagctccacc tcctggccag cctcgtcacg aaccgggatc   180
aagttgccgg acgactcagg tcaaggaatg ggcggctatc ctctggaccg cccgagccgg   240
agcacagggc gagggctggg cggtgccccg gaccctgccg taaaactaca gcttcaagcg   300
gaagagagag gggtcgtgtc tatcaaagga gtgtgtgcaa accgttacct ggccatgaag   360
gaggatgggc gactgctggc ttctaaatgt gttacagatg agtgtttctt ttttgaacga   420
ctggaatcta ataactacaa tacttaccgg tcccgaaagt actccagctg gtatgtggca   480
ctgaaacgaa ctgggcagta taaacttgga tccaaaacag gacctgggca gaaagctata   540
cttttttcttc caatgtctgc taaaagc                                     567
```

<210> SEQ ID NO 211
<211> LENGTH: 465
<212> TYPE: DNA
<213> ORGANISM: Western clawed frog

<400> SEQUENCE: 211

| | | | | | |
|---|---|---|---|---|---|
| atggcagcag | gaagcatcac | aaccctacca | accgaatctg | aggatggaaa | cactcctttc | 60 |
| ccaccgggga | actttaagga | ccccaagagg | ctctactgca | agaatggggg | ctacttcctc | 120 |
| aggattaact | cagacgggag | agtggacgga | tcaagggata | aaagtgactt | acacataaaa | 180 |
| ttacagctac | aagcagtaga | gcggggagtg | gtatcaataa | agggaatcac | tgcaaatcgc | 240 |
| taccttgcca | tgaaggaaga | tgggagatta | acatcgctga | agtgtataac | agatgaatgc | 300 |
| ttcttttatg | aacgattgga | agctaataac | tacaacactt | accggtctcg | gaaaaacaac | 360 |
| agctggtatg | tggcactaaa | gcgaactggg | cagtataaaa | atggatcgac | cactggacca | 420 |
| ggacaaaaag | ctattttgtt | tctcccaatg | tcagcaaaaa | gctga | | 465 |

<210> SEQ ID NO 212
<211> LENGTH: 468
<212> TYPE: DNA
<213> ORGANISM: Coelacanth

<400> SEQUENCE: 212

| | | | | | |
|---|---|---|---|---|---|
| atggctgcgg | gaggaatcac | taccctgccg | gcggtacctg | aggatggagg | cagcagcacc | 60 |
| ttccctccag | gaaacttcaa | ggagcccaag | agactttact | gtaagaatgg | aggctatttc | 120 |
| ttaaggataa | acccccgatgg | aagagtggat | ggaacaaggg | agaaaaatga | tccttatata | 180 |
| aaattacaac | tgcaagctga | atctatagga | gtggtgtcga | taagggagt | ttgttcaaac | 240 |
| cgttacctag | cgatgaatga | agactgtaga | cttttggat | tgaaatatcc | aacggatgaa | 300 |
| tgtttcttcc | atgagaggct | ggagtccaac | aactacaata | cttatcgttc | aaagaagtat | 360 |
| tcggattggt | atgtggcgct | gaaacggact | ggtcagtaca | aacctgggcc | aaaaactgga | 420 |
| ctgggacaaa | aagcaatcct | tttccttccg | atgtctgcca | agagttga | | 468 |

<210> SEQ ID NO 213
<211> LENGTH: 468
<212> TYPE: DNA
<213> ORGANISM: Spotted green pufferfish

<400> SEQUENCE: 213

| | | | | | |
|---|---|---|---|---|---|
| atggccacgg | gagggatcac | gacgcttcca | tccacacctg | aagacggcgg | cagcagcggc | 60 |
| tttcctcccg | gcagcttcaa | ggatcccaaa | aggctctact | gtaaaaacgg | aggtttcttc | 120 |
| ctgaggatca | agtccgacgg | ggtcgtggac | ggaatccggg | agaagagtga | ccccacata | 180 |
| aagcttcagc | tccaggcgac | ctctgtgggg | gaggtggtca | tcaaggggggt | gtgcgctaac | 240 |
| cgctatctgg | ccatgaacag | agatggacgg | ctgttcggaa | cgaaacgagc | cacggacgaa | 300 |
| tgccatttct | tagagcggct | tgagagcaac | aactacaaca | cttaccgctc | caggaagtac | 360 |
| ccaaccatgt | ttgtgggact | gacgcggacg | ggccagtaca | agtctgggag | caaaactgga | 420 |
| ccgggccaaa | aggccatcct | ttttcttccg | atgtccgcca | aatgctaa | | 468 |

<210> SEQ ID NO 214
<211> LENGTH: 468
<212> TYPE: DNA
<213> ORGANISM: Stickleback

<400> SEQUENCE: 214

```
atggccacgg caggcttcgc gacgcttccc tccacgcccg aagacggcgg cagcggcggc    60
ttcaccccgg ggggattcaa ggatcccaag aggctgtact gcaaaaacgg gggcttcttc   120
ttgaggatca ggtccgacgg aggtgtagat ggaatcaggg agaagagcga cgcccacata   180
aagctccaaa tccaggcgac gtcggtgggg gaggtggtca tcaaggagt ctgtgccaac    240
cgctatctgg ccatgaacag agacggccgg ctgttcggag tgagacgggc gacggacgaa   300
tgctacttcc tggagcggct ggagagtaac aactacaaca cctaccgctc caggaagtac   360
cccggcatgt acgtggctct gaagcggacc ggccagtaca agtccgggag caaaaccgga   420
cccggtcaaa aggccattct gttcctcccc atgtcggcta agtgctaa                468
```

<210> SEQ ID NO 215
<211> LENGTH: 468
<212> TYPE: DNA
<213> ORGANISM: Fugu rubripes

<400> SEQUENCE: 215

```
atggccacgg gagggatcac aacacttcca tccacacctg aagacggcgg cagcggcggt    60
tttcctcccg ggagcttcaa ggatcccaaa aggctgtact gtaaaaacgg cggcttcttc   120
ctgaggatca ggtccgacgg ggccgtgggac ggaacccggg agaagactga ccccccacata  180
aagcttcagc tccaggcgac ctctgtgggg gaggtggtca tcaagggggt ttgtgctaat   240
cgttatctgg ccatgaacag agatggacga ctgtttggaa tgaaacgagc gacggatgaa   300
tgccacttct tagagcggct cgagagcaac aactacaaca cctaccgctc caggaagtac   360
cccaacatgt ttgtgggact gacgcgaact ggcaactaca agtctgggac taaaactgga   420
ccgggccaaa aggccatcct ctttcttccg atgtcggcca aatactaa                468
```

<210> SEQ ID NO 216
<211> LENGTH: 468
<212> TYPE: DNA
<213> ORGANISM: Rainbow trout

<400> SEQUENCE: 216

```
atggccacag gagaaatcac cactctaccc gccacacctg aagatggagg cagtggcggc    60
ttccttccag gaaactttaa ggagcccaag aggttgtact gtaaaaatgg aggctacttc   120
ttgaggataa actctaacgg aagcgtggac gggatcagag ataagaacga cccccacaat   180
aagcttcaac tccaggcgac ctcagtgggg gaagtagtaa tcaaggggt ctcagccaac    240
cgctatctgg ccatgaatgc agatggaaga ctgtttggac cgagacggac aacagatgaa   300
tgctacttca tggagaggct ggagagtaac aactacaaca cctaccgctc tcgaaagtac   360
cctgaaatgt atgtggcact gaaaaggact ggccagtaca agtcaggatc caaaactgga   420
cccggccaaa aagccatcct cttcctcccc atgtcagcca gacgctga                468
```

<210> SEQ ID NO 217
<211> LENGTH: 453
<212> TYPE: DNA
<213> ORGANISM: Salmon

<400> SEQUENCE: 217

```
atggccacag gagaaatcac cactctaccc gccacacctg aagatggagg cagtggcggc    60
ttccctccag gaaactttaa ggatcccaag aggctgtact gtaaaaacgg gggctacttc   120
ttgagaataa actctaatgg aagcgtggac gggatccgag agaagaacga ccccccacaaa  180
```

```
cagcctcaat tgtcagggc atggactctt caaggtgtca aacgttccac agggatgctg      240
gcccatgttg actccaacgc ttcccacaat tgtgtcaagg tggctggatg ttctttggga      300
gaatttggca gtatgtccaa ccggcctcat aaccgcagac cacgtgtagc tacaccagcc      360
caggacctcc acatccggct tcttcatcta cgggatcgtc tgaaaccagc cacccgaaca      420
gctgataaaa ctgaggagta tttctgtctg taa                                   453
```

```
<210> SEQ ID NO 218
<211> LENGTH: 465
<212> TYPE: DNA
<213> ORGANISM: Zebrafish

<400> SEQUENCE: 218
atggccaccg agggatcac cacactcccg gccgctccgg acgccgaaaa cagcagcttt       60
cccgcgggca gcttcaggga tcccaagcgc ctgtactgca aaaacggagg attcttcctg     120
cggatcaacg cggacggccg agtggacgga gcccgagaca agagcgaccc gcacattcgt     180
ctgcagctgc aggcgacggc agtgggtgaa gtactcatta aaggcatctg taccaaccgt     240
ttccttgcca tgaacgcaga cggacgactg ttcgggacga aaaggaccac agatgaatgt     300
tatttcctgg agcgcctgga gtccaacaac tacaacacat acagatcccg caagtatccc     360
gactggtacg tggctctgaa agaaccggc cagtataaaa gcggctctaa aaccagcccg      420
ggacagaagg ccatcctgtt tctgcccatg tcggccaaat gctga                     465
```

```
<210> SEQ ID NO 219
<211> LENGTH: 468
<212> TYPE: DNA
<213> ORGANISM: Nile tilapia

<400> SEQUENCE: 219
atggccacgg aggaatcac aacacttccc gctacacctg aagacggcgg cagcagcggc       60
tttcctcctg ggaacttcaa ggaccctaaa aggctgtact gtaaaaatgg tggcttcttc     120
ttgaggataa aatctgatgg aggagtggat ggaatacgag agaaaaacga cccccacata     180
aagcttcaac tccaggcgac ctcagtggga gaagtggtca tcaaagggat tgtgcaaac      240 cgatatctgg caatgaacag agatggacga ctgtttggag cgagaagagc aacagatgag     300
tgctacttct tagagcggct cgagagcaac aactacaaca cctaccgctc caggaagtac     360
ccaaacatgt acgtggcgct gaagcggact ggccagtaca gtctggaag caaaactgga      420 ccgggtcaaa aggcaattct ctttctccca atgtctgcta aatgctaa                  468
```

```
<210> SEQ ID NO 220
<211> LENGTH: 468
<212> TYPE: DNA
<213> ORGANISM: Medaka

<400> SEQUENCE: 220
atggctacgg agaaatcac aacacttccc tccccagctg aaaacagcag aagcgatggc       60
tttcctccag ggaactacaa ggatcctaag aggctctact gtaaaaatgg aggtttgttt     120
ttgaggatta aacctgatgg aggagtggat ggaatccggg aaaaaaaga tccccacgtt      180 aagcttcgcc ttcaggctac ctcagcggga gaggtggtga tcaaaggagt tgttcaaac     240 agatatctgg cgatgcatgg agatggacgt ctatttggag tgagacaagc aacagaggaa     300 tgctactttct tggagcgact agagagcaac aactataaca cctatcgctc taaaaagtac    360
```

```
ccaaacatgt acgtggcact gaagcggaca ggccagtaca aacctggaaa caaaactgga    420
ccaggtcaaa aggccattct ctttctgcct atgtctgcca agtactaa                 468
```

<210> SEQ ID NO 221
<211> LENGTH: 206
<212> TYPE: PRT
<213> ORGANISM: Homo sapiens

<400> SEQUENCE: 221

```
Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Gly Ala Ala Ala Pro
            20                  25                  30

Thr Ala Pro Asn Gly Thr Leu Glu Ala Glu Leu Glu Arg Arg Trp Glu
        35                  40                  45

Ser Leu Val Ala Leu Ser Leu Ala Arg Leu Pro Val Ala Ala Gln Pro
    50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
                85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
        115                 120                 125

Phe Gly Val Ala Ser Arg Phe Phe Val Ala Met Ser Ser Lys Gly Lys
    130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
            180                 185                 190

Val Ser Pro Thr Met Lys Val Thr His Phe Leu Pro Arg Leu
        195                 200                 205
```

<210> SEQ ID NO 222
<211> LENGTH: 268
<212> TYPE: PRT
<213> ORGANISM: Homo sapiens

<400> SEQUENCE: 222

```
Met Ser Leu Ser Phe Leu Leu Leu Phe Phe Ser His Leu Ile Leu
1               5                   10                  15

Ser Ala Trp Ala His Gly Glu Lys Arg Leu Ala Pro Lys Gly Gln Pro
            20                  25                  30

Gly Pro Ala Ala Thr Asp Arg Asn Pro Arg Gly Ser Ser Ser Arg Gln
        35                  40                  45

Ser Ser Ser Ser Ala Met Ser Ser Ser Ala Ser Ser Pro Ala
    50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
                85                  90                  95

Ile Gly Phe His Leu Gln Ile Tyr Pro Asp Gly Lys Val Asn Gly Ser
            100                 105                 110
```

His Glu Ala Asn Met Leu Ser Val Leu Glu Ile Phe Ala Val Ser Gln
            115                 120                 125

Gly Ile Val Gly Ile Arg Gly Val Phe Ser Asn Lys Phe Leu Ala Met
        130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
            180                 185                 190

Asn Lys Arg Gly Lys Ala Lys Arg Gly Cys Ser Pro Arg Val Lys Pro
        195                 200                 205

Gln His Ile Ser Thr His Phe Leu Pro Arg Phe Lys Gln Ser Glu Gln
    210                 215                 220

Pro Glu Leu Ser Phe Thr Val Thr Val Pro Glu Lys Lys Pro Pro
225                 230                 235                 240

Ser Pro Ile Lys Pro Lys Ile Pro Leu Ser Ala Pro Arg Lys Asn Thr
                245                 250                 255

Asn Ser Val Lys Tyr Arg Leu Lys Phe Arg Phe Gly
            260                 265

<210> SEQ ID NO 223
<211> LENGTH: 208
<212> TYPE: PRT
<213> ORGANISM: Homo sapiens

<400> SEQUENCE: 223

Met Ala Leu Gly Gln Lys Leu Phe Ile Thr Met Ser Arg Gly Ala Gly
1               5                   10                  15

Arg Leu Gln Gly Thr Leu Trp Ala Leu Val Phe Leu Gly Ile Leu Val
            20                  25                  30

Gly Met Val Val Pro Ser Pro Ala Gly Thr Arg Ala Asn Asn Thr Leu
        35                  40                  45

Leu Asp Ser Arg Gly Trp Gly Thr Leu Leu Ser Arg Ser Arg Ala Gly
50                  55                  60

Leu Ala Gly Glu Ile Ala Gly Val Asn Trp Glu Ser Gly Tyr Leu Val
65                  70                  75                  80

Gly Ile Lys Arg Gln Arg Arg Leu Tyr Cys Asn Val Gly Ile Gly Phe
                85                  90                  95

His Leu Gln Val Leu Pro Asp Gly Arg Ile Ser Gly Thr His Glu Glu
            100                 105                 110

Asn Pro Tyr Ser Leu Leu Glu Ile Ser Thr Val Glu Arg Gly Val Val
        115                 120                 125

Ser Leu Phe Gly Val Arg Ser Ala Leu Phe Val Ala Met Asn Ser Lys
130                 135                 140

Gly Arg Leu Tyr Ala Thr Pro Ser Phe Gln Glu Glu Cys Lys Phe Arg
145                 150                 155                 160

Glu Thr Leu Leu Pro Asn Asn Tyr Asn Ala Tyr Glu Ser Asp Leu Tyr
                165                 170                 175

Gln Gly Thr Tyr Ile Ala Leu Ser Lys Tyr Gly Arg Val Lys Arg Gly
            180                 185                 190

Ser Lys Val Ser Pro Ile Met Thr Val Thr His Phe Leu Pro Arg Ile
        195                 200                 205

<210> SEQ ID NO 224
<211> LENGTH: 208
<212> TYPE: PRT
<213> ORGANISM: Homo sapiens

<400> SEQUENCE: 224

```
Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Gly Leu Pro Arg Gly
        35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205
```

<210> SEQ ID NO 225
<211> LENGTH: 207
<212> TYPE: PRT
<213> ORGANISM: Homo sapiens

<400> SEQUENCE: 225

```
Met Ala Glu Val Gly Gly Val Phe Ala Ser Leu Asp Trp Asp Leu His
1               5                   10                  15

Gly Phe Ser Ser Leu Gly Asn Val Pro Leu Ala Asp Ser Pro Gly
            20                  25                  30

Phe Leu Asn Glu Arg Leu Gly Gln Ile Glu Gly Lys Leu Gln Arg Gly
        35                  40                  45

Ser Pro Thr Asp Phe Ala His Leu Lys Gly Ile Leu Arg Arg Arg Gln
    50                  55                  60

Leu Tyr Cys Arg Thr Gly Phe His Leu Glu Ile Phe Pro Asn Gly Thr
65                  70                  75                  80

Val His Gly Thr Arg His Asp His Ser Arg Phe Gly Ile Leu Glu Phe
                85                  90                  95

Ile Ser Leu Ala Val Gly Leu Ile Ser Ile Arg Gly Val Asp Ser Gly
            100                 105                 110

Leu Tyr Leu Gly Met Asn Glu Arg Gly Glu Leu Tyr Gly Ser Lys Lys
        115                 120                 125

Leu Thr Arg Glu Cys Val Phe Arg Glu Gln Phe Glu Glu Asn Trp Tyr
```

```
            130                 135                 140
Asn Thr Tyr Ala Ser Thr Leu Tyr Lys His Ser Asp Ser Glu Arg Gln
145                 150                 155                 160

Tyr Tyr Val Ala Leu Asn Lys Asp Gly Ser Pro Arg Glu Gly Tyr Arg
                165                 170                 175

Thr Lys Arg His Gln Lys Phe Thr His Phe Leu Pro Arg Pro Val Asp
                180                 185                 190

Pro Ser Lys Leu Pro Ser Met Ser Arg Asp Leu Phe His Tyr Arg
            195                 200                 205

<210> SEQ ID NO 226
<211> LENGTH: 211
<212> TYPE: PRT
<213> ORGANISM: Homo sapiens

<400> SEQUENCE: 226

Met Ala Pro Leu Ala Glu Val Gly Gly Phe Leu Gly Gly Leu Glu Gly
1               5                   10                  15

Leu Gly Gln Gln Val Gly Ser His Phe Leu Pro Pro Ala Gly Glu
                20                  25                  30

Arg Pro Pro Leu Leu Gly Glu Arg Arg Ser Ala Ala Glu Arg Ser Ala
            35                  40                  45

Arg Gly Gly Pro Gly Ala Ala Gln Leu Ala His Leu His Gly Ile Leu
        50                  55                  60

Arg Arg Arg Gln Leu Tyr Cys Arg Thr Gly Phe His Leu Gln Ile Leu
65                  70                  75                  80

Pro Asp Gly Ser Val Gln Gly Thr Arg Gln Asp His Ser Leu Phe Gly
                85                  90                  95

Ile Leu Glu Phe Ile Ser Val Ala Val Gly Leu Val Ser Ile Arg Gly
                100                 105                 110

Val Asp Ser Gly Leu Tyr Leu Gly Met Asn Asp Lys Gly Glu Leu Tyr
            115                 120                 125

Gly Ser Glu Lys Leu Thr Ser Glu Cys Ile Phe Arg Glu Gln Phe Glu
130                 135                 140

Glu Asn Trp Tyr Asn Thr Tyr Ser Ser Asn Ile Tyr Lys His Gly Asp
145                 150                 155                 160

Thr Gly Arg Arg Tyr Phe Val Ala Leu Asn Lys Asp Gly Thr Pro Arg
                165                 170                 175

Asp Gly Ala Arg Ser Lys Arg His Gln Lys Phe Thr His Phe Leu Pro
                180                 185                 190

Arg Pro Val Asp Pro Glu Arg Val Pro Glu Leu Tyr Lys Asp Leu Leu
            195                 200                 205

Met Tyr Thr
    210

<210> SEQ ID NO 227
<211> LENGTH: 621
<212> TYPE: DNA
<213> ORGANISM: Homo sapiens

<400> SEQUENCE: 227
atgtcggggc ccgggacggc cgcggtagcg ctgctcccgg cggtcctgct ggccttgctg      60
gcgccctggg cgggccgagg gggcgccgcc gcacccactg cacccaacgg cacgctggag     120
gccgagctgg agcgccgctg ggagagcctg gtggcgctct cgttggcgcg cctgccggtg     180
gcagcgcagc ccaaggaggc ggccgtccag agcggcgccg cgactacctg ctgggcatc      240
```

```
aagcggctgc ggcggctcta ctgcaacgtg ggcatcggct tccacctcca ggcgctcccc    300
gacggccgca tcggcggcgc gcacgcggac acccgcgaca gcctgctgga gctctcgccc    360
gtggagcggg gcgtggtgag catcttcggc gtggccagcc ggttcttcgt ggccatgagc    420
agcaagggca agctctatgg ctcgcccttc ttcaccgatg agtgcacgtt caaggagatt    480
ctccttccca caactacaa cgcctacgag tcctacaagt accccggcat gttcatcgcc     540
ctgagcaaga tgggaagac caagaagggg aaccgagtgt cgcccaccat gaaggtcacc     600
cacttcctcc ccaggctgtg a                                              621
```

<210> SEQ ID NO 228
<211> LENGTH: 807
<212> TYPE: DNA
<213> ORGANISM: Homo sapiens

<400> SEQUENCE: 228

```
atgagcttgt ccttcctcct cctcctcttc ttcagccacc tgatcctcag cgcctgggct     60
cacggggaga agcgtctcgc ccccaaaggg caacccggac ccgctgccac tgataggaac    120
cctagaggct ccagcagcag acagagcagc agtagcgcta tgtcttcctc ttctgcctcc    180
tcctcccccg cagcttctct gggcagccaa ggaagtggct tggagcagag cagtttccag    240
tggagcccct cggggcgccg gaccggcagc ctctactgca gagtgggcat cggtttccat    300
ctgcagatct acccggatgg caaagtcaat ggatcccacg aagccaatat gttaagtgtt    360
ttggaaatat ttgctgtgtc tcaggggatt gtaggaatac gaggagtttt cagcaacaaa    420
tttttagcga tgtcaaaaaa aggaaaactc catgcaagtg ccaagttcac agatgactgc    480
aagttcaggg agcgttttca agaaaatagc tataatacct atgcctcagc aatacataga    540
actgaaaaaa caggcggga gtggtatgtg gccctgaata aaagaggaaa agccaaacga    600
gggtgcagcc cccgggttaa accccagcat atctctaccc atttcctgcc aagattcaag    660
cagtcggagc agccagaact ttctttcacg gttactgttc ctgaaaagaa aaagccacct    720
agccctatca agccaaagat tccccttcct gcacctcgga aaaataccaa ctcagtgaaa    780
tacagactca agtttcgctt tggataa                                         807
```

<210> SEQ ID NO 229
<211> LENGTH: 627
<212> TYPE: DNA
<213> ORGANISM: Homo sapiens

<400> SEQUENCE: 229

```
atggccctgg acagaaaact gttcatcact atgtcccggg gagcaggacg tctgcagggc     60
acgctgtggg ctctcgtctt cctaggcatc ctagtgggca tggtggtgcc ctcgcctgca    120
ggcacccgtg ccaacaacac gctgctggac tcgaggggct ggggcaccct gctgtccagg    180
tctcgcgcgg ggctagctgg agagattgcc ggggtgaact gggaaagtgg ctatttggtg    240
gggatcaagc ggcagcggag gctctactgc aacgtgggca tcggctttca cctccaggtg    300
ctccccgacg gccggatcag cgggacccac gaggagaacc cctacagcct gctggaaatt    360
tccactgtgg agcgaggcgt ggtgagtctc tttggagtga agtgccct cttcgttgcc     420 atgaacagta aaggaagatt gtacgcaacg cccagcttcc aagaagaatg caagttcaga    480
gaaaccctcc tgcccaacaa ttacaatgcc tacgagtcag acttgtacca agggacctac    540
attgccctga gcaaatacgg acgggtaaag cggggcagca aggtgtcccc gatcatgact    600
```
gtcactcatt tccttcccag gatctaa                                                  627

<210> SEQ ID NO 230
<211> LENGTH: 627
<212> TYPE: DNA
<213> ORGANISM: Homo sapiens

<400> SEQUENCE: 230
atggctccct taggtgaagt tgggaactat ttcggtgtgc aggatgcggt accgtttggg    60
aatgtgcccg tgttgccggt ggacagcccg gttttgttaa gtgaccacct gggtcagtcc   120
gaagcagggg ggctccccag gggacccgca gtcacggact tggatcattt aaagggatt   180 ctcaggcgga ggcagctata ctgcaggact ggatttcact tagaaatctt ccccaatggt   240
actatccagg gaaccaggaa agaccacagc cgatttggca ttctggaatt tatcagtata   300
gcagtgggcc tggtcagcat tcgaggcgtg gacagtggac tctacctcgg gatgaatgag   360 aaggggagc tgtatggatc agaaaaacta acccaagagt gtgtattcag agaacagttc   420
gaagaaaact ggtataatac gtactcatca aacctatata agcacgtgga cactggaagg   480
cgatactatg ttgcattaaa taaagatggg accccgagag aagggactag gactaaacgg   540
caccagaaat tcacacattt tttacctaga ccagtggacc ccgacaaagt acctgaactg   600
tataaggata ttctaagcca aagttga                                        627

<210> SEQ ID NO 231
<211> LENGTH: 624
<212> TYPE: DNA
<213> ORGANISM: Homo sapiens

<400> SEQUENCE: 231
atggcagagg tgggggggcgt cttcgcctcc ttggactggg atctacacgg cttctcctcg    60
tctctgggga acgtgcccctt agctgactcc ccaggtttcc tgaacgagcg cctgggccaa   120
atcgagggga agctgcagcg tggctcaccc acagacttcg cccacctgaa ggggatcctg   180
cggcgccgcc agctctactg ccgcaccggc ttccacctgg agatcttccc caacggcacg   240
gtgcacggga cccgccacga ccacagccgc ttcgaatcc tggagtttat cagcctggct   300 gtgggctga tcagcatccg gggagtggac tctggcctgt acctaggaat gaatgagcga   360
ggagaactct atgggtcgaa gaaactcaca cgtgaatgtg ttttccggga cagtttgaa   420 gaaaactggt acaacaccta tgcctcaacc ttgtacaaac attcggactc agagagacag   480
tattacgtgg ccctgaacaa agatggctca ccccggagg gatacaggac taaacgacac   540
cagaaattca ctcactttt acccaggcct gtagatcctt ctaagttgcc ctccatgtcc   600
agagacctct tcactatag gtaa                                            624

<210> SEQ ID NO 232
<211> LENGTH: 636
<212> TYPE: DNA
<213> ORGANISM: Homo sapiens

<400> SEQUENCE: 232
atggctccct tagccgaagt cgggggcttt ctgggcggcc tggagggctt gggccagcag    60
gtgggttcgc atttcctgtt gcctcctgcc ggggagcggc cgccgctgct gggcgagcgc   120
aggagcgcgg cggagcggag cgcgcgcggc gggccggggg ctgcgcagct ggcgcacctg   180
cacggcatcc tgcgccgccg gcagctctat tgccgcaccg cttccacct gcagatcctg   240 cccgacggca gcgtgcaggg caccggcag gaccacagcc tcttcggtat cttggaattc   300

```
atcagtgtgg cagtgggact ggtcagtatt agaggtgtgg acagtggtct ctatcttgga    360
atgaatgaca aggagaact  ctatggatca gagaaactta cttccgaatg catctttagg    420
gagcagtttg aagagaactg gtataacacc tattcatcta acatatataa acatggagac    480
actggccgca ggtattttgt ggcacttaac aaagacggaa ctccaagaga tggcgccagg    540
tccaagaggc atcagaaatt tacacatttc ttacctagac cagtggatcc agaaagagtt    600
ccagaattgt acaaggacct actgatgtac acttga                              636
```

<210> SEQ ID NO 233
<211> LENGTH: 209
<212> TYPE: PRT
<213> ORGANISM: Homo sapiens

<400> SEQUENCE: 233

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 234
<211> LENGTH: 209
<212> TYPE: PRT
<213> ORGANISM: Pongo abelii

<400> SEQUENCE: 234

Met Asp Ser Asp Glu Thr Gly Phe Glu His Ser Gly Leu Trp Val Pro
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
                115                 120                 125

Glu Asp Gly Tyr Asn Val Tyr Gln Ser Glu Ala His Gly Leu Pro Leu
130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
                180                 185                 190

Pro Leu Ser Met Val Gly Pro Ser Gln Gly Arg Ser Pro Ser Tyr Ala
                195                 200                 205

Ser

<210> SEQ ID NO 235
<211> LENGTH: 209
<212> TYPE: PRT
<213> ORGANISM: Pan troglodytes

<400> SEQUENCE: 235

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
                115                 120                 125

Glu Asp Gly Tyr Asn Val Tyr Gln Ser Glu Ala His Gly Leu Pro Leu
130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
                180                 185                 190

Pro Leu Ser Met Val Gly Pro Ser Gln Gly Arg Ser Pro Ser Tyr Thr
                195                 200                 205

Ser

<210> SEQ ID NO 236
<211> LENGTH: 209
<212> TYPE: PRT
<213> ORGANISM: Canis lupus familiaris

<400> SEQUENCE: 236

```
Met Gly Trp Ala Glu Ala Gly Phe Glu His Leu Gly Leu Trp Val Pro
1               5                   10                  15
Val Leu Ala Val Leu Leu Glu Ala Cys Arg Ala His Pro Ile Pro
            20                  25                  30
Asp Ser Ser Pro Leu Leu Gln Phe Gly Gly Gln Val Arg Gln Arg Tyr
            35                  40                  45
Leu Tyr Thr Asp Asp Ala Gln Glu Thr Glu Ala His Leu Glu Ile Arg
    50                  55                  60
Ala Asp Gly Thr Val Val Gly Ala Ala Arg Gln Ser Pro Glu Ser Leu
65                  70                  75                  80
Leu Glu Leu Lys Ala Leu Lys Pro Gly Val Ile Gln Ile Leu Gly Val
                85                  90                  95
Lys Thr Ser Arg Phe Leu Cys Gln Gly Pro Asp Gly Thr Leu Tyr Gly
                100                 105                 110
Ser Leu His Phe Asp Pro Val Ala Cys Ser Phe Arg Glu Leu Leu Leu
            115                 120                 125
Glu Asp Gly Tyr Asn Ile Tyr His Ser Glu Thr Leu Gly Leu Pro Leu
    130                 135                 140
Arg Leu Arg Pro His Asn Ser Ala Tyr Arg Asp Leu Ala Pro Arg Gly
145                 150                 155                 160
Pro Ala Arg Phe Leu Pro Leu Pro Gly Leu Leu Pro Ala Pro Pro Glu
                165                 170                 175
Pro Pro Gly Ile Leu Ala Pro Glu Pro Pro Asp Val Gly Ser Ser Asp
                180                 185                 190
Pro Leu Ser Met Val Gly Pro Ser Gln Gly Arg Ser Pro Ser Tyr Ala
            195                 200                 205
Ser
```

<210> SEQ ID NO 237
<211> LENGTH: 209
<212> TYPE: PRT
<213> ORGANISM: Bos taurus

<400> SEQUENCE: 237

```
Met Gly Trp Asp Glu Ala Lys Phe Lys His Leu Gly Leu Trp Val Pro
1               5                   10                  15
Val Leu Ala Val Leu Leu Leu Gly Thr Cys Arg Ala His Pro Ile Pro
            20                  25                  30
Asp Ser Ser Pro Leu Leu Gln Phe Gly Gly Gln Val Arg Gln Arg Tyr
            35                  40                  45
Leu Tyr Thr Asp Asp Ala Gln Glu Thr Glu Ala His Leu Glu Ile Arg
    50                  55                  60
Ala Asp Gly Thr Val Val Gly Ala Ala Arg Gln Ser Pro Glu Ser Leu
65                  70                  75                  80
Leu Glu Leu Lys Ala Leu Lys Pro Gly Val Ile Gln Ile Leu Gly Val
                85                  90                  95
Lys Thr Ser Arg Phe Leu Cys Gln Gly Pro Asp Gly Lys Leu Tyr Gly
                100                 105                 110
```

```
Ser Leu His Phe Asp Pro Lys Ala Cys Ser Phe Arg Glu Leu Leu Leu
        115                 120                 125

Glu Asp Gly Tyr Asn Val Tyr Gln Ser Glu Thr Leu Gly Leu Pro Leu
    130                 135                 140

Arg Leu Pro Pro Gln Arg Ser Ser Asn Arg Asp Pro Ala Pro Arg Gly
145                 150                 155                 160

Pro Ala Arg Phe Leu Pro Leu Pro Gly Leu Pro Ala Ala Pro Pro Asp
                165                 170                 175

Pro Pro Gly Ile Leu Ala Pro Glu Pro Pro Asp Val Gly Ser Ser Asp
            180                 185                 190

Pro Leu Ser Met Val Gly Pro Ser Tyr Gly Arg Ser Pro Ser Tyr Thr
        195                 200                 205

Ser

<210> SEQ ID NO 238
<211> LENGTH: 209
<212> TYPE: PRT
<213> ORGANISM: Equus caballus

<400> SEQUENCE: 238

Met Asp Trp Asp Lys Thr Gly Phe Lys Tyr Gln Gly Leu Trp Val Pro
1               5                   10                  15

Val Leu Ala Val Leu Leu Gly Ala Cys Gln Ser His Pro Ile Pro
            20                  25                  30

Asp Ser Ser Pro Leu Leu Gln Phe Gly Gly Gln Val Arg Gln Arg His
            35                  40                  45

Leu Tyr Thr Asp Asp Ala Gln Glu Thr Glu Ala His Leu Glu Ile Arg
    50                  55                  60

Ala Asp Gly Thr Val Ala Gly Ala Val His Arg Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Thr Leu Tyr Gly
            100                 105                 110

Ser Leu His Phe Asp Pro Val Ala Cys Ser Phe Arg Glu Leu Leu Leu
        115                 120                 125

Glu Asp Gly Tyr Asn Val Tyr Gln Ser Glu Thr Leu Gly Leu Pro Leu
    130                 135                 140

Arg Leu Pro His His Ser Ser Pro Tyr Gln Asp Pro Ala Pro Arg Ala
145                 150                 155                 160

Pro Ala Arg Phe Leu Pro Leu Pro Gly Phe Pro Ala Pro Pro Glu
                165                 170                 175

Pro Pro Gly Ile Pro Ala Pro Glu Pro Pro Asp Val Gly Ser Ser Asp
            180                 185                 190

Pro Leu Ser Met Val Gly Pro Ser Arg Ser Arg Ser Pro Ser Tyr Thr
        195                 200                 205

Ser

<210> SEQ ID NO 239
<211> LENGTH: 209
<212> TYPE: PRT
<213> ORGANISM: Ailuropoda melanoleuca

<400> SEQUENCE: 239

Met Gly Trp Asp Glu Ala Arg Ser Glu Gln Leu Gly Leu Trp Val Pro
```

-continued

```
1               5                   10                  15
Val Leu Ala Val Leu Leu Glu Ala Cys Gln Ala His Pro Ile Pro
            20                  25                  30
Asp Ser Ser Pro Leu Leu Gln Phe Gly Gly Gln Val Arg Gln Arg Tyr
            35                  40                  45
Leu Tyr Thr Asp Asp Ala Gln Glu Thr Glu Ala His Leu Ala Ile Arg
    50                  55                  60
Ala Asp Gly Thr Val Val Gly Ala Ala Ser Arg Ser Pro Glu Ser Leu
65                  70                  75                  80
Leu Glu Leu Lys Ala Leu Lys Pro Gly Val Ile Gln Ile Leu Gly Val
                85                  90                  95
Lys Thr Ser Arg Phe Leu Cys Gln Gly Pro Asp Gly Thr Leu Tyr Gly
                100                 105                 110
Ser Val Arg Phe Asp Pro Val Ala Cys Ser Phe Arg Glu Leu Leu Leu
                115                 120                 125
Glu Asp Gly Tyr Asn Ile Tyr His Ser Glu Thr Leu Gly Leu Pro Leu
            130                 135                 140
Arg Leu Pro Ala His Asn Ser Pro Tyr Arg Asp Ser Ala Pro Arg Gly
145                 150                 155                 160
Pro Ala Arg Phe Leu Pro Leu Pro Gly Leu Pro Val Pro Pro Asp
                165                 170                 175
Pro Pro Gly Ile Leu Gly Pro Glu Pro Pro Asp Val Gly Ser Ser Asp
            180                 185                 190
Pro Leu Ser Met Val Gly Pro Ser Gln Gly Arg Ser Pro Ser Tyr Ala
                195                 200                 205
Ser
```

<210> SEQ ID NO 240
<211> LENGTH: 209
<212> TYPE: PRT
<213> ORGANISM: Oryctolagus cuniculus

<400> SEQUENCE: 240

```
Met Asp Trp Gly Lys Ala Lys Cys Arg Pro Pro Gly Leu Trp Val Pro
1               5                   10                  15
Ala Leu Ala Ala Leu Leu Leu Gly Ala Cys Gln Ala His Pro Ile Pro
            20                  25                  30
Asp Ser Ser Pro Leu Leu Gln Phe Gly Asp Gln Val Arg Gln Gln His
            35                  40                  45
Leu Tyr Thr Asp Asp Ala Gln Glu Thr Glu Ala His Leu Glu Ile Arg
    50                  55                  60
Ala Asp Gly Thr Val Val Gly Ala Ala Arg Arg Ser Pro Glu Ser Leu
65                  70                  75                  80
Leu Gln Met Lys Ala Leu Gln Pro Gly Ile Ile Gln Ile Leu Gly Val
                85                  90                  95
Gln Thr Ser Arg Phe Leu Cys Gln Arg Pro Asp Gly Thr Leu Tyr Gly
                100                 105                 110
Ser Leu His Phe Asp Arg Glu Ala Cys Ser Phe Arg Glu Leu Leu Arg
                115                 120                 125
Glu Asp Gly Tyr Asn Val Tyr Leu Ser Glu Ala Leu Gly Leu Pro Leu
            130                 135                 140
Arg Leu Ser Pro Gly Ser Ser Pro Arg Arg Ala Pro Ala Pro Arg Gly
145                 150                 155                 160
Pro Ala Arg Phe Leu Pro Leu Pro Gly Leu Pro Pro Asp Leu Pro Glu
```

```
                    165                 170                 175
Pro Pro Gly Leu Leu Ala Ala Pro Pro Asp Val Asp Ser Pro Asp
            180                 185                 190
Pro Leu Ser Met Val Gln Pro Ala Leu Asp Gln Ser Pro Ser Tyr Thr
            195                 200                 205
Ser

<210> SEQ ID NO 241
<211> LENGTH: 209
<212> TYPE: PRT
<213> ORGANISM: Gorilla gorilla

<400> SEQUENCE: 241

Met Asp Ser Asp Glu Thr Gly Phe Glu His Ser Gly Leu Trp Val Ser
1               5                   10                  15
Val Leu Ala Gly Leu Leu Gly Ala Cys Gln Ala His Pro Ile Pro
            20                  25                  30
Asp Ser Ser Pro Leu Leu Gln Phe Gly Gly Gln Val Arg Gln Arg Tyr
        35                  40                  45
Leu Tyr Thr Asp Asp Ala Gln Gln Thr Glu Ala His Leu Glu Ile Arg
    50                  55                  60
Glu Asp Gly Thr Val Gly Gly Ala Ala Asp Gln Ser Pro Glu Ser Leu
65                  70                  75                  80
Leu Gln Leu Lys Ala Leu Lys Pro Gly Val Ile Gln Ile Leu Gly Val
                85                  90                  95
Lys Thr Ser Arg Phe Leu Cys Gln Arg Pro Asp Gly Ala Leu Tyr Gly
            100                 105                 110
Ser Leu His Phe Asp Pro Glu Ala Cys Ser Phe Arg Glu Leu Leu Leu
        115                 120                 125
Glu Asp Gly Tyr Asn Val Tyr Gln Ser Glu Ala His Gly Leu Pro Leu
    130                 135                 140
His Leu Pro Gly Asn Lys Ser Pro His Arg Asp Pro Ala Pro Arg Gly
145                 150                 155                 160
Pro Ala Arg Phe Leu Pro Leu Pro Gly Leu Pro Pro Ala Pro Pro Glu
                165                 170                 175
Pro Pro Gly Ile Leu Ala Pro Gln Pro Pro Asp Val Gly Ser Ser Asp
            180                 185                 190
Pro Leu Ser Met Val Gly Pro Ser Gln Gly Arg Ser Pro Ser Tyr Ala
        195                 200                 205
Ser

<210> SEQ ID NO 242
<211> LENGTH: 209
<212> TYPE: PRT
<213> ORGANISM: Nomascus leucogenys

<400> SEQUENCE: 242

Met Asp Ser Asp Glu Thr Gly Phe Glu His Ser Gly Leu Trp Val Pro
1               5                   10                  15
Val Leu Ala Gly Leu Leu Gly Ala Cys Gln Ala His Pro Ile Pro
            20                  25                  30
Asp Ser Ser Pro Leu Leu Gln Phe Gly Gly Gln Val Arg Gln Arg Tyr
        35                  40                  45
Leu Tyr Thr Asp Asp Ala Gln Gln Thr Glu Ala His Leu Glu Ile Arg
    50                  55                  60
```

```
Glu Asp Gly Thr Val Gly Ala Ala Asp Gln Ser Pro Glu Ser Leu
 65                  70                  75                  80

Leu Gln Leu Lys Ala Leu Lys Pro Gly Val Ile Gln Ile Leu Gly Val
             85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
            130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
                180                 185                 190

Pro Leu Ser Met Val Gly Pro Ser Gln Gly Arg Ser Pro Ser Tyr Ala
            195                 200                 205

Ser
```

<210> SEQ ID NO 243
<211> LENGTH: 209
<212> TYPE: PRT
<213> ORGANISM: Procavia capensis

<400> SEQUENCE: 243

```
Met Asp Trp Ala Lys Phe Gly Ile Glu His Pro Gly Leu Trp Val Pro
  1               5                  10                  15

Val Met Ala Val Leu Leu Leu Gly Ala Cys Gln Gly Tyr Pro Ile Pro
             20                  25                  30

Asp Ser Ser Pro Leu Leu Gln Phe Gly Gly Gln Val Arg Gln Arg Tyr
         35                  40                  45

Leu Tyr Thr Asp Asp Ala Gln Glu Thr Glu Ala His Leu Glu Ile Arg
 50                  55                  60

Ala Asp Gly Thr Val Val Gly Ala Ala His Arg Ser Pro Glu Ser Leu
 65                  70                  75                  80

Leu Glu Leu Lys Ala Leu Lys Pro Gly Ile Ile Gln Ile Leu Gly Val
             85                  90                  95

Lys Thr Ser Arg Phe Leu Cys Gln Gly Pro Asp Gly Val Leu Tyr Gly
            100                 105                 110

Ser Leu Arg Phe Asp Pro Val Ala Cys Ser Phe Arg Glu Leu Leu Leu
            115                 120                 125

Glu Asp Gly Tyr Asn Val Tyr Gln Ser Glu Ala His Gly Leu Pro Leu
            130                 135                 140

Arg Leu Pro Ser His Asn Ser Pro Gln Arg Asp Leu Ala Ser Arg Val
145                 150                 155                 160

Pro Ala Arg Phe Leu Pro Leu Pro Gly Arg Leu Thr Val Leu Pro Glu
                165                 170                 175

Pro Ser Gly Val Leu Gly Pro Glu Pro Pro Asp Val Asp Ser Ser Asp
            180                 185                 190

Pro Leu Ser Met Val Gly Pro Ser Gln Gly Arg Ser Pro Ser Tyr Ala
            195                 200                 205

Ser
```

<210> SEQ ID NO 244
<211> LENGTH: 209
<212> TYPE: PRT
<213> ORGANISM: Cavia porcellus

<400> SEQUENCE: 244

```
Met Asp Trp Ala Arg Thr Glu Cys Glu Arg Pro Arg Leu Trp Val Ser
1               5                   10                  15

Met Leu Ala Ile Leu Leu Val Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Asp Thr Glu Val His Leu Glu Ile Arg
    50                  55                  60

Ala Asp Gly Ser Val Arg Gly Ile Ala His Arg Ser Pro Glu Ser Leu
65                  70                  75                  80

Leu Glu Leu Lys Ala Leu Lys Pro Gly Val Ile Gln Ile Leu Gly Ile
                85                  90                  95

Arg Thr Ser Arg Phe Leu Cys Gln Arg Pro Asp Gly Ser Leu Tyr Gly
            100                 105                 110

Ser Leu His Phe Asp Pro Glu Ala Cys Ser Phe Arg Glu Leu Leu Leu
        115                 120                 125

Ala Asp Gly Tyr Asn Val Tyr Lys Ser Glu Ala His Gly Leu Pro Leu
    130                 135                 140

His Leu Leu Arg Gly Asp Ser Leu Ser Gln Glu Pro Ala Pro Pro Gly
145                 150                 155                 160

Pro Ala Arg Phe Leu Pro Leu Pro Gly Leu Pro Ala Thr Pro Pro Glu
                165                 170                 175

Pro Pro Arg Met Leu Pro Pro Gly Pro Pro Asp Val Gly Ser Ser Asp
            180                 185                 190

Pro Leu Ser Met Val Gly Pro Leu Trp Asp Arg Ser Pro Ser Tyr Thr
        195                 200                 205

Ser
```

<210> SEQ ID NO 245
<211> LENGTH: 209
<212> TYPE: PRT
<213> ORGANISM: Tupaia belangeri

<400> SEQUENCE: 245

```
Met Gly Trp Asp Lys Ala Arg Phe Glu His Leu Gly Ala Trp Ala Pro
1               5                   10                  15

Val Leu Ala Val Leu Leu Gly Ala Cys Gln Ala Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Thr Gln Asp Thr Glu Ala His Leu Glu Ile Arg
    50                  55                  60

Ala Asp Gly Thr Val Val Gly Ala Ala His Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125
```

-continued

```
Glu Asp Gly Tyr Asn Ile Tyr Gln Ser Glu Ala Arg Gly Leu Pro Leu
        130                 135                 140

Arg Leu Pro Pro His Asp Ser Pro His Arg Asp Arg Thr Pro Arg Gly
145                 150                 155                 160

Pro Ala Arg Phe Leu Pro Leu Pro Gly Leu Pro Leu Val Pro Pro Glu
                165                 170                 175

Leu Pro Gly Val Leu Ala Leu Glu Pro Pro Asp Val Gly Ser Ser Asp
                180                 185                 190

Pro Leu Ser Met Met Gly Pro Ser Gln Gly Gln Ser Pro Ser Tyr Ala
                195                 200                 205

Ser

<210> SEQ ID NO 246
<211> LENGTH: 210
<212> TYPE: PRT
<213> ORGANISM: Sorex araneus

<400> SEQUENCE: 246

Met Val Trp Asp Lys Ala Arg Gly Gln Gln Leu Gly Leu Trp Ala Pro
1               5                   10                  15

Met Leu Leu Gly Leu Leu Gly Ala Cys Gln Ala His Pro Leu Pro
            20                  25                  30

Asp Ser Ser Pro Leu Leu Gln Phe Gly Gly Val Arg Leu Arg Phe
            35                  40                  45

Leu Tyr Thr Asp Asp Ala Gln Arg Thr Gly Ala His Leu Glu Ile Arg
    50                  55                  60

Ala Asp Gly Thr Val Gln Gly Ala Ala His Arg Thr Pro Glu Cys Leu
65                  70                  75                  80

Leu Glu Leu Lys Ala Leu Lys Pro Gly Val Ile Gln Ile Leu Gly Val
                85                  90                  95

Ser Thr Ser Arg Phe Leu Cys Gln Arg Pro Asp Gly Val Leu Tyr Gly
            100                 105                 110

Ser Leu Arg Phe Asp Pro Glu Ala Cys Ser Phe Arg Glu Leu Leu Leu
            115                 120                 125

Gln Asp Gly Tyr Asn Val Tyr Gln Ser Glu Ala Leu Gly Leu Pro Leu
        130                 135                 140

Tyr Leu His Pro Pro Ser Ala Pro Val Ser Gln Glu Pro Ala Ser Arg
145                 150                 155                 160

Gly Ala Val Arg Phe Leu Pro Leu Pro Gly Leu Pro Pro Ala Ser Leu
                165                 170                 175

Glu Pro Pro Arg Pro Pro Ala Pro Val Pro Asp Val Gly Ser Ser
                180                 185                 190

Asp Pro Leu Ser Met Val Gly Pro Pro Glu Arg His Ser Pro Ser Tyr
                195                 200                 205

Thr Ser
    210

<210> SEQ ID NO 247
<211> LENGTH: 208
<212> TYPE: PRT
<213> ORGANISM: Ictidomys tridecemlineatus

<400> SEQUENCE: 247

Met Asp Trp Val Lys Ala Lys Leu Glu Pro Leu Gly Leu Trp Val Leu
1               5                   10                  15
```

```
Val Leu Ala Ala Leu Val Leu Gly Ala Cys Gln Ala Tyr Pro Ile Pro
             20                  25                  30

Asp Ser Ser Pro Leu Leu Gln Phe Gly Gly Gln Val Arg Gln Arg Tyr
         35                  40                  45

Leu Tyr Thr Asp Asp Ala Gln Glu Thr Glu Ala His Leu Glu Ile Arg
     50                  55                  60

Ala Asp Gly Thr Val Val Gly Ala Ala His Gln Ser Pro Glu Ser Leu
 65                  70                  75                  80

Leu Glu Leu Lys Ala Leu Lys Pro Gly Val Ile Gln Ile Leu Gly Val
                 85                  90                  95

Lys Thr Ser Arg Phe Leu Cys Gln Arg Pro Asp Gly Val Leu Tyr Gly
            100                 105                 110

Ser Leu His Phe Asp Pro Glu Ala Cys Ser Phe Arg Glu Gln Leu Leu
        115                 120                 125

Glu Asp Gly Tyr Asn Val Tyr Gln Ser Glu Ser His Gly Leu Pro Val
    130                 135                 140

Arg Leu Pro Pro Asn Ser Pro Tyr Arg Asp Pro Ala Pro Pro Gly Pro
145                 150                 155                 160

Ala Arg Phe Leu Pro Leu Pro Gly Leu Pro Pro Ala Leu Glu Pro
                165                 170                 175

Pro Gly Ile Leu Gly Pro Glu Pro Pro Asp Val Gly Ser Ser Asp Pro
            180                 185                 190

Leu Ser Met Val Gly Pro Leu Gln Gly Arg Ser Pro Ser Tyr Ala Ser
        195                 200                 205

<210> SEQ ID NO 248
<211> LENGTH: 208
<212> TYPE: PRT
<213> ORGANISM: Loxodonta africana

<400> SEQUENCE: 248

Met Asp Trp Ala Lys Phe Gly Leu Glu His Pro Gly Leu Trp Val Pro
  1               5                  10                  15

Val Met Ala Val Leu Leu Gly Ala Cys Gln Gly His Pro Ile Pro
             20                  25                  30

Asp Ser Ser Pro Leu Leu Gln Phe Gly Gly Gln Val Arg Gln Arg Tyr
         35                  40                  45

Leu Tyr Thr Asp Asp Gln Glu Thr Glu Ala His Leu Glu Ile Arg Ala
     50                  55                  60

Asp Gly Thr Val Ala Gly Ala Ala His Arg Ser Ser Glu Ser Leu Leu
 65                  70                  75                  80

Glu Leu Lys Ala Leu Lys Pro Gly Ile Ile Gln Ile Leu Gly Val Lys
                 85                  90                  95

Thr Ser Arg Phe Leu Cys Gln Gly Pro Asp Gly Val Leu Tyr Gly Ser
            100                 105                 110

Leu His Phe Asp Pro Ala Ala Cys Ser Phe Arg Glu Leu Leu Leu Glu
        115                 120                 125

Asp Gly Tyr Asn Val Tyr Trp Ser Glu Ala His Gly Leu Pro Ile Arg
    130                 135                 140

Leu Pro Ser His Asn Ser Pro Tyr Arg Asp Pro Ala Ser Arg Val Pro
145                 150                 155                 160

Ala Arg Phe Leu Pro Leu Pro Gly Leu Leu Pro Met Leu Gln Glu Pro
                165                 170                 175

Pro Gly Val Leu Ala Pro Glu Pro Pro Asp Val Asp Ser Ser Asp Pro
            180                 185                 190
```

```
Leu Ser Met Val Gly Pro Ser Gln Gly Arg Ser Pro Ser Tyr Ala Ser
        195                 200                 205
```

<210> SEQ ID NO 249
<211> LENGTH: 208
<212> TYPE: PRT
<213> ORGANISM: Sus scrofa

<400> SEQUENCE: 249

```
Met Gly Trp Ala Glu Ala Lys Phe Glu Arg Leu Gly Leu Trp Val Pro
1               5                   10                  15
Val Leu Ala Val Leu Leu Gly Ala Cys Gln Ala Arg Pro Ile Pro Asp
            20                  25                  30
Ser Ser Pro Leu Leu Gln Phe Gly Gly Gln Val Arg Gln Arg Tyr Leu
        35                  40                  45
Tyr Thr Asp Asp Ala Gln Glu Thr Glu Ala His Leu Glu Ile Arg Ala
    50                  55                  60
Asp Gly Thr Val Ala Gly Val Ala Arg Gln Ser Pro Glu Ser Leu Leu
65                  70                  75                  80
Glu Leu Lys Ala Leu Lys Pro Gly Val Ile Gln Ile Leu Gly Val Gln
                85                  90                  95
Thr Ser Arg Phe Leu Cys Gln Gly Pro Asp Gly Arg Leu Tyr Gly Ser
            100                 105                 110
Leu His Phe Asp Pro Glu Ala Cys Ser Phe Arg Glu Leu Leu Leu Glu
        115                 120                 125
Asp Gly Tyr Asn Val Tyr Gln Ser Glu Ala Leu Gly Leu Pro Leu Arg
    130                 135                 140
Leu Pro Pro His Arg Ser Ser Asn Arg Asp Leu Ala Pro Arg Gly Pro
145                 150                 155                 160
Ala Arg Phe Leu Pro Leu Pro Gly Leu Pro Pro Ala Pro Pro Glu Pro
                165                 170                 175
Pro Gly Ile Leu Ala Pro Glu Pro Pro Asp Val Gly Ser Ser Asp Pro
            180                 185                 190
Leu Ser Met Val Gly Pro Ser His Gly Arg Ser Pro Ser Tyr Thr Ser
        195                 200                 205
```

<210> SEQ ID NO 250
<211> LENGTH: 208
<212> TYPE: PRT
<213> ORGANISM: Felis catus

<400> SEQUENCE: 250

```
Met Asp Trp Asp Glu Ala Gly Ser Gln Arg Leu Gly Leu Trp Val Val
1               5                   10                  15
Leu Gly Val Leu Leu Pro Glu Ala Cys Gln Ala His Pro Ile Pro Asp
            20                  25                  30
Ser Ser Pro Leu Leu Gln Phe Gly Gly Gln Val Arg Gln Arg Phe Leu
        35                  40                  45
Tyr Thr Asp Asp Ala Gln Glu Thr Glu Val His Leu Glu Ile Lys Ala
    50                  55                  60
Asp Gly Thr Val Val Gly Thr Ala Arg Arg Ser Pro Glu Ser Leu Leu
65                  70                  75                  80
Glu Leu Lys Ala Leu Lys Pro Gly Val Ile Gln Ile Leu Gly Val Lys
                85                  90                  95
Thr Ser Arg Phe Leu Cys Gln Gly Pro Asp Gly Thr Leu Tyr Gly Ser
            100                 105                 110
```

```
Leu Arg Phe Asp Pro Ala Ala Cys Ser Phe Arg Glu Leu Leu Leu Glu
            115                 120                 125

Asp Gly Tyr Asn Ile Tyr His Ser Glu Thr Leu Gly Leu Pro Leu Arg
        130                 135                 140

Leu Pro Pro His Asn Ser Pro Tyr Arg Asp Leu Ala Pro Arg Ala Pro
145                 150                 155                 160

Ala Arg Phe Leu Pro Leu Pro Gly Leu Leu Pro Ala Pro Pro Glu Pro
                165                 170                 175

Pro Gly Ile Leu Ala Pro Glu Pro Pro Asp Val Gly Ser Ser Asp Pro
            180                 185                 190

Leu Ser Met Val Gly Pro Ser Gln Gly Arg Ser Pro Ser Tyr Ala Ser
        195                 200                 205

<210> SEQ ID NO 251
<211> LENGTH: 208
<212> TYPE: PRT
<213> ORGANISM: Otolemur garnettii

<400> SEQUENCE: 251

Asp Lys Ala Arg Thr Gly Phe Lys His Pro Gly Pro Trp Phe Pro Leu
1               5                   10                  15

Leu Ala Val Leu Leu Leu Gly Ala Cys Gln Ala His Pro Ile Pro Asp
                20                  25                  30

Ser Ser Pro Leu Leu Gln Phe Gly Gln Val Arg Gln Arg Tyr Leu
            35                  40                  45

Tyr Thr Asp Asp Ala Gln Glu Thr Glu Ala His Leu Glu Ile Arg Glu
    50                  55                  60

Asp Gly Thr Val Val Gly Ala Ala Gln Gln Ser Pro Glu Ser Leu Leu
65                  70                  75                  80

Glu Leu Lys Ala Leu Lys Pro Gly Val Ile Gln Ile Leu Gly Val Lys
                85                  90                  95

Thr Ser Arg Phe Leu Cys Gln Arg Pro Asp Gly Gly Leu Tyr Gly Ser
            100                 105                 110

Leu Tyr Phe Asp Pro Lys Ala Cys Ser Phe Arg Glu Leu Leu Leu Glu
        115                 120                 125

Asp Gly Tyr Asn Val Tyr Trp Ser Glu Thr Tyr Gly Leu Pro Leu His
    130                 135                 140

Leu Pro Pro Ala Asn Ser Pro Tyr Trp Gly Pro Ser Leu Arg Ser Pro
145                 150                 155                 160

Ala Arg Phe Leu Pro Leu Pro Gly Pro Pro Ala Ala Ser Pro Glu Leu
                165                 170                 175

Pro Gly Ile Leu Ala Leu Glu Pro Pro Asp Val Gly Ser Ser Asp Pro
            180                 185                 190

Leu Ser Met Val Gly Pro Ser Gln Gly Arg Ser Pro Ser Tyr Ala Ser
        195                 200                 205

<210> SEQ ID NO 252
<211> LENGTH: 208
<212> TYPE: PRT
<213> ORGANISM: Rattus norvegicus

<400> SEQUENCE: 252

Met Asp Trp Met Lys Ser Arg Val Gly Ala Pro Gly Leu Trp Val Cys
1               5                   10                  15

Leu Leu Leu Pro Val Phe Leu Leu Gly Val Cys Glu Ala Tyr Pro Ile
                20                  25                  30
```

```
Ser Asp Ser Ser Pro Leu Leu Gln Phe Gly Gly Gln Val Arg Gln Arg
            35                  40                  45

Tyr Leu Tyr Thr Asp Asp Gln Asp Thr Glu Ala His Leu Glu Ile
 50                  55                  60

Arg Glu Asp Gly Thr Val Val Gly Thr Ala His Arg Ser Pro Glu Ser
 65                  70                  75                  80

Leu Leu Glu Leu Lys Ala Leu Lys Pro Gly Val Ile Gln Ile Leu Gly
                 85                  90                  95

Val Lys Ala Ser Arg Phe Leu Cys Gln Gln Pro Asp Gly Thr Leu Tyr
                100                 105                 110

Gly Ser Pro His Phe Asp Pro Glu Ala Cys Ser Phe Arg Glu Leu Leu
                115                 120                 125

Leu Lys Asp Gly Tyr Asn Val Tyr Gln Ser Glu Ala His Gly Leu Pro
            130                 135                 140

Leu Arg Leu Pro Gln Lys Asp Ser Gln Asp Pro Ala Thr Arg Gly Pro
145                 150                 155                 160

Val Arg Phe Leu Pro Met Pro Gly Leu Pro His Glu Pro Gln Glu Gln
                165                 170                 175

Pro Gly Val Leu Pro Pro Glu Pro Pro Asp Val Gly Ser Ser Asp Pro
                180                 185                 190

Leu Ser Met Val Glu Pro Leu Gln Gly Arg Ser Pro Ser Tyr Ala Ser
            195                 200                 205

<210> SEQ ID NO 253
<211> LENGTH: 210
<212> TYPE: PRT
<213> ORGANISM: Mus musculus

<400> SEQUENCE: 253

Met Glu Trp Met Arg Ser Arg Val Gly Thr Leu Gly Leu Trp Val Arg
 1               5                  10                  15

Leu Leu Leu Ala Val Phe Leu Leu Gly Val Tyr Gln Ala Tyr Pro Ile
                 20                  25                  30

Pro Asp Ser Ser Pro Leu Leu Gln Phe Gly Gly Gln Val Arg Gln Arg
            35                  40                  45

Tyr Leu Tyr Thr Asp Asp Gln Asp Thr Glu Ala His Leu Glu Ile
 50                  55                  60

Arg Glu Asp Gly Thr Val Val Gly Ala Ala His Arg Ser Pro Glu Ser
 65                  70                  75                  80

Leu Leu Glu Leu Lys Ala Leu Lys Pro Gly Val Ile Gln Ile Leu Gly
                 85                  90                  95

Val Lys Ala Ser Arg Phe Leu Cys Gln Gln Pro Asp Gly Ala Leu Tyr
                100                 105                 110

Gly Ser Pro His Phe Asp Pro Glu Ala Cys Ser Phe Arg Glu Leu Leu
                115                 120                 125

Leu Glu Asp Gly Tyr Asn Val Tyr Gln Ser Glu Ala His Gly Leu Pro
            130                 135                 140

Leu Arg Leu Pro Gln Lys Asp Ser Pro Asn Gln Asp Ala Thr Ser Trp
145                 150                 155                 160

Gly Pro Val Arg Phe Leu Pro Met Pro Gly Leu Leu His Glu Pro Gln
                165                 170                 175

Asp Gln Ala Gly Phe Leu Pro Pro Glu Pro Pro Asp Val Gly Ser Ser
            180                 185                 190

Asp Pro Leu Ser Met Val Glu Pro Leu Gln Gly Arg Ser Pro Ser Tyr
```

Ala Ser
    210

<210> SEQ ID NO 254
<211> LENGTH: 107
<212> TYPE: PRT
<213> ORGANISM: Vicugna pacos

<400> SEQUENCE: 254

Met Asp Trp Asp Glu Ala Lys Phe Glu His Arg Gly Leu Trp Val Pro
1               5                   10                  15

Val Leu Thr Val Leu Leu Leu Gly Ala Cys Gln Ala Arg Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Val Ala Arg Gln Pro Glu Gly Ile Pro
65                  70                  75                  80

Pro Glu Pro Pro Asp Val Gly Ser Ser Asp Pro Leu Ser Met Val Gly
                85                  90                  95

Pro Ser Tyr Ser Arg Ser Pro Ser Tyr Thr Ser
            100                 105

<210> SEQ ID NO 255
<211> LENGTH: 211
<212> TYPE: PRT
<213> ORGANISM: Anolis carolinensis

<400> SEQUENCE: 255

Cys Lys Ser Lys Gly Gly Gly Lys Gly Gly Glu Arg Met Trp Val Asp
1               5                   10                  15

Leu Val Phe Trp Ala Ala Leu Leu Arg Thr Ala Pro Ala Leu Pro Leu
            20                  25                  30

Arg Asn Ser Asn Pro Ile Tyr Gln Phe Asp Gly Gln Val Arg Leu Arg
        35                  40                  45

His Leu Tyr Thr Ala Asp Glu Gln Thr His Leu His Leu Glu Ile Leu
    50                  55                  60

Pro Asp Gly Thr Val Gly Gly Ser Arg Phe Gln Asn Pro Phe Ser Leu
65                  70                  75                  80

Met Glu Ile Lys Ala Val Lys Pro Gly Val Ile Arg Met Gln Ala Lys
                85                  90                  95

Lys Thr Ser Arg Phe Leu Cys Met Lys Pro Asn Gly Arg Leu Tyr Gly
            100                 105                 110

Ser Leu Phe Tyr Ser Glu Glu Ala Cys Asn Phe His Glu Lys Val Leu
        115                 120                 125

Ser Asp Gly Tyr Asn Leu Tyr Tyr Ser Glu Asn Tyr Asn Ile Pro Val
    130                 135                 140

Ser Leu Ser Ser Ala Gly Asn Leu Gly Gln Ser Arg Gln Leu Pro Pro
145                 150                 155                 160

Phe Ser Gln Phe Leu Pro Leu Val Asn Lys Ile Pro Leu Glu Pro Val
                165                 170                 175

Leu Glu Asp Phe Asp Phe Tyr Gly His Gln Leu Asp Val Glu Ser Ala
            180                 185                 190

Asp Pro Leu Ser Ile Leu Gly Gln Asn Pro Gly Phe Met Ser Pro Ser

```
                        195                 200                 205

Tyr Val Phe
    210

<210> SEQ ID NO 256
<211> LENGTH: 188
<212> TYPE: PRT
<213> ORGANISM: Gadus morhua

<400> SEQUENCE: 256

Leu Leu Leu Ala Thr Leu Leu His Ile Gly Leu Ser Phe Tyr Val Pro
1               5                   10                  15

Asp Ser Gly Pro Leu Leu Trp Leu Gly Asp Gln Val Arg Glu Arg His
            20                  25                  30

Leu Tyr Thr Ala Glu Ser His Arg Arg Gly Leu Phe Leu Glu Met Ser
        35                  40                  45

Pro Asp Gly Gln Val Thr Gly Ser Ala Ala Gln Thr Pro Leu Ser Val
    50                  55                  60

Leu Glu Leu Arg Ser Val Arg Ala Gly Asp Thr Val Ile Arg Ala Arg
65                  70                  75                  80

Leu Ser Ser Leu Tyr Leu Cys Val Asp Arg Ala Gly His Leu Thr Gly
                85                  90                  95

Gln Arg Gln Tyr Thr Glu Ser Asp Cys Thr Phe Arg Glu Val Ile Leu
            100                 105                 110

Glu Asp Gly Tyr Thr His Phe Leu Ser Val His His Gly Leu Pro Ile
        115                 120                 125

Ser Leu Ala Pro Arg His Ser Pro Gly Arg Gln Gly Leu Arg Phe Ser
    130                 135                 140

Arg Phe Leu Pro Leu Arg Ser Ser Leu Ser Glu Asp Arg Val Ala Glu
145                 150                 155                 160

Pro Pro Asp Ser Pro Leu Asn Leu Asp Ser Glu Asp Pro Leu Gly Met
                165                 170                 175

Gly Leu Gly Ser Leu Leu Ser Pro Ala Phe Ser Met
            180                 185

<210> SEQ ID NO 257
<211> LENGTH: 216
<212> TYPE: PRT
<213> ORGANISM: Latimeria chalumnae

<400> SEQUENCE: 257

Met Leu Cys Gln Ser Phe Val Ile Leu Ser Gln Lys Phe Ile Phe Gly
1               5                   10                  15

Leu Phe Leu Thr Gly Leu Gly Leu Thr Gly Leu Ala Trp Thr Arg Pro
            20                  25                  30

Phe Gln Asp Ser Asn Pro Ile Leu Gln Tyr Ser Asp Ser Ile Arg Leu
        35                  40                  45

Arg His Leu Tyr Thr Ala Ser Glu Ser Arg His Leu His Leu Gln Ile
    50                  55                  60

Asn Ser Asp Gly Gln Val Gly Gly Thr Thr Lys Gln Ser Pro Tyr Ser
65                  70                  75                  80

Leu Leu Glu Met Lys Ala Val Lys Thr Gly Phe Val Val Ile Arg Gly
                85                  90                  95

Lys Lys Ser Ala Arg Tyr Leu Cys Met Glu Arg Ser Gly Arg Leu Tyr
            100                 105                 110

Gly Ser Leu Gln Tyr Thr Glu Lys Asp Cys Thr Phe Lys Glu Val Val
```

```
            115                 120                 125
Leu Ala Asp Gly Tyr Asn Leu Tyr Val Ser Glu Glu His Gln Ala Thr
        130                 135                 140
Val Thr Leu Ser Pro Met Arg Ala Arg Ile Ala Gln Gly Lys Lys Ile
145                 150                 155                 160
Pro Pro Phe Ser His Phe Leu Pro Met Val Asn Lys Val Pro Val Glu
                165                 170                 175
Asp Val Ala Ala Glu Met Glu Phe Val Gln Val Leu Arg Glu Met Thr
            180                 185                 190
Ala Asp Val Asp Ser Pro Asp Pro Phe Gly Met Thr Trp Glu Glu Ser
        195                 200                 205
Val His Ser Pro Ser Phe Phe Ala
    210                 215

<210> SEQ ID NO 258
<211> LENGTH: 192
<212> TYPE: PRT
<213> ORGANISM: Tursiops truncates

<400> SEQUENCE: 258

Met Gly Trp Asp Lys Thr Lys Leu Glu His Leu Gly Leu Trp Val Pro
1               5                   10                  15
Val Leu Ala Val Leu Leu Gly Pro Cys Gln Ala His Pro Ile Pro Asp
            20                  25                  30
Ser Ser Pro Leu Leu Gln Phe Gly Gly Gln Val Arg Gln Arg Tyr Leu
        35                  40                  45
Tyr Thr Asp Asp Ala Gln Glu Thr Glu Ala His Leu Glu Ile Arg Ala
    50                  55                  60
Asp Gly Thr Val Val Gly Thr Ala Arg Arg Ser Pro Glu Gly Val Lys
65                  70                  75                  80
Thr Ser Arg Phe Leu Cys Gln Gly Pro Glu Gly Arg Leu Tyr Gly Ser
                85                  90                  95
Leu His Phe Asn Pro Gln Ala Cys Ser Phe Arg Glu Leu Leu Leu Glu
            100                 105                 110
Asp Gly Tyr Asn Val Tyr Gln Ser Glu Ala Leu Gly Ile Pro Leu Arg
        115                 120                 125
Leu Pro Pro His Arg Ser Ser Asn Trp Asp Leu Ala Pro Arg Gly Pro
    130                 135                 140
Ala Arg Phe Leu Pro Leu Pro Gly Phe Leu Pro Pro Leu Glu Pro
145                 150                 155                 160
Pro Gly Ile Leu Ala Pro Glu Pro Pro Asn Val Gly Ser Ser Asp Pro
                165                 170                 175
Leu Ser Met Val Gly Pro Ser His Gly Arg Ser Pro Ser Tyr Thr Ser
            180                 185                 190

<210> SEQ ID NO 259
<211> LENGTH: 209
<212> TYPE: PRT
<213> ORGANISM: Mustela putorius furo

<400> SEQUENCE: 259

Met Gly Trp Glu Glu Ala Arg Ser Glu His Leu Gly Leu Trp Val Pro
1               5                   10                  15
Val Leu Ala Val Leu Leu Leu Gly Ala Cys Gln Ala Tyr Pro Ile Pro
            20                  25                  30
Asp Ser Ser Pro Leu Leu Gln Phe Gly Gly Gln Val Arg Gln Arg Tyr
```

-continued

```
                35                  40                  45
Leu Tyr Thr Asp Asp Ala Gln Glu Thr Glu Ala His Leu Glu Ile Arg
 50                  55                  60

Ala Asp Gly Thr Val Val Gly Ala Ala Arg Arg Ser Pro Glu Ser Leu
 65                  70                  75                  80

Leu Glu Leu Lys Ala Leu Lys Pro Gly Val Ile Gln Ile Leu Gly Val
                 85                  90                  95

Lys Thr Ser Arg Phe Leu Cys Gln Gly Pro Asn Gly Thr Leu Tyr Gly
                100                 105                 110

Ser Phe His Phe Asp Pro Val Ala Cys Ser Phe Arg Glu Val Leu Leu
                115                 120                 125

Glu Asp Gly Tyr Asn Ile Tyr His Ser Glu Thr Leu Gly Leu Pro Leu
            130                 135                 140

Arg Leu Pro Pro His Asn Ser Pro His Arg Asp Leu Ala Pro Arg Gly
145                 150                 155                 160

Pro Ala Arg Phe Leu Pro Leu Pro Gly Leu Leu Pro Ala Thr Pro Glu
                165                 170                 175

Ser Arg Gly Ile Pro Ala Pro Glu Pro Pro Asn Val Gly Ser Ser Asp
            180                 185                 190

Pro Leu Ser Met Val Gly Pro Leu Gln Gly Gln Ser Pro Ser Tyr Thr
            195                 200                 205

Ser

<210> SEQ ID NO 260
<211> LENGTH: 198
<212> TYPE: PRT
<213> ORGANISM: Takifugu rubripes

<400> SEQUENCE: 260

Phe Ile Tyr Leu Phe Ile Gln Thr Ala Leu Phe Ser Pro Ser Lys Trp
  1               5                  10                  15

Phe Asn Phe Tyr Leu Pro Asp Ser Asn Pro Leu Leu Ser Phe Asp Ser
                 20                  25                  30

His Gly Arg Gly Ile His Leu Tyr Thr Asp Asn Gln Arg Arg Gly Met
             35                  40                  45

Tyr Leu Gln Met Ser Thr Asp Gly Ser Val Ser Gly Ser Asp Val Gln
 50                  55                  60

Thr Ala Asn Ser Val Leu Glu Leu Lys Ser Val Arg Asn Gly His Val
 65                  70                  75                  80

Val Ile Arg Gly Lys Ser Ser Ser Leu Phe Leu Cys Met Asp Ser Arg
                 85                  90                  95

Gly Arg Leu Trp Gly Gln Arg His Pro Thr Glu Ala Asp Cys Thr Phe
                100                 105                 110

Arg Glu Val Leu Leu Ala Asp Gly Tyr Thr Arg Phe Leu Ser Leu His
            115                 120                 125

Asn Gly Thr Pro Val Ser Leu Ala Pro Lys Gln Ser Pro Asp Gln His
            130                 135                 140

Thr Val Pro Phe Thr Arg Phe Leu Pro Leu Arg Asn Thr Leu Ala Glu
145                 150                 155                 160

Glu Ser Met Ser Glu Pro Pro Ser Asn Gln Arg Tyr Phe Asn Ile
                165                 170                 175

Asp Ser Asp Asp Leu Leu Gly Met Asp Leu Asn Ala Met Val Ser Pro
            180                 185                 190

Gln Phe Ser Gly Asp Lys
```

195

<210> SEQ ID NO 261
<211> LENGTH: 203
<212> TYPE: PRT
<213> ORGANISM: Dipodomys ordii

<400> SEQUENCE: 261

```
Met Asp Gln Ala Lys Thr Arg Val Gly Ala Arg Gly Leu Gly Gly Leu
1               5                   10                  15

Val Leu Ala Val Ile Ile Leu Gly Ala Cys Lys Ala Arg Pro Ile Pro
                20                  25                  30

Asp Ser Ser Pro Leu Leu Gln Phe Gly Gly Gln Val Arg Leu Arg His
            35                  40                  45

Leu Tyr Thr Asp Asp Thr Gln Glu Thr Glu Ala His Leu Glu Ile Arg
        50                  55                  60

Ala Asp Gly Thr Val Val Gly Thr Ala His Arg Ser Pro Glu Ser Leu
65                  70                  75                  80

Leu Glu Leu Lys Ala Leu Lys Pro Gly Val Ile Gln Ile Leu Gly Ile
                85                  90                  95

Lys Thr Ser Arg Phe Leu Cys Gln Arg Pro Asp Gly Thr Leu Tyr Gly
            100                 105                 110

Ser Leu His Phe Asp Pro Glu Val Cys Ser Phe Gln Glu Leu Leu Leu
        115                 120                 125

Glu Asp Gly Tyr Asn Ile Tyr Arg Ser Glu Ala Leu Gly Leu Pro Leu
    130                 135                 140

Arg Leu Ser Pro Asp Pro Ala Pro Trp Gly Pro Ala Arg Phe Leu Pro
145                 150                 155                 160

Leu Pro Gly Val Pro Pro Ala Pro Pro Glu Pro Pro Gly Ile Leu Ala
                165                 170                 175

Pro Glu Pro Pro Asp Val Gly Ser Ser Asp Pro Leu Ser Met Val Gly
            180                 185                 190

Leu Leu Gln Gly Arg Ser Pro Ser Tyr Ala Ser
        195                 200
```

<210> SEQ ID NO 262
<211> LENGTH: 184
<212> TYPE: PRT
<213> ORGANISM: Echinops telfairi

<400> SEQUENCE: 262

```
Met Gly Cys Thr Lys Ser Gly Trp Lys Ser Pro Gly Leu Trp Val Pro
1               5                   10                  15

Val Leu Ala Ser Leu Leu Gly Gly Cys Gly Ala His Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Thr Thr Glu Ala His Leu Glu Ile Arg
        50                  55                  60

Ala Asp Gly Thr Val Gly Gly Val Ala His Gln Ser Pro Glu Lys Phe
65                  70                  75                  80

Leu Ser Gln Trp Arg Glu Lys Pro Leu Arg Ser Leu His Phe Asp Pro
                85                  90                  95

Ala Ala Cys Ser Phe Arg Glu Lys Leu Leu Glu Asp Gly Tyr Asn Leu
            100                 105                 110

Tyr His Ser Glu Thr His Gly Leu Pro Leu Arg Leu Pro Pro Arg Gly
```

```
            115                 120                 125
Gly Asp Pro Ser Ser Gln Pro Gly Ala Arg Phe Pro Leu Pro Gly
        130                 135                 140

Gln Leu Pro Gln Leu Gln Glu Thr Pro Gly Val Leu Ala Pro Glu Pro
145                 150                 155                 160

Pro Asp Val Gly Ser Ser Asp Pro Leu Ser Met Val Gly Pro Trp Arg
                165                 170                 175

Gly Gln Ser Pro Ser Tyr Ala Ser
            180

<210> SEQ ID NO 263
<211> LENGTH: 210
<212> TYPE: PRT
<213> ORGANISM: Macaca mulatta

<400> SEQUENCE: 263

Met Asp Ser Asp Glu Thr Gly Phe Glu His Ser Gly Leu Trp Val Pro
1               5                   10                  15

Val Leu Ala Gly Leu Leu Leu Gly Ala Cys Gln Ala His Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
50                  55                  60

Glu Asp Gly Thr Val Gly Gly Ala Ala His Gln Ser Pro Glu Ser Glu
65                  70                  75                  80

Cys Gly Pro Glu Pro Gly Ser Glu Gly Gly Ala Val Gly Gly Ala
                85                  90                  95

Glu Gly Pro Gly Leu Leu Gly Leu Arg Glu Ala Gly Leu Gly Pro Gly
            100                 105                 110

Ser Trp Leu His Phe Asp Pro Glu Ala Cys Ser Phe Arg Glu Leu Leu
        115                 120                 125

Leu Glu Asn Gly Tyr Asn Val Tyr Gln Ser Glu Ala His Gly Leu Pro
130                 135                 140

Leu His Leu Pro Gly Asn Lys Ser Pro His Arg Asp Pro Ala Ser Gln
145                 150                 155                 160

Gly Pro Ala Arg Phe Leu Pro Leu Pro Gly Leu Pro Pro Ala Pro Pro
                165                 170                 175

Glu Pro Pro Gly Ile Leu Ala Pro Gln Pro Pro Asp Val Gly Ser Ser
            180                 185                 190

Asp Pro Leu Ser Met Val Gly Pro Ser Gln Ala Arg Ser Pro Ser Tyr
        195                 200                 205

Ala Ser
    210

<210> SEQ ID NO 264
<211> LENGTH: 193
<212> TYPE: PRT
<213> ORGANISM: Microcebus murinus

<400> SEQUENCE: 264

Met Gly Trp Asp Glu Ala Gly Ala Gly Phe Glu His Pro Gly Leu Trp
1               5                   10                  15

Phe Pro Met Leu Gly Val Leu Leu Gly Ala Cys Gln Ala Tyr Pro
                20                  25                  30

Ile Pro Asp Ser Ser Pro Leu Leu Gln Phe Gly Gly Gln Val Arg Gln
```

```
                 35                  40                  45
Arg His Leu Tyr Thr Asp Asp Ile Gln Glu Thr Glu Ala His Leu Glu
 50                  55                  60

Ile Arg Ala Asp Gly Thr Val Val Gly Ala Arg Gln Ser Pro Glu
 65                  70                  75                  80

Leu Glu Leu Lys Ala Leu Lys Pro Gly Val Ile Gln Ile Leu Gly Val
                 85                  90                  95

Lys Thr Ser Arg Phe Leu Cys Gln Arg Pro Asp Gly Ala Leu Tyr Gly
                100                 105                 110

Ser Leu His Phe Asp Pro Glu Cys Ser Phe Arg Glu Leu Leu Glu
                115                 120                 125

Asp Gly Tyr Asn Val Tyr Cys Pro Tyr Leu Pro Leu His Leu Ser Pro
130                 135                 140

Arg Ile Glu Leu Ala Gly Ser Arg Ser Ala Leu Pro Leu Pro Pro Ala
145                 150                 155                 160

Pro Glu Arg Arg Ile Leu Ala Pro Glu Pro Pro Asp Gly Ser Ser Asp
                165                 170                 175

Pro Leu Ser Met Val Gly Pro Ser Gln Gly Arg Ser Pro Ser Tyr Ala
                180                 185                 190

Ser

<210> SEQ ID NO 265
<211> LENGTH: 204
<212> TYPE: PRT
<213> ORGANISM: Ochotona princeps

<400> SEQUENCE: 265

Lys Asp Met Asp Gly Leu Gln Pro Pro Gly Leu Arg Val Pro Val Leu
 1               5                  10                  15

Ala Ala Leu Leu Leu Gly Val Gly Gln Ala Arg Pro Ile Pro Asp Ser
                 20                  25                  30

Ser Pro Leu Leu Gln Phe Gly Gly Gln Val Arg Gln Arg His Leu Tyr
                 35                  40                  45

Thr Asp Asp Ala Gln Glu Ser Glu Val His Leu Glu Ile Arg Ala Asp
 50                  55                  60

Gly Thr Val Ala Gly Thr Ala Arg Arg Ser Pro Glu Ser Leu Leu Glu
 65                  70                  75                  80

Met Lys Ala Leu Lys Pro Gly Val Ile Gln Ile Leu Gly Val His Thr
                 85                  90                  95

Ser Arg Phe Leu Cys Gln Arg Pro Asp Gly Thr Leu Tyr Gly Ser Leu
                100                 105                 110

His Phe Asp His Lys Ala Cys Ser Phe Arg Glu Gln Leu Leu Glu Asp
                115                 120                 125

Gly Tyr Asn Val Tyr His Ser Glu Thr His Gly Leu Pro Leu Arg Leu
130                 135                 140

Ser Pro Asp Arg Ala Pro Arg Gly Pro Ala Arg Phe Leu Pro Leu Pro
145                 150                 155                 160

Gly Pro Pro Pro Asp Leu Leu Val Pro Leu Pro Asp Val Leu
                165                 170                 175

Ala Pro Glu Pro Pro Asp Val Asp Ser Pro Asp Pro Leu Ser Met Val
                180                 185                 190

Gly Pro Leu Gln Gly Gln Ser Pro Ser Tyr Thr Ser
                195                 200
```

-continued

<210> SEQ ID NO 266
<211> LENGTH: 182
<212> TYPE: PRT
<213> ORGANISM: Xiphophorus maculatus

<400> SEQUENCE: 266

Cys Pro Phe Pro Phe Leu Phe Leu Ile Leu Ser Leu Pro Phe Phe Ser
1               5                   10                  15

Ser Ser Phe Tyr Ile Pro Glu Ser Asn Pro Ile Phe Ala Phe Arg Asn
            20                  25                  30

Gln Leu Arg Glu Val His Leu Tyr Thr Glu Asn His Arg Arg Gly Leu
        35                  40                  45

Tyr Val Glu Ile His Leu Asp Gly Arg Val Thr Gly Ser Asp Ala Gln
    50                  55                  60

Ser Pro Tyr Ser Val Leu Gln Ile Lys Ser Val Lys Pro Gly His Val
65                  70                  75                  80

Val Ile Lys Gly Gln Thr Ser Ser Leu Phe Leu Cys Met Asp Asp Ser
                85                  90                  95

Gly Asn Leu Arg Gly Gln Thr Thr Tyr Asp Glu Ala Asp Cys Ser Phe
            100                 105                 110

Arg Glu Leu Leu Leu Ala Asp Gly Tyr Thr Arg Phe Leu Asn Ser Gln
        115                 120                 125

His Gly Val Pro Leu Ser Leu Ala Ser Arg Asn Ser Pro Asp Arg His
    130                 135                 140

Ser Val Pro Phe Thr Arg Phe Leu Pro Leu Arg Asn Thr Leu Thr Val
145                 150                 155                 160

Ser Glu Glu Ser Thr Lys Thr Gln Arg Asp Phe Asn Leu Asp Ser Asp
                165                 170                 175

Asp Leu Leu Gly Met Gly
            180

<210> SEQ ID NO 267
<211> LENGTH: 192
<212> TYPE: PRT
<213> ORGANISM: Gasterosteus aculeatus

<400> SEQUENCE: 267

Ser Leu Leu Leu Met Val Pro Leu Pro Phe Cys Ser Ser Phe Tyr Leu
1               5                   10                  15

Thr Asp Ser Ser Pro Leu Leu Pro Phe Asn Asn Gln Val Lys Glu Val
            20                  25                  30

His Leu Tyr Thr Ala Glu Asn His Arg Arg Ala Met Tyr Leu Gln Ile
        35                  40                  45

Ala Leu Asp Gly Ser Val Ser Gly Ser Asp Ala Arg Ser Thr Tyr Ser
    50                  55                  60

Val Leu Gln Leu Lys Ser Ile Gln Pro Gly His Val Val Ile Arg Gly
65                  70                  75                  80

Lys Ala Ser Ser Met Phe Leu Cys Val Asp Ser Gly Gly Arg Leu Arg
                85                  90                  95

Gly Gln Gly Pro Tyr Ser Glu Ala Asp Cys Ser Phe Arg Glu Leu Leu
            100                 105                 110

Leu Gly Asp Gly Tyr Thr Arg Phe Leu Ser Ser Gln His Gly Ser Pro
        115                 120                 125

Leu Ser Leu Ala Ser Arg Pro Ser Pro Asp Pro Asn Ser Val Pro Phe
    130                 135                 140

Thr Arg Phe Leu Pro Ile Arg Thr Ala Pro Glu Ala Glu Ser Val Ile

```
                145                 150                 155                 160
Glu Glu Pro Pro Ser Asn Gln Arg Tyr Val Asn Val Asp Ser Glu Asp
                    165                 170                 175

Leu Leu Gly Met Gly Leu Asn Thr Val Val Ser Pro Gln Phe Ser Ala
                180                 185                 190

<210> SEQ ID NO 268
<211> LENGTH: 165
<212> TYPE: PRT
<213> ORGANISM: Sarcophilus harrisii

<400> SEQUENCE: 268

Val Ser Ala Met Gly Leu Arg Glu Arg Ala Pro Arg Tyr Leu Ala Pro
1               5                   10                  15

Leu Leu Ser Leu Leu Leu Ala Cys Arg Ala Ser Gly His Pro Leu Pro
                20                  25                  30

Asp Ser Ser Pro Met Leu Leu Phe Gly Gly Gln Val Arg Leu Arg His
            35                  40                  45

Leu Tyr Thr Asp Val Gly Gln Glu Ala Glu Ala His Val Glu Leu Ala
        50                  55                  60

Ser Asp Gly Thr Val Arg Ala Ala Arg Arg Ser Pro Asn Ser Leu
65                  70                  75                  80

Leu Glu Leu Lys Ala Val Lys Pro Gly Ile Val Arg Ile Leu Ala Val
                85                  90                  95

His Ser Ser Arg Phe Leu Cys Met Arg Pro Asn Gly Glu Leu Tyr Gly
                100                 105                 110

Ala Ile His Tyr Asp Pro Ser Ala Cys Asn Phe Arg Glu Arg Leu Leu
            115                 120                 125

Gly Asp Gly Tyr Asn Val Tyr Glu Ser Glu Ala His Gly Arg Thr Leu
        130                 135                 140

Arg Leu Pro Pro Lys Ala Ala Pro Gly Pro Ala Gly Pro Ser Arg Phe
145                 150                 155                 160

Leu Pro Leu Pro Gly
                165

<210> SEQ ID NO 269
<211> LENGTH: 208
<212> TYPE: PRT
<213> ORGANISM: Macropus eugenii

<400> SEQUENCE: 269

Thr Glu Glu Pro Ser Thr Gly Ser Arg His Leu Gly Gln Trp Ala Pro
1               5                   10                  15

Gly Leu Pro Gly Pro Leu Leu Ser Leu Leu Leu Ala Tyr Arg Gly Trp
                20                  25                  30

Gly Ser Pro Ile Pro Asp Ser Ser Pro Met Leu Leu Phe Gly Gly Gln
            35                  40                  45

Val Arg Leu Arg His Leu Tyr Thr Asp Asp Gly Gln Asp Thr Glu Ala
        50                  55                  60

His Val Glu Leu Gly Pro Asp Gly Val Val Arg Ala Val Ala Glu Arg
65                  70                  75                  80

Ser Pro Asn Ser Leu Leu Glu Leu Lys Ala Val Lys Pro Gly Val Ile
                85                  90                  95

Arg Ile Leu Ala Val Gln Ser Ser Arg Phe Leu Cys Met Arg Pro Asn
                100                 105                 110

Gly Glu Leu Tyr Gly Ala Val His Tyr Asp Pro Ser Ala Cys Asn Phe
```

```
              115                 120                 125
Arg Glu His Leu Leu Gly Asp Gly Tyr Asn Val Tyr Glu Ser Glu Thr
        130                 135                 140

His Arg Arg Thr Leu Arg Leu Ser Pro Ser Leu Gly Gln Ala Gly Pro
145                 150                 155                 160

Ser Arg Phe Leu Pro Leu Pro Gly Asp Trp Leu Pro Gly Pro Asp Pro
                165                 170                 175

Pro Trp Ala Gln Gly Pro Glu Pro Pro Asp Val Gly Ser Ala Asp Pro
            180                 185                 190

Leu Ser Met Val Gly Ala Val Gln Gly Leu Ser Pro Ser Tyr Ser Ser
        195                 200                 205

<210> SEQ ID NO 270
<211> LENGTH: 160
<212> TYPE: PRT
<213> ORGANISM: Xenopus tropicalis

<400> SEQUENCE: 270

Arg Gly Gly Arg Thr Lys Lys Thr Leu Arg Lys Trp Leu Cys
1               5                   10                  15

Leu Leu Ala Ile Met Leu Ser Arg Ser Arg Phe Ser Leu Ala Asn Pro
            20                  25                  30

Ile Gln Asn Ser Asn Pro Ile Leu Ser Asn Asp Asn Gln Val Arg Thr
        35                  40                  45

Gln Tyr Leu Tyr Thr Asp Asn Asn Met His Leu Tyr Leu Gln Ile
    50                  55                  60

Thr His Asn Gly Val Val Thr Gly Thr Glu Glu Lys Asn Asp Tyr Gly
65                  70                  75                  80

Val Leu Glu Ile Lys Ala Val Lys Ala Gly Val Val Ile Lys Gly
                85                  90                  95

Ile Arg Ser Asn Leu Tyr Leu Cys Met Asp Ser Arg His Gln Leu Tyr
            100                 105                 110

Ala Ser Ala Tyr Asp Lys Asp Cys His Phe His Glu Lys Ile Thr
        115                 120                 125

Pro Asp Asn Tyr Asn Met Tyr Ser Ser Glu Lys His Ser Glu Tyr Val
    130                 135                 140

Ser Leu Ala Pro Leu Lys Gly Ser Gln Met Ala Arg Phe Leu Pro Ile
145                 150                 155                 160

<210> SEQ ID NO 271
<211> LENGTH: 194
<212> TYPE: PRT
<213> ORGANISM: Danio rerio

<400> SEQUENCE: 271

Met Leu Leu Ala Cys Phe Phe Ile Phe Phe Ala Leu Phe Pro His Leu
1               5                   10                  15

Arg Trp Cys Met Tyr Val Pro Ala Gln Asn Val Leu Leu Gln Phe Gly
            20                  25                  30

Thr Gln Val Arg Glu Arg Leu Leu Tyr Thr Asp Gly Leu Phe Leu Glu
        35                  40                  45

Met Asn Pro Asp Gly Ser Val Lys Gly Ser Pro Glu Lys Asn Leu Asn
    50                  55                  60

Cys Val Leu Glu Leu Arg Ser Val Lys Ala Gly Glu Thr Val Ile Gln
65                  70                  75                  80

Ser Ala Ala Thr Ser Leu Tyr Leu Cys Val Asp Asp Gln Asp Lys Leu
```

85                  90                  95
Lys Gly Gln His His Tyr Ser Ala Leu Asp Cys Thr Phe Gln Glu Leu
                100                 105                 110

Leu Leu Asp Gly Tyr Ser Phe Phe Leu Ser Pro His Thr Asn Leu Pro
                115                 120                 125

Val Ser Leu Leu Ser Lys Arg Gln Lys His Gly Asn Pro Leu Ser Arg
            130                 135                 140

Phe Leu Pro Val Ser Arg Ala Glu Asp Ser Arg Thr Gln Glu Val Lys
145                 150                 155                 160

Gln Tyr Ile Gln Asp Ile Asn Leu Asp Ser Asp Pro Leu Gly Met
                165                 170                 175

Gly His Arg Ser His Leu Gln Thr Val Phe Ser Pro Ser Leu His Thr
            180                 185                 190

Lys Lys

<210> SEQ ID NO 272
<211> LENGTH: 209
<212> TYPE: PRT
<213> ORGANISM: Bos grunniens mutus

<400> SEQUENCE: 272

Met Gly Trp Asp Glu Ala Lys Phe Lys His Leu Gly Leu Trp Val Pro
1               5                   10                  15

Val Leu Ala Val Leu Leu Gly Thr Cys Arg Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala Arg Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Lys Leu Tyr Gly
                100                 105                 110

Ser Leu His Phe Asp Pro Lys Ala Cys Ser Phe Arg Glu Leu Leu Leu
            115                 120                 125

Glu Asp Gly Tyr Asn Val Tyr Gln Ser Glu Thr Leu Gly Leu Pro Leu
        130                 135                 140

Arg Leu Pro Pro Gln Arg Ser Ser Asn Arg Asp Pro Ala Pro Arg Gly
145                 150                 155                 160

Pro Ala Arg Phe Leu Pro Leu Pro Gly Leu Pro Ala Glu Pro Pro Asp
                165                 170                 175

Pro Pro Gly Ile Leu Ala Pro Glu Pro Pro Asp Val Gly Ser Ser Asp
            180                 185                 190

Pro Leu Ser Met Val Gly Pro Ser Tyr Gly Arg Ser Pro Ser Tyr Thr
        195                 200                 205

Ser

<210> SEQ ID NO 273
<211> LENGTH: 209
<212> TYPE: PRT
<213> ORGANISM: Saimiri boliviensis boliviensis

<400> SEQUENCE: 273

```
Met Gly Ser Glu Glu Val Ala Leu Glu Arg Pro Ala Leu Trp Val Ser
1               5                   10                  15

Val Leu Ala Gly Leu Leu Leu Gly Thr Cys Gln Ala Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Ala Gly Ala Ala His Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu Tyr Phe Asp Pro Glu Ala Cys Ser Phe Arg Glu Leu Leu Leu
        115                 120                 125

Glu Asp Gly Tyr Asn Val Tyr Gln Ser Val Ala His Ser Leu Pro Leu
    130                 135                 140

His Leu Pro Gly Gly Arg Ser Pro Pro Trp Asp Pro Ala Pro Arg Gly
145                 150                 155                 160

Pro Ala Arg Phe Leu Pro Leu Pro Gly Leu Pro Pro Glu Pro Pro Glu
                165                 170                 175

Ala Pro Gly Ile Leu Ala Pro Glu Pro Pro Asp Val Gly Ser Ser Asp
            180                 185                 190

Pro Leu Ser Met Val Gly Pro Ser Gln Gly Gln Ser Pro Ser Tyr Thr
        195                 200                 205

Ser

<210> SEQ ID NO 274
<211> LENGTH: 210
<212> TYPE: PRT
<213> ORGANISM: Callithrix jacchus
<220> FEATURE:
<221> NAME/KEY: misc_feature
<222> LOCATION: (64)..(64)
<223> OTHER INFORMATION: Xaa can be any naturally occurring amino acid

<400> SEQUENCE: 274

Met Gly Ser Glu Glu Val Gly Leu Glu His Pro Ala Leu Trp Val Ser
1               5                   10                  15

Val Leu Ala Gly Leu Leu Leu Gly Thr Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Lys Glu Ala His Leu Glu Ile Xaa
    50                  55                  60

Glu Asp Gly Thr Val Ala Gly Ala Ala Thr Lys Val Pro Lys Val Ser
65                  70                  75                  80

Leu Leu Gln Leu Lys Ala Leu Lys Pro Gly Val Ile Gln Ile Leu Gly
                85                  90                  95

Val Lys Thr Ser Arg Phe Leu Cys Gln Arg Pro Asp Gly Ala Leu Tyr
            100                 105                 110

Gly Ser Leu His Phe Asp Pro Glu Ala Cys Ser Phe Arg Glu Leu Leu
        115                 120                 125

Leu Glu Asp Gly Tyr Asn Val Tyr Gln Ser Val Ala His Gly Leu Pro
    130                 135                 140
```

```
Leu His Leu Pro Glu Ser Arg Ser Pro Pro Arg Asp Pro Ala Pro Arg
145                 150                 155                 160

Gly Pro Ala Arg Phe Leu Pro Leu Pro Gly Leu Pro Glu Pro Pro
                165                 170                 175

Glu Pro Pro Gly Ile Leu Ala Pro Glu Pro Pro Asp Val Gly Ser Ser
            180                 185                 190

Asp Pro Leu Ser Met Val Gly Pro Ser Gln Gly Gln Ser Pro Ser Tyr
        195                 200                 205

Ala Ser
    210
```

<210> SEQ ID NO 275
<211> LENGTH: 209
<212> TYPE: PRT
<213> ORGANISM: Tupaia chinensis

<400> SEQUENCE: 275

```
Met Gly Trp Asp Lys Ala Arg Phe Glu His Leu Gly Trp Ala Pro
1               5                   10                  15

Val Leu Ala Val Leu Leu Leu Gly Ala Cys Gln Ala Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Thr Gln Asp Thr Glu Ala His Leu Glu Ile Arg
    50                  55                  60

Ala Asp Gly Thr Val Val Gly Ala Ala His Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Ile Tyr Gln Ser Glu Ala Arg Gly Leu Pro Leu
    130                 135                 140

Arg Leu Pro Pro His Asp Ser Pro His Arg Asp Arg Thr Pro Gln Gly
145                 150                 155                 160

Pro Ala Arg Phe Leu Pro Leu Pro Gly Leu Pro Leu Val Pro Pro Glu
                165                 170                 175

Leu Pro Gly Val Leu Ala Leu Glu Pro Pro Asp Val Gly Ser Ser Asp
            180                 185                 190

Pro Leu Ser Met Met Gly Pro Ser Gln Gly Gln Ser Pro Ser Tyr Ala
        195                 200                 205

Ser
```

<210> SEQ ID NO 276
<211> LENGTH: 188
<212> TYPE: PRT
<213> ORGANISM: Papio Anubis

<400> SEQUENCE: 276

```
Met Asp Ser Asp Glu Thr Gly Phe Glu His Ser Gly Leu Trp Val Pro
1               5                   10                  15

Val Leu Ala Gly Leu Leu Leu Gly Ala Cys Gln Ala His Pro Ile Pro
            20                  25                  30
```

Asp Ser Ser Pro Leu Leu Gln Phe Gly Gly Gln Val Arg Gln Arg Tyr
                35                  40                  45

Leu Tyr Thr Asp Asp Ala Gln Gln Thr Glu Ala His Leu Glu Ile Arg
 50                  55                  60

Glu Asp Gly Thr Val Gly Gly Ala Ala His Gln Ser Pro Glu Ser Lys
 65                  70                  75                  80

Cys Gly Pro Glu Pro Gly Ser Glu Gly Gly Ala Leu His Phe Asp
                 85                  90                  95

Pro Glu Ala Cys Ser Phe Arg Glu Leu Leu Leu Glu Asn Gly Tyr Asn
                100                 105                 110

Val Tyr Gln Ser Glu Ala His Gly Leu Pro Leu His Leu Pro Gly Asn
                115                 120                 125

Lys Ser Pro His Arg Asp Pro Ala Ser Arg Gly Pro Ala Arg Phe Leu
130                 135                 140

Pro Leu Pro Gly Leu Pro Ala Pro Pro Glu Pro Gly Ile Leu
145                 150                 155                 160

Ala Pro Gln Pro Pro Asp Val Gly Ser Ser Asp Pro Leu Ser Met Val
                165                 170                 175

Gly Pro Ser Gln Ala Arg Ser Pro Ser Tyr Ala Ser
                180                 185

<210> SEQ ID NO 277
<211> LENGTH: 208
<212> TYPE: PRT
<213> ORGANISM: Pteropus alecto

<400> SEQUENCE: 277

Met Gly Trp Gly Lys Ala Arg Leu Gln His Pro Gly Leu Trp Gly Pro
 1               5                  10                  15

Val Leu Ala Val Leu Leu Gly Ala Cys Gln Ala His Pro Ile Leu Asp
                20                  25                  30

Ser Ser Pro Leu Phe Gln Phe Gly Ser Gln Val Arg Arg Arg Tyr Leu
                35                  40                  45

Tyr Thr Asp Asp Ala Gln Asp Thr Glu Ala His Leu Glu Ile Arg Ala
 50                  55                  60

Asp Gly Thr Val Ala Gly Ala Ala Arg Arg Ser Pro Glu Ser Leu Leu
 65                  70                  75                  80

Glu Leu Lys Ala Leu Lys Pro Gly Val Ile Gln Val Leu Gly Val Lys
                 85                  90                  95

Thr Ser Arg Phe Leu Cys Gln Arg Pro Asp Gly Thr Leu Tyr Gly Ser
                100                 105                 110

Leu His Phe Asp Pro Ala Ala Cys Ser Phe Arg Glu Leu Leu Leu Lys
                115                 120                 125

Asp Gly Tyr Asn Val Tyr Gln Ser Glu Ala Leu Ala Arg Pro Leu Arg
130                 135                 140

Leu Pro Pro Tyr Ser Ser Pro Ser Ser Asp Pro Ala Arg Arg Gly Pro
145                 150                 155                 160

Ala Arg Phe Leu Pro Leu Pro Gly Pro Pro Pro Glu Pro Pro Gln Pro
                165                 170                 175

Pro Gly Arg Leu Ala Pro Glu Pro Asp Val Gly Ser Ser Asp Pro
                180                 185                 190

Leu Ser Met Val Trp Pro Ser Arg Gly Arg Ser Pro Ser Tyr Thr Ser
                195                 200                 205

<210> SEQ ID NO 278

```
<211> LENGTH: 210
<212> TYPE: PRT
<213> ORGANISM: Heterocephalus glaber

<400> SEQUENCE: 278

Met Asp Trp Ala Arg Ala Glu Ser Glu Arg Pro Gly Leu Trp Val Pro
1               5                   10                  15

Ala Val Leu Ala Val Leu Leu Leu Gly Ala Cys Gln Ala His Pro Ile
            20                  25                  30

Pro Asp Ser Ser Pro Leu Leu Gln Phe Gly Gly Gln Val Arg Gln Arg
        35                  40                  45

His Leu Tyr Thr Asp Asp Ala Gln Asp Thr Glu Val His Leu Glu Ile
    50                  55                  60

Arg Ala Asp Gly Ser Val Gly Ala Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Arg Thr Ser Arg Phe Leu Cys Gln Arg Pro Asp Gly Thr Leu Tyr
            100                 105                 110

Gly Ser Leu His Phe Asp Pro Glu Ala Cys Ser Phe Arg Glu Leu Leu
        115                 120                 125

Leu Ala Asp Gly Tyr Asn Ile Tyr Gln Ser Glu Ala Tyr Gly Leu Pro
    130                 135                 140

Leu Arg Met Leu Pro Ser Asp Ser Ala Ser Arg Asp Pro Val Pro Pro
145                 150                 155                 160

Gly Pro Ala Arg Phe Leu Pro Leu Pro Gly Leu His Pro Pro Leu
                165                 170                 175

Glu Pro Pro Gly Met Leu Pro Pro Glu Pro Pro Asp Val Gly Ser Ser
            180                 185                 190

Asp Pro Leu Ser Met Val Gly Pro Leu Gln Gly Arg Ser Pro Ser Tyr
        195                 200                 205

Ala Phe
    210

<210> SEQ ID NO 279
<211> LENGTH: 209
<212> TYPE: PRT
<213> ORGANISM: Cricetulus griseus

<400> SEQUENCE: 279

Met Asp Trp Met Lys Ser Gly Val Gly Val Pro Gly Leu Trp Val Pro
1               5                   10                  15

Leu Leu Pro Ile Phe Leu Leu Gly Val Ser Gln Ala His Pro Ile Pro
            20                  25                  30

Asp Ser Ser Pro Leu Leu Gln Phe Gly Gly Gln Val Arg His Arg His
        35                  40                  45

Leu Tyr Thr Asp Asp Asn Gln Glu Thr Glu Val His Leu Glu Ile Arg
    50                  55                  60

Gln Asp Gly Thr Val Ile Gly Thr Thr His Arg Ser Pro Glu Ser Leu
65                  70                  75                  80

Leu Glu Leu Lys Ala Leu Lys Pro Glu Val Ile Pro Val Leu Gly Val
                85                  90                  95

Lys Ala Ser Arg Phe Leu Cys Gln Gln Pro Asp Gly Thr Leu Tyr Gly
            100                 105                 110

Ser Pro His Phe Asp Pro Glu Ala Cys Ser Phe Arg Glu Leu Leu Leu
        115                 120                 125
```

```
Glu Asp Gly Tyr Asn Val Tyr Gln Ser Glu Val His Gly Leu Pro Leu
            130                 135                 140

Arg Leu Pro Gln Arg Asp Ser Pro Asn Gln Ala Pro Ala Ser Trp Gly
145                 150                 155                 160

Pro Val Pro Pro Leu Pro Val Pro Gly Leu Leu His Gln Pro Gln Glu
                165                 170                 175

Leu Pro Gly Phe Leu Ala Pro Glu Pro Pro Asp Val Gly Ser Ser Asp
            180                 185                 190

Pro Leu Ser Met Val Gly Pro Leu Gln Gly Arg Ser Pro Ser Tyr Ala
                195                 200                 205

Ser

<210> SEQ ID NO 280
<211> LENGTH: 192
<212> TYPE: PRT
<213> ORGANISM: Ovis aries

<400> SEQUENCE: 280

Met Gly Trp Asp Glu Ala Lys Phe Lys His Leu Gly Leu Trp Val Pro
1               5                   10                  15

Val Leu Ala Val Leu Leu Gly Thr Cys Arg Ala His Pro Ile Pro
            20                  25                  30

Asp Ser Ser Pro Leu Leu Gln Phe Gly Gly Gln Val Arg Gln Arg Tyr
            35                  40                  45

Leu Tyr Thr Asp Asp Ala Gln Glu Thr Glu Ala His Leu Glu Ile Arg
        50                  55                  60

Ala Asp Gly Thr Val Val Gly Ala Ala Arg Gln Ser Pro Glu Ser Leu
65                  70                  75                  80

Leu Glu Leu Lys Ala Leu Lys Pro Gly Val Ile Gln Ile Phe Gly Val
                85                  90                  95

Lys Thr Ser Arg Phe Leu Cys Gln Gly Pro Asp Gly Lys Leu Tyr Gly
            100                 105                 110

Ser Leu His Phe Asp Pro Lys Ala Cys Ser Phe Arg Glu Leu Leu Leu
        115                 120                 125

Glu Asp Gly Tyr Asn Val Tyr Gln Ser Glu Thr Leu Gly Leu Pro Leu
    130                 135                 140

Arg Leu Pro Pro Gln Arg Ser Ser Asn Arg Asp Pro Ala Pro Arg Gly
145                 150                 155                 160

Pro Pro Lys Pro Gln Leu His Phe Leu Lys Thr Ser Ala Val Gln Tyr
                165                 170                 175

Trp Pro Arg Tyr Glu Lys Val Pro Ala Phe Leu His Pro Phe Pro Gly
            180                 185                 190

<210> SEQ ID NO 281
<211> LENGTH: 135
<212> TYPE: PRT
<213> ORGANISM: Pan paniscus

<400> SEQUENCE: 281

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
            35                  40                  45
```

```
Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
 65                  70                  75                  80

Leu Gln Leu Lys Ala Leu Lys Pro Gly Val Ile Gln Ile Leu Gly Val
                 85                  90                  95

Lys Thr Ser Arg Phe Leu Cys Gln Arg Pro Asp Gly Ala Leu Tyr Gly
                100                 105                 110

Ser Val Ser Phe Gln Asp Pro Pro His His Pro Pro Cys Ser Ser Tyr
            115                 120                 125

Met Ser Pro Ser Gln Pro Gly
    130                 135

<210> SEQ ID NO 282
<211> LENGTH: 116
<212> TYPE: PRT
<213> ORGANISM: Macaca fascicularis

<400> SEQUENCE: 282

Met Asp Ser Asp Glu Thr Gly Phe Glu His Ser Gly Leu Trp Val Pro
 1               5                  10                  15

Val Leu Ala Gly Leu Leu Leu Gly Ala Cys Gln Ala His Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala His Gln Ser Pro Glu Ser Leu
 65                  70                  75                  80

Leu Gln Leu Lys Ala Leu Lys Pro Gly Val Ile Gln Ile Leu Gly Val
                 85                  90                  95

Lys Thr Ser Arg Phe Leu Cys Gln Lys Pro Asp Gly Ala Leu Tyr Gly
                100                 105                 110

Ser Val Ser Phe
            115

<210> SEQ ID NO 283
<211> LENGTH: 104
<212> TYPE: PRT
<213> ORGANISM: Mesocricetus auratus

<400> SEQUENCE: 283

Val Ile Gln Ile Leu Gly Val Lys Ala Ala Arg Phe Pro Cys Gln Gln
 1               5                  10                  15

Pro Asp Gly Ser Leu Tyr Gly Ser Pro His Phe Asp Pro Glu Ala Cys
                20                  25                  30

Ser Phe Arg Glu Leu Leu Leu Glu Asp Gly Tyr Asn Val Tyr Gln Ser
            35                  40                  45

Glu Ala His Gly Leu Pro Leu Arg Leu Pro Gln Arg Asp Ala Pro Ser
    50                  55                  60

Gln Pro Pro Ala Ser Trp Gly Pro Val Arg Phe Leu Pro Val Pro Gly
 65                  70                  75                  80

Leu Phe Gln Pro Pro His Asp Leu Pro Gly Arg Pro Ala Pro Glu Pro
                 85                  90                  95

Pro Asp Val Gly Ser Ser Asp Pro
                100
```

<210> SEQ ID NO 284
<211> LENGTH: 151
<212> TYPE: PRT
<213> ORGANISM: Oreochromis niloticus

<400> SEQUENCE: 284

Met Tyr Leu Gln Met Asn Met Asp Gly Arg Val Thr Gly Ser Asp Ala
1               5                   10                  15

Gln Thr Pro Tyr Ser Leu Met Gln Leu Lys Ser Val Lys Pro Gly His
            20                  25                  30

Val Ile Ile Lys Gly Pro Ser Ser Leu Phe Leu Cys Val Asp Ser
        35                  40                  45

Glu Gly Asn Leu Arg Gly Gln Ser His Tyr Ser Glu Thr Ser Cys Thr
50                  55                  60

Phe Arg Glu Met Leu Leu Ala Asp Gly Tyr Thr Arg Phe Ile Ser Ser
65                  70                  75                  80

Gln Tyr Gly Phe Pro Met Ser Leu Ala Ser Arg His Ser Pro Asp Arg
                85                  90                  95

His Ala Leu Pro Phe Thr Arg Phe Leu Pro Leu Arg Asn Asn Leu Lys
            100                 105                 110

Thr Asp Ser Val Ser Glu Gln Leu Pro Asn Asn Gln Arg Leu Phe Asn
        115                 120                 125

Val Asp Ser Asp Asp Leu Leu Gly Met Gly Leu Asn Ser Met Gly Ser
130                 135                 140

Pro Gln Phe Ser Met Asp Lys
145                 150

<210> SEQ ID NO 285
<211> LENGTH: 630
<212> TYPE: DNA
<213> ORGANISM: Homo sapiens

<400> SEQUENCE: 285
atggactcgg acgagaccgg gttcgagcac tcaggactgt gggtttctgt gctggctggt      60
cttctgctgg agcctgcca ggcacacccc atccctgact ccagtcctct cctgcaattc     120
gggggccaag tccggcagcg gtacctctac acagatgatg cccagcagac agaagcccac    180
ctggagatca ggaggatgg gacggtgggg ggcgctgctg accagagccc cgaaagtctc     240
ctgcagctga aagccttgaa gccgggagtt attcaaatct gggagtcaa gacatccagg     300 ttcctgtgcc agcggccaga tggggccctg tatggatcgc tccactttga ccctgaggcc    360
tgcagcttcc gggagctgct tcttgaggac ggatacaatg tttaccagtc cgaagcccac    420
ggcctcccgc tgcacctgcc agggaacaag tccccacacc gggaccctgc accccgagga    480
ccagctcgct tcctgccact accaggcctg ccccccgcac tcccggagcc acccggaatc    540 ctggccccc agcccccga tgtgggctcc tcggaccctc tgagcatggt gggaccttcc      600
cagggccgaa gccccagcta cgcttcctga                                     630

<210> SEQ ID NO 286
<211> LENGTH: 630
<212> TYPE: DNA
<213> ORGANISM: Pongo abelii

<400> SEQUENCE: 286
atggactcgg acgagaccgg gttcgagcac tcaggactgt gggttcctgt gctggctggt      60
cttctgctgg agcctgcca ggcacacccc atccctgact ccagtcctct cctgcaattc     120

```
ggggggccaag tccggcagcg gtacctctac acagatgatg cccagcagac agaagcccac    180
ctggagatca gggaggatgg gacggtgggg ggcgctgctg accagagccc cgaaagtctc    240
ctgcagctga aagccttgaa gccgggagtt attcaaatct tgggagtcaa gacatccagg    300
ttcctgtgcc agaggccaga tggggccctg tatggatcgc tccactttga ccctgaggcc    360
tgcagcttcc gggagctgct tcttgaggac ggatacaatg tttatcagtc cgaggcccat    420
ggcctcccgc tgcacctgcc gggaaacaag tccccacacc gggaccctgc accccgagga    480
ccagctcgct tcctgccact accaggcctg ccccccgcac cccagagccg cccggaatc     540 ctggcccccc agcccccga tgtgggctcc tcggaccctc tgagcatggt gggaccttcc    600
cagggccgaa gccccagcta tgcttcctga                                    630

<210> SEQ ID NO 287
<211> LENGTH: 630
<212> TYPE: DNA
<213> ORGANISM: Pan troglodytes

<400> SEQUENCE: 287
atggactcgg acgagaccgg gttcgagcac tcaggactgt gggtttctgt gctggctggt     60
cttctgctag gagcctgcca ggcacacccc atccctgact ccagtcctct cctgcaattc    120 ggggggccaag tccggcagcg gtacctctac acagatgatg cccagcagac agaagcccac   180
ctggagatca gggaggatgg gacggtgggg ggcgctgctg accagagccc cgaaagtctc    240
ctgcagctga aagccttgaa gccgggagtt attcaaatct tgggagtcaa gacatccagg    300
ttcctgtgcc agaggccaga tggggccctg tatggatcgc tccactttga ccctgaggcc    360
tgcagcttcc gggagctgct tcttgaggac ggatacaatg tttaccagtc cgaggcccac    420
ggcctcccgc tgcacctgcc ggggaacaag tccccacacc gggaccctgc accccgagga   480
ccagctcgct tcctgccact accaggcctg ccccccgcac cccggagcc acccggaatc    540 ctggcccccc agcccccga tgtgggctcc tcagaccctc tgagcatggt gggaccttcc    600
cagggccgaa gccccagcta cacttcctga                                    630

<210> SEQ ID NO 288
<211> LENGTH: 630
<212> TYPE: DNA
<213> ORGANISM: Canis lupus familiaris

<400> SEQUENCE: 288
atgggctggg ccgaggccgg gttcgagcac ctgggactgt gggtccctgt gctggctgtg     60
cttttgctgg aagcctgccg ggcacatccg atccctgact ccagcccct cctacaattt    120 ggaggtcaag ttcgacagcg gtacctctac accgacgatg cccaggagac agaggccac    180 ctagagatca gggccgatgg cacagtggtg ggggctgccc gccagagccc tgaaagtctc    240
ctggagctga aagccctaaa gccagggggtc attcaaatct tgggagtcaa acatccagg    300 ttcctgtgcc agggcccaga tgggacacta tatggctcgc tccatttcga ccctgtggcc    360
tgcagtttcc gagaactgct tcttgaggat gggtacaaca tctaccactc cgagaccctt    420
ggtctcccgc ttcgcctgcg ccccacaac tccgcatacc gggacttggc accccgcggg    480
cctgcccgct tcctgccact gccaggcctg cttccagcac cccagagcc tccagggatc    540 ctggccccgg agcctcctga cgtgggctcc tcggaccctc tgagcatggt ggggccttca   600
cagggccgga gtcccagcta tgcttcctaa                                    630
```

<210> SEQ ID NO 289
<211> LENGTH: 630
<212> TYPE: DNA
<213> ORGANISM: Bos taurus

<400> SEQUENCE: 289

```
atgggctggg acgaggccaa gttcaagcac ttgggactgt gggtccctgt gctggctgtc    60
ctcctgctag gaacctgccg ggcgcatccc attccagact ccagcccccct cctccagttt   120
ggggccaag tccgccagcg gtacctctac acggatgatg cccaggagac agaggcccac    180
ctggagatca gggccgatgg cacagtggtg ggggcagccc gccagagccc cgaaagtctc    240
ttggagctga agccctgaa gccaggcgtc attcagatct gggagttaa acatccagg     300
tttctctgcc aggggccaga tgggaagctg tacggatcgc tgcactttga ccccaaagcc    360
tgcagctttc gggagctgct tcttgaagat ggatacaacg tctaccagtc ggagaccctg    420
ggccttccac tccgcctgcc ccccagcgc tcgtccaacc gggacccggc ccgcgggga    480
cctgctcgct tccttccact gccgggcctg cccgcgcgc cccgatcc tcagggatc      540
ttggcccccg agcctcccga cgtgggctcc tcggatcccc tgagtatggt gggaccctcg    600
tatggccgaa gccccagcta cacttcttga                                    630
```

<210> SEQ ID NO 290
<211> LENGTH: 630
<212> TYPE: DNA
<213> ORGANISM: Equus caballus

<400> SEQUENCE: 290

```
atggactggg acaagacggg gttcaagtac cagggactgt gggtccctgt gctggctgtc    60
cttctgctgg gagcctgcca gtcacacccc atccctgact ccagtcccct cctccaattc   120
ggggccaag tcaggcagcg ccacctctac acagatgatg cccaggagac agaggcgcac    180
ctggagatca gggctgacgg cactgtggca ggggctgtcc accggagccc agaaagtctc    240
ttggagctga agccctgaa gccaggggta attcaaatct gggagtcaa gacatccagg    300
tttctgtgcc aggggccaga cgggacgctg tacggatcgc tccacttcga ccccgtggcc    360
tgcagcttcc gggagctgct tctcgaagac ggctacaacg tttaccagtc tgagaccctt    420
ggcctcccac tccgcctgcc caccacagc tccccatacc aggatccggc ccctcgggca    480
cccgcccgct tcctgccgct gccaggcttt ccccagcac cccggagcc tcagggatc     540
ccggccccg agccccgga cgtgggctcc tcggacccc tgagcatggt ggggccttca     600
cgcagccgga gccccagcta cacttcctga                                   630
```

<210> SEQ ID NO 291
<211> LENGTH: 630
<212> TYPE: DNA
<213> ORGANISM: Ailuropoda melanoleuca

<400> SEQUENCE: 291

```
atgggctggg acgaggccag gtccgagcag ctggggctgt gggtccctgt gctggctgtc    60
cttttgctgg aagcttgcca ggcacaccct atccctgact ccagcccccct cctccaattc   120
ggaggccaag ttcgacagcg gtacctctac acggacgatg cccaggagac agaggcccac    180
ctagcgatca gggctgatgg cacagtggtg gggctgcca gccggagccc agaaagtctc    240
ttggagctga agccctgaa accgggggtc attcaaatcc tggagtgaa acatctagg     300
ttcctgtgcc agggcccaga tgggacactg tacggatcgg tccgcttcga ccccgtagcc    360
```

```
tgcagcttcc gggaactgct cctggaggat gggtacaaca tctaccactc tgagaccctc    420
ggcctcccac ttcgcctgcc cgcccacaac tctccatacc gggactcggc gccccggggg    480
cctgcccgct tcctgcccct gccaggcctg cttccggtcc ccccggaccc ccagggatc     540 ctgggccccg agcctcccga cgtgggctcc tcggacccc tgagcatggt ggggccttca    600
cagggccgaa gtcccagcta cgcttcctga                                     630
```

<210> SEQ ID NO 292
<211> LENGTH: 630
<212> TYPE: DNA
<213> ORGANISM: Oryctolagus cuniculus

<400> SEQUENCE: 292

```
atggactggg gcaaggccaa gtgccggccc ccggggctgt gggtcccgc gctcgctgcc     60 ctgctgctgg gggcctgcca ggcacacccc atccccgact ccagcccct cctccagttt    120 ggggaccaag tgcggcagca gcacctgtac acggacgatg cgcaggaaac agaagcccac   180
ctggagatca gggcggatgg cacggtggtg ggggctgccc ggaggagccc agaaagtctc   240
ttgcagatga aagccttaca accggggatc attcagatct ggggggtcca gacgtccagg   300
ttcctctgcc agaggccgga tggcacgctc tacggctcgc tccacttcga ccgcgaggcc   360
tgcagcttcc gggagctgct gcgtgaggat gggtacaacg tttacctctc ggaggccctg   420
ggcctgcccc tgcgcctgtc ccccggcagc tccccacgca gggcgccggc ccccggggga   480
ccagcccgct tcctgccgct gcccggcctg ccgccagacc ttccggaacc gccaggcctc   540
ctggccgccg cgcccccga tgtcgactcc ccggaccccc tgagcatggt gcagcctgcg    600
ctggaccaga gccccagcta cacctcctga                                     630
```

<210> SEQ ID NO 293
<211> LENGTH: 630
<212> TYPE: DNA
<213> ORGANISM: Gorilla gorilla

<400> SEQUENCE: 293

```
atggactcgg acgagaccgg gttcgagcac tcaggactgt gggtttctgt gctggctggt     60
cttctgctgg gagcctgcca ggcacacccc atccctgact ccagtcctct cctgcaattc    120
gggggccaag tccggcagcg gtacctctac acagatgatg cccagcagac agaagcccac   180
ctggagatca gggaggatgg gacggtgggg ggtgctgctg accagagccc tgaaagtctc   240
ctgcagctga aagccttgaa gccgggagtt attcaaatct gggagtcaa gacatccagg    300 ttcctgtgcc agaggccaga tggggccctg tatggatcgc tccactttga ccctgaggcc   360
tgcagcttcc gggagctgct tcttgaggac ggatacaatg tttaccagtc cgaggcccac   420
ggcctcccgc tgcacctgcc ggggaacaag tccccacacc gggaccctgc accccgagga   480
ccagctcgct tcctgccact accaggcctg ccccccgcac cccggagcc acccggaatc    540 ctggcccccc agccccccga tgtgggctcc tcggaccctc tgagcatggt gggaccttcc   600
cagggccgaa gccccagcta cgcttcctga                                     630
```

<210> SEQ ID NO 294
<211> LENGTH: 630
<212> TYPE: DNA
<213> ORGANISM: Nomascus leucogenys

<400> SEQUENCE: 294

```
atggactcgg acgagaccgg gttcgagcac tcaggactgt gggttcctgt gctggctggt    60
cttctgctgg agcctgcca ggcacacccc atccctgact ccagtcctct cctgcaattc   120
gggggccaag tccggcagcg gtacctctac acagatgatg cccagcagac agaagcccac   180
ctggagatca gggaggatgg gacggtgggg ggcgctgctg accagagccc tgaaagtctc   240
ctgcagctga agccttgaa gccgggagtt attcaaatct gggagtcaa gacatccagg    300
ttcctatgcc agaggccaga tggggccctg tatggatcgc tccactttga ccctgaggcc   360
tgcagcttcc gggagctgct tcttgaggac ggatacaatg tttaccagtc cgaggcccat   420
ggcctcccgc tgcacctgcc ggggaacaag tccccacacc gggaccctgc accccgagga   480
ccagctcgct tcctgccact accaggcctg cccctgcac cccagagcc gcccggaatc    540
ctggcccccc agcccccga tgtgggctcc tcggaccctc tgagcatggt gggaccttcc   600
cagggccgaa gccccagcta cgcttcctga                                   630
```

<210> SEQ ID NO 295
<211> LENGTH: 630
<212> TYPE: DNA
<213> ORGANISM: Procavia capensis

<400> SEQUENCE: 295

```
atgactggg ccaagtttgg gatcgagcac ccggactgt gggtcccggt gatggcagta     60
cttctgctgg agcctgcca aggataccct attcctgact ccagccccct ctccaattc    120
ggaggccagg tccggcaacg ttacctctac acagatgacg cgcaggagac cgaggcccac   180
ctggagatcc gagcagacgg cacggtggtg ggggctgccc accggagccc cgagagtctc   240
ttggagctga aagctttgaa gcccggcata attcagatct gggagtcaa gacatccaga    300
ttcctctgcc agggtcctga tggggtgctg tatggatcgc tccgttttga cccagtggcc   360
tgcagcttcc gggagctgct tcttgaagat ggatacaatg tttaccagtc tgaggcccac   420
ggcctcccgc ttcgcctacc atcccacaat tccccacaga gggacctggc gtcccgggtg   480
ccagcccgct tcctgccact gccaggccgg ctcacggtgc tcccagaacc ttcggggtc    540
ctgggcccctg agccccccga tgtggactcc tcagaccccc tgagcatggt ggggccttcg   600
cagggccgaa gccccagtta cgcctcctga                                   630
```

<210> SEQ ID NO 296
<211> LENGTH: 630
<212> TYPE: DNA
<213> ORGANISM: Cavia porcellus

<400> SEQUENCE: 296

```
atggactggg cccggactga gtgtgagcgc ccaaggctgt gggtctccat gctggccatc    60
cttctggtgg agcctgcca ggcacaccct atccctgact ccagccccct cctccagttt   120
gggggccagg tccggcagcg gtacctctac acagatgatg ctcaggacac tgaagtgcac   180
ctggagatca gggccgatgg ctcagtacgg ggcattgccc acaggagccc tgaaagtctc   240
ctggagctga agccttgaa gccaggagtc attcagatct gggaatcag acttccagg     300
ttcctgtgcc agaggcccga tgggagtctg tatggatcac tccactttga tcctgaggcc   360
tgcagcttcc gggagctgct gcttgctgat ggctacaatg tctacaagtc tgaagcccac   420
ggcctccctc tgcacctgct gcgcggtgac tctctatcgc aggaaccagc accccagga    480
ccagcccgat ttctgccact accaggcctg cccgcaacac cccgagcc acccaggatg    540
ctgcccccag ggcccccaga tgtgggctcc tcggacccct tgagcatggt ggggcctttta   600
```

```
                                                         tgggaccgaa gccccagcta tacttcctga                              630

<210> SEQ ID NO 297
<211> LENGTH: 583
<212> TYPE: DNA
<213> ORGANISM: Tupaia belangeri

<400> SEQUENCE: 297
atgggctggg acaaggcccg gttcgagcac ctgggagcgt gggctcctgt gctggctgtc      60
ctcctcctgg gagcctgcca ggcatacccc atccctgact ccagcccct cctacaattc      120 gggggccagg tccggcagcg gtacctctac acggacgaca cgcaggacac agaagcccac     180
cttgagatca gggccgacgg caccgtggtg ggggccgccc accaaagccc ggaaagtctc     240
ctggagctga aagccttgaa gccggggggtc attcaaatcc tgggagtcaa gacctccagg     300
ttcctgtgcc agaggccaga cggggccctg tacgggtcgc ttcacttcga ccccgaggcc     360
tgcagcttcc gggagctgct tctcgaggat ggatacaaca tttaccagtc tgaggctcgt     420
ggcctccccc tgcgcctgcc gccccacgac tccccacatc gggaccggac ccctcgggga     480
ccagctcgtt tcctgccgct gcctggcctg ccctggttc ctccagagct gccagggggtc      540 ctggcccttg agccccccga cgtgggctcc tcagacccgc tga                     583

<210> SEQ ID NO 298
<211> LENGTH: 586
<212> TYPE: DNA
<213> ORGANISM: Sorex araneus

<400> SEQUENCE: 298
atggtctggg acaaggccag ggggcagcag ttgggactgt gggcccccat gctgctgggc      60
ttgctgctgg gtgcctgcca ggcacacccc ctccctgact ccagcccct cctccaattt      120 gggggccaag tccgactgag gttcctgtac accgacgatg cccagaggac aggggcgcac     180
ctggagatca gggccgacgg cacagtgcag ggtgcggccc acaggacccc agaatgtctc     240
ctggagctga aagccttgaa gccaggcgta attcaaatcc ttggggtcag cacatccaga     300
ttcctgtgcc agcggcccga tggggtcctg tatggatcgc ttcgctttga cccagaggcc     360
tgcagtttcc gggaacttct tctccaggat ggatataacg tttaccagtc tgaggccctg     420
ggtctcccgc tctacctaca cccgcccagt gccccagtgt cccaggaacc agcctcacgg     480
ggcgccgtcc gcttcctgcc actgccagga ctgccacctg cctccctgga gccccccagg     540 cccccgccc cggtgcctcc agacgtgggt tcctcagacc ccctga                   586

<210> SEQ ID NO 299
<211> LENGTH: 546
<212> TYPE: DNA
<213> ORGANISM: Ictidomys tridecemlineatus

<400> SEQUENCE: 299
atgtacccca tccctgactc aagccccctc ctccaatttg ggggccaagt ccggcagcgg      60
tacctgtaca cagatgatgc ccaggagact gaggcccacc tggagatcag gctgatggc     120 accgtggtgg gggctgccca tcaaagcccg gaaagtctct tggaactgaa agccttgaag     180
cctggggtca ttcaaatctt ggggggtcaaa acatccaggt tcctgtgcca gaggccagat     240
ggagtgctgt atggatcgct ccactttgac cctgaggcct gcagcttccg ggagcagctt     300
ctggaggacg ggtacaacgt ttaccagtca gaatcccacg gcctcccgt gcgcctgccc      360
```

| | |
|---|---|
| cctaactcac ataccggga cccagcgccg ccaggaccag cccgcttcct tccactgcca | 420 |
| ggcctgcccc cagcagccct ggagccgcca gggatcctgg gccctgagcc ccctgatgtg | 480 |
| ggctcctccg acccactcag catggtgggg cctttgcagg gccgaagccc cagttacgct | 540 |
| tcctga | 546 |

<210> SEQ ID NO 300
<211> LENGTH: 627
<212> TYPE: DNA
<213> ORGANISM: Loxodonta Africana

<400> SEQUENCE: 300

| | |
|---|---|
| atggactggg ccaagtttgg gttggagcac ccaggactgt gggtccctgt gatggctgtc | 60 |
| cttctgctgg gagcctgcca gggacacccc atccctgact ccagcccct cctccaattc | 120 |
| gggggccagg tccggcaacg ttacctctac acagatgatc aggagaccga ggcccacctg | 180 |
| gagatcagag cagatggcac agtggcggga gccgctcacc ggagctctga gagtctcttg | 240 |
| gagctgaaag ctttgaagcc tggaataatt cagatcttgg gggtcaagac atcccggttc | 300 |
| ctgtgccagg ggcctgatgg ggtgctgtac ggatcgctcc atttcgaccc agccgcctgc | 360 |
| agcttccggg agctgcttct tgaagatgga tacaatgttt actggtccga ggcccatgga | 420 |
| ctcccaatcc gcctgccctc ccacaactcc ccatataggg acccagcatc ccgggtacca | 480 |
| gcccgcttc tgccactgcc aggcctgctc ccaatgctcc aagaacctcc aggggtcctg | 540 |
| gccctgagc ccctgatgt ggactcctca gacccctga gcatggtggg gccttcacag | 600 |
| ggccgaagcc ccagctatgc ctcctga | 627 |

<210> SEQ ID NO 301
<211> LENGTH: 627
<212> TYPE: DNA
<213> ORGANISM: Sus scrofa

<400> SEQUENCE: 301

| | |
|---|---|
| atgggctggg ccgaggccaa gttcgagcgc ttgggactgt gggtccctgt gctggctgtc | 60 |
| ctgctgggag cctgccaggc acgtcccatt cctgactcca gccccctcct ccaatttggg | 120 |
| ggccaagtgc gccaacgata cctctacacg gatgatgccc aggaaactga agcccacctg | 180 |
| gagatcagag ctgatggcac cgtggcaggg gtagcccgcc agagccctga agtctcttg | 240 |
| gagctgaaag ccctgaagcc aggggtcatt caaattttgg gagtccagac atcccggttc | 300 |
| ctgtgccagg ggccagacgg gagactgtac ggatcgctcc acttcgaccc tgaggcctgc | 360 |
| agcttccggg agctgcttct tgaggatggc tacaacgttt accagtctga ggcccttggc | 420 |
| ctcccactcc ggctgcctcc gcaccgctcc tccaaccggg acctggcccc cgggggacct | 480 |
| gctcgcttcc tgccactgcc aggcctgccc ccggcacccc cggagccgcc agggatcttg | 540 |
| gcccctgaac ctcccgacgt gggctcctcg dacccctga gcatggtggg gccttcacac | 600 |
| ggccggagcc ccagctacac ttcttga | 627 |

<210> SEQ ID NO 302
<211> LENGTH: 627
<212> TYPE: DNA
<213> ORGANISM: Felis catus

<400> SEQUENCE: 302

| | |
|---|---|
| atgggctggg acgaggccgg gtcccagcgc ctgggactgt gggtcgtgct ggggtccttt | 60 |
| ttgccggaag cctgccaggc acaccctatc cctgactcca gccccctcct ccaattcggg | 120 |

```
ggccaagttc dacagcggtt cctctacacg gacgacgccc aggagacaga ggtccacctc    180
gagatcaagg ctgatggcac agtggtgggg accgctcgcc ggagccctga gagtctcttg    240
gagctaaaag ccctgaagcc gggggtaatt caaatcttgg gggtcaaaac gtccaggttc    300
ctgtgccagg gccagatgg gacactgtat ggatcgctcc gctttgaccc cgcagcctgc    360
agcttccggg aactgctcct ggaggacgga tacaacatct accactcgga gaccctcggg    420
ctcccactcc gcctgccccc ccacaactcc ccataccggg acttggcccc ccgggcacct    480
gcccgcttcc tgccgctgcc aggcctgctt ccggcacccc cggagcctcc agggatcctg    540
gcccccgagc cccggacgt gggctcctcg gaccctctga gcatggtggg gccttcccag    600
ggccgaagtc ccagctacgc ttcctga                                        627
```

<210> SEQ ID NO 303
<211> LENGTH: 627
<212> TYPE: DNA
<213> ORGANISM: Otolemur garnettii

<400> SEQUENCE: 303

```
gacaaggcca ggactgggtt caagcaccca ggaccatggt ttcccctgct ggctgtactt     60
ttgttgggag cctgccaggc acccctatc cctgactcca gccccctact ccagtttggt    120
ggccaagtcc ggcagcggta cctctacaca gatgatgccc aggagacaga agcccacctg    180
gagatcaggg aagatggcac agtggtgggg gctgcacaac agagccctga aagtctcttg    240
gagctgaaag ctttaaagcc aggggtcatt caaatcttgg gagtcaagac atccaggttc    300
ctgtgccaga ggcagatgg gggcctatat ggatcgctct actttgaccc caaggcctgc    360
agtttccggg agctgcttct tgaggatgga tacaacgttt actggtctga gacctatggc    420
ctcccactgc acctgcctcc tgccaattcc ccatactggg gccatcccct tcggagccca    480
gcccgcttcc tgccactgcc aggccctcct gcagcatccc cagagctgcc ggggatcttg    540
gccctggaac ccccgatgt gggctcctcg gaccctctga gcatggtggg gccttcgcag    600
ggccgaagcc ccagctatgc ttcctga                                        627
```

<210> SEQ ID NO 304
<211> LENGTH: 627
<212> TYPE: DNA
<213> ORGANISM: Rattus norvegicus

<400> SEQUENCE: 304

```
atggactgga tgaaatctag agttgggggcc ccgggactgt gggtctgtct cctgctgcct     60
gtcttcctgc tgggggtgtg cgaggcatac cccatctctg actccagccc cctcctccag    120
tttgggggtc aagtccgaca gaggtatctc tacacagatg acgaccagga caccgaagcc    180
cacctggaga tcagggagga cggaacagtg gtgggcacag cacaccgcag tccagaaagt    240
ctcctggagc tcaaagcctt gaagccaggg tcattcaaa tcctgggtgt caaagcctct    300
aggtttcttt gccaacaacc agatggaact ctctatggat cgcctcactt tgatcctgag    360
gcctgcagtt tcagagagct gctgcttaag gacggataca atgtgtacca gtctgaggcc    420
catggcctgc cctgcgtctg ccccagaag actcccagg atccagcaac ccggggacct    480
gtgcgcttcc tgcccatgcc aggcctgccc cacgagcccc aagagcaacc aggagtcctt    540
cccccagagc cccagatgt gggttcctcc gaccccctga gcatggtaga gccttgcaa    600 ggccgaagcc ccagctatgc atcttga                                        627
```

<210> SEQ ID NO 305
<211> LENGTH: 633
<212> TYPE: DNA
<213> ORGANISM: Mus musculus

<400> SEQUENCE: 305

| | |
|---|---|
| atggaatgga tgagatctag agttgggacc ctgggactgt gggtccgact gctgctggct | 60 |
| gtcttcctgc tgggggtcta ccaagcatac cccatccctg actccagccc cctcctccag | 120 |
| tttgggggtc aagtccggca gaggtacctc tacacagatg acgaccaaga cactgaagcc | 180 |
| cacctggaga tcagggagga tggaacagtg gtaggcgcag cacaccgcag tccagaaagt | 240 |
| ctcctggagc tcaaagcctt gaagccaggg gtcattcaaa tcctgggtgt caaagcctct | 300 |
| aggtttcttt gccaacagcc agatggagct ctctatggat cgcctcactt tgatcctgag | 360 |
| gcctgcagct tcagagaact gctgctggag gacggttaca atgtgtacca gtctgaagcc | 420 |
| catggcctgc ccctgcgtct gcctcagaag gactccccaa accaggatgc aacatcctgg | 480 |
| ggacctgtgc gcttcctgcc catgccaggc ctgctccacg agcccaagga ccaagcagga | 540 |
| ttcctgcccc cagagccccc agatgtgggc tcctctgacc ccctgagcat ggtagagcct | 600 |
| ttacagggcc aagccccag ctatgcgtcc tga | 633 |

<210> SEQ ID NO 306
<211> LENGTH: 324
<212> TYPE: DNA
<213> ORGANISM: Vicugna pacos

<400> SEQUENCE: 306

| | |
|---|---|
| atggactggg acgaggccaa gttcgagcat cggggactgt gggtcccagt gctcactgtc | 60 |
| cttctgctgg gagcctgcca ggcacgcccc attcctgact ccagcccct cctccaattc | 120 |
| gggggccaag tccggcagcg gtacctctac acggatgacg cccaggagac agaagcccac | 180 |
| ctggagatca gggctgatgg cacagtggtg gggtggccc gccagcccga aggaattcct | 240 |
| cccgagcctc ctgacgtggg ctcctcagac cccctgagca tggtggggcc ttcatacagc | 300 |
| agaagcccca gctacacttc ctga | 324 |

<210> SEQ ID NO 307
<211> LENGTH: 633
<212> TYPE: DNA
<213> ORGANISM: Anolis carolinensis

<400> SEQUENCE: 307

| | |
|---|---|
| tgtaaaagca agggaggagg aaggggggga gagaggatgt gggtagacct agttttctgg | 60 |
| gctgccttgc tccgcacagc tcctgctctt cccttgcgga attccaaccc catctaccaa | 120 |
| tttgatgggc aggtccggct tcggcacctc tacacagcag atgaacagac gcacctccac | 180 |
| ttggagatct tgccagacgg taccgtgggt ggatccaggt ttcagaatcc cttcagtttg | 240 |
| atggagatca aagctgtgaa gccaggagtc attcgcatgc aggccaagaa gacctctaga | 300 |
| tttctctgta tgaaacccaa tggacgactg tatggctcgc tgttctactc tgaggaggca | 360 |
| tgcaacttcc atgagaaggt tctcagcgat ggctacaacc tctactattc tgaaaactac | 420 |
| aacatacctg tcagcctcag ctcggcaggg aacctgggtc agagccgtca gttgcctccc | 480 |
| ttctcccaat tcctgccgtt agtcaacaaa attcctcttg agctgtgct tgaagacttt | 540 |
| gacttctatg acatcaatt ggatgttgaa tcagctgatc ctttgagcat tttaggacaa | 600 |
| aaccctggtt tcatgagtcc gagctatgtc ttc | 633 |

<210> SEQ ID NO 308
<211> LENGTH: 564
<212> TYPE: DNA
<213> ORGANISM: Gadus morhua

<400> SEQUENCE: 308

```
ctcctcctcg ccaccctcct ccacatcggc ctctccttct acgtccccga ctccggcccc      60
ctgctgtggc tgggcgacca ggtcagggag agacacctct acacagcaga gagccaccgg     120
aggggggctgt tcctggagat gagcccggac ggtcaggtga caggaagtgc tgctcagacg     180
ccgctcagtg ttctggagct gaggtcggtc agagcaggag atacggtcat cagagcgcgc     240
ctctcctctc tctacctgtg tgtggacagg gcaggtcacc tgacaggaca gagacagtac     300
acagagtccg actgcacctt cagagaggtc atccttgagg acggctacac ccacttcctg     360
tccgtgcacc acggacttcc tatttcgctg gcgccgagac actccccagg gagacagggg     420
ctgcgcttca gcaggttcct cccgctgagg agcagtctgt cagaggatag ggtcgccgag     480
cccccagaca gcccactgaa cctggactct gaagaccccc tggggatggg tctgggttcg     540
ctcctcagcc cggccttctc catg                                           564
```

<210> SEQ ID NO 309
<211> LENGTH: 648
<212> TYPE: DNA
<213> ORGANISM: Latimeria chalumnae

<400> SEQUENCE: 309

```
atgttatgcc agagttttgt gatattaagt cagaaattca tttttgggct cttttttgact      60
ggattggggc taacaggatt ggcttggaca aggcccttcc aggattccaa tcccatcctg     120
cagtattccg attccatccg gctccgacat ctgtacactg ccagtgagag tcggcacctt     180
cacctacaaa tcaactcgga tggacaggtg ggagggacaa ccaagcaaag cccttacagt     240
ctgttggaga tgaaggcggt gaagacaggt tttgtggtca tcaggggcaa gaaaagcgcc     300
cgttacctct gtatggaacg tagtggacgg ctctatggat cgctgcagta tacagaaaaa     360
gactgcacct tcaaagaggt tgtgttggca gatggataca acctgtatgt ctcagaggaa     420
caccaggcca cagtgacgct gagccccatg agggcgagga tagcgcaagg gaaaaagatc     480
ccacccttt cccatttcct tccaatggtg aacaaggtgc ctgtggagga tgttgccgct     540
gagatggagt ttgtccaggt gctgcgggaa atgacggccg acgtggactc tccggatccc     600
tttggaatga cctgggaaga atcggttcac agtccgagct ttttttgcc                 648
```

<210> SEQ ID NO 310
<211> LENGTH: 579
<212> TYPE: DNA
<213> ORGANISM: Tursiops truncates

<400> SEQUENCE: 310

```
atgggctggg acaagaccaa actcgagcac ctgggactgt gggtccctgt gctagctgtc      60
ctgctgggac cctgccaggc acatcccatt cctgactcca gccccctcct ccaatttggg     120
ggccaagtcc gccagcgata cctctacacg gatgacgccc aggagacgga ggcccacctg     180
gagatcaggg ctgatggcac agtggtgggg acggcccgcc ggagcccga aggagttaaa     240
acatccaggt tcctgtgcca ggggccagag ggaggctgt atggatcgct ccacttcaac     300
ccccaggcct gcagcttccg ggagctgctt cttgaggatg gatacaacgt ttaccagtct     360
```

```
gaggctcttg gcattcccct ccgcctgccc ccgcaccgct cctccaactg ggacctggcc    420 cccgggac   ctgctcgctt cctgccgctg ccaggcttcc tcccgccacc cctggagcct    480
ccagggatct tggccccga  gcctcccaac gtaggttcct cggaccccctt gagcatggtg    540 ggaccttcac atggccgaag ccccagctac acttcctga                           579
```

<210> SEQ ID NO 311
<211> LENGTH: 630
<212> TYPE: DNA
<213> ORGANISM: Mustela putorius furo

<400> SEQUENCE: 311

```
atgggctggg aagaggccag gtccgagcac ctggggctgt gggtccctgt gctggcggtc    60
cttttgctgg gagcctgcca ggcatacccct attcctgact ccagccccct cctccaattt   120
ggaggccaag ttcgacagcg gtacctctac acagacgacg ctcaggagac ggaggcccac    180
ctagagatca gggctgatgg cacggtggtg ggggctgccc gccggagccc cgaaagtctc    240
ttggagctga aagccctgaa gccagggggtc attcagatct gggagtgaa  acatccagg    300 ttcctgtgcc agggcccgaa tgggacactg tacggatcgt ccacttcga  ccccgtagcc    360 tgcagcttcc gggaagtgct tctgaagat  ggatacaaca tctaccactc tgagaccctg    420
ggcctcccac tgcgcctgcc cccccacaac tccccacaca gggacctggc gccccggggg    480
cctgcccgct tcctgcccct gcaggcctg  cttccggcca ccccgagtc  ccgggggatc    540 ccagcccccg agcctcccaa cgtgggctcc tcagacccccc tgagcatggt ggggcctttg    600
cagggtcaaa gtcccagcta cacttcctga                                      630
```

<210> SEQ ID NO 312
<211> LENGTH: 597
<212> TYPE: DNA
<213> ORGANISM: Takifugu rubripes

<400> SEQUENCE: 312

```
tttatttatt tatttattca aactgcactt ttttcccctt ccaaatggtt caacttttat    60
ctccctgact ccaacccgct cttatccttt gacagtcatg gcagaggcat ccacctctac   120
acagataatc aaaggcgagg gatgtatctg cagatgagca cagatggaag cgtttccggg   180
agtgatgtcc agacggcgaa cagtgtgctg gaactgaagt cagtcagaaa cggccacgtc   240
gtcatccgag gaaaatcgtc ttctctgttt ctctgtatgg acagcagagg ccgtttatgg   300
gggcagaggc accccactga ggccgactgc actttcaggg aagtgttgct ggcagatgga   360
tacactcgct tcctgtccct gcacaacgga actcctgtgt ctctggcacc taaacaatct   420
ccagaccagc acacagtccc cttcactcgt ttcctgccgc tcaggaatac actggcagag   480
gagagcatgt ctgaaccacc atcaaaccaa cagagatatt ttaacattga ctctgatgat   540
cttcttggaa tggatttaaa tgcgatggtc agtcctcagt tttcagggga caagtga     597
```

<210> SEQ ID NO 313
<211> LENGTH: 612
<212> TYPE: DNA
<213> ORGANISM: Dipodomys ordii

<400> SEQUENCE: 313

```
atggaccagg caaagaccag ggttggggcc cggggggctgg ggggccttgt gctggctgtc    60
ataattctgg gagcatgcaa ggcacggcct atccctgact ccagccccct cctccaattt   120
gggggtcaag ttcggcttcg gcacctctac acagatgaca ctcaggagac ggaagcccat   180
```

```
ctggagatca gggcagatgg cacggtagtg gggactgccc accggagccc tgaaagtctc      240
ttggagctga aagccttgaa gccaggagtc attcaaatct tagggatcaa gacatccaga      300
ttcttatgcc agagaccaga cggacactg tatggatcac tccactttga ccctgaggtt       360
tgcagcttcc aggagctgct tctgaagat ggatacaaca tttaccgttc tgaagccctg       420
ggtctccccc tgcgcctgtc cccagatcca gcaccctggg ggccagcccg cttcctgccc      480
ctgcctggtg tgccccccgc accgccgag cccccggga tcctggctcc cgaacccct         540 gatgtcggct cctccgaccc tctgagtatg gtgggactgt tgcagggccg aagccccagc      600
tatgcatcct ga                                                         612

<210> SEQ ID NO 314
<211> LENGTH: 555
<212> TYPE: DNA
<213> ORGANISM: Echinops telfairi

<400> SEQUENCE: 314
atgggttgca ccaaatctgg gtggaagtcc ccgggactgt gggtccctgt gctggccagc      60
cttctgctgg gaggctgcgg agcacacccc atccctgact ccagcccct cctccaattc       120 gggggccaag tccggcagcg atacctctat acggatgacg cccagaccac cgaggcccac      180
ctggagatca gagcggatgg cacagtgggg ggcgtcgccc accagagccc agagaagttc      240
ctgagtcaat ggcgtgaaaa gcccctgaga tcactccatt tcgacccagc cgcctgcagc      300
ttccgggaga agcttctaga agacggatac aacttgtacc actctgagac ccacggcctc      360
cccctccgcc tcccacccg tgggggcgac ccctcttctc agcctggggc ccgcttccca      420
ccgctgccgg gccagctccc acaactccaa gagacgccag gggtcctcgc ccccgaaccc      480
cccgacgtgg gctcttcaga ccccctgagc atggtggggc cttggcgagg gcaaagtccc      540
agttatgcct cctga                                                      555

<210> SEQ ID NO 315
<211> LENGTH: 633
<212> TYPE: DNA
<213> ORGANISM: Macaca mulatta

<400> SEQUENCE: 315
atggactcgg acgagaccgg gttcgagcac tcaggactgt gggttcctgt gctggctggt      60
cttctgctgg gagcctgcca ggcacacccc atccctgact ccagtcctct cctgcaattc      120
ggggcccaag tccggcaacg gtacctctac acagatgatg cccagcagac agaagcccac      180
ctggagatca gggaggatgg gacagtgggg ggcgctgctc accagagccc cgaaagtgag      240
tgtgggccag agcctgggtc tgaggagga ggggctgtgg gaggtgctga gggacctgga       300
ctcctgggtc tgagggaggc agggctgggg cctggatcct ggctccactt tgaccctgag      360
gcctgcagct ccggagct gcttcttgag aacggataca atgtttacca gtccgaggcc        420
cacggcctcc cactgcacct gccgggaaac aagtccccac accgggaccc tgcatcccaa      480
ggaccagctc gcttcctgcc actaccaggc ctgcccccg cacccccgga gccgccagga       540
atcctcgccc ccagccccc cgatgtgggc tcctcggacc ctctgagcat ggtgggacct       600
tcccaggccc gaagcccag ctatgcttcc tga                                    633

<210> SEQ ID NO 316
<211> LENGTH: 582
<212> TYPE: DNA
```

<213> ORGANISM: Microcebus murinus

<400> SEQUENCE: 316

| | | |
|---|---|---|
| atgggctggg acgaggccgg cgccgggttc gagcacccag gactgtggtt tcccatgctg | 60 |
| ggtgtcctgc tgctgggagc ctgccaggcg tacccatcc ctgactccag ccccctcctc | 120 |
| caatttggcg gccaagtccg gcagcggcac ctctacacag acgatatcca ggagacagaa | 180 |
| gcccacctgg agatcagggc ggacggcaca gtggtggggg ccgcccgaca gagccctgag | 240 |
| ttggagctga aagccttaaa gccaggggtc attcaaatct gggagtcaa gacctccagg | 300 |
| ttcctgtgcc agaggccaga cggggccctg tacggatcgc tccactttga ccccgagtgc | 360 |
| agcttccggg agctgcttct tgaggatgga tacaacgtct actgtcccta cctcccgctg | 420 |
| cacctgtccc cacgcatcga actggccgga tcacgctctg cgctgccact gccccagca | 480 |
| cctgaacgca ggattttggc cccggagccc ccggatggct cctcggaccc tctgagcatg | 540 |
| gtggggcctt cgcagggccg aagtcccagc tatgcttcct ga | 582 |

<210> SEQ ID NO 317
<211> LENGTH: 615
<212> TYPE: DNA
<213> ORGANISM: Ochotona princeps

<400> SEQUENCE: 317

| | | |
|---|---|---|
| aaagacatgg acgggctcca gcctccgggg ctgcgggttc ctgtgctggc tgccctgctt | 60 |
| ttgggagttg gccaggcacg ccccatccct gattctagcc ctctcctcca attcggggc | 120 |
| caggtccggc agaggcacct ctacacggat gacgcccagg aatcggaagt acacctggag | 180 |
| atccgggcag acggcaccgt ggcagggact gcccgccgga gccctgaaag tctcttagaa | 240 |
| atgaaagcgt tgaagccagg cgtcattcag atcctggggg tccacacatc caggttcctg | 300 |
| tgccagagac cagacgggac gctgtacggc tcgctccact tcgaccacaa ggcctgcagc | 360 |
| ttccgggagc agctgctgga ggatgggtac aacgtgtacc actcagagac acacggcctc | 420 |
| ccgctgcgcc tgtctccaga ccgagccccc cggggcccag cccgcttcct gccactgcca | 480 |
| ggccctcctc ctgacctcct ggtgccaccc ctgccaccgg acgtcctagc ccctgagccc | 540 |
| cccgacgtgg actccccaga cccctgagc atggtggggc ccttgcaggg ccaaagcccc | 600 |
| agctacactt cctga | 615 |

<210> SEQ ID NO 318
<211> LENGTH: 546
<212> TYPE: DNA
<213> ORGANISM: Xiphophorus maculates

<400> SEQUENCE: 318

| | | |
|---|---|---|
| tgcccgttcc ccttcctttt cttaatcctc tctcttccct ttttctcttc ctcgttttac | 60 |
| atcccagaat ccaacccaat ctttgccttc aggaatcagc tcagagaggt gcatctctac | 120 |
| acagaaaatc acagacgggg tttgtatgtg agatacatc tggatgggag agtgactgga | 180 |
| agtgatgctc agagtcctta tagtgtgttg cagataaagt ctgttaaacc gggtcatgtg | 240 |
| gtcataaagg gacagacatc gtccctgttc tctgcatgg acgactccgg aatctaaga | 300 |
| ggacagacaa cctatgacga ggctgactgc tccttcaggg aactgctgct ggccgatggc | 360 |
| tacacccgtt tcctgaactc acaacatggc gttcctttat cactggcatc cagaaactct | 420 |
| ccagatcgac actccgttcc tttcacaaga ttttttacctc tcaggaatac tttaacggtt | 480 |
| tcagaagaat caacaaaaac tcagagggac ttcaacctgg actcggacga ccttctcggg | 540 |

```
atggga                                                                      546
```

<210> SEQ ID NO 319
<211> LENGTH: 576
<212> TYPE: DNA
<213> ORGANISM: Gasterosteus aculeatus

<400> SEQUENCE: 319

```
tctctcctcc tcatggtccc acttcctttc tgttcatcct tttatctcac tgactccagc    60
ccacttctac ccttcaataa tcaagtcaaa gaggtgcacc tctacacagc agagaatcac   120
agaagagcga tgtacctgca gatcgctctg gacgggagcg tgtcgggaag cgacgctcgg   180
tccacttaca gtgtgctgca gctgaaatct atccagccgg ccacgtggt catcagaggg    240
aaggcctcct ccatgttcct ctgcgtggac agcggggggcc gtttgagagg acaggggccg   300
tactcagagg ccgactgcag cttcaggag ctgctgctgg gggatggcta cacccggttc    360
ctgtcctcgc agcacgggtc cccgctgtct ctggcgtcga ggccttcccc ggatcccaac   420
tcggtgccct tcactcgatt cctacccatc cggaccgccc ccgaggctga gagcgtgatc   480
gaagagccac cgagcaatca gagatacgtc aacgtggact ccgaggatct tcttggaatg   540
ggcctgaaca ctgtggtcag tcctcagttc tcggcg                             576
```

<210> SEQ ID NO 320
<211> LENGTH: 495
<212> TYPE: DNA
<213> ORGANISM: Sarcophilus harrisii

<400> SEQUENCE: 320

```
gtgtctgcca tgggcctgag ggagcgagct cccaggtacc tggccccgct gctgtccttg    60
ctcttggcct gcagggcctc gggtcacccc ctcccggatt ccagccccat gctcctgttt   120
gggggggcagg tccgcctccg gcacctctac acggatgtgg gccaggaggc cgaggcccac   180
gtggaactgg cgtccgacgg cacagtccgg gcggcagcgc ggaggagtcc caacagtctc   240
ctggagctga aggctgtgaa gccgggcatc gtccgaatcc tggccgtcca cagctctcgg   300
tttctgtgta tgaggcccaa cggggagctg tacgagcga tacactacga cccttccgcc    360
tgcaactttc gggagcgcct gctgggggac ggctacaacg tgtacgagtc cgaggctcac   420
gggaggaccc tccgcctgcc ccccaaggcc gcaccgggac ccgccggacc ttctcgcttc   480
ctgccgctcc ccggc                                                   495
```

<210> SEQ ID NO 321
<211> LENGTH: 627
<212> TYPE: DNA
<213> ORGANISM: Macropus eugenii

<400> SEQUENCE: 321

```
acagaggagc cttctactgg gtccaggcac ctgggacaat gggctcccgg gctgcctggt    60
cctctgctgt ccttgctcct ggcctacagg ggctggggct ccccccatccc tgattccagc   120
cccatgctcc tgtttggtgg ccaggtccgc ctccgacacc tgtacacaga tgatggccag   180
gacacggagc cccatgtgga gctggggcca gatggagtgg ttcgagctgt ggctgagagg   240
agccccaaca gtcttctgga actgaaggcg gtgaagcctg gagtcatccg aatcctcgct   300
gtccagagct ctcggtttct gtgtatgagg cccaacgggg aactgtatgg agcggtacac   360
tatgacccctt ctgcctgcaa ctttcgggaa catctgctgg gggatggtta taatgtgtat   420
```

```
gaatcagaga ctcacagaag gaccctccgt ctgtccccat ccctgggtca ggctggcccc    480
tctcgcttcc tgccacttcc aggcgactgg ctgcccggcc ctgatccacc ttgggcacag    540
ggccctgagc ccccagacgt gggctctgca gaccccctga gcatggtggg ggccgtgcag    600
ggcctcagcc ccagctactc ctcctga                                       627
```

<210> SEQ ID NO 322
<211> LENGTH: 480
<212> TYPE: DNA
<213> ORGANISM: Xenopus tropicalis

<400> SEQUENCE: 322

```
agaggggta ggaccaaaaa aaagacgtta ctcaggaaat ggctttgcct tttagccatt      60
atgttgagta ggtcaaggtt ttctttagca aatcctatcc agaattcgaa cccaatctta    120
tccaacgaca accaagtacg gactcagtat ttatacacag ataacaataa catgcacctg    180
tatcttcaga tcacccacaa tggagtagta actggtaccg aagaaaagaa tgactatggt    240
gtgctggaaa taaaggcagt aaaagctggg gttgtagtta taaaaggaat tcgaagcaat    300
ctctacctat gcatggattc tagacaccaa ttgtatgcgt cggcatatga taaagatgac    360
tgccatttcc atgaaaagat cacaccagat aattacaaca tgtatagctc agagaagcat    420
tcagaatacg tgtccttagc tccattaaaa ggaagccaga tggctcgttt tctacctata    480
```

<210> SEQ ID NO 323
<211> LENGTH: 585
<212> TYPE: DNA
<213> ORGANISM: Danio rerio

<400> SEQUENCE: 323

```
atgcttcttg cctgcttttt tatattttt gctctttttc ctcatcttcg gtggtgtatg       60
tatgttcctg cacagaacgt gcttctgcag tttggcacac aagtcaggga acgcctgctt    120
tacacagatg ggttgtttct tgaaatgaat ccagatggct ccgtcaaagg ctctcctgaa    180
aagaatctaa attgtgtgct ggagctgcgt tcagtcaaag cgggtgaaac cgtcatccag    240
agtgcagcta catctctcta cctctgcgtc gatgatcaag acaagctgaa aggacagcat    300
cattactctg cactagactg caccctttcag gaattgctac tggatggata ttcgtttttc    360
ctttctccac acactaatct tcccgtatcg ctcctctcga aacgtcagaa acacggcaat    420
cctctttctc gcttcctccc tgttagcaga gcagaggaca gccggacaca ggaggtgaaa    480
cagtatattc aggatataaa cctggactct gacgacccac taggaatggg acatcggtca    540
cacttacaga ccgtcttcag tcccagtctg catactaaaa aatga                    585
```

<210> SEQ ID NO 324
<211> LENGTH: 630
<212> TYPE: DNA
<213> ORGANISM: Bos grunniens mutus

<400> SEQUENCE: 324

```
atgggctggg atgaagcgaa atttaaacat ctgggcctgt gggtgccggt gctggcggtg       60
ctgctgctgg gcacctgccg cgcgcatccg attccggata gcagcccgct gctgcagttt    120
ggcggccagg tgcgccagcg ctatctgtat accgatgatg cgcaggaaac cgaagcgcat    180
ctggaaattc gcgcggatgg caccgtggtg ggcgcggcgc gccagagccc ggaaaagcctg    240 ctggaactga aagcgctgaa accgggcgtg attcagattc tgggcgtgaa aaccagccgc    300
tttctgtgcc agggcccgga tggcaaactg tatggcagcc tgcattttga tccgaaagcg    360
```

```
                                            -continued tgcagctttc gcgaactgct gctggaagat ggctataacg tgtatcagag cgaaaccctg      420
ggcctgccgc tgcgcctgcc gccgcagcgc agcagcaacc gcgatccggc gccgcgggc      480 ccggcgcgct ttctgccgct gccgggcctg ccggcggaac cgccggatcc gccgggcatt      540
ctggcgccgg aaccgccgga tgtgggcagc agcgatccgc tgagcatggt gggcccgagc      600
tatggccgca gcccgagcta taccagctaa                                      630

<210> SEQ ID NO 325
<211> LENGTH: 630
<212> TYPE: DNA
<213> ORGANISM: Saimiri boliviensis boliviensis

<400> SEQUENCE: 325
atgggctcgg aggaggtcgc gttggagcgc cctgcactgt gggtctctgt gttggctggt       60
ctcctgctgg gaacctgcca ggcataccc atccctgact ctagtcccct cctgcaattt      120
ggaggccaag tccggcagcg gtacctctac acagatgacg ctcagcagac agaagcccac      180
ctggagatca gggaagatgg cacggtggcg ggggctgccc accagagccc gaaagtctc      240 ttgcagctga aagccttaaa gccaggggtt attcaaatct gggagtcaa gacctccagg      300 ttcctgtgcc agaggccgga cggggccctg tacggatcgc tctactttga ccccgaggcc      360
tgcagcttcc gggagctgct tcttgaggac ggatacaatg tgtaccagtc cgtgcccac      420 agcctcccgc tgcacctgcc aggggggcagg tccccaccct gggaccctgc acctcgagga      480
ccagctcgct tcctgccgct accaggcctg cccccgaac cccccgaggc gccaggaatc      540
ctggcccccg agccccccga tgtgggctcc tcagaccctc tgagcatggt ggggccttcc      600
caaggccaaa gccccagcta cacttcctga                                      630

<210> SEQ ID NO 326
<211> LENGTH: 633
<212> TYPE: DNA
<213> ORGANISM: Callithrix jacchus
<220> FEATURE:
<221> NAME/KEY: misc_feature
<222> LOCATION: (190)..(190)
<223> OTHER INFORMATION: n is a, c, g, or t

<400> SEQUENCE: 326
atgggctcgg aggaggtcgg gttggagcac cctgcactgt gggtttctgt gctggctggt       60
ctcctgctgg gaacctgcca ggcgcacccc atccctgact ccagtcccct cctgcaattt      120
ggaggccaag tccggcagcg gtacctctac acagatgacg cccagcagaa agaagcccac      180
ctggagatcn aggaagatgg cacagtggcc ggggctgcca ccaaagtccc gaaagtgagt      240
ctcttgcagc tgaaagcctt aaagccaggg gttattcaaa tcttgggagt caagacatcc      300
aggttcctgt gccagaggcc agacggggcg ctgtatggat cgctccactt tgaccccgag      360
gcctgcagct ccggggagct gcttcttgag gacggataca atgtgtacca gtctgtggcc      420
cacggcctcc cgctgcacct gccagagagc aggtcaccac cccgggaccc tgcaccccga      480
ggaccagctc gcttcctgcc actaccaggc ctgccccctg aaccccccaga gccgccagga      540 atcctggccc ctgagccccc cgacgtgggc tcctcagacc ctctgagcat ggtgggggcct      600 tcccaaggcc aaagccccag ctacgcttcc tga                                  633

<210> SEQ ID NO 327
<211> LENGTH: 630
<212> TYPE: DNA
```

<213> ORGANISM: Tupaia chinensis

<400> SEQUENCE: 327

| | | | | | |
|---|---|---|---|---|---|
| atgggctggg | ataaagcgcg | ctttgaacat | ctgggcgcgt | gggcgccggt | gctggcggtg | 60 |
| ctgctgctgg | gcgcgtgcca | ggcgtatccg | attccggata | gcagcccgct | gctgcagttt | 120 |
| ggcggccagg | tgcgccagcg | ctatctgtat | accgatgata | cccaggatac | cgaagcgcat | 180 |
| ctggaaattc | gcgcggatgg | caccgtggtg | ggcgcggcgc | atcagagccc | ggaaaagcctg | 240 |
| ctggaactga | aagcgctgaa | accgggcgtg | attcagattc | tgggcgtgaa | aaccagccgc | 300 |
| tttctgtgcc | agcgcccgga | tggcgcgctg | tatggcagcc | tgcattttga | tccggaagcg | 360 |
| tgcagctttc | gcgaactgct | gctggaagat | ggctataaca | tttatcagag | cgaagcgcgc | 420 |
| ggcctgccgc | tgcgcctgcc | gccgcatgat | agcccgcatc | gcgatcgcac | cccgcagggc | 480 |
| ccggcgcgct | ttctgccgct | gccgggcctg | ccgctggtgc | cgccggaact | gccgggcgtg | 540 |
| ctggcgctgg | aaccgccgga | tgtgggcagc | agcgatccgc | tgagcatgat | gggcccgagc | 600 |
| cagggccaga | gcccgagcta | tgcgagctaa | | | | 630 |

<210> SEQ ID NO 328
<211> LENGTH: 567
<212> TYPE: DNA
<213> ORGANISM: Papio anubis

<400> SEQUENCE: 328

| | | | | | |
|---|---|---|---|---|---|
| atggactcgg | acgagaccgg | gttcgagcac | tcaggactgt | gggttcctgt | gctggctggt | 60 |
| cttctgctgg | gagcctgcca | ggcacacccc | atccctgact | ccagtcctct | cctgcaattc | 120 |
| gggggccaag | tccggcaacg | gtacctctac | acagatgatg | cccagcagac | agaagcccac | 180 |
| ctggagatca | ggaggatgg | gacagtgggg | ggcgctgctc | accagagccc | cgaaagtaag | 240 |
| tgtgggccag | agcctgggtc | tgagggagga | ggggctctcc | actttgaccc | tgaggcctgc | 300 |
| agcttccgcg | agctgcttct | tgagaacgga | tacaatgttt | accagtccga | ggcccacggc | 360 |
| ctcccactgc | acctgccggg | aaacaagtcc | ccacaccggg | accctgcatc | ccgaggacca | 420 |
| gctcgcttcc | tgccactacc | aggcctgccc | ccgcacccc | cagagccacc | aggaatcctc | 480 |
| gccccccagc | ccccgatgt | gggctcctcg | accctctga | gcatggtggg | accttcccag | 540 |
| gcccgaagcc | ctagctacgc | ttcctga | | | | 567 |

<210> SEQ ID NO 329
<211> LENGTH: 627
<212> TYPE: DNA
<213> ORGANISM: Pteropus alecto

<400> SEQUENCE: 329

| | | | | | |
|---|---|---|---|---|---|
| atgggctggg | gcaaagcgcg | cctgcagcat | ccgggcctgt | ggggcccggt | gctggcggtg | 60 |
| ctgctgggcg | cgtgccaggc | gcatccgatt | ctggatagca | gcccgctgtt | tcagtttggc | 120 |
| agccaggtgc | gccgccgcta | tctgtatacc | gatgatgcgc | aggataccga | agcgcatctg | 180 |
| gaaattcgcg | cggatggcac | cgtggcgggc | gcggcgcgcc | gcagcccgga | aagcctgctg | 240 |
| gaactgaaag | cgctgaaacc | gggcgtgatt | caggtgctgg | gcgtgaaaac | cagccgcttt | 300 |
| ctgtgccagc | gcccggatgg | caccctgtat | ggcagcctgc | attttgatcc | ggcggcgtgc | 360 |
| agctttcgcg | aactgctgct | gaaagatggc | tataacgtgt | atcagagcga | agcgctggcg | 420 |
| cgcccgctgc | gcctgccgcc | gtatagcagc | ccgagcagcg | atccggcgcg | ccgcggcccg | 480 |
| gcgcgctttc | tgccgctgcc | gggcccgccg | ccggaaccgc | cgcagccgcc | gggccgcctg | 540 |

```
gcgccggaac cgccggatgt gggcagcagc gatccgctga gcatggtgtg ccgagccgc    600 ggccgcagcc cgagctatac cagctaa                                      627

<210> SEQ ID NO 330
<211> LENGTH: 633
<212> TYPE: DNA
<213> ORGANISM: Heterocephalus glaber

<400> SEQUENCE: 330
atggattggg cgcgcgcgga aagcgaacgc ccgggcctgt gggtgccggc ggtgctggcg    60
gtgctgctgc tgggcgcgtg ccaggcgcat ccgattccgg atagcagccc gctgctgcag   120
tttggcggcc aggtgcgcca cgccatctg tataccgatg atgcgcagga taccgaagtg   180
catctggaaa ttcgcgcgga tgcagcgtg gcggcgcgg cgcatcgcag cccggaaagc    240
ctgctggaac tgaaagcgct gaaaccgggc gtgattcaga ttctgggcgt gcgcaccagc   300
cgctttctgt gccagcgccc ggatggcacc ctgtatggca gcctgcattt tgatccggaa   360
gcgtgcagct ttcgcgaact gctgctggcg gatggctata acatttatca gagcgaagcg   420
tatgccctgc cgctgcgcat gctgccgagc gatagcgcga ccgcgatcc ggtgccgccg    480 ggcccggcgc gctttctgcc gctgccgggc ctgcatccgc cgccgctgga accgccgggc   540
atgctgccgc cggaaccgcc ggatgtgggc agcagcgatc cgctgagcat ggtgggcccg   600
ctgcagggcc gcagcccgag ctatgcgttt taa                               633

<210> SEQ ID NO 331
<211> LENGTH: 630
<212> TYPE: DNA
<213> ORGANISM: Cricetulus griseus

<400> SEQUENCE: 331
atggactgga tgaaatctgg agttggggtc ccgggactgt gggtccctct gctgcctatc    60
ttcctgctgg gggtctccca ggcacacccc atccctgact ccagcccct cctccagttt    120 gggggtcaag tccggcacag gcacctctac acagatgaca accaggaaac tgaagtccac   180
ctggagatta ggcaggatgg cacggtgata gggaccacac accgcagccc agaaagtctc   240
ctggagctca aagccttgaa gccagaggtc atcccagtgc tgggtgtcaa ggcctccagg    300
tttctttgcc aacaaccaga cggaaccctg tatggatcgc ctcactttga tcctgaggcc   360
tgcagtttca gggagctctt gcttgaggat ggatacaatg tgtaccaatc tgaagtccat   420
ggcctgcccc tgcgcctgcc ccagagggac tctccaaacc aggccccagc atcctgggga   480
cctgtgcccc ccctgccagt gccaggactg ctccaccagc ccaggagct accagggttc    540 ctggccccag aacctccaga tgtgggctcc tctgacccac tgagcatggt gggacctttg    600
cagggccgaa gccccagcta tgcttcctga                                    630

<210> SEQ ID NO 332
<211> LENGTH: 579
<212> TYPE: DNA
<213> ORGANISM: Ovis aries

<400> SEQUENCE: 332
atgggctggg acgaggccaa gttcaagcac ttgggactgt gggtccctgt gctggctgtc     60
ctcctgctag gaacctgccg ggcgcatcca attccagact ccagcccct cctccagttt    120 gggggccaag tccgccagcg gtacctctac acggatgatg cccaggagac agaggcccac    180
```

| | |
|---|---|
| ctggagatca gggccgatgg cacagtggtg ggggcggccc gccagagtcc cgaaagtctc | 240 |
| ttggagctga aagccctgaa gccaggagtc attcagatct ttggagttaa acatccagg | 300 |
| ttcctgtgcc aggggccaga tgggaagctg tatggatcgc tgcactttga ccccaaagcc | 360 |
| tgcagcttcc gggagctgct tcttgaagat gggtacaatg tctaccagtc ggagaccctg | 420 |
| ggccttccac tccgcctgcc gccgcagcgc tcatccaacc gggacccggc ccgcgggga | 480 |
| cctccgaagc cccagctaca cttcttgaag acgtccgctg tgcagtactg gccacgttat | 540 |
| gagaaggtcc cagcttttct gcacccttc cccggctga | 579 |

<210> SEQ ID NO 333
<211> LENGTH: 405
<212> TYPE: DNA
<213> ORGANISM: Pan paniscus

<400> SEQUENCE: 333

| | |
|---|---|
| atggactcgg acgagaccgg gttcgagcac tcaggactgt gggtttctgt gctggctggt | 60 |
| cttctgctgg gagcctgcca ggcacacccc atccctgact ccagtcctct cctgcaattc | 120 |
| gggggccaag tccggcagcg gtacctctac acagatgatg cccagcagac agaagcccac | 180 |
| ctggagatca ggaggatgg gacggtgggg ggcgctgctg accagagccc cgaaagtctc | 240 |
| ctgcagctga agccttgaa gccgggagtt attcaaatct gggagtcaa gacatccagg | 300 |
| ttcctgtgcc agaggccaga tggggccctg tatggatcgg tgagtttcca ggaccctcct | 360 |
| caccacccac catgctcctc ctatatgtcg ccctcacagc ctggg | 405 |

<210> SEQ ID NO 334
<211> LENGTH: 351
<212> TYPE: DNA
<213> ORGANISM: Macaca fascicularis

<400> SEQUENCE: 334

| | |
|---|---|
| atggatagcg atgaaaccgg ctttgaacat agcggcctgt gggtgccggt gctggcgggc | 60 |
| ctgctgctgg gcgcgtgcca ggcgcatccg attccggata gcagcccgct gctgcagttt | 120 |
| ggcggccagg tgcgccagcg ctatctgtat accgatgatg cgcagcagac cgaagcgcat | 180 |
| ctggaaattc gcgaagatgg caccgtgggc ggcgcggcgc atcagagccc ggaaagcctg | 240 |
| ctgcagctga aagcgctgaa accgggcgtg attcagattc tgggcgtgaa accagccgc | 300 |
| tttctgtgcc agaaaccgga tggcgcgctg tatggcagcg tgagctttta a | 351 |

<210> SEQ ID NO 335
<211> LENGTH: 314
<212> TYPE: DNA
<213> ORGANISM: Mesocricetus auratus

<400> SEQUENCE: 335

| | |
|---|---|
| ggtcatccaa atcctgggtg tcaaggctgc taggtttcct tgccagcaac cagacggaag | 60 |
| cctgtacgga tcgcctcact tcgatcccga ggcctgcagt ttccgggagc tcctgcttga | 120 |
| ggatggatac aatgtgtacc agtcggaagc ccacggcctg ccctgcgcc tgccccagag | 180 |
| ggacgctccg agccagcccc cagcatcctg ggaccggtg cgcttcctgc cagtgcccgg | 240 |
| actgttccag ccgccccacg acctcccagg gcgcccggcc ccagagcctc cggacgtggg | 300 |
| ctcctccgac ccac | 314 |

<210> SEQ ID NO 336
<211> LENGTH: 456

```
<212> TYPE: DNA
<213> ORGANISM: Nile tilapia

<400> SEQUENCE: 336
atgtatttgc agatgaacat ggatgggaga gtcacaggaa gtgatgctca gacaccttac    60
agtttgatgc agctgaaatc agttaaacca ggccatgtaa tcattaaagg accatcatca   120
tctcttttc tctgtgtgga cagcgaaggc aatctgagag gcagagtca ctactcagaa     180
accagctgca ccttcagaga aatgctgctg gctgacggat acacccgttt catttcctca   240
caatatggat ttcccatgtc actggcatca agacattccc cagatcgaca cgcgcttccc   300
tttacgcggt tcctaccact gaggaataac ttgaaaacgg atagcgtatc agagcagctg   360
ccaaacaatc agagactctt caacgtggac tctgatgacc ttcttggaat gggtctaaat   420
tctatgggca gtcctcagtt ttctatggac aaataa                             456

<210> SEQ ID NO 337
<211> LENGTH: 216
<212> TYPE: PRT
<213> ORGANISM: Homo sapiens

<400> SEQUENCE: 337

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
                35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
                100                 105                 110

Leu Gln Tyr Ser Glu Glu Asp Cys Ala Phe Glu Glu Ile Arg Pro
            115                 120                 125

Asp Gly Tyr Asn Val Tyr Arg Ser Glu Lys His Arg Leu Pro Val Ser
            130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
                180                 185                 190

Glu Thr Asp Ser Met Asp Pro Phe Gly Leu Val Thr Gly Leu Glu Ala
                195                 200                 205

Val Arg Ser Pro Ser Phe Glu Lys
            210                 215

<210> SEQ ID NO 338
<211> LENGTH: 651
<212> TYPE: DNA
<213> ORGANISM: Homo sapiens

<400> SEQUENCE: 338
```

```
atgcggagcg ggtgtgtggt ggtccacgta tggatcctgg ccggcctctg gctggccgtg      60
gccgggcgcc ccctcgcctt ctcggacgcg gggccccacg tgcactacgg ctggggcgac     120
cccatccgcc tgcggcacct gtacacctcc ggcccccacg gctctccag ctgcttcctg      180
cgcatccgtg ccgacggcgt cgtggactgc gcgcggggcc agagcgcgca cagtttgctg     240
gagatcaagg cagtcgctct gcggaccgtg gccatcaagg gcgtgcacag cgtgcggtac     300
ctctgcatgg cgccgacgg caagatgcag gggctgcttc agtactcgga ggaagactgt      360
gctttcgagg aggagatccg cccagatggc tacaatgtgt accgatccga aagcaccgc      420
ctcccggtct ccctgagcag tgccaaacag cggcagctgt acaagaacag aggctttctt     480
ccactctctc atttcctgcc catgctgccc atggtcccag aggagcctga ggacctcagg     540
ggccacttgg aatctgacat gttctcttcg cccctggaga ccgacagcat ggacccattt     600
gggcttgtca ccggactgga ggccgtgagg agtcccagct tgagaagta a               651
```

<210> SEQ ID NO 339
<211> LENGTH: 192
<212> TYPE: PRT
<213> ORGANISM: Artificial
<220> FEATURE:
<223> OTHER INFORMATION: Chimeric protein

<400> SEQUENCE: 339

Met Ala Glu Gly Glu Ile Thr Thr Phe Thr Ala Leu Thr Glu Lys Phe
1               5                   10                  15
Asn Leu Pro Pro Gly Asn Tyr Lys Lys Pro Lys Leu Leu Tyr Cys Ser
            20                  25                  30
Asn Gly Gly His Phe Leu Arg Ile Leu Pro Asp Gly Thr Val Asp Gly
        35                  40                  45
Thr Arg Asp Arg Ser Asp Gln His Ile Gln Leu Gln Leu Ser Ala Glu
    50                  55                  60
Ser Val Gly Glu Val Tyr Ile Lys Ser Thr Glu Thr Gly Gln Tyr Leu
65                  70                  75                  80
Ala Met Asp Thr Asp Gly Leu Leu Tyr Gly Ser Gln Thr Pro Asn Glu
                85                  90                  95
Glu Cys Leu Phe Leu Glu Arg Leu Glu Glu Asn His Tyr Asn Thr Tyr
            100                 105                 110
Ile Ser Lys Lys His Ala Glu Lys Asn Trp Phe Val Gly Leu Asp Gln
        115                 120                 125
Asn Gly Ser Cys Val Arg Gly Pro Arg Thr His Tyr Gly Gln Lys Ala
    130                 135                 140
Ile Leu Phe Leu Pro Leu Pro Gly Leu Pro Pro Ala Leu Pro Glu Pro
145                 150                 155                 160
Pro Gly Ile Leu Ala Pro Gln Pro Pro Asp Val Gly Ser Ser Asp Pro
                165                 170                 175
Leu Ser Met Val Gly Pro Ser Gln Gly Arg Ser Pro Ser Tyr Ala Ser
            180                 185                 190

<210> SEQ ID NO 340
<211> LENGTH: 168
<212> TYPE: PRT
<213> ORGANISM: Artificial
<220> FEATURE:
<223> OTHER INFORMATION: Chimeric protein

<400> SEQUENCE: 340

Lys Pro Lys Leu Leu Tyr Cys Ser Asn Gly Gly His Phe Leu Arg Ile

```
              1               5                  10                 15
Leu Pro Asp Gly Thr Val Asp Gly Thr Arg Asp Arg Ser Asp Gln His
              20                 25                 30

Ile Gln Leu Gln Leu Ser Ala Glu Ser Val Gly Glu Val Tyr Ile Lys
              35                 40                 45

Ser Thr Glu Thr Gly Gln Tyr Leu Ala Met Asp Thr Asp Gly Leu Leu
              50                 55                 60

Tyr Gly Ser Gln Thr Pro Asn Glu Glu Cys Leu Phe Leu Glu Arg Leu
 65                 70                 75                 80

Glu Glu Asn His Tyr Asn Thr Tyr Ile Ser Lys Lys His Ala Glu Lys
                     85                 90                 95

Asn Trp Phe Val Gly Leu Asp Gln Asn Gly Ser Cys Val Arg Gly Pro
                100                105                110

Arg Thr His Tyr Gly Gln Lys Ala Ile Leu Phe Leu Pro Leu Pro Gly
                115                120                125

Leu Pro Pro Ala Leu Pro Glu Pro Pro Gly Ile Leu Ala Pro Gln Pro
130                135                140

Pro Asp Val Gly Ser Ser Asp Pro Leu Ser Met Val Gly Pro Ser Gln
145                150                155                160

Gly Arg Ser Pro Ser Tyr Ala Ser
                165
```

<210> SEQ ID NO 341
<211> LENGTH: 193
<212> TYPE: PRT
<213> ORGANISM: Artificial
<220> FEATURE:
<223> OTHER INFORMATION: Chimeric protein

<400> SEQUENCE: 341

```
Met Ala Ala Gly Ser Ile Thr Thr Leu Pro Ala Leu Pro Glu Asp Gly
 1               5                  10                 15

Gly Ser Gly Ala Phe Pro Pro Gly His Phe Lys Asp Pro Lys Arg Leu
              20                 25                 30

Tyr Cys Lys Asn Gly Gly Phe Phe Leu Arg Ile His Pro Asp Gly Arg
              35                 40                 45

Val Asp Gly Val Arg Glu Lys Ser Asp Pro His Ile Lys Leu Gln Leu
              50                 55                 60

Gln Ala Glu Glu Arg Gly Val Val Ser Ile Lys Gly Val Cys Ala Asn
 65                 70                 75                 80

Arg Tyr Leu Ala Met Lys Glu Asp Gly Arg Leu Leu Ala Ser Lys Cys
                     85                 90                 95

Val Thr Asp Glu Cys Phe Phe Phe Glu Arg Leu Glu Ser Asn Asn Tyr
                100                105                110

Asn Thr Tyr Arg Ser Arg Lys Tyr Thr Ser Trp Tyr Val Ala Leu Asp
                115                120                125

Gln Thr Gly Gln Tyr Val Leu Gly Ser Lys Thr Gly Pro Gly Gln Lys
                130                135                140

Ala Ile Leu Phe Leu Pro Met Pro Gly Leu Pro Ala Leu Pro Glu
145                150                155                160

Pro Pro Gly Ile Leu Ala Pro Gln Pro Asp Val Gly Ser Ser Asp
                165                170                175

Pro Leu Ser Met Val Gly Pro Ser Gln Gly Arg Ser Pro Ser Tyr Ala
                180                185                190

Ser
```

<210> SEQ ID NO 342
<211> LENGTH: 169
<212> TYPE: PRT
<213> ORGANISM: Artificial
<220> FEATURE:
<223> OTHER INFORMATION: Chimeric protein

<400> SEQUENCE: 342

His Phe Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Asp Gln Thr Gly Gln Tyr Val Leu Gly
            100                 105                 110

Ser Lys Thr Gly Pro Gly Gln Lys Ala Ile Leu Phe Leu Pro Met Pro
        115                 120                 125

Gly Leu Pro Pro Ala Leu Pro Glu Pro Pro Gly Ile Leu Ala Pro Gln
    130                 135                 140

Pro Pro Asp Val Gly Ser Ser Asp Pro Leu Ser Met Val Gly Pro Ser
145                 150                 155                 160

Gln Gly Arg Ser Pro Ser Tyr Ala Ser
                165

<210> SEQ ID NO 343
<211> LENGTH: 576
<212> TYPE: DNA
<213> ORGANISM: Artificial
<220> FEATURE:
<223> OTHER INFORMATION: Nucleic acid sequence encoding chimeric protein

<400> SEQUENCE: 343
atggctgaag gggaaatcac caccttcaca gccctgaccg agaagtttaa tctgcctcca      60
gggaattaca gaagcccaa actcctctac tgtagcaacg ggggccactt cctgaggatc      120
cttccggatg gcacagtgga tgggacaagg acaggagcg accagcacat tcagctgcag      180
ctcagtgcgg aaagcgtggg ggaggtgtat ataaagagta ccgagactgg ccagtacttg      240
gccatggaca ccgacgggct tttatacggc tcacagacac aaatgaggat gtttgttc      300 ctggaaaggc tggaggagaa ccattacaac acctatatat ccaagaagca tgcagagaag      360
aattggtttg ttggcctcga tcagaatggg agctgcgttc gcggtcctcg gactcactat      420
ggccagaaag caatcttgtt tctcccctg ccaggcctgc ccccgcact cccggagcca       480 cccggaatcc tggcccccca gccccccgat gtgggctcct cggaccctct gagcatggtg      540
ggaccttccc agggccgaag cccagctac gcttcc                                 576

<210> SEQ ID NO 344
<211> LENGTH: 504
<212> TYPE: DNA
<213> ORGANISM: Artificial
<220> FEATURE:
<223> OTHER INFORMATION: Nucleic acid sequence encoding chimeric protein

<400> SEQUENCE: 344

```
aagcccaaac tcctctactg tagcaacggg ggccacttcc tgaggatcct tccggatggc      60
acagtggatg ggacaaggga caggagcgac cagcacattc agctgcagct cagtgcggaa     120
agcgtggggg aggtgtatat aaagagtacc gagactggcc agtacttggc catggacacc     180
gacgggcttt tatacggctc acagacacca aatgaggaat gtttgttcct ggaaaggctg     240
gaggagaacc attacaacac ctatatatcc aagaagcatg cagagaagaa ttggtttgtt     300
ggcctcgatc agaatgggag ctgcgttcgc ggtcctcgga ctcactatgg ccagaaagca     360
atcttgtttc tccccctgcc aggcctgccc cccgcactcc cggagccacc cggaatcctg     420
gccccccagc cccccgatgt gggctcctcg gaccctctga gcatggtggg accttcccag     480
ggccgaagcc ccagctacgc ttcc                                            504
```

<210> SEQ ID NO 345
<211> LENGTH: 579
<212> TYPE: DNA
<213> ORGANISM: Artificial
<220> FEATURE:
<223> OTHER INFORMATION: Nucleic acid sequence encoding chimeric protein

<400> SEQUENCE: 345

```
atggcagccg ggagcatcac cacgctgccc gccttgcccg aggatggcgg cagcggcgcc      60
ttcccgcccg gccacttcaa ggaccccaag cggctgtact gcaaaaacgg ggcttcttc      120
ctgcgcatcc accccgacgg ccgagttgac ggggtccggg agaagagcga ccctcacatc     180
aagctacaac ttcaagcaga agagaggagt tgtgtctatc aaaggagtgt gtgctaac      240
cgttacctgg ctatgaagga gatggaaga ttactggctt ctaaatgtgt tacggatgag      300
tgttttcttt ttgaacgatt ggaatctaat aactacaata cttaccggtc aaggaaatac     360
accagttggt atgtggcact ggatcagact gggcagtatg ttcttggatc caaaacagga     420
cctgggcaga aagctatact ttttcttcca atgccaggcc tgcccccgc actcccggag     480
ccacccggaa tcctggcccc ccagcccccc gatgtgggct cctcggaccc tctgagcatg     540
gtgggacctt cccagggccg aagccccagc tacgcttcc                            579
```

<210> SEQ ID NO 346
<211> LENGTH: 507
<212> TYPE: DNA
<213> ORGANISM: Artificial
<220> FEATURE:
<223> OTHER INFORMATION: Nucleic acid sequence encoding chimeric protein

<400> SEQUENCE: 346

```
cacttcaagg accccaagcg gctgtactgc aaaaacgggg cttcttcct gcgcatccac       60
cccgacggcc gagttgacgg ggtccgggag aagagcgacc tcacatcaa gctacaactt     120
caagcagaag agaggagt tgtgtctatc aaaggagtgt gtgctaaccg ttacctggct     180
atgaaggaag atggaagatt actggcttct aaatgtgtta cggatgagtg ttttcttttt     240
gaacgattgg aatctaataa ctacaatact taccggtcaa ggaaatacac cagttggtat     300
gtggcactgg atcagactgg gcagtatgtt cttggatcca aaacaggacc tgggcagaaa     360
gctatacttt ttcttccaat gccaggcctg cccccgcac tcccggagcc acccggaatc     420
ctggccccc agccccccga tgtgggctcc tcggaccctc tgagcatggt gggaccttcc      480
```
cagggccgaa gccccagcta cgcttcc 507

<210> SEQ ID NO 347
<211> LENGTH: 1044
<212> TYPE: PRT
<213> ORGANISM: Homo sapiens

<400> SEQUENCE: 347

```
Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
        35                  40                  45

Ala Val Thr Gly Phe Ser Gly Asp Gly Arg Ala Ile Trp Ser Lys Asn
    50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
    290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
        355                 360                 365
```

```
Phe Phe Ala Phe Ser Phe Gly Pro Asn Asn Phe Lys Pro Leu Asn Thr
    370             375                 380
Met Ala Lys Met Gly Gln Asn Val Ser Leu Asn Leu Arg Glu Ala Leu
385                 390                 395                 400
Asn Trp Ile Lys Leu Glu Tyr Asn Asn Pro Arg Ile Leu Ile Ala Glu
                405                 410                 415
Asn Gly Trp Phe Thr Asp Ser Arg Val Lys Thr Glu Asp Thr Thr Ala
            420                 425                 430
Ile Tyr Met Met Lys Asn Phe Leu Ser Gln Val Leu Gln Ala Ile Arg
        435                 440                 445
Leu Asp Glu Ile Arg Val Phe Gly Tyr Thr Ala Trp Ser Leu Leu Asp
450                 455                 460
Gly Phe Glu Trp Gln Asp Ala Tyr Thr Ile Arg Arg Gly Leu Phe Tyr
465                 470                 475                 480
Val Asp Phe Asn Ser Lys Gln Lys Glu Arg Lys Pro Lys Ser Ser Ala
                485                 490                 495
His Tyr Tyr Lys Gln Ile Ile Arg Glu Asn Gly Phe Ser Leu Lys Glu
            500                 505                 510
Ser Thr Pro Asp Val Gln Gly Gln Phe Pro Cys Asp Phe Ser Trp Gly
        515                 520                 525
Val Thr Glu Ser Val Leu Lys Pro Glu Ser Val Ala Ser Ser Pro Gln
530                 535                 540
Phe Ser Asp Pro His Leu Tyr Val Trp Asn Ala Thr Gly Asn Arg Leu
545                 550                 555                 560
Leu His Arg Val Glu Gly Val Arg Leu Lys Thr Arg Pro Ala Gln Cys
                565                 570                 575
Thr Asp Phe Val Asn Ile Lys Lys Gln Leu Glu Met Leu Ala Arg Met
            580                 585                 590
Lys Val Thr His Tyr Arg Phe Ala Leu Asp Trp Ala Ser Val Leu Pro
        595                 600                 605
Thr Gly Asn Leu Ser Ala Val Asn Arg Gln Ala Leu Arg Tyr Tyr Arg
610                 615                 620
Cys Val Val Ser Glu Gly Leu Lys Leu Gly Ile Ser Ala Met Val Thr
625                 630                 635                 640
Leu Tyr Tyr Pro Thr His Ala His Leu Gly Leu Pro Glu Pro Leu Leu
                645                 650                 655
His Ala Asp Gly Trp Leu Asn Pro Ser Thr Ala Glu Ala Phe Gln Ala
            660                 665                 670
Tyr Ala Gly Leu Cys Phe Gln Glu Leu Gly Asp Leu Val Lys Leu Trp
        675                 680                 685
Ile Thr Ile Asn Glu Pro Asn Arg Leu Ser Asp Ile Tyr Asn Arg Ser
690                 695                 700
Gly Asn Asp Thr Tyr Gly Ala Ala His Asn Leu Leu Val Ala His Ala
705                 710                 715                 720
Leu Ala Trp Arg Leu Tyr Asp Arg Gln Phe Arg Pro Ser Gln Arg Gly
                725                 730                 735
Ala Val Ser Leu Ser Leu His Ala Asp Trp Ala Glu Pro Ala Asn Pro
            740                 745                 750
Tyr Ala Asp Ser His Trp Arg Ala Ala Glu Arg Phe Leu Gln Phe Glu
        755                 760                 765
Ile Ala Trp Phe Ala Glu Pro Leu Phe Lys Thr Gly Asp Tyr Pro Ala
770                 775                 780
Ala Met Arg Glu Tyr Ile Ala Ser Lys His Arg Arg Gly Leu Ser Ser
```

Ser Ala Leu Pro Arg Leu Thr Glu Ala Glu Arg Arg Leu Leu Lys Gly
785                 790                 795                 800

Thr Val Asp Phe Cys Ala Leu Asn His Phe Thr Thr Arg Phe Val Met
            805                 810                 815

His Glu Gln Leu Ala Gly Ser Arg Tyr Asp Ser Arg Asp Ile Gln
        820                 825                 830

Phe Leu Gln Asp Ile Thr Arg Leu Ser Ser Pro Thr Arg Leu Ala Val
835                 840                 845

Ile Pro Trp Gly Val Arg Lys Leu Leu Arg Trp Val Arg Arg Asn Tyr
    850                 855                 860

Gly Asp Met Asp Ile Tyr Ile Thr Ala Ser Gly Ile Asp Asp Gln Ala
865                 870                 875                 880

Leu Glu Asp Asp Arg Leu Arg Lys Tyr Tyr Leu Gly Lys Tyr Leu Gln
            885                 890                 895

Glu Val Leu Lys Ala Tyr Leu Ile Asp Lys Val Arg Ile Lys Gly Tyr
        900                 905                 910

Tyr Ala Phe Lys Leu Ala Glu Glu Lys Ser Lys Pro Arg Phe Gly Phe
915                 920                 925

Phe Thr Ser Asp Phe Lys Ala Lys Ser Ser Ile Gln Phe Tyr Asn Lys
    930                 935                 940

Val Ile Ser Ser Arg Gly Phe Pro Phe Glu Asn Ser Ser Arg Cys
945                 950                 955                 960

Ser Gln Thr Gln Glu Asn Thr Glu Cys Thr Val Cys Leu Phe Leu Val
            965                 970                 975

Gln Lys Lys Pro Leu Ile Phe Leu Gly Cys Cys Phe Phe Ser Thr Leu
        980                 985                 990

Val Leu Leu Leu Ser Ile Ala Ile Phe Gln Arg Gln Lys Arg Arg
995                 1000                1005

Lys Phe Trp Lys Ala Lys Asn Leu Gln His Ile Pro Leu Lys Lys
    1010                1015                1020

Gly Lys Arg Val Val Ser
1025                1030                1035

Gly Lys Arg Val Val Ser
    1040

<210> SEQ ID NO 348
<211> LENGTH: 1043
<212> TYPE: PRT
<213> ORGANISM: Mus musculus

<400> SEQUENCE: 348

Met Lys Thr Gly Cys Ala Ala Gly Ser Pro Gly Asn Glu Trp Ile Phe
1               5                   10                  15

Phe Ser Asp Glu Arg Asn Thr Arg Ser Arg Lys Thr Met Ser Asn
            20                  25                  30

Arg Ala Leu Gln Arg Ser Ala Val Leu Ser Ala Phe Val Leu Leu Arg
        35                  40                  45

Ala Val Thr Gly Phe Ser Gly Asp Gly Lys Ala Ile Trp Asp Lys Lys
    50                  55                  60

Gln Tyr Val Ser Pro Val Asn Pro Ser Gln Leu Phe Leu Tyr Asp Thr
65                  70                  75                  80

Phe Pro Lys Asn Phe Ser Trp Gly Val Gly Thr Gly Ala Phe Gln Val
            85                  90                  95

Glu Gly Ser Trp Lys Thr Asp Gly Arg Gly Pro Ser Ile Trp Asp Arg
        100                 105                 110

-continued

Tyr Val Tyr Ser His Leu Arg Gly Val Asn Gly Thr Asp Arg Ser Thr
            115                 120                 125

Asp Ser Tyr Ile Phe Leu Glu Lys Asp Leu Leu Ala Leu Asp Phe Leu
130                 135                 140

Gly Val Ser Phe Tyr Gln Phe Ser Ile Ser Trp Pro Arg Leu Phe Pro
145                 150                 155                 160

Asn Gly Thr Val Ala Ala Val Asn Ala Gln Gly Leu Arg Tyr Tyr Arg
                165                 170                 175

Ala Leu Leu Asp Ser Leu Val Leu Arg Asn Ile Glu Pro Ile Val Thr
            180                 185                 190

Leu Tyr His Trp Asp Leu Pro Leu Thr Leu Gln Glu Glu Tyr Gly Gly
        195                 200                 205

Trp Lys Asn Ala Thr Met Ile Asp Leu Phe Asn Asp Tyr Ala Thr Tyr
210                 215                 220

Cys Phe Gln Thr Phe Gly Asp Arg Val Lys Tyr Trp Ile Thr Ile His
225                 230                 235                 240

Asn Pro Tyr Leu Val Ala Trp His Gly Phe Gly Thr Gly Met His Ala
                245                 250                 255

Pro Gly Glu Lys Gly Asn Leu Thr Ala Val Tyr Thr Val Gly His Asn
            260                 265                 270

Leu Ile Lys Ala His Ser Lys Val Trp His Asn Tyr Asp Lys Asn Phe
        275                 280                 285

Arg Pro His Gln Lys Gly Trp Leu Ser Ile Thr Leu Gly Ser His Trp
    290                 295                 300

Ile Glu Pro Asn Arg Thr Asp Asn Met Glu Asp Val Ile Asn Cys Gln
305                 310                 315                 320

His Ser Met Ser Ser Val Leu Gly Trp Phe Ala Asn Pro Ile His Gly
                325                 330                 335

Asp Gly Asp Tyr Pro Glu Phe Met Lys Thr Gly Ala Met Ile Pro Glu
            340                 345                 350

Phe Ser Glu Ala Glu Lys Glu Glu Val Arg Gly Thr Ala Asp Phe Phe
        355                 360                 365

Ala Phe Ser Phe Gly Pro Asn Asn Phe Arg Pro Ser Asn Thr Val Val
    370                 375                 380

Lys Met Gly Gln Asn Val Ser Leu Asn Leu Arg Gln Val Leu Asn Trp
385                 390                 395                 400

Ile Lys Leu Glu Tyr Asp Asp Pro Gln Ile Leu Ile Ser Glu Asn Gly
                405                 410                 415

Trp Phe Thr Asp Ser Tyr Ile Lys Thr Glu Asp Thr Thr Ala Ile Tyr
            420                 425                 430

Met Met Lys Asn Phe Leu Asn Gln Val Leu Gln Ala Ile Lys Phe Asp
        435                 440                 445

Glu Ile Arg Val Phe Gly Tyr Thr Ala Trp Thr Leu Leu Asp Gly Phe
    450                 455                 460

Glu Trp Gln Asp Ala Tyr Thr Thr Arg Arg Gly Leu Phe Tyr Val Asp
465                 470                 475                 480

Phe Asn Ser Glu Gln Lys Glu Arg Lys Pro Lys Ser Ser Ala His Tyr
                485                 490                 495

Tyr Lys Gln Ile Ile Gln Asp Asn Gly Phe Pro Leu Lys Glu Ser Thr
            500                 505                 510

Pro Asp Met Lys Gly Arg Phe Pro Cys Asp Phe Ser Trp Gly Val Thr
        515                 520                 525

Glu Ser Val Leu Lys Pro Glu Phe Thr Val Ser Ser Pro Gln Phe Thr

```
            530                 535                 540
Asp Pro His Leu Tyr Val Trp Asn Val Thr Gly Asn Arg Leu Leu Tyr
545                 550                 555                 560

Arg Val Glu Gly Val Arg Leu Lys Thr Arg Pro Ser Gln Cys Thr Asp
                    565                 570                 575

Tyr Val Ser Ile Lys Lys Arg Val Glu Met Leu Ala Lys Met Lys Val
                580                 585                 590

Thr His Tyr Gln Phe Ala Leu Asp Trp Thr Ser Ile Leu Pro Thr Gly
            595                 600                 605

Asn Leu Ser Lys Val Asn Arg Gln Val Leu Arg Tyr Tyr Arg Cys Val
        610                 615                 620

Val Ser Glu Gly Leu Lys Leu Gly Val Phe Pro Met Val Thr Leu Tyr
625                 630                 635                 640

His Pro Thr His Ser His Leu Gly Leu Pro Leu Pro Leu Leu Ser Ser
                    645                 650                 655

Gly Gly Trp Leu Asn Met Asn Thr Ala Lys Ala Phe Gln Asp Tyr Ala
                660                 665                 670

Glu Leu Cys Phe Arg Glu Leu Gly Asp Leu Val Lys Leu Trp Ile Thr
            675                 680                 685

Ile Asn Glu Pro Asn Arg Leu Ser Asp Met Tyr Asn Arg Thr Ser Asn
690                 695                 700

Asp Thr Tyr Arg Ala Ala His Asn Leu Met Ile Ala His Ala Gln Val
705                 710                 715                 720

Trp His Leu Tyr Asp Arg Gln Tyr Arg Pro Val Gln His Gly Ala Val
                    725                 730                 735

Ser Leu Ser Leu His Cys Asp Trp Ala Glu Pro Ala Asn Pro Phe Val
                740                 745                 750

Asp Ser His Trp Lys Ala Ala Glu Arg Phe Leu Gln Phe Glu Ile Ala
            755                 760                 765

Trp Phe Ala Asp Pro Leu Phe Lys Thr Gly Asp Tyr Pro Ser Val Met
770                 775                 780

Lys Glu Tyr Ile Ala Ser Lys Asn Gln Arg Gly Leu Ser Ser Ser Val
785                 790                 795                 800

Leu Pro Arg Phe Thr Ala Lys Glu Ser Arg Leu Val Lys Gly Thr Val
                805                 810                 815

Asp Phe Tyr Ala Leu Asn His Phe Thr Thr Arg Phe Val Ile His Lys
            820                 825                 830

Gln Leu Asn Thr Asn Arg Ser Val Ala Asp Arg Asp Val Gln Phe Leu
        835                 840                 845

Gln Asp Ile Thr Arg Leu Ser Ser Pro Ser Arg Leu Ala Val Thr Pro
850                 855                 860

Trp Gly Val Arg Lys Leu Leu Ala Trp Ile Arg Arg Asn Tyr Arg Asp
865                 870                 875                 880

Arg Asp Ile Tyr Ile Thr Ala Asn Gly Ile Asp Asp Leu Ala Leu Glu
                    885                 890                 895

Asp Asp Gln Ile Arg Lys Tyr Tyr Leu Glu Lys Tyr Val Gln Glu Ala
                900                 905                 910

Leu Lys Ala Tyr Leu Ile Asp Lys Val Lys Ile Lys Gly Tyr Tyr Ala
            915                 920                 925

Phe Lys Leu Thr Glu Glu Lys Ser Lys Pro Arg Phe Gly Phe Phe Thr
        930                 935                 940

Ser Asp Phe Arg Ala Lys Ser Ser Val Gln Phe Tyr Ser Lys Leu Ile
945                 950                 955                 960
```

Ser Ser Ser Gly Leu Pro Ala Glu Asn Arg Ser Pro Ala Cys Gly Gln
            965                 970                 975

Pro Ala Glu Asp Thr Asp Cys Thr Ile Cys Ser Phe Leu Val Glu Lys
            980                 985                 990

Lys Pro Leu Ile Phe Phe Gly Cys  Cys Phe Ile Ser Thr  Leu Ala Val
            995                 1000                1005

Leu Leu  Ser Ile Thr Val Phe  His His Gln Lys Arg  Arg Lys Phe
        1010                1015                1020

Gln Lys  Ala Arg Asn Leu Gln  Asn Ile Pro Leu Lys  Lys Gly His
        1025                1030                1035

Ser Arg  Val Phe Ser
        1040

<210> SEQ ID NO 349
<211> LENGTH: 3135
<212> TYPE: DNA
<213> ORGANISM: Homo sapiens

<400> SEQUENCE: 349
atgaagccag gctgtgcggc aggatctcca gggaatgaat ggattttctt cagcactgat      60
gaaataacca cacgctatag aatacaatg tccaacgggg gattgcaaag atctgtcatc     120
ctgtcagcac ttattctgct acgagctgtt actggattct ctggagatgg aagagctata     180
tggtctaaaa atcctaattt tactccggta atgaaagtc agctgtttct ctatgacact     240
ttccctaaaa acttttttctg gggtattggg actggagcat gcaagtggaa agggagttgg     300
aagaaggatg gaaaaggacc ttctatatgg gatcatttca tccacacaca ccttaaaaat     360
gtcagcagca cgaatggttc cagtgacagt tatattttc tggaaaaaga cttatcagcc     420
ctggatttta taggagtttc ttttttatcaa ttttcaattt cctggccaag gcttttcccc     480
gatggaatag taacagttgc caacgcaaaa ggtctgcagt actacagtac tcttctggac     540
gctctagtgc ttagaaacat tgaacctata gttacttat accactggga tttgcctttg     600
gcactacaag aaaaatatgg ggggtggaaa aatgatacca taatagatat cttcaatgac     660
tatgccacat actgtttcca gatgtttggg accgtgtca atattggat tacaattcac     720
aacccatatc tagtggcttg gcatgggtat gggacaggta tgcatgcccc tggagagaag     780
ggaaatttag cagctgtcta cactgtggga cacaacttga tcaaggctca ctcgaaagtt     840
tggcataact acaacacaca tttccgccca catcagaagg gttggttatc gatcacgttg     900
ggatctcatt ggatcgagcc aaaccggtcg gaaaacacga tggatatatt caatgtcaa     960
caatccatgg tttctgtgct tggatggttt gccaacccta tccatgggga tggcgactat    1020
ccagagggga tgagaaagaa gttgttctcc gttctaccca ttttctctga agcagagaag    1080
catgagatga gaggcacagc tgatttcttt gcctttttctt ttggacccaa caacttcaag    1140
cccctaaaca ccatggctaa aatgggacaa atgtttcac ttaatttaag agaagcgctg    1200
aactggatta aactggaata caacaaccct cgaatcttga ttgctgagaa tggctggttc    1260
acagacagtc gtgtgaaaac agaagacacc acggccatct acatgatgaa gaatttcctc    1320
agccaggtgc ttcaagcaat aaggttagat gaaatacgag tgtttggtta tactgcctgg    1380
tctctcctgg atggctttga atggcaggat gcttacacca tccgccgagg attatttat    1440
gtggatttta acagtaaaca gaaagagcgg aaacctaagt cttcagcaca ctactacaaa    1500
cagatcatac gagaaaatgg tttttcttta aaagagtcca cgccagatgt gcagggccag    1560

```
tttccctgtg acttctcctg gggtgtcact gaatctgttc ttaagcccga gtctgtggct    1620
tcgtccccac agttcagcga tcctcatctg tacgtgtgga acgccactgg caacagactg    1680
ttgcaccgag tggaaggggt gaggctgaaa acacgacccg ctcaatgcac agattttgta    1740
aacatcaaaa aacaacttga gatgttggca agaatgaaag tcacccacta ccggtttgct    1800
ctggattggg cctcggtcct tcccactggc aacctgtccg cggtgaaccg acaggccctg    1860
aggtactaca ggtgcgtggt cagtgagggg ctgaagcttg catctccgc gatggtcacc     1920
ctgtattatc cgacccacgc ccacctaggc ctccccgagc ctctgttgca tgccgacggg    1980
tggctgaacc catcgacggc cgaggccttc caggcctacg ctgggctgtg cttccaggag    2040
ctgggggacc tggtgaagct ctggatcacc atcaacgagc ctaaccggct aagtgacatc    2100
tacaaccgct ctggcaacga cacctacggg gcggcgcaca acctgctggt ggcccacgcc    2160
ctggcctggc gcctctacga ccggcagttc aggccctcac agcgcggggc cgtgtcgctg    2220
tcgctgcacg cggactgggc ggaacccgcc aaccccatg ctgactcgca ctggagggcg     2280
gccgagcgct tcctgcagtt cgagatcgcc tggttcgccg agccgctctt caagaccggg    2340
gactacccc g cggccatgag ggaatacatt gcctccaagc accgacgggg gctttccagc    2400
tcggccctgc cgcgcctcac cgaggccgaa aggaggctgc tcaagggcac ggtcgacttc    2460
tgcgcgctca accacttcac cactaggttc gtgatgcacg agcagctggc cggcagccgc    2520
tacgactcgg acagggacat ccagtttctg caggacatca cccgcctgag ctcccccacg    2580
cgcctggctg tgattcctg ggggggtgcgc aagctgctgc ggtgggtccg gaggaactac    2640
ggcgacatgg acatttacat caccgccagt ggcatcgacg accaggctct ggaggatgac    2700
cggctccgga gtactacct agggaagtac cttcaggagg tgctgaaagc atacctgatt    2760
gataaagtca gaatcaaagg ctattatgca ttcaaactgg ctgaagagaa atctaaaccc    2820
agatttggat tcttcacatc tgattttaaa gctaaatcct caatacaatt ttacaacaaa    2880
gtgatcagca gcaggggctt ccctttgag aacagtagtt ctagatgcag tcagacccaa     2940
gaaaatacag agtgcactgt ctgcttattc cttgtgcaga gaaaccact gatattcctg     3000
ggttgttgct tcttctccac cctggttcta ctcttatcaa ttgccatttt tcaaaggcag    3060
aagagaagaa agttttggaa agcaaaaaac ttacaacaca taccattaaa gaaaggcaag    3120
agagttgtta gctaa                                                     3135
```

<210> SEQ ID NO 350
<211> LENGTH: 3132
<212> TYPE: DNA
<213> ORGANISM: House mouse

<400> SEQUENCE: 350

```
atgaagacag gctgtgcagc agggtctccg gggaatgaat ggattttctt cagctctgat     60
gaaagaaaca cacgctctag gaaaacaatg tccaacaggg cactgcaaag atctgccgtg    120
ctgtctgcgt ttgttctgct gcgagctgtt accggcttct ccggagacgg gaaagcaata    180
tgggataaaa aacagtacgt gagtccggta aacccaagtc agctgttcct ctatgacact    240
ttccctaaaa acttttcctg gggcgttggg accggagcat ttcaagtgga agggagttgg    300
aagacagatg gaagaggacc ctcgatctgg gatcggtacg tctactcaca cctgagaggt    360
gtcaacggca cagacagatc cactgacagt tacatctttc tggaaaaaga cttgttggct    420
ctggattttt taggagtttc ttttttatcag ttctcaatct cctggccacg gttgtttccc    480
aatggaacag tagcagcagt gaatgcgcaa ggtctccggt actaccgtgc acttctggac    540
```

```
tcgctggtac ttaggaatat cgagcccatt gttaccttgt accattggga tttgcctctg    600
acgctccagg aagaatatgg gggctggaaa aatgcaacta tgatagatct cttcaacgac    660
tatgccacat actgcttcca gacctttgga gaccgtgtca aatattggat tacaattcac    720
aacccttacc ttgttgcttg gcatgggttt ggcacaggta tgcatgcacc aggagagaag    780
ggaaatttaa cagctgtcta cactgtggga cacaacctga tcaaggcaca ttcgaaagtg    840
tggcataact acgacaaaaa cttccgccct catcagaagg gttggctctc catcaccttg    900
gggtcccatt ggatagagcc aaacagaaca gacaacatgg aggacgtgat caactgccag    960
cactccatgt cctctgtgct tggatggttc gccaaccccc tccacgggga cggcgactac   1020
cctgagttca tgaagacggg cgccatgatc cccgagttct ctgaggcaga aaggaggag    1080
gtgaggggca cggctgattt cttttgcctt tccttcgggc ccaacaactt caggccctca   1140
aacaccgtgg tgaaaatggg acaaaatgta tcactcaact taaggcaggt gctgaactgg   1200
attaaactgg aatacgatga ccctcaaatc ttgatttcgg agaacggctg gttcacagat   1260
agctatataa agacagagga caccacggcc atctacatga tgaagaattt cctaaaccag   1320
gttcttcaag caataaaatt tgatgaaatc cgcgtgtttg ttatacggc ctggactctc    1380
ctggatggct ttgagtggca ggatgcctat acgacccgac gagggctgtt ttatgtggac   1440
tttaacagtg agcagaaaga gaggaaaccc aagtcctcgg ctcattacta caagcagatc   1500
atacaagaca acggcttccc tttgaaagag tccacgccag acatgaaggg tcggttcccc   1560
tgtgatttct cttggggagt cactgagtct gttcttaagc ccgagtttac ggtctcctcc   1620
ccgcagttta ccgatcctca cctgtatgtg tggaatgtca ctggcaacag attgctctac   1680
cgagtggaag gggtaaggct gaaaacaaga ccatcccagt gcacagatta tgtgagcatc   1740
aaaaaacgag ttgaaatgtt ggcaaaaatg aaagtcaccc actaccagtt tgctctggac   1800
tggacctcta tccttcccac tggcaatctg tccaaagtta acagacaagt gttaaggtac   1860
tataggtgtg tggtgagcga aggactgaag ctgggcgtct tccccatggt gacgttgtac   1920
cacccaaccc actcccatct cggcctcccc ctgccactc tgagcagtgg ggggtggcta    1980
aacatgaaca cagccaaggc cttccaggac tacgctgagc tgtgcttccg ggagttgggg   2040
gacttggtga agctctggat caccatcaat gagcctaaca ggctgagtga catgtacaac   2100
cgcacgagta atgacaccta ccgtgcagcc cacaacctga tcgcccca tgcccaggtc    2160
tggcacctct atgataggca gtataggccg gtccagcatg gggctgtgtc gctgtcctta   2220
cattgcgact gggcagaacc tgccaacccc tttgtggatt cacactggaa ggcagccgag   2280
cgcttcctcc agtttgagat cgcctggttt gcagatccgc tcttcaagac tggcgactat   2340
ccatcggtta tgaaggaata catcgcctcc aagaaccagc gagggctgtc tagctcagtc   2400
ctgccgcgct tcaccgcgaa ggagagcagg ctggtgaagg gtaccgtcga cttctacgca   2460
ctgaaccact tcactacgag gttcgtgata cacaagcagc tgaacaccaa ccgctcagtt   2520
gcagacaggg acgtccagtt cctgcaggac atcacccgcc taagctcgcc cagccgcctg   2580
gctgtaacac cctggggagt gcgcaagctc cttgcgtgga tccggaggaa ctacagagac   2640
agggatatct acatcacagc caatggcatc gatgacctgg ctctagagga tgatcagatc   2700
cgaaagtact acttggagaa gtatgtccag gaggctctga agcatatct cattgacaag    2760
gtcaaaatca aaggctacta tgcattcaaa ctgactgaag agaaatctaa gcctagattt   2820
ggatttttca cctctgactt cagagctaag tcctctgtcc agttttacag caagctgatc   2880
```

-continued

```
agcagcagtg gcctccccgc tgagaacaga agtcctgcgt gtggtcagcc tgcggaagac    2940
acagactgca ccatttgctc atttctcgtg gagaagaaac cactcatctt cttcggttgc    3000
tgcttcatct ccactctggc tgtactgcta tccatcaccg ttttcatca tcaaaagaga    3060 agaaaattcc agaaagcaag gaacttacaa aatataccat tgaagaaagg ccacagcaga    3120
gttttcagct aa                                                        3132

<210> SEQ ID NO 351
<211> LENGTH: 251
<212> TYPE: PRT
<213> ORGANISM: Homo sapiens

<400> SEQUENCE: 351

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 352
<211> LENGTH: 42
<212> TYPE: PRT
<213> ORGANISM: Artificial
<220> FEATURE:
<223> OTHER INFORMATION: FGF21 variant

<400> SEQUENCE: 352

Pro Gly Leu Pro Pro Ala Leu Pro Glu Pro Gly Ile Leu Ala Pro
1               5                   10                  15
```

-continued

Gln Pro Pro Asp Val Gly Ser Ser Asp Pro Leu Ser Met Val Gly Pro
            20                  25                  30

Ser Gln Gly Arg Ser Pro Ser Tyr Ala Lys
        35                  40

<210> SEQ ID NO 353
<211> LENGTH: 42
<212> TYPE: PRT
<213> ORGANISM: Artificial
<220> FEATURE:
<223> OTHER INFORMATION: FGF21 variant

<400> SEQUENCE: 353

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Glu Ser
        35                  40

<210> SEQ ID NO 354
<211> LENGTH: 42
<212> TYPE: PRT
<213> ORGANISM: Artificial
<220> FEATURE:
<223> OTHER INFORMATION: FGF21 variant

<400> SEQUENCE: 354

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Phe Ala Ser
        35                  40

<210> SEQ ID NO 355
<211> LENGTH: 42
<212> TYPE: PRT
<213> ORGANISM: Artificial
<220> FEATURE:
<223> OTHER INFORMATION: FGF21 variant

<400> SEQUENCE: 355

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Val Arg Ser Pro Ser Tyr Ala Ser
        35                  40

<210> SEQ ID NO 356
<211> LENGTH: 42
<212> TYPE: PRT
<213> ORGANISM: Artificial
<220> FEATURE:
<223> OTHER INFORMATION: FGF21 variant

<400> SEQUENCE: 356

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

```
Ser Ala Gly Arg Ser Pro Ser Tyr Ala Ser
        35                  40

<210> SEQ ID NO 357
<211> LENGTH: 42
<212> TYPE: PRT
<213> ORGANISM: Artificial
<220> FEATURE:
<223> OTHER INFORMATION: FGF21 variant

<400> SEQUENCE: 357

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Glu Gln Gly Arg Ser Pro Ser Tyr Ala Ser
        35                  40

<210> SEQ ID NO 358
<211> LENGTH: 42
<212> TYPE: PRT
<213> ORGANISM: Artificial
<220> FEATURE:
<223> OTHER INFORMATION: FGF21 variant

<400> SEQUENCE: 358

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Leu
            20                  25                  30

Ser Gln Gly Arg Ser Pro Ser Tyr Ala Ser
        35                  40

<210> SEQ ID NO 359
<211> LENGTH: 43
<212> TYPE: PRT
<213> ORGANISM: Artificial
<220> FEATURE:
<223> OTHER INFORMATION: FGF21 variant

<400> SEQUENCE: 359

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Thr Gly
            20                  25                  30

Pro Ser Gln Gly Arg Ser Pro Ser Tyr Ala Ser
        35                  40

<210> SEQ ID NO 360
<211> LENGTH: 42
<212> TYPE: PRT
<213> ORGANISM: Artificial
<220> FEATURE:
<223> OTHER INFORMATION: FGF21 variant

<400> SEQUENCE: 360

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Leu Val Gly Pro
            20                  25                  30

Ser Gln Gly Arg Ser Pro Ser Tyr Ala Ser
        35                  40
```

<210> SEQ ID NO 361
<211> LENGTH: 42
<212> TYPE: PRT
<213> ORGANISM: Artificial
<220> FEATURE:
<223> OTHER INFORMATION: FGF21 variant

<400> SEQUENCE: 361

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Gly Met Val Gly Pro
            20                  25                  30

Ser Gln Gly Arg Ser Pro Ser Tyr Ala Ser
        35                  40

<210> SEQ ID NO 362
<211> LENGTH: 42
<212> TYPE: PRT
<213> ORGANISM: Artificial
<220> FEATURE:
<223> OTHER INFORMATION: FGF21 variant

<400> SEQUENCE: 362

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Phe Ser Met Val Gly Pro
            20                  25                  30

Ser Gln Gly Arg Ser Pro Ser Tyr Ala Ser
        35                  40

<210> SEQ ID NO 363
<211> LENGTH: 42
<212> TYPE: PRT
<213> ORGANISM: Artificial
<220> FEATURE:
<223> OTHER INFORMATION: FGF21 variant

<400> SEQUENCE: 363

Pro Gly Leu Pro Pro Ala Leu Pro Glu Pro Pro Gly Ile Leu Ala Pro
1               5                   10                  15

Gln Pro Pro Asp Val Gly Ser Met Asp Pro Leu Ser Met Val Gly Pro
            20                  25                  30

Ser Gln Gly Arg Ser Pro Ser Tyr Ala Ser
        35                  40

<210> SEQ ID NO 364
<211> LENGTH: 42
<212> TYPE: PRT
<213> ORGANISM: Artificial
<220> FEATURE:
<223> OTHER INFORMATION: FGF21 variant

<400> SEQUENCE: 364

Pro Gly Leu Pro Pro Ala Leu Pro Glu Pro Pro Gly Ile Leu Ala Pro
1               5                   10                  15

Gln Pro Pro Asp Val Asp Ser Ser Asp Pro Leu Ser Met Val Gly Pro
            20                  25                  30

Ser Gln Gly Arg Ser Pro Ser Tyr Ala Ser
        35                  40

<210> SEQ ID NO 365
<211> LENGTH: 42

<212> TYPE: PRT
<213> ORGANISM: Artificial
<220> FEATURE:
<223> OTHER INFORMATION: FGF21 variant

<400> SEQUENCE: 365

Pro Gly Leu Pro Pro Ala Leu Pro Glu Pro Pro Gly Ile Leu Ala Pro
1               5                   10                  15
Gln Pro Pro Asp Thr Gly Ser Ser Asp Pro Leu Ser Met Val Gly Pro
            20                  25                  30
Ser Gln Gly Arg Ser Pro Ser Tyr Ala Ser
        35                  40

<210> SEQ ID NO 366
<211> LENGTH: 42
<212> TYPE: PRT
<213> ORGANISM: Artificial
<220> FEATURE:
<223> OTHER INFORMATION: FGF21 variant

<400> SEQUENCE: 366

Pro Gly Leu Pro Pro Ala Leu Pro Glu Pro Pro Gly Ile Leu Ala Pro
1               5                   10                  15
Gln Pro Pro Glu Val Gly Ser Ser Asp Pro Leu Ser Met Val Gly Pro
            20                  25                  30
Ser Gln Gly Arg Ser Pro Ser Tyr Ala Ser
        35                  40

<210> SEQ ID NO 367
<211> LENGTH: 42
<212> TYPE: PRT
<213> ORGANISM: Artificial
<220> FEATURE:
<223> OTHER INFORMATION: FGF21 variant

<400> SEQUENCE: 367

Pro Gly Leu Pro Pro Ala Leu Pro Glu Pro Pro Gly Ile Leu Ala Pro
1               5                   10                  15
Gln Pro Leu Asp Val Gly Ser Ser Asp Pro Leu Ser Met Val Gly Pro
            20                  25                  30
Ser Gln Gly Arg Ser Pro Ser Tyr Ala Ser
        35                  40

<210> SEQ ID NO 368
<211> LENGTH: 42
<212> TYPE: PRT
<213> ORGANISM: Artificial
<220> FEATURE:
<223> OTHER INFORMATION: FGF21 variant

<400> SEQUENCE: 368

Pro Gly Leu Pro Pro Ala Leu Pro Glu Pro Pro Gly Ile Leu Ala Pro
1               5                   10                  15
Ser Pro Pro Asp Val Gly Ser Ser Asp Pro Leu Ser Met Val Gly Pro
            20                  25                  30
Ser Gln Gly Arg Ser Pro Ser Tyr Ala Ser
        35                  40

<210> SEQ ID NO 369
<211> LENGTH: 42
<212> TYPE: PRT
<213> ORGANISM: Artificial
<220> FEATURE:

<223> OTHER INFORMATION: FGF21 variant

<400> SEQUENCE: 369

Pro Gly Leu Pro Pro Ala Leu Pro Glu Pro Pro Gly Ile Leu Ala Ser
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 370
<211> LENGTH: 42
<212> TYPE: PRT
<213> ORGANISM: Artificial
<220> FEATURE:
<223> OTHER INFORMATION: FGF21 variant

<400> SEQUENCE: 370

Pro Gly Leu Pro Pro Ala Leu Pro Glu Pro Pro Gly Ile Leu Phe Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 371
<211> LENGTH: 42
<212> TYPE: PRT
<213> ORGANISM: Artificial
<220> FEATURE:
<223> OTHER INFORMATION: FGF21 variant

<400> SEQUENCE: 371

Pro Gly Leu Pro Pro Ala Leu Pro Glu Pro Pro Gly Ile Met Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 372
<211> LENGTH: 42
<212> TYPE: PRT
<213> ORGANISM: Artificial
<220> FEATURE:
<223> OTHER INFORMATION: FGF21 variant

<400> SEQUENCE: 372

Pro Gly Leu Pro Pro Ala Leu Pro Glu Pro Pro Gly Asp Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 373
<211> LENGTH: 42
<212> TYPE: PRT
<213> ORGANISM: Artificial
<220> FEATURE:
<223> OTHER INFORMATION: FGF21 variant

<400> SEQUENCE: 373

-continued

Pro Gly Leu Pro Pro Ala Leu Pro Glu Pro Pro Ser Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 374
<211> LENGTH: 42
<212> TYPE: PRT
<213> ORGANISM: Artificial
<220> FEATURE:
<223> OTHER INFORMATION: FGF21 variant

<400> SEQUENCE: 374

Pro Gly Leu Pro Pro Ala Leu Pro Glu Pro Glu Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 375
<211> LENGTH: 42
<212> TYPE: PRT
<213> ORGANISM: Artificial
<220> FEATURE:
<223> OTHER INFORMATION: FGF21 variant

<400> SEQUENCE: 375

Pro Gly Leu Pro Pro Ala Leu Pro Glu Leu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 376
<211> LENGTH: 43
<212> TYPE: PRT
<213> ORGANISM: Artificial
<220> FEATURE:
<223> OTHER INFORMATION: FGF21 variant

<400> SEQUENCE: 376

Pro Gly Leu Pro Pro Ala Leu Pro Glu His Pro Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40

<210> SEQ ID NO 377
<211> LENGTH: 43
<212> TYPE: PRT
<213> ORGANISM: Artificial
<220> FEATURE:
<223> OTHER INFORMATION: FGF21 variant

<400> SEQUENCE: 377

Pro Gly Leu Pro Pro Ala Leu Pro Glu Gly Pro Pro Gly Ile Leu Ala
1               5                   10                  15

-continued

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40

<210> SEQ ID NO 378
<211> LENGTH: 43
<212> TYPE: PRT
<213> ORGANISM: Artificial
<220> FEATURE:
<223> OTHER INFORMATION: FGF21 variant

<400> SEQUENCE: 378

Pro Gly Leu Pro Pro Ala Leu Pro Glu Arg Pro Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40

<210> SEQ ID NO 379
<211> LENGTH: 43
<212> TYPE: PRT
<213> ORGANISM: Artificial
<220> FEATURE:
<223> OTHER INFORMATION: FGF21 variant

<400> SEQUENCE: 379

Pro Gly Leu Pro Pro Ala Leu Pro Glu Leu Pro Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40

<210> SEQ ID NO 380
<211> LENGTH: 43
<212> TYPE: PRT
<213> ORGANISM: Artificial
<220> FEATURE:
<223> OTHER INFORMATION: FGF21 variant

<400> SEQUENCE: 380

Pro Gly Leu Pro Pro Ala Leu Pro Glu Asp Pro Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40

<210> SEQ ID NO 381
<211> LENGTH: 42
<212> TYPE: PRT
<213> ORGANISM: Artificial
<220> FEATURE:
<223> OTHER INFORMATION: FGF21 variant

<400> SEQUENCE: 381

Pro Gly Leu Pro Pro Ala Glu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 382
<211> LENGTH: 42
<212> TYPE: PRT
<213> ORGANISM: Artificial
<220> FEATURE:
<223> OTHER INFORMATION: FGF21 variant

<400> SEQUENCE: 382

Pro Gly Leu Pro Pro Glu Leu Pro Glu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 383
<211> LENGTH: 42
<212> TYPE: PRT
<213> ORGANISM: Artificial
<220> FEATURE:
<223> OTHER INFORMATION: FGF21 variant

<400> SEQUENCE: 383

Pro Gly Leu Val Pro Ala Leu Pro Glu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 384
<211> LENGTH: 42
<212> TYPE: PRT
<213> ORGANISM: Artificial
<220> FEATURE:
<223> OTHER INFORMATION: FGF21 variant

<400> SEQUENCE: 384

Pro Gly Met Pro Pro Ala Leu Pro Glu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 385
<211> LENGTH: 42
<212> TYPE: PRT
<213> ORGANISM: Artificial
<220> FEATURE:
<223> OTHER INFORMATION: FGF21 variant

<400> SEQUENCE: 385

Pro Pro Leu Pro Pro Ala Leu Pro Glu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 386
<211> LENGTH: 42
<212> TYPE: PRT
<213> ORGANISM: Artificial
<220> FEATURE:
<223> OTHER INFORMATION: FGF21 variant

<400> SEQUENCE: 386

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
                20                  25                  30

Ser Gln Gly Arg Ser Pro Ser Tyr Glu Lys
            35                  40

<210> SEQ ID NO 387
<211> LENGTH: 42
<212> TYPE: PRT
<213> ORGANISM: Artificial
<220> FEATURE:
<223> OTHER INFORMATION: FGF21 variant

<400> SEQUENCE: 387

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
                20                  25                  30

Ser Gln Gly Arg Ser Pro Ser Phe Glu Lys
            35                  40

<210> SEQ ID NO 388
<211> LENGTH: 42
<212> TYPE: PRT
<213> ORGANISM: Artificial
<220> FEATURE:
<223> OTHER INFORMATION: FGF21 variant

<400> SEQUENCE: 388

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
                20                  25                  30

Ser Gln Val Arg Ser Pro Ser Phe Glu Lys
            35                  40

<210> SEQ ID NO 389
<211> LENGTH: 42
<212> TYPE: PRT
<213> ORGANISM: Artificial
<220> FEATURE:
<223> OTHER INFORMATION: FGF21 variant

<400> SEQUENCE: 389

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
                20                  25                  30

Ser Ala Val Arg Ser Pro Ser Phe Glu Lys
            35                  40

<210> SEQ ID NO 390

```
<211> LENGTH: 42
<212> TYPE: PRT
<213> ORGANISM: Artificial
<220> FEATURE:
<223> OTHER INFORMATION: FGF21 variant

<400> SEQUENCE: 390

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Glu Ala Val Arg Ser Pro Ser Phe Glu Lys
        35                  40

<210> SEQ ID NO 391
<211> LENGTH: 42
<212> TYPE: PRT
<213> ORGANISM: Artificial
<220> FEATURE:
<223> OTHER INFORMATION: FGF21 variant

<400> SEQUENCE: 391

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Leu
            20                  25                  30

Glu Ala Val Arg Ser Pro Ser Phe Glu Lys
        35                  40

<210> SEQ ID NO 392
<211> LENGTH: 42
<212> TYPE: PRT
<213> ORGANISM: Artificial
<220> FEATURE:
<223> OTHER INFORMATION: FGF21 variant

<400> SEQUENCE: 392

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Thr Gly
            20                  25                  30

Leu Glu Ala Val Arg Ser Pro Phe Glu Lys
        35                  40

<210> SEQ ID NO 393
<211> LENGTH: 43
<212> TYPE: PRT
<213> ORGANISM: Artificial
<220> FEATURE:
<223> OTHER INFORMATION: FGF21 variant

<400> SEQUENCE: 393

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Leu Val Thr Gly
            20                  25                  30

Leu Glu Ala Val Arg Ser Pro Ser Phe Glu Lys
        35                  40

<210> SEQ ID NO 394
<211> LENGTH: 43
<212> TYPE: PRT
<213> ORGANISM: Artificial
```

<220> FEATURE:
<223> OTHER INFORMATION: FGF21 variant

<400> SEQUENCE: 394

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Gly Leu Val Thr Gly
            20                  25                  30

Leu Glu Ala Val Arg Ser Pro Ser Phe Glu Lys
        35                  40

<210> SEQ ID NO 395
<211> LENGTH: 43
<212> TYPE: PRT
<213> ORGANISM: Artificial
<220> FEATURE:
<223> OTHER INFORMATION: FGF21 variant

<400> SEQUENCE: 395

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Phe Gly Leu Val Thr Gly
            20                  25                  30

Leu Glu Ala Val Arg Ser Pro Ser Phe Glu Lys
        35                  40

<210> SEQ ID NO 396
<211> LENGTH: 43
<212> TYPE: PRT
<213> ORGANISM: Artificial
<220> FEATURE:
<223> OTHER INFORMATION: FGF21 variant

<400> SEQUENCE: 396

Pro Gly Leu Pro Pro Ala Leu Pro Glu Pro Pro Gly Ile Leu Ala Pro
1               5                   10                  15

Gln Pro Pro Asp Val Gly Ser Met Asp Pro Phe Gly Leu Val Thr Gly
            20                  25                  30

Leu Glu Ala Val Arg Ser Pro Ser Phe Glu Lys
        35                  40

<210> SEQ ID NO 397
<211> LENGTH: 43
<212> TYPE: PRT
<213> ORGANISM: Artificial
<220> FEATURE:
<223> OTHER INFORMATION: FGF21 variant

<400> SEQUENCE: 397

Pro Gly Leu Pro Pro Ala Leu Pro Glu Pro Pro Gly Ile Leu Ala Pro
1               5                   10                  15

Gln Pro Pro Asp Val Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 398
<211> LENGTH: 43
<212> TYPE: PRT
<213> ORGANISM: Artificial
<220> FEATURE:
<223> OTHER INFORMATION: FGF21 variant

```
<400> SEQUENCE: 398

Pro Gly Leu Pro Pro Ala Leu Pro Glu Pro Pro Gly Ile Leu Ala Pro
1               5                   10                  15

Gln Pro Pro Asp Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 399
<211> LENGTH: 43
<212> TYPE: PRT
<213> ORGANISM: Artificial
<220> FEATURE:
<223> OTHER INFORMATION: FGF21 variant

<400> SEQUENCE: 399

Pro Gly Leu Pro Pro Ala Leu Pro Glu Pro Pro Gly Ile Leu Ala Pro
1               5                   10                  15

Gln Pro Pro Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 400
<211> LENGTH: 43
<212> TYPE: PRT
<213> ORGANISM: Artificial
<220> FEATURE:
<223> OTHER INFORMATION: FGF21 variant

<400> SEQUENCE: 400

Pro Gly Leu Pro Pro Ala Leu Pro Glu Pro Pro Gly Ile Leu Ala Pro
1               5                   10                  15

Gln Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 401
<211> LENGTH: 43
<212> TYPE: PRT
<213> ORGANISM: Artificial
<220> FEATURE:
<223> OTHER INFORMATION: FGF21 variant

<400> SEQUENCE: 401

Pro Gly Leu Pro Pro Ala Leu Pro Glu Pro Pro Gly Ile Leu Ala Pro
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 402
<211> LENGTH: 43
<212> TYPE: PRT
<213> ORGANISM: Artificial
<220> FEATURE:
<223> OTHER INFORMATION: FGF21 variant

<400> SEQUENCE: 402

Pro Gly Leu Pro Pro Ala Leu Pro Glu Pro Pro Gly Ile Leu Ala Ser
```

1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 403
<211> LENGTH: 43
<212> TYPE: PRT
<213> ORGANISM: Artificial
<220> FEATURE:
<223> OTHER INFORMATION: FGF21 variant

<400> SEQUENCE: 403

Pro Gly Leu Pro Pro Ala Leu Pro Glu Pro Pro Gly Ile Leu Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 404
<211> LENGTH: 43
<212> TYPE: PRT
<213> ORGANISM: Artificial
<220> FEATURE:
<223> OTHER INFORMATION: FGF21 variant

<400> SEQUENCE: 404

Pro Gly Leu Pro Pro Ala Leu Pro Glu Pro Pro Gly Ile Met Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 405
<211> LENGTH: 43
<212> TYPE: PRT
<213> ORGANISM: Artificial
<220> FEATURE:
<223> OTHER INFORMATION: FGF21 variant

<400> SEQUENCE: 405

Pro Gly Leu Pro Pro Ala Leu Pro Glu Pro Pro Gly Asp Met Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 406
<211> LENGTH: 43
<212> TYPE: PRT
<213> ORGANISM: Artificial
<220> FEATURE:
<223> OTHER INFORMATION: FGF21 variant

<400> SEQUENCE: 406

Pro Gly Leu Pro Pro Ala Leu Pro Glu Pro Pro Ser Asp Met Phe Ser
1               5                   10                  15

Ser Pro Leu Glu Thr Asp Ser Met Asp Pro Phe Gly Leu Val Thr Gly

```
            20                  25                  30

Leu Glu Ala Val Arg Ser Pro Ser Phe Glu Lys
        35                  40

<210> SEQ ID NO 407
<211> LENGTH: 43
<212> TYPE: PRT
<213> ORGANISM: Artificial
<220> FEATURE:
<223> OTHER INFORMATION: FGF21 variant

<400> SEQUENCE: 407

Pro Gly Leu Pro Pro Ala Leu Pro Glu Pro Glu Ser Asp Met Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 408
<211> LENGTH: 43
<212> TYPE: PRT
<213> ORGANISM: Artificial
<220> FEATURE:
<223> OTHER INFORMATION: FGF21 variant

<400> SEQUENCE: 408

Pro Gly Leu Pro Pro Ala Leu Pro Glu Leu Glu Ser Asp Met Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 409
<211> LENGTH: 44
<212> TYPE: PRT
<213> ORGANISM: Artificial
<220> FEATURE:
<223> OTHER INFORMATION: FGF21 variant

<400> SEQUENCE: 409

Pro Gly Leu Pro Pro Ala Leu Pro Glu His Leu Glu Ser Asp Met Phe
1               5                   10                  15

Ser Ser Pro Leu Glu Thr Asp Ser Met Asp Pro Phe Gly Leu Val Thr
            20                  25                  30

Gly Leu Glu Ala Val Arg Ser Pro Ser Phe Glu Lys
        35                  40

<210> SEQ ID NO 410
<211> LENGTH: 45
<212> TYPE: PRT
<213> ORGANISM: Artificial
<220> FEATURE:
<223> OTHER INFORMATION: FGF21 variant

<400> SEQUENCE: 410

Pro Gly Leu Pro Pro Ala Leu Pro Glu Gly His Leu Glu Ser Asp Met
1               5                   10                  15

Phe Ser Ser Pro Leu Glu Thr Asp Ser Met Asp Pro Phe Gly Leu Val
            20                  25                  30

Thr Gly Leu Glu Ala Val Arg Ser Pro Ser Phe Glu Lys
```

35                  40                  45

<210> SEQ ID NO 411
<211> LENGTH: 46
<212> TYPE: PRT
<213> ORGANISM: Artificial
<220> FEATURE:
<223> OTHER INFORMATION: FGF21 variant

<400> SEQUENCE: 411

Pro Gly Leu Pro Pro Ala Leu Pro Glu Arg Gly His Leu Glu Ser Asp
1               5                   10                  15

Met Phe Ser Ser Pro Leu Glu Thr Asp Ser Met Asp Pro Phe Gly Leu
                20                  25                  30

Val Thr Gly Leu Glu Ala Val Arg Ser Pro Ser Phe Glu Lys
            35                  40                  45

<210> SEQ ID NO 412
<211> LENGTH: 47
<212> TYPE: PRT
<213> ORGANISM: Artificial
<220> FEATURE:
<223> OTHER INFORMATION: FGF21 variant

<400> SEQUENCE: 412

Pro Gly Leu Pro Pro Ala Leu Pro Glu Leu Arg Gly His Leu Glu Ser
1               5                   10                  15

Asp Met Phe Ser Ser Pro Leu Glu Thr Asp Ser Met Asp Pro Phe Gly
                20                  25                  30

Leu Val Thr Gly Leu Glu Ala Val Arg Ser Pro Ser Phe Glu Lys
            35                  40                  45

<210> SEQ ID NO 413
<211> LENGTH: 48
<212> TYPE: PRT
<213> ORGANISM: Artificial
<220> FEATURE:
<223> OTHER INFORMATION: FGF21 variant

<400> SEQUENCE: 413

Pro Gly Leu Pro Pro Ala Leu Pro Glu Asp Leu Arg Gly His Leu Glu
1               5                   10                  15

Ser Asp Met Phe Ser Ser Pro Leu Glu Thr Asp Ser Met Asp Pro Phe
                20                  25                  30

Gly Leu Val Thr Gly Leu Glu Ala Val Arg Ser Pro Ser Phe Glu Lys
            35                  40                  45

<210> SEQ ID NO 414
<211> LENGTH: 48
<212> TYPE: PRT
<213> ORGANISM: Artificial
<220> FEATURE:
<223> OTHER INFORMATION: FGF21 variant

<400> SEQUENCE: 414

Pro Gly Leu Pro Pro Ala Glu Pro Glu Asp Leu Arg Gly His Leu Glu
1               5                   10                  15

Ser Asp Met Phe Ser Ser Pro Leu Glu Thr Asp Ser Met Asp Pro Phe
                20                  25                  30

Gly Leu Val Thr Gly Leu Glu Ala Val Arg Ser Pro Ser Phe Glu Lys
            35                  40                  45

```
<210> SEQ ID NO 415
<211> LENGTH: 48
<212> TYPE: PRT
<213> ORGANISM: Artificial
<220> FEATURE:
<223> OTHER INFORMATION: FGF21 variant

<400> SEQUENCE: 415

Pro Gly Leu Pro Pro Glu Glu Pro Glu Asp Leu Arg Gly His Leu Glu
1               5                   10                  15
Ser Asp Met Phe Ser Ser Pro Leu Glu Thr Asp Ser Met Asp Pro Phe
            20                  25                  30
Gly Leu Val Thr Gly Leu Glu Ala Val Arg Ser Pro Ser Phe Glu Lys
        35                  40                  45

<210> SEQ ID NO 416
<211> LENGTH: 48
<212> TYPE: PRT
<213> ORGANISM: Artificial
<220> FEATURE:
<223> OTHER INFORMATION: FGF21 variant

<400> SEQUENCE: 416

Pro Gly Leu Val Pro Glu Glu Pro Glu Asp Leu Arg Gly His Leu Glu
1               5                   10                  15
Ser Asp Met Phe Ser Ser Pro Leu Glu Thr Asp Ser Met Asp Pro Phe
            20                  25                  30
Gly Leu Val Thr Gly Leu Glu Ala Val Arg Ser Pro Ser Phe Glu Lys
        35                  40                  45

<210> SEQ ID NO 417
<211> LENGTH: 48
<212> TYPE: PRT
<213> ORGANISM: Artificial
<220> FEATURE:
<223> OTHER INFORMATION: FGF21 variant

<400> SEQUENCE: 417

Pro Gly Met Val Pro Glu Glu Pro Glu Asp Leu Arg Gly His Leu Glu
1               5                   10                  15
Ser Asp Met Phe Ser Ser Pro Leu Glu Thr Asp Ser Met Asp Pro Phe
            20                  25                  30
Gly Leu Val Thr Gly Leu Glu Ala Val Arg Ser Pro Ser Phe Glu Lys
        35                  40                  45

<210> SEQ ID NO 418
<211> LENGTH: 48
<212> TYPE: PRT
<213> ORGANISM: Artificial
<220> FEATURE:
<223> OTHER INFORMATION: FGF21 variant

<400> SEQUENCE: 418

Pro Pro Met Val Pro Glu Glu Pro Glu Asp Leu Arg Gly His Leu Glu
1               5                   10                  15
Ser Asp Met Phe Ser Ser Pro Leu Glu Thr Asp Ser Met Asp Pro Phe
            20                  25                  30
Gly Leu Val Thr Gly Leu Glu Ala Val Arg Ser Pro Ser Phe Glu Lys
        35                  40                  45
```